US012457900B2

(12) United States Patent
Zheng et al.

(10) Patent No.: US 12,457,900 B2
(45) Date of Patent: Oct. 28, 2025

(54) ORGANIC COMPOUND, AND ELECTRONIC ELEMENT AND ELECTRONIC DEVICE USING SAME

(71) Applicant: Shaanxi Lighte Optoelectronics Material Co., Ltd., Xi'an (CN)

(72) Inventors: Yiyi Zheng, Xi'an (CN); Xinying Liu, Xi'an (CN); Tiantian Ma, Xi'an (CN)

(73) Assignee: Shaanxi Lighte Optoelectronics Material Co., Ltd., Xi'an (CN)

( * ) Notice: Subject to any disclaimer, the term of this patent is extended or adjusted under 35 U.S.C. 154(b) by 199 days.

(21) Appl. No.: 18/011,991

(22) PCT Filed: Jul. 9, 2021

(86) PCT No.: PCT/CN2021/105554
§ 371 (c)(1),
(2) Date: Dec. 21, 2022

(87) PCT Pub. No.: WO2022/012439
PCT Pub. Date: Jan. 20, 2022

(65) Prior Publication Data

US 2023/0217825 A1 Jul. 6, 2023

(30) Foreign Application Priority Data

Jul. 17, 2020 (CN) ........................ 202010695858.X

(51) Int. Cl.
*H10K 85/60* (2023.01)
*C07D 239/26* (2006.01)
(Continued)

(52) U.S. Cl.
CPC ....... *H10K 85/6574* (2023.02); *C07D 239/26* (2013.01); *C07D 251/24* (2013.01); *C07D 307/94* (2013.01); *C07D 333/76* (2013.01); *C07D 405/04* (2013.01); *C07D 405/10* (2013.01); *C07D 405/14* (2013.01); *C07D 409/04* (2013.01); *C07D 409/10* (2013.01);
(Continued)

(58) Field of Classification Search
CPC ............. H10K 85/6574; H10K 85/624; H10K 85/654; H10K 85/6576; H10K 85/615; H10K 85/626; H10K 85/6572; H10K 85/40; C07D 239/26; C07D 251/24; C07D 307/94; C07D 333/76; C07D 405/04; C07D 405/10; C07D 405/14; C07D 409/04; C07D 409/10; C07D 409/14; C07F 7/0816; C09K 11/06; C09K 2211/1018; H01L 51/0071; H01L 51/0072; H01L 51/0073; H01L 51/0074; H01L 51/0054; H01L 51/0055; H01L 51/0056; H01L 51/0058
See application file for complete search history.

(56) References Cited

U.S. PATENT DOCUMENTS 6,322,909 B1 * 11/2001 Sakaguchi ........... H10K 85/626 313/506
2003/0068526 A1 * 4/2003 Kamatani .............. C09K 11/06 546/10

(Continued)

FOREIGN PATENT DOCUMENTS

CN 111018797 A 4/2020
CN 111848588 A 10/2020

(Continued)

OTHER PUBLICATIONS

Fukagawa H et al., machine translation of JP-2020068235-A (2020) pp. 1-17. (Year: 2020).*

(Continued)

*Primary Examiner* — Dylan C Kershner
(74) *Attorney, Agent, or Firm* — Tucker Ellis LLP

(57) ABSTRACT

The present disclosure relates to an organic compound. The structure of the organic compound consists of a structure represented by formula (I) and a structure represented by formula (II); the structure represented by formula (I) is fused with the structure represented by formula (II); and * represents a connection point, in formula (I), capable of being fused with formula (II). When being used to the organic light-emitting layer of an organic electroluminescent device, the organic compound of the present application can effectively improve the device efficiency of the device and prolong the service life of the organic electroluminescent device.

Formula I

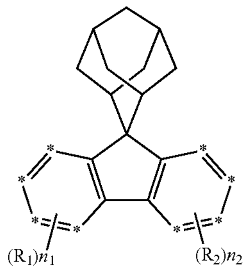

Formula II

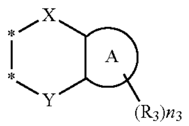

8 Claims, 1 Drawing Sheet

(51) Int. Cl.

| | |
|---|---|
| ***C07D 251/24*** | (2006.01) |
| ***C07D 307/94*** | (2006.01) |
| ***C07D 333/76*** | (2006.01) |
| ***C07D 405/04*** | (2006.01) |
| ***C07D 405/10*** | (2006.01) |
| ***C07D 405/14*** | (2006.01) |
| ***C07D 409/04*** | (2006.01) |
| ***C07D 409/10*** | (2006.01) |
| ***C07D 409/14*** | (2006.01) |
| ***C07F 7/08*** | (2006.01) |
| ***C09K 11/06*** | (2006.01) |
| ***H10K 50/12*** | (2023.01) |
| ***H10K 85/40*** | (2023.01) |

(52) U.S. Cl.

CPC .......... *C07D 409/14* (2013.01); *C07F 7/0816* (2013.01); *C09K 11/06* (2013.01); *H10K 85/40* (2023.02); *H10K 85/615* (2023.02); *H10K 85/624* (2023.02); *H10K 85/626* (2023.02); *H10K 85/654* (2023.02); *H10K 85/6572* (2023.02); *H10K 85/6576* (2023.02); *C09K 2211/1018* (2013.01); *H10K 50/121* (2023.02)

(56) References Cited

U.S. PATENT DOCUMENTS

2015/0349270 A1* 12/2015 Lee ...................... C07D 409/10 546/281.1
2018/0040834 A1* 2/2018 Choi .................. H10K 85/6574
2022/0017544 A1* 1/2022 Yoon .................... H10K 85/636

FOREIGN PATENT DOCUMENTS

JP 2020068235 A * 4/2020
WO WO-2020045924 A1 * 3/2020 ........... C07C 211/61

OTHER PUBLICATIONS

International Search Report from corresponding International Application No. PCT/CN2021/105554, dated Sep. 28, 2021, 4 pages with translation.

* cited by examiner

ORGANIC COMPOUND, AND ELECTRONIC ELEMENT AND ELECTRONIC DEVICE USING SAME

CROSS REFERENCE TO RELATED APPLICATIONS

The present application claims the priority of Chinese Patent Application No. 202010695858.X, filed on Jul. 17, 2020, the contents of which are incorporated herein by reference in their entirety as a part of the present application.

FIELD OF THE TECHNOLOGY

The present disclosure belongs to the technical field of organic materials, and in particular provides an organic compound, and an electronic element and electronic device using the same.

BACKGROUND

Organic electroluminescent materials (OLEDs) have the advantages of ultra-thinness, self-luminescence, wide viewing angle, fast response, high luminous efficiency, good temperature adaptability, simple production process, low driving voltage, low energy consumption, and the like as a new-generation display technology, and have been widely used in industries such as flat panel display, flexible display, solid state lighting, and vehicle display.

An organic light-emitting device generally includes an anode, a cathode and an organic material layer between them. The organic material layer is typically formed in a multilayer structure composed of different materials to improve the brightness, efficiency, and service life of an organic electroluminescent device, and the organic material layer may be composed of a hole injection layer, a hole transport layer, a light-emitting layer, an electron transport layer, an electron injection layer, and the like. In an organic light-emitting device structure, when a voltage is applied between two electrodes, holes and electrons are injected into the organic material layer from the anode and the cathode, respectively, and excitons are formed when the injected holes and electrons meet, and light is emitted when these excitons return to a ground state.

In the existing organic electroluminescent device, the most major problem is the service life and efficiency, as the area of the display increases, the driving voltage is also increased, the luminous efficiency and the power efficiency are also required to be increased, and thus, it is necessary to continue to develop new materials to further improve the performance of the organic electroluminescent device.

SUMMARY

The present disclosure aims to provide an organic compound, and an electronic element and electronic device using the same. The organic compound can be used in an organic electroluminescent device, so that the performance of the device can be improved.

To achieve the above purpose, in a first aspect, the present disclosure provides an organic compound, having a structure consisting of a structure represented by a formula I and a structure represented by a formula II:

Formula I

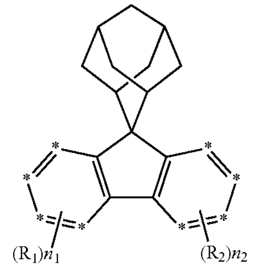

Formula II

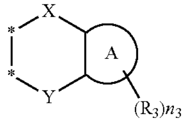

where the structure represented by the formula I is fused with at least one structure represented by the formula II;

* represents a site where the formula I is fused with the formula II;

a ring A is selected from a benzene ring or a fused aromatic ring with 10 to 14 ring-forming carbon atoms;

$n_1$ represents the number of $R_1$, $n_2$ represents the number of $R_2$, and $n_3$ represents the number of $R_3$;

$R_1$, $R_2$ and $R_3$ are represented by $R_k$, $n_1$ to $n_3$ are represented by $n_k$, and k is a variable and represents 1, 2 or 3; when k is 1, $n_k$ is selected from 0, 1, 2, 3 or 4; when k is 2, $n_k$ is selected from 0, 1 or 2; when k is 3, $n_k$ is selected from 0, 1, 2, 3, 4, 5, 6, 7 or 8; and when $n_k$ is greater than 1, any two $n_k$ are the same or different; and optionally, any two adjacent $R_k$ are connected to each other to form a ring, and the formed ring is optionally substituted with R';

$R_1$, $R_2$, $R_3$, and R' are the same or different, and are each independently selected from an alkyl with 1 to 5 carbon atoms or a structure represented by a formula III:

Formula III

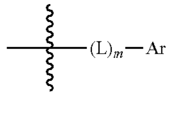

represents a chemical bond;

m represents the number of L, and m is selected from 1, 2 or 3; and when m is 2 or 3, any two L are the same or different;

Ar is selected from a substituted or unsubstituted aryl with 6 to 30 carbon atoms, a substituted or unsubstituted heteroaryl with 3 to 30 carbon atoms, a triarylsilyl with 18 to 30 carbon atoms, a triarylphosphinyloxy with 12 to 20 carbon atoms, or a cycloalkyl with 3 to 10 carbon atoms;

L is selected from a single bond, a substituted or unsubstituted arylene with 6 to 30 carbon atoms, or a substituted or unsubstituted heteroarylene with 3 to 30 carbon atoms;

substituents in L and Ar are one or more, where the substituents in L and Ar are each independently selected from deuterium, a halogen group, cyano, a heteroaryl with 3 to 12 carbon atoms, an aryl with 6 to 12 carbon atoms, an alkyl with 1 to 5 carbon atoms, a cycloalkyl with 3 to 10 carbon atoms, trimethylsilyl, or triphenylsilyl; and X and Y are the same or different, and are each independently selected from a single bond, O, S, $C(R_4R_5)$, and $Si(R_6R_7)$, and X and Y are not simultaneously a single bond; where $R_4$-$R_7$ are the same or different, and are each independently selected from an alkyl with 1 to 5 carbon atoms, an aryl with 6 to 30 carbon atoms, or a heteroaryl with 2 to 30 carbon atoms; optionally, $R_4$ and $R_5$ are connected to each other to form a 3- to 15-membered saturated or unsaturated ring together with the atoms to which they are commonly connected; and optionally, $R_6$ and $R_7$ are connected to each other to form a 3- to 15-membered saturated or unsaturated ring together with the atoms to which they are commonly connected.

In a second aspect, the present disclosure provides an electronic element, including an anode and a cathode which are oppositely disposed, and a functional layer disposed between the anode and the cathode; and the functional layer includes the organic compound provided by the present disclosure.

In a third aspect, the present disclosure provides an electronic device, including the electronic element according to the second aspect of the present disclosure.

The organic compound of the present disclosure has a large planar structure formed by spiro[adamantane-fluorene] as a core structure fused with a benzoheteroaromatic ring; in this structure, an aromatic ring is fused on spiro[adamantane-fluorene], which greatly enhances the rigidity of the compound, improves the hole mobility, and possesses a high first triplet energy level, and the fused benzoheteroaromatic ring can efficiently promote energy transfer, and thus the organic compound can be applied to a host material of an organic light-emitting layer in an organic electroluminescent material; the compound can be applied to a single-component host material or one of a two-component mixed-type host material, which can ensure that the organic electroluminescent device has high luminous efficiency and service life; and adamantane is spiro-bonded to the fused planar structure, which may effectively reduce intermolecular stacking, improve the film-forming properties of the compound, and thus further improve the service life of the device.

Other features and advantages of the present disclosure will be described in detail in the Detailed Description that follows.

BRIEF DESCRIPTION OF THE DRAWINGS

The accompanying drawings are used to provide a further understanding of the present disclosure, and constitute a part of this description, and together with the following specific examples, are used to explain the present disclosure, but do not constitute a limitation to the present disclosure.

DESCRIPTION OF REFERENCE SIGNS

Figure 1:
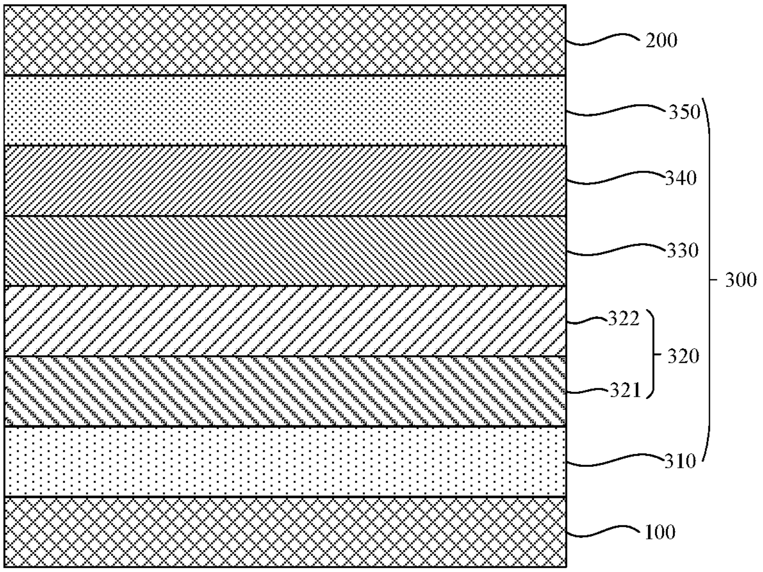
FIG. 1 is a structural schematic diagram of an organic electroluminescent device according to one example of the present disclosure.

100, anode; 200, cathode; 300, functional layer; 310, hole injection layer; 320, hole transport layer; 321, first hole transport layer; 322, second hole transport layer; 330, organic light-emitting layer; 340, electron transport layer; 350, electron injection layer; and 400, electronic device.

DETAILED DESCRIPTION

Specific examples of the present disclosure will be described in detail below. It should be understood that the specific examples described here are only used to illustrate and explain the present disclosure, but are not intended to limit the present disclosure.

In a first aspect, the present disclosure provides an organic compound, having a structure consisting of a structure represented by a formula I and a structure represented by a formula II:

Formula I

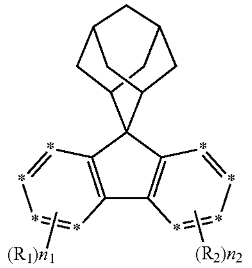

Formula II

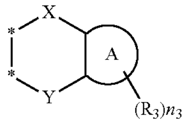

where the structure represented by the formula I is fused with at least one structure represented by the formula II;

* represents a site where the formula I is fused with the formula II;

a ring A is selected from a benzene ring or a fused aromatic ring with 10 to 14 ring-forming carbon atoms;

$n_1$ represents the number of $R_1$, $n_2$ represents the number of $R_2$, and $n_3$ represents the number of $R_3$;

$R_1$, $R_2$ and $R_3$ are represented by $R_k$, $n_1$ to $n_3$ are represented by $n_k$, and k is a variable and represents 1, 2 or 3; when k is 1, $n_k$ is selected from 0, 1, 2, 3 or 4; when k is 2, $n_k$ is selected from 0, 1 or 2; when k is 3, $n_k$ is selected from 0, 1, 2, 3, 4, 5, 6, 7 or 8; and when $n_k$ is greater than 1, any two $n_k$ are the same or different; and optionally, any two adjacent $R_k$ are connected to each other to form a ring, and the formed ring is optionally substituted with R';

$R_1$, $R_2$, $R_3$, and R' are the same or different, and are each independently selected from an alkyl with 1 to 5 carbon atoms or a structure represented by a formula III:

Formula III

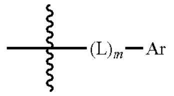

represents a chemical bond;

m represents the number of L, and m is selected from 1, 2 or 3; and when m is 2 or 3, any two L are the same or different;

Ar is selected from a substituted or unsubstituted aryl with 6 to 30 carbon atoms, a substituted or unsubstituted heteroaryl with 3 to 30 carbon atoms, a triarylsilyl with 18 to 30 carbon atoms, a triarylphosphinyloxy with 12 to 20 carbon atoms, or a cycloalkyl with 3 to 10 carbon atoms;

L is selected from a single bond, a substituted or unsubstituted arylene with 6 to 30 carbon atoms, or a substituted or unsubstituted heteroarylene with 3 to 30 carbon atoms;

substituents in L and Ar are one or more (when L and Ar include substituents), and the substituents in L and Ar are each independently selected from deuterium, a halogen group, cyano, a heteroaryl with 3 to 12 carbon atoms, an aryl with 6 to 12 carbon atoms, an alkyl with 1 to 5 carbon atoms, a cycloalkyl with 3 to 10 carbon atoms, trimethylsilyl, or triphenylsilyl; and X and Y are the same or different, and are each independently selected from a single bond, O, S, $C(R_4R_5)$, and $Si(R_6R_7)$, and X and Y are not simultaneously a single bond; $R_4$ to $R_7$ are the same or different, and are each independently selected from an alkyl with 1 to 5 carbon atoms, an aryl with 6 to 30 carbon atoms, or a heteroaryl with 2 to 30 carbon atoms; optionally, $R_4$ and $R_5$ are connected to each other to form a 3- to 15-membered saturated or unsaturated ring together with the atoms to which they are commonly connected; and optionally, $R_6$ and $R_7$ are connected to each other to form a 3- to 15-membered saturated or unsaturated ring together with the atoms to which they are commonly connected.

In the present disclosure, $R_1$, $R_2$, $R_3$, and R' may also each independently be selected from deuterium, a halogen group, and cyano.

In the present disclosure "* represents a site where the formula I is fused with the formula II", which means that the formula II is connected to any two adjacent fused positions of eight fused sites of the formula I.

Optionally, the structure represented by the formula I is fused with one structure represented by the formula II.

Optionally, the structure represented by the formula I is fused with two structures represented by the formula II.

Optionally, the structure represented by the formula I is fused with three structures represented by the formula II.

In the present disclosure,

“ 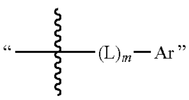 ”

means that m L are linked together in sequence, and are linked to Ar, specifically, when m is 1,

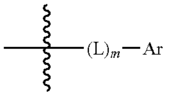

represents

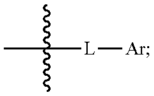

when m is 2,

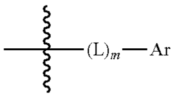

represents

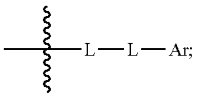

when m is 3,

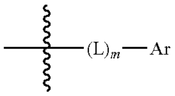

represents

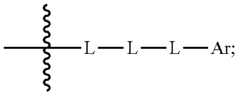

and when m is 2 or 3, each L may be the same or different.

In the present disclosure, the terms “optional” and “optionally” mean that the subsequently described event or circumstance can but need not occur, and that the description includes occasions where the event or circumstance occurs or does not occur. For example, “optionally, two adjacent substituents xx form a ring”, which means that the two substituents can, but need not, form a ring, including a scenario in which two adjacent substituents form a ring and a scenario in which two adjacent substituents do not form a ring. For another example, “optionally, $R_4$ and $R_5$ are connected to each other to form a 3- to 15-membered saturated or unsaturated ring together with the atoms to which they are commonly connected”, which means that $R_4$ and $R_5$ may be connected to each other to form a 3- to 15-membered saturated or unsaturated ring together with the atoms to which they are commonly connected, or $R_4$ and $R_5$ may also each independently be present.

In the present disclosure, if a group is not specifically indicated to be substituted, it indicates that the group is unsubstituted.

In the present disclosure, the used descriptions modes "each . . . is independently", " . . . is respectively and independently" and " . . . is independently selected from" can be interchanged, which should be understood in a broad sense, and may mean that specific options expressed by a same symbol in different groups do not influence each other, or may also mean that specific options expressed by a same symbol in a same group do not influence each other. For example, the meaning of

Q-1

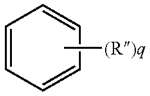

Q-2

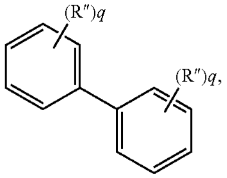

where each q is independently 0, 1, 2 or 3 and each R" is independently selected from hydrogen, deuterium, fluorine, and chlorine" is as follows: a formula Q-1 represents that a benzene ring has q substituents R", each R" can be the same or different, and options of each R" do not influence each other; and a formula Q-2 represents that each benzene ring of biphenyl has q substituents R", the number q of the substituents R" on the two benzene rings can be the same or different, each R" can be the same or different, and options of each R" do not influence each other.

In the present disclosure, the term "substituted or unsubstituted" means that a functional group described behind the term may or may not have substituents (the substituents are collectively referred to as Rc below for ease of description). For example, "substituted or unsubstituted aryl" refers to aryl with a substituent Rc or unsubstituted aryl. The above substituent, i.e. Rc, can be, for example, deuterium, a halogen group, cyano, heteroaryl, aryl, trimethylsilyl, triphenylsilyl, alkyl or cycloalkyl.

In the present disclosure, in the expression that "any two adjacent substituents form a ring", "any adjacent" can include the condition that there are two substituents on a same atom and can also include the condition that two adjacent atoms each have one substituent; when there are two substituents on the same atom, the two substituents may form a saturated or unsaturated ring (e.g., a 3- to 18-membered saturated or unsaturated ring) with the atom to which they are commonly connected; when two adjacent atoms each have one substituent, the two substituents may be fused to form a ring, e.g., a naphthalene ring, a phenanthrene ring, or an anthracene ring. For example, "any two adjacent $R_i$ form a ring", which includes the condition that any two adjacent $R_1$ are connected to each other to form a ring with the atoms to which they are commonly connected, or the condition that any two adjacent $R_2$ are connected to each other to form a ring with the atoms to which they are commonly connected, or the condition that any two adjacent $R_3$ are connected to each other to form a ring with the atoms to which they are commonly connected. For example: any two adjacent $R_i$ may form a ring having 6 to 15 carbon atoms, or a ring having 6 to 10 carbon atoms; the ring may be saturated (e.g., a five-membered ring

, a six-membered ring

, etc.) or unsaturated, (for example, an aromatic ring, and specific examples of the aromatic ring include a benzene ring

, a naphthalene ring

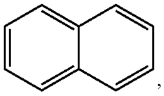, a phenanthrene ring

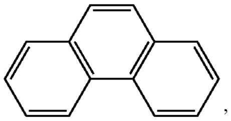 [SMILES: c1ccc2c(c1)ccc1ccccc12], etc.).

In the present disclosure, the number of carbon atoms of a substituted or unsubstituted functional group refers to the number of all carbon atoms. For example, if Ar is a substituted aryl with 12 carbon atoms, then the number of all carbon atoms of the aryl and substituents on the aryl is 12.

In the present disclosure, aryl refers to an optional functional group or substituent derived from an aromatic carbocyclic ring. The aryl can be monocyclic aryl (e.g., phenyl) or polycyclic aryl, in other words, the aryl can be monocyclic aryl, fused aryl, two or more monocyclic aryl conjugatedly linked by carbon-carbon bonds, monocyclic aryl and fused aryl which are conjugatedly linked by a carbon-carbon bond, and two or more fused aryl conjugatedly linked by carbon-carbon bonds. That is, unless specified otherwise, two or more aromatic groups conjugatedly linked by carbon-carbon bonds can also be regarded as aryl of the present disclosure. The fused aryl may, for example, include bicyclic fused aryl (e.g., naphthyl), tricyclic fused aryl (e.g., phenanthryl, fluorenyl, and anthryl), and the like. The aryl does not contain heteroatoms such as B, N, O, S, P, Se, and Si. For example, in the present disclosure, biphenyl, terphenyl, and the like are aryl. Examples of the aryl can include, but are not limited to, phenyl, naphthyl, fluorenyl, anthryl, phenanthryl, biphenyl, terphenyl, quaterphenyl, quinquephenyl, benzo[9,10]phenanthryl, pyrenyl, benzofluoranthenyl, chrysenyl, and the like. In the present disclosure, involved arylene refers to a divalent group formed by further loss of one hydrogen atom of the aryl.

In the present disclosure, substituted aryl can be that one or two or more hydrogen atoms in the aryl are substituted with groups such as a deuterium atom, a halogen group, —CN, aryl, heteroaryl, trialkylsilyl, alkyl, cycloalkyl, and the like. Specific examples of heteroaryl-substituted aryl include, but are not limited to, dibenzofuranyl-substituted phenyl, dibenzothiophenyl-substituted phenyl, pyridinyl-substituted phenyl, and the like. It should be understood that the number of carbon atoms of the substituted aryl refers to the total number of carbon atoms of the aryl and substituents on the aryl, for example, substituted aryl with 18 carbon atoms means that the total number of carbon atoms of the aryl and substituents is 18.

In the present disclosure, examples of aryl as a substituent include, but are not limited to, phenyl, biphenyl, naphthyl, 9,9-dimethylfluorenyl, anthryl, phenanthryl, and chrysenyl.

In the present disclosure, heteroaryl refers to a monovalent aromatic ring containing at least one heteroatom in the ring or its derivative, and the heteroatom can be at least one of B, 0, N, P, Si, Se, and S. The heteroaryl may be monocyclic heteroaryl or polycyclic heteroaryl, in other words, the heteroaryl may be a single aromatic ring system or a plurality of aromatic ring systems conjugatedly connected via carbon-carbon bonds, and any one aromatic ring system is one aromatic monocyclic ring or one aromatic fused ring. For example, the heteroaryl may include thienyl, furyl, pyrrolyl, imidazolyl, thiazolyl, oxazolyl, oxadiazolyl, triazolyl, pyridyl, bipyridyl, pyrimidinyl, triazinyl, acridinyl, pyridazinyl, pyrazinyl, quinolyl, quinazolinyl, quinoxalinyl, phenoxazinyl, phthalazinyl, pyridopyrimidinyl, pyridopyrazinyl, pyrazinopyrazinyl, isoquinolyl, indolyl, carbazolyl, benzoxazolyl, benzimidazolyl, benzothiazolyl, benzocarbazolyl, benzothienyl, dibenzothienyl, thienothienyl, benzofuranyl, phenanthrolinyl, isoxazolyl, thiadiazolyl, benzothiazolyl, phenothiazinyl, silafluorenyl, dibenzofuranyl, as well as N-phenylcarbazolyl, N-pyridylcarbazolyl, N-methylcarbazolyl and the like, but is not limited to this. Thienyl, furyl, phenanthrolinyl, etc. are heteroaryl of the single aromatic ring system, and N-arylcarbazolyl, and N-heteroarylcarbazolyl are heteroaryl of the plurality of aromatic ring systems conjugatedly connected via carbon-carbon bonds. In the present disclosure, involved heteroarylene refers to a divalent group formed by further loss of one hydrogen atom of the heteroaryl.

In the present disclosure, substituted heteroaryl can be that one or two or more hydrogen atoms in the heteroaryl are substituted with groups such as a deuterium atom, a halogen group, —CN, aryl, heteroaryl, trialkylsilyl, alkyl, cycloalkyl, and the like. Specific examples of aryl-substituted heteroaryl include, but are not limited to, phenyl-substituted dibenzofuranyl, phenyl-substituted dibenzothienyl, phenyl-substituted pyridyl, and the like. It should be understood that the number of carbon atoms of the substituted heteroaryl refers to the total number of carbon atoms of the heteroaryl and substituents on the heteroaryl.

In the present disclosure, heteroaryl as a substituent includes, for example, but is not limited to, pyridyl, pyrimidinyl, carbazolyl, dibenzofuranyl, dibenzothienyl, quinolyl, quinazolinyl, quinoxalinyl, and isoquinolyl.

In the present disclosure, an unpositioned connecting bond refers to a single bond

extending from a ring system, which indicates that one end of the connecting bond can be connected to any position in the ring system through which the bond penetrates, and the other end of the connecting bond is connected to the remaining part of a compound molecule.

For example, as shown in a formula (f) below, naphthyl represented by the formula (f) is connected to other positions of a molecule by two unpositioned connecting bonds penetrating a bicyclic ring, and its meaning includes any one possible connection mode represented by formulae (f-1) to (f-10).

(f)

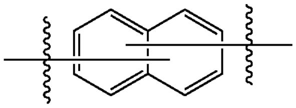

(f-1)

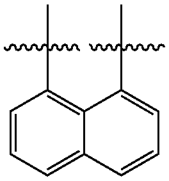

(f-2)

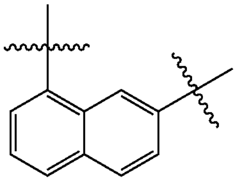

(f-3)

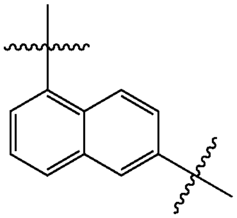

(f-4)

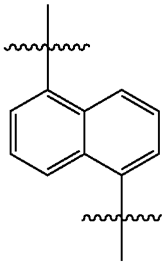

-continued (f-5)

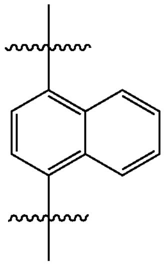

(f-6)

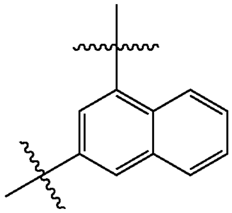

(f-7)

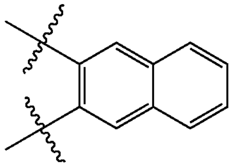

(f-8)

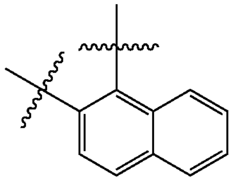

(f-9)

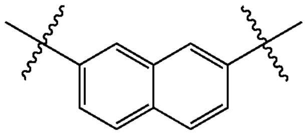

(f-10)

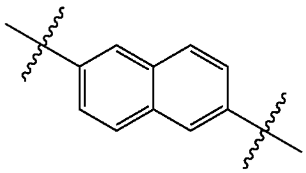

For another example, as shown in a formula (X') below, phenanthryl represented by the formula (X') is connected to other positions of a molecule via one unpositioned connecting bond extending from the middle of a benzene ring on one side, and its meaning includes any one possible connection mode represented by formulae (X'-1) to (X'-4).

(X')

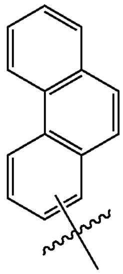

(X'-1)

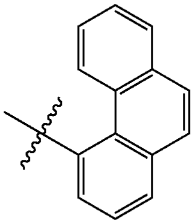

(X'-2)

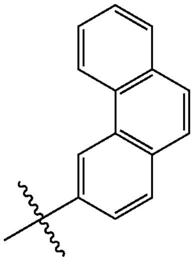

(X'-3)

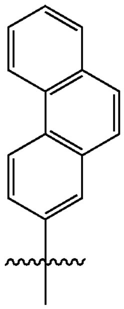

(X'-4)

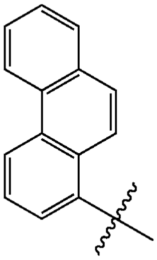

An unpositioned substituent in the present disclosure refers to a substituent connected through a single bond extending from the center of a ring system, which means that the substituent can be connected to any possible position in the ring system. For example, as shown in a formula (Y) below, a substituent R' as shown in the formula (Y) is connected to a quinoline ring via one unpositioned connecting bond, and its meaning includes any one possible connection mode represented by formulae (Y-1) to (Y-7).

(Y)

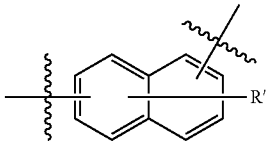

(Y-1)

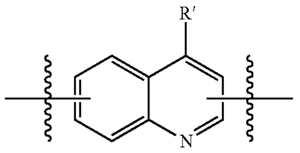

(Y-2)

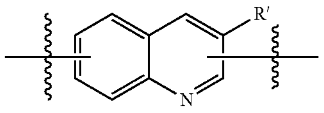

(Y-3)

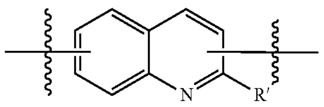

(Y-4)

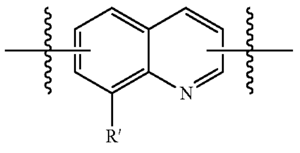

(Y-5)

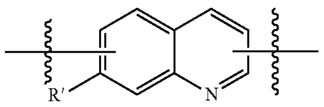

(Y-6)

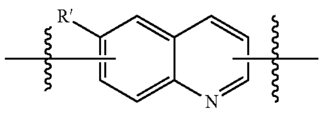

(Y-7)

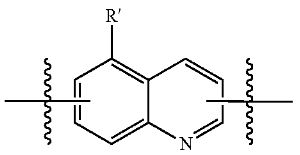

In the present disclosure, the number of carbon atoms of alkyl may be 1 to 5, and the alkyl may include linear alkyl with 1 to 5 carbon atoms and branched alkyl with 3 to 5 carbon atoms. The number of carbon atoms may be any integer of 1, 2, 3, 4, or 5; and specific examples of the alkyl can include, methyl, ethyl, n-propyl, isopropyl, n-butyl, isobutyl, tert-butyl, n-pentyl, isopentyl, neopentyl, and the like.

In the present disclosure, the number of carbon atoms of cycloalkyl can be, for example, 3, 5, 6, 7, 8, 9 or 10. Specific examples of the cycloalkyl include, but are not limited to, cyclopentyl, cyclohexyl, and adamantyl.

In the present disclosure, the halogen group can be, for example, fluorine, chlorine, bromine or iodine.

In the present disclosure, specific examples of trialkylsilyl include, but are not limited to, trimethylsilyl, triethylsilyl, and the like.

In the present disclosure, specific examples of triarylsilyl include, but are not limited to, triphenylsilyl and the like.

In the present disclosure, in the above two groups of groups $R_4$ and $R_5$, as well as $R_6$ and $R_7$, two groups in each group are connected to each other to form a 3- to 15-membered saturated or unsaturated ring together with the atoms to which they are commonly connected. For example, in the formula II

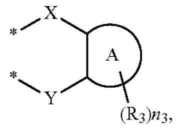

when Y is a single bond, $n_3$ is 0, and X is $C(R_4R_5)$, and when $R_4$ and $R_5$ are connected to each other to form a 5-membered ring together with the atoms to which they are commonly connected, the formula II is

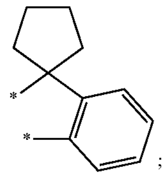 [SMILES: *c1ccccc1C1(*)CCCC1]

;

likewise, the formula II may also represent

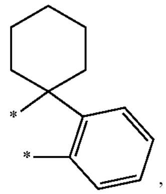 [SMILES: *c1ccccc1C1(*)CCCCC1]

, that is, $R_4$ and $R_5$ are connected to each other to form a 6-membered ring together with the atoms to which they are commonly connected; likewise, the formula II may also represent

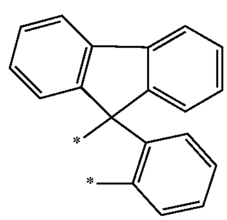

or

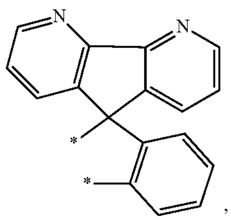

, that is, $R_4$ and $R_5$ are connected to each other to form a partially unsaturated 13-membered ring together with the atoms to which they are commonly connected; and likewise, the formula II may also represent

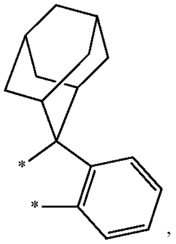 [SMILES: *c1ccccc1C1(*)C2CC3CC(C2)CC1C3]
that is, $R_4$ and $R_5$ are connected to each other to form a 10-membered ring together with the atoms to which they are commonly connected.
In one example of the present disclosure, the organic compound has a structure shown in any one of formulae 1-1 to 1-17:
1-1
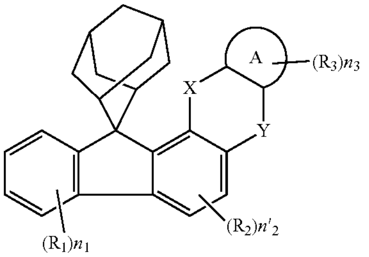
1-2
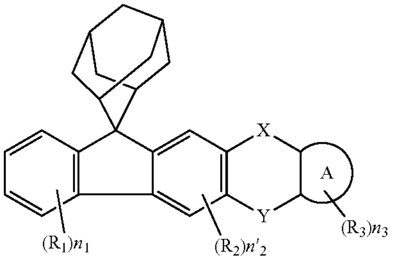
1-3
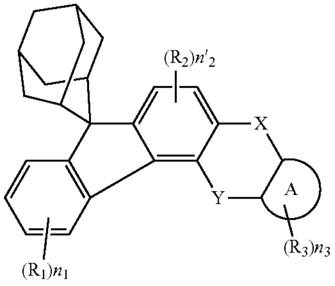
1-4
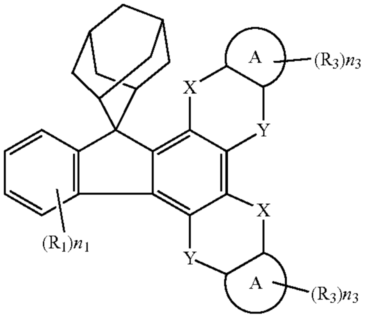
-continued
1-5
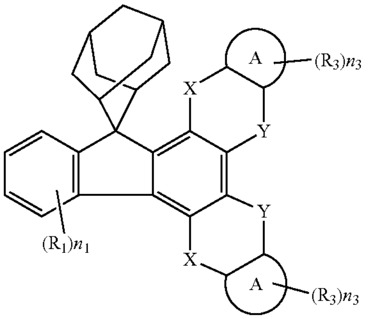
1-6
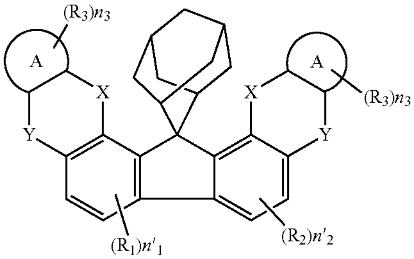
1-7
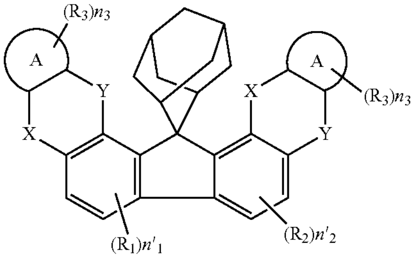
1-8
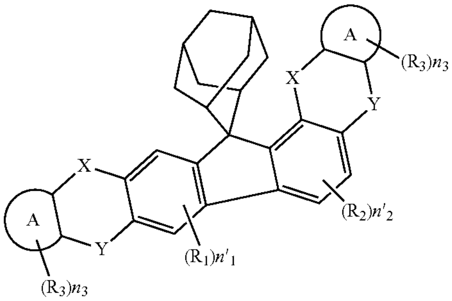
1-9
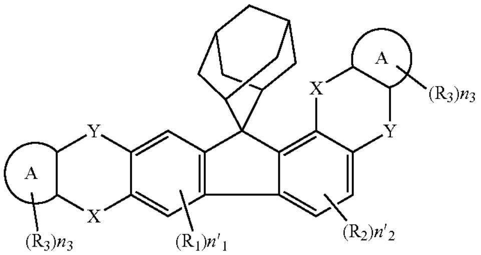

-continued
1-10
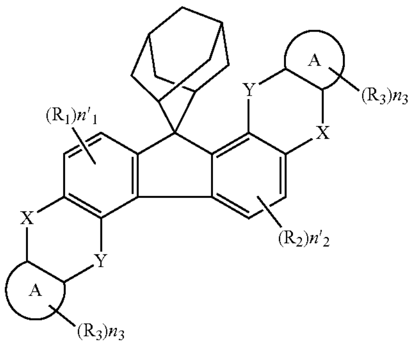
1-11
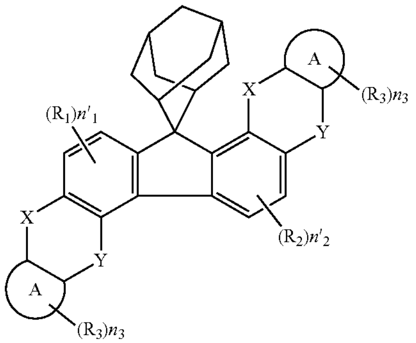
1-12
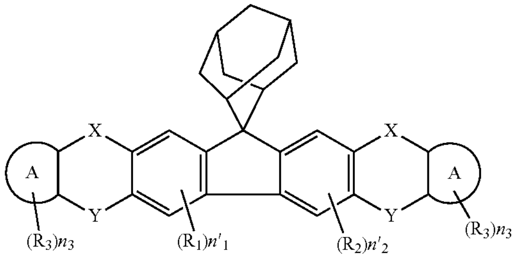
1-13
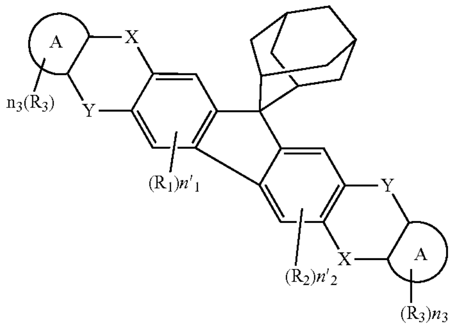
-continued
1-14
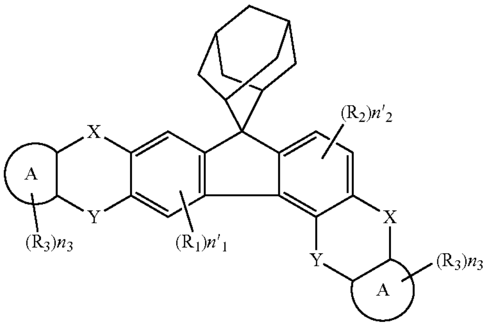
1-15
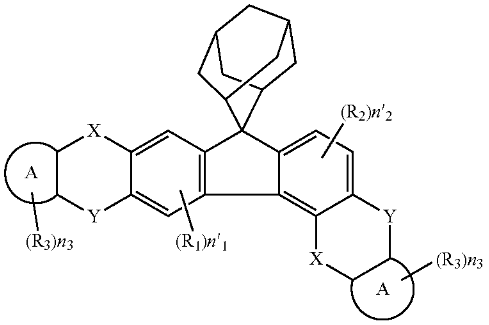
1-16
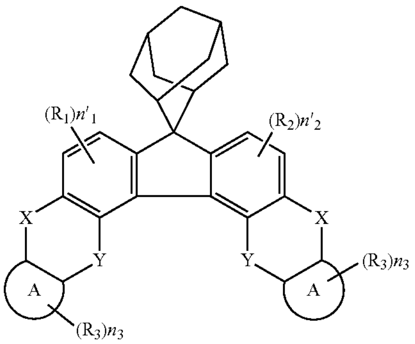
1-17
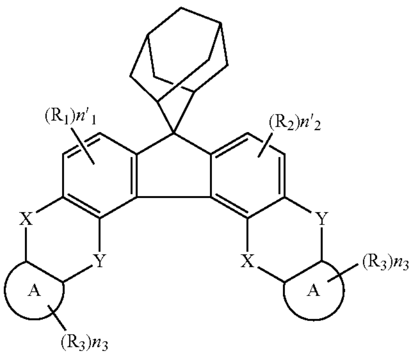
where $n'_1$ is selected from 0, 1 or 2; and $n'_2$ is selected from 0, 1 or 2. X and Y may be the same or different.
In one example of the present disclosure, the organic compound has a structure shown in any one of 2-1 to 2-41:

2-1
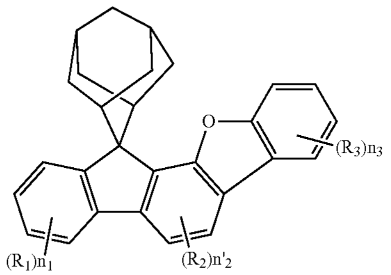
2-2
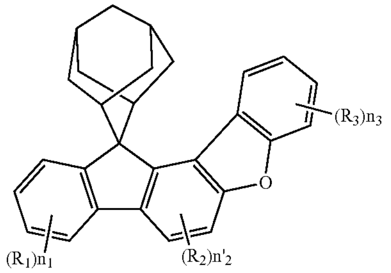
2-3
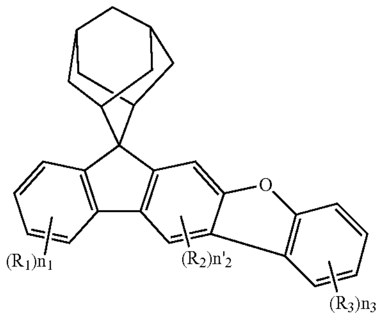
2-4
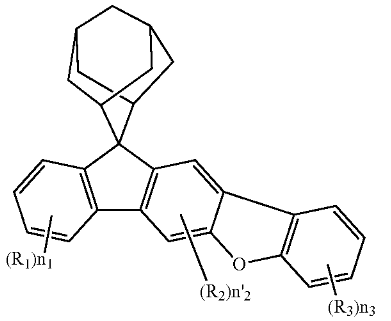
2-5
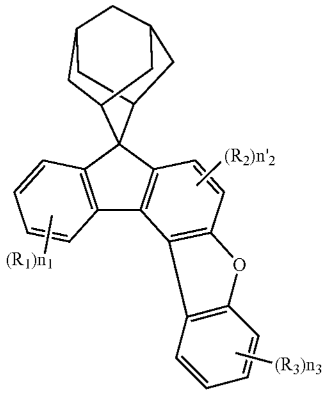
-continued
2-6
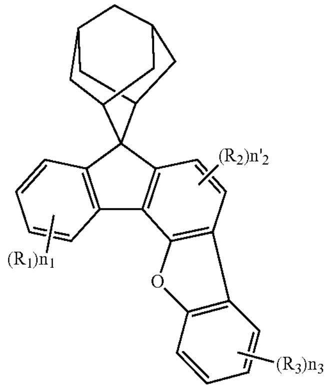
2-7
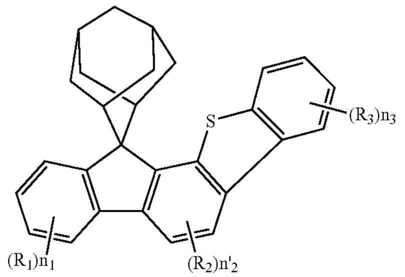
2-8
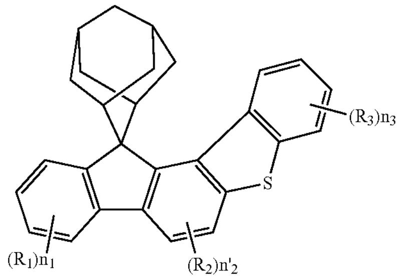
2-9
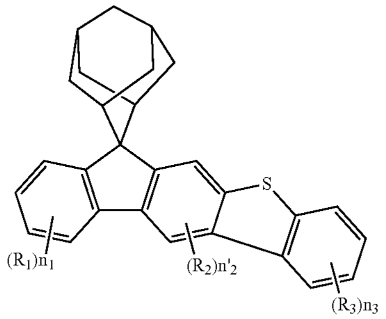
2-10
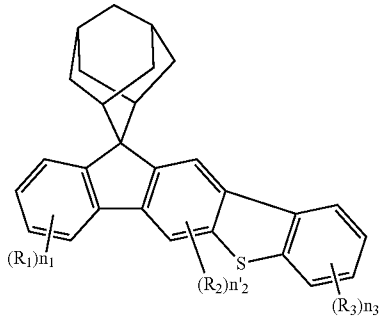

-continued
2-11
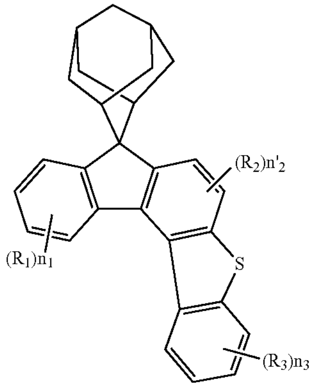
2-12
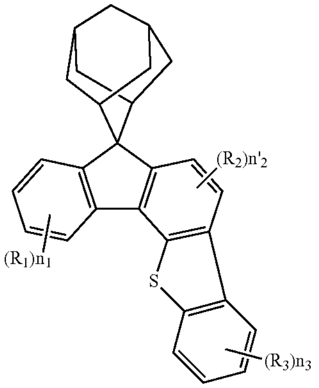
2-13
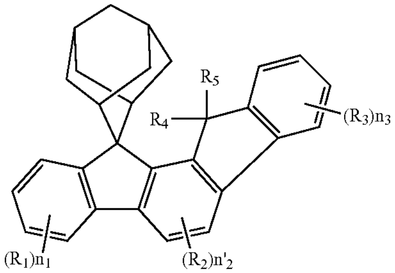
2-14
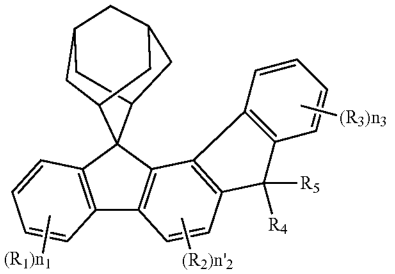
-continued
2-15
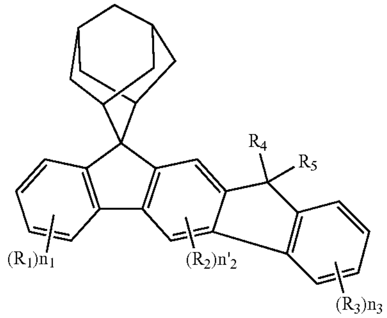
2-16
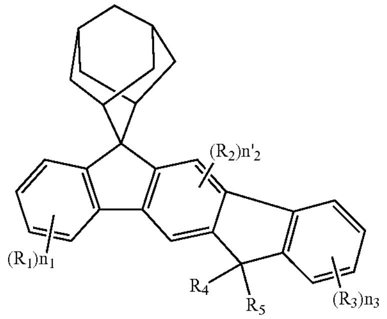
2-17
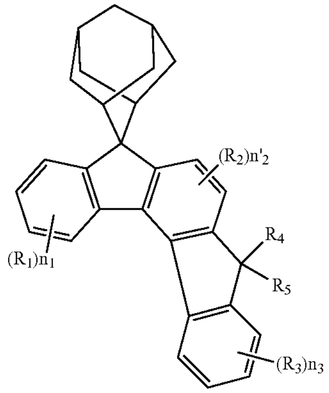
2-18
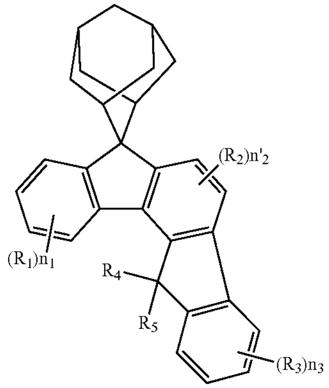

-continued
2-19
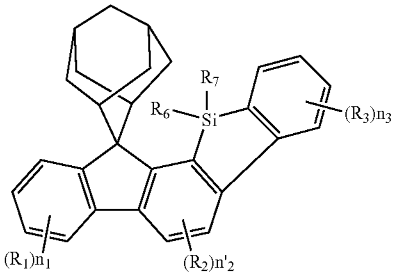
2-20
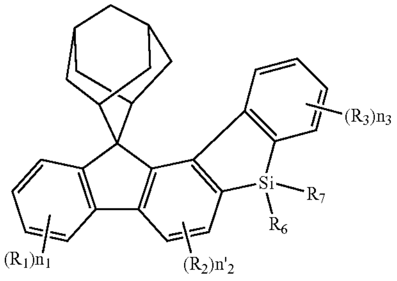
2-21
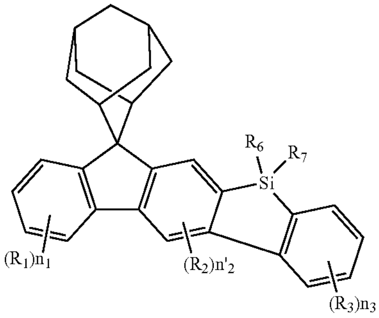
2-22
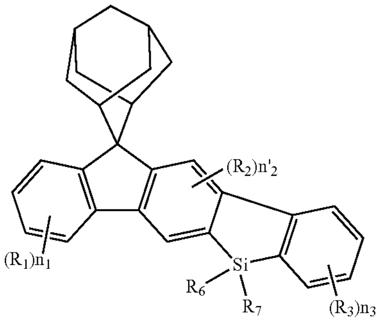
2-23
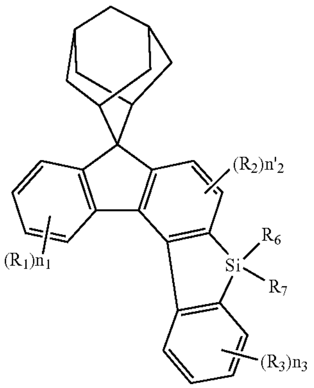
-continued
2-24
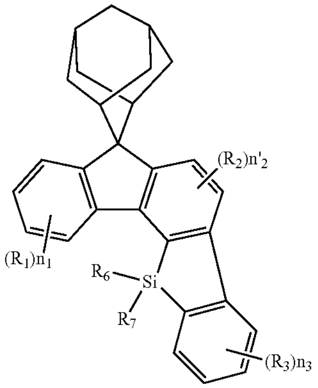
2-25
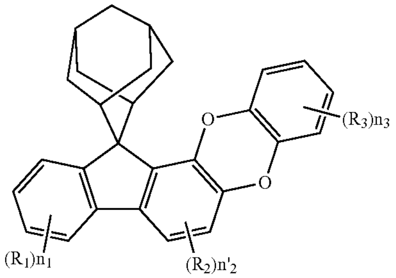
2-26
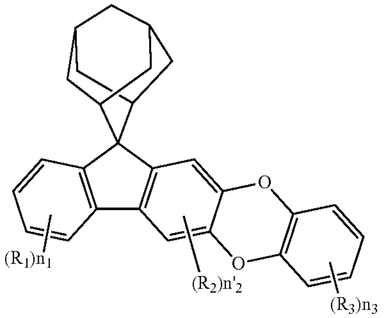
2-27
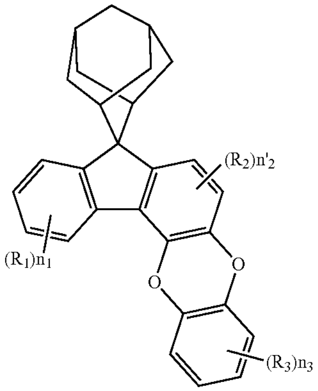

-continued
2-28
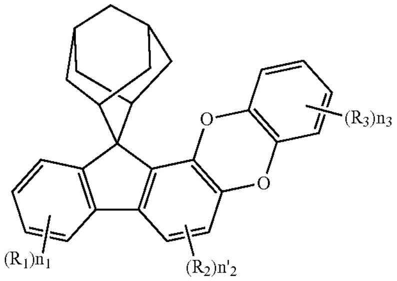
2-29
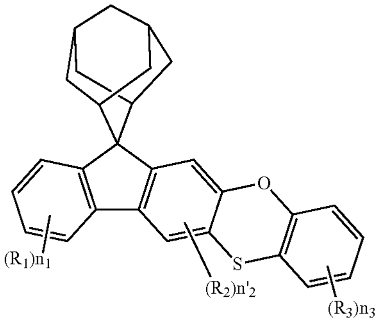
2-30
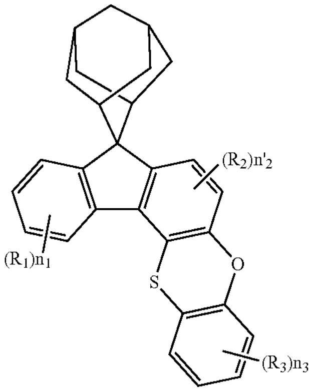
2-31
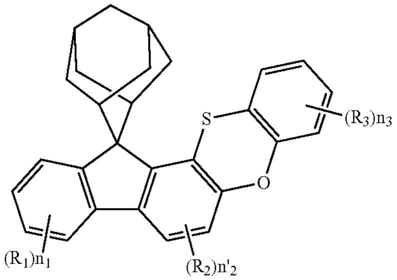
2-32
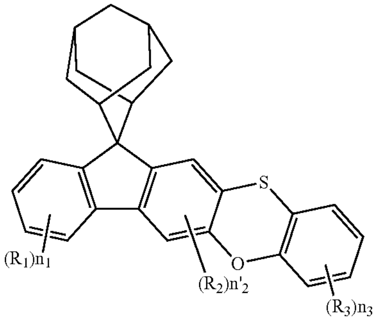
-continued
2-33
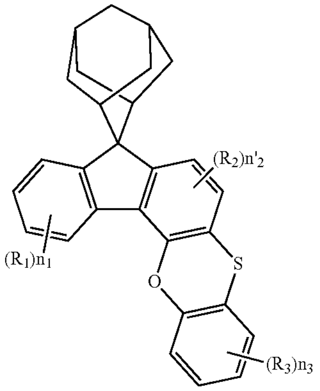
2-34
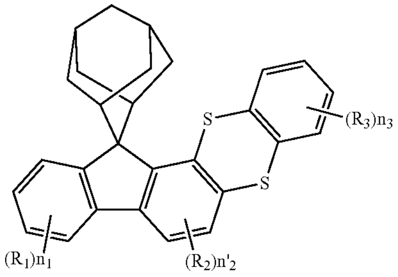
2-35
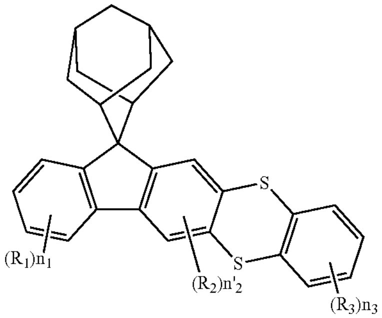
2-36
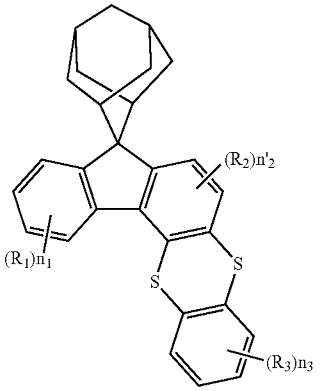

-continued
2-37
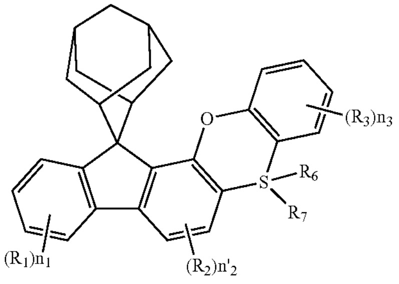
2-38
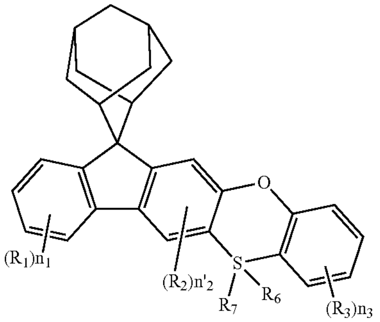
2-39
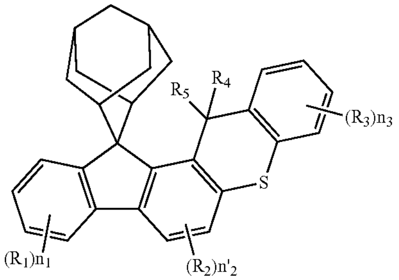
2-40
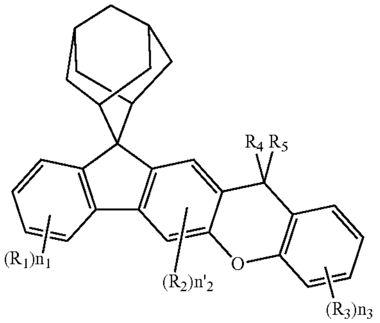
2-41
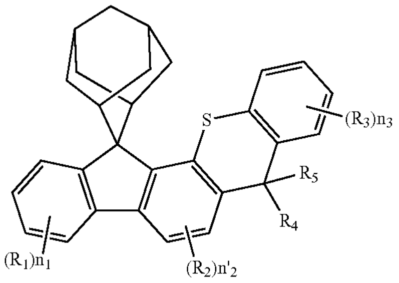
where $n'_2$ is selected from 0, 1 or 2.
In one example of the present disclosure, the formula II has a structure shown in any one of formulae II-1 to II-11:
II-1
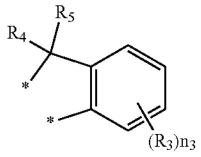
II-2
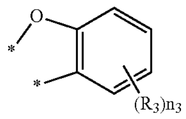
II-3
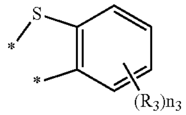
II-4
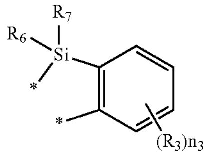
II-5
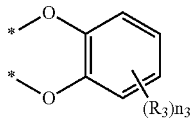
II-6
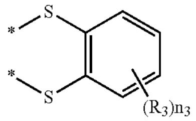
II-7
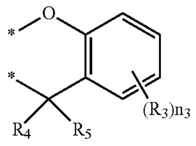
II-8
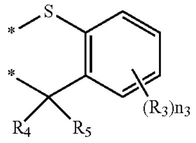
II-9
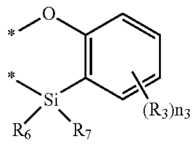
II-10
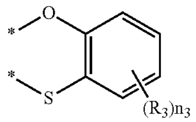
II-11
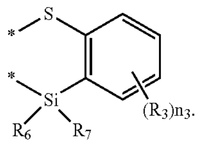

Optionally, $n_1$, $n_2$, and $n_3$ are not simultaneously 0, and at least one $R_k$, if present, has the structure represented by the formula III. For example, $n_1=1$, and $R_1$ has the structure represented by the formula III; or $n_2=1$, and $R_2$ has the structure represented by the formula III; or $n_3=1$, and $R_3$ has the structure represented by the formula III.

In the present disclosure, a ring A refers to

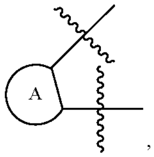

, where the ring A is a benzene ring or a fused aromatic ring with 10 to 14 ring-forming carbon atoms. The fused aromatic ring may be, for example, a naphthalene ring, an anthracene ring, or a phenanthrene ring. Where

represents a chemical bond. For example, in a compound

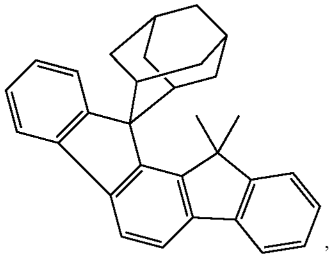 [SMILES: CC1(C)c2ccccc2-c2ccc3c(c21)C1(c2ccccc2-3)C2CC3CC(C2)CC1C3]

, the ring A is a benzene ring, the number of a substituent $R_3$ on the ring A is 0 (i.e., $n_3=0$), X represents $C(R_4R_5)$, $R_4$ and $R_5$ are each methyl, Y is a single bond, and the number of a substituent $R_1$ and the number of a substituent $R_2$ are also 0 (i.e., $n_1$ and $n_2$ are both 0).

In one example of the present disclosure, $n_1$, $n_2$ and $n_3$ may each independently be selected from 0, 1 or 2.

In the present disclosure, when $R_1$, $R_2$, and $R_3$ respectively have the structure represented by the formula III, Ar in $R_1$, $R_2$, and $R_3$ may each be the same or different, and L may each also be the same or different.

In some examples, L is selected from a single bond or the group consisting of groups represented by formulae j-1 to j-15:

j-1

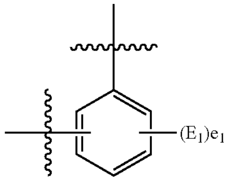

-continued j-2

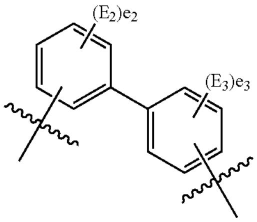

j-3

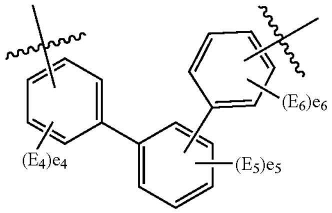

j-4

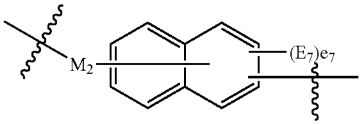

j-5

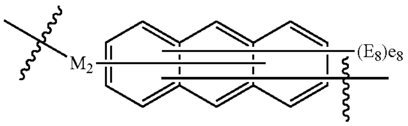

j-6

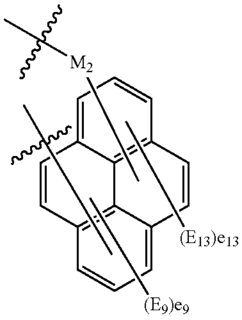

j-7

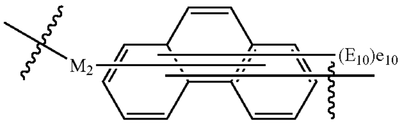

j-8

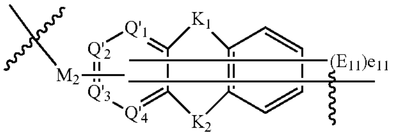

j-9

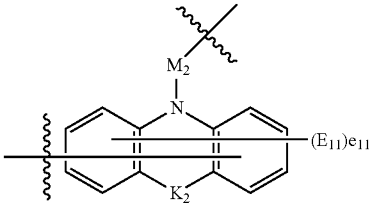

-continued j-10

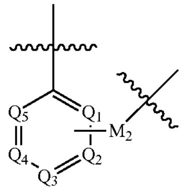

j-11

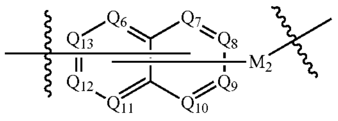

j-12

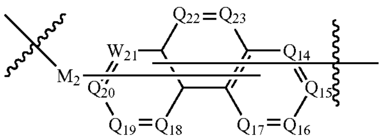

j-13

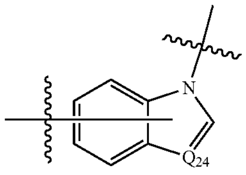

j-14

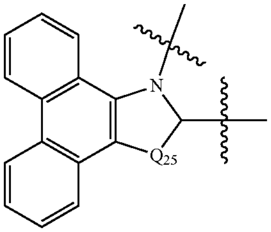

j-15

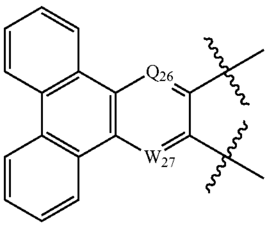

where $M_2$ is selected from a single bond or

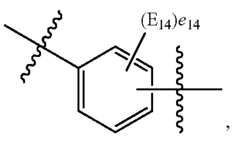

, and

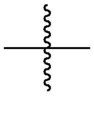

represents a chemical bond;

$Q_1$ to $Q_5$ and $Q'_1$ to $Q'_4$ are each independently selected from N, C or $C(J_1)$, and at least one of $Q_1$ to $Q_5$ is selected from N; when two or more of $Q_1$ to $Q_5$ are selected from $C(J_1)$, any two $J_1$ are the same or different; and when two or more of $Q'_1$ to $Q'_4$ are selected from $C(J_1)$, any two $J_1$ are the same or different;

$Q_6$ to $Q_{13}$ are each independently selected from N, C or $C(J_2)$, and at least one of $Q_6$ to $Q_{13}$ is selected from N; and when two or more of $Q_6$ to $Q_{13}$ are selected from $C(J_2)$, any two $J_2$ are the same or different;

$Q_{14}$ to $Q_{23}$ are each independently selected from N, C or $C(J_3)$, and at least one of $Q_{14}$ to $Q_{23}$ is selected from N; and when two or more of $Q_{14}$ to $Q_{23}$ are selected from $C(J_3)$, any two $J_3$ are the same or different;

$Q_{24}$ to $Q_{25}$ are each independently selected from N, C or $C(J_4)$;

$Q_{26}$ and $Q_{27}$ are each selected from N, C or $C(J_5)$, and at least one of $Q_{26}$ to $Q_{27}$ is selected from N; and when $Q_{26}$ and $Q_{27}$ are both selected from $C(J_5)$, both $J_5$ are the same or different;

$E_1$ to $E_{14}$, and $J_1$ to $J_5$ are each independently selected from hydrogen, deuterium, fluorine, chlorine, bromine, cyano, a heteroaryl with 3 to 10 carbon atoms, an aryl with 6 to 12 carbon atoms, trimethylsilyl, triphenylsilyl, an alkyl with 1 to 5 carbon atoms, or a cycloalkyl with 3 to 10 carbon atoms;

e1 to e14 are represented by $e_r$, $E_1$ to $E_{14}$ are represented by $E_r$, r is a variable, and represents any integer from 1 to 14, and $e_r$ represents the number of a substituent $E_r$; when r is selected from 1, 2, 3, 4, 5, 6, 9, 13 or 14, $e_r$ is selected from 1, 2, 3 or 4; when r is selected from 7 or 11, $e_r$ is selected from 1, 2, 3, 4, 5 or 6; when r is 12, $e_r$ is selected from 1, 2, 3, 4, 5, 6, or 7; when r is selected from 8 or 10, $e_r$ is selected from 1, 2, 3, 4, 5, 6, 7 or 8; and when $e_r$ is greater than 1, any two $E_r$ are the same or different, and optionally, any two adjacent $E_r$ are connected to each other to form a ring;

$K_1$ is selected from O, S, Se, $N(E_{15})$, $C(E_{16}E_{17})$ or $Si(E_{18}E_{19})$; where $E_{15}$, $E_{16}$, $E_{17}$, $E_{18}$ and $E_{19}$ are each independently selected from an aryl with 6 to 20 carbon atoms, a heteroaryl with 3 to 20 carbon atoms, an alkyl with 1 to 5 carbon atoms, or a cycloalkyl with 3 to 10 carbon atoms, or $E_{16}$ and $E_{17}$ are connected to each other to form a saturated or unsaturated ring having 3 to 15 carbon atoms together with the atoms to which they are commonly connected, or $E_{18}$ and $E_{19}$ are connected to each other to form a saturated or unsaturated ring having 3 to 15 carbon atoms together with the atoms to which they are commonly connected; and $K_2$ is selected from a single bond, O, S, Se, $N(E_{20})$, $C(E_{21}E_{22})$ or $Si(E_{23}E_{24})$; where $E_{20}$ to $E_{24}$ are each independently selected from an aryl with 6 to 20 carbon atoms, a heteroaryl with 3 to 20 carbon atoms, an alkyl with 1 to 5 carbon atoms, or a cycloalkyl with 3 to 10 carbon atoms, or $E_{21}$ and $E_{22}$ are connected to each other to form a saturated or unsaturated ring having 3 to 15 carbon atoms together with the atoms to which they are commonly connected, or $E_{23}$ and $E_{24}$ are connected to each other to form a saturated or unsaturated ring having 3 to 15 carbon atoms together with the atoms to which they are commonly connected.

In the present disclosure, in the four groups of groups $E_{16}$ and $E_{17}$, $E_{18}$ and $E_{19}$, $E_{21}$ and $E_{22}$, as well as $E_{23}$ and $E_{24}$, a ring formed by connecting two groups in each group to each other can be a saturated or unsaturated ring having 3 to 15 carbon atoms. For example, in the formula j-8 j-8

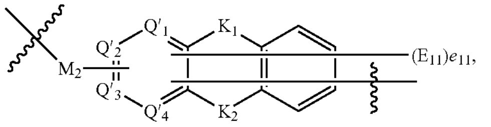

when both $K_4$ and $M_1$ are a single bond, $Q'_1$, $Q'_2$, $Q'_3$, $Q'_4$, and $E_{11}$ are hydrogen, and $K_1$ is $C(E_{16}E_{17})$, and when $E_{16}$ and $E_{17}$ are connected to each other to form a 5-membered ring together with the atoms to which they are commonly connected, the formula j-8 is

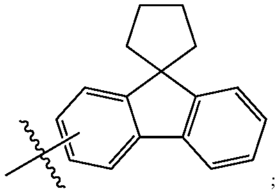

;

likewise, the formula j-8 may also represent

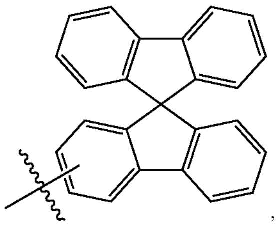

, that is, $E_{16}$ and $E_{17}$ are connected to each other to form a partially unsaturated 13-membered ring together with the atoms to which they are commonly connected.

In the present disclosure, in the formulae j-10 to j-12, $J_1$ to $J_3$ may be represented by $J_j$, where j is a variable and represents 1, 2, or 3. For example, when j is 2, $J_j$ refers to $J_2$. It should be understood that $J_j$ in $C(J_j)$ is not present when an unpositioned connecting bond is connected to $C(J_j)$. For example, in the chemical formula i-11, when

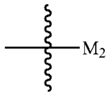

is connected to $Q_{12}$, $Q_{12}$ can only represent a C atom, i.e. the structure of the formula i-11 is specifically:

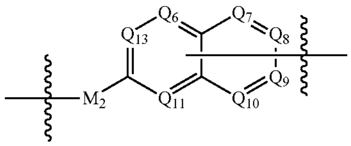

Optionally, L is selected from a single bond, substituted or unsubstituted arylene with 6 to 25 carbon atoms, and substituted or unsubstituted heteroarylene with 3 to 25 carbon atoms. For example, L can be selected from a single bond, substituted or unsubstituted arylene with 6, 7, 8, 9, 10, 11, 12, 13, 14, 15, 16, 17, 18, 19, 20, 21, 22, 23, 24, or 25 carbon atoms, and substituted or unsubstituted heteroarylene with 3, 4, 5, 6, 7, 8, 9, 10, 11, 12, 13, 14, 15, 16, 17, 18, 19, 20, 21, 22, 23, 24, or 25 carbon atoms.

Optionally, L is selected from a single bond, a substituted or unsubstituted arylene with 6 to 15 carbon atoms, or a substituted or unsubstituted heteroarylene with 3 to 20 carbon atoms.

Optionally, L is selected from a single bond or a substituted or unsubstituted group $T_1$, and the unsubstituted group $T_1$ is selected from the group consisting of:

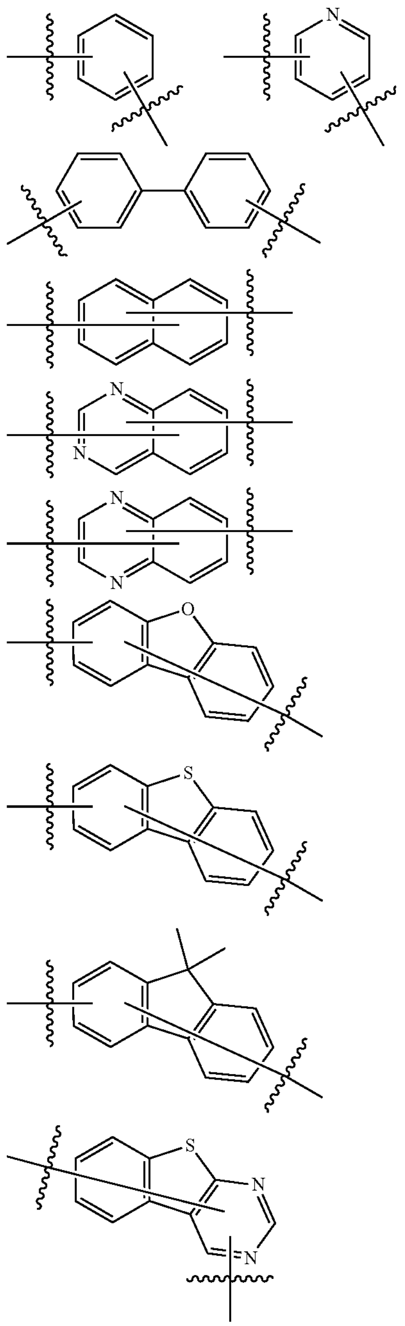

-continued
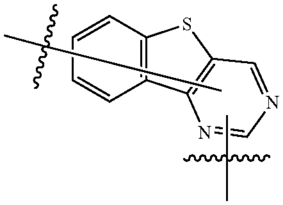
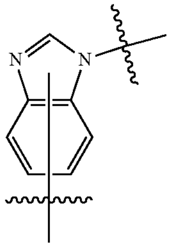
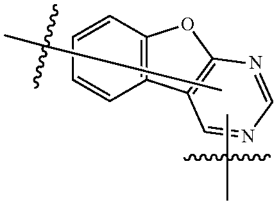
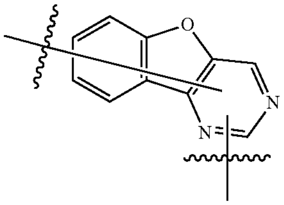
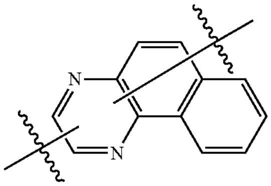
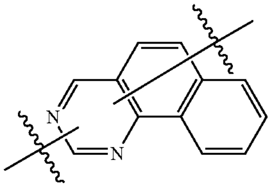
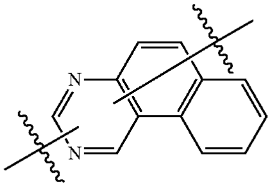
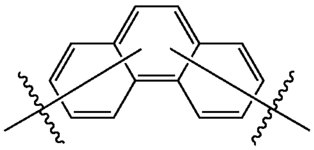
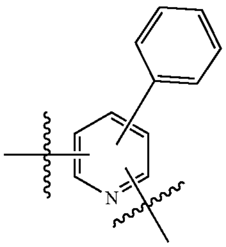
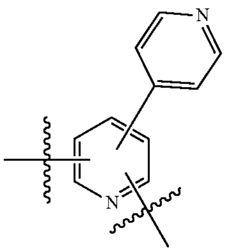
-continued
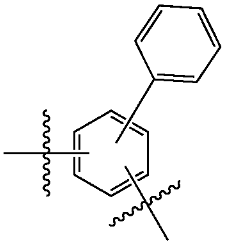
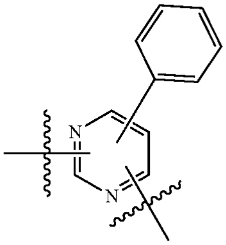
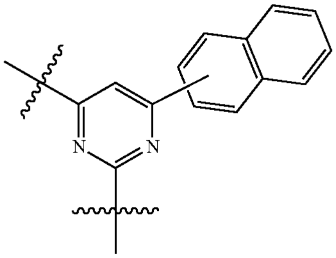
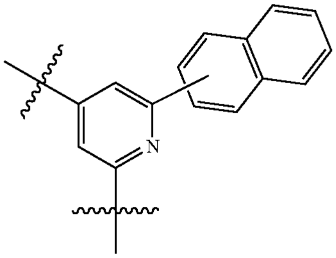
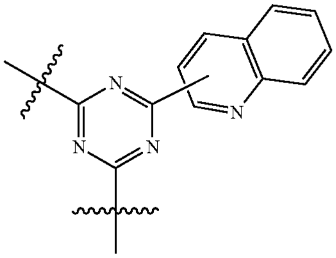
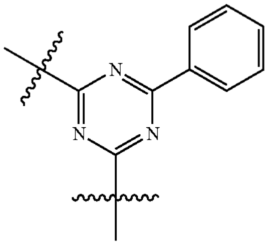
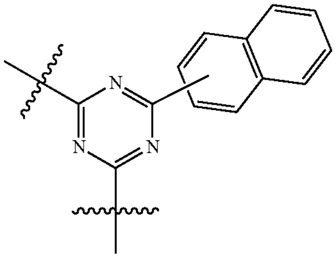

-continued

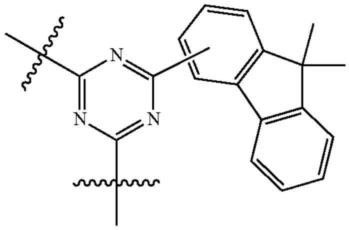

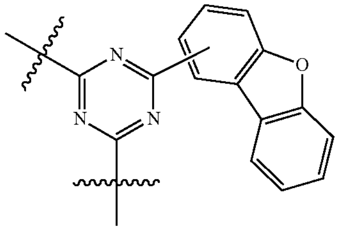

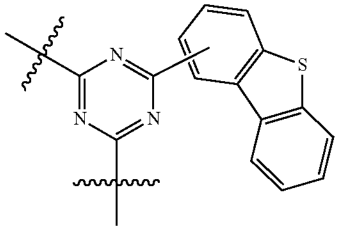

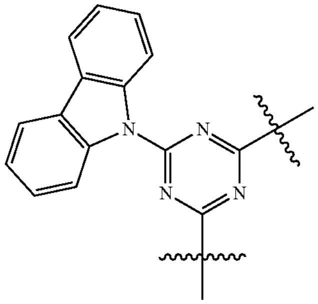

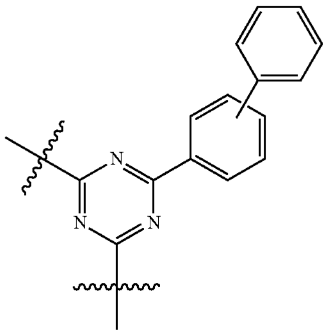

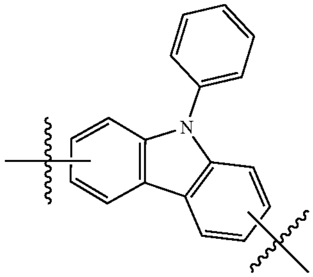

-continued

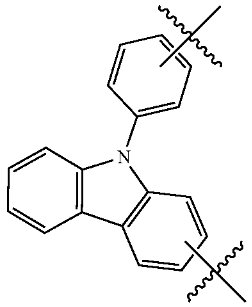

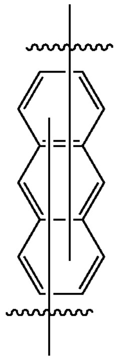

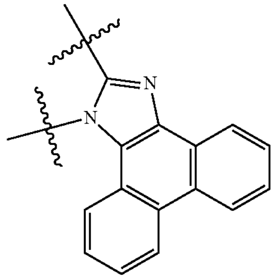

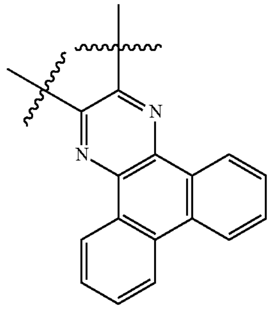

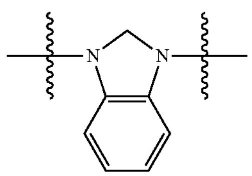

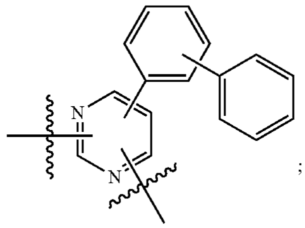

;

the substituted group $T_1$ has one or two or more substituents, and the substituents in substituted group $T_1$ are independently selected from deuterium, fluorine, cyano, trimethylsilyl, triphenylsilyl, methyl, ethyl, isopropyl, tert-butyl, phenyl, biphenyl, pyridyl, naphthyl, carbazolyl, dibenzofuranyl or dibenzothienyl.

Further optionally, L is selected from a single bond or the group consisting of:

-continued
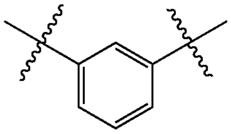
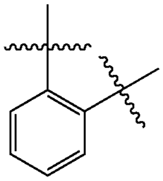
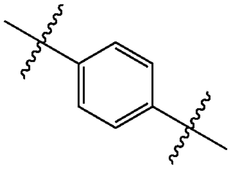
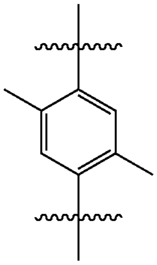
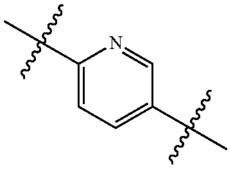
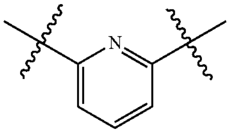
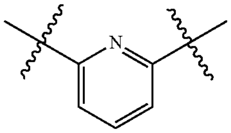
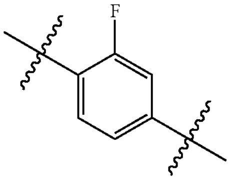
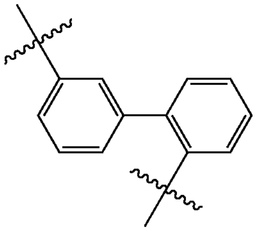
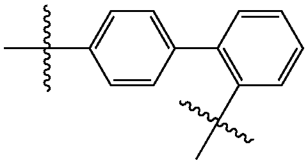
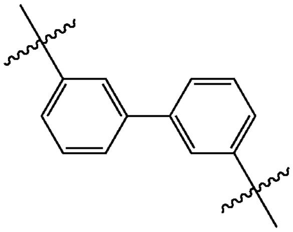
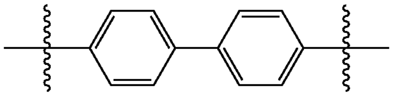
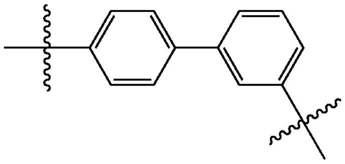
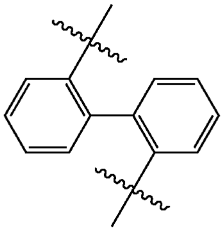
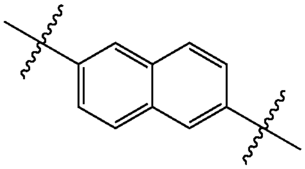
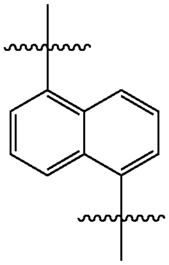
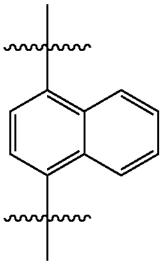
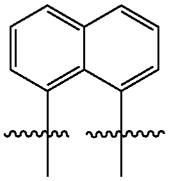
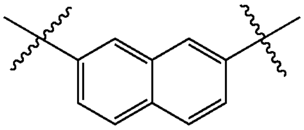
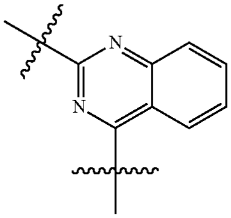
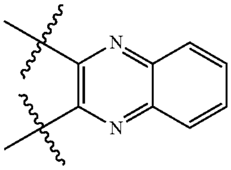
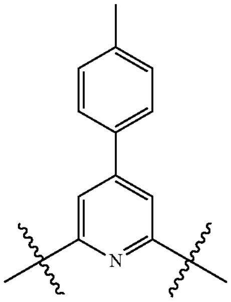
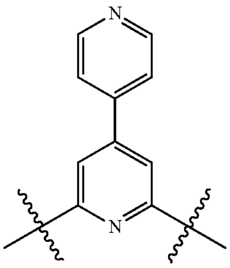
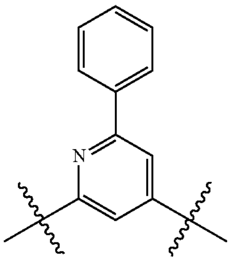
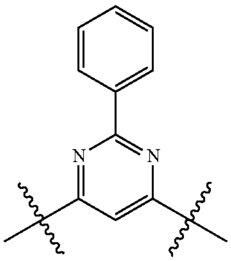

-continued
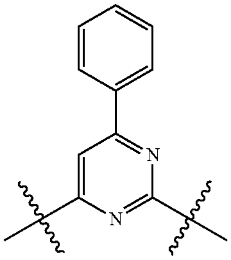
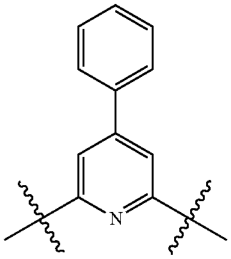
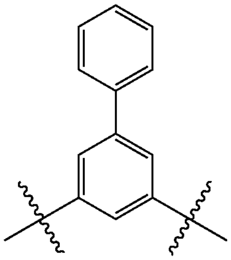
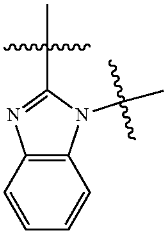
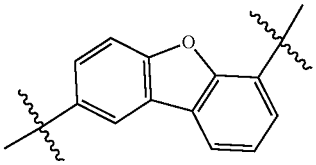
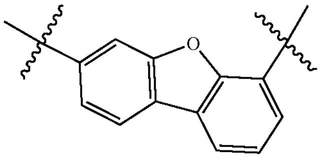
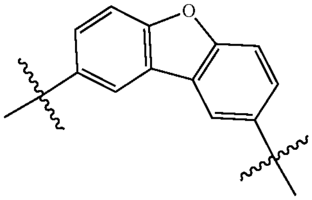
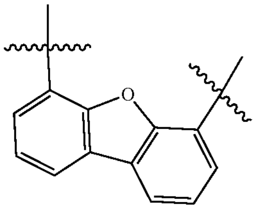
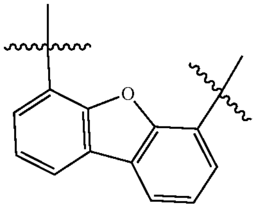
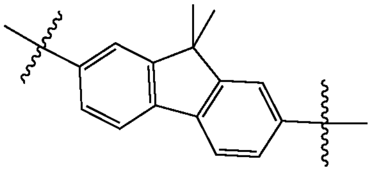
-continued
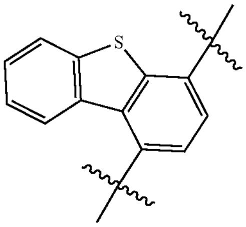
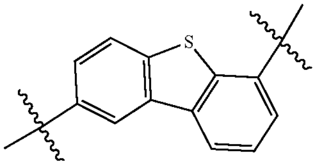
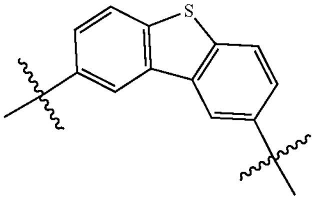
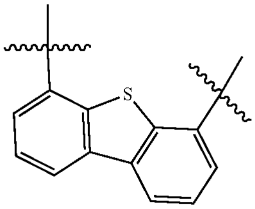
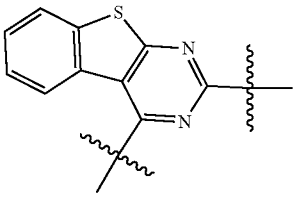
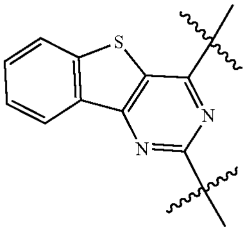
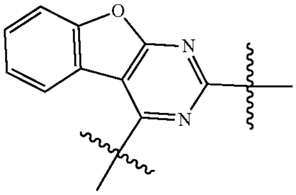
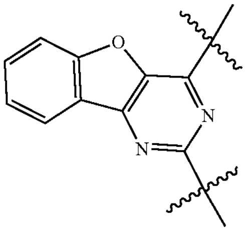

-continued
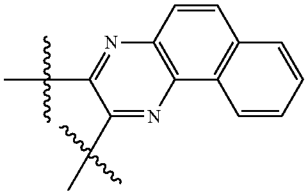
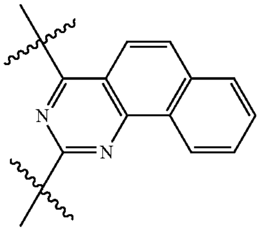
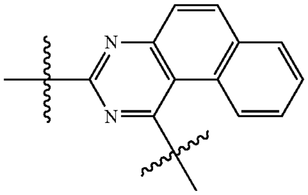
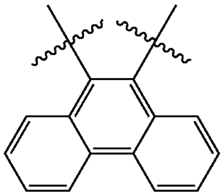
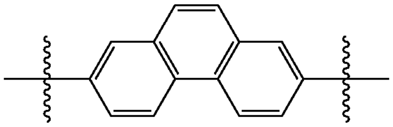
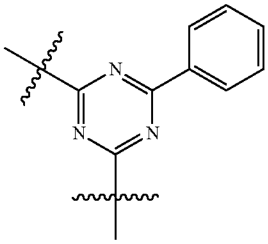
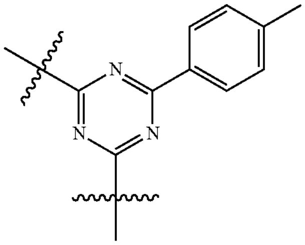
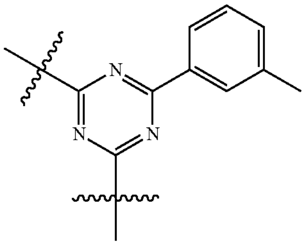
-continued
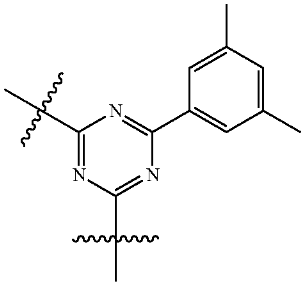
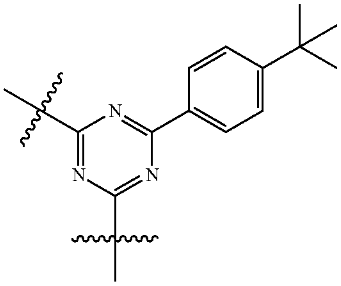
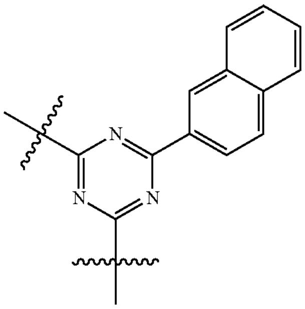
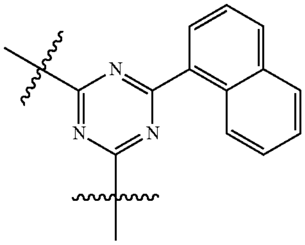
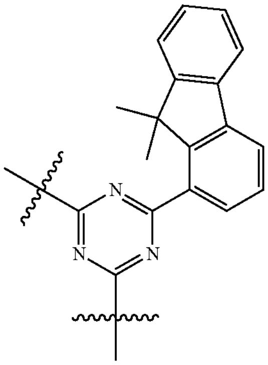

-continued
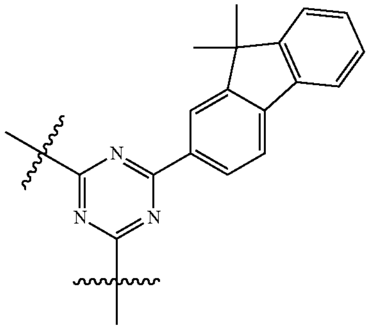
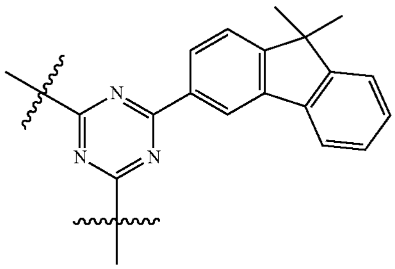
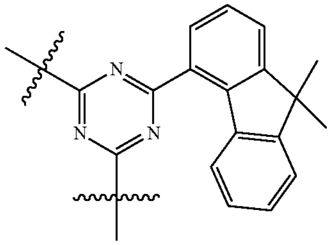
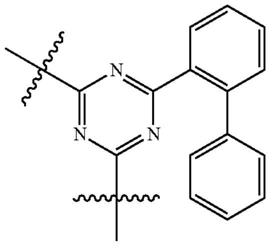
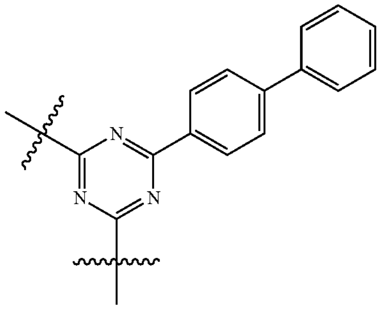
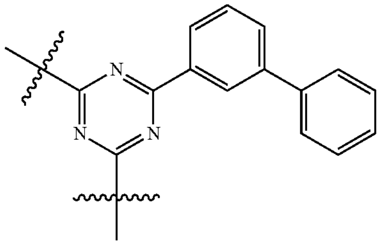
-continued
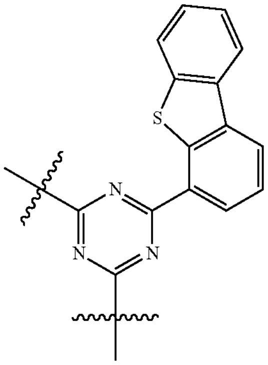
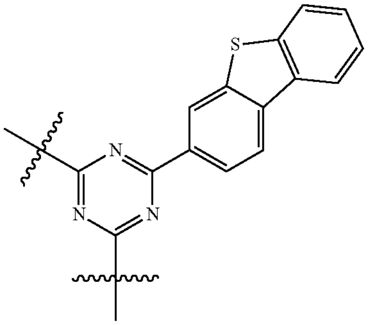
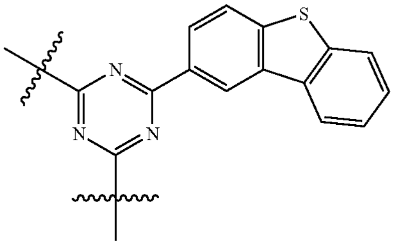
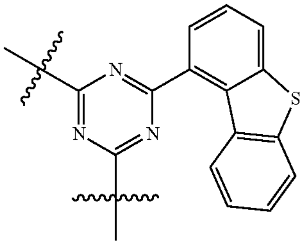
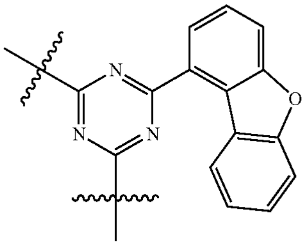
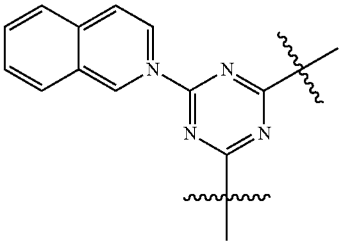

-continued
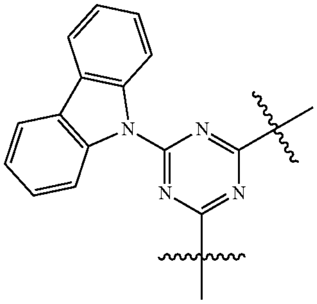
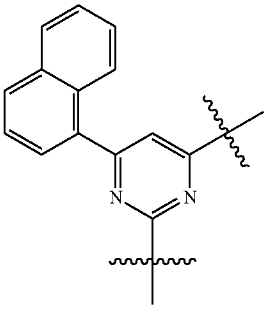
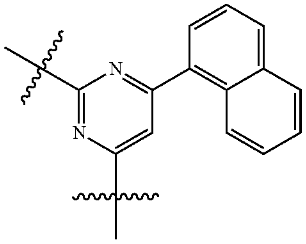
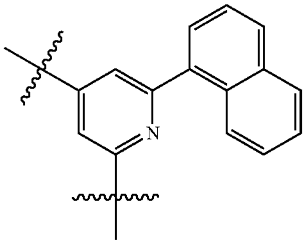
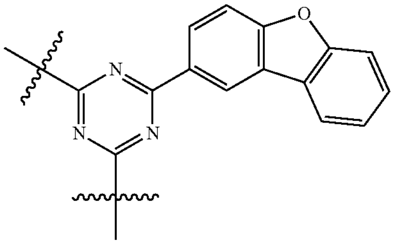
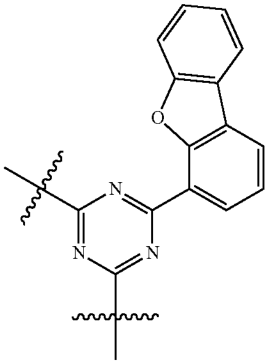
-continued
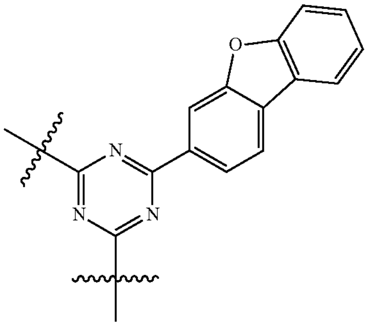
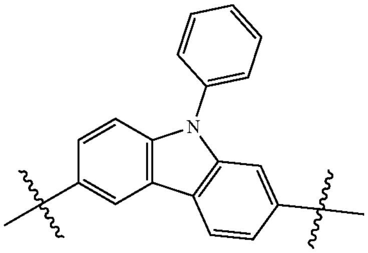
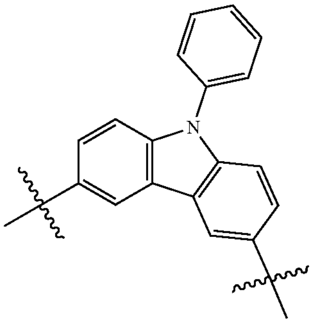
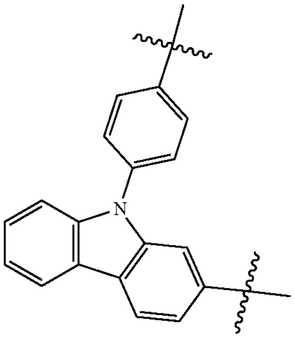
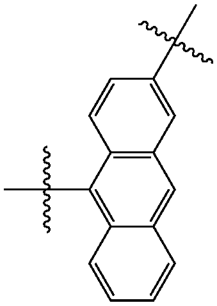
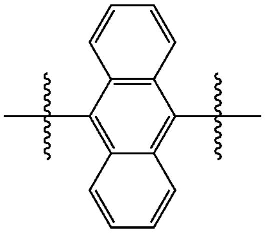

-continued
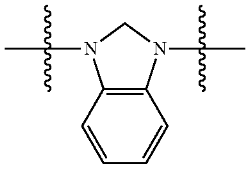
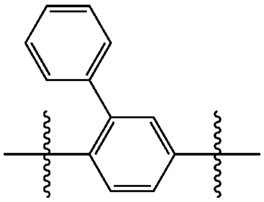
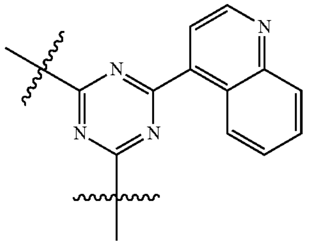
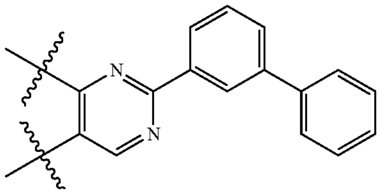
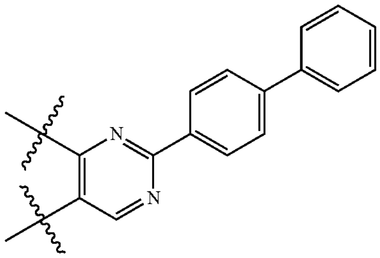
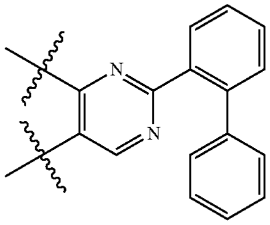
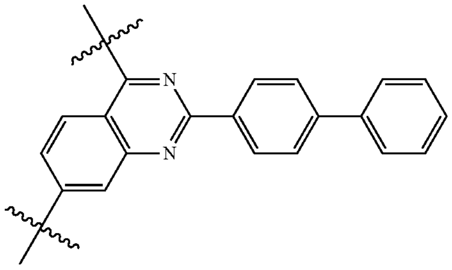
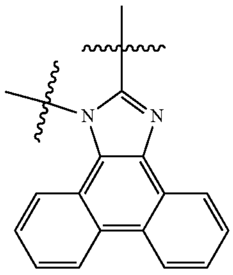
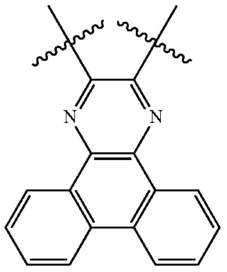
-continued
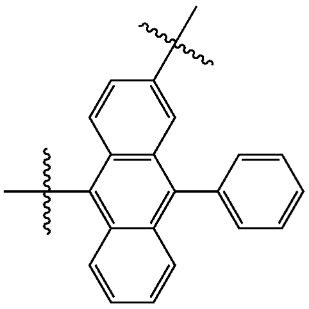
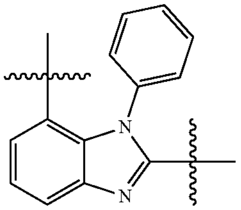
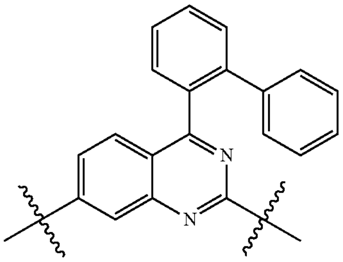
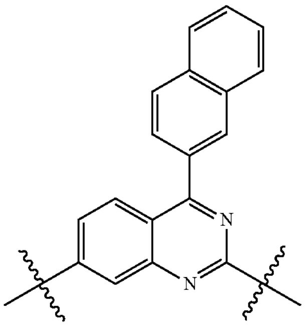
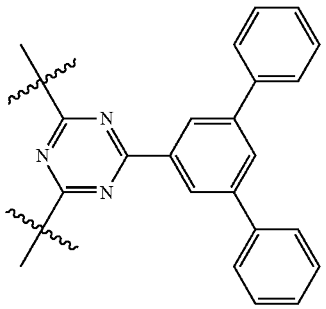
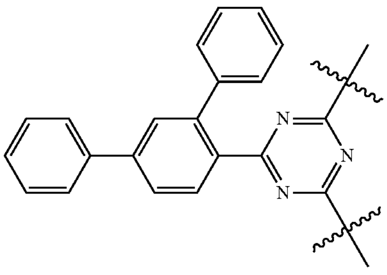

-continued

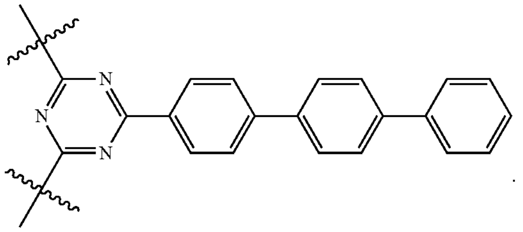

Optionally, L is selected from a single bond, or substituted or unsubstituted phenylene, substituted or unsubstituted naphthylene, substituted or unsubstituted anthrylene, substituted or unsubstituted dibenzofuranylene, substituted or unsubstituted dibenzothienylene, substituted or unsubstituted benzothiazolylene, substituted or unsubstituted benzoxazolylene, substituted or unsubstituted biphenylene, substituted or unsubstituted quinolylene, substituted or unsubstituted quinazolinylene, substituted or unsubstituted benzo[f]quinoxalinylene, substituted or unsubstituted benzo[f]quinazolinylene, substituted or unsubstituted benzo[h]quinazolinylene, substituted or unsubstituted fluorenylene, substituted or unsubstituted benzimidazolylene, substituted or unsubstituted phenanthro[9,10-d]imidazolylene, substituted or unsubstituted pyridylene, substituted or unsubstituted carbazolylene, substituted or unsubstituted triazinylene, substituted or unsubstituted quinoxalinylene, substituted or unsubstituted phenanthrylene, substituted or unsubstituted pyrimidylene, substituted or unsubstituted benzothienopyrimidinylene, substituted or unsubstituted benzofuropyrimidinylene, and substituted or unsubstituted dibenzo[f,h]quinoxalinylene; or is a group formed by connecting two or three of the above groups by a single bond; and substituents in the above groups are the same or different, and are each independently selected from deuterium, fluorine, cyano, methyl, ethyl, isopropyl, tert-butyl, phenyl, phenyl substituted with methyl, ethyl, isopropyl, and tert-butyl, naphthyl, dimethylfluorenyl, biphenyl, biphenyl substituted with phenyl, dibenzofuranyl, dibenzothienyl, carbazolyl, quinolyl, and pyridyl.

In some examples, Ar is selected from the group consisting of groups represented by any one of formulae i-1 to i-15:

i-1

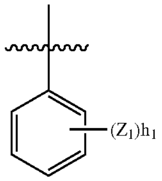

i-2

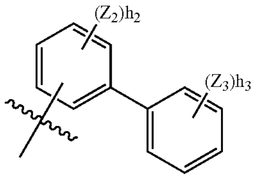

-continued i-3

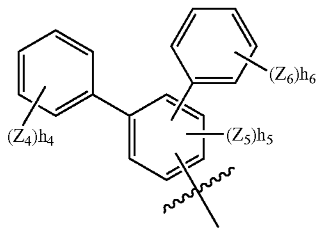

i-4

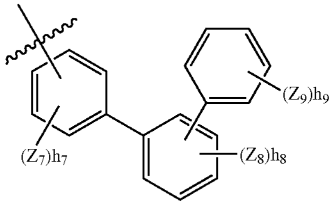

i-5

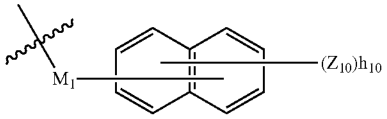

i-6

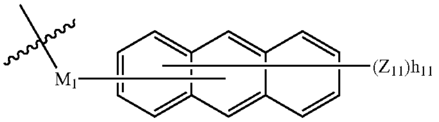

i-7

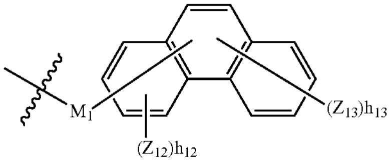

i-8

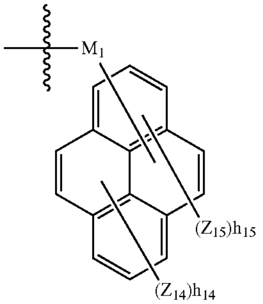

i-9

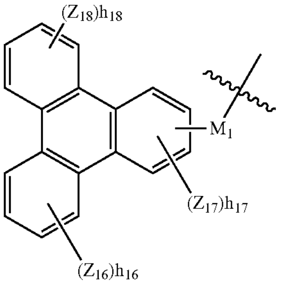

i-10

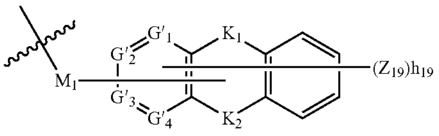

-continued i-11

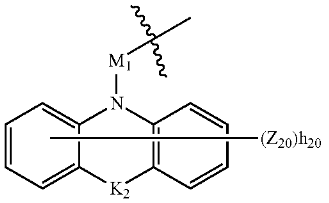

i-12

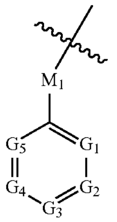

i-13

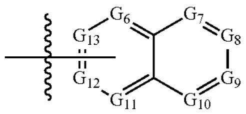

i-14

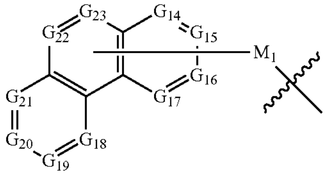

i-15

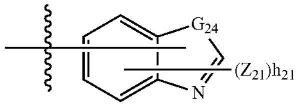

where $M_1$ is selected from a single bond or

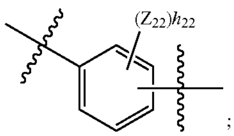

;

$G_1$ to $G_5$ and $G'_1$ to $G'_4$ are each independently selected from N, C, or $C(J_6)$, and at least one of $G_1$ to $G_5$ is selected from N; when two or more of $G_1$ to $G_5$ are selected from $C(J_6)$, any two $J_6$ are the same or different; and when two or more of $G'_1$ to $G'_4$ are selected from $C(J_6)$, any two $J_6$ are the same or different;

$G_6$ to $G_{13}$ are each independently selected from N, C or $C(J_7)$, and at least one of $G_6$ to $G_{13}$ is selected from N; and when two or more of $G_6$ to $G_{13}$ are selected from $C(J_7)$, any two $J_7$ are the same or different;

$G_{14}$ to $G_{23}$ are each independently selected from N, C or $C(J_8)$, and at least one of $G_{14}$ to $G_{23}$ is selected from N; and when two or more of $G_{14}$ to $G_{23}$ are selected from $C(J_8)$, any two $J_8$ are the same or different;

$G_{24}$ is selected from O, S, $N(J_9)$ or $C(J_{10})$;

$Z_1$ is selected from hydrogen, deuterium, a halogen group, cyano, trimethylsilyl, an alkyl with 1 to 5 carbon atoms, a cycloalkyl with 3 to 10 carbon atoms, or triphenylsilyl;

$Z_2$ to $Z_9$, and $Z_{22}$ are each independently selected from hydrogen, deuterium, a halogen group, cyano, trimethylsilyl, an alkyl with 1 to 5 carbon atoms, a cycloalkyl with 3 to 10 carbon atoms, a heteroaryl with 3 to 18 carbon atoms, or triphenylsilyl;

$Z_{10}$ to $Z_{21}$, and $J_1$ to $J_{10}$ are each independently selected from hydrogen, deuterium, a halogen group, cyano, trimethylsilyl, an alkyl with 1 to 5 carbon atoms, a cycloalkyl with 3 to 10 carbon atoms, an aryl with 6 to 18 carbon atoms, a heteroaryl with 3 to 18 carbon atoms, or triphenylsilyl;

$h_1$ to $h_{22}$ are represented by $h_k$, $Z_1$ to $Z_{22}$ are represented by $Z_k$, k is a variable and represents any integer from 1 to 22, and $h_k$ represents the number of a substituent $Z_k$; when k is selected from 5 or 17, $h_k$ is selected from 1, 2 or 3; when k is selected from 2, 7, 8, 12, 15, 16, 18, 21 or 22, $h_k$ is selected from 1, 2, 3 or 4; when k is selected from 1, 3, 4, 6, 9 or 14, $h_k$ is selected from 1, 2, 3, 4 or 5; when k is 13, $h_k$ is selected from 1, 2, 3, 4, 5, or 6; when k is selected from 10 or 19, $h_k$ is selected from 1, 2, 3, 4, 5, 6 or 7; when k is 20, $h_k$ is selected from 1, 2, 3, 4, 5, 6, 7, or 8; when k is 11, $h_k$ is selected from 1, 2, 3, 4, 5, 6, 7, 8 or 9; and when $h_k$ is greater than 1, any two $Z_k$ are the same or different;

$K_1$ is selected from O, S, $N(Z_{23})$, $C(Z_{24}Z_{25})$, and $Si(Z_{26}Z_{27})$; where $Z_{23}$, $Z_{24}$, $Z_{25}$, $Z_{26}$, and $Z_{27}$ are each independently selected from an aryl with 6 to 18 carbon atoms, a heteroaryl with 3 to 18 carbon atoms, an alkyl with 1 to 5 carbon atoms, or cycloalkyl with 3 to 10 carbon atoms, or $Z_{24}$ and $Z_{25}$ are connected to each other to form a saturated or unsaturated ring having 3 to 15 carbon atoms together with the atoms to which they are commonly connected, or $Z_{26}$ and $Z_{27}$ are connected to each other to form a saturated or unsaturated ring having 3 to 15 carbon atoms together with the atoms to which they are commonly connected; and $K_2$ is selected from a single bond, O, S, $N(Z_{28})$, $C(Z_{29}Z_{30})$, and $Si(Z_{31}Z_{32})$; where $Z_{28}$, $Z_{29}$, $Z_{30}$, $Z_{31}$, and $Z_{32}$ are each independently selected from an aryl with 6 to 18 carbon atoms, a heteroaryl with 3 to 18 carbon atoms, an alkyl with 1 to 5 carbon atoms, or cycloalkyl with 3 to 10 carbon atoms, or $Z_{29}$ and $Z_{30}$ are connected to each other to form a saturated or unsaturated ring having 3 to 15 carbon atoms together with the atoms to which they are commonly connected, or $Z_{31}$ and $Z_{32}$ are connected to each other to form a saturated or unsaturated ring having 3 to 15 carbon atoms together with the atoms to which they are commonly connected.

Optionally, Ar is selected from a substituted or unsubstituted aryl with 6 to 25 carbon atoms or a substituted or unsubstituted heteroaryl with 3 to 20 carbon atoms. For example, Ar may be selected from substituted or unsubstituted aryl with 6, 7, 8, 9, 10, 11, 12, 13, 14, 15, 16, 17, 18, 19, 20, 21, 22, 23, 24, or 25 carbon atoms, and substituted or unsubstituted heteroaryl with 3, 4, 5, 6, 7, 8, 9, 10, 11, 12, 13, 14, 15, 16, 17, 18, 19, or 20 carbon atoms.

Optionally, Ar is selected from a substituted or unsubstituted group $T_2$, and the unsubstituted group $T_2$ is selected from the group consisting of:

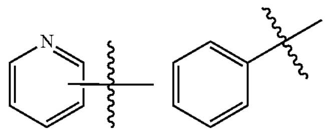

-continued
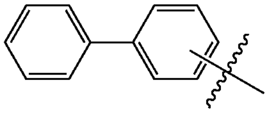
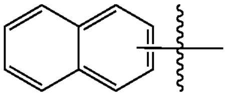
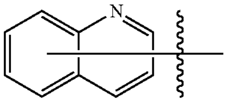
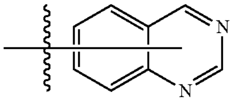
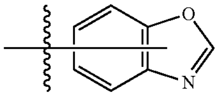
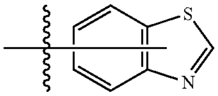
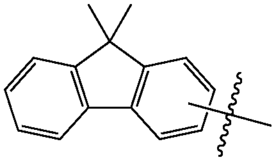
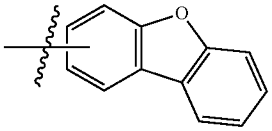
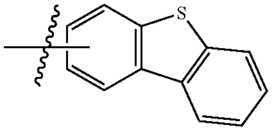
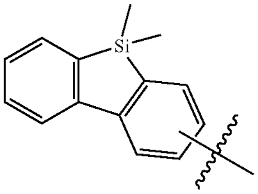
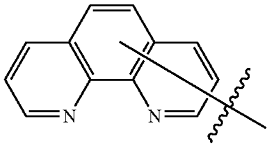
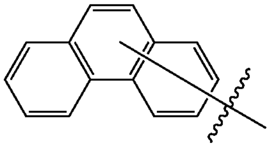
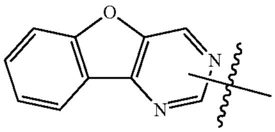
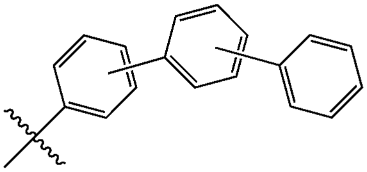
-continued
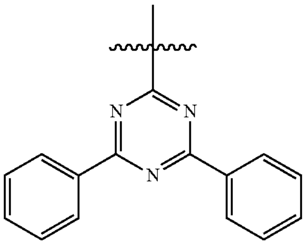
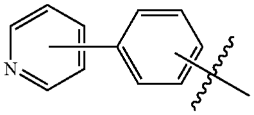
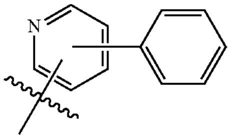
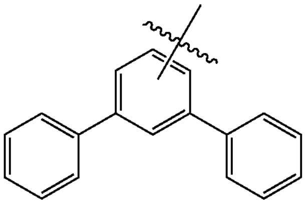
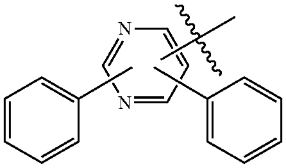
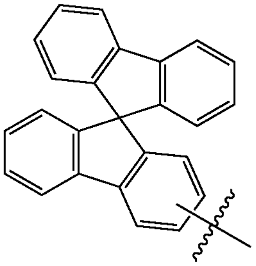
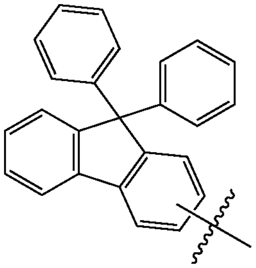
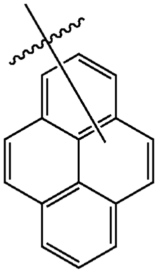
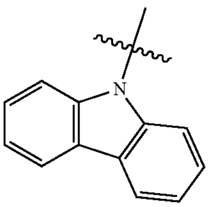
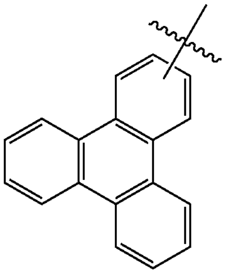
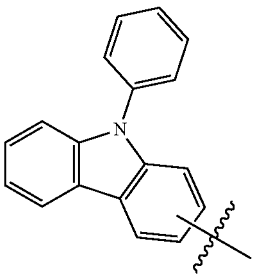

-continued

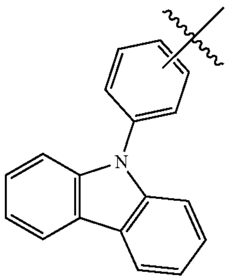

;

the substituted group $T_2$ has one or two or more substituents, and the substituents in the substituted group $T_2$ are independently selected from deuterium, fluorine, cyano, methyl, ethyl, isopropyl, tert-butyl, phenyl, biphenyl, pyridyl, naphthyl, carbazolyl, cyclohexyl, dibenzofuranyl or dibenzothienyl.

Further optionally, Ar is selected from the group consisting of:

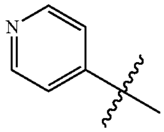
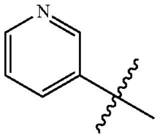
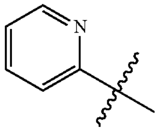
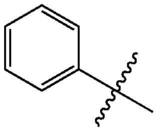
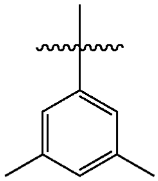
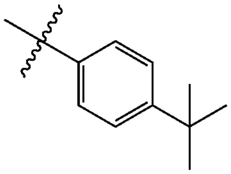
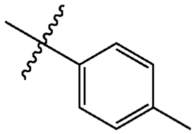
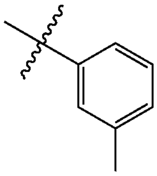
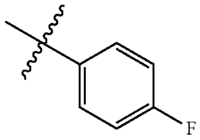
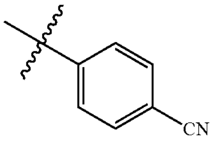
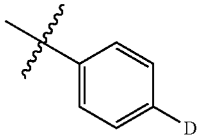
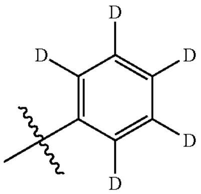
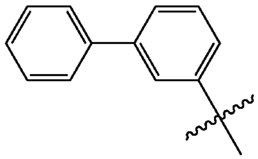

-continued

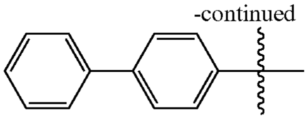
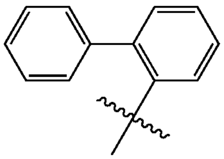
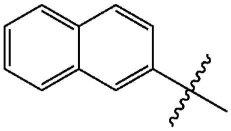
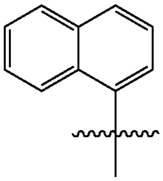
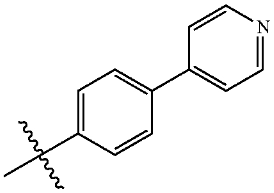
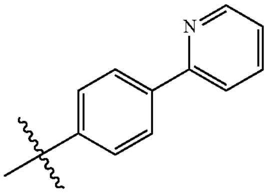
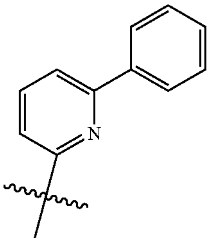
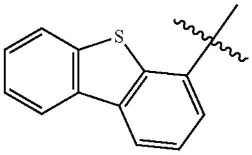
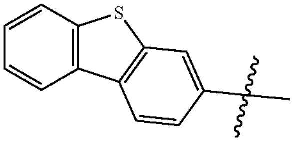
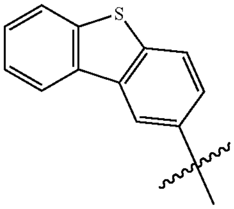
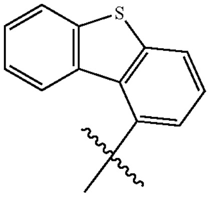
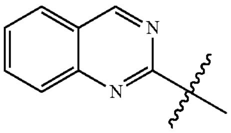
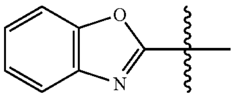
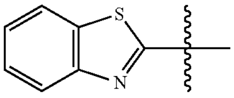
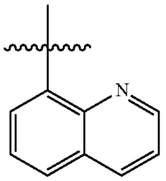
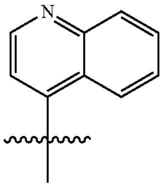
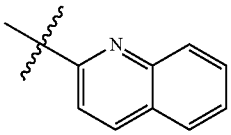

-continued
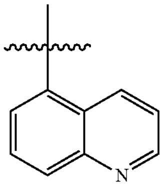
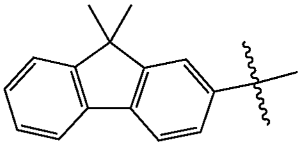
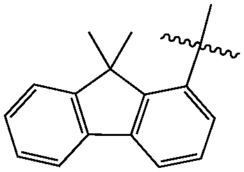
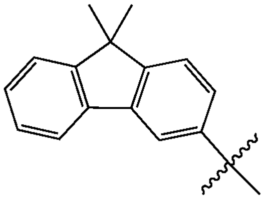
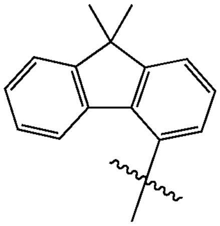
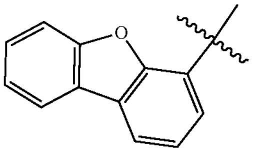
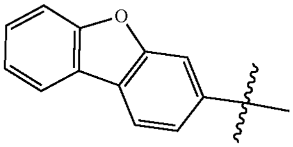
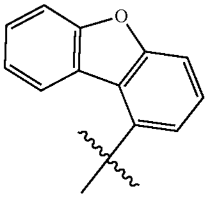
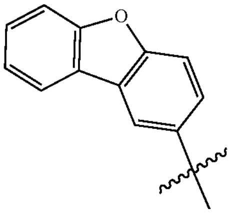
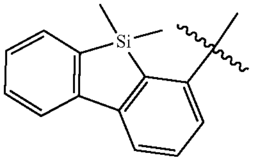
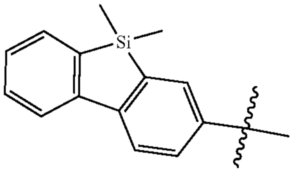
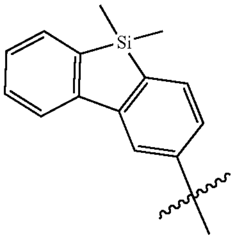
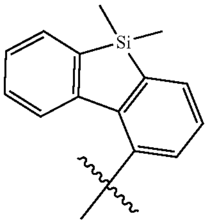
-continued
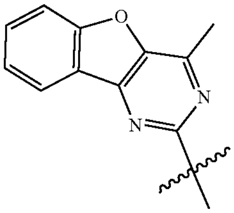
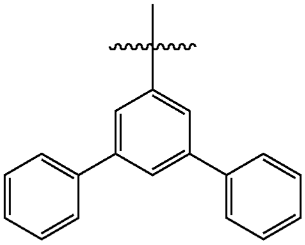
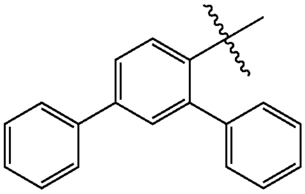
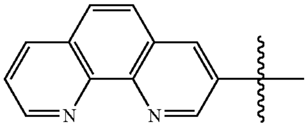
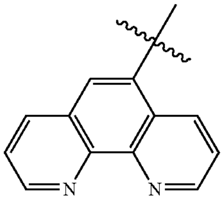
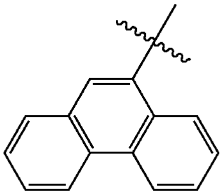
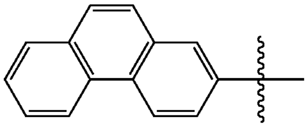
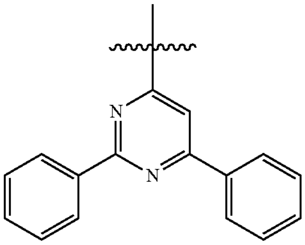
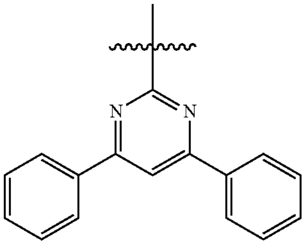

-continued
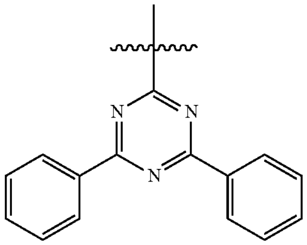
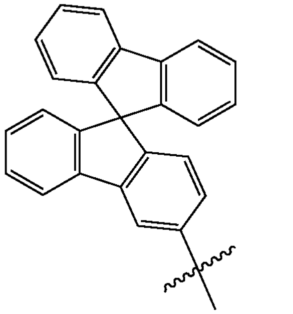
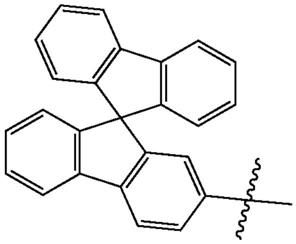
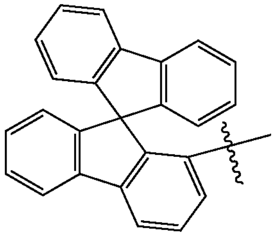
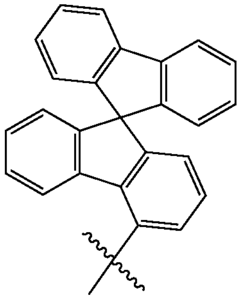
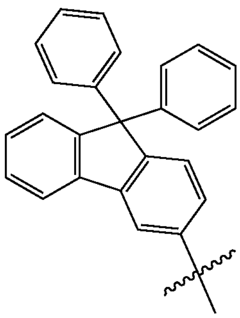
-continued
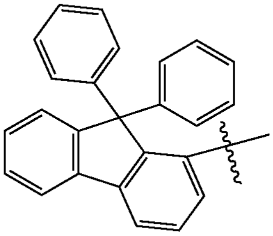
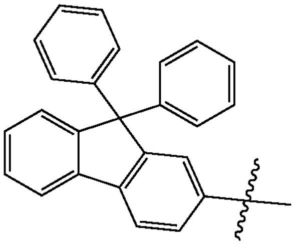
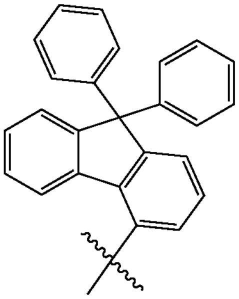
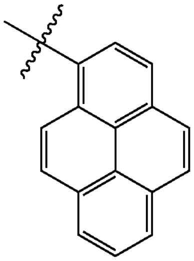
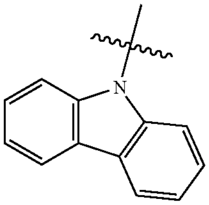
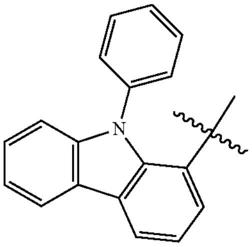
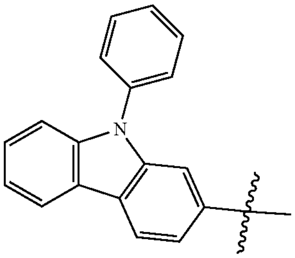
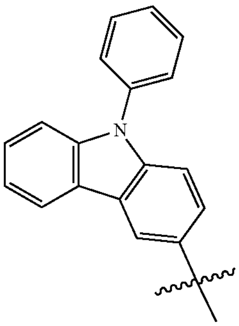
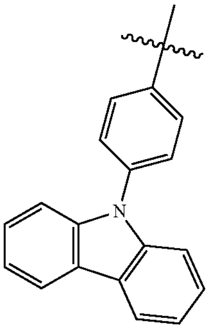

-continued

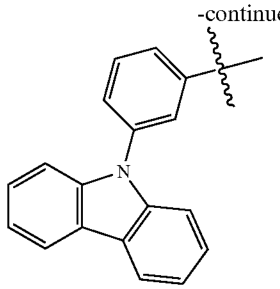

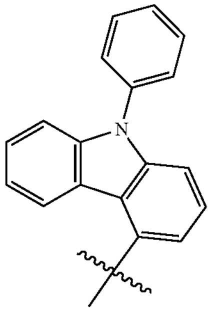

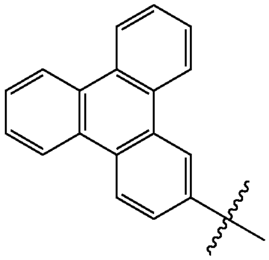

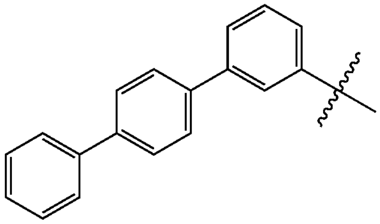

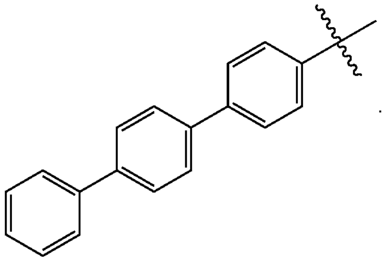

.

In one example, Ar is selected from substituted or unsubstituted phenyl, substituted or unsubstituted pyridyl, substituted or unsubstituted pyrimidinyl, substituted or unsubstituted triazinyl, substituted or unsubstituted naphthyl, substituted or unsubstituted anthryl, substituted or unsubstituted benzothiazolyl, substituted or unsubstituted benzoxazolyl, substituted or unsubstituted phenanthryl, substituted or unsubstituted biphenyl, substituted or unsubstituted quinolyl, substituted or unsubstituted 1,10-phenanthrolinyl, substituted or unsubstituted 9,9-dimethylfluorenyl, substituted or unsubstituted dibenzofuranyl, substituted or unsubstituted dibenzothienyl, substituted or unsubstituted 9,10-benzophenanthryl, substituted or unsubstituted N-phenylcarbazolyl, substituted or unsubstituted terphenyl, substituted or unsubstituted carbazolyl, substituted or unsubstituted pyrenyl, substituted or unsubstituted fluoranthenyl, 1-phenyl-1H-benzimidazolyl, substituted or unsubstituted 9,9-spirobifluorenyl, substituted or unsubstituted 9,9-diphenylfluorenyl, substituted or unsubstituted 4,5-diaza-9,9'-spirodifluorenyl, substituted or unsubstituted silafluorenyl, and substituted or unsubstituted benzofuropyrimidinyl, and substituents in the above groups are the same or different, and are each independently selected from deuterium, cyano, fluorine, trimethylsilyl, methyl, ethyl, isopropyl, tert-butyl, phenyl, biphenyl, pyridyl, carbazolyl, and naphthyl.

Optionally, $R_4$ to $R_7$ are each independently selected from an alkyl with 1 to 5 carbon atoms, an aryl with 6 to 20 carbon atoms, or a heteroaryl with 3 to 20 carbon atoms.

Further optionally, $R_4$ to $R_7$ are each independently selected from methyl, ethyl, isopropyl, tert-butyl, phenyl, naphthyl, biphenyl, pyridyl, and quinolyl.

Optionally, the organic compound is selected from the group consisting of the following compounds:

1

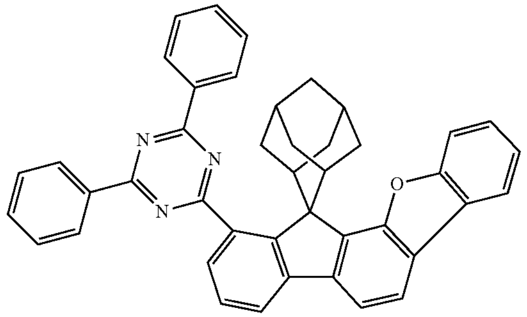

2

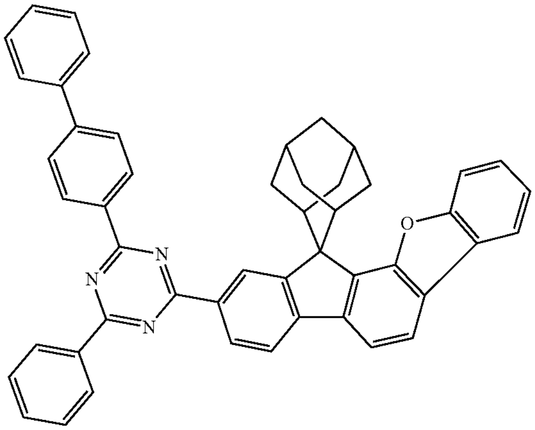

3

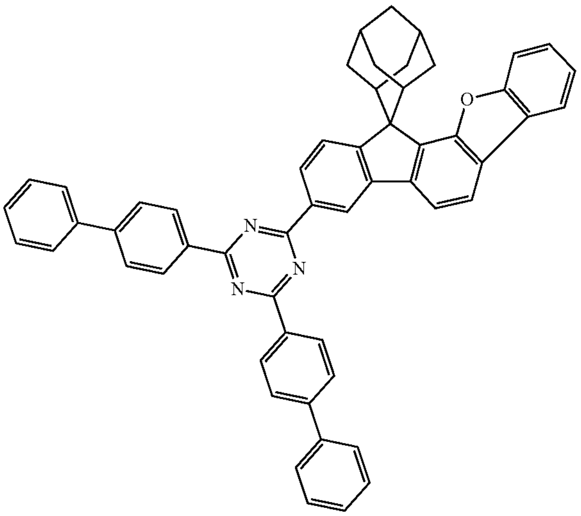

-continued
4
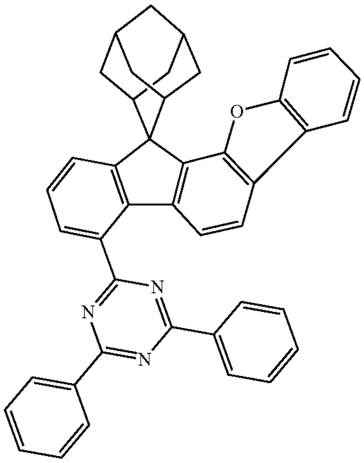
5
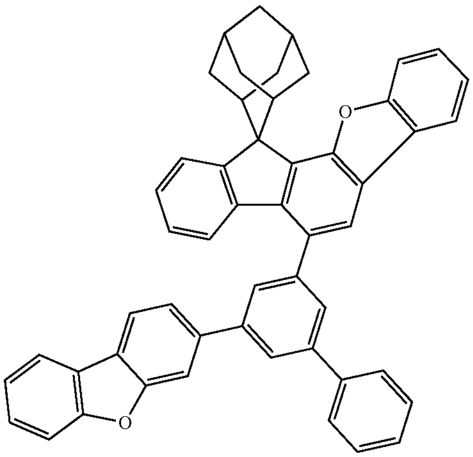
6
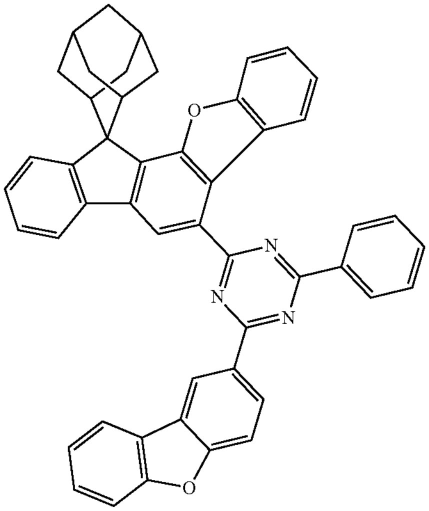
-continued
7
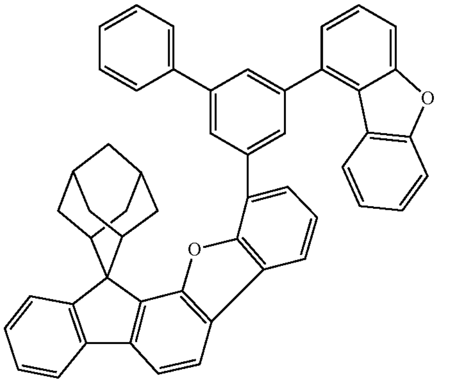
8
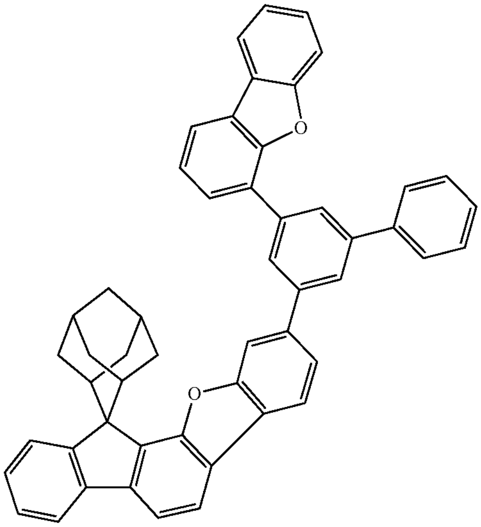
9
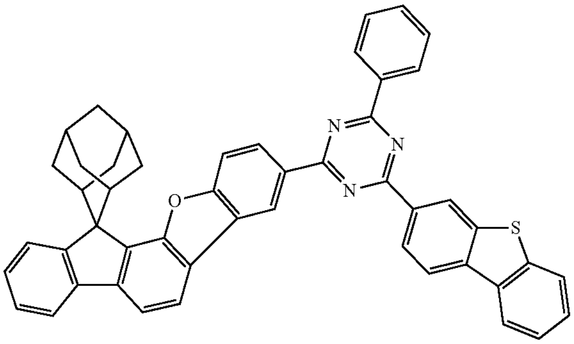

-continued
10
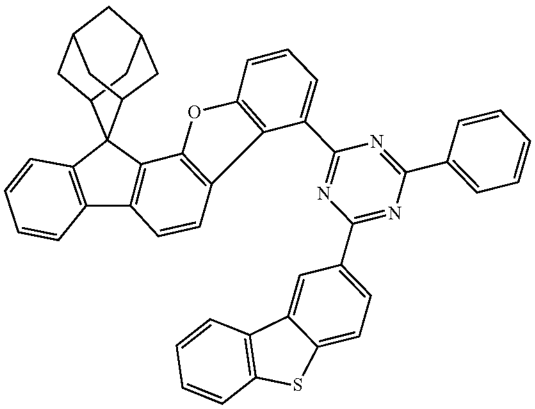
11
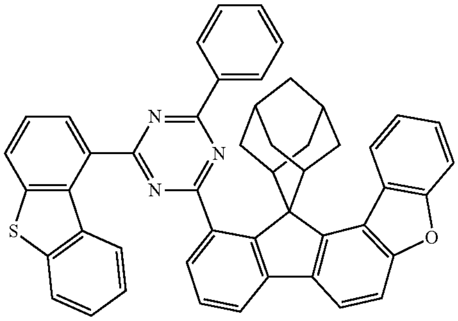
12
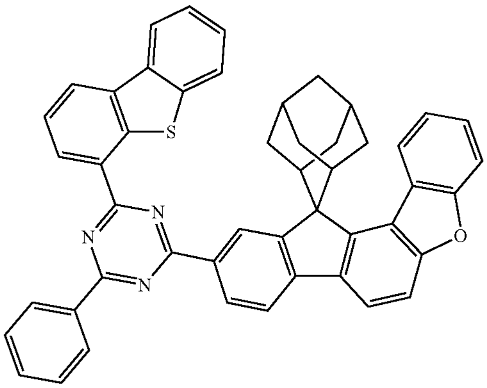
-continued
13
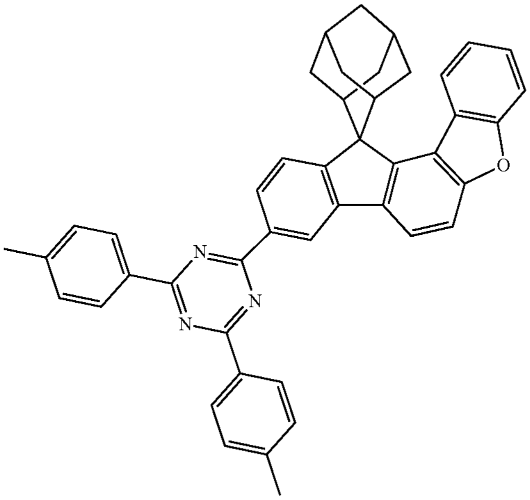
14
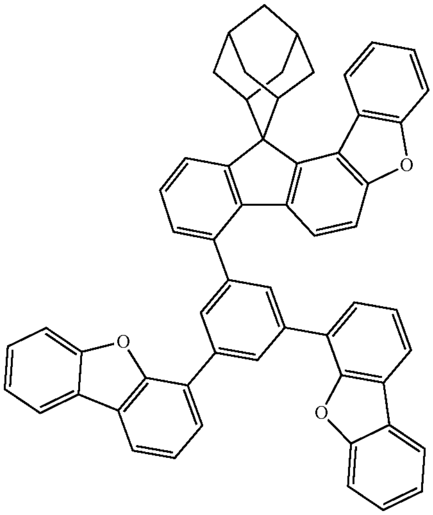
15
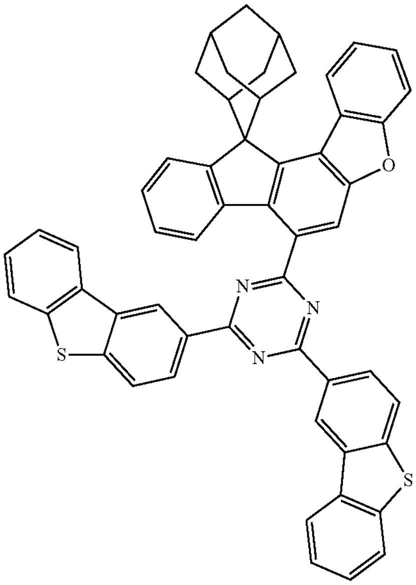

-continued
16
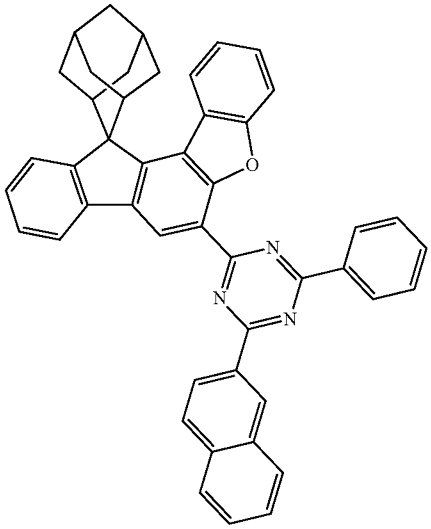
17
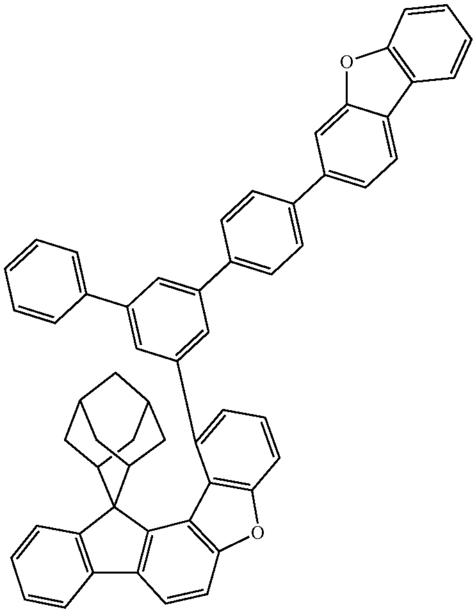
-continued
18
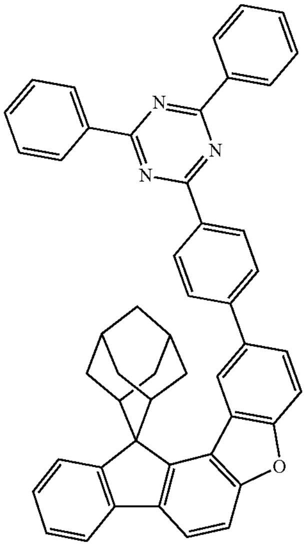
19
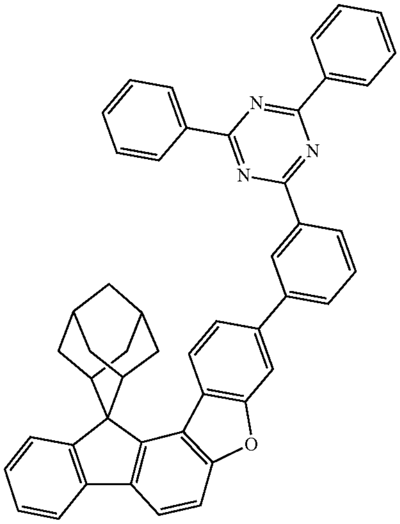
20
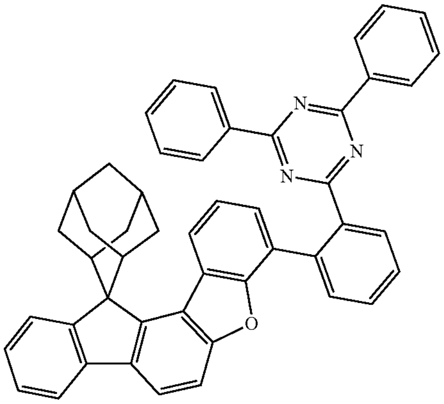

-continued
21
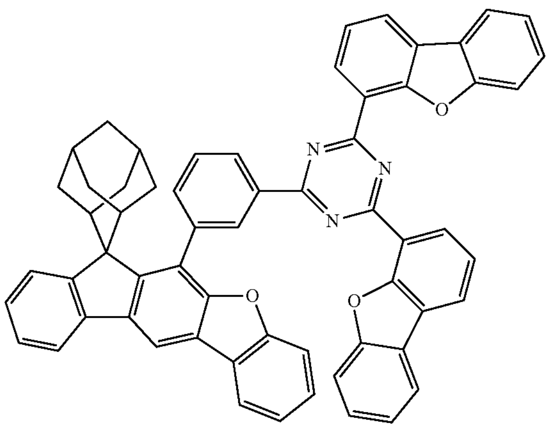
22
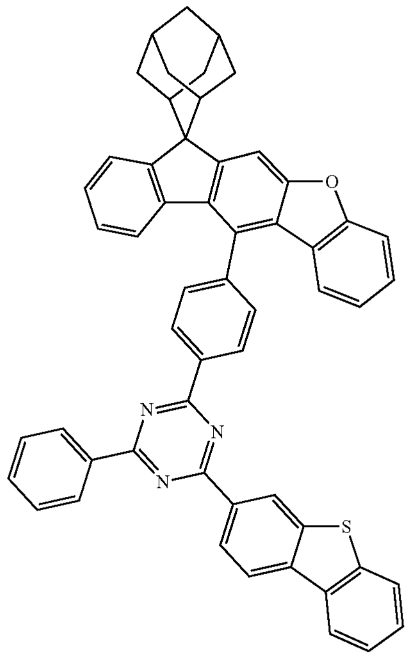
23
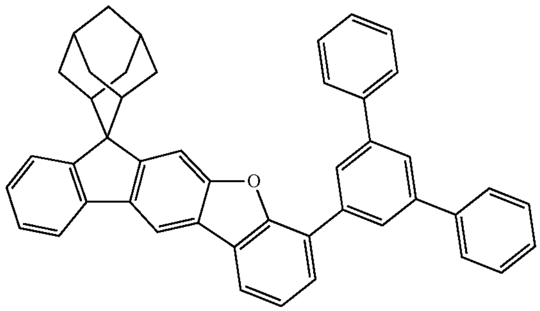
-continued
24
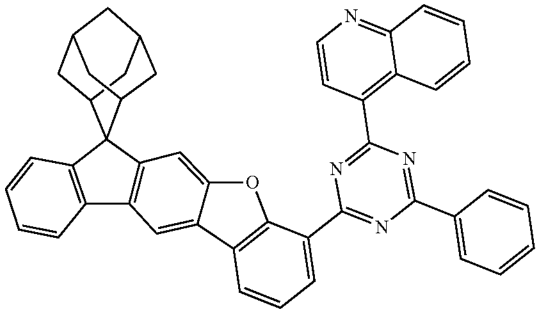
25
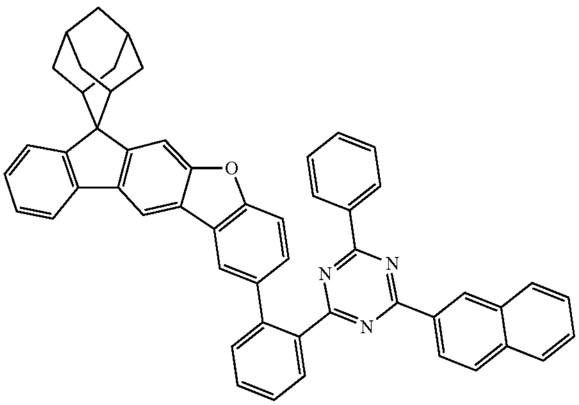
26
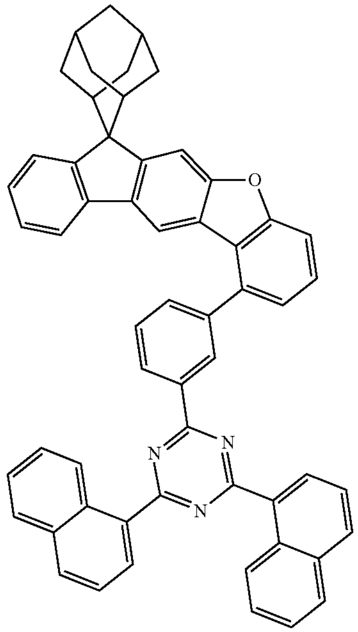

-continued
27
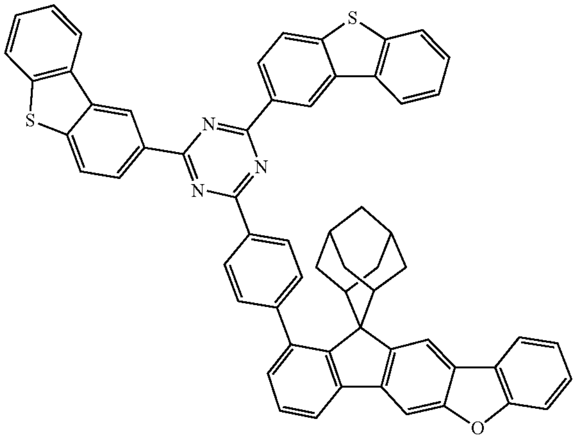
28
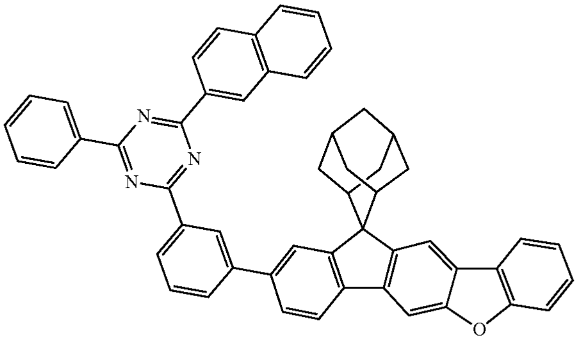
29
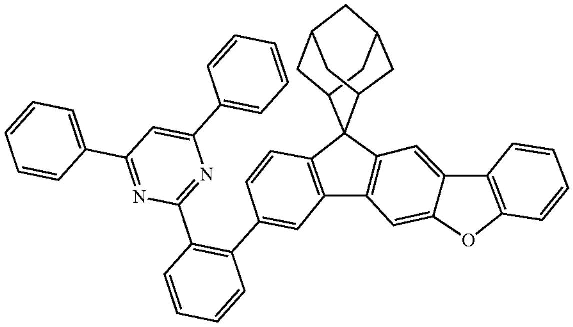
30
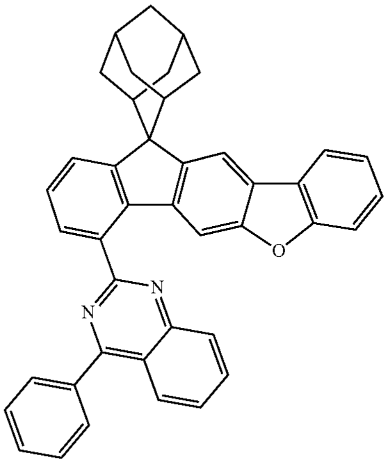
-continued
31
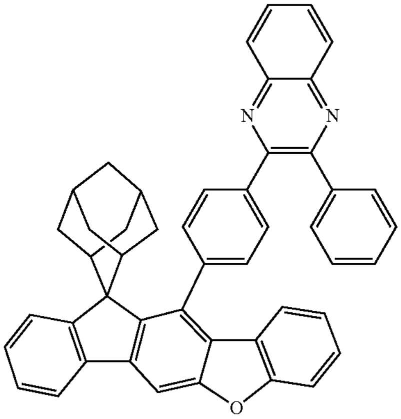
32
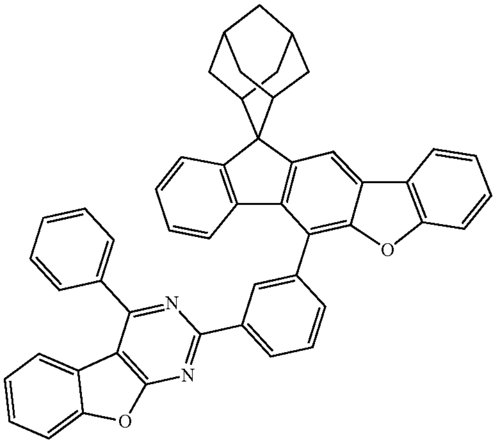
33
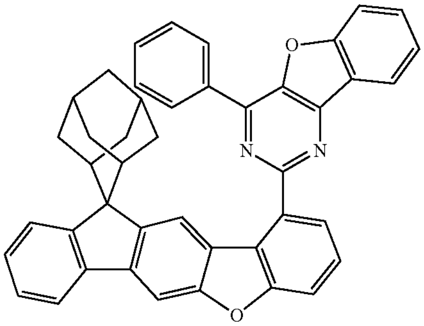
34
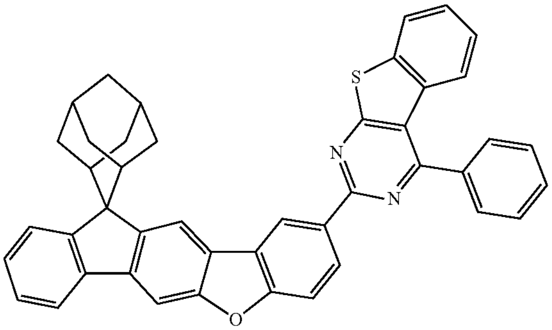

-continued
35
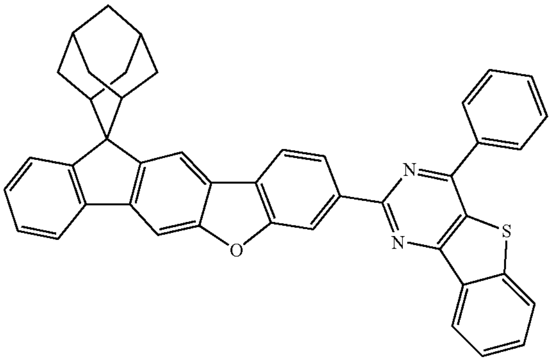
36
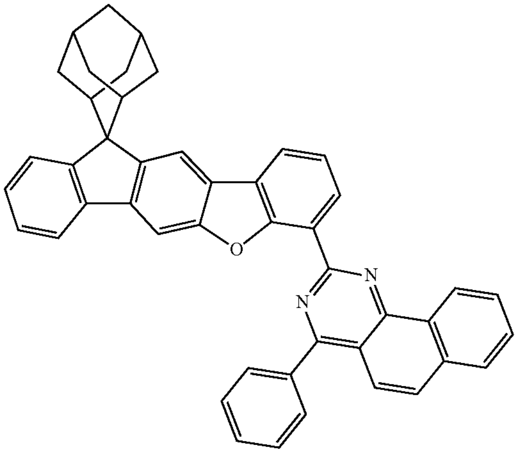
37
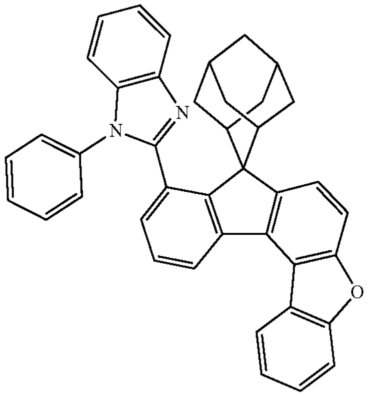
38
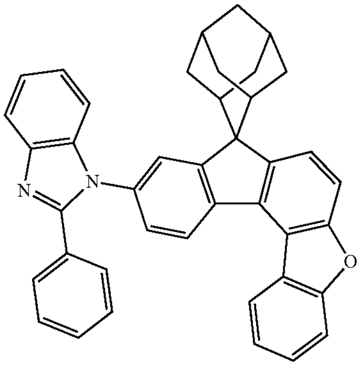
-continued
39
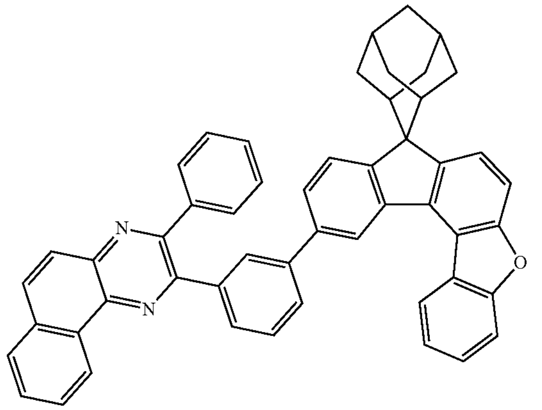
40
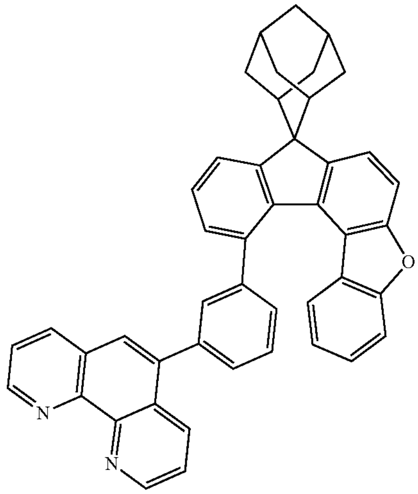
41
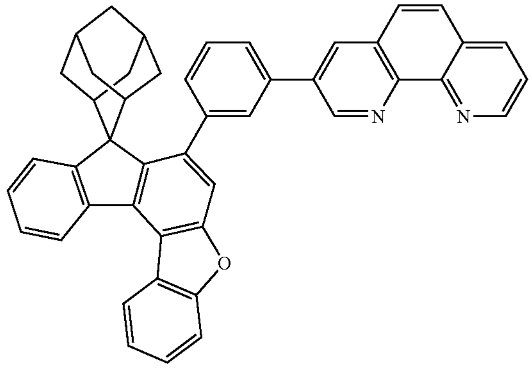

-continued
42
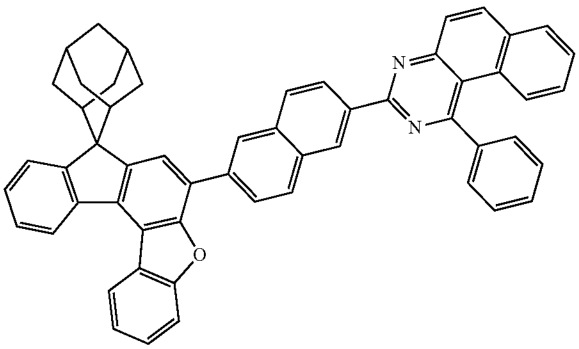
43
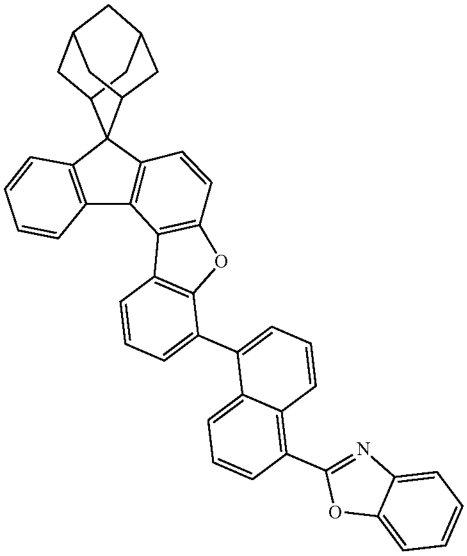
44
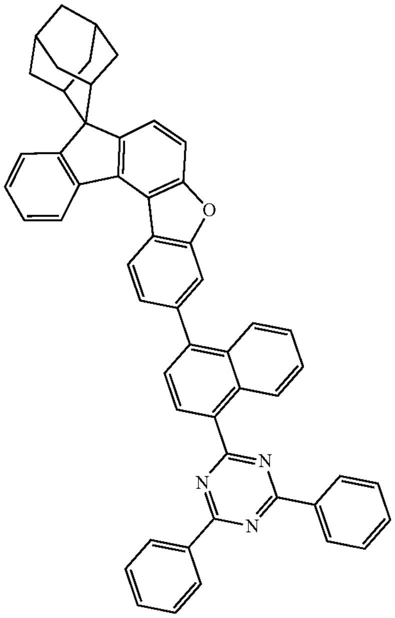
-continued
45
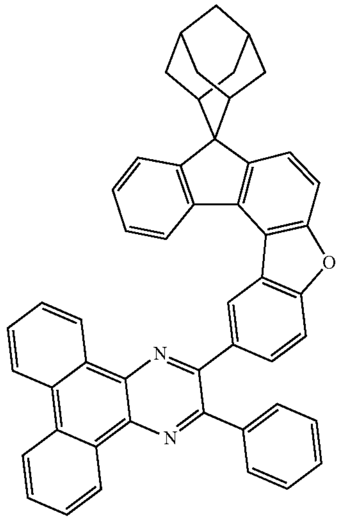
46
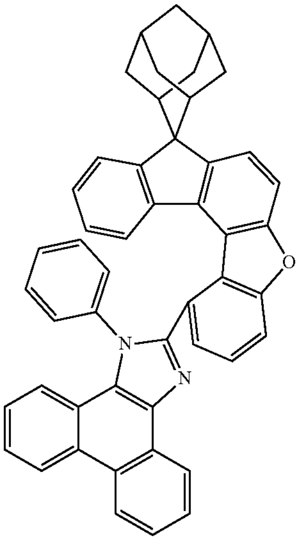
47
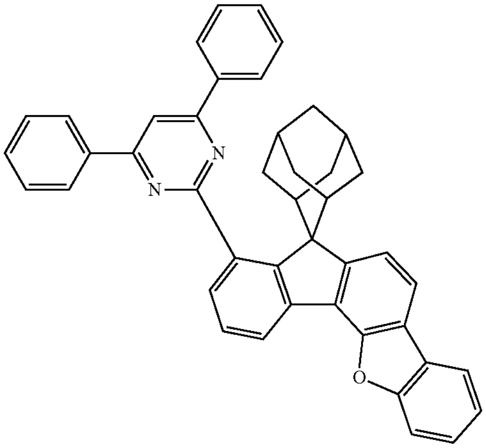

-continued
48
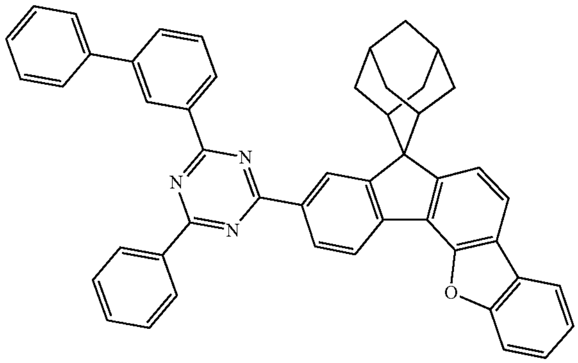
49
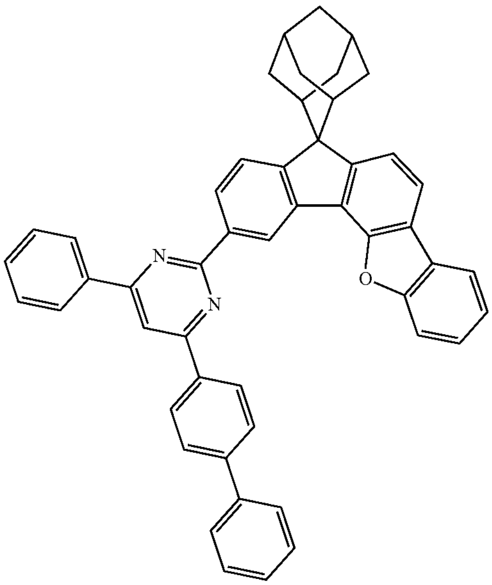
50
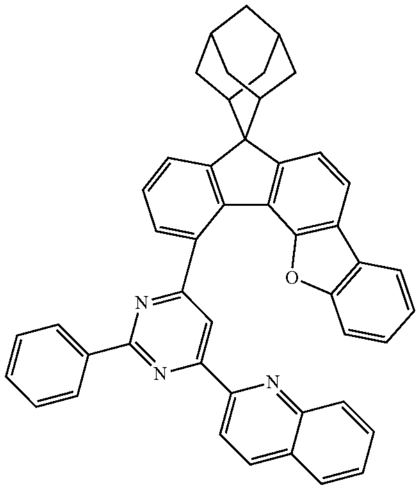
-continued
51
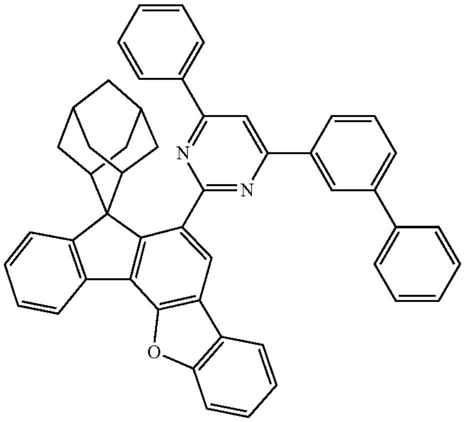
52
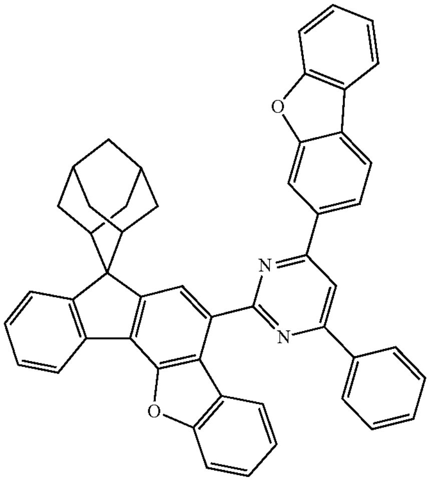
53
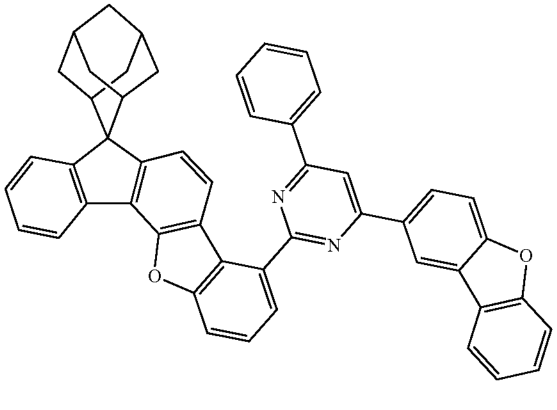

-continued
54
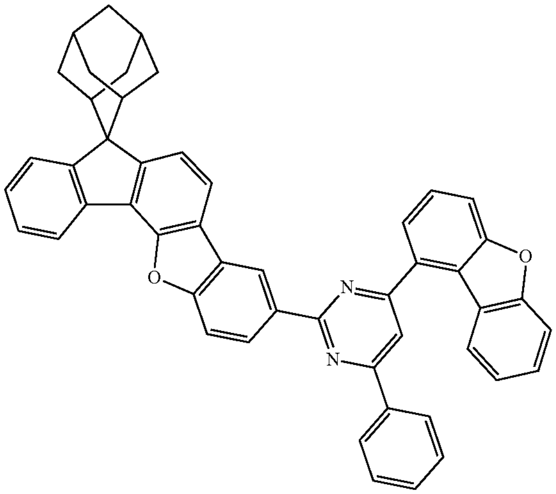
55
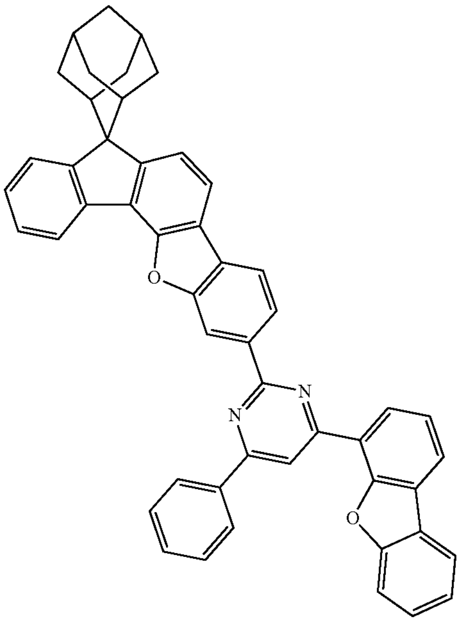
-continued
56
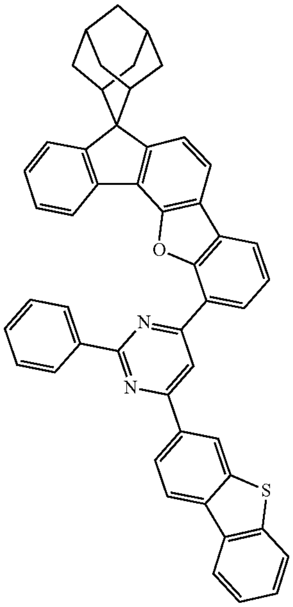
57
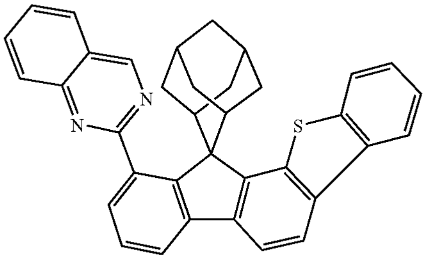
58
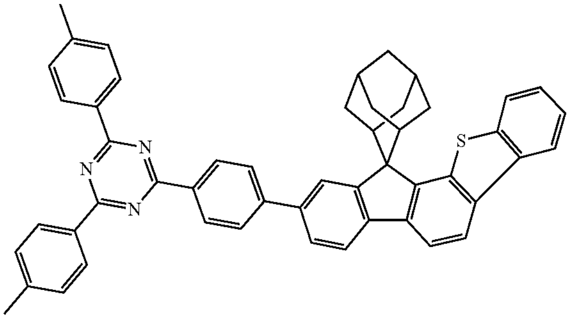

-continued
59
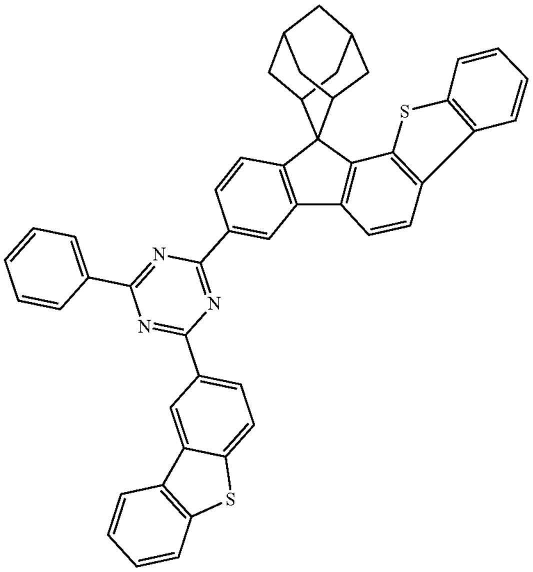
60
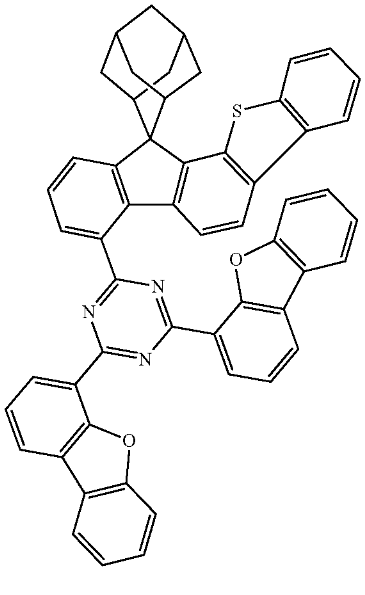
-continued
61
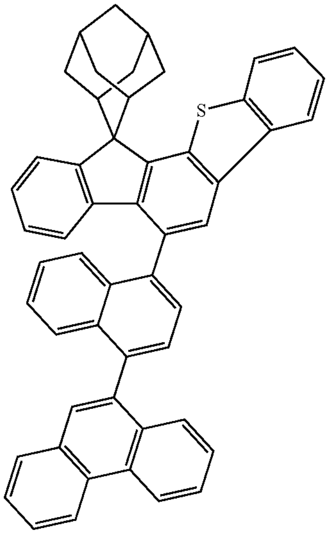
62
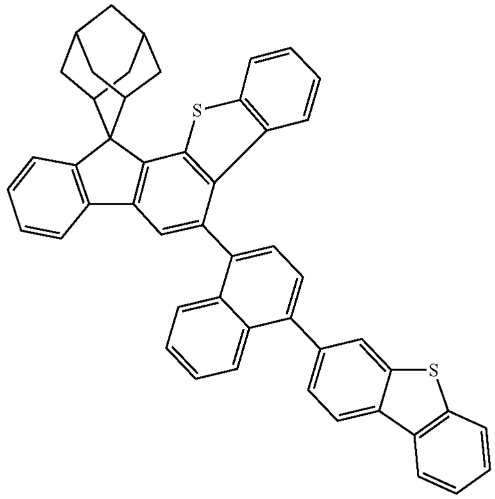
63
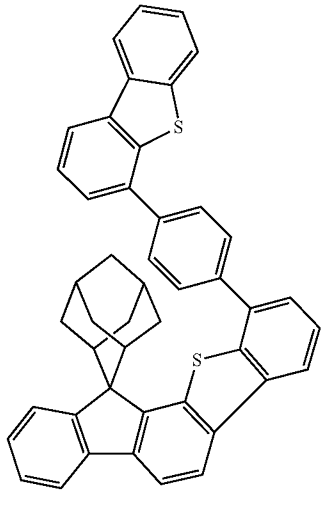

-continued
64
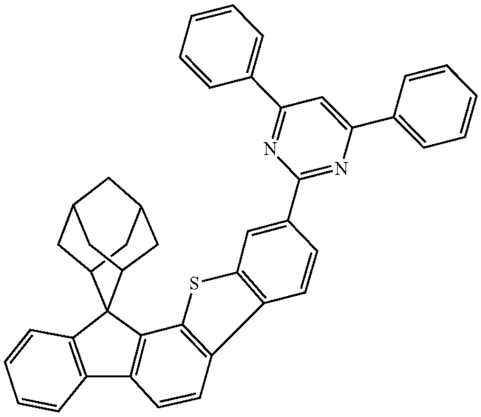
65
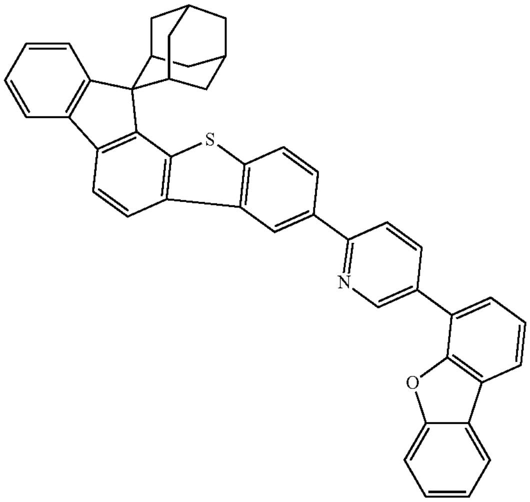
66
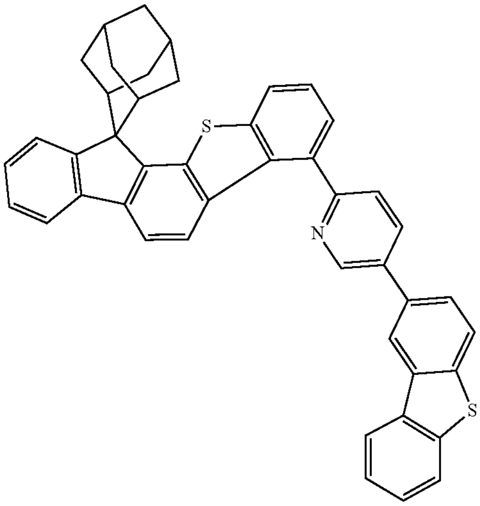
-continued
67
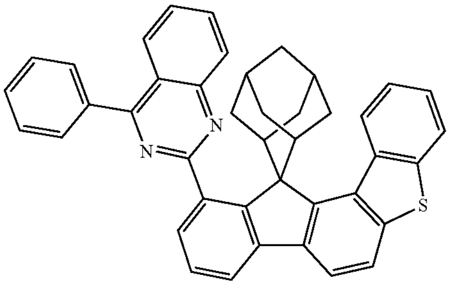
68
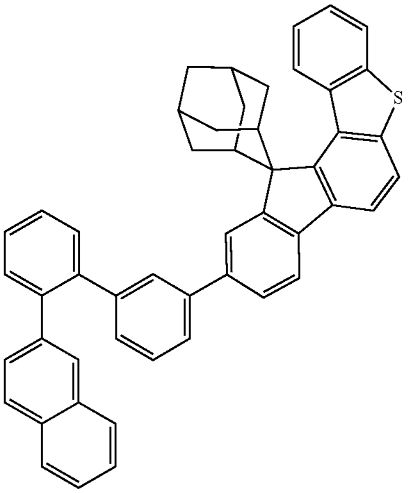
69
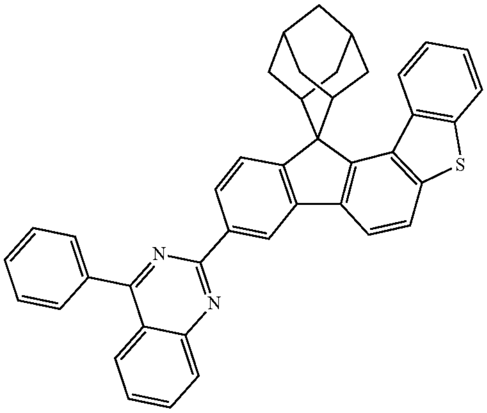
70
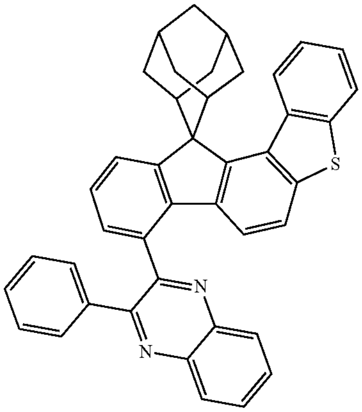

-continued
71
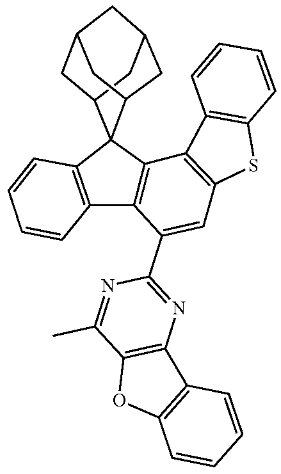
72
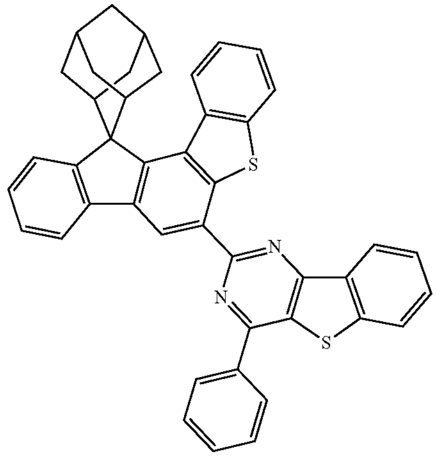
73
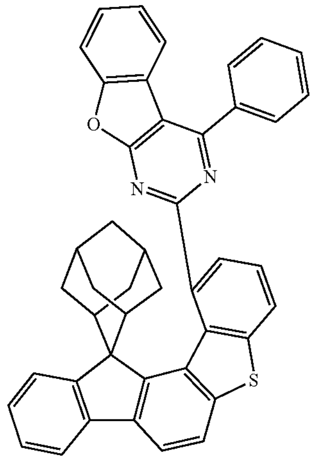
-continued
74
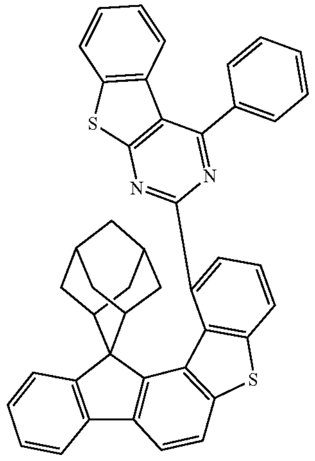
75
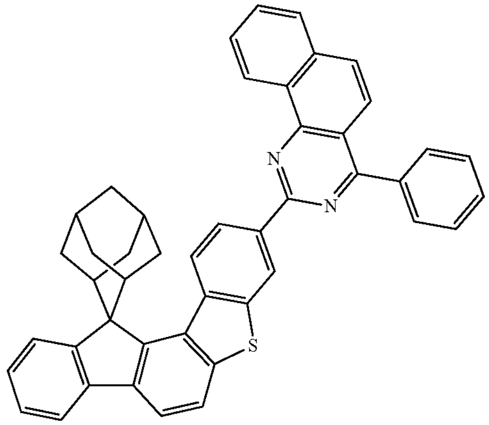
76
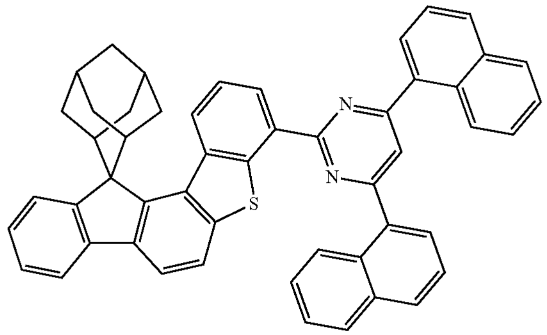

-continued
77
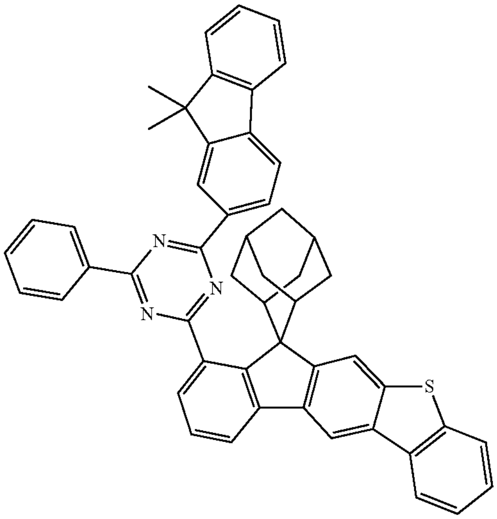
78
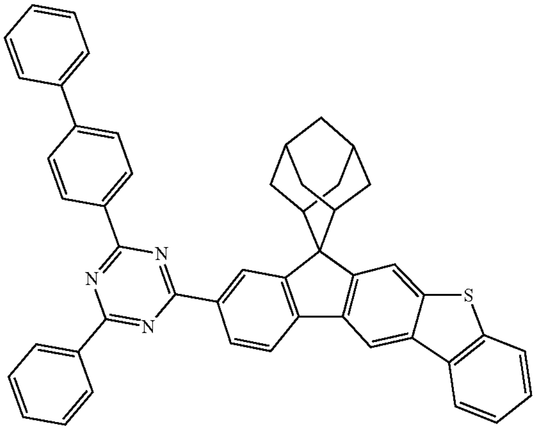
79
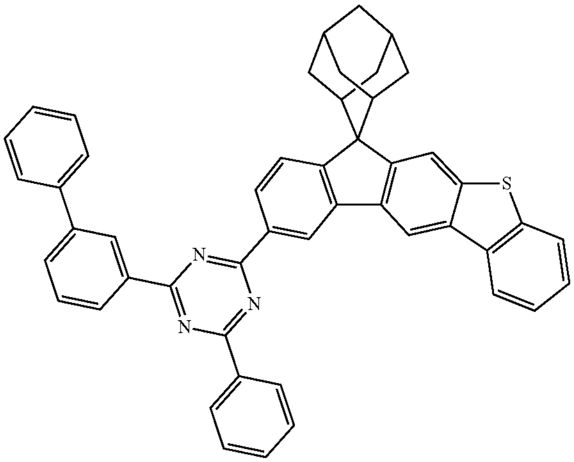
-continued
80
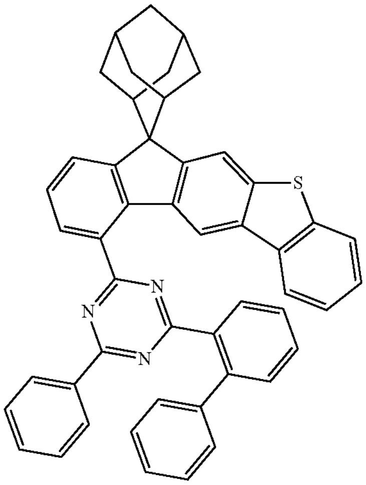
81
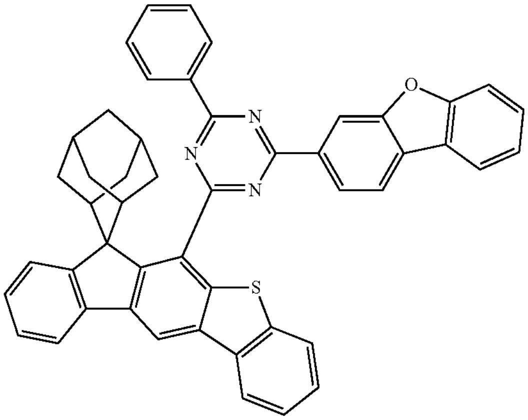
82
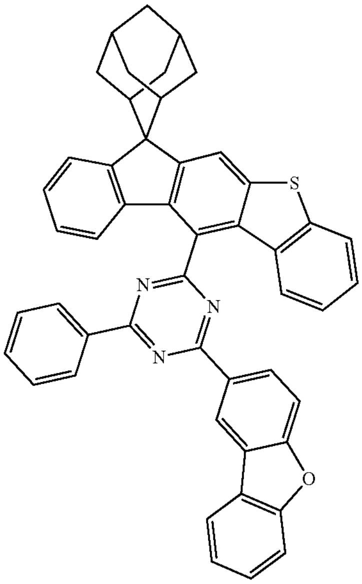

-continued
83
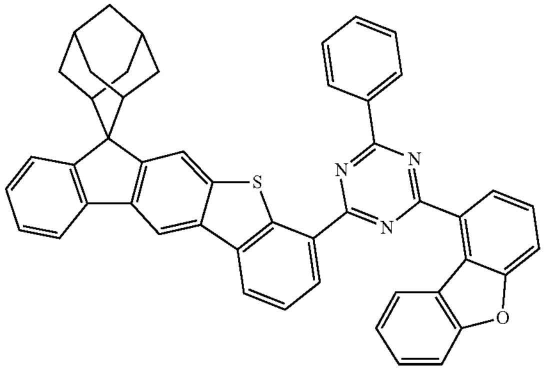
84
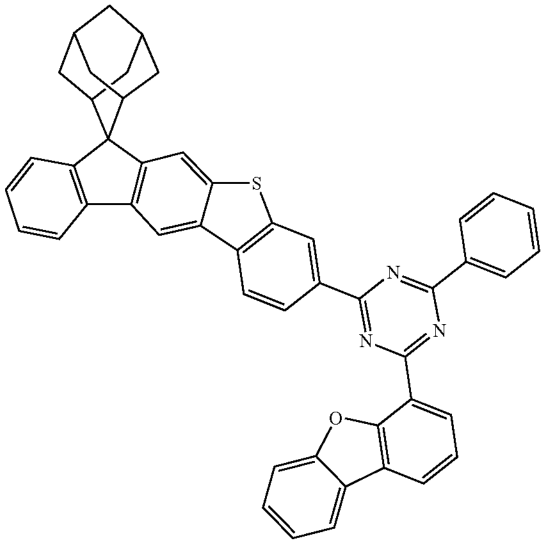
85
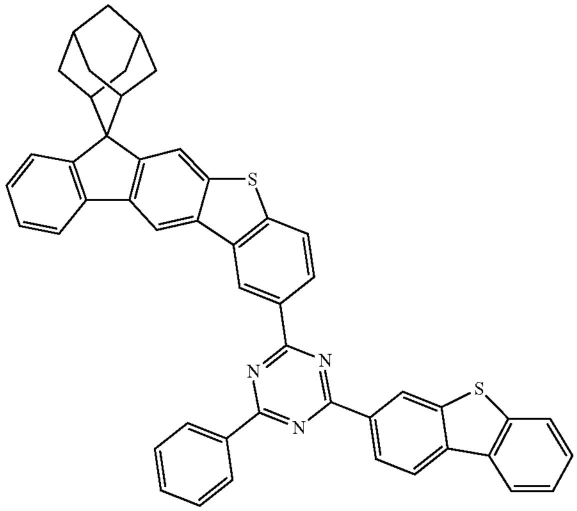
-continued
86
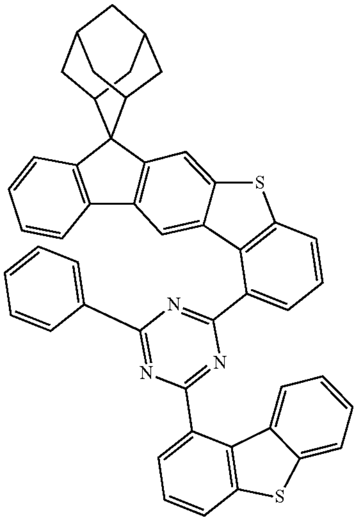
87
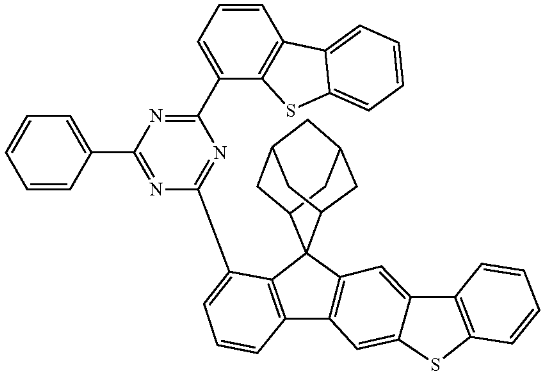
88
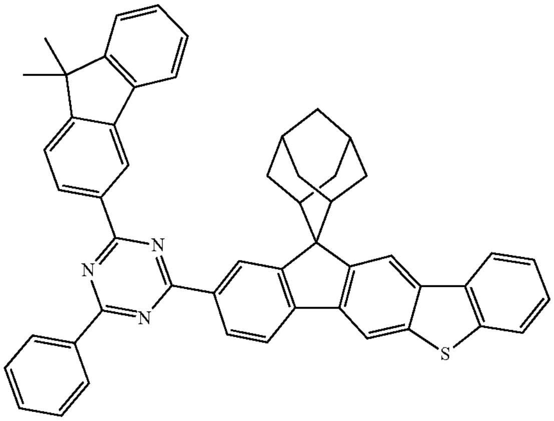

-continued
89
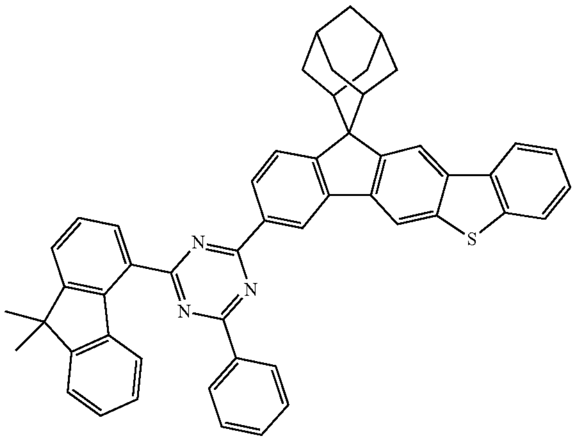
90
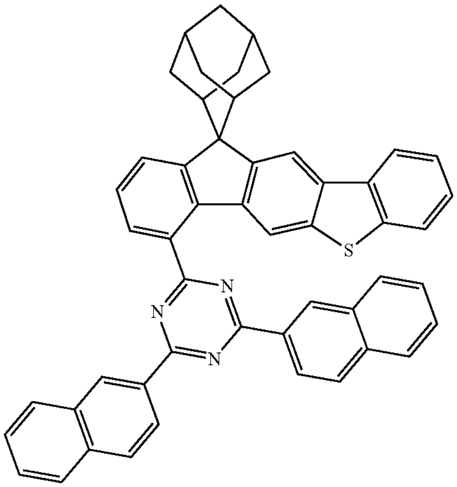
91
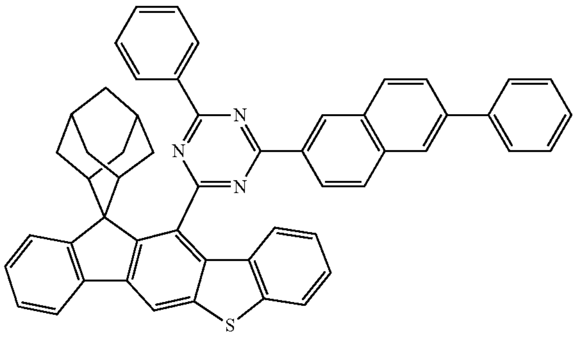
-continued
92
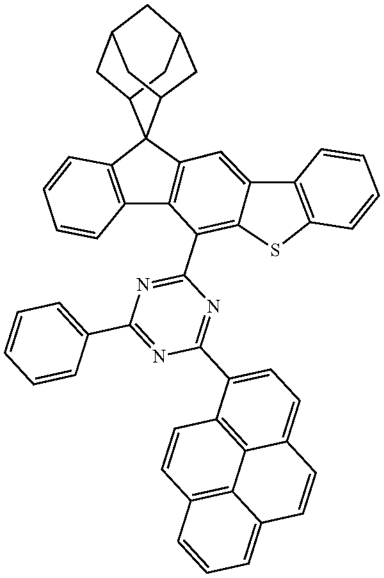
93
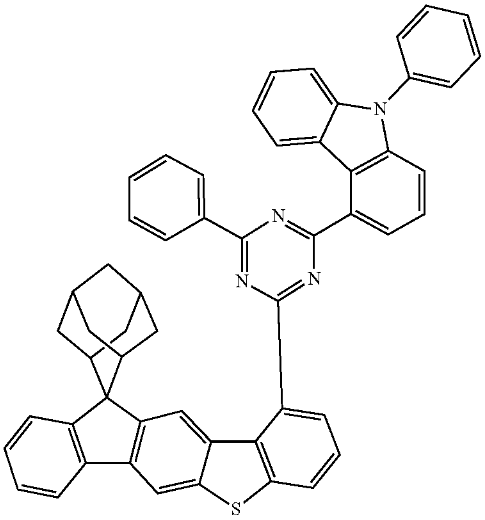
94
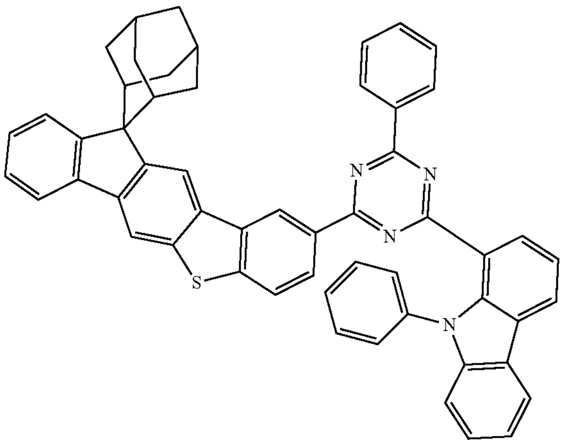

-continued
95
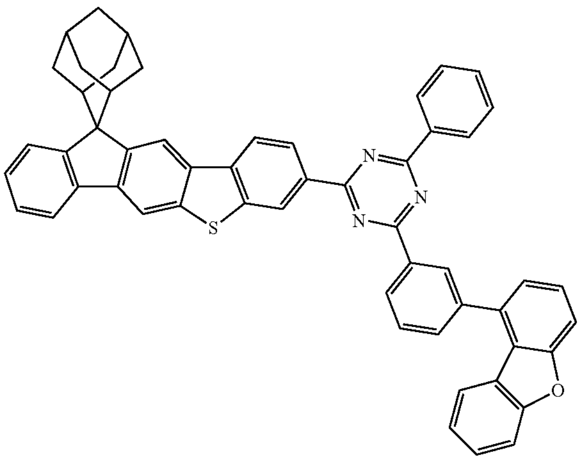
96
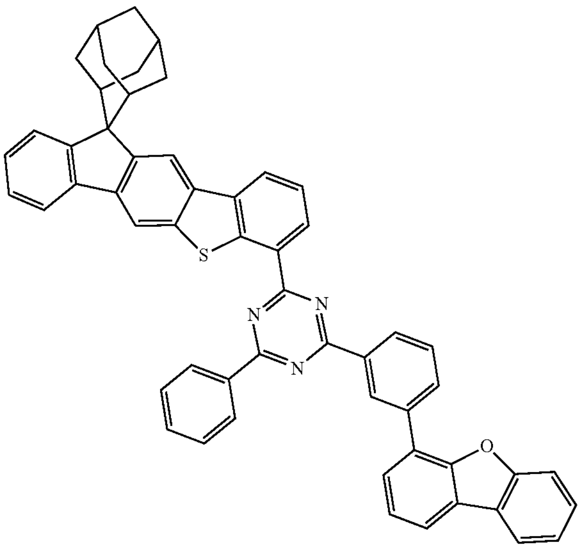
97
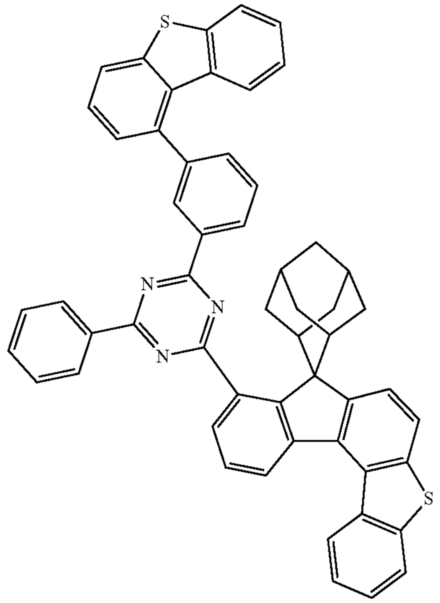
-continued
98
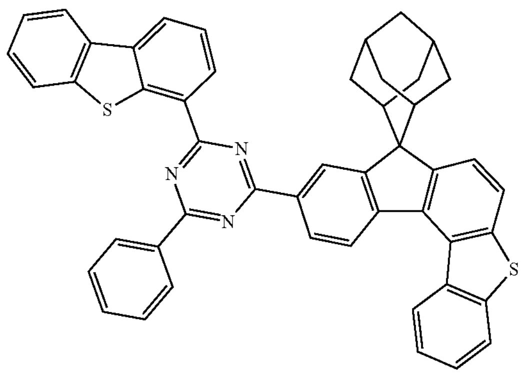
99
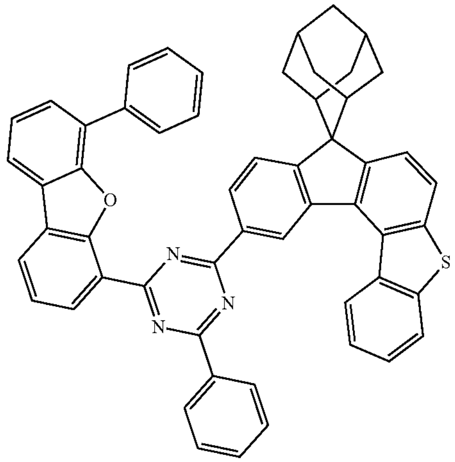
100
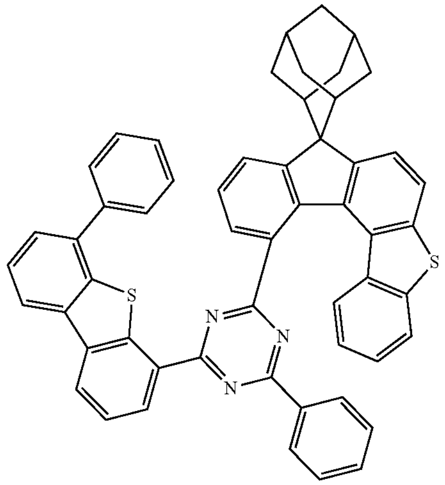

101
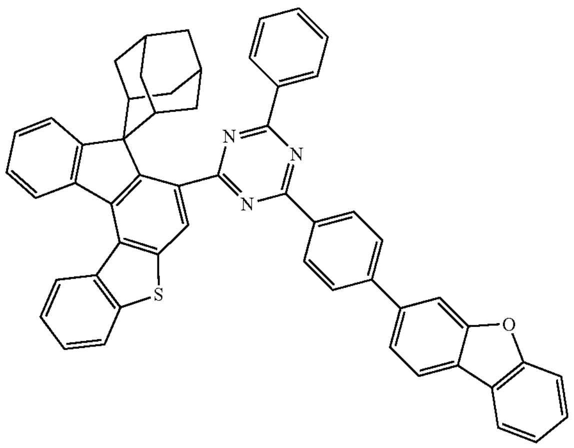
102
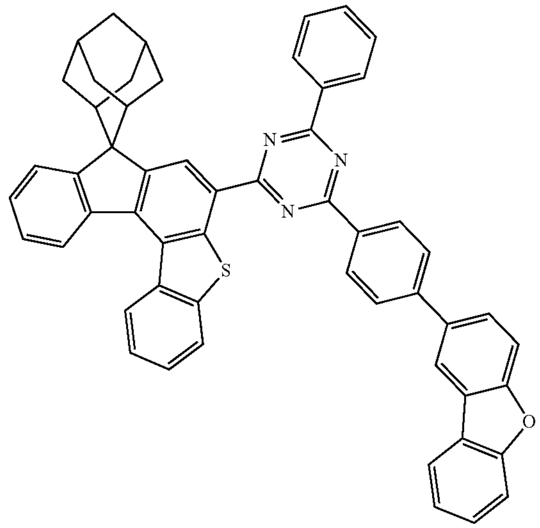
103
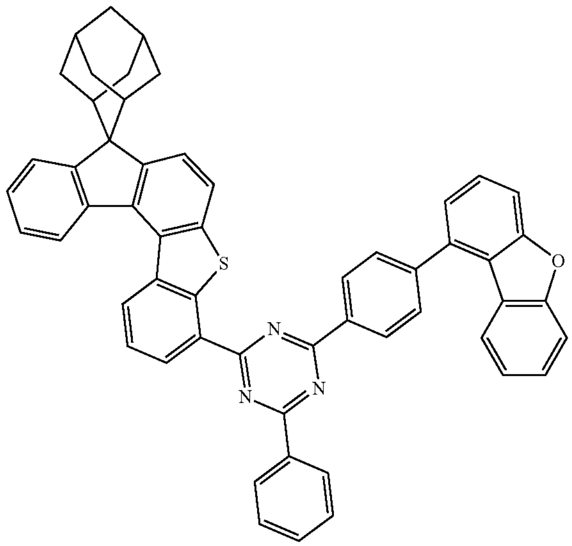
104
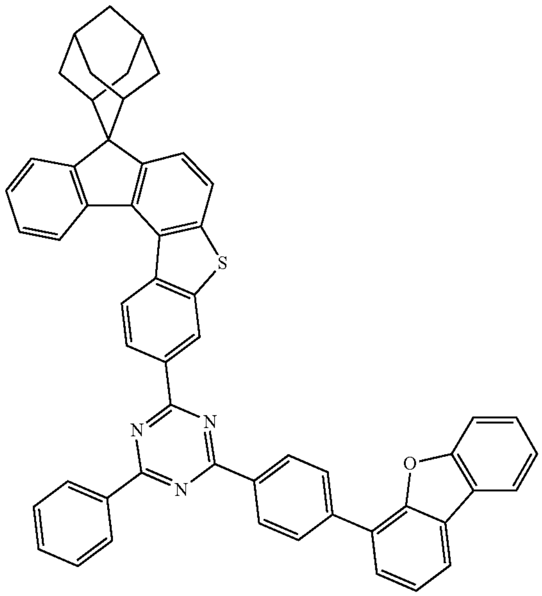
105
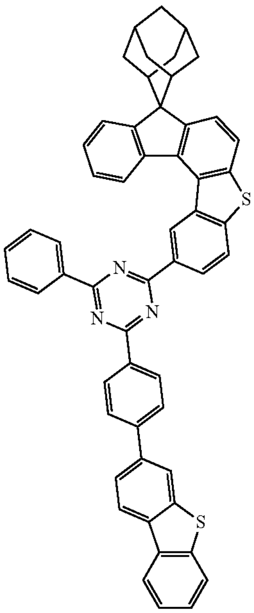

-continued
106
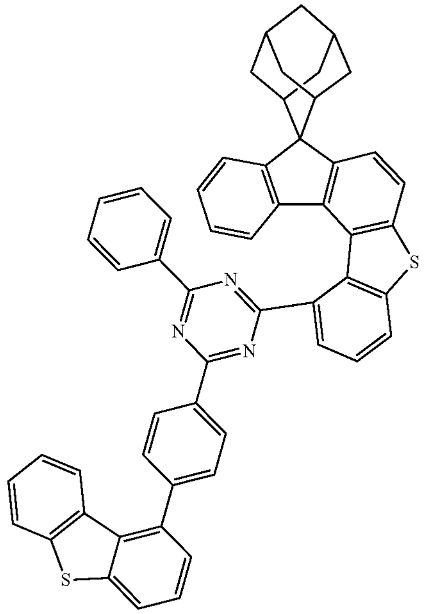
107
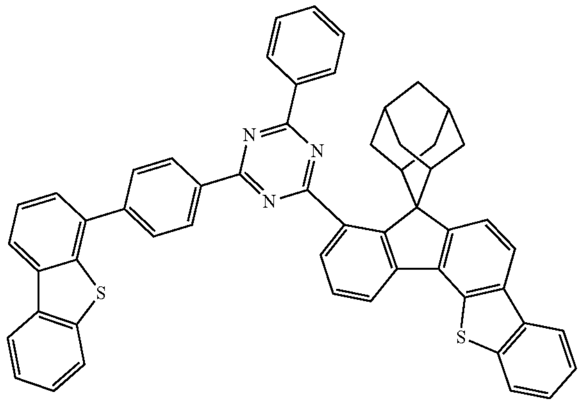
108
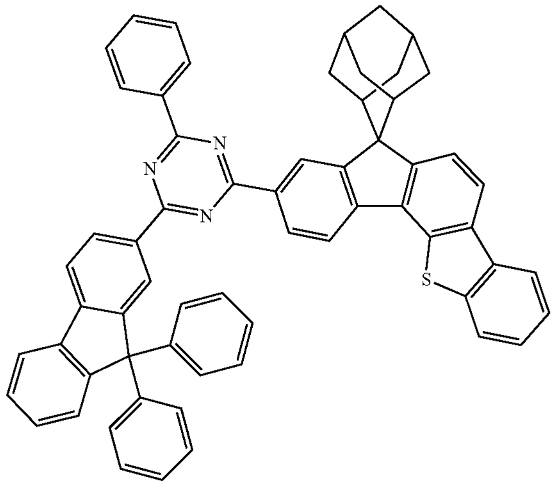
-continued
109
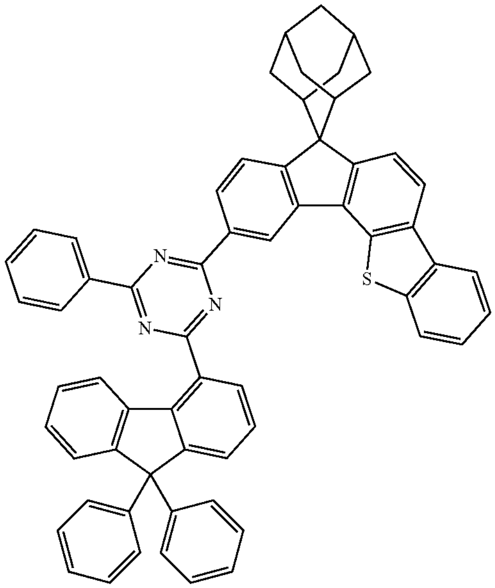
110
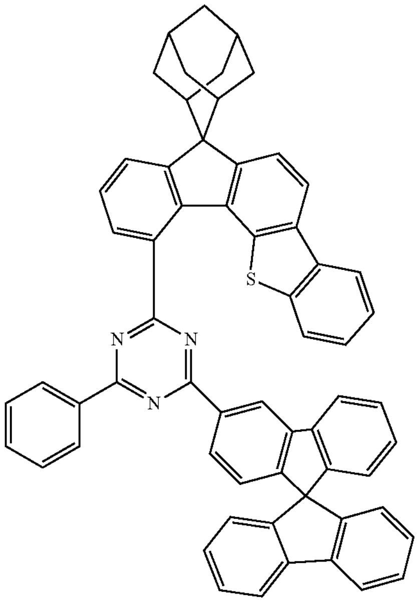

-continued
111
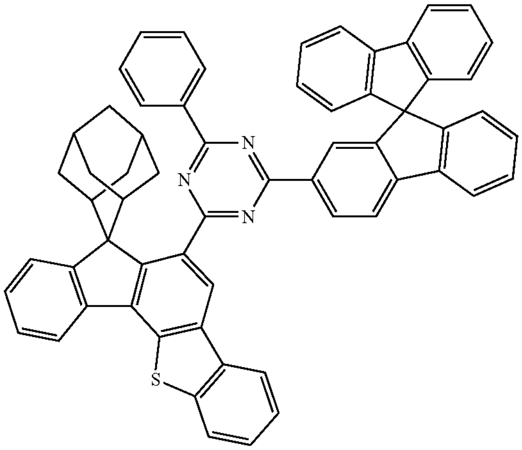
112
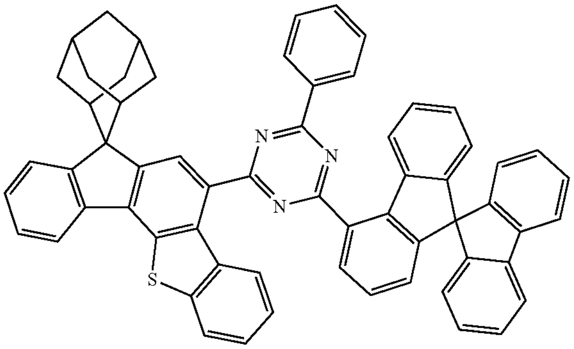
113
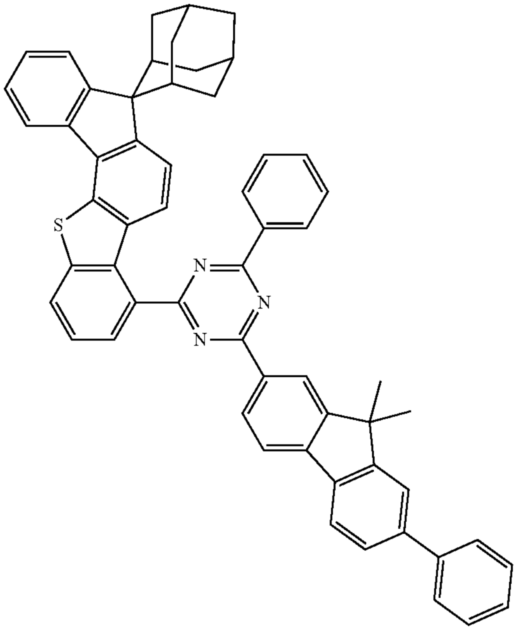
-continued
114
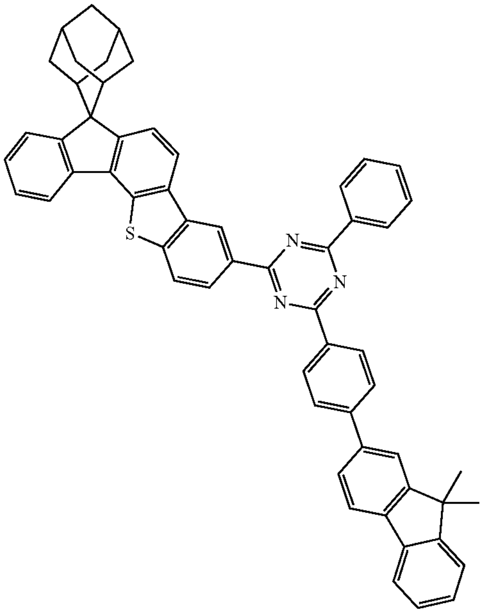
115
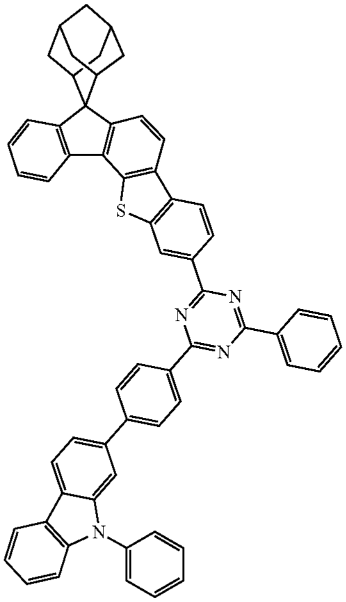

-continued
116
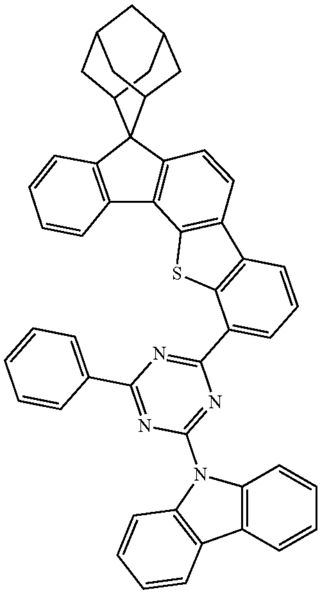
117
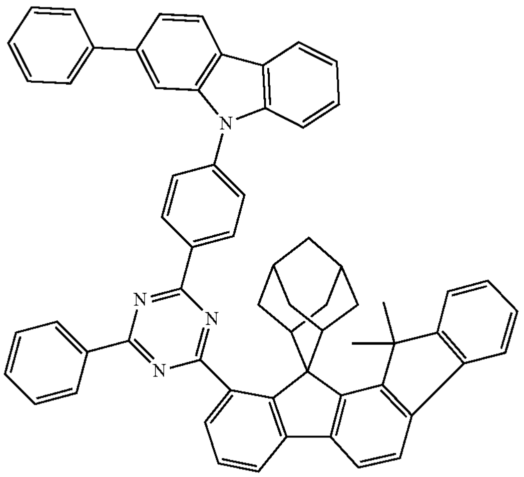
118
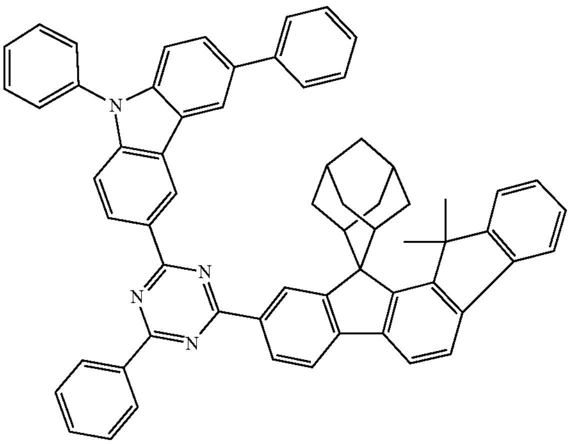
-continued
119
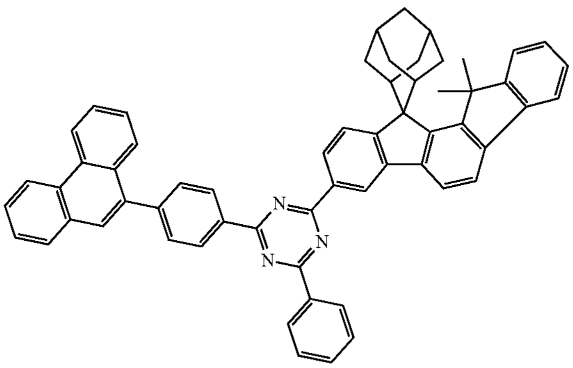
120
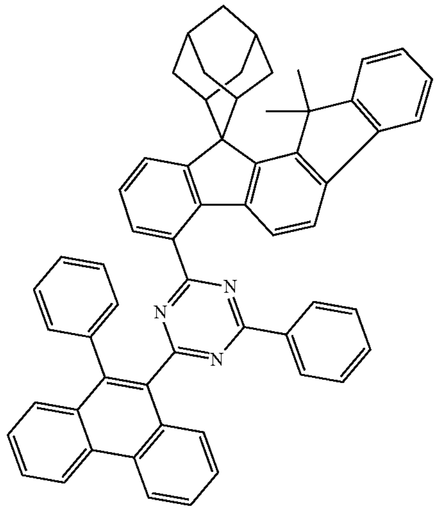
121
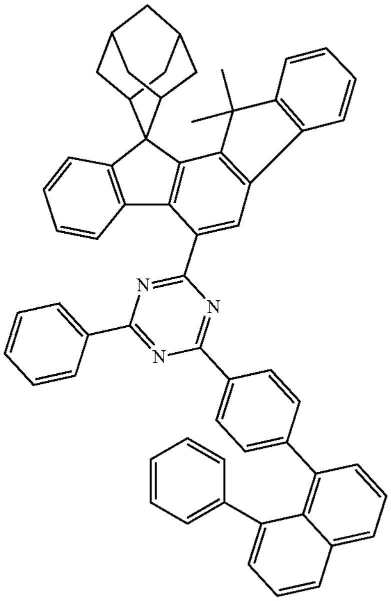

-continued
122
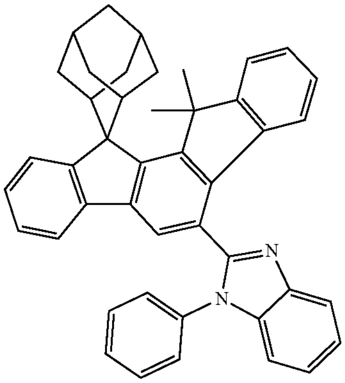
123
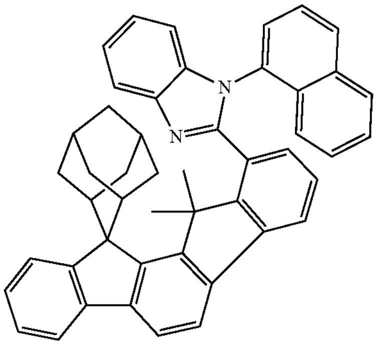
124
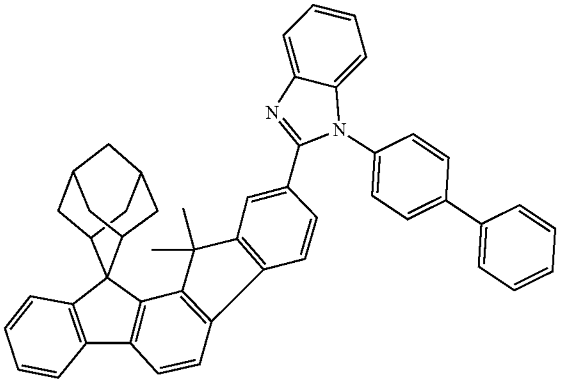
125
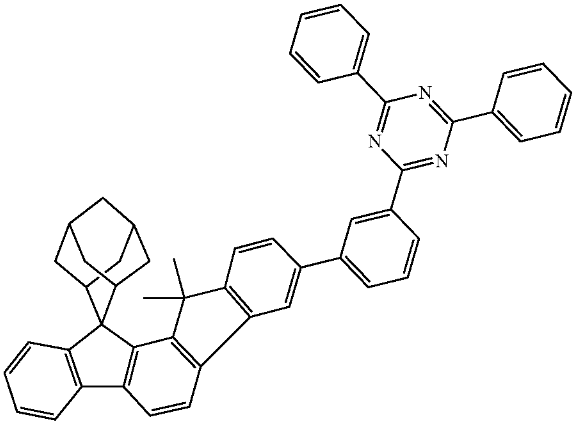
-continued
126
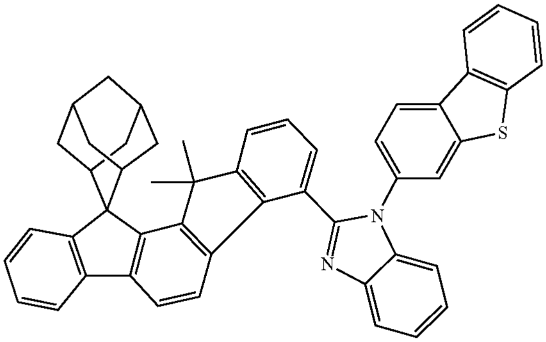
127
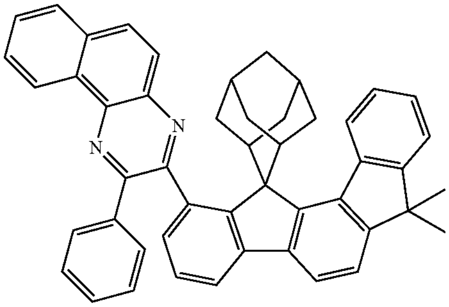
128
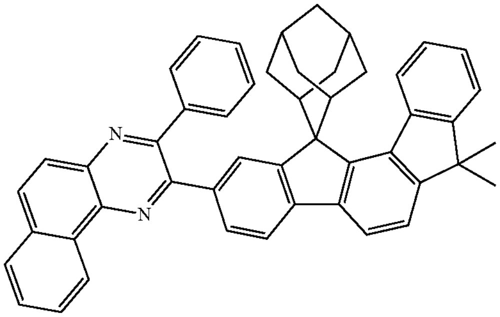
129
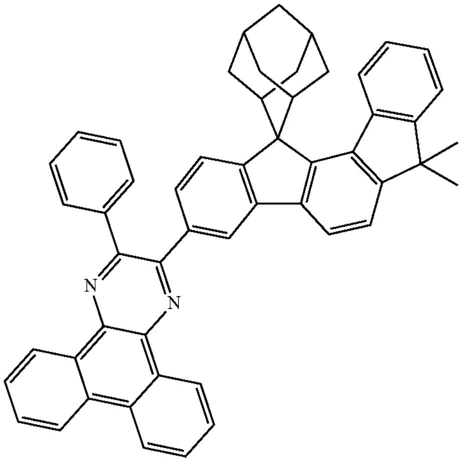

-continued
130
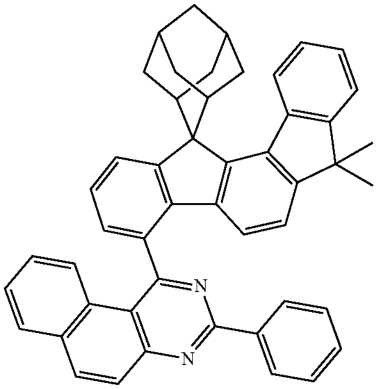
131
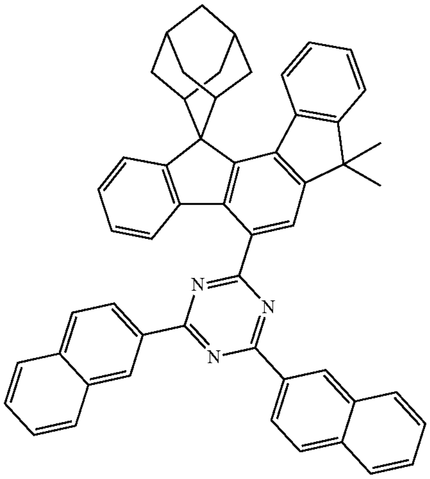
132
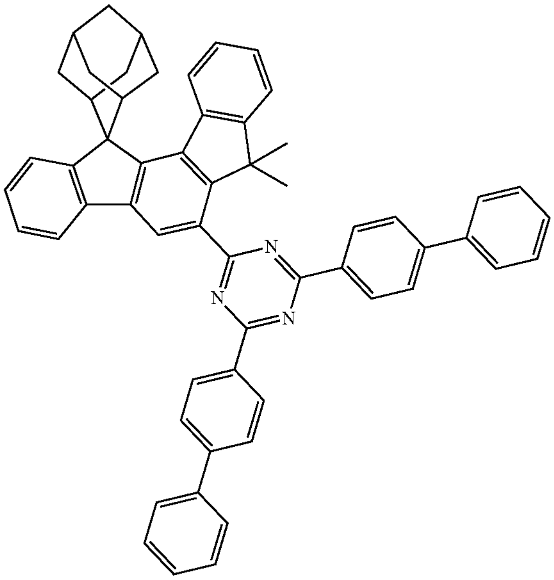
-continued
133
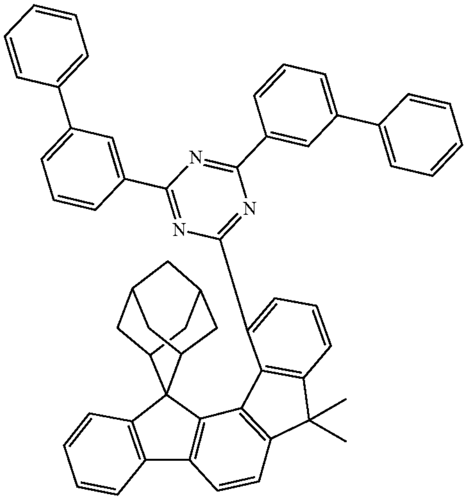
134
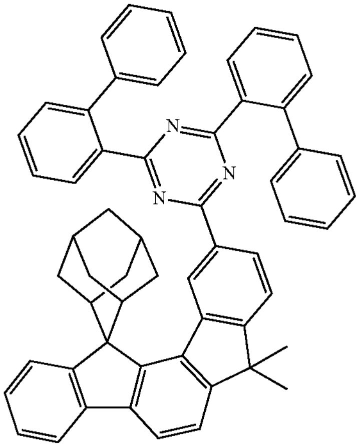
135
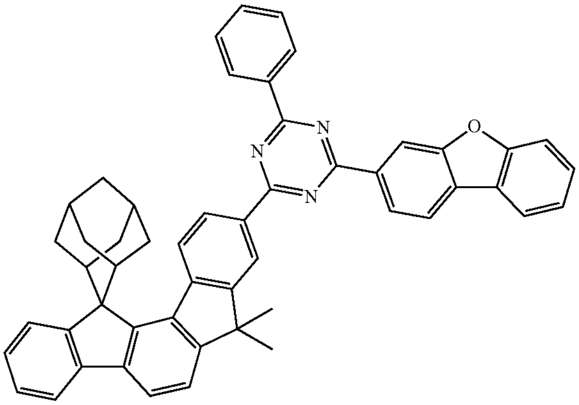

-continued
136
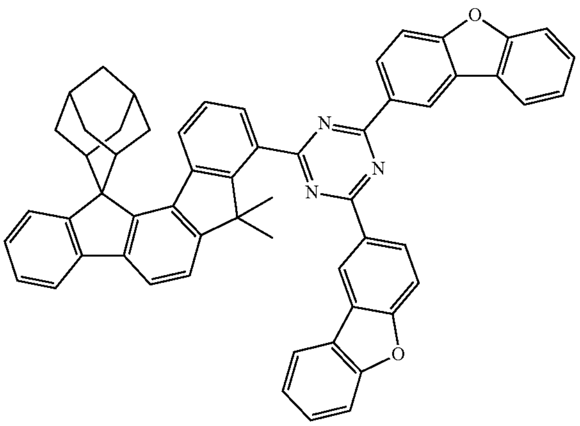
137
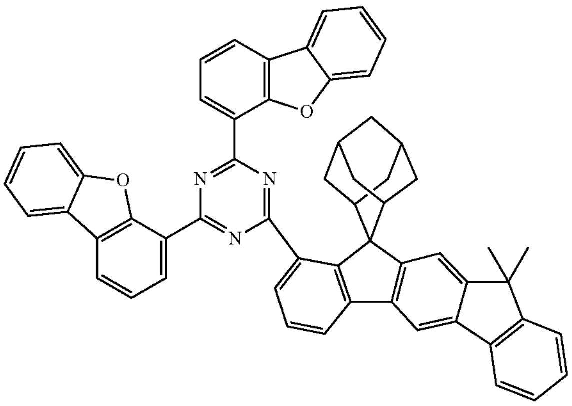
138
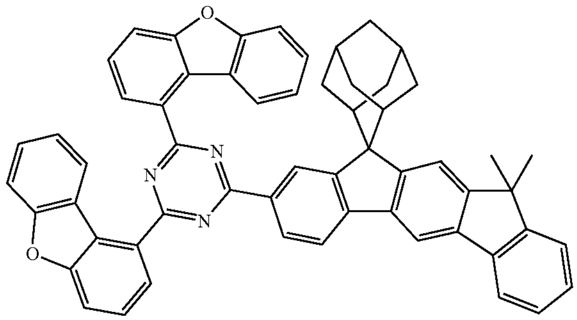
-continued
139
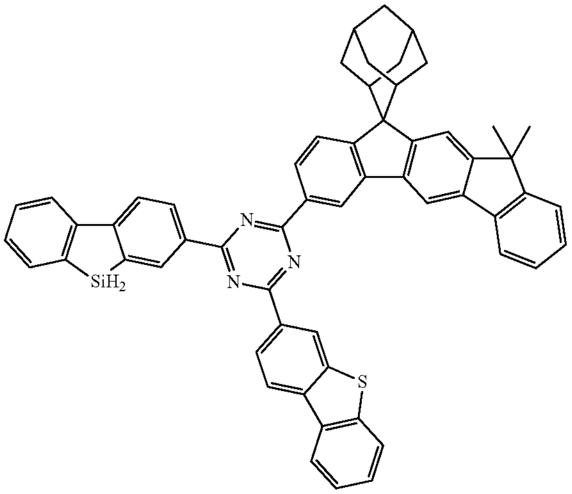
140
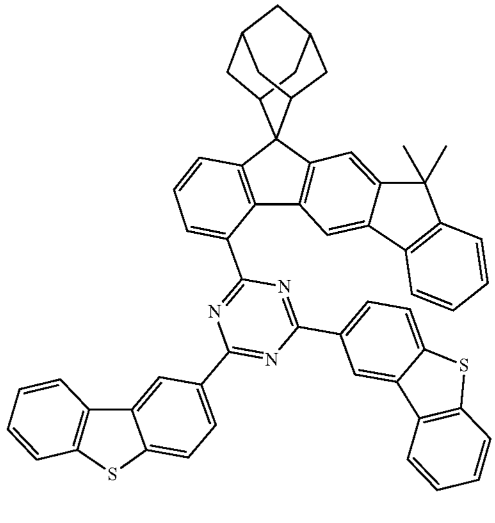
141
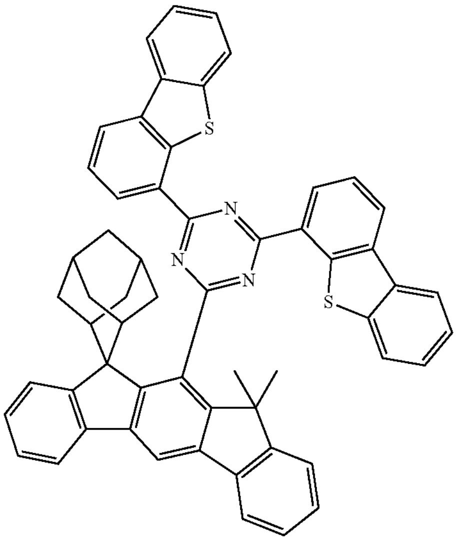

142
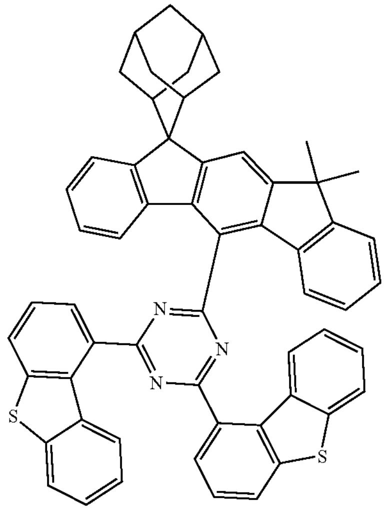
143
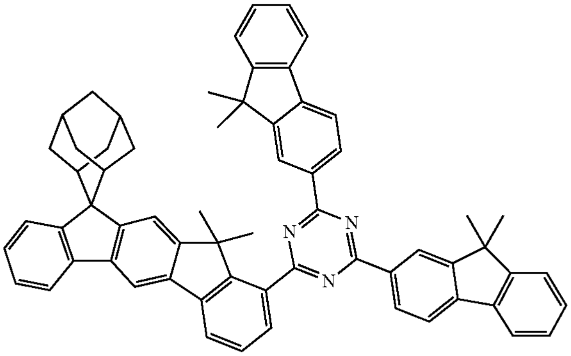
144
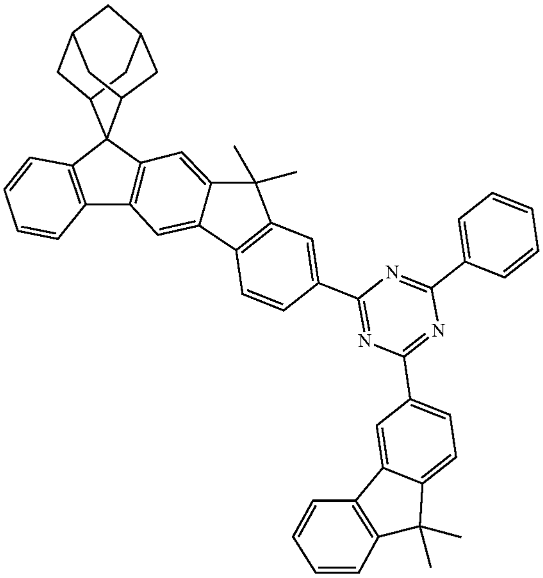
145
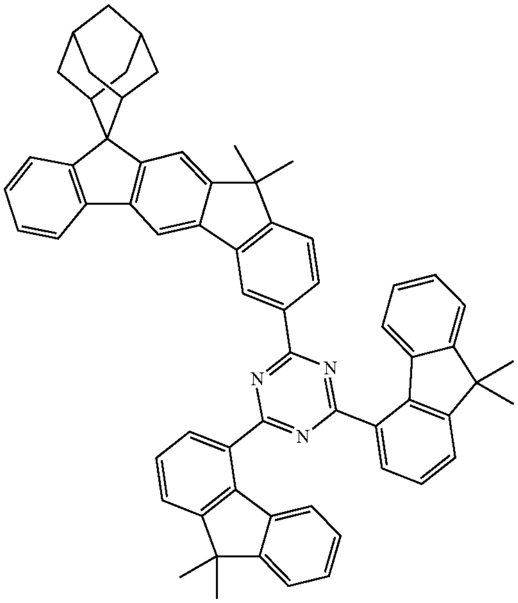
146
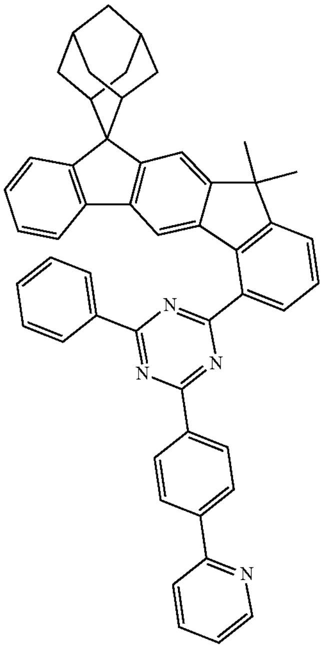

147
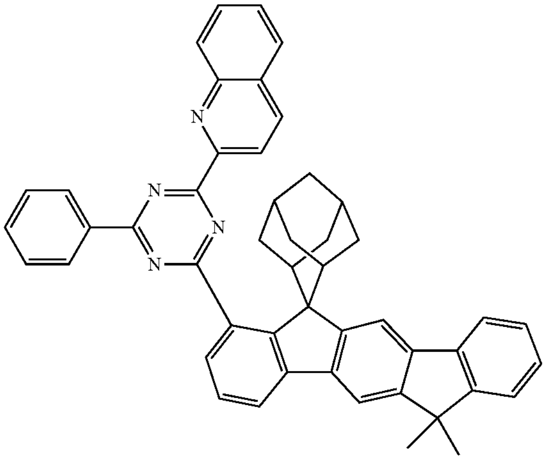
148
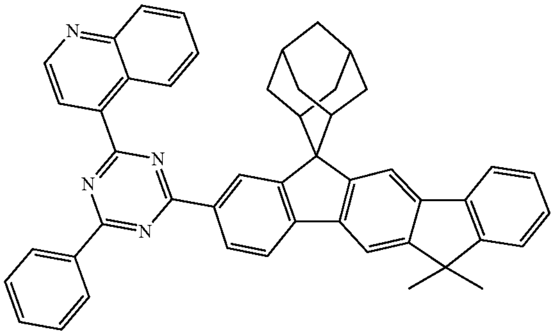
149
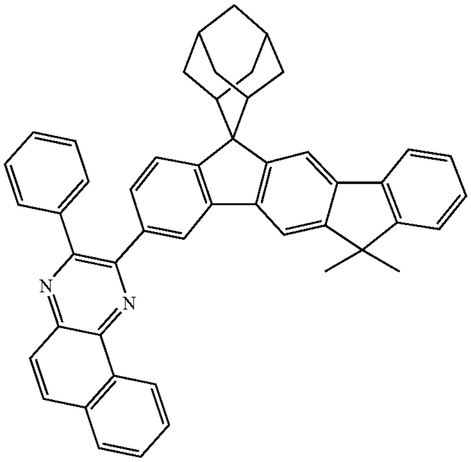
150
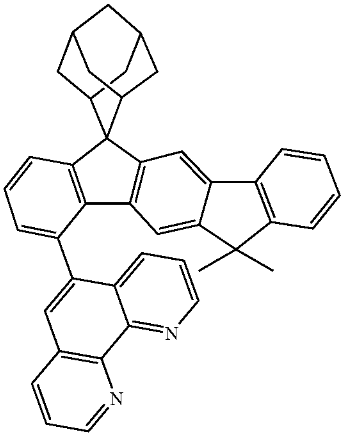
151
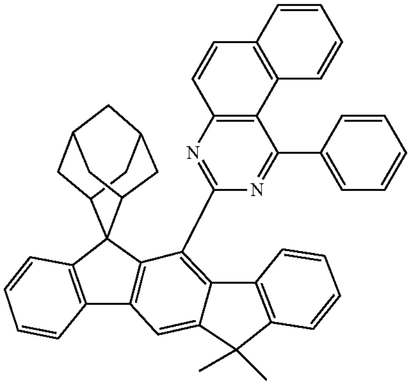
152
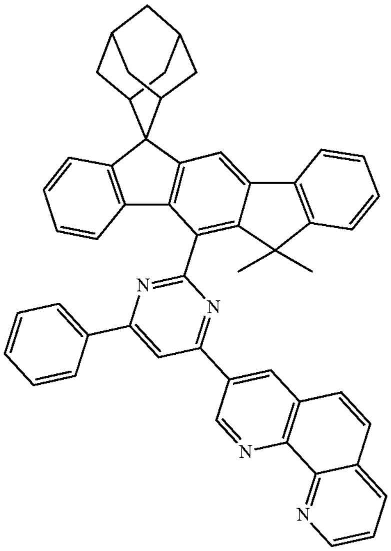

-continued
153
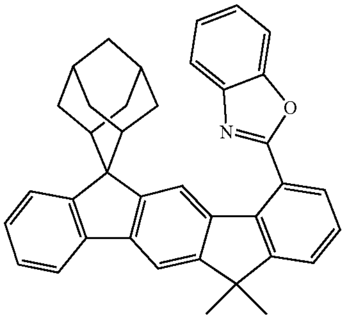
154
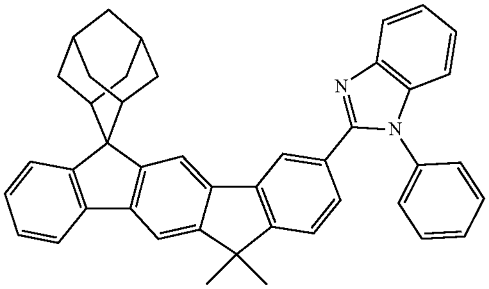
155
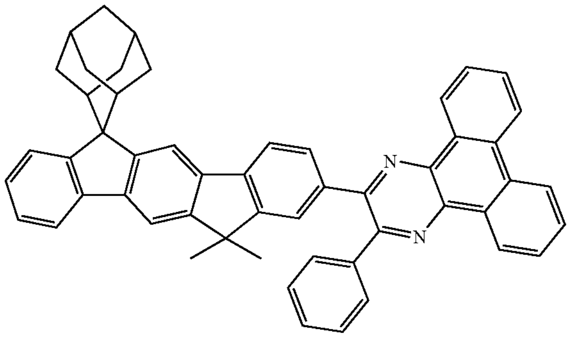
156
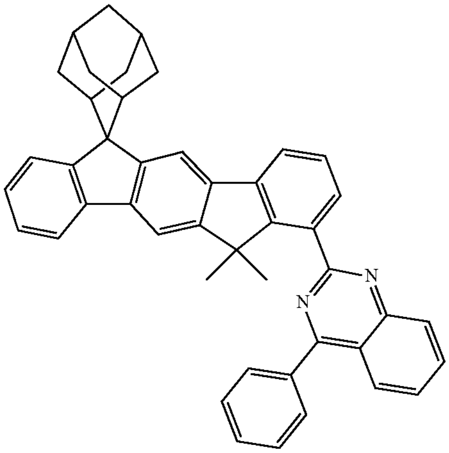
-continued
157
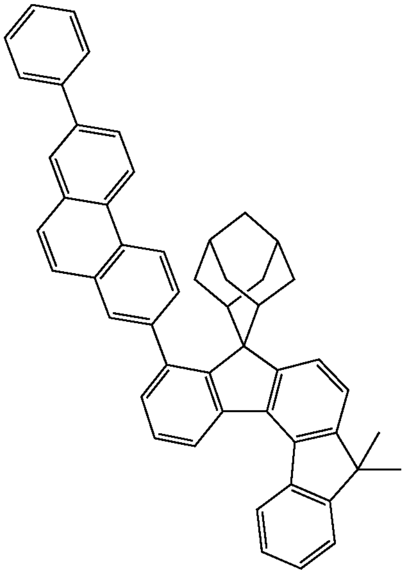
158
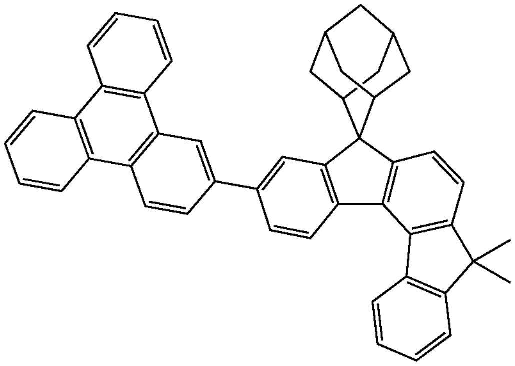
159
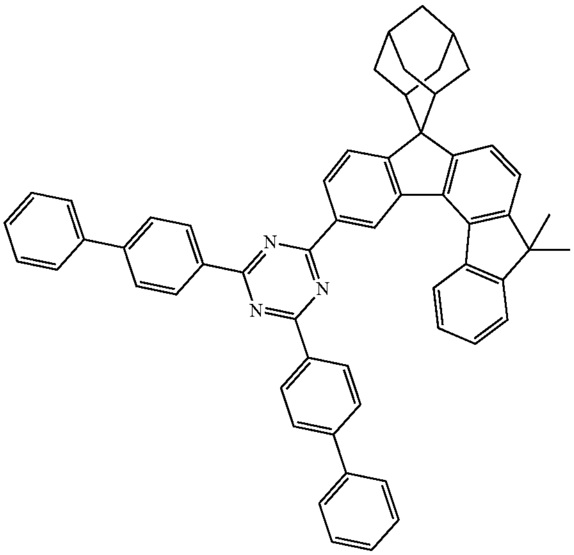

-continued
160
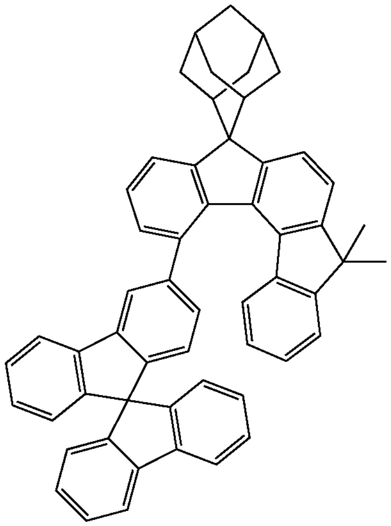
161
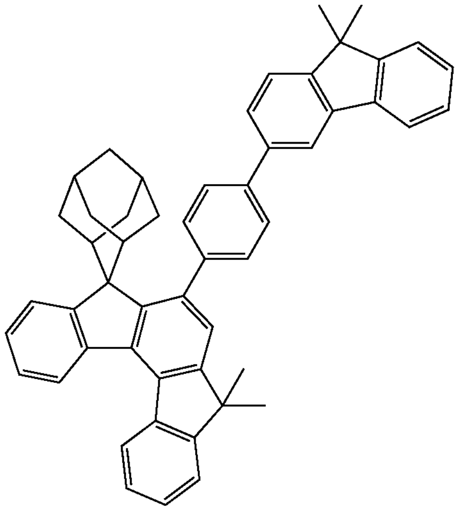
162
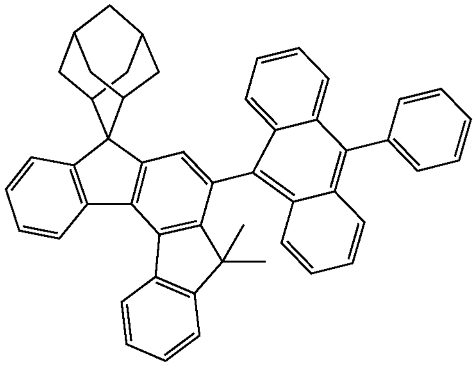
-continued
163
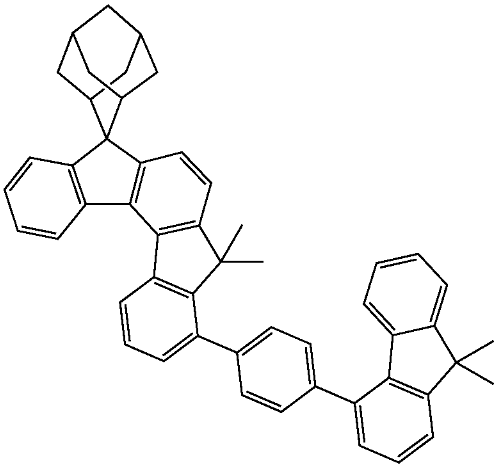
164
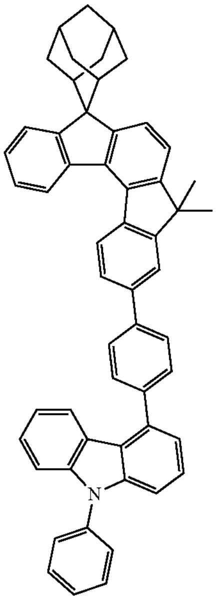

-continued
165
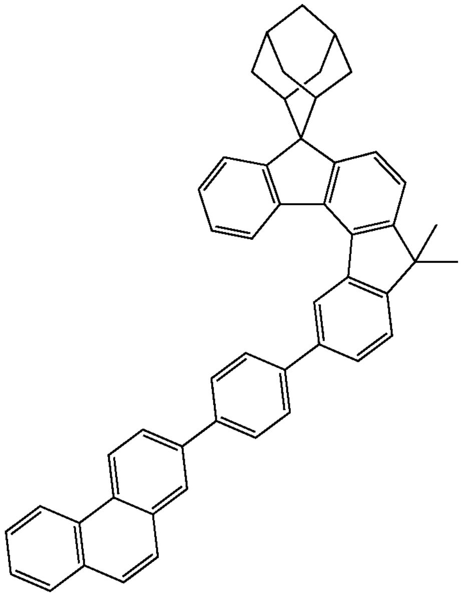
166
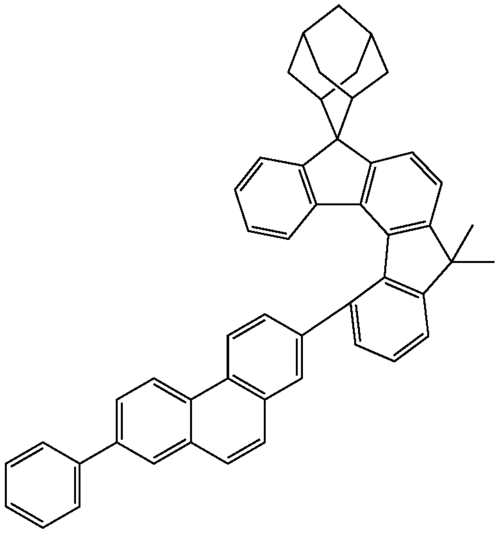
167
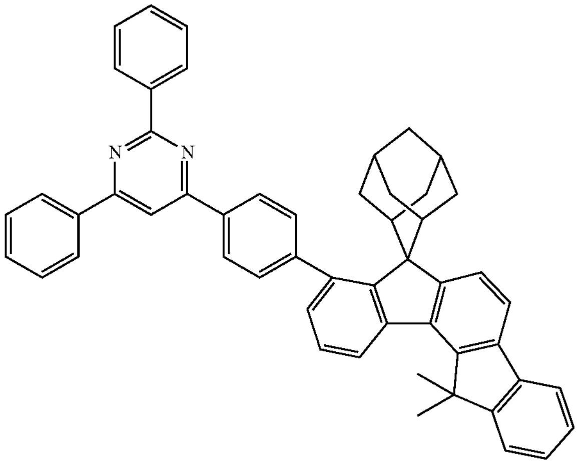
-continued
168
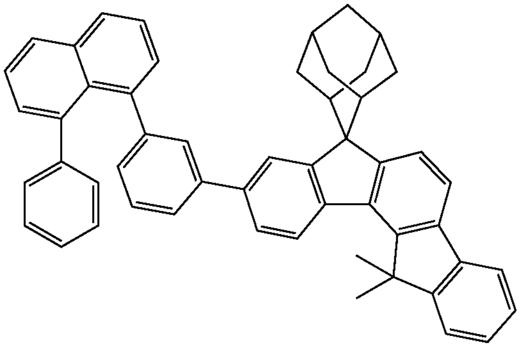
169
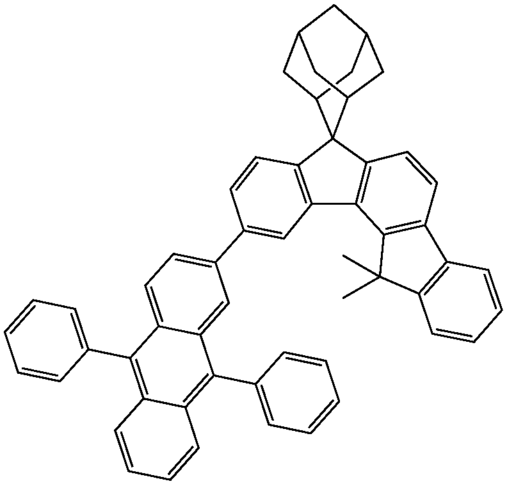
170
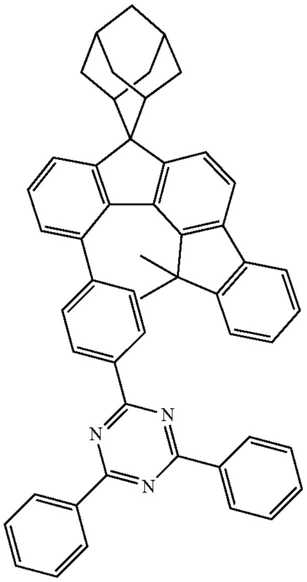

-continued
171
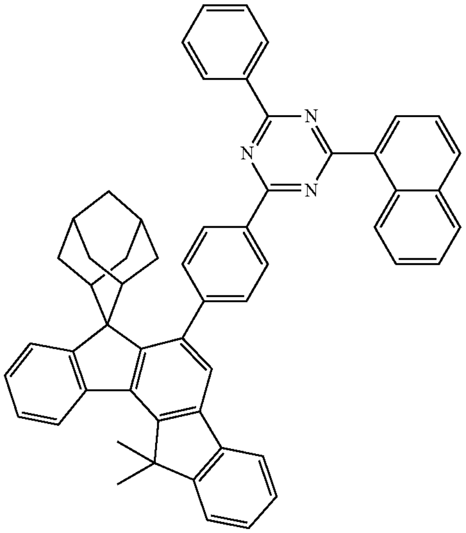
172
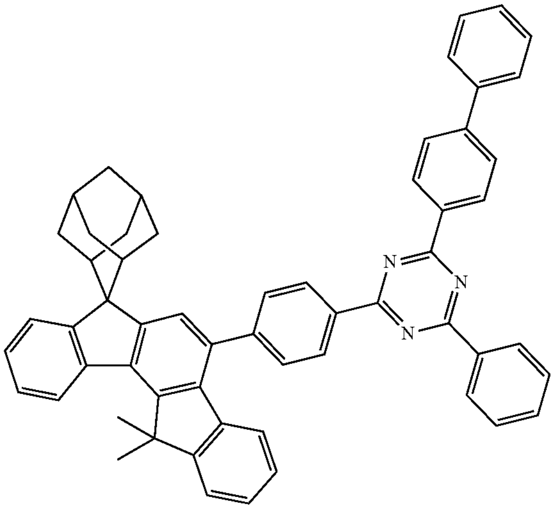
173
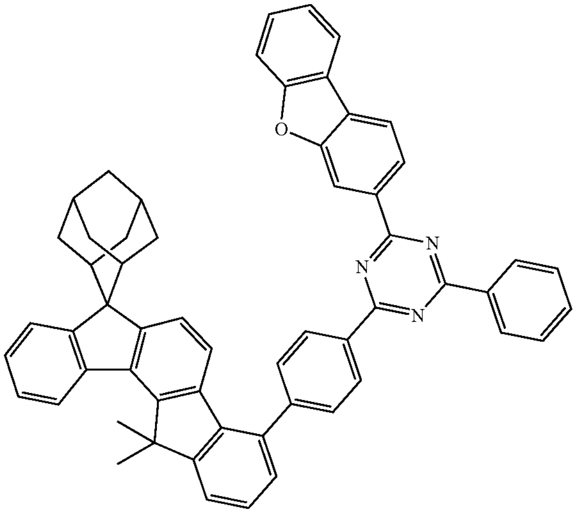
-continued
174
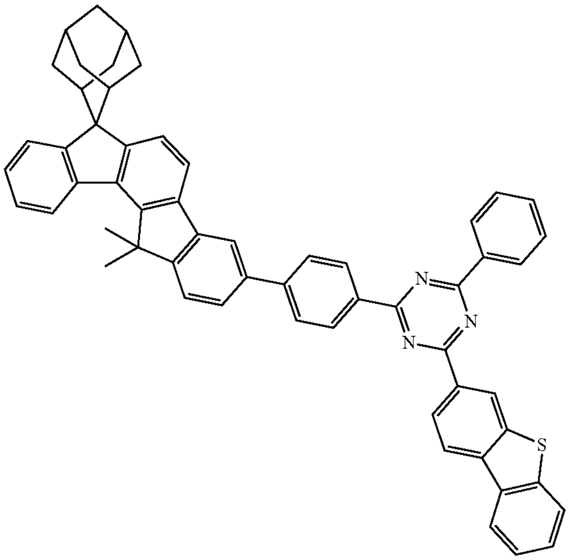
175
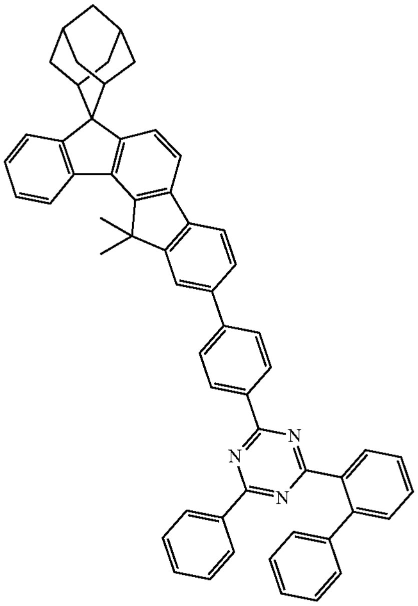

-continued
176
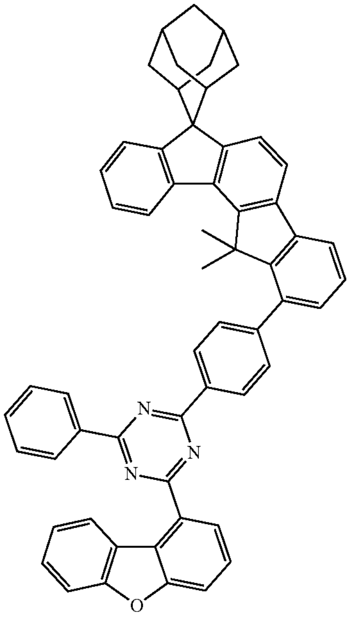
177
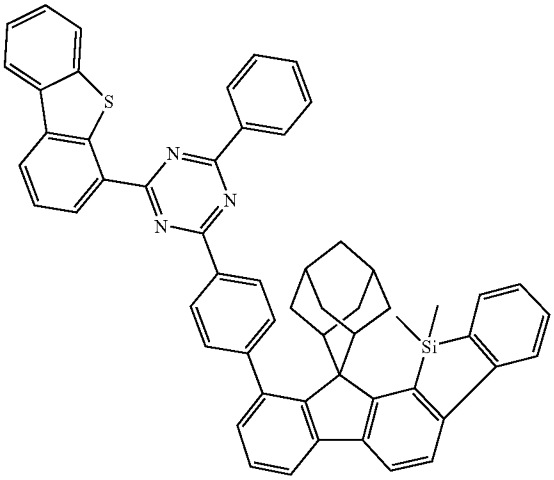
178
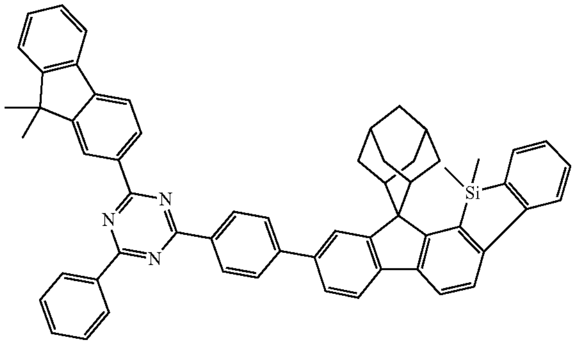
-continued
179
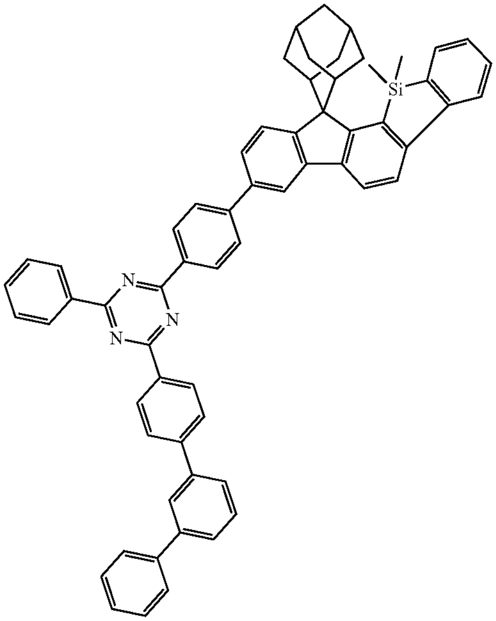
180
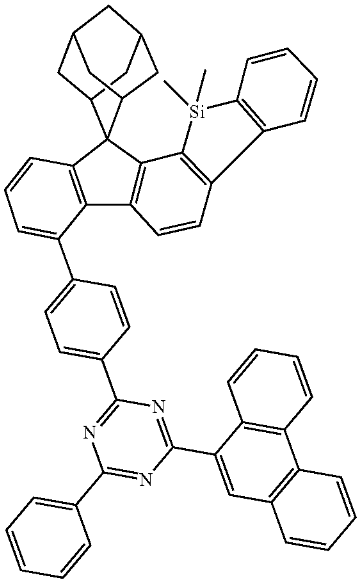

-continued
181
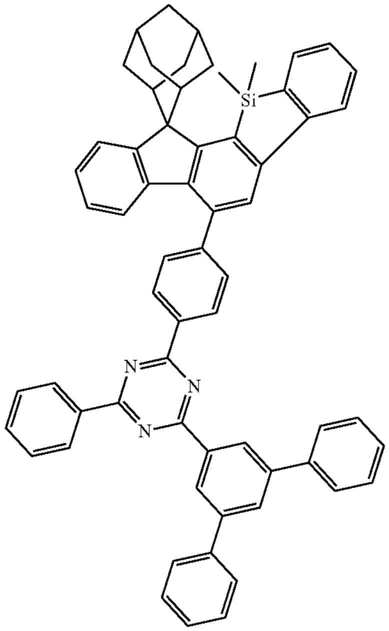
182
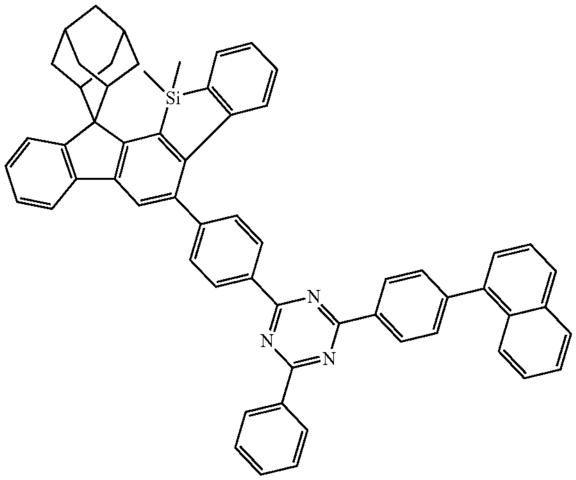
-continued
183
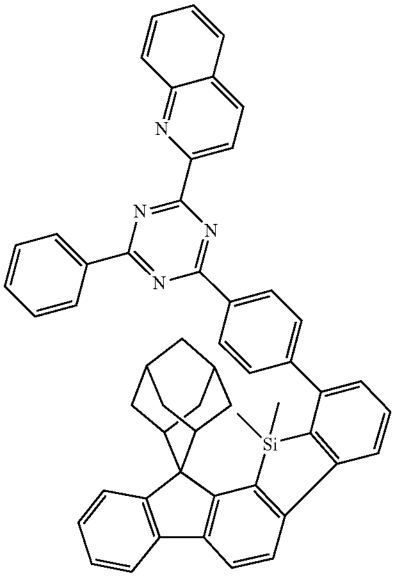
184
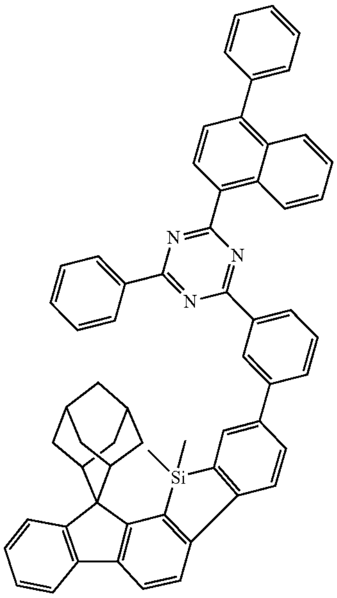
185
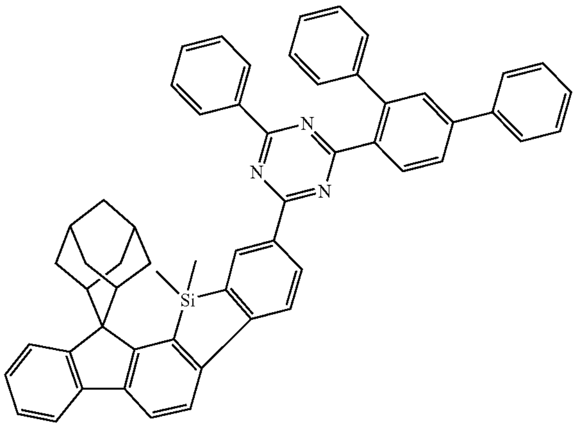

-continued
186
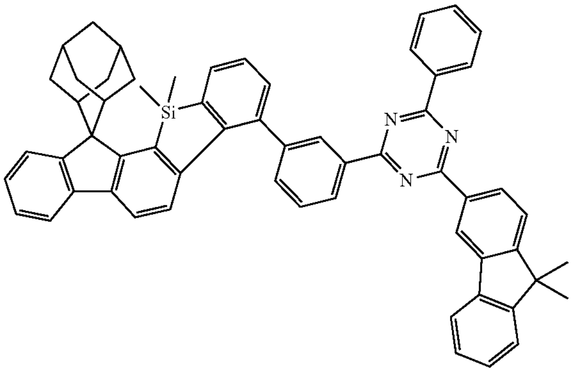
187
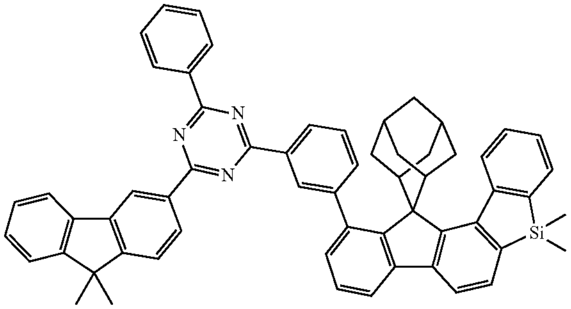
188
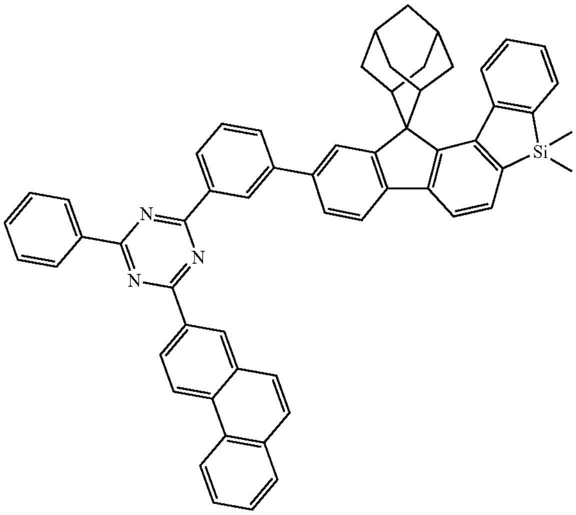
-continued
189
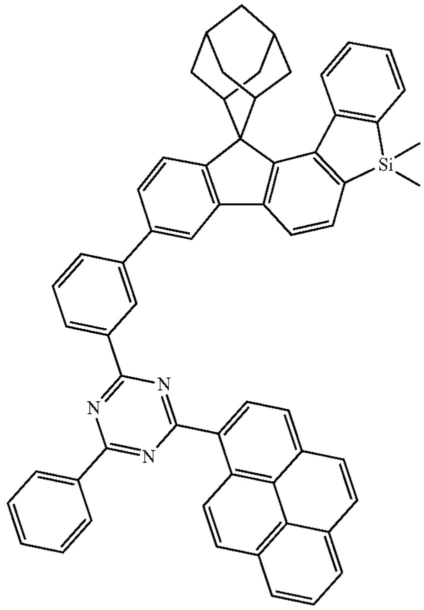
190
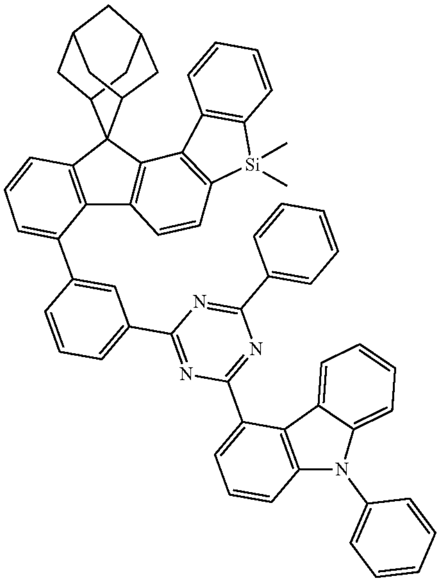

191
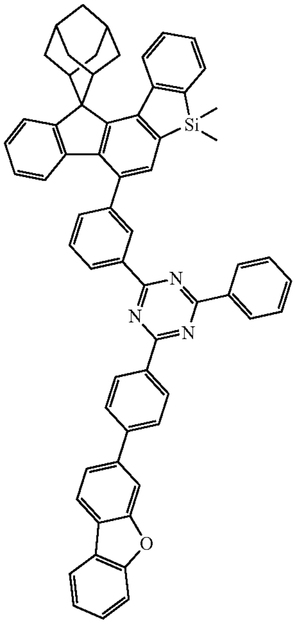
192
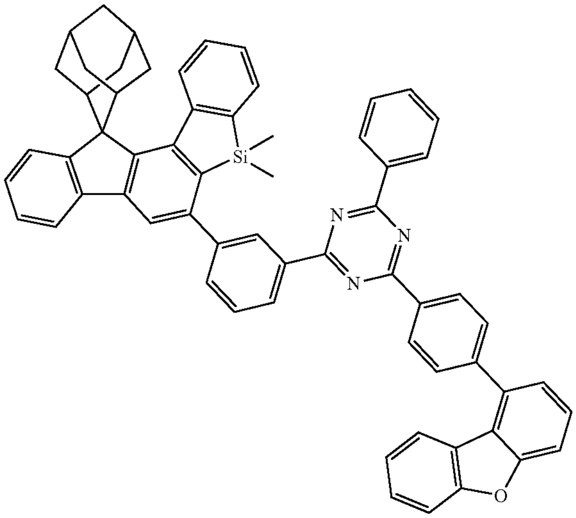
193
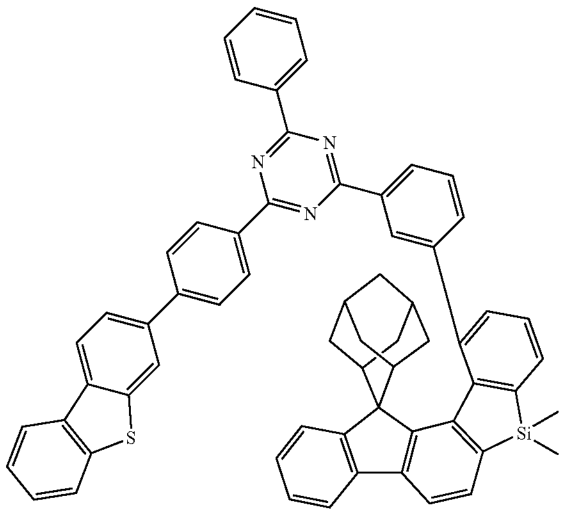
194
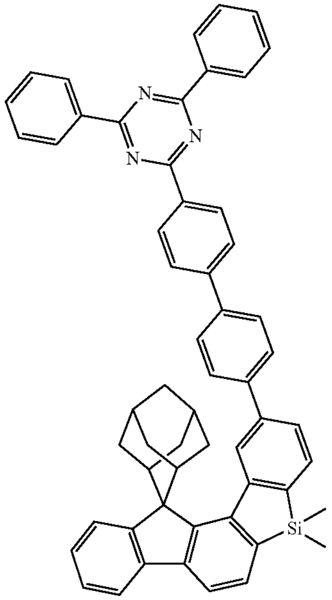
195
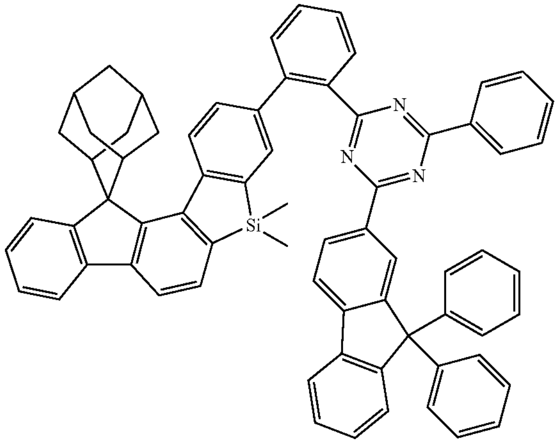

196
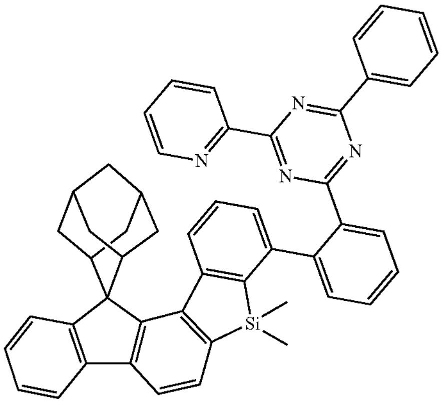
197
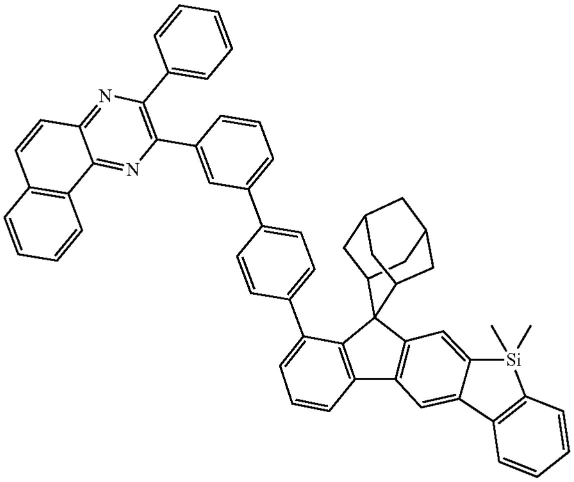
198
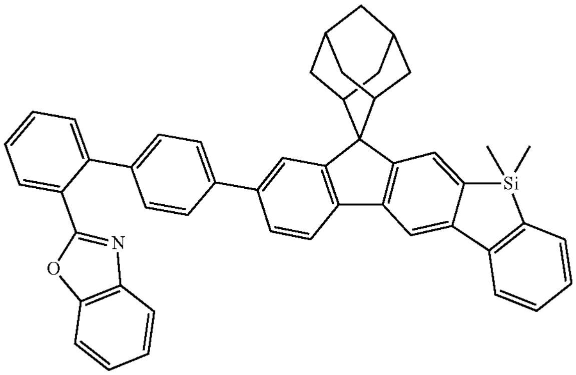
199
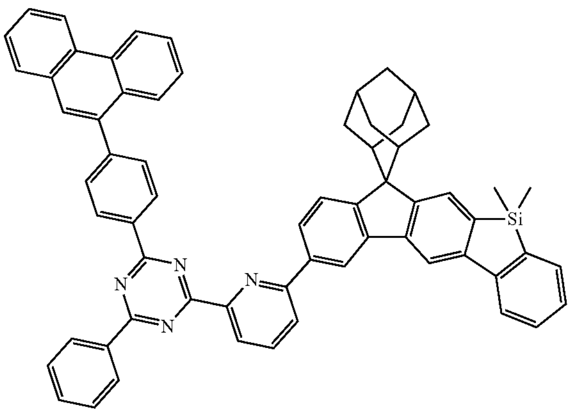
200
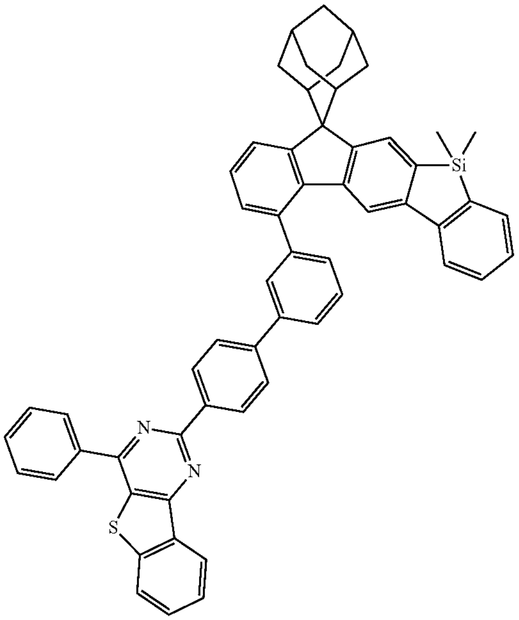
201
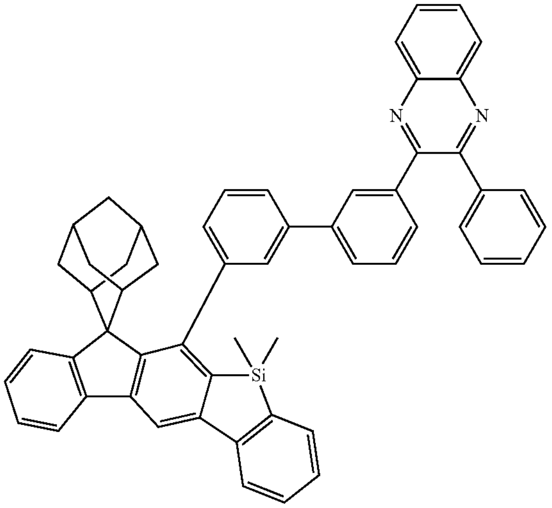

-continued
202
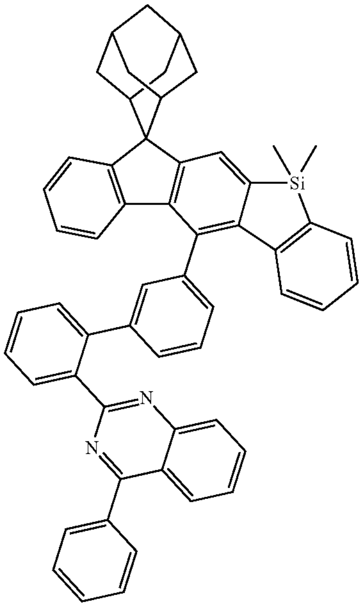
203
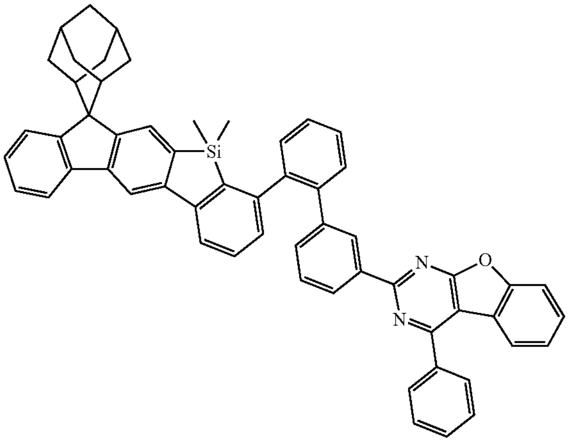
204
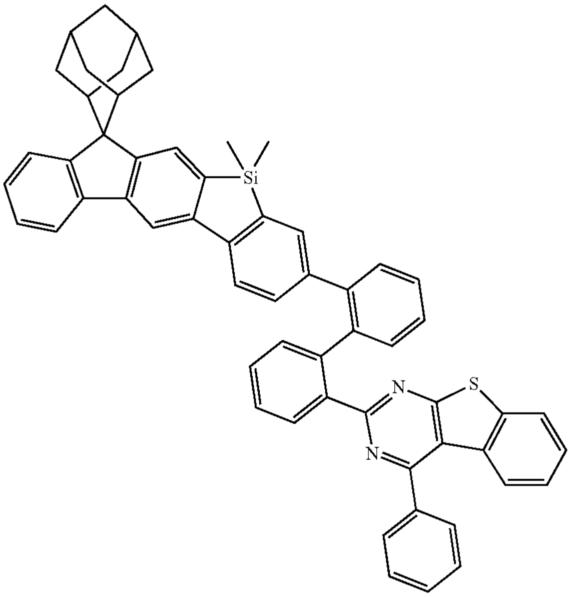
-continued
205
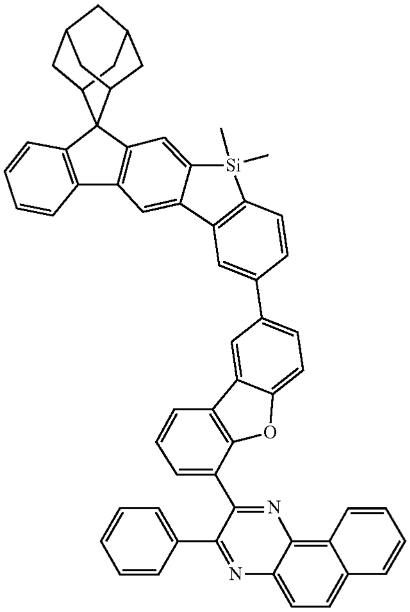
206
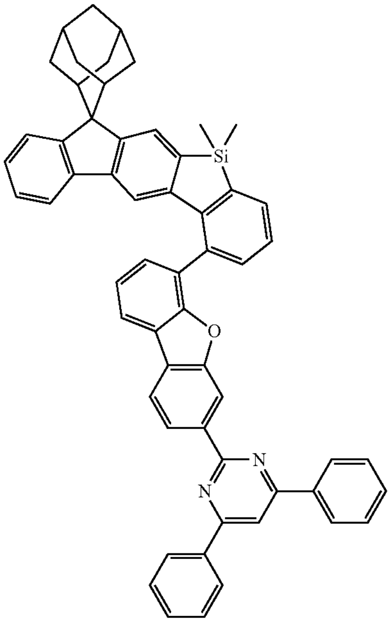

-continued
207
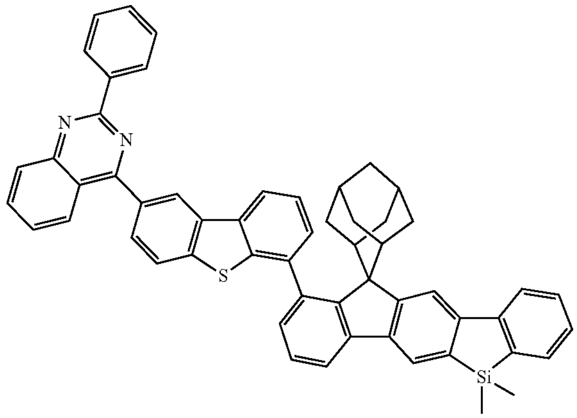
208
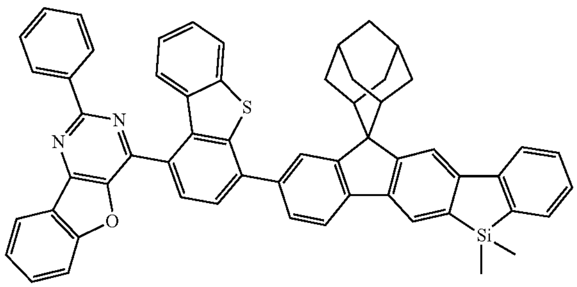
209
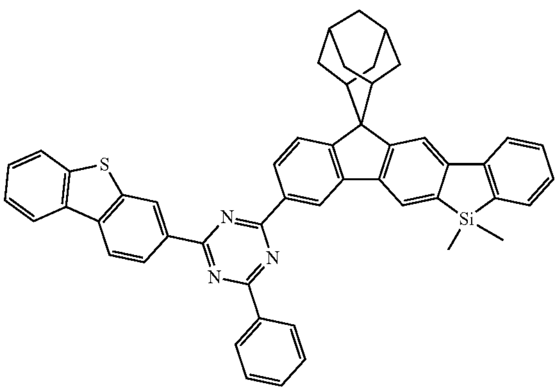
210
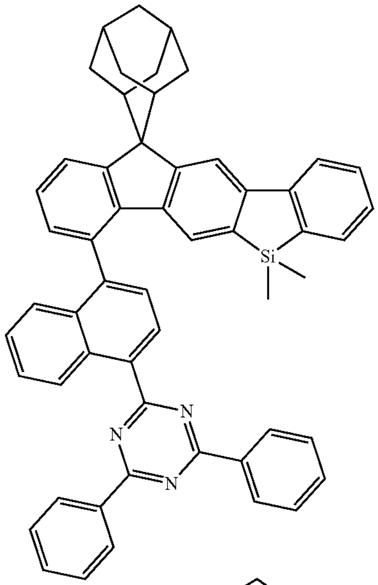
211
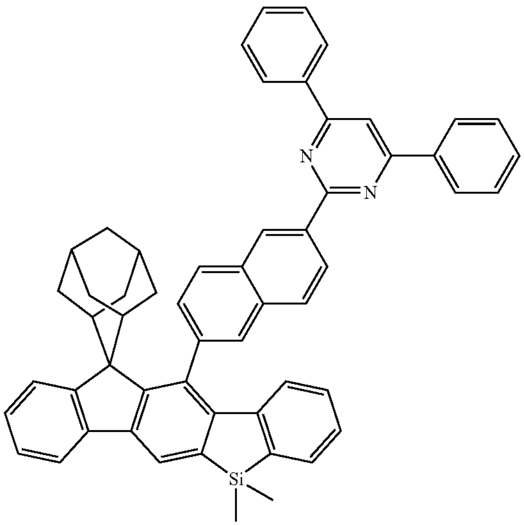
212
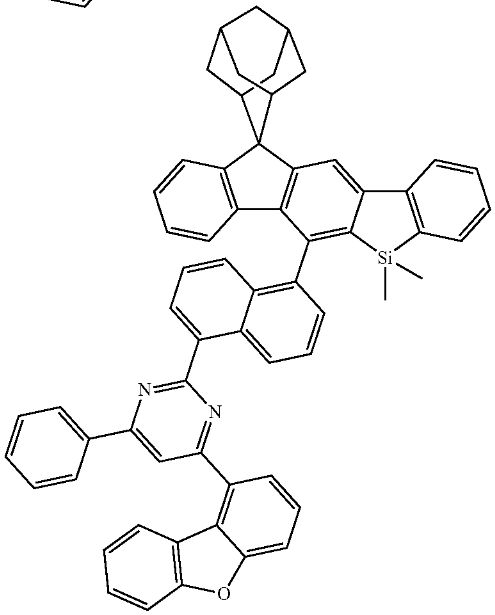

-continued
213
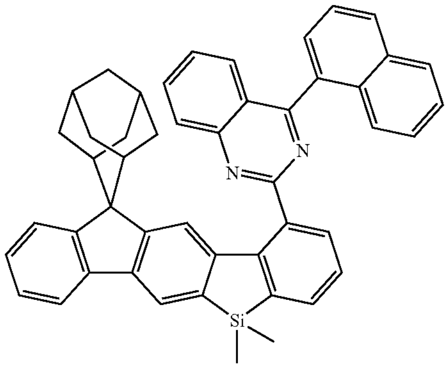
214
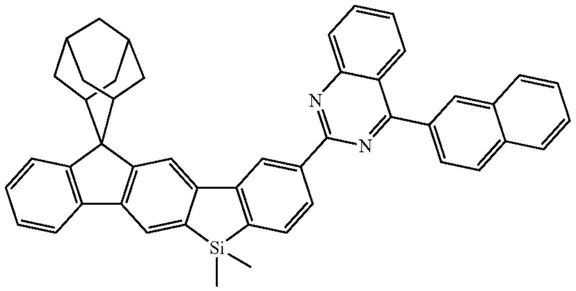
215
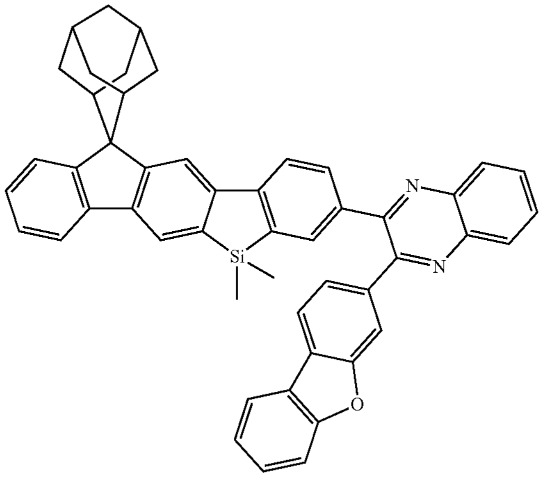
216
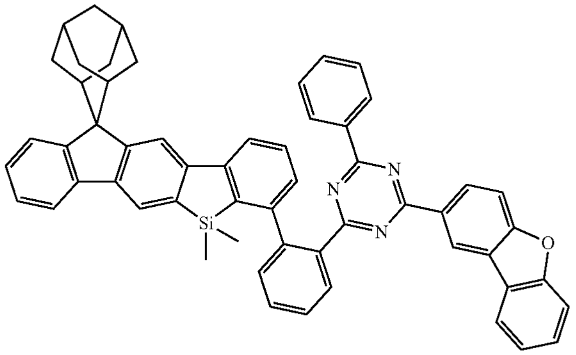
217
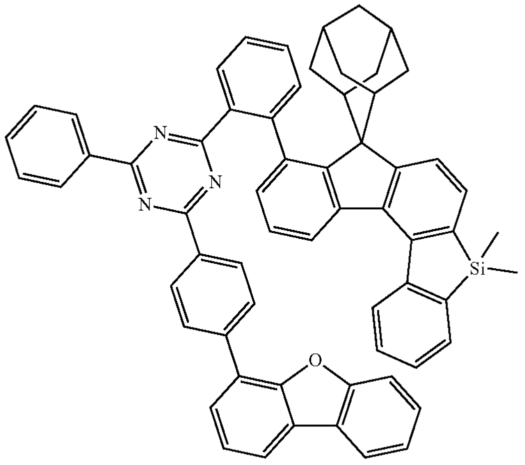
218
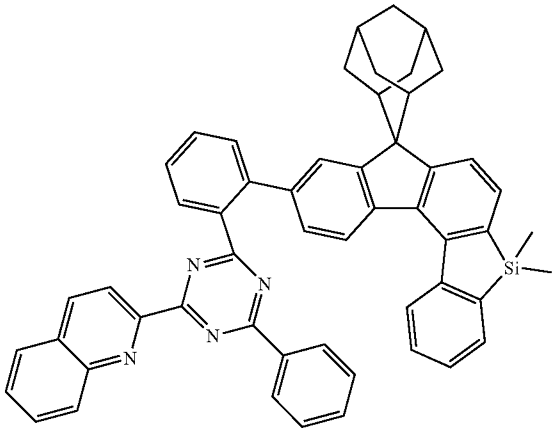

-continued
219
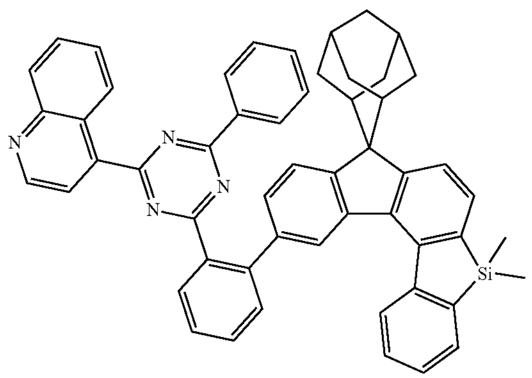
220
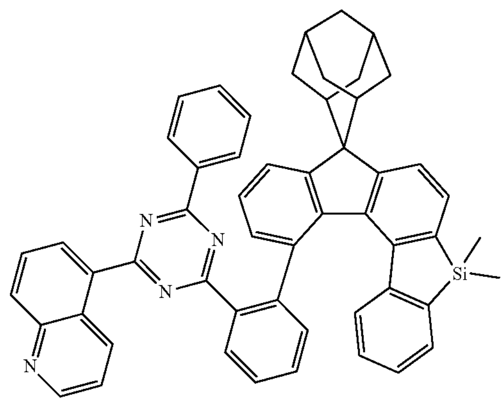
221
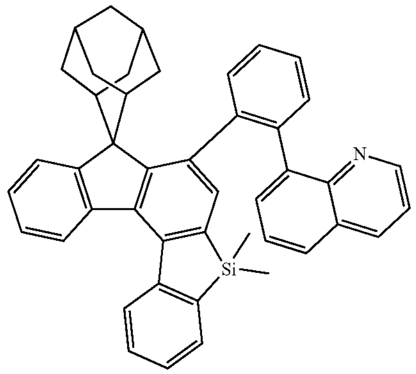
222
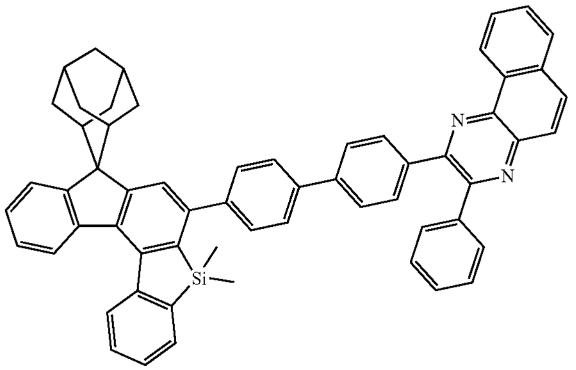
223
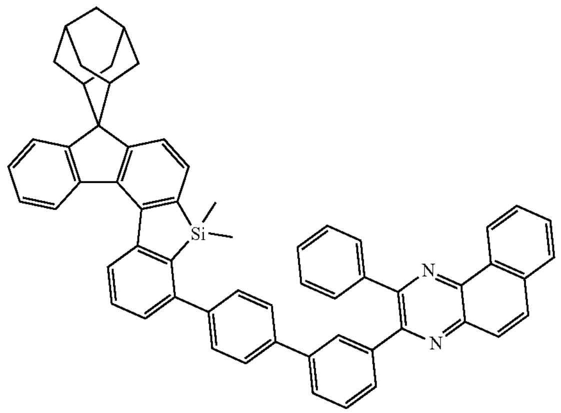
224
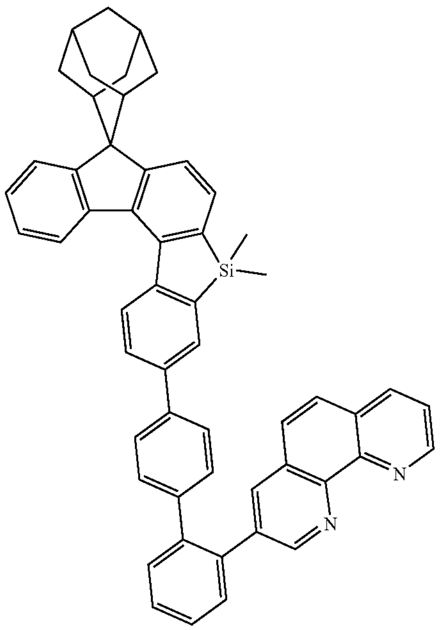

-continued
225
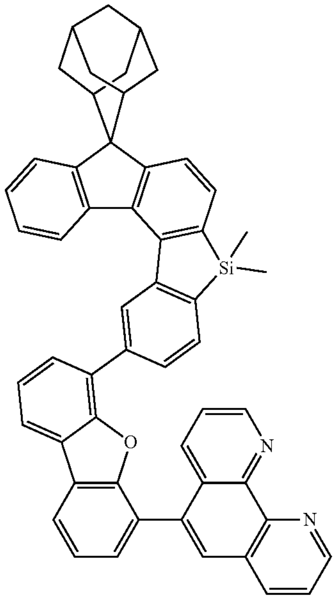
226
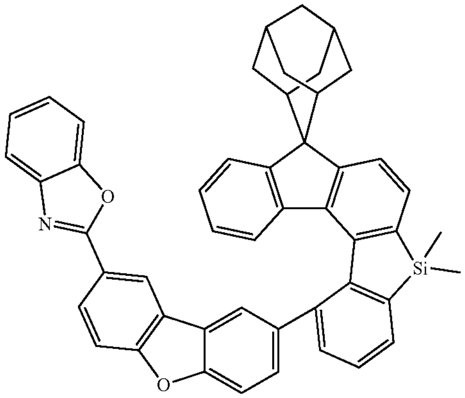
227
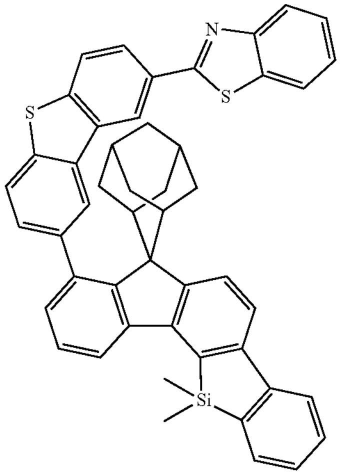
228
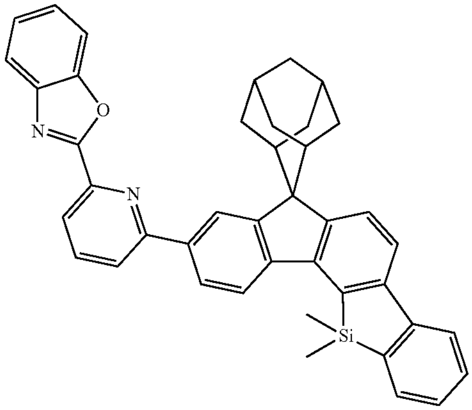

-continued
229
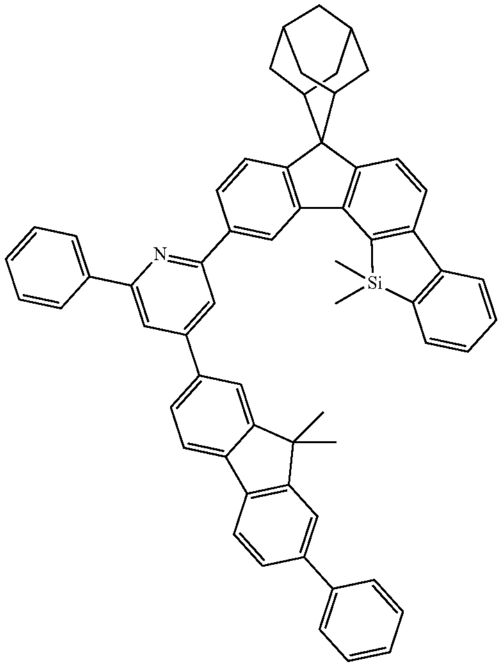
230
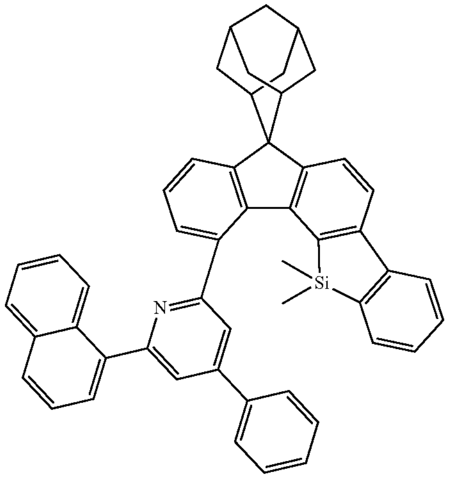
231
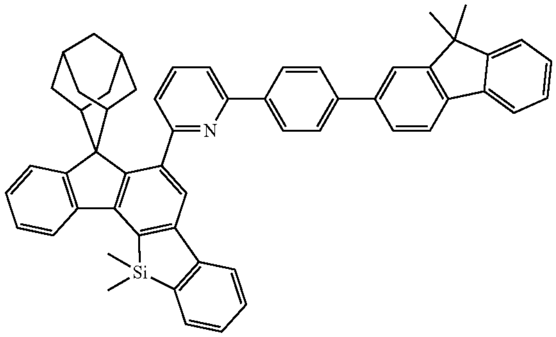
232
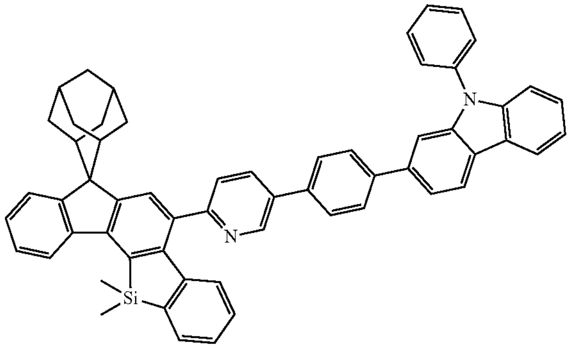

-continued
233
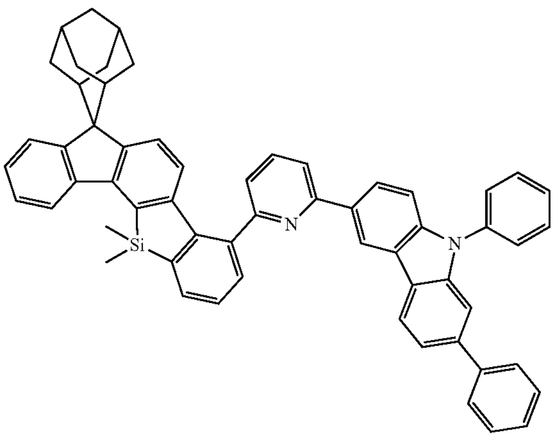
234
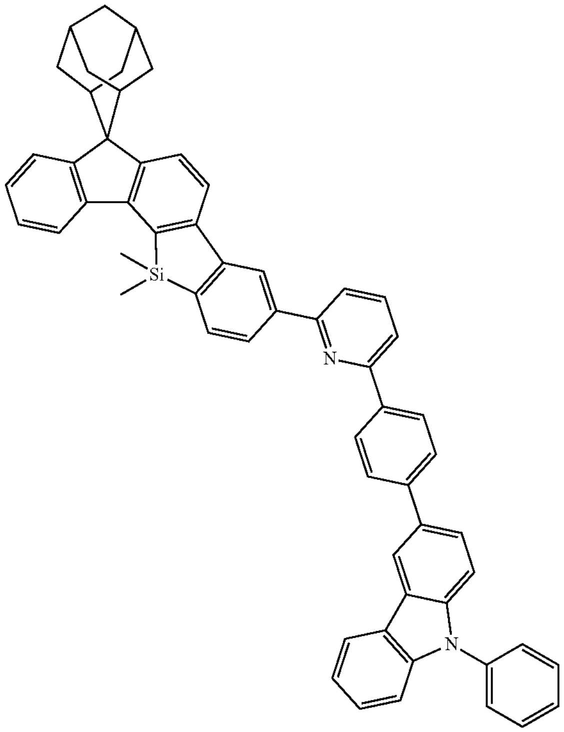
235
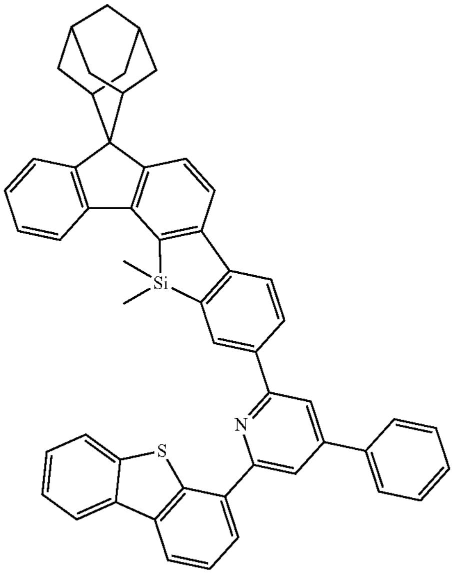
236
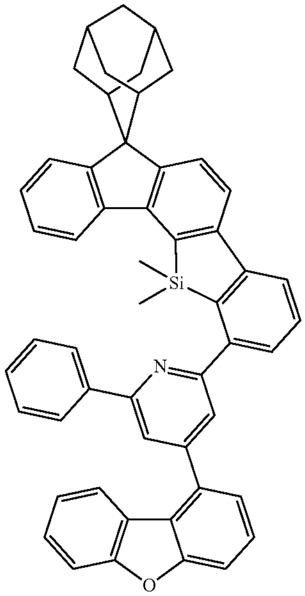

-continued
237
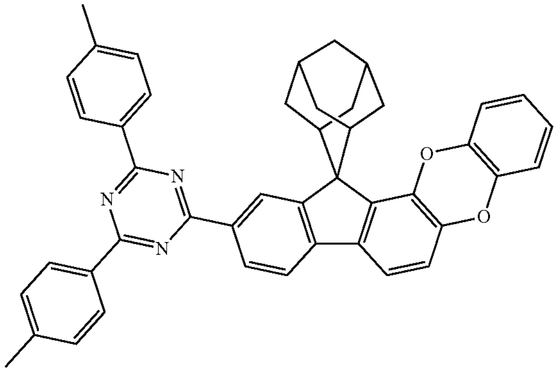
238
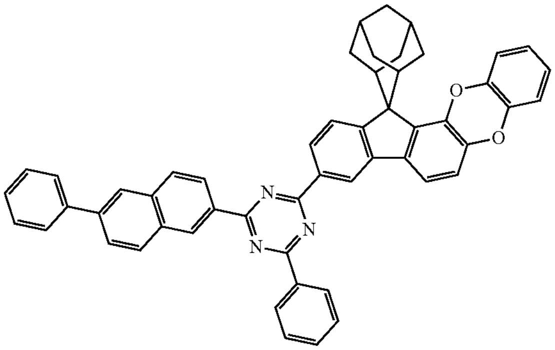
239
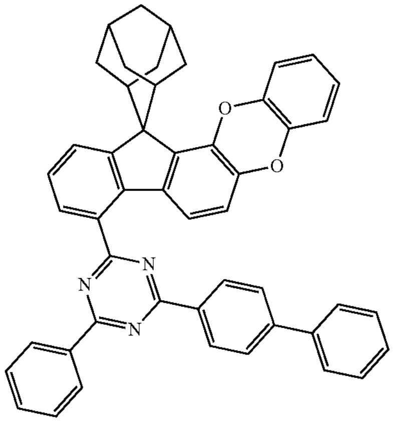
240
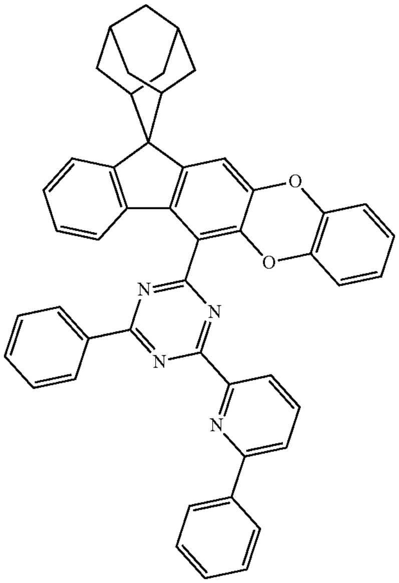
241
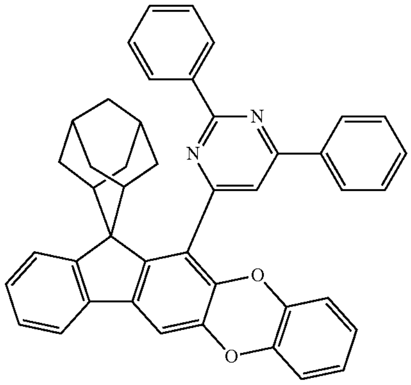
242
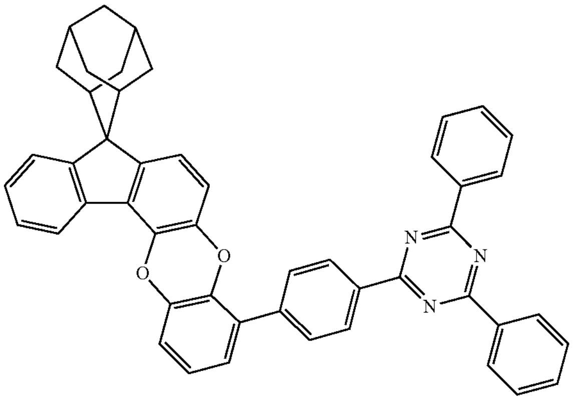

-continued
243
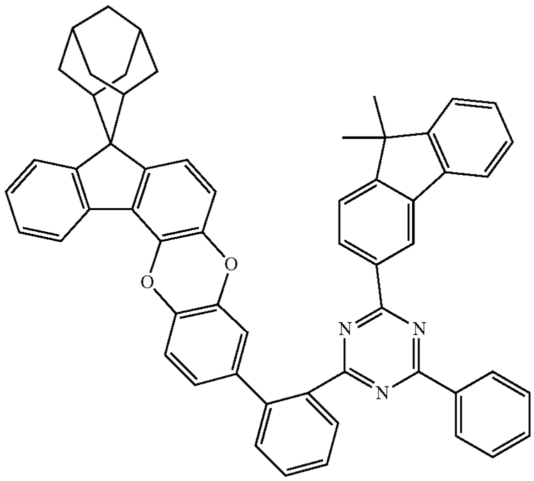
244
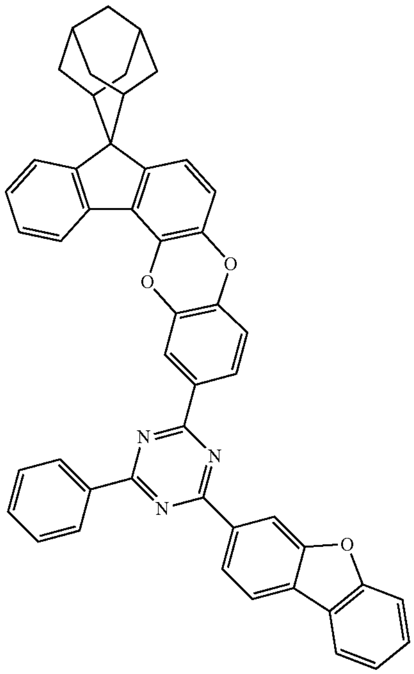
245
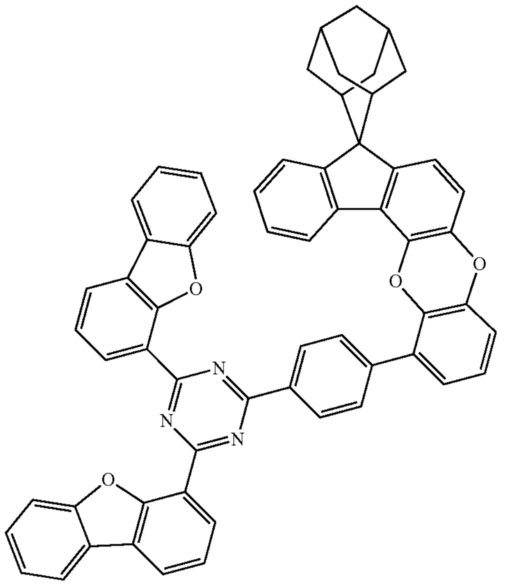
246
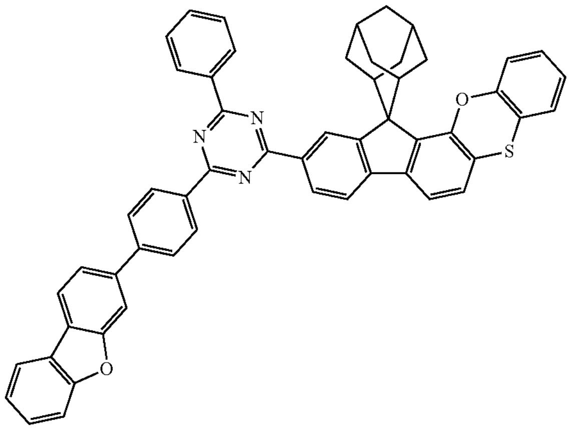

-continued
247
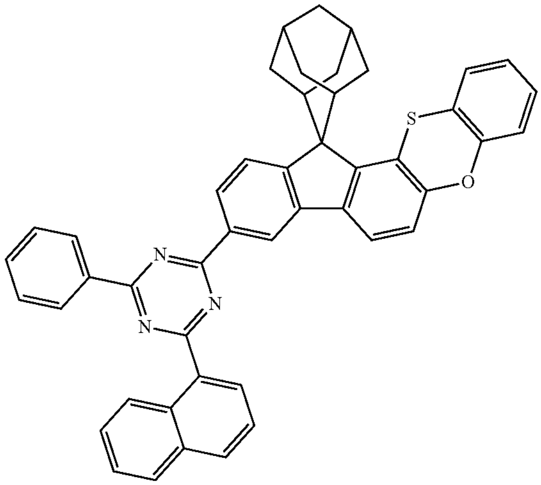
248
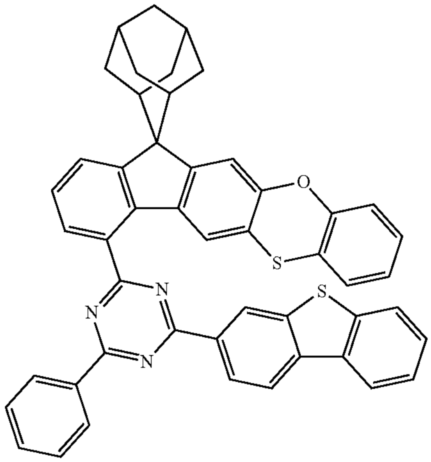
249
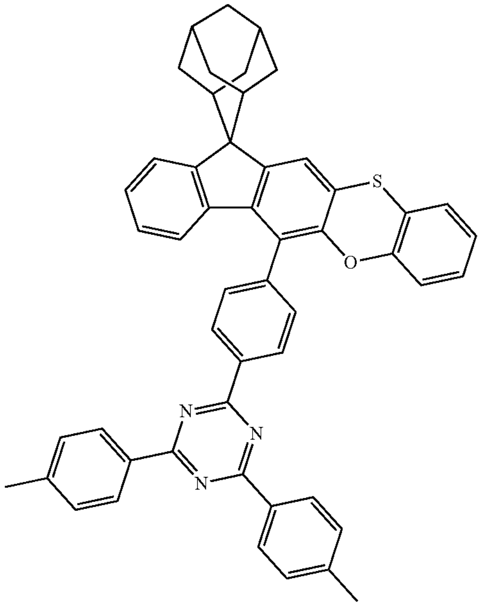
250
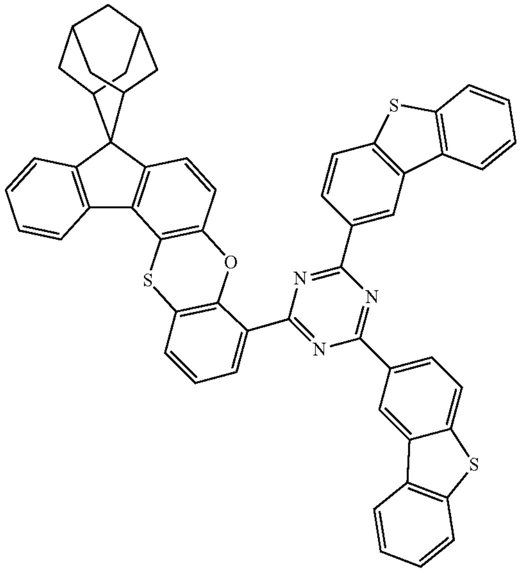

-continued
251
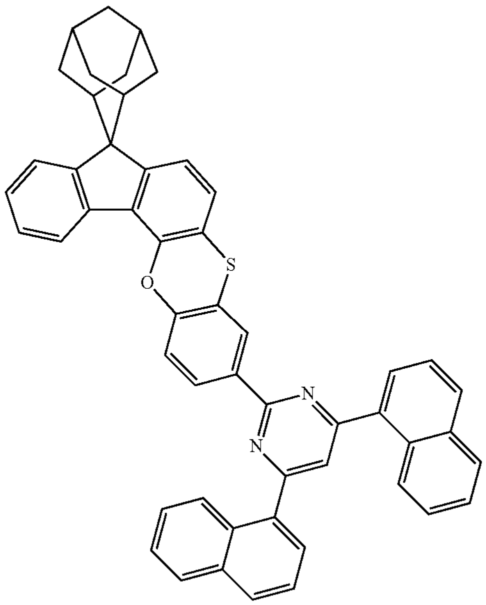
252
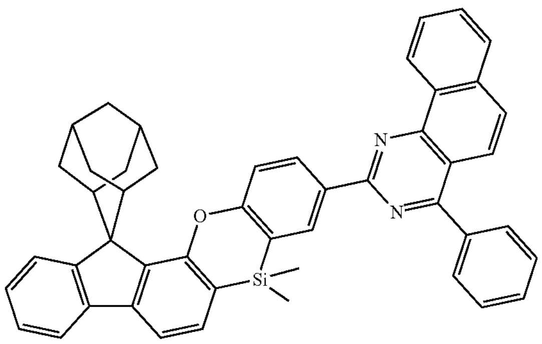
253
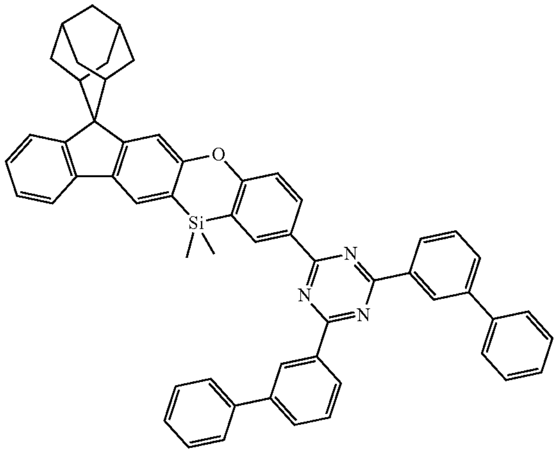
254
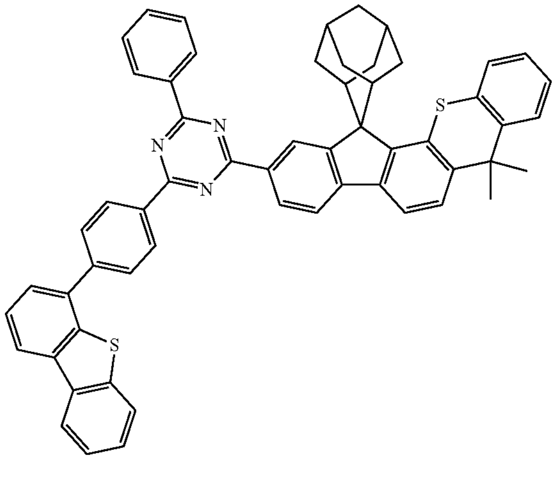

-continued
255
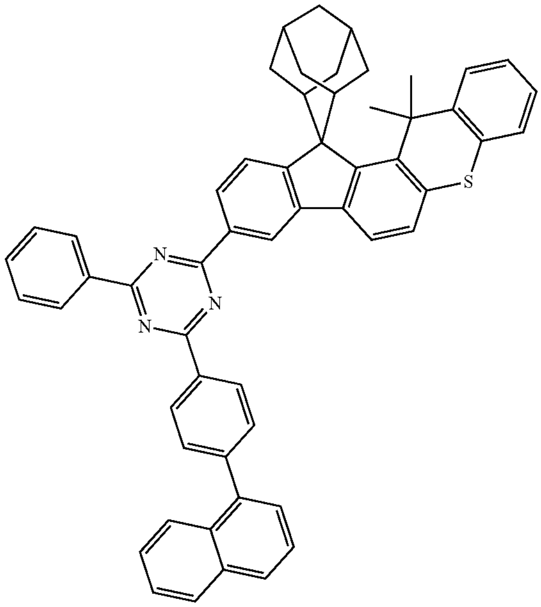
256
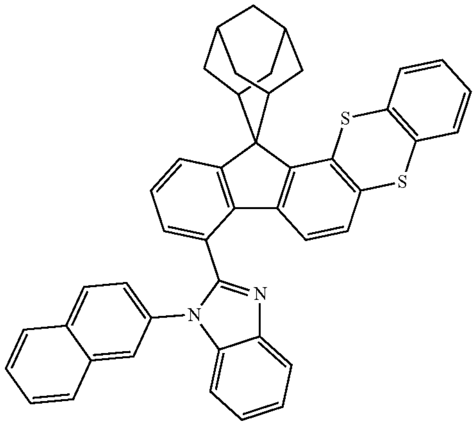
257
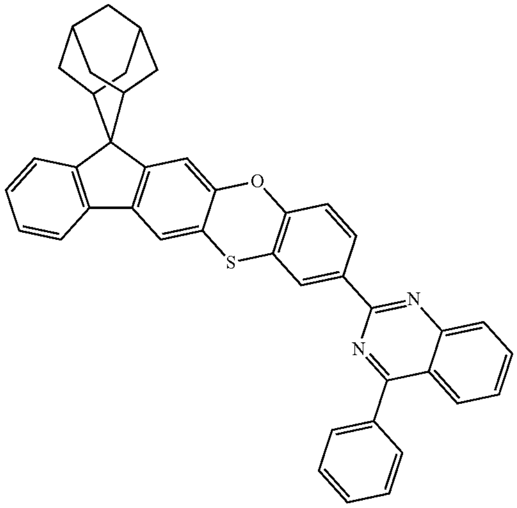
258
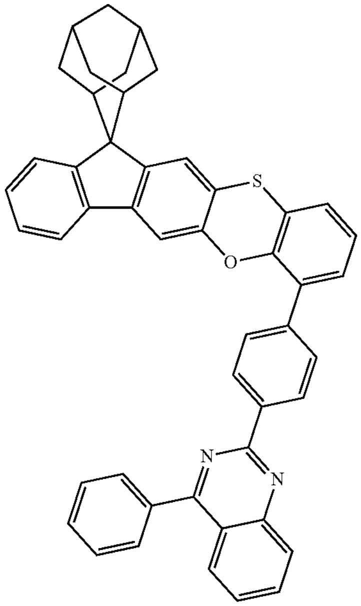
259
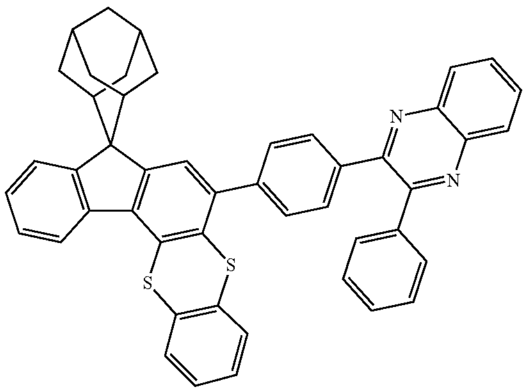
260
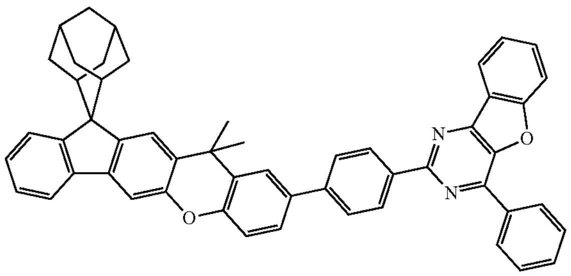

-continued
261
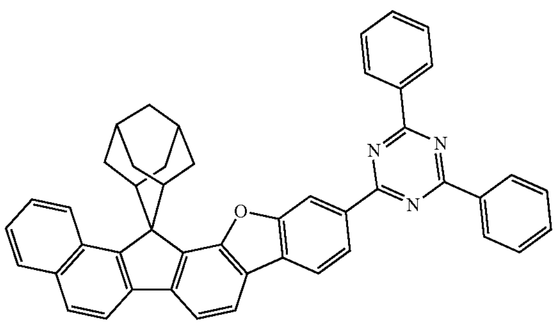
262
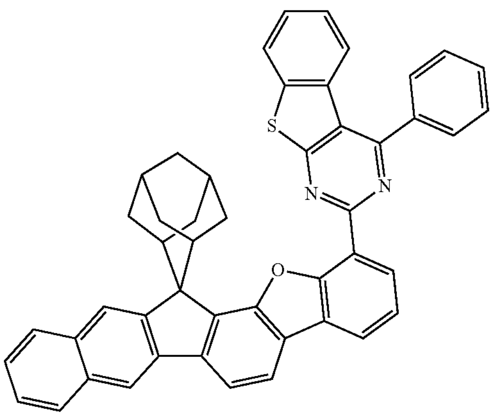
263
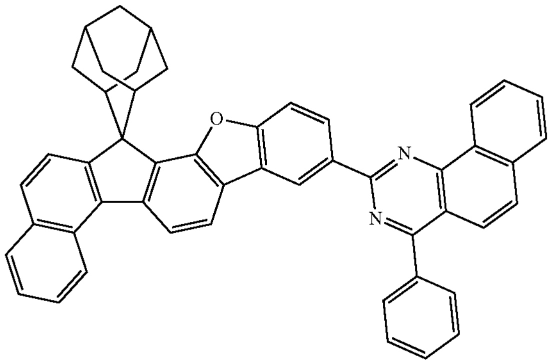
264
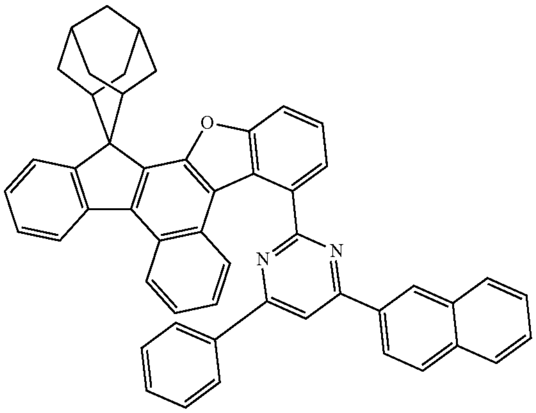
265
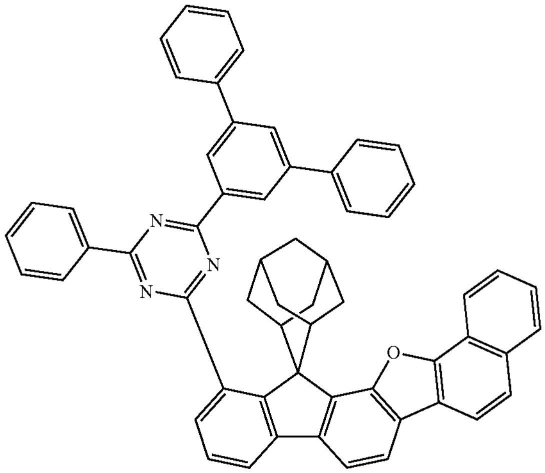
266
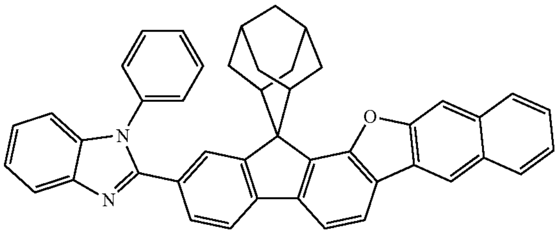

-continued
267
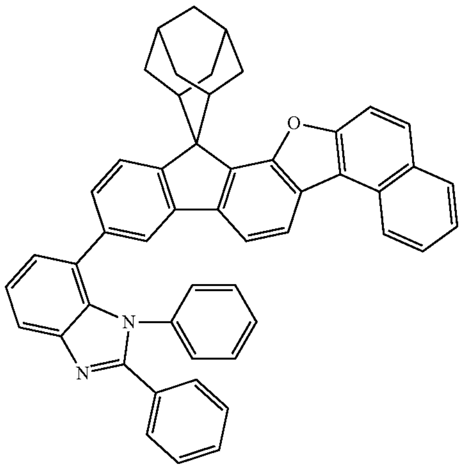
268
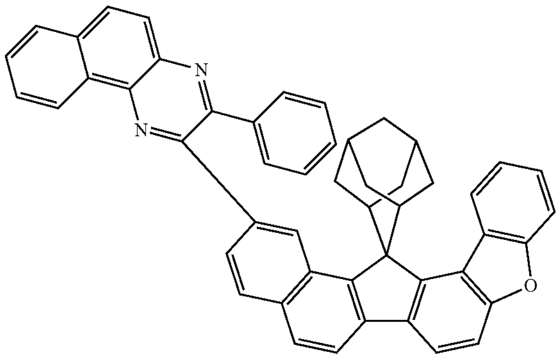
269
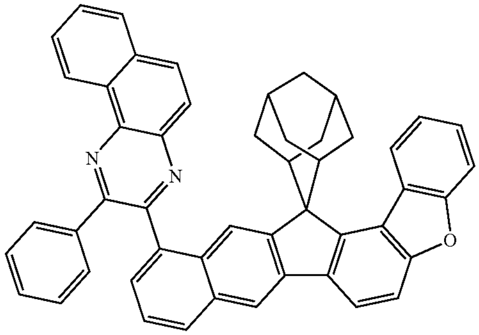
270
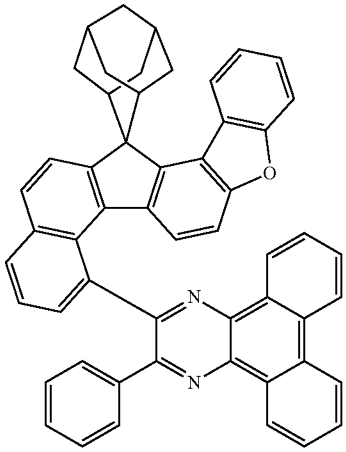
271
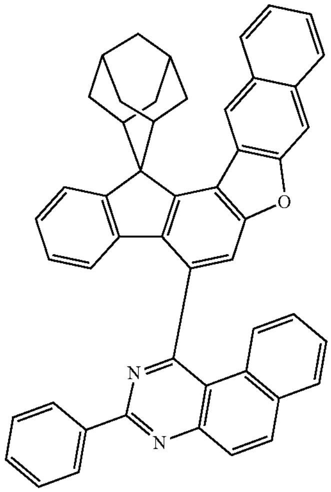
272
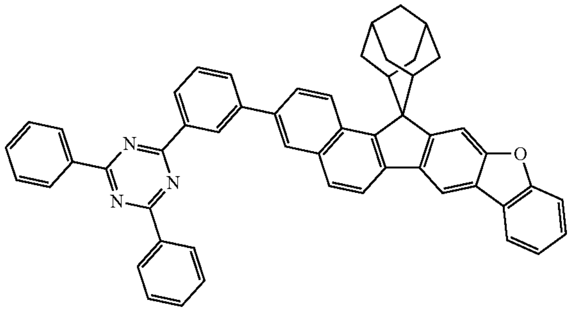

-continued
273
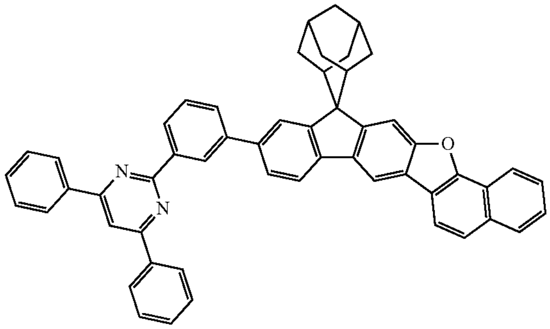
274
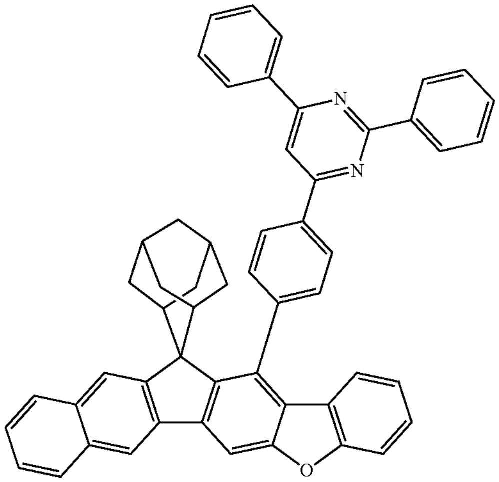
275
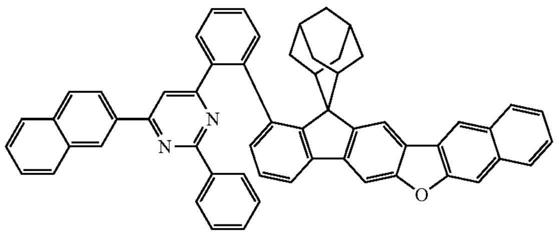
276
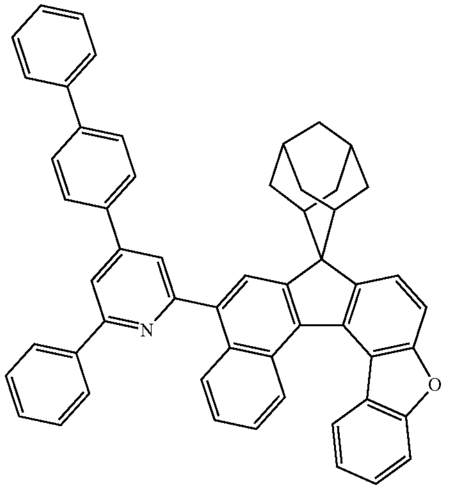
277
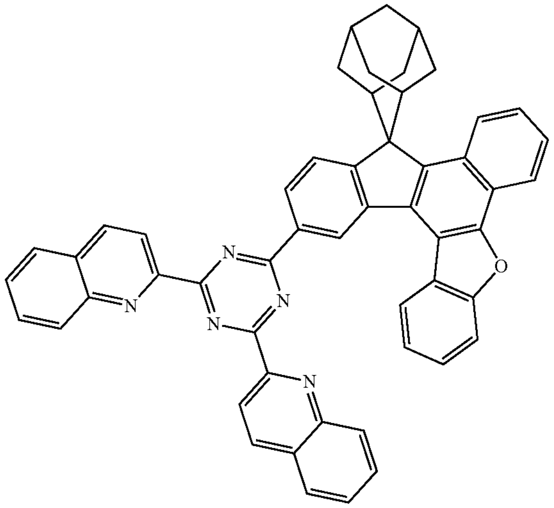
278
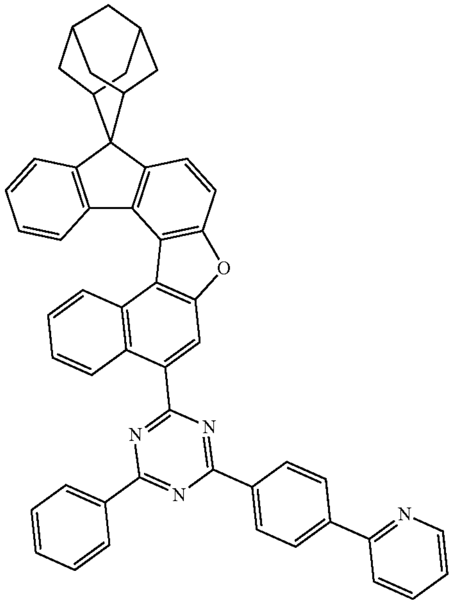

-continued
279
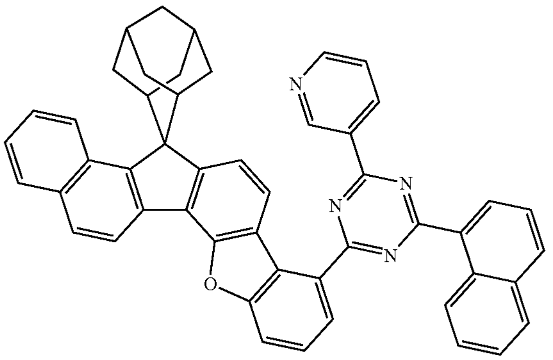
280
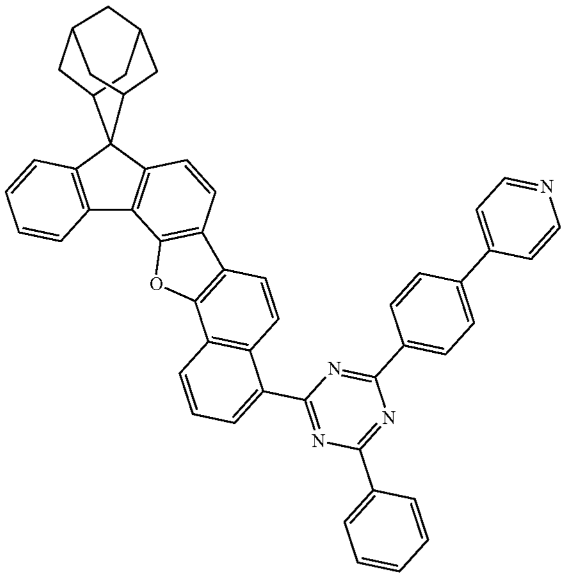
281
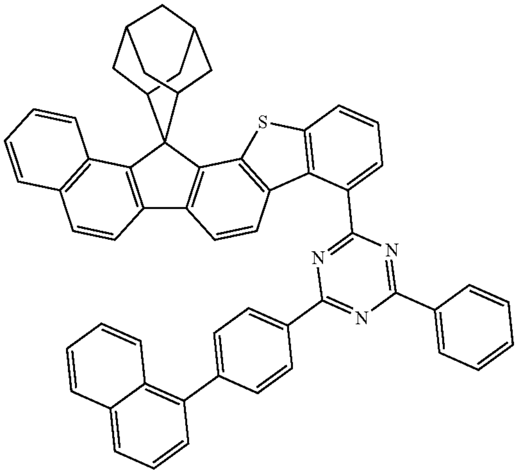
282
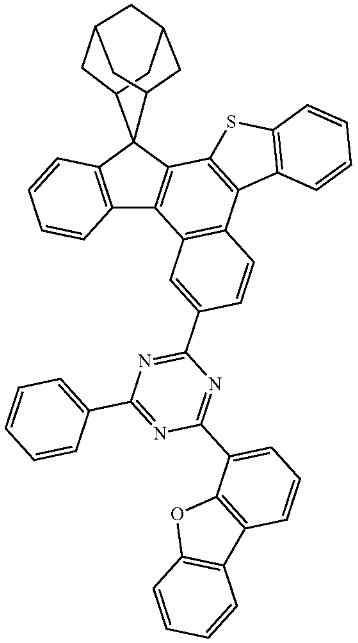

-continued
283
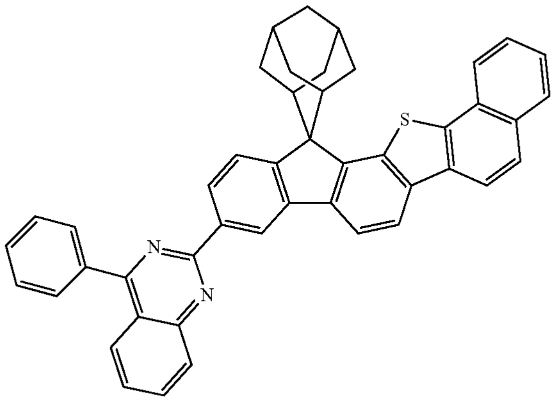
284
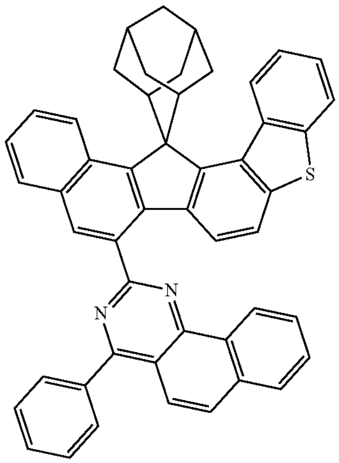
285
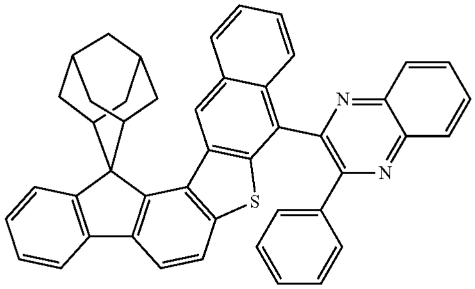
286
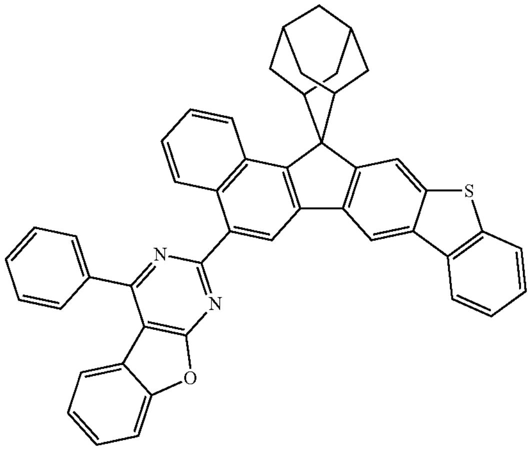
287
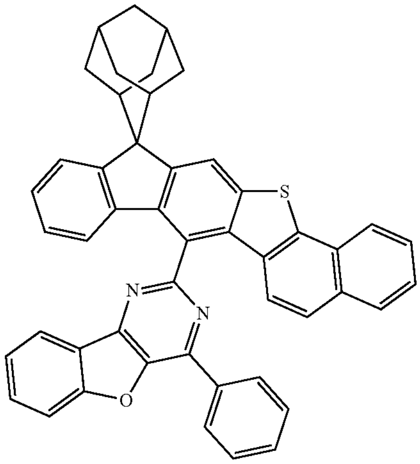
288
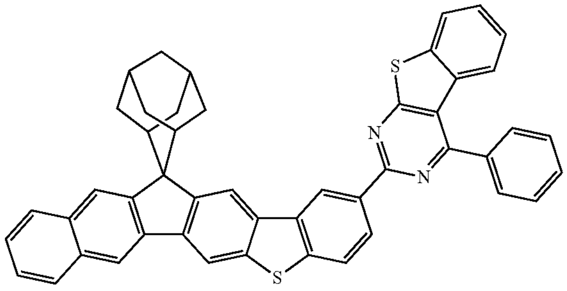

-continued
289
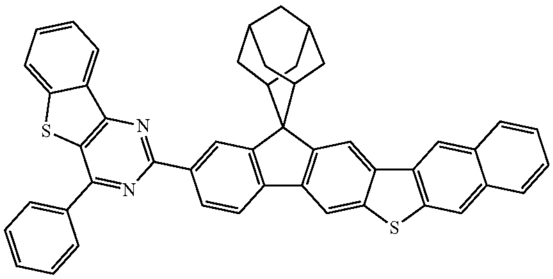
290
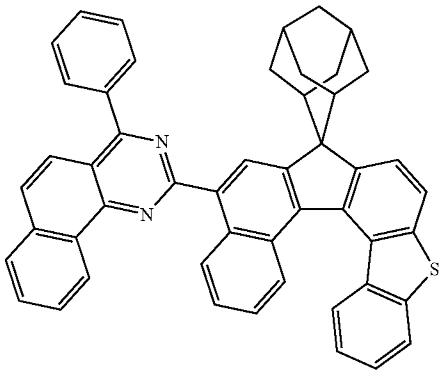
291
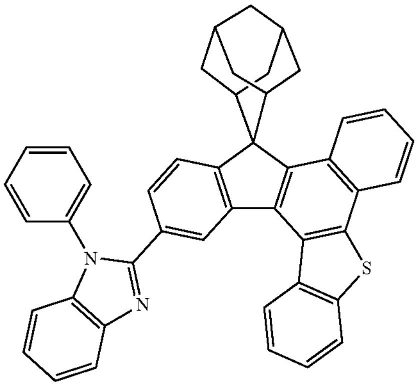
292
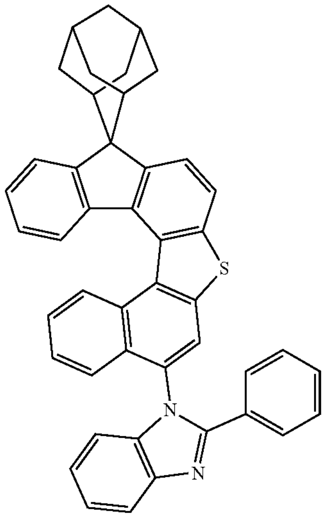
293
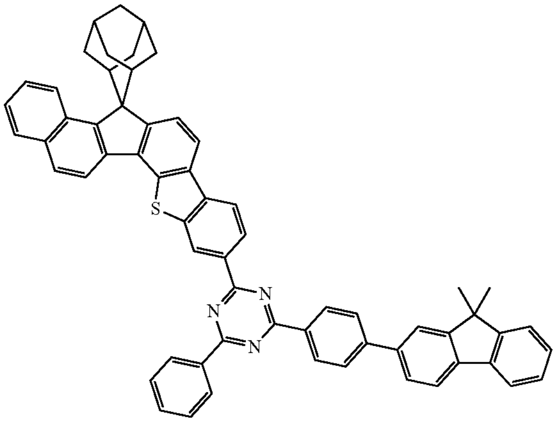
294
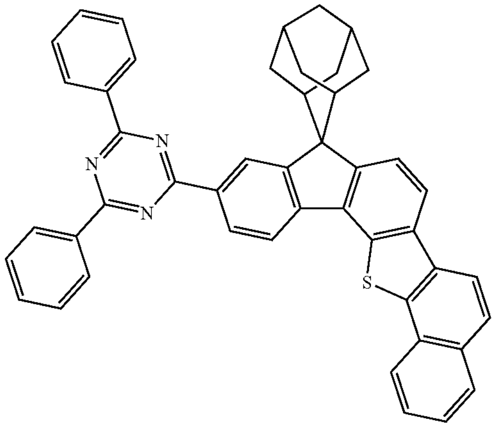

-continued
295
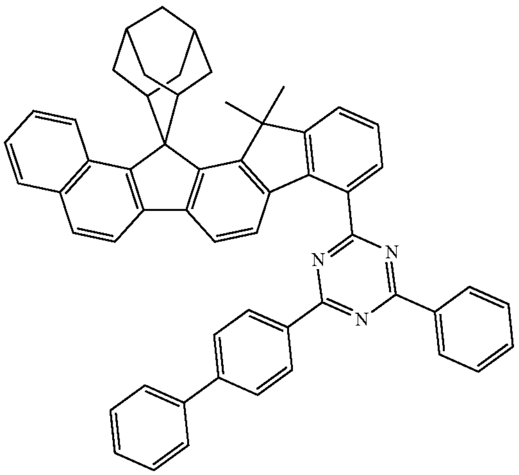
296
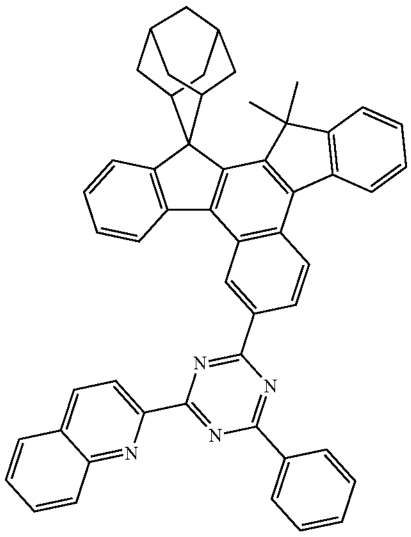
297
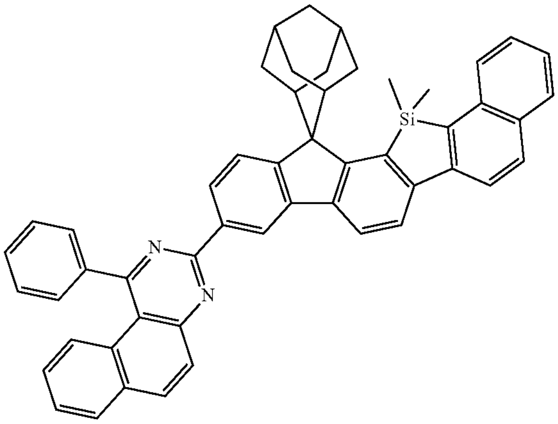
298
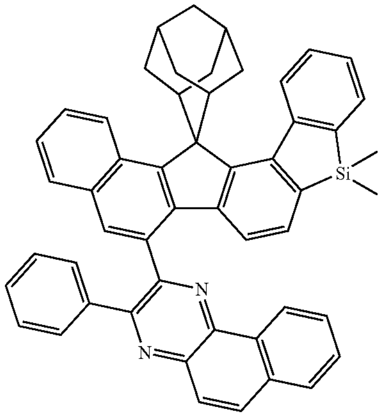
299
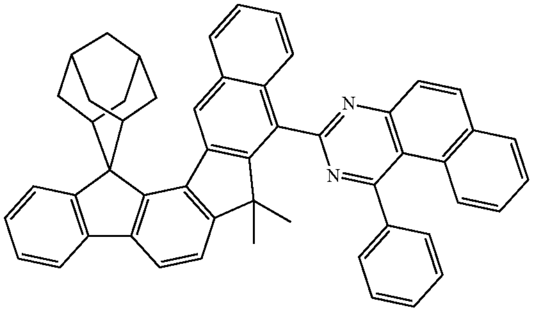
300
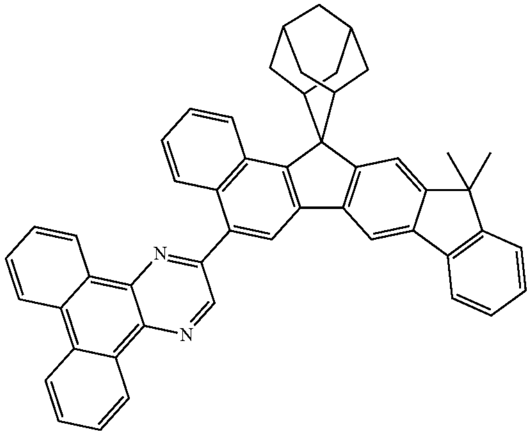

-continued
301
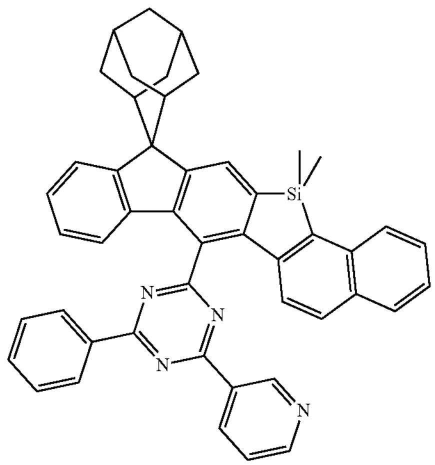
302
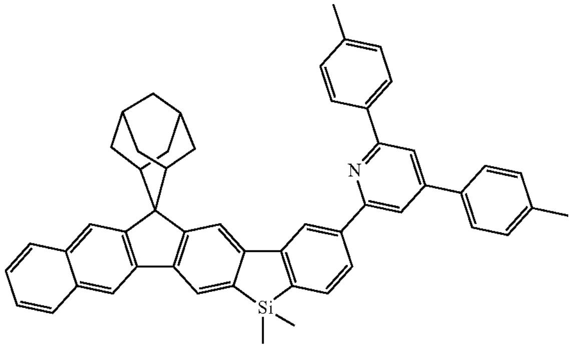
303
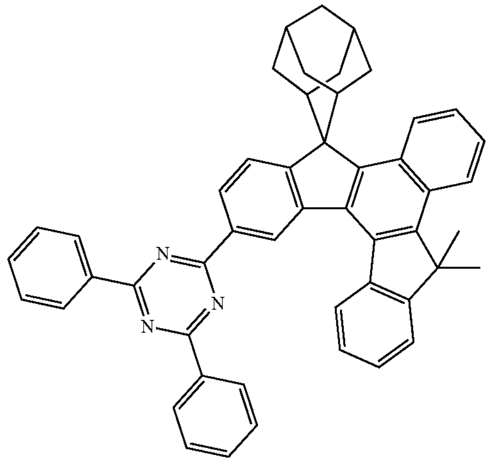
304
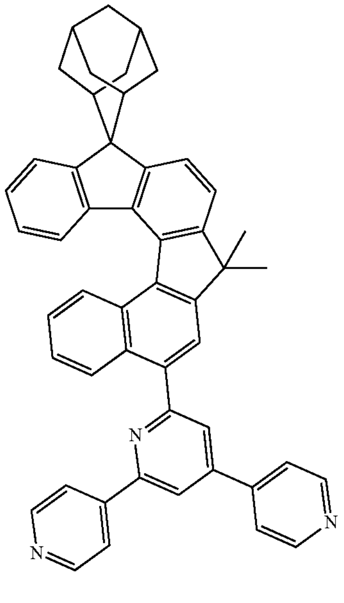
305
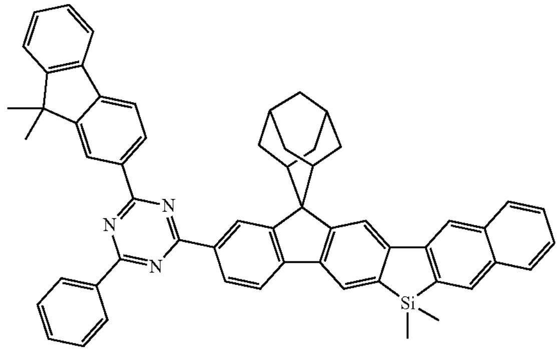
306
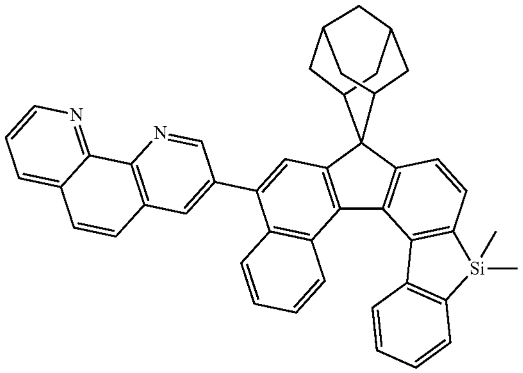

-continued
307
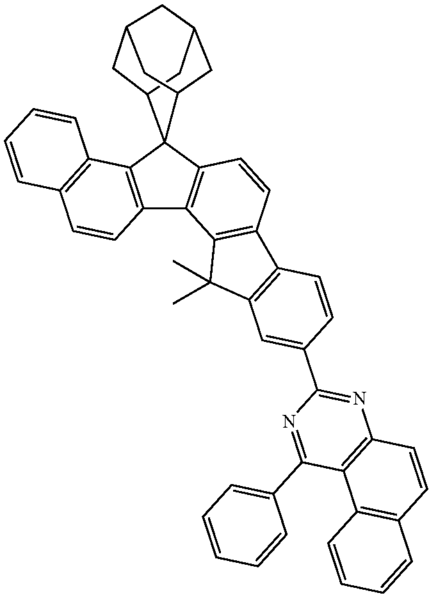
308
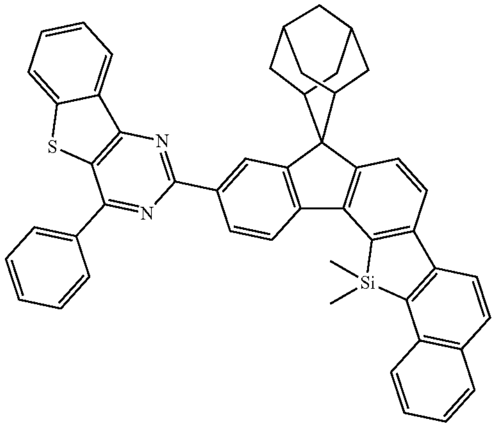
309
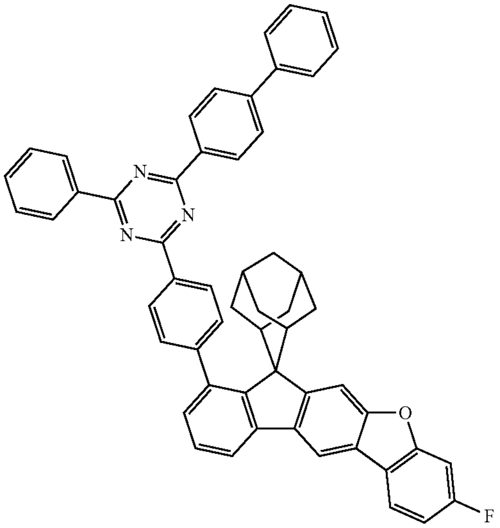
310
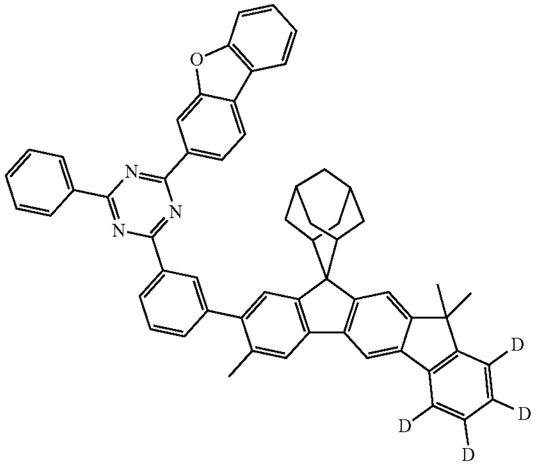

-continued
311
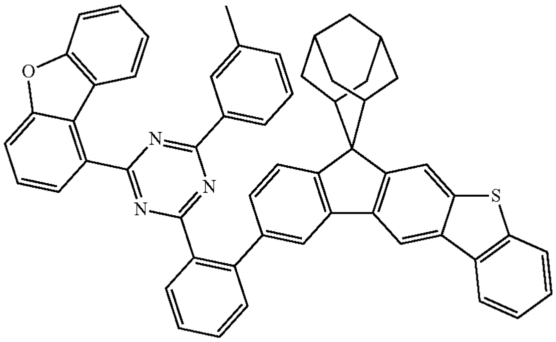
312
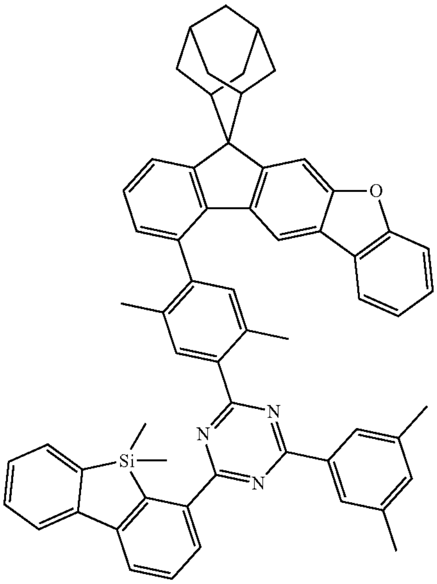
314
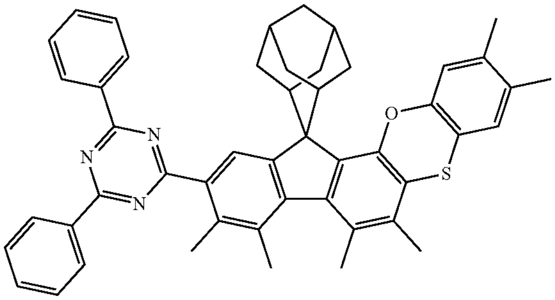
315
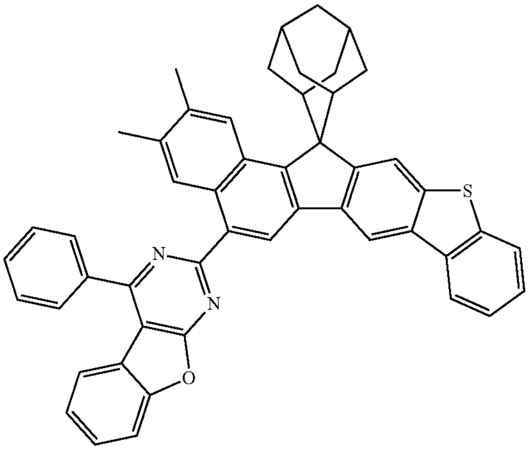
316
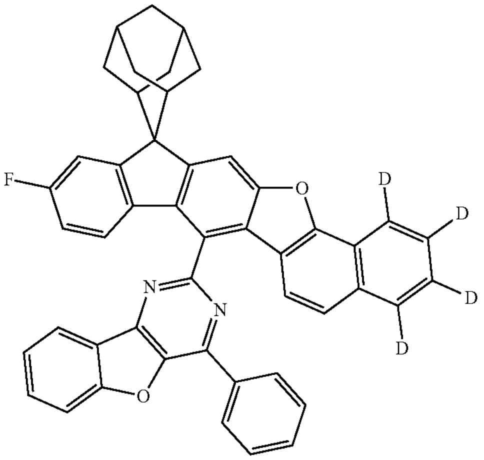
317
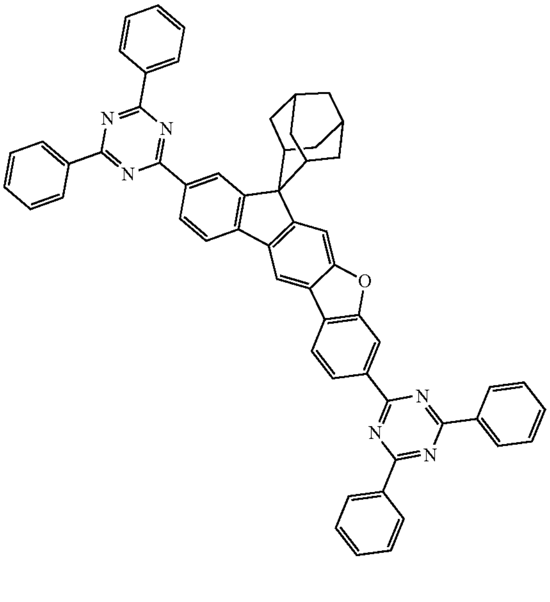

-continued
318
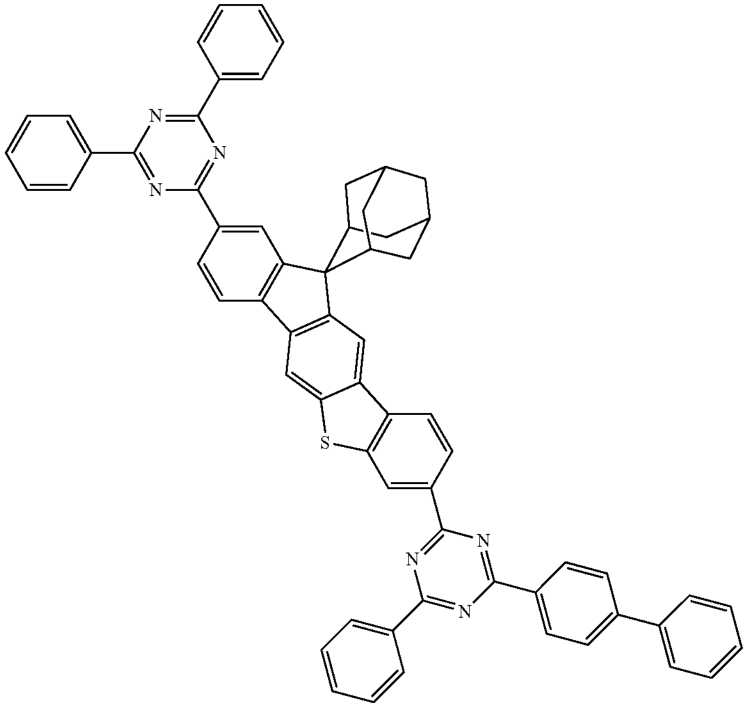
319
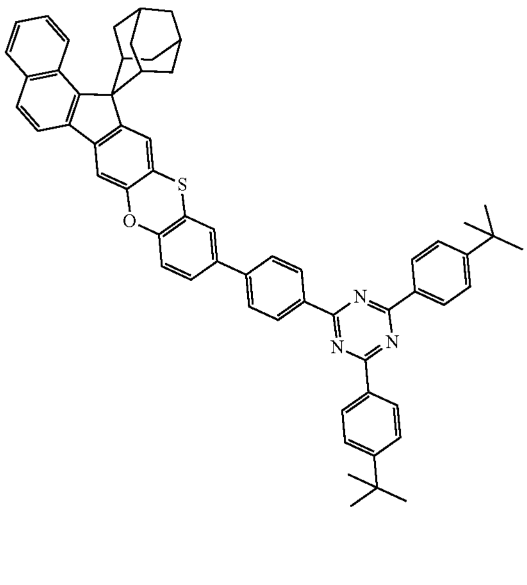
320
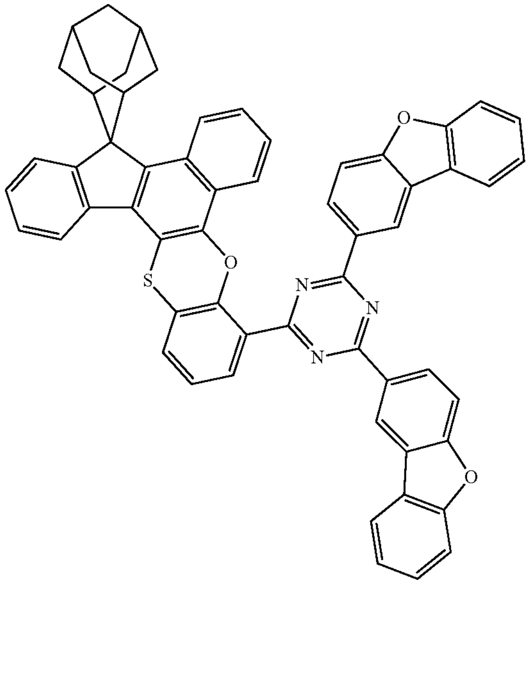

-continued
321
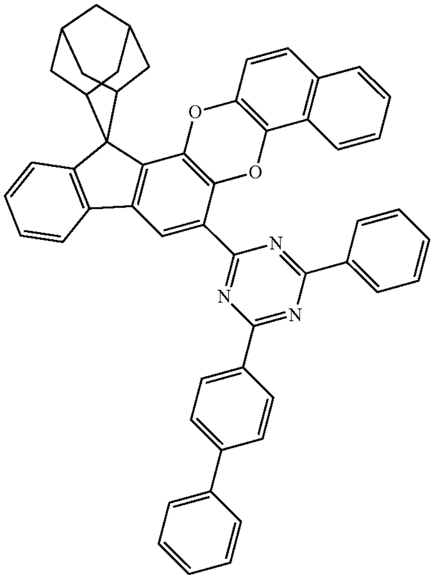
322
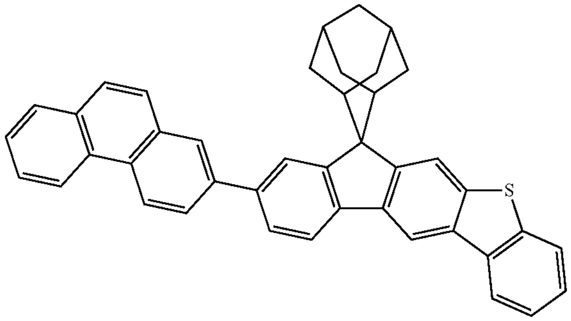
323
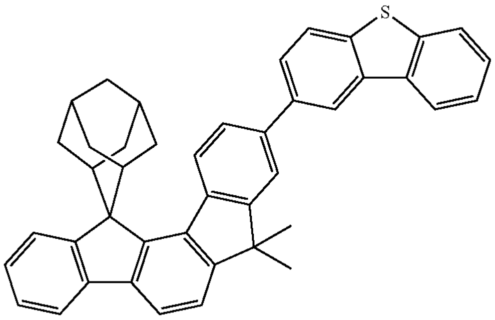
324
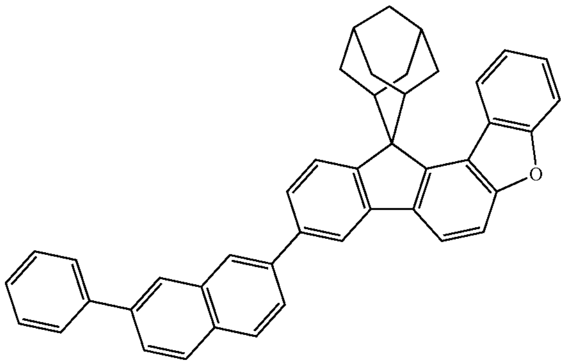
325
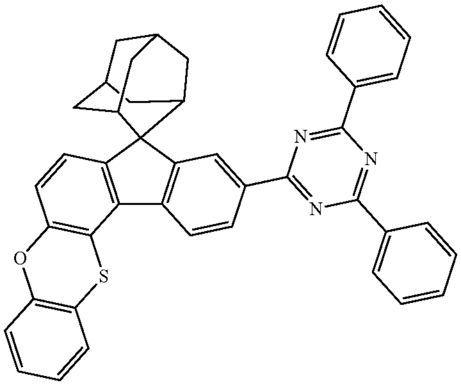
326
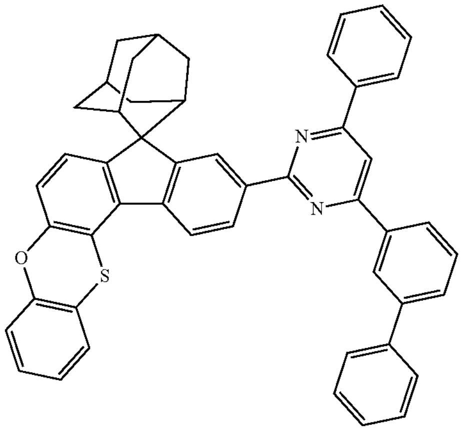

-continued
327
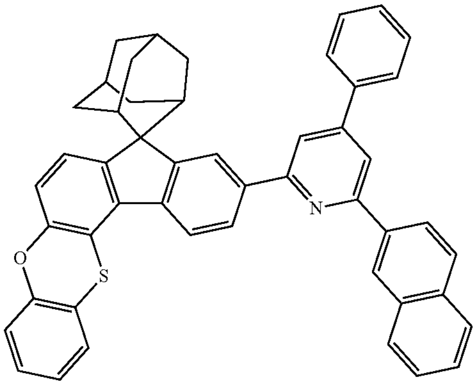
328
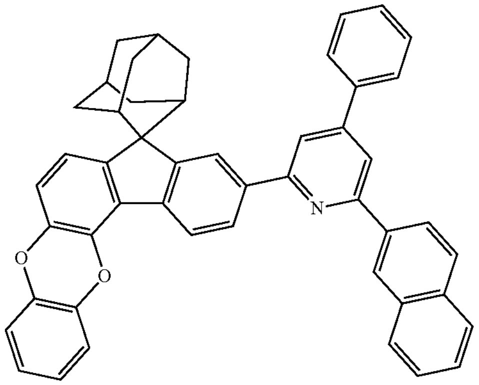
329
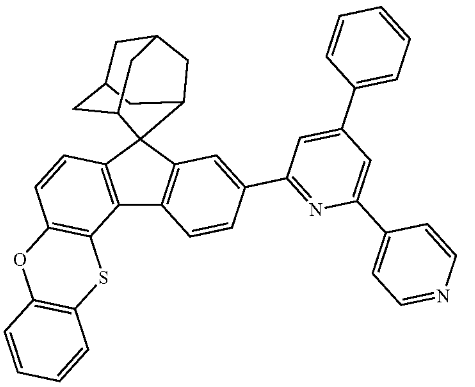
330
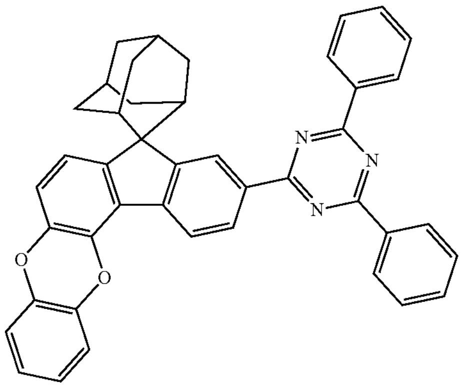
331
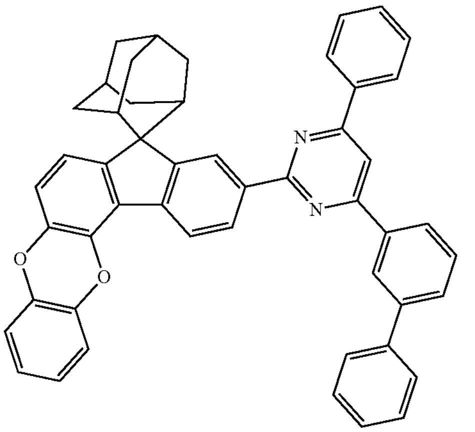
332
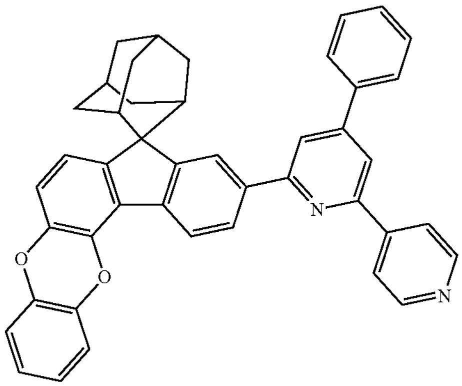
333
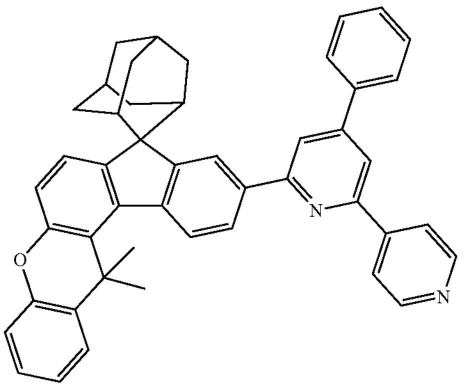
334
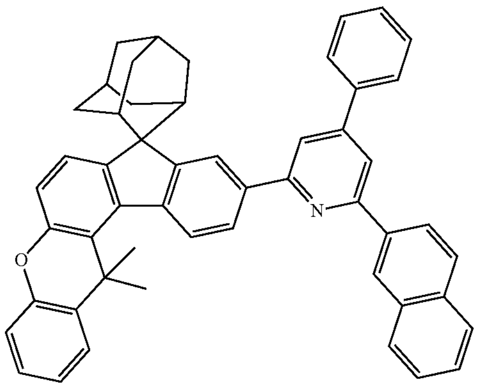

-continued
335
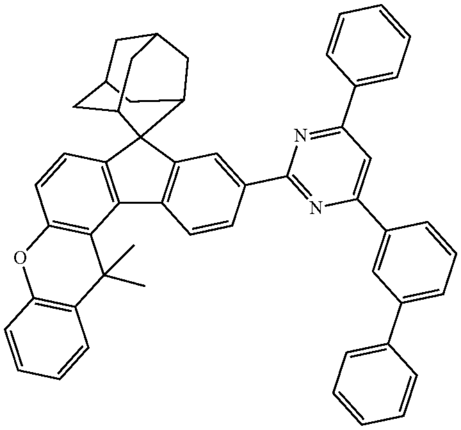
336
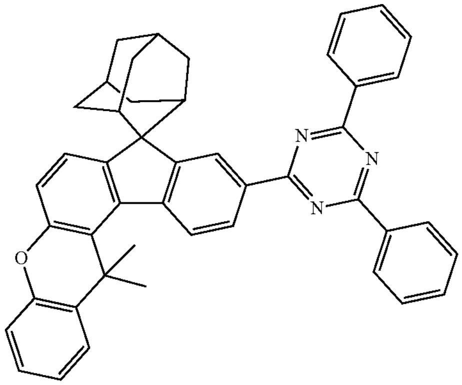
337
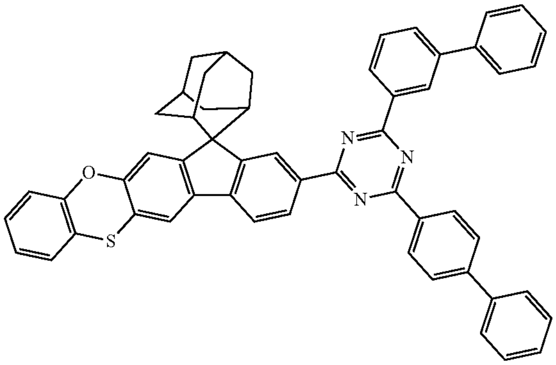
338
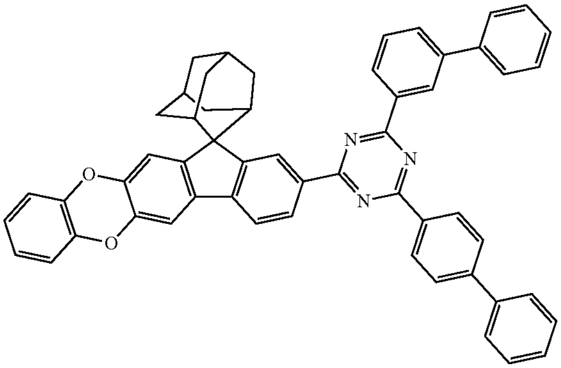
339
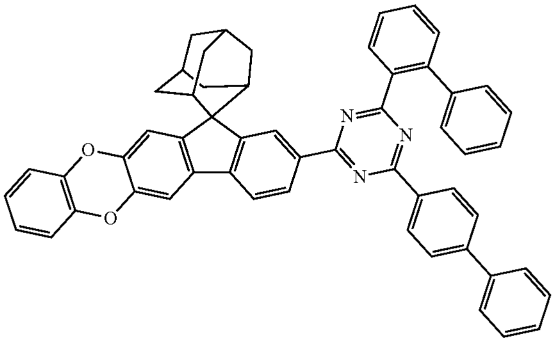
340
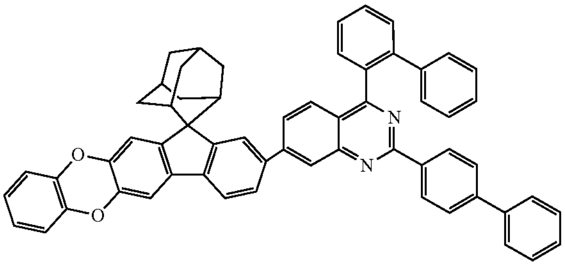

-continued
341
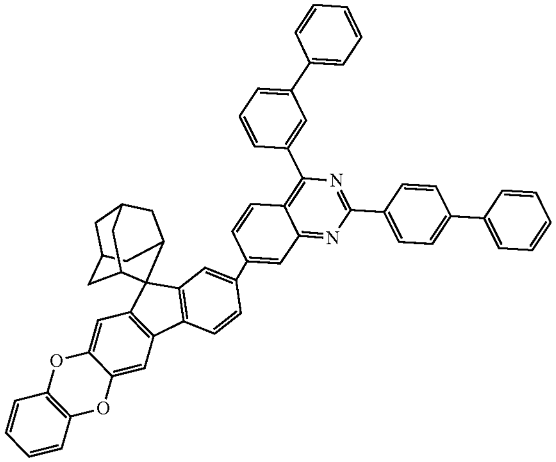
342
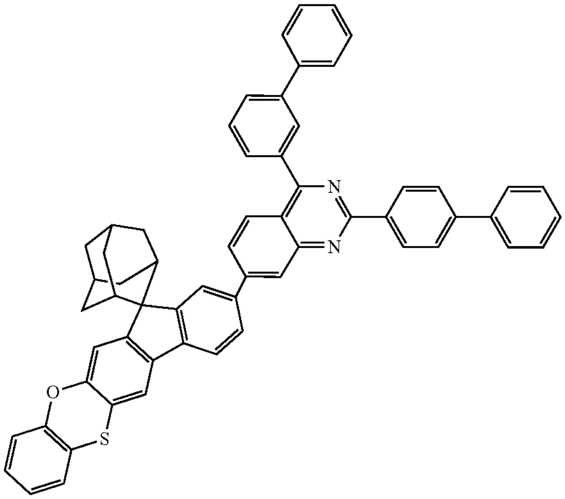
343
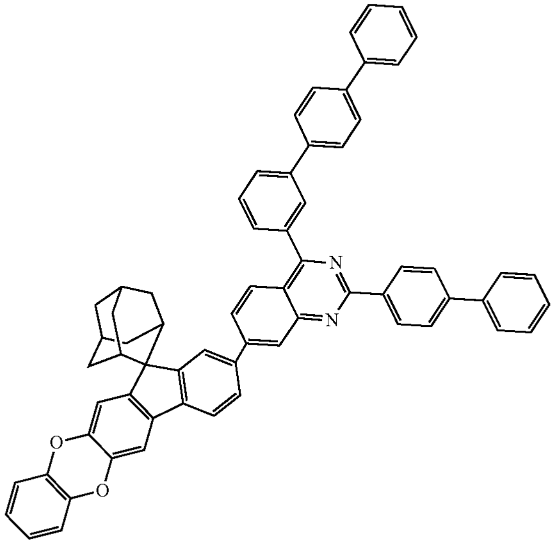
344
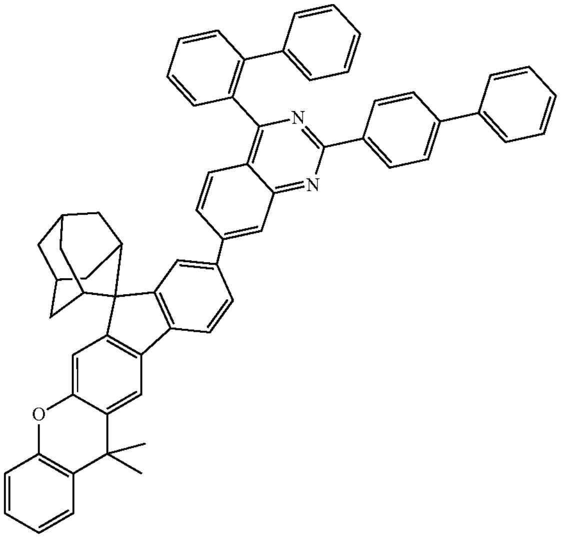
345
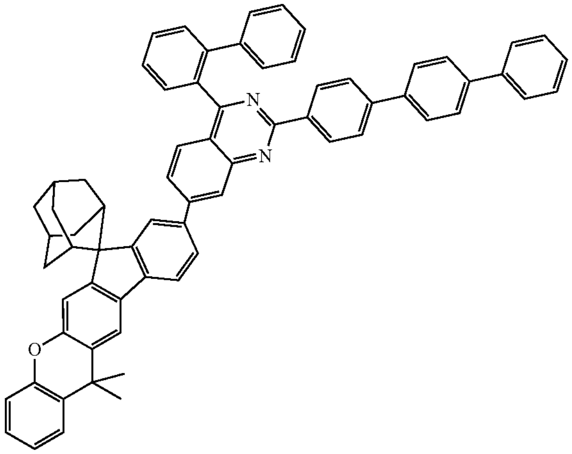

-continued
346
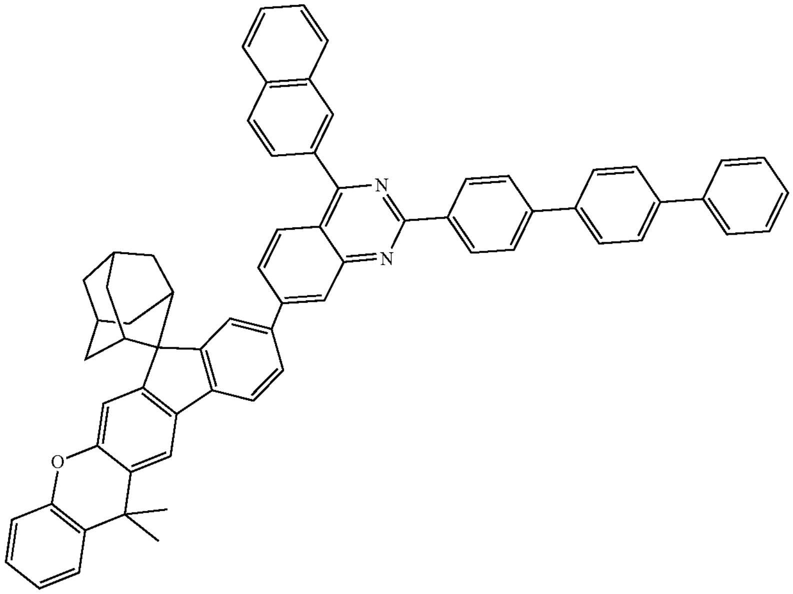
347
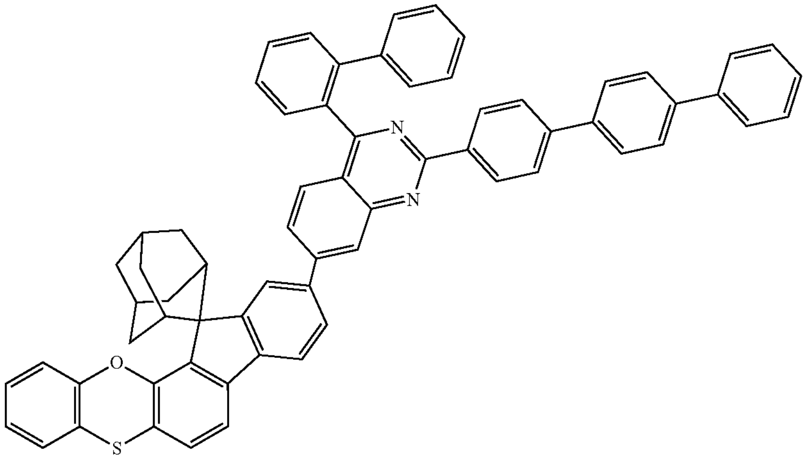
348
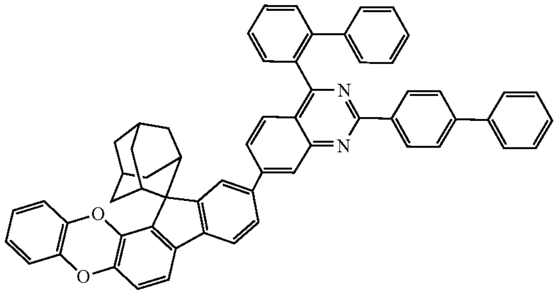
349
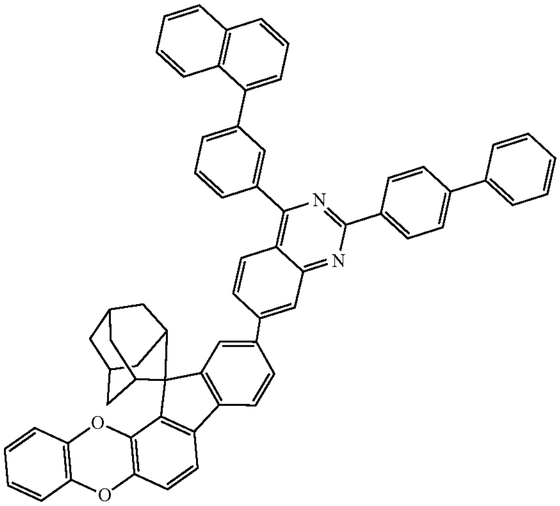

-continued
350
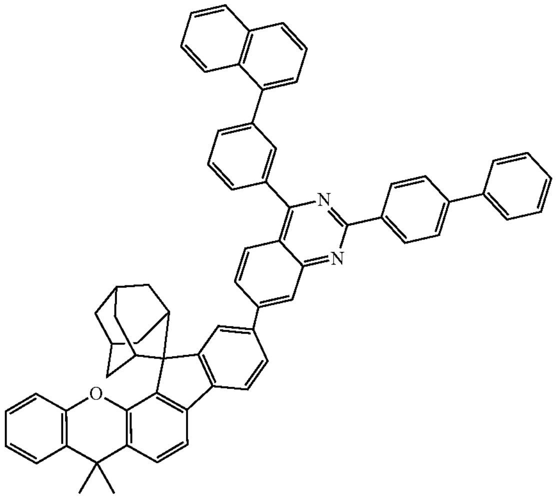
351
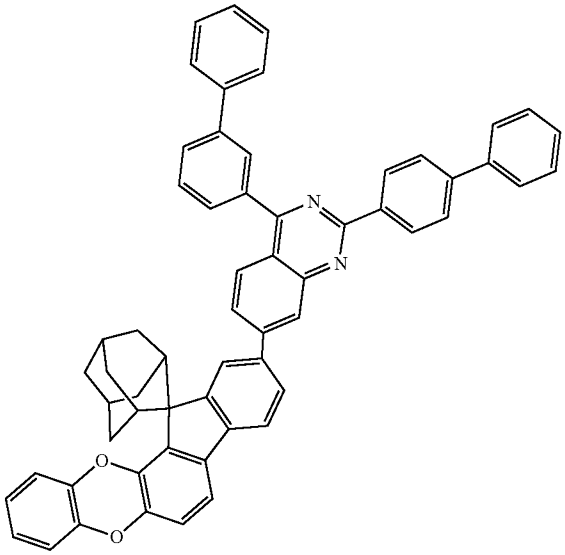
352
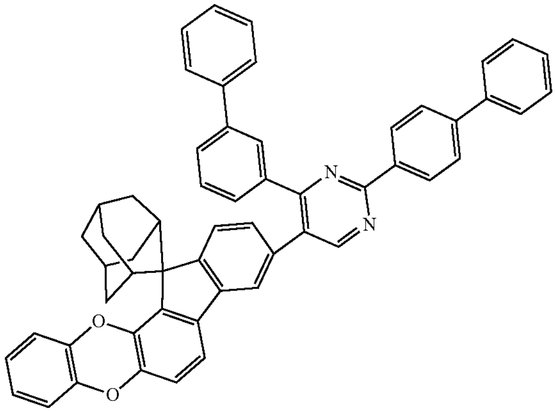
353
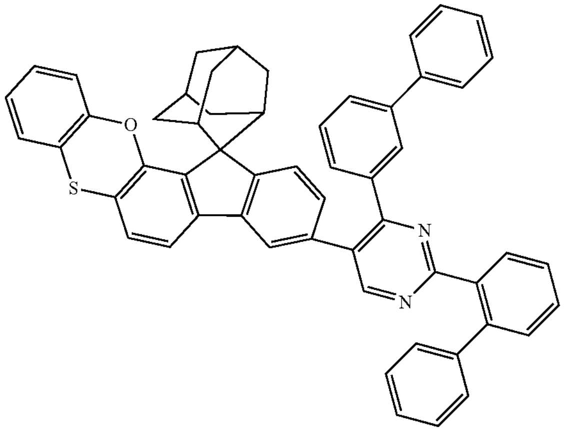
354
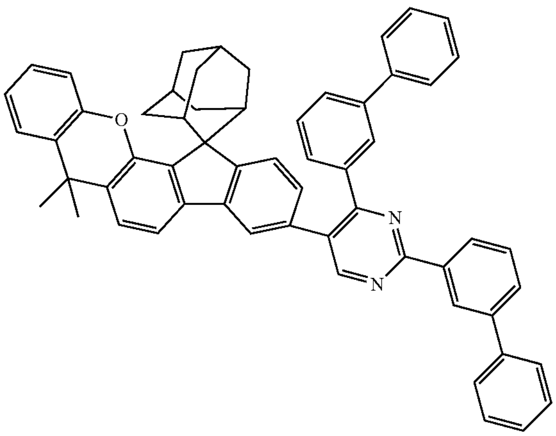
355
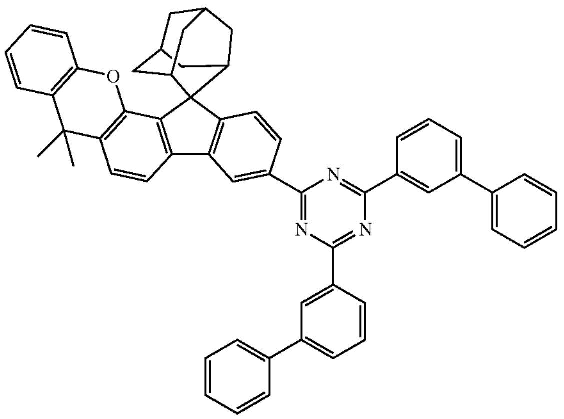

-continued
356
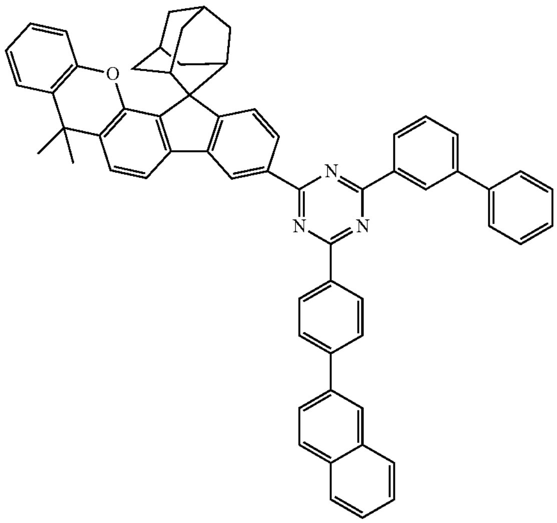
357
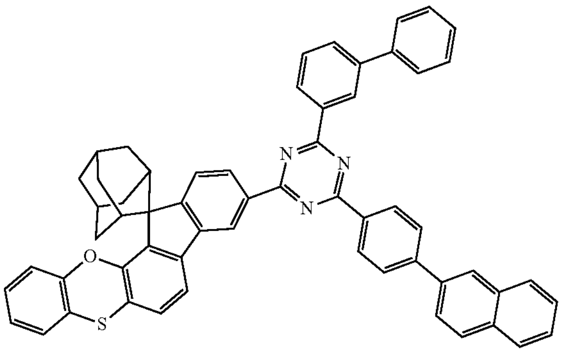
358
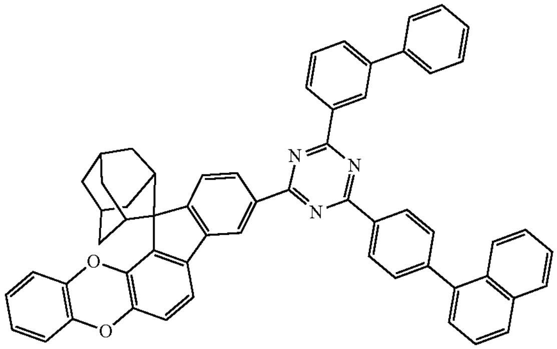
359
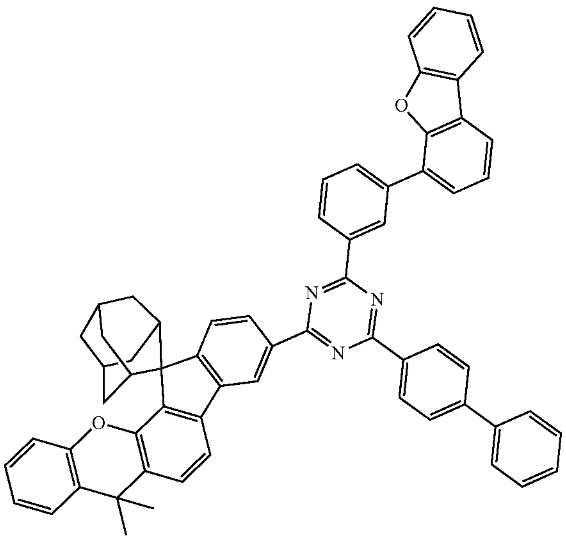

-continued
360
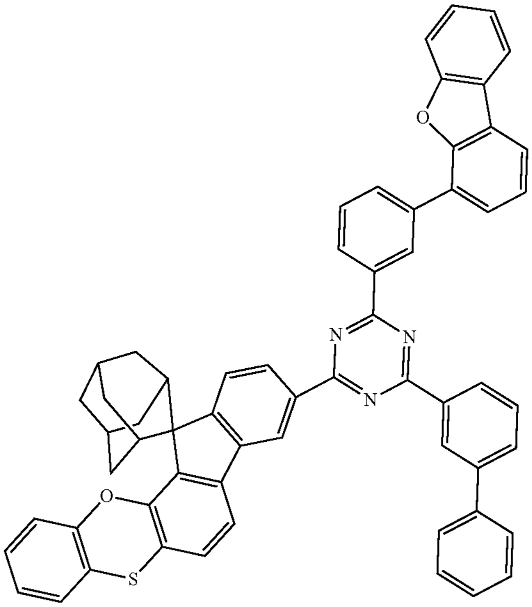
361
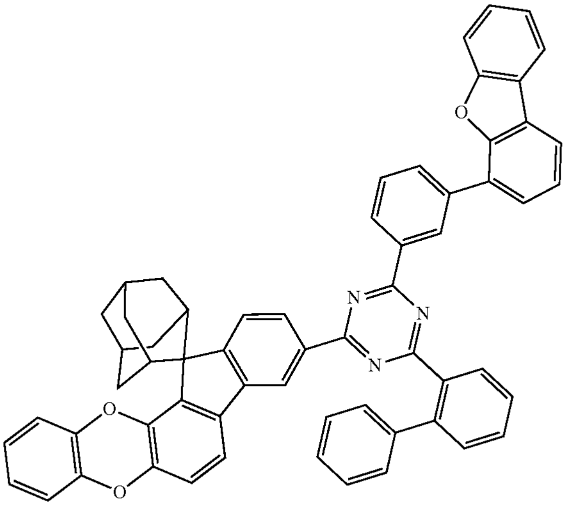
362
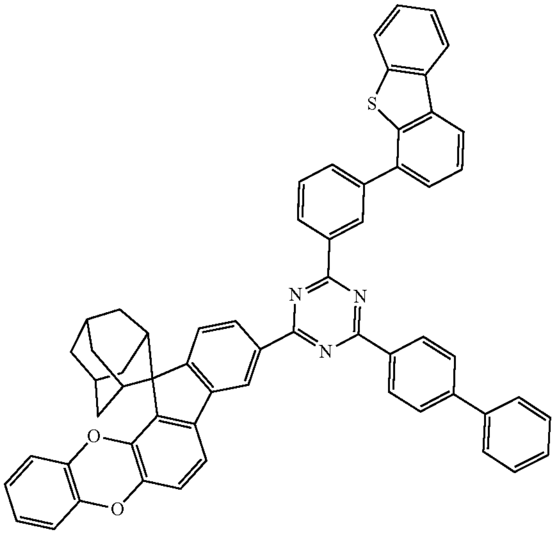
363
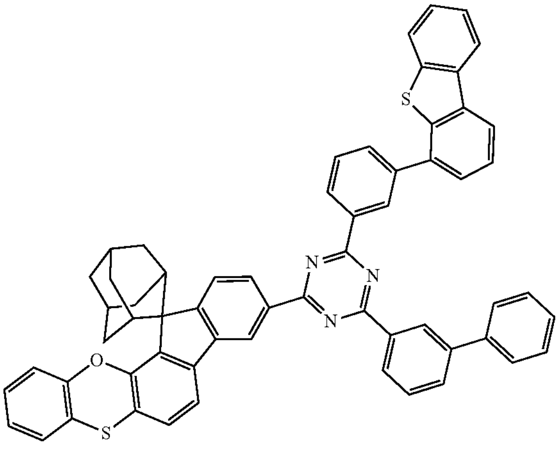

-continued
364
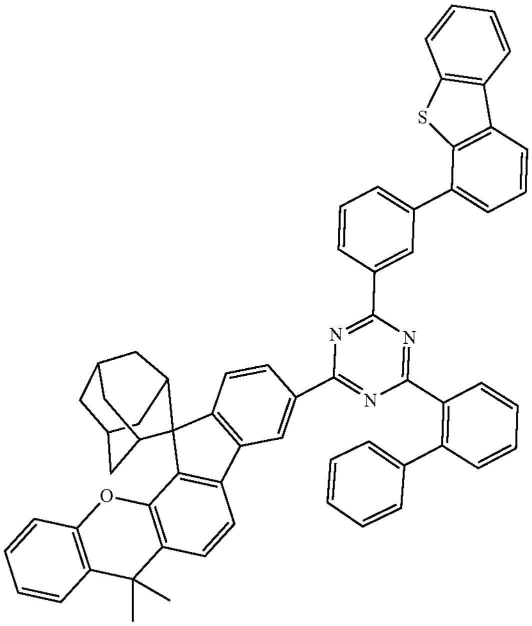
365
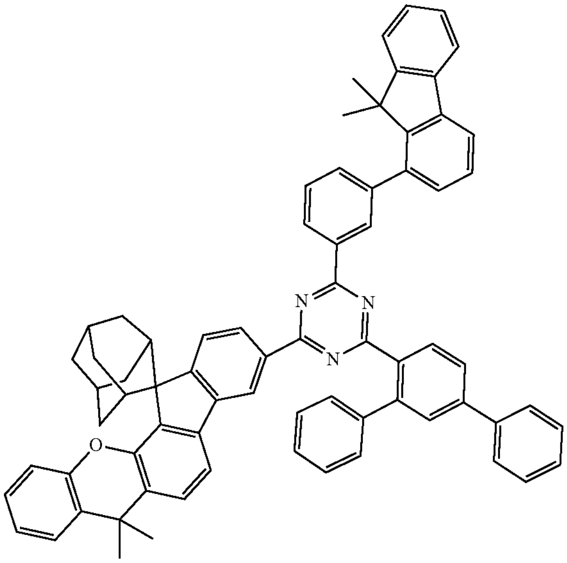
366
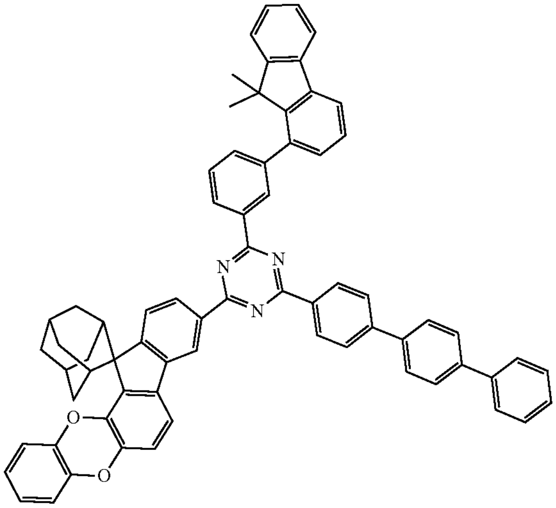
367
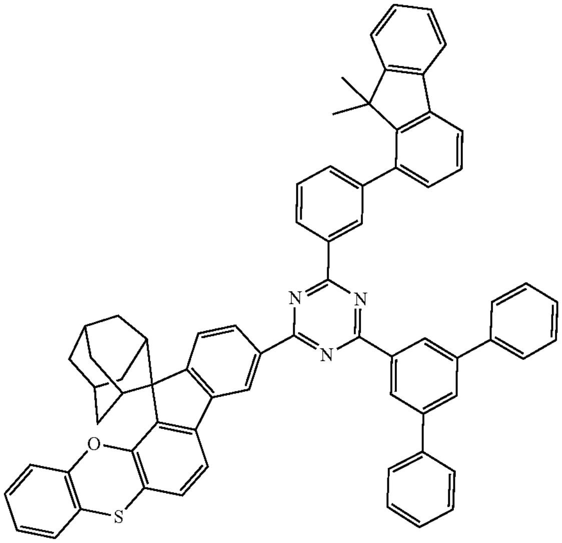

-continued
368
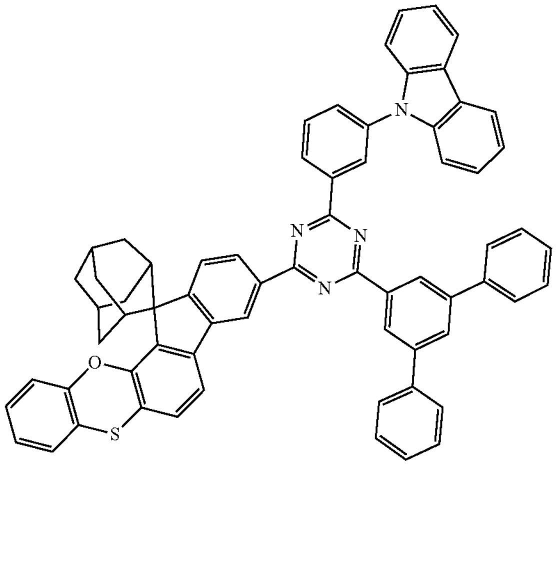
369
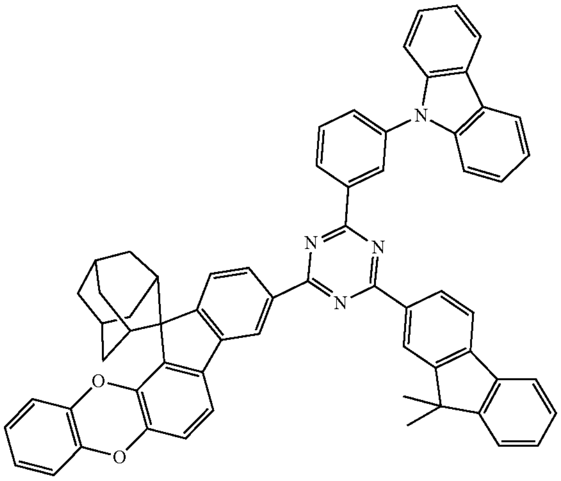
370
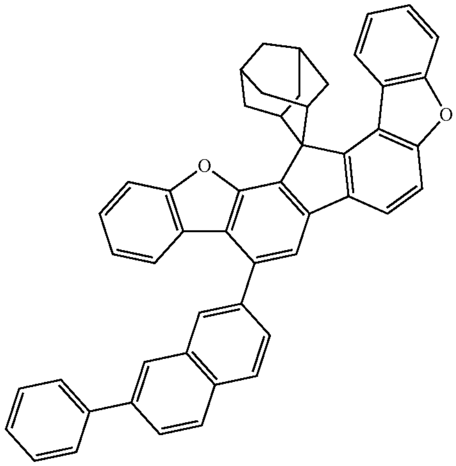
371
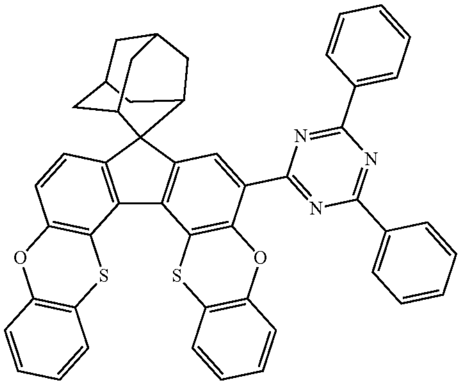
372
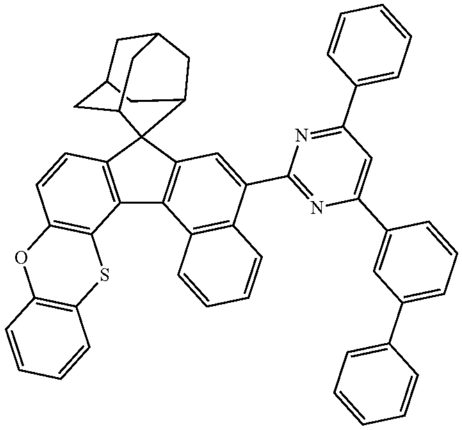
373
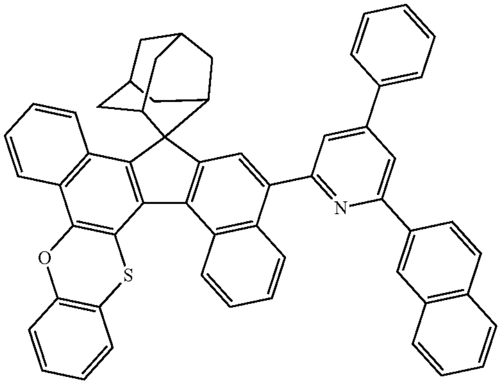

-continued

374

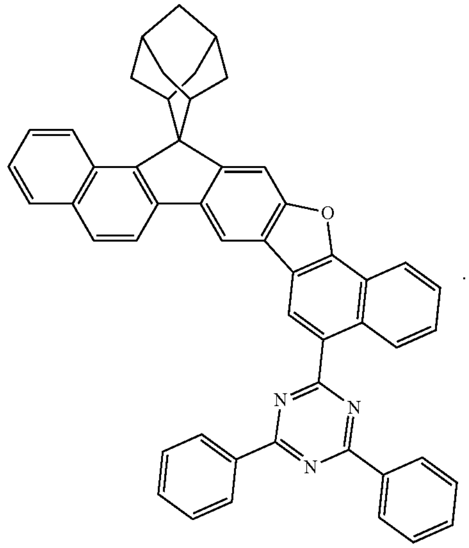

A synthetic method of the organic compound provided is not particularly limited in the present disclosure, and those skilled in the art can determine a suitable synthetic method according to the organic compound of the present disclosure in combination with synthetic methods provided in Synthesis examples. In other words, the Synthesis examples of the present disclosure exemplarily provide methods for the preparation of the organic compounds, and the used raw materials may be commercially obtained or obtained by a method well known in the art. All organic compounds provided by the present disclosure can be obtained according to these exemplary synthetic methods by those skilled in the art, and all specific synthetic methods for preparing such organic compounds are not described in detail here, which should not be understood by those skilled in the art as limiting the present disclosure.

In a second aspect, the present disclosure provides an electronic element, including an anode and a cathode which are oppositely disposed, and a functional layer disposed between the anode and the cathode; and the functional layer includes the organic compound described above.

The organic compound provided by the present disclosure can be used to form at least one organic film layer in the functional layer to improve the efficiency and service life characteristics of the electronic element.

In one example of the present disclosure, the functional layer includes an organic light-emitting layer including the organic compound. The organic light-emitting layer may be composed of the organic compound provided by the present disclosure or may be composed of the organic compound provided by the present disclosure together with other materials.

Optionally, the electronic element is an organic electroluminescent device.

According to one example of the present disclosure, the organic electroluminescent device can be a green device or a red device. As shown in FIG. 1, the organic electroluminescent device may include an anode 100, a first hole transport layer 321, a second hole transport layer 322, an organic light-emitting layer 330 as an energy conversion layer, an electron transport layer 340, and a cathode 200 which are sequentially stacked.

Optionally, the anode 100 includes the following anode materials, which are preferably materials having a large work function that facilitate hole injection into the functional layer. Specific examples of the anode materials include metals such as nickel, platinum, vanadium, chromium, copper, zinc, and gold or their alloys; metal oxides such as zinc oxide, indium oxide, indium tin oxide (ITO), and indium zinc oxide (IZO); combined metals and oxides such as ZnO:Al or $SnO_2$:Sb; or conducting polymers such as poly(3-methylthiophene), poly[3,4-(ethylene-1,2-dioxy)thiophene] (PEDT), polypyrrole, and polyaniline, but are not limited to this. A transparent electrode containing indium tin oxide (ITO) as the anode is preferably included.

Optionally, the hole transport layer 320 includes a first hole transport layer 321 and a second hole transport layer 322 which are sequentially stacked, and the first hole transport layer 321 is closer to the anode 100 than the second hole transport layer 322.

Optionally, the first hole transport layer 321 and the second hole transport layer 322 each include one or more hole transport materials, and the hole transport materials may be selected from a carbazole polymer, carbazole-linked triarylamine compounds, or other types of compounds, which are not particularly limited in the present disclosure. For example, the first hole transport layer 321 may be composed of a compound NPB, HT-01 or HT-03; and the second hole transport layer 322 may be composed of a compound HT-02 or HT-04. The structures of HT-01 to HT-04 are shown below.

Optionally, the organic light-emitting layer 330 may be composed of a single light-emitting material, and may also include a host material and a guest material. The host material and/or the guest material of the organic light-emitting layer may contain the organic compound of the present disclosure. Further optionally, the organic light-emitting layer 330 is composed of the host material and the guest material, and holes injected into the organic light-emitting layer 330 and electrons injected into the organic light-emitting layer 330 may be recombined in the organic light-emitting layer 330 to form excitons, the excitons transfer energy to the host material, and the host material transfers energy to the guest material, thus enabling the guest material to emit light. In one example of the present disclosure, the host material of the organic light-emitting layer contains the organic compound of the present disclosure.

The guest material of the organic light-emitting layer 330 may be a compound having a condensed aryl ring or its derivative, a compound having a heteroaryl ring or its derivative, an aromatic amine derivative, or other materials, which is not specially limited in the present disclosure.

The electron transport layer 340 may be of a single-layer structure or a multi-layer structure, and may include one or more electron transport materials, and the electron transport materials may be selected from, but are not limited to, a benzimidazole derivative, an oxadiazole derivative, a quinoxaline derivative, or other electron transport materials. In one example of the present disclosure, the electron transport layer 340 may be composed of TPBi and LiQ or ET-01 (with a structure shown below) and LiQ.

In the present disclosure, the cathode 200 may include a cathode material, which is a material having a small work function that facilitates electron injection into the functional layer. Specific examples of the cathode material include, but are not limited to, metals such as magnesium, calcium, sodium, potassium, titanium, indium, yttrium, lithium, gadolinium, aluminum, silver, tin, and lead or their alloys; or multilayer materials such as LiF/Al, Liq/Al, $LiO_2$/Al, LiF/Ca, LiF/Al, and $BaF_2$/Ca. A metal electrode containing magnesium and silver as the cathode is preferably included.

Optionally, as shown in FIG. 1, a hole injection layer 310 may also be arranged between the anode 100 and the first hole transport layer 321 to enhance the ability to inject holes into the first hole transport layer 321. The hole injection layer 310 can be made of a benzidine derivative, a starburst arylamine compound, a phthalocyanine derivative or other materials, which is not specially limited in the present disclosure. For example, the hole injection layer 310 may be composed of HAT-CN or F4-TCNQ.

Optionally, as shown in FIG. 1, an electron injection layer 350 may also be arranged between the cathode 200 and the electron transport layer 340 to enhance the ability to inject electrons into the electron transport layer 340. The electron injection layer 350 may include an inorganic material such as an alkali metal sulfide and an alkali metal halide, or may include a complex of an alkali metal and an organic substance. For example, the electron injection layer 350 may include LiQ or Yb.

In a third aspect, the present disclosure provides an electronic device, including the electronic element according to the second aspect of the present disclosure.

Figure 2:
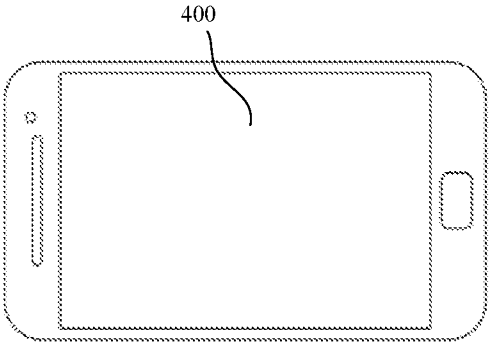
FIG. 2 is a structural schematic diagram of an electronic device according to one example of the present disclosure.

According to one example, as shown in FIG. 2, the electronic device is an electronic device 400 including the organic electroluminescent device described above. The electronic device 400 may be, for example, a display device, a lighting device, an optical communication device, or other types of electronic devices, and may include, for example, but is not limited to, a computer screen, a mobile phone screen, a television, electronic paper, an emergency lighting lamp, an optical module, and the like.

Compounds of which synthetic methods are not mentioned in the present disclosure are all raw material products obtained by commercial routes.

The synthetic methods of the organic compounds of the present disclosure are specifically described below in conjunction with synthesis examples.

SYNTHESIS EXAMPLES

1. Preparation of Intermediate IM a-1

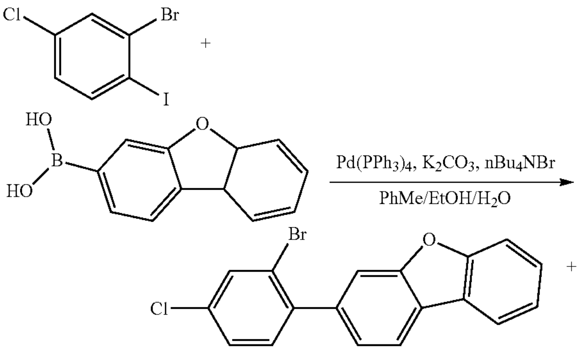

IM a-1

2-Bromo-4-chloro-1-iodobenzene (50.0 g, 157.5 mmol), dibenzofuran-3-boronic acid (30.4 g, 157.5 mmol), tetrakis (triphenylphosphine)palladium (3.6 g, 3.1 mmol), potassium carbonate (54.3 g, 393.8 mmol), and tetrabutylammonium bromide (10.1 g, 31.5 mmol) were added to a flask, and a mixed solvent of toluene (440 mL), ethanol (200 mL) and water (100 mL) was added, and the mixture was heated to 80° C. under nitrogen protection, and stirred for 24 h while maintaining the temperature, after cooling to room temperature, stirring was stopped, the reaction solution was washed with water, the obtained organic phase was separated, and dried by anhydrous magnesium sulfate, and a solvent was removed under reduced pressure to give a crude product; and the crude product was purified by silica gel column chromatography using dichloromethane/n-heptane as a mobile phase to obtain a white solid intermediate IM a-1 (33.8 g, yield: 60%).

Intermediates IM x-1 listed in Table 1 were synthesized by the same method as that for synthesis of the intermediate IM a-1 except that a reactant A was used instead of 2-bromo-4-chloro-1-iodobenzene and a reactant B was used instead of dibenzofuran-3-boronic acid. The used main reactants, the synthesized intermediates and their yields are shown in Table 1.

TABLE 1

| Reactant A | Reactant B | Intermediate IM x-1 | Yield/% |
|---|---|---|---|
| 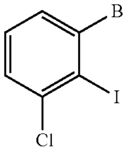 | 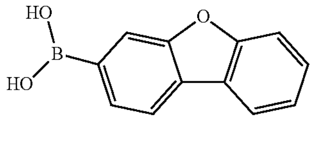 [SMILES: OB(O)c1ccc2c(c1)oc1ccccc12] | 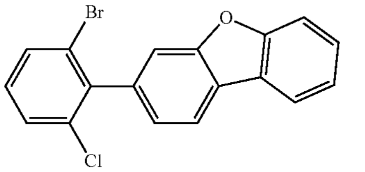 [SMILES: Clc1cccc(Br)c1-c1ccc2c(c1)oc1ccccc12] | 60 |

TABLE 1-continued
| Reactant A | Reactant B | Intermediate IM x-1 | Yield/ % |
|---|---|---|---|
| 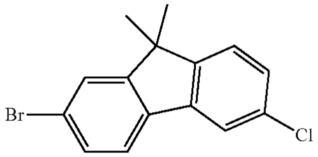 [SMILES: CC1(C)c2ccc(Cl)cc2-c2ccc(Br)cc21] | 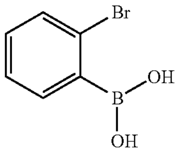 | 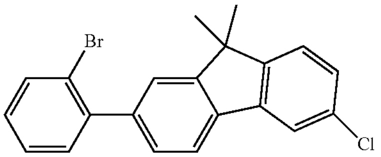 IM c-1 | 58 |
| 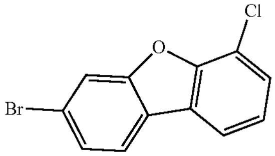 | 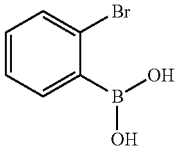 | 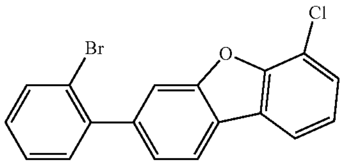 IM d-1 | 61 |
| 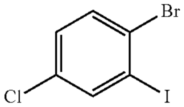 | 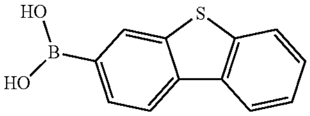 [SMILES: OB(O)c1ccc2c(c1)sc1ccccc12] | 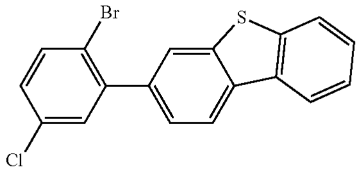 IM e-1 | 63 |
| 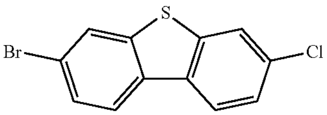 [SMILES: Clc1ccc2c(c1)sc1cc(Br)ccc12] | 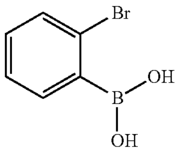 | 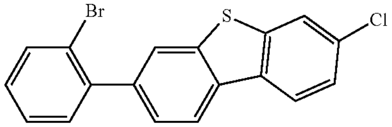 IM f-1 | 57 |
| 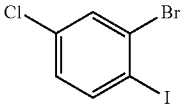 | 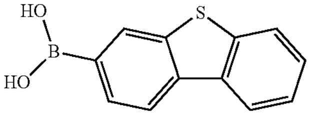 [SMILES: OB(O)c1ccc2c(c1)sc1ccccc12] | 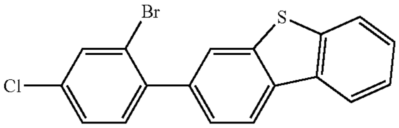 IM g-1 | 59 |
| 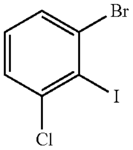 | 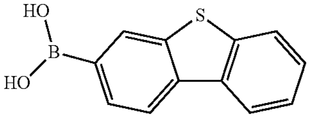 [SMILES: OB(O)c1ccc2c(c1)sc1ccccc12] | 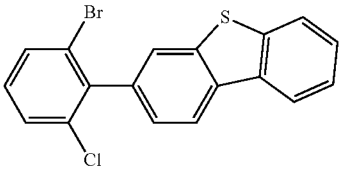 | 60 |
| 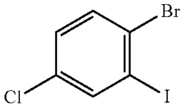 | 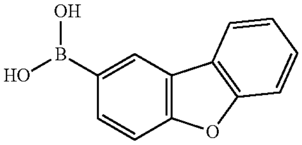 [SMILES: OB(O)c1ccc2oc3ccccc3c2c1] | 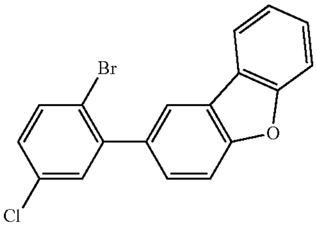 IM i-1 | 64 |

TABLE 1-continued
| Reactant A | Reactant B | Intermediate IM x-1 | Yield/ % |
|---|---|---|---|
| 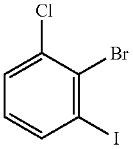 | 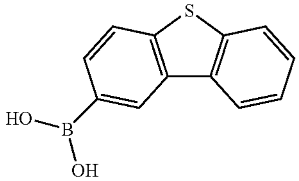 [SMILES: OB(O)c1ccc2sc3ccccc3c2c1] | 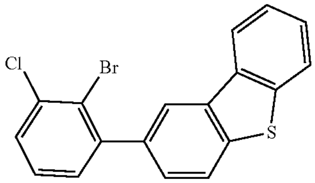 [SMILES: Clc1cccc(-c2ccc3sc4ccccc4c3c2)c1Br] | 56 |
| 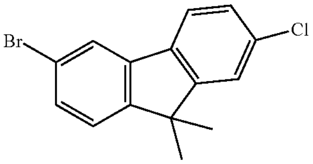 [SMILES: CC1(C)c2ccc(Br)cc2-c2ccc(Cl)cc21] | 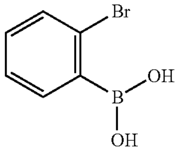 | 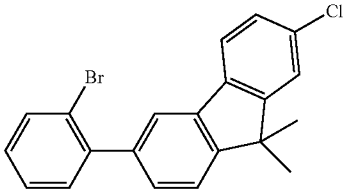 IM k-1 | 67 |
| 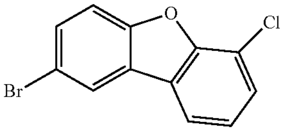 [SMILES: Clc1cccc2c1oc1ccc(Br)cc12] | 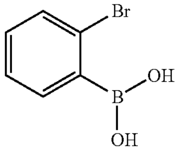 | 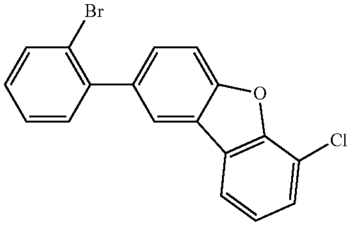 [SMILES: Clc1cccc2c1oc1ccc(-c3ccccc3Br)cc12] | 62 |
| 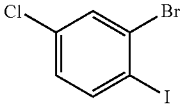 | 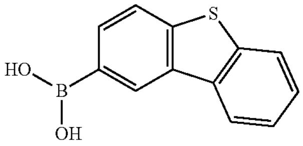 [SMILES: OB(O)c1ccc2sc3ccccc3c2c1] | 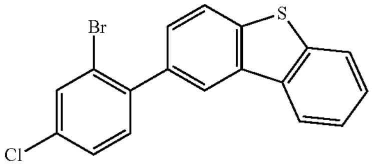 IM m-1 | 64 |
| 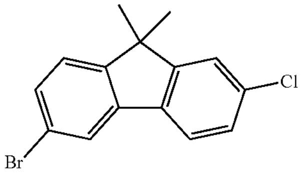 [SMILES: CC1(C)c2ccc(Br)cc2-c2ccc(Cl)cc21] | 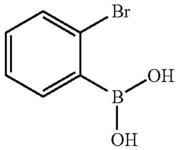 | 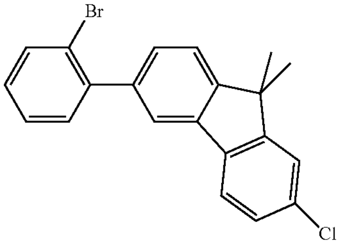 [SMILES: CC1(C)c2ccc(-c3ccccc3Br)cc2-c2ccc(Cl)cc21] | 66 |
| 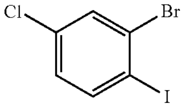 | 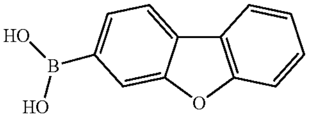 | 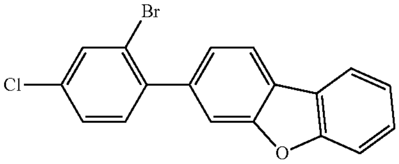 IM o-1 | 63 |
| 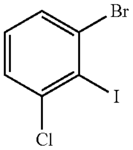 | 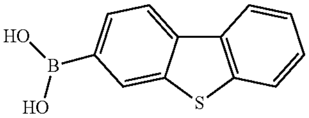 [SMILES: OB(O)c1ccc2c(c1)sc1ccccc12] | 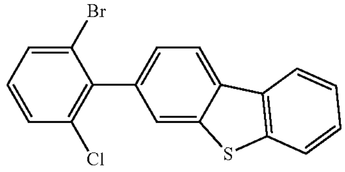 [SMILES: Clc1cccc(Br)c1-c1ccc2c(c1)sc1ccccc12] | 62 |

TABLE 1-continued
| Reactant A | Reactant B | Intermediate IM x-1 | Yield/ % |
|---|---|---|---|
| 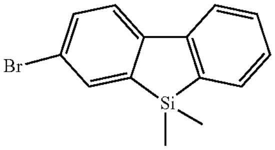 [SMILES: C[Si]1(C)c2ccccc2-c2ccc(Br)cc21] | 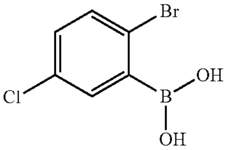 [SMILES: OB(O)c1cc(Cl)ccc1Br] | 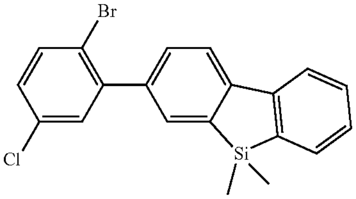 IM q-1 | 61 |
| 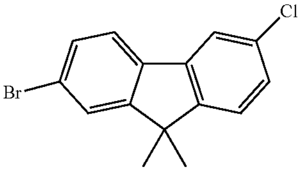 [SMILES: CC1(C)c2ccc(Cl)cc2-c2ccc(Br)cc21] | 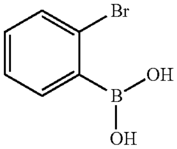 | 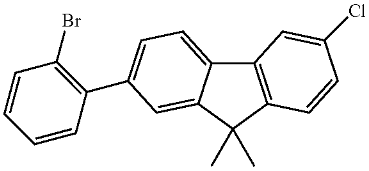 [SMILES: CC1(C)c2ccc(Cl)cc2-c2ccc(-c3ccccc3Br)cc21] | 60 |
| 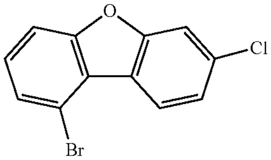 [SMILES: Clc1ccc2c(c1)oc1cccc(Br)c12] | 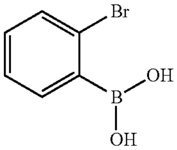 | 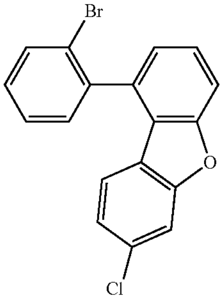 IM s-1 | 59 |
| 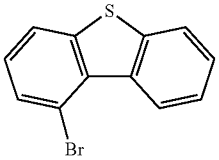 [SMILES: Brc1cccc2sc3ccccc3c12] | 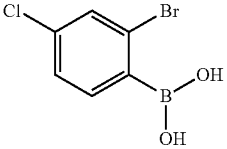 [SMILES: OB(O)c1ccc(Cl)cc1Br] | 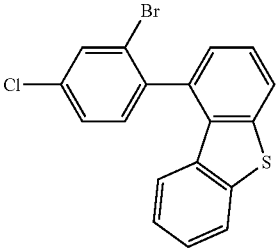 IM t-1 | 64 |
| 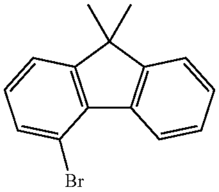 [SMILES: CC1(C)c2ccccc2-c2c(Br)cccc21] | 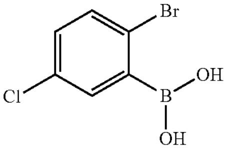 [SMILES: OB(O)c1cc(Cl)ccc1Br] | 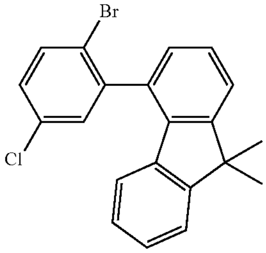 IM u-1 | 65 |

TABLE 1-continued
| Reactant A | Reactant B | Intermediate IM x-1 | Yield/ % |
|---|---|---|---|
| 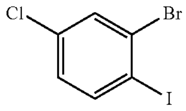 | 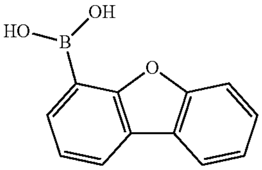 [SMILES: OB(O)c1cccc2c1oc1ccccc12] | 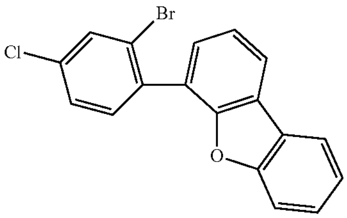 [SMILES: Clc1ccc(-c2cccc3c2oc2ccccc23)c(Br)c1] | 63 |
| 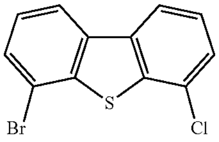 [SMILES: Clc1cccc2c1sc1c(Br)cccc12] | 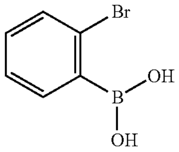 | 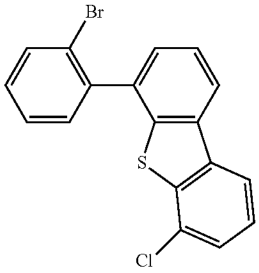 IM w-1 | 58 |
| 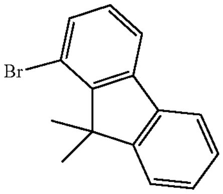 [SMILES: CC1(C)c2ccccc2-c2cccc(Br)c21] | 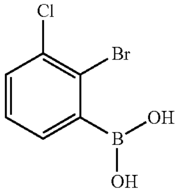 [SMILES: OB(O)c1cccc(Cl)c1Br] | 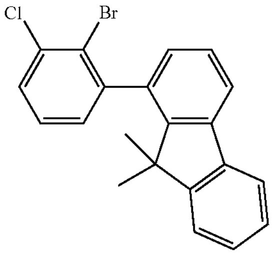 IM x-1 | 58 |
| 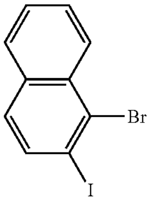 [SMILES: Brc1c(I)ccc2ccccc12] | 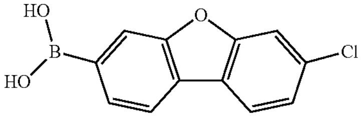 [SMILES: OB(O)c1ccc2c(c1)oc1cc(Cl)ccc12] | 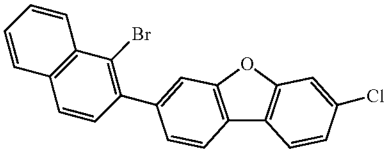 IM y-1 | 59 |
| 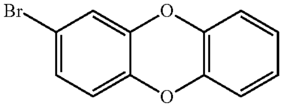 [SMILES: Brc1ccc2c(c1)Oc1ccccc1O2] | 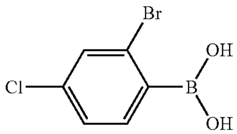 [SMILES: OB(O)c1ccc(Cl)cc1Br] | 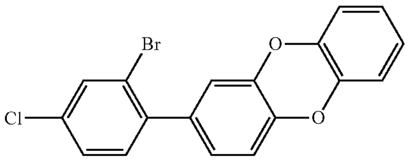 | 61 |
2. Preparation of Intermediate-IM a-2
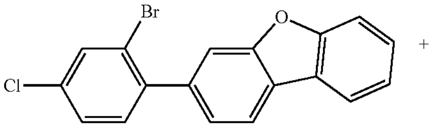
IM a-1
-continued
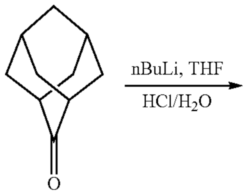

-continued

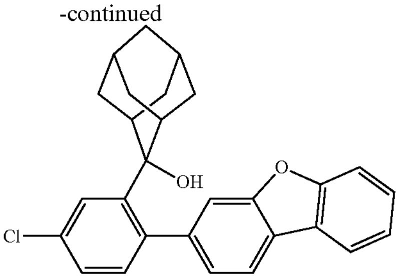

IM a-2

The intermediate IM a-1 (33.8 g, 94.5 mmol) and tetrahydrofuran (280 mL) were added to a flask, and cooled to −78° C. under nitrogen protection, a solution (2.5 M) of n-butyllithium (57 mL, 141.75 mmol) in tetrahydrofuran was added dropwise under stirring, after the dropwise addition was complete, stirring was performed for 1 h while heat preservation, a solution of adamantanone (11.3 g, 75.6 mmol) in tetrahydrofuran (56 mL) was added dropwise while maintaining at −78° C., after the addition was complete, heat preservation was performed for 1 $h_1$, then the system was heated to room temperature, stirring was performed for 24 $h_1$, hydrochloric acid (12M) (17.7 mL, 212.59 mmol) (100 mL) was added to the reaction solution, stirring was performed for 1 h, liquid separation was performed, the obtained organic phase was washed with water to be neutral, and dried by anhydrous magnesium sulfate, and a solvent was removed under reduced pressure to obtain a crude product, and the crude product was purified by silica gel column chromatography using a dichloromethane/n-heptane system to obtain a white solid intermediate IM a-2 (20.3 g, yield: 50%).

Intermediates IM x-2 listed in Table 2 were synthesized by the same method as that for synthesis of the intermediate IM a-2 except that a reactant C was used instead of the intermediate IM a-1. The used main reactants, the synthesized intermediates and their yields are shown in Table 2.

TABLE 2

| Reactant C | Intermediate IM x-2 | Yield/% |
|---|---|---|
| 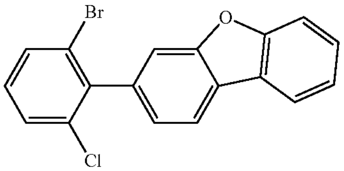 IM b-1 | 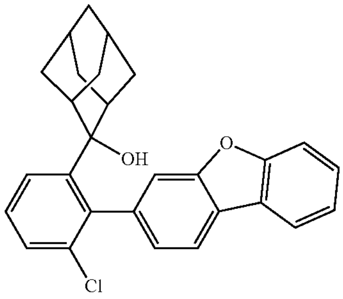 IM b-2 | 56 |
| 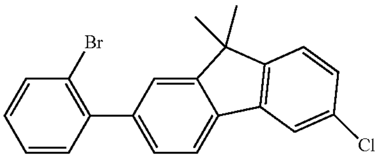 IM c-1 | 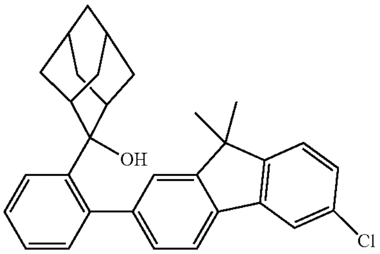 IM c-2 | 54 |
| 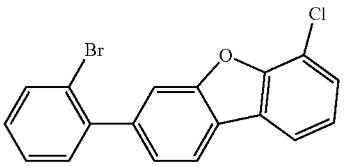 IM d-1 | 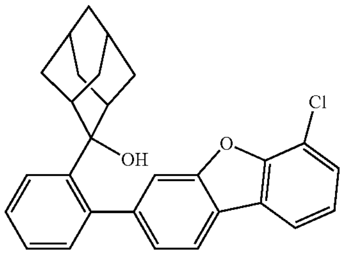 IM d-2 | 53 |

TABLE 2-continued
| Reactant C | Intermediate IM x-2 | Yield/% |
| --- | --- | --- |
| 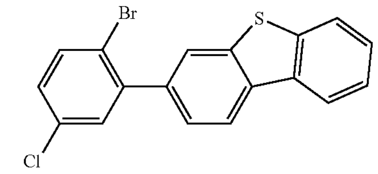 IM e-1 | 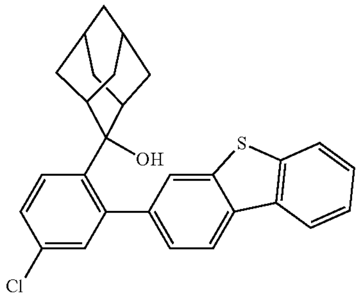 IM e-2 | 52 |
| 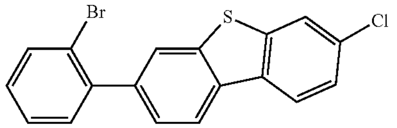 IM f-1 | 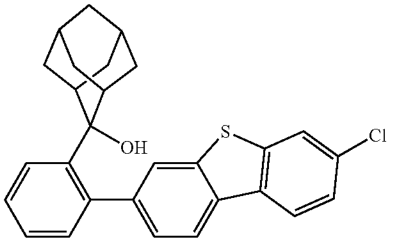 IM f-2 | 51 |
| 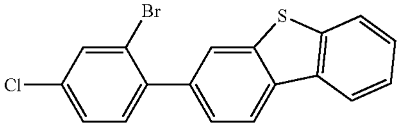 IM g-1 | 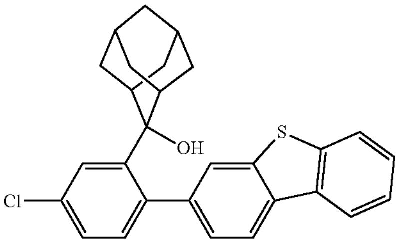 IM g-2 | 57 |
| 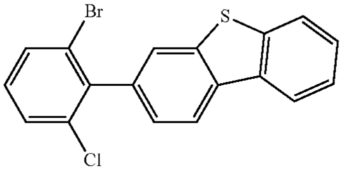 IM h-1 | 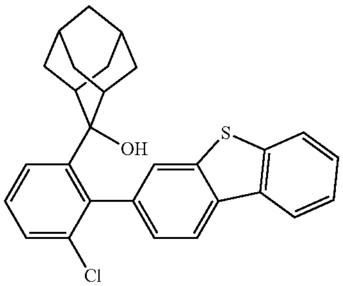 IM h-2 | 50 |

TABLE 2-continued
| Reactant C | Intermediate IM x-2 | Yield/% |
|---|---|---|
| 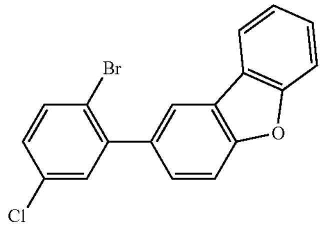 IM i-1 | 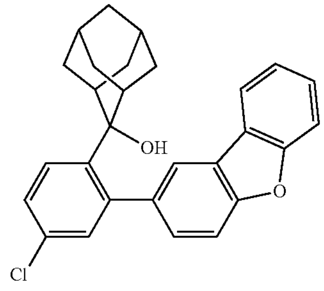 IM i-2 | 59 |
| 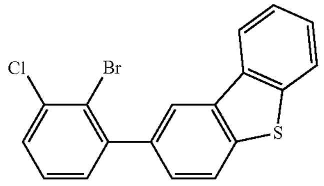 IM j-1 | 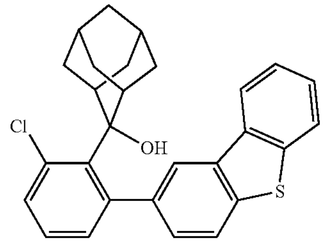 IM j-2 | 57 |
| 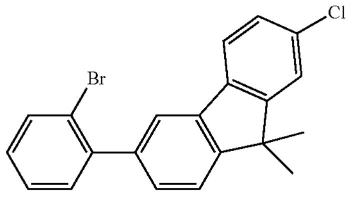 IM k-1 | 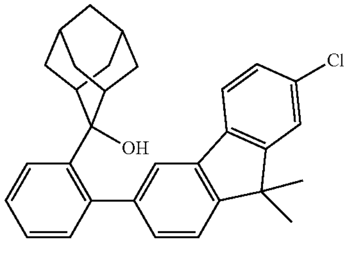 IM k-2 | 55 |
| 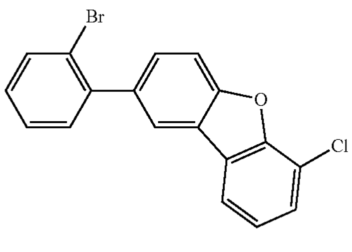 IM l-1 | 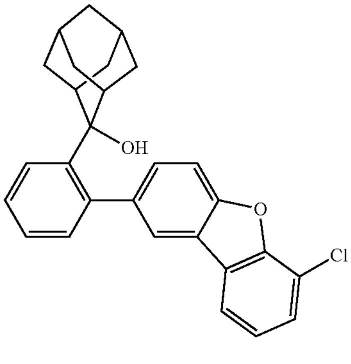 IM l-2 | 54 |

TABLE 2-continued
| Reactant C | Intermediate IM x-2 | Yield/% |
|---|---|---|
| 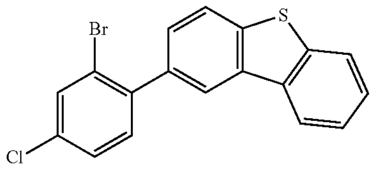 IM m-1 | 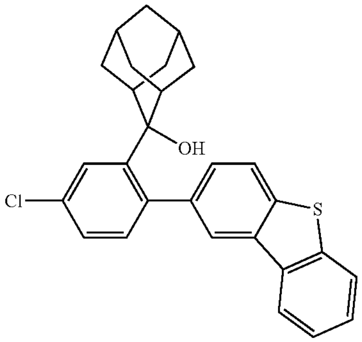 IM m-2 | 52 |
| 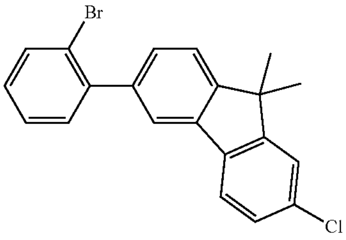 IM n-1 | 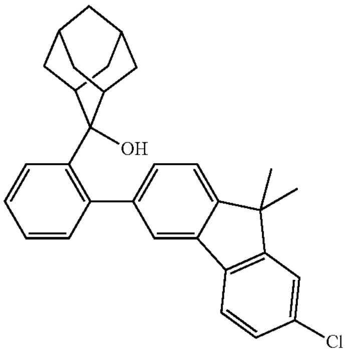 IM n-2 | 54 |
| 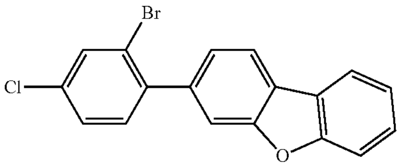 IM o-1 | 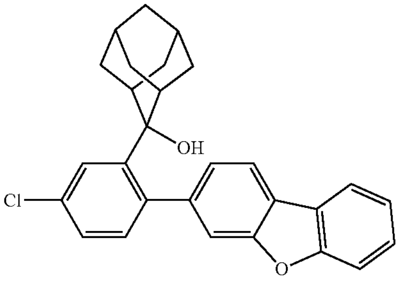 IM o-2 | 56 |
| 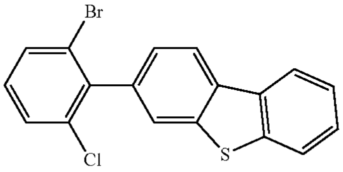 IM p-1 | 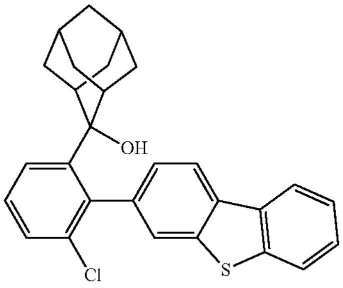 IM p-2 | 53 |

TABLE 2-continued
| Reactant C | Intermediate IM x-2 | Yield/% |
|---|---|---|
| 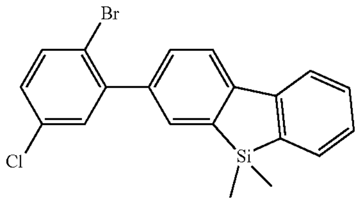 IM q-1 | 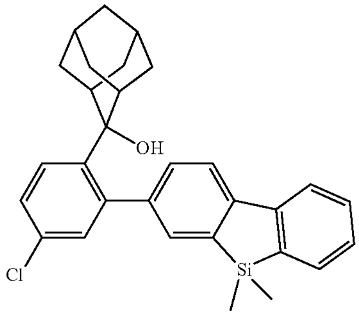 IM q-2 | 52 |
| 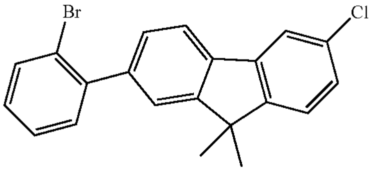 IM r-1 | 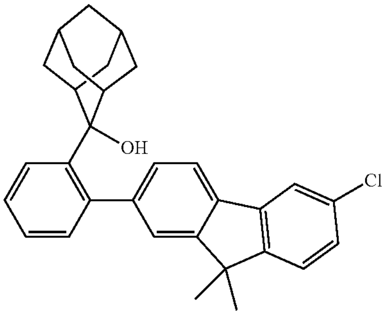 IM r-2 | 53 |
| 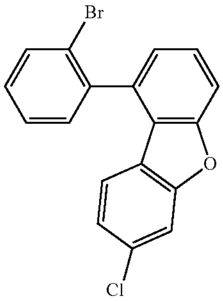 IM s-1 | 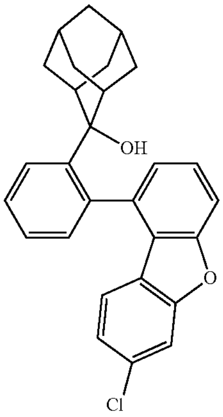 IM s-2 | 59 |

TABLE 2-continued
| Reactant C | Intermediate IM x-2 | Yield/% |
|---|---|---|
| 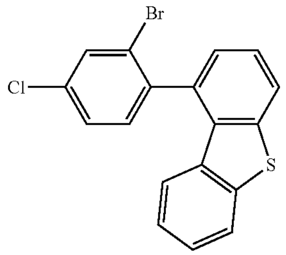<br>IM t-1 | 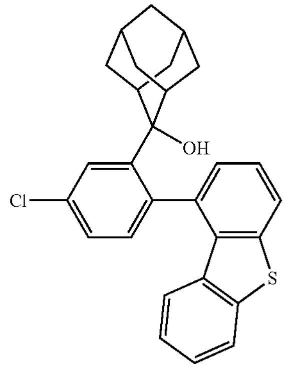<br>IM t-2 | 58 |
| 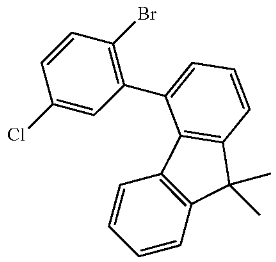<br>IM u-1 | 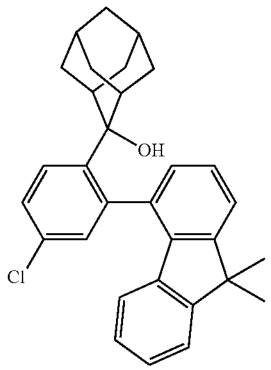<br>IM u-2 | 60 |
| 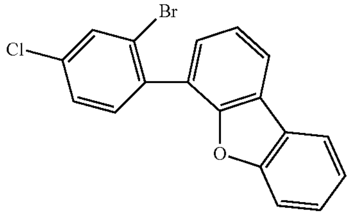<br>IM v-1 | 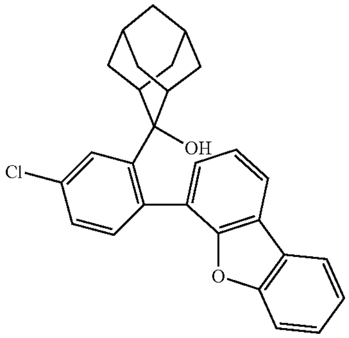<br>IM v-2 | 63 |

TABLE 2-continued
| Reactant C | Intermediate IM x-2 | Yield/% |
| --- | --- | --- |
| 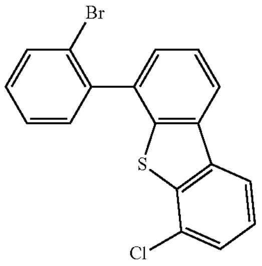 IM w-1 | 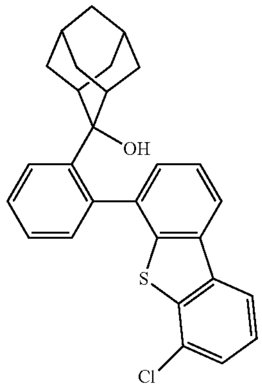 IM w-2 | 59 |
| 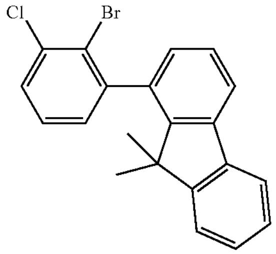 IM x-1 | 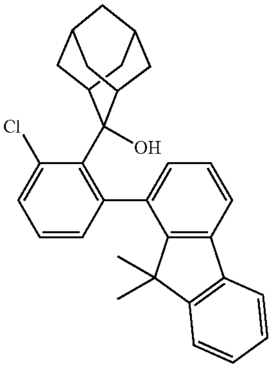 IM x-2 | 61 |
| 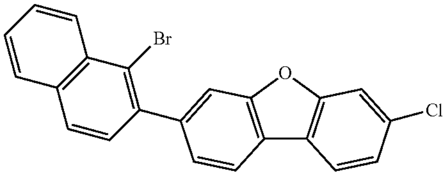 IM y-1 | 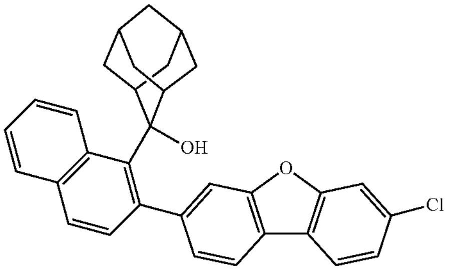 IM y-2 | 59 |
| 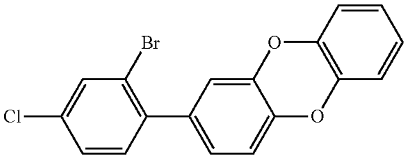 [SMILES: Clc1ccc(-c2ccc3c(c2)Oc2ccccc2O3)c(Br)c1] IM z-1 | 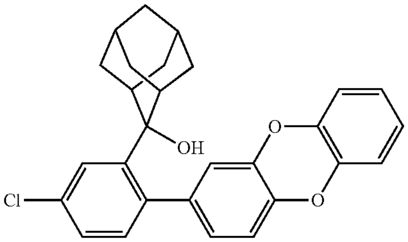 IM z-2 | 58 |

Preparation of Intermediate IM a-3

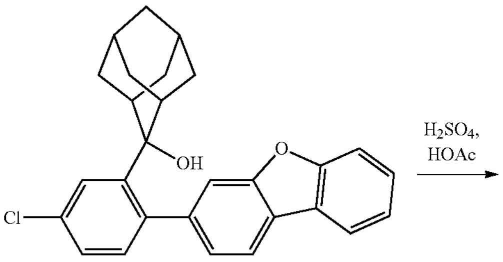

IM a-2

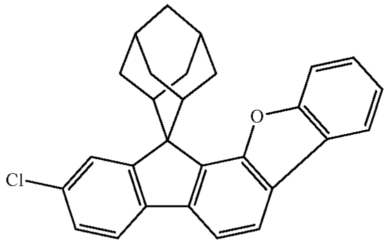

IM a-3

The intermediate IM a-2 (20.3 g, 47.3 mmol) and glacial acetic acid (200 mL) were added into a flask, a solution of concentrated sulfuric acid (98%) (0.9 mL, 9.5 mmol) in acetic acid (20 mL) was slowly added dropwise under stirring at room temperature under nitrogen protection, and after the dropwise addition was complete, the mixture was heated to 60° C., and stirred for 2 h; the resulting reaction solution was cooled to room temperature, the precipitated solid was filtered, and a filter cake was rinsed with water and ethanol, and oven-dried to obtain a crude product; and the crude product was purified by silica gel column chromatography using a dichloromethane/n-heptane system to obtain a white solid intermediate IM a-3 (15.5 g, yield: 80%).

Intermediates IM x-3 listed in Table 3 were synthesized by the same method as that for synthesis of the intermediate IM a-3 except that the reactant D was used instead of the intermediate IM a-2. The used main reactants, the synthesized intermediates and their yields are shown in Table 3.

TABLE 3

| Reactant D | Intermediate x-3 | Yield/% |
|---|---|---|
| 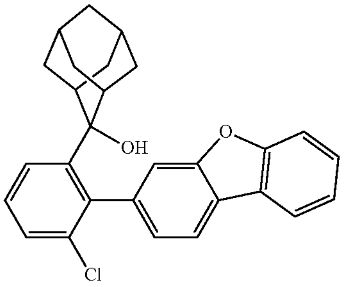 IM b-2 | 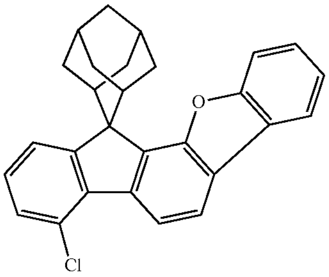 [SMILES: Clc1cccc2c1oc1c3c(ccc12)-c1ccccc1C31C2CC3CC(C2)CC1C3] IM b-3 | 76 |
| 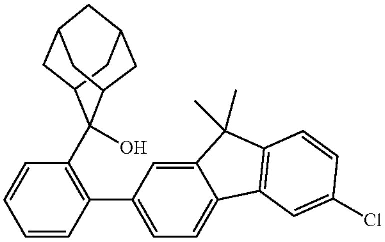 IM c-2 | 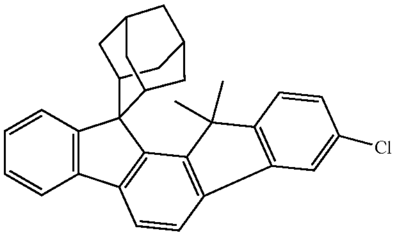 IM c-3 | 77 |
| 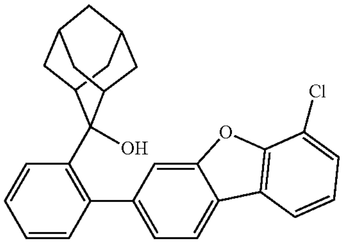 IM d-2 | 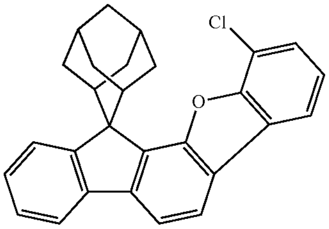 IM d-3 | 73 |

TABLE 3-continued
| Reactant D | Intermediate x-3 | Yield/% |
|---|---|---|
| 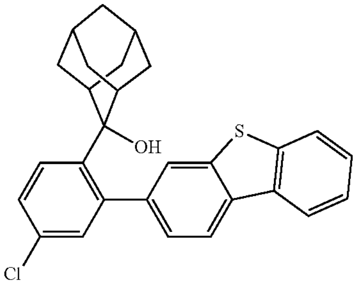 IM e-2 | 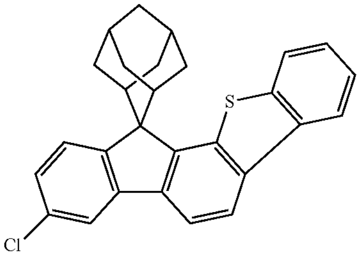 IM e-3 | 72 |
| 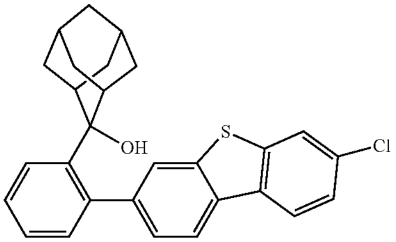 IM f-2 | 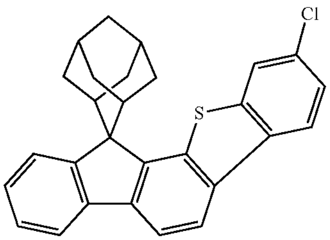 IM f-3 | 79 |
| 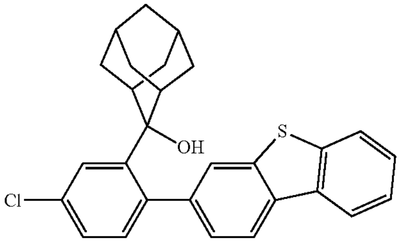 IM g-2 | 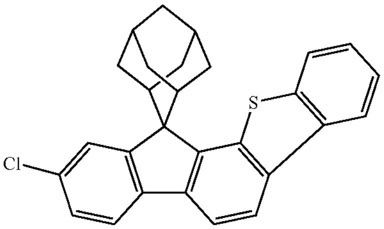 IM g-3 | 80 |
| 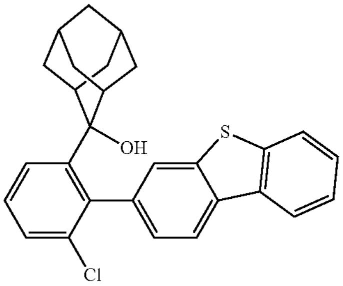 IM h-2 | 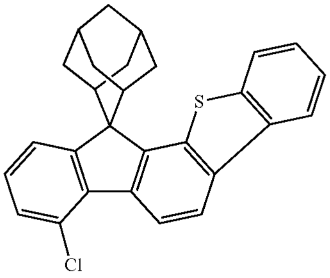 IM h-3 | 75 |

TABLE 3-continued
| Reactant D | Intermediate x-3 | Yield/% |
| --- | --- | --- |
| 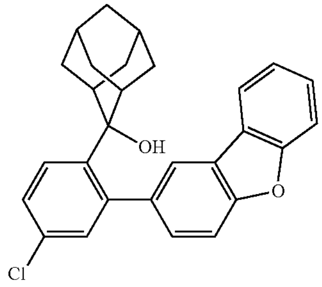 IM i-2 | 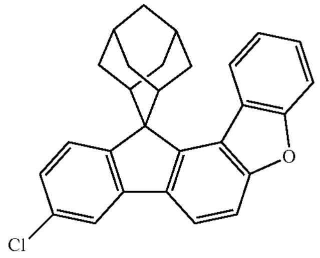 IM i-3 | 73 |
| 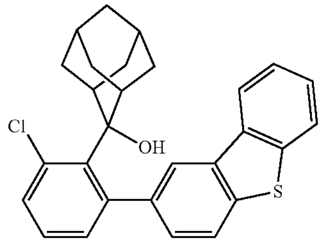 IM j-2 | 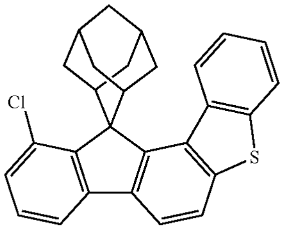 IM j-3 | 75 |
| 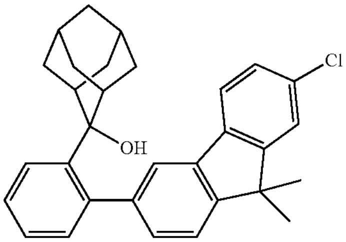 IM k-2 | 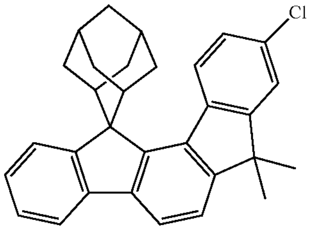 IM k-3 | 72 |
| 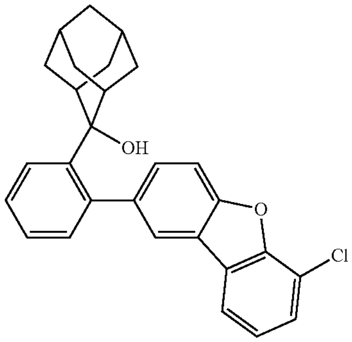 IM l-2 | 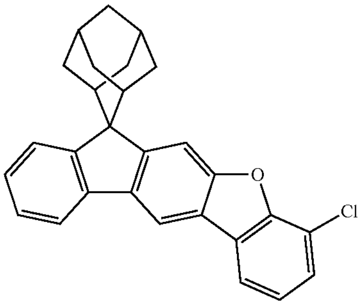 IM l-3 | 69 |

TABLE 3-continued
| Reactant D | Intermediate x-3 | Yield/% |
|---|---|---|
| 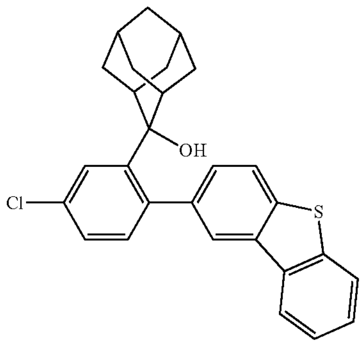 IM m-2 | 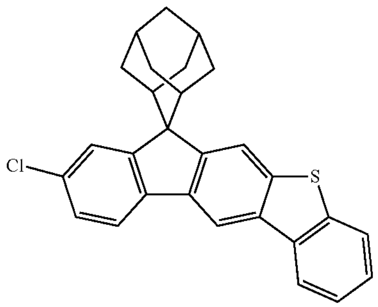 IM m-3 | 68 |
| 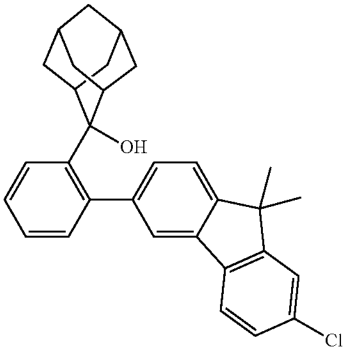 IM n-2 | 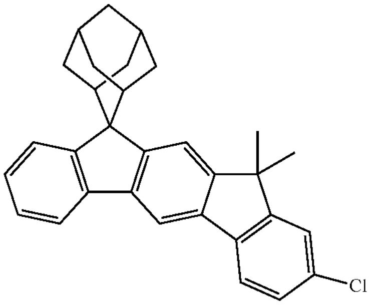 IM n-3 | 79 |
| 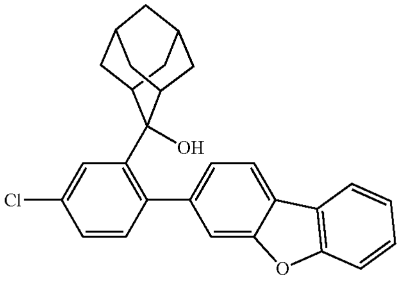 IM o-2 | 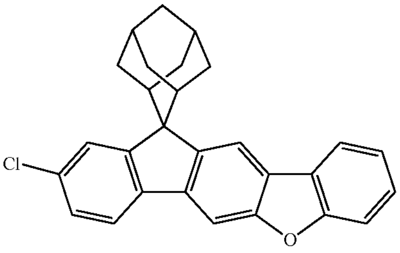 IM o-3 | 76 |
| 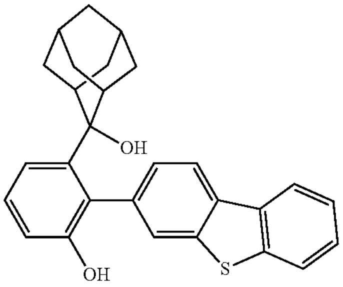 IM p-2 | 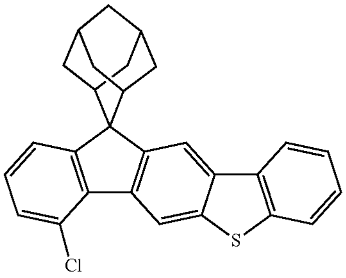 IM p-3 | 73 |

TABLE 3-continued
| Reactant D | Intermediate x-3 | Yield/% |
| --- | --- | --- |
| 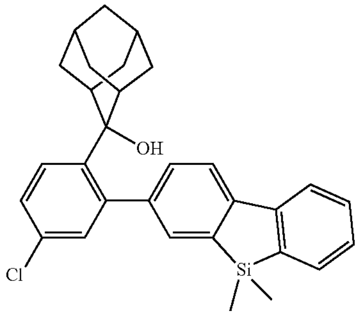 IM q-2 | 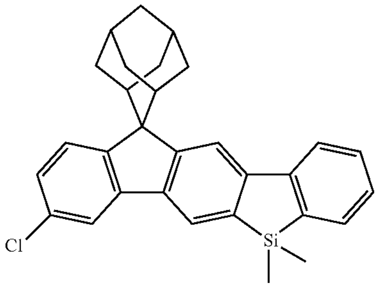 IM q-3 | 71 |
| 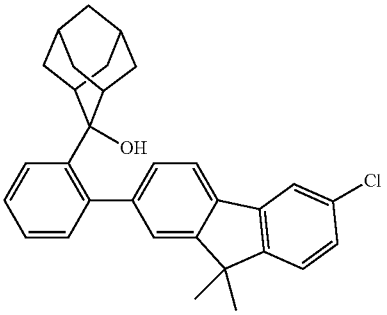 IM r-2 | 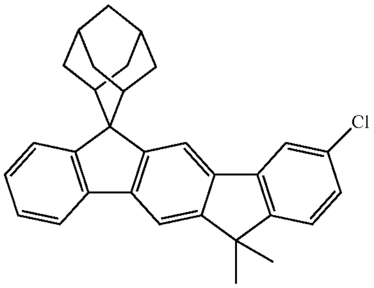 IM r-3 | 70 |
| 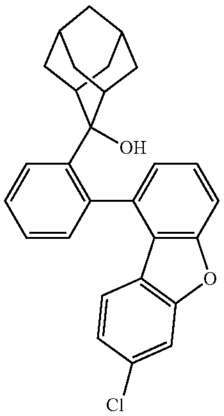 IM s-2 | 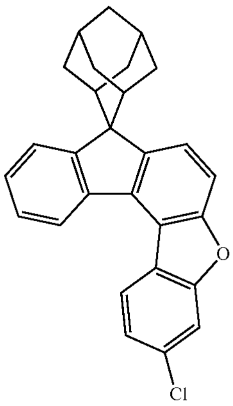 IM s-3 | 79 |

TABLE 3-continued
| Reactant D | Intermediate x-3 | Yield/% |
|---|---|---|
| 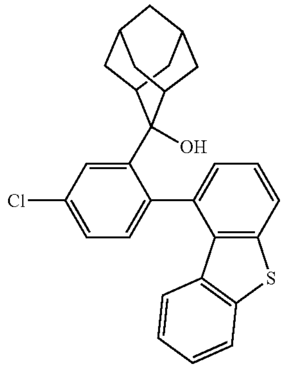 IM t-2 | 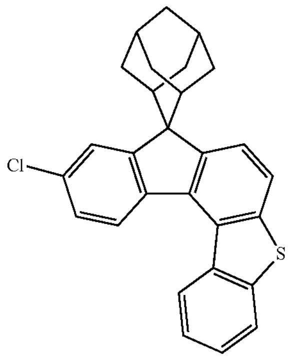 IM t-3 | 80 |
| 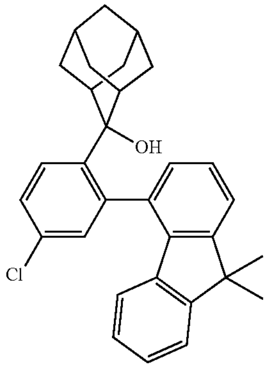 IM u-2 | 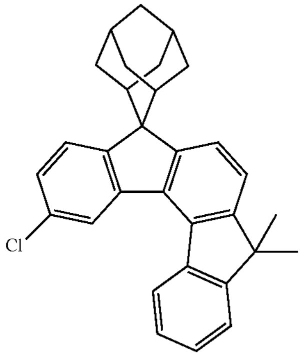 IM u-3 | 81 |
| 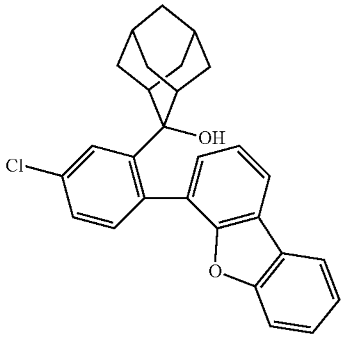 IM v-2 | 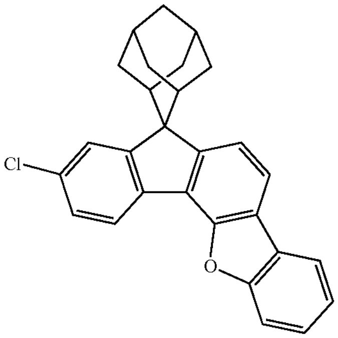 IM v-3 | 77 |

TABLE 3-continued
| Reactant D | Intermediate x-3 | Yield/% |
| --- | --- | --- |
| 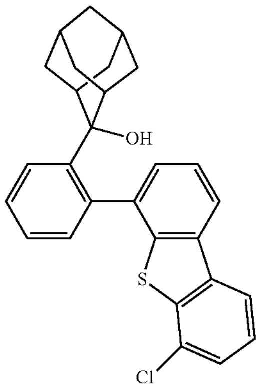 IM w-2 | 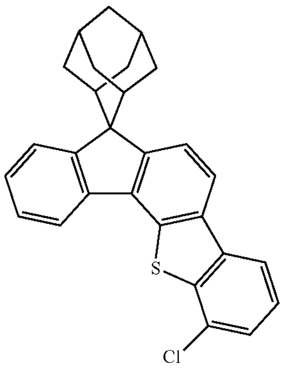 IM w-3 | 78 |
| 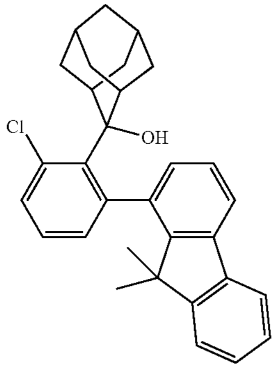 IM x-2 | 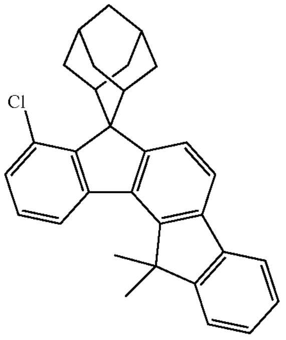 IM x-3 | 74 |
| 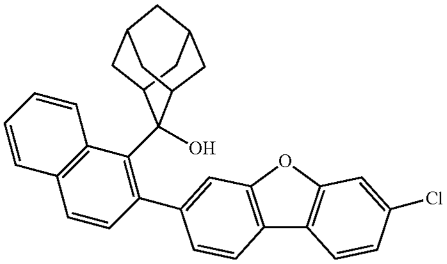 IM y-2 | 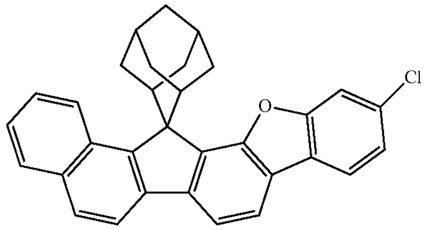 IM y-3 | 73 |
| 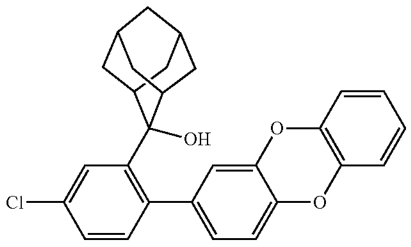 IM z-2 | 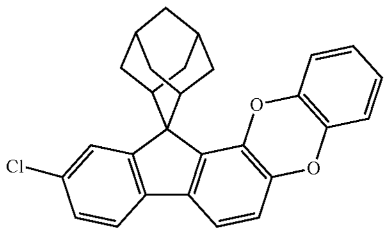 IM z-3 | 72 |

4. Preparation of Intermediate IM a-4

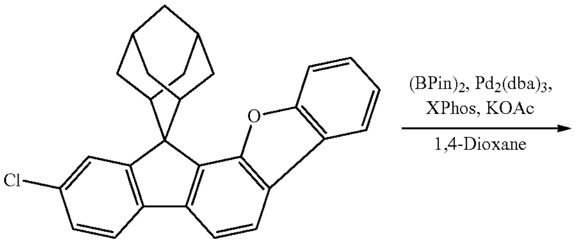

IM a-3

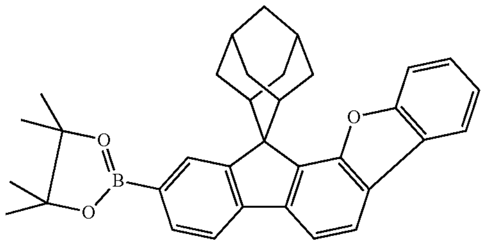

IM a-4

The intermediate IM a-3 (15.5 g, 37.7 mmol), bis(pinacolato)diboron (11.5 g, 45.3 mmol), tris(dibenzylideneacetone)dipalladium (0.35 g, 0.38 mmol), 2-dicyclohexylphosphino-2',4',6'-triisopropylbiphenyl (0.35 g, 0.75 mmol), potassium acetate (11.1 g, 113.1 mmol) and 1,4-dioxane (150 mL) were added to a flask, and stirred under reflux at 100° C. for 12 h under nitrogen protection; the resulting reaction solution was cooled to room temperature, dichloromethane and water were added to the reaction solution, liquid separation was performed, the obtained organic phase was washed with water and dried by anhydrous magnesium sulfate, and a solvent was removed under reduced pressure to obtain a crude product; and the crude product was purified by silica gel column chromatography using a dichloromethane/n-heptane system to obtain a white solid intermediate IM a-4 (10.0 g, yield: 53%).

Intermediates IM x-4 listed in Table 4 were synthesized by the same method as that for synthesis of the intermediate IM a-4 except that a reactant E was used instead of the intermediate IM a-3. The used main reactants, the synthesized intermediates and their yields are shown in Table 4.

TABLE 4

| Reactant E | Intermediate IM x-4 | Yield/% |
|---|---|---|
| 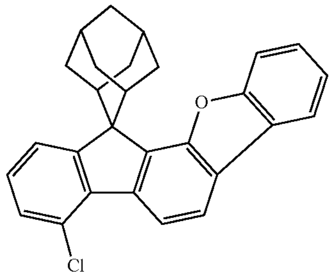 [SMILES: Clc1cccc2c1oc1c3c(ccc12)-c1ccccc1C31C2CC3CC(C2)CC1C3] IM b-3 | 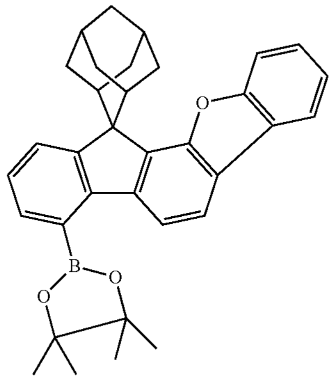 IM b-4 | 53 |
| 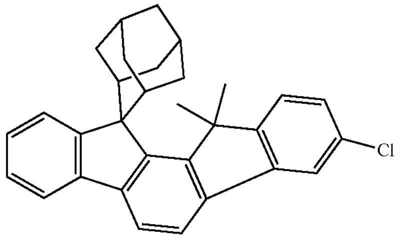 IM c-3 | 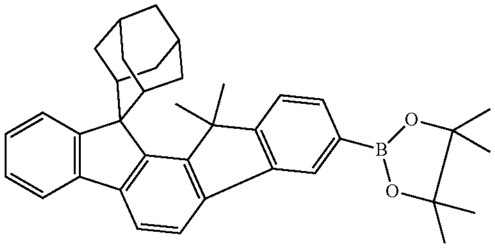 IM c-4 | 52 |

TABLE 4-continued
| Reactant E | Intermediate IM x-4 | Yield/% |
|---|---|---|
| 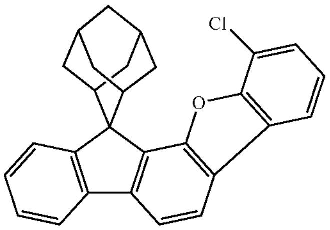 IM d-3 | 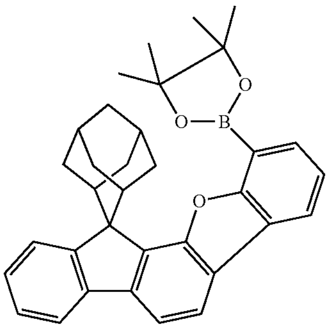 IM d-4 | 50 |
| 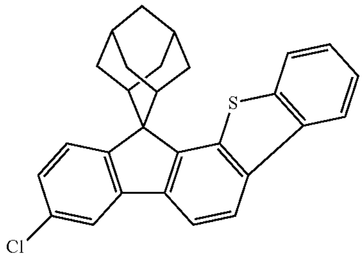 IM e-3 | 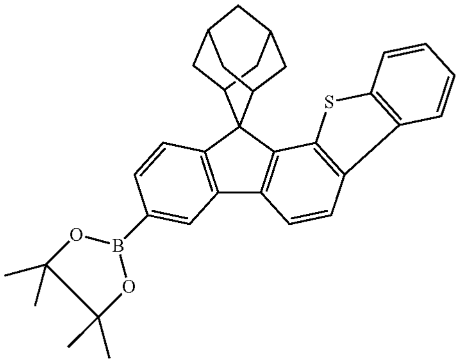 IM e-4 | 56 |
| 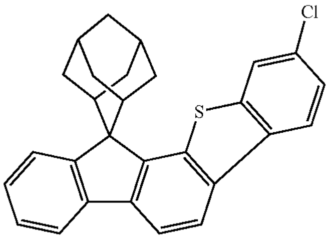 IM f-3 | 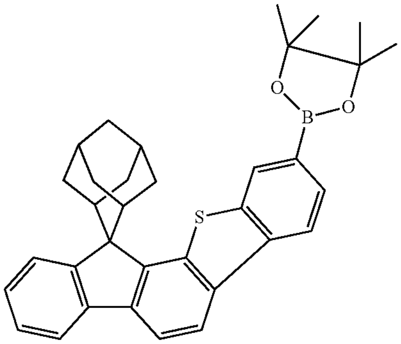 IM f-4 | 57 |
| 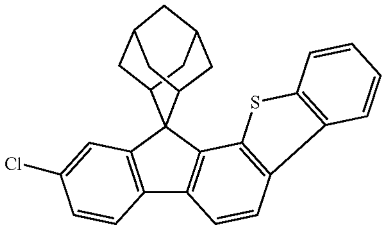 IM g-3 | 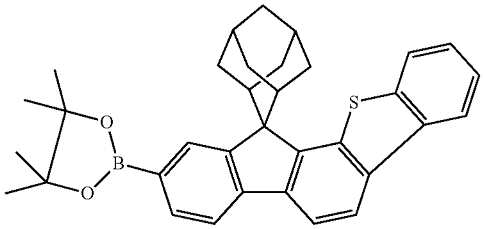 IM g-4 | 58 |

TABLE 4-continued
| Reactant E | Intermediate IM x-4 | Yield/% |
|---|---|---|
| 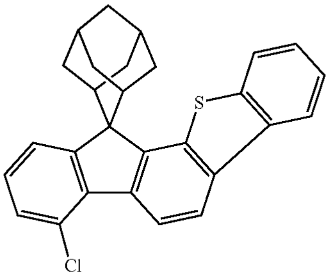 IM h-3 | 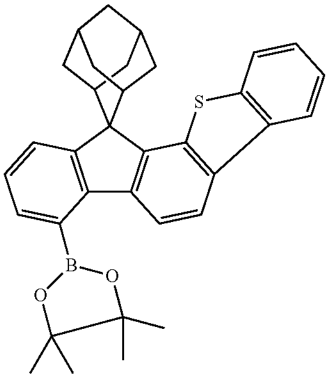 IM h-4 | 55 |
| 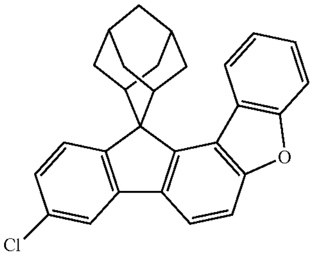 IM i-3 | 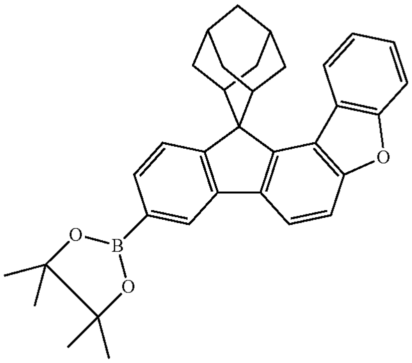 IM i-4 | 59 |
| 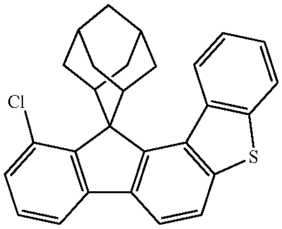 IM j-3 | 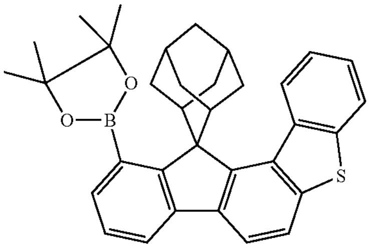 IM j-4 | 58 |
| 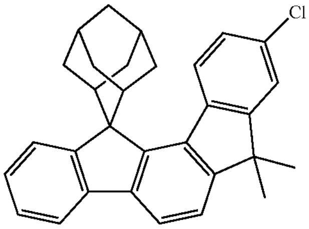 IM k-3 | 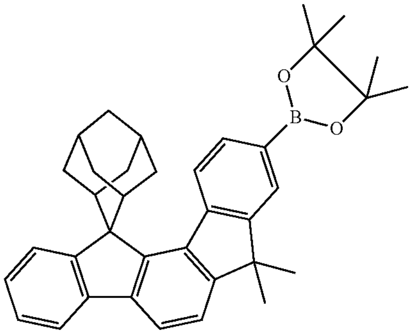 IM k-4 | 58 |

TABLE 4-continued
| Reactant E | Intermediate IM x-4 | Yield/% |
|---|---|---|
| 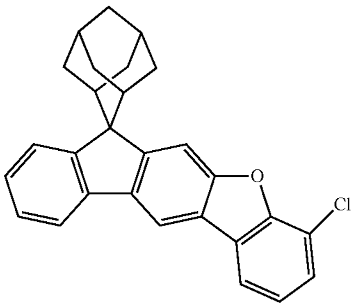 IM l-3 | 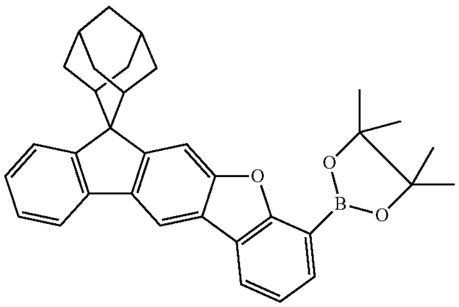 IM l-4 | 56 |
| 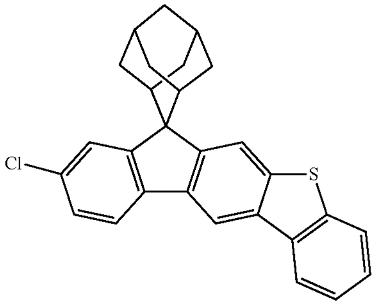 IM m-3 | 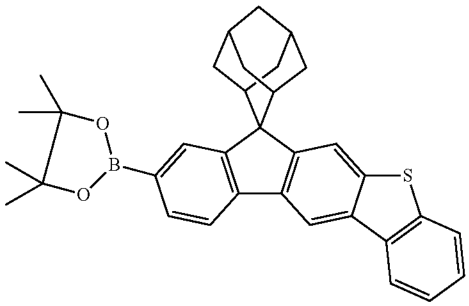 IM m-4 | 54 |
| 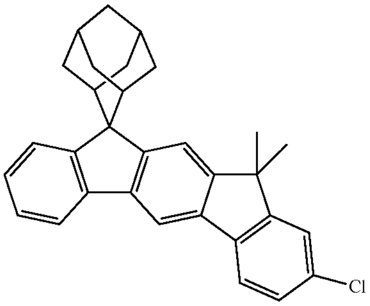 IM n-3 | 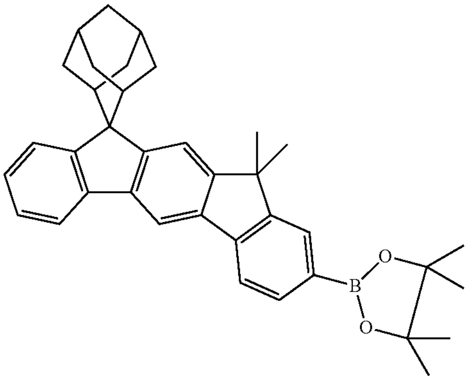 IM n-4 | 60 |
| 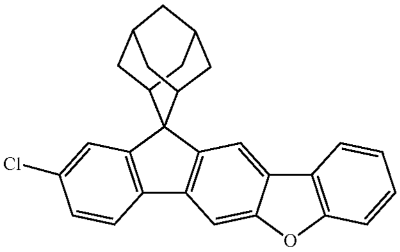 IM o-3 | 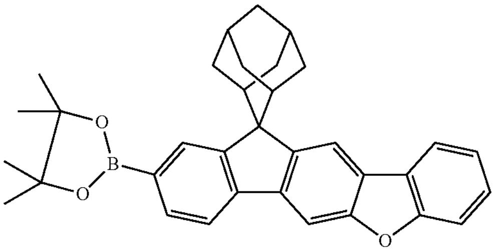 IM o-4 | 59 |

TABLE 4-continued
| Reactant E | Intermediate IM x-4 | Yield/% |
|---|---|---|
| 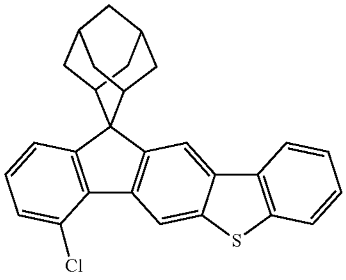 IM p-3 | 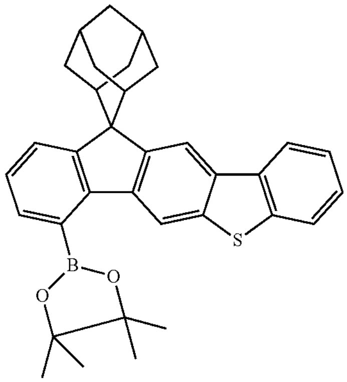 IM p-4 | 56 |
| 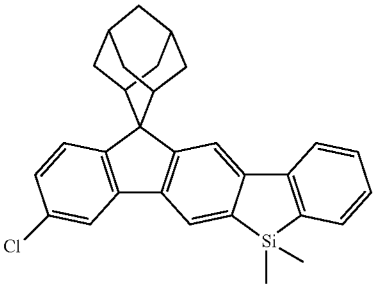 IM q-3 | 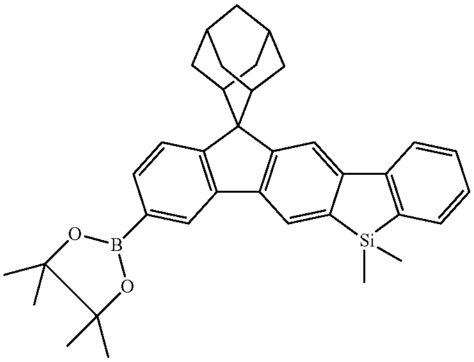 IM q-4 | 55 |
| 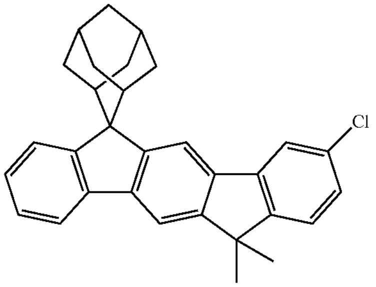 IM r-3 | 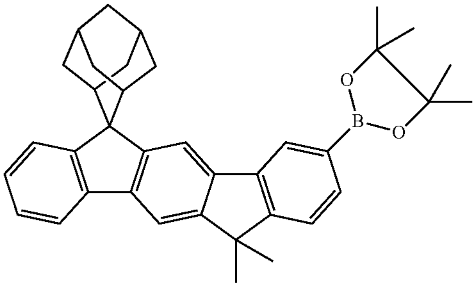 IM r-4 | 57 |

TABLE 4-continued
| Reactant E | Intermediate IM x-4 | Yield/% |
| --- | --- | --- |
| 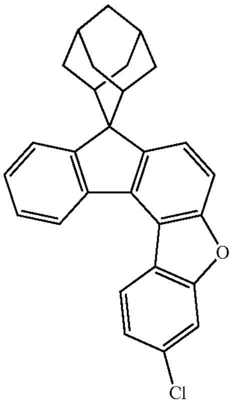 IM s-3 | 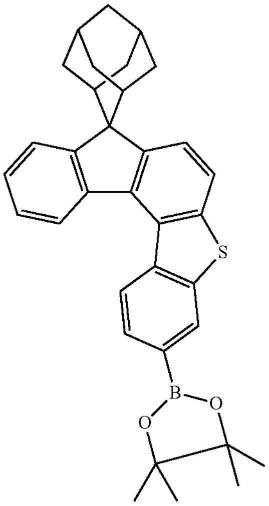 IM s-4 | 58 |
| 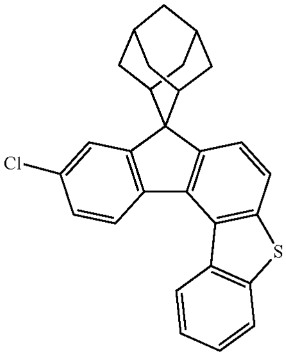 IM t-3 | 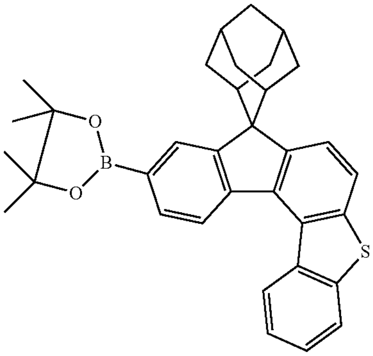 IM t-4 | 57 |
| 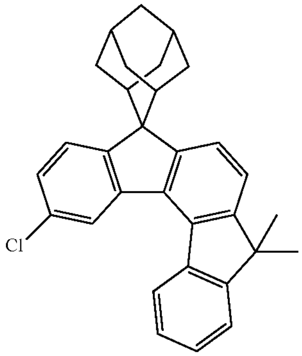 IM u-3 | 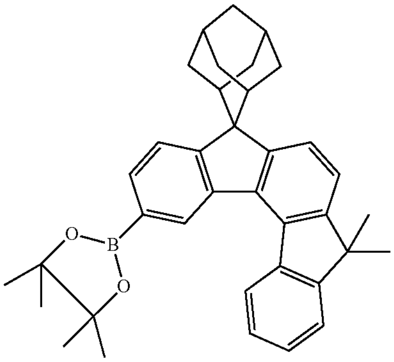 IM u-4 | 55 |

TABLE 4-continued
| Reactant E | Intermediate IM x-4 | Yield/% |
| --- | --- | --- |
| 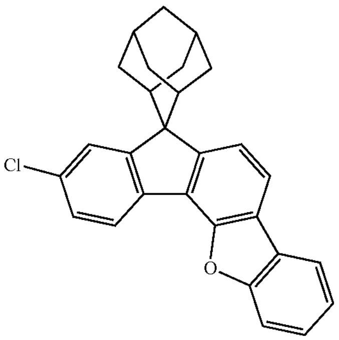 IM v-3 | 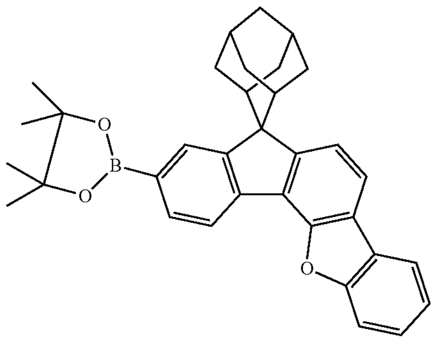 IM v-4 | 54 |
| 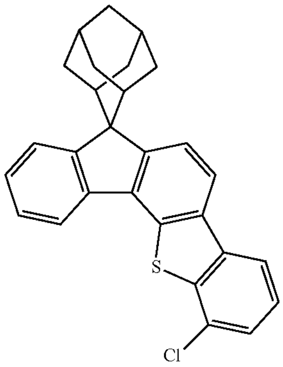 IM w-3 | 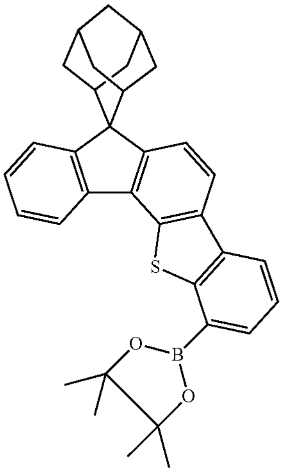 IM w-4 | 57 |
| 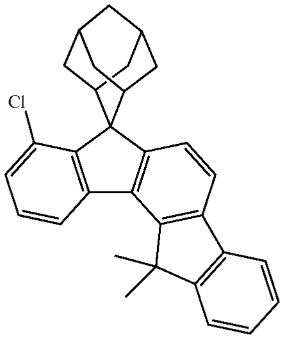 IM x-3 | 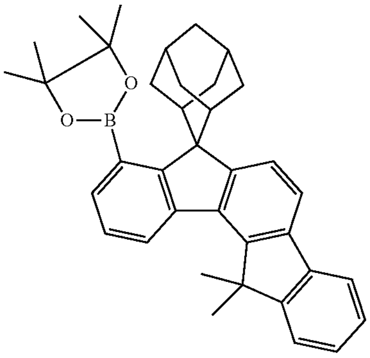 IM x-4 | 52 |

TABLE 4-continued

| Reactant E | Intermediate IM x-4 | Yield/% |
|---|---|---|
| 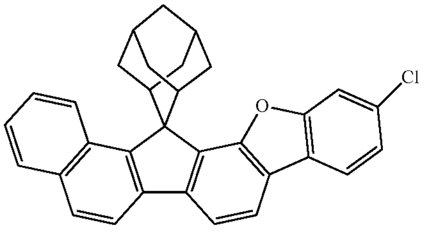 IM y-3 | 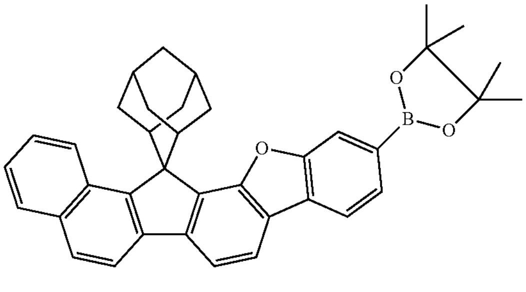 IM y-4 | 59 |
| 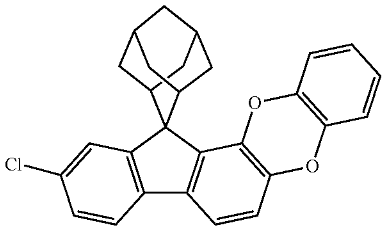 IM z-3 | 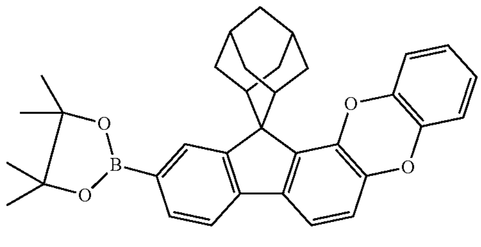 IM z-4 | 58 |

5. Preparation of Compounds

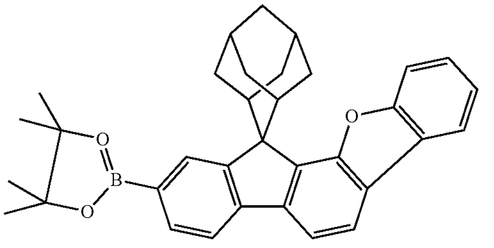

IM a-4

+

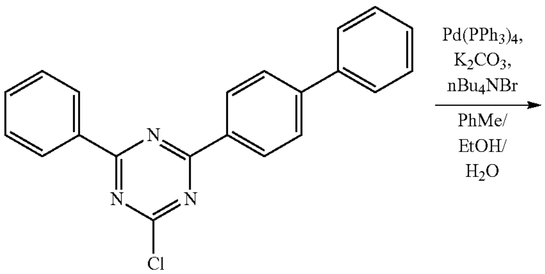

-continued

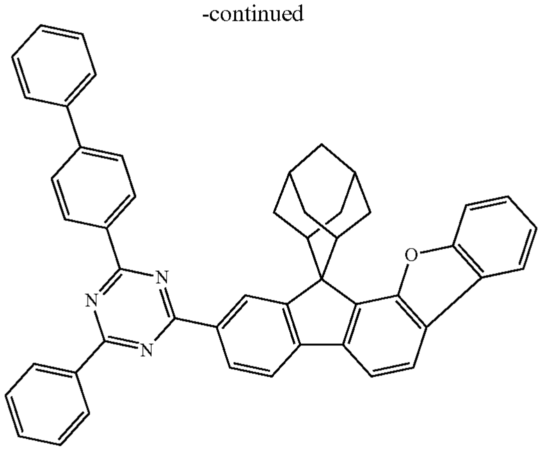

2

The intermediate IM a-4 (10 g, 19.9 mmol), 2-(4-biphenyl)-4-chloro-6-phenyl-1,3,5-triazine (6.2 g, 18.1 mmol), tetrakis(triphenylphosphine)palladium (0.41 g, 0.36 mmol), potassium carbonate (6.2 g, 45.2 mmol), and tetrabutylammonium bromide (1.1 g, 3.6 mmol) were added to a flask, and a mixed solvent of toluene (80 mL), ethanol (20 mL) and water (20 mL) was added, and the mixture was heated to 80° C. under nitrogen protection, and stirred for 8 h while maintaining the temperature; then cooling to room temperature, stirring was stopped, the reaction solution was washed with water, the obtained organic phase was separated, and dried by anhydrous magnesium sulfate, and a solvent was removed under reduced pressure to obtain a crude product; and the crude product was purified by silica gel column chromatography using a dichloromethane/n-heptane mixed solvent as a mobile phase to obtain a white solid compound 2 (8.6 g, yield: 70%).

Compounds listed in Table 5 were synthesized by the same synthesis method as that for the synthesis of the compound 2 except that a reactant F was used instead of the intermediate IM a-4, and a reactant G was used instead of 2-(4-biphenyl)-4-chloro-6-phenyl-1,3,5-triazine. The used main reactants, the synthesized compounds and their yields are shown in Table 5.

TABLE 5
| Reactant F | Reactant G | Compound | Yield/ % |
|---|---|---|---|
| 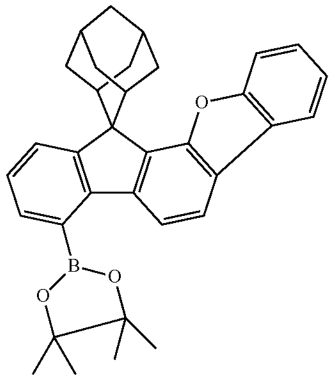 IM b-4 | 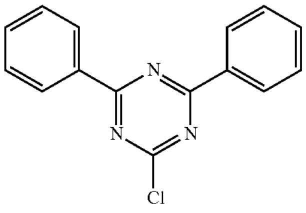 [SMILES: Clc1nc(-c2ccccc2)nc(-c2ccccc2)n1] | 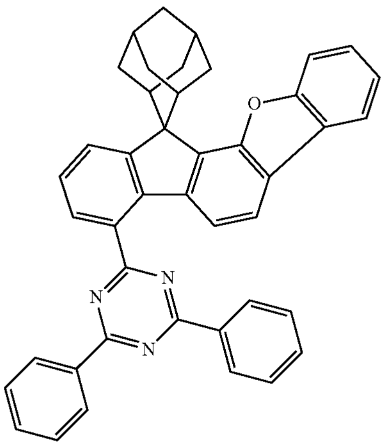 4 | 69 |
| 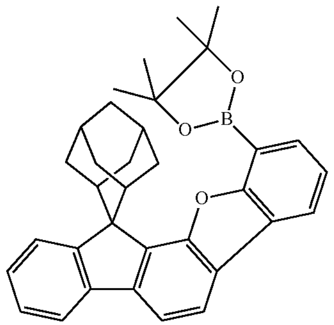 IM d-4 | 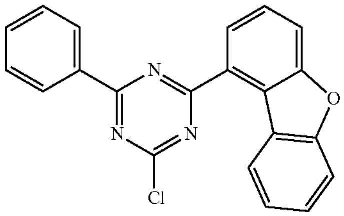 [SMILES: Clc1nc(-c2ccccc2)nc(-c2cccc3oc4ccccc4c23)n1] | 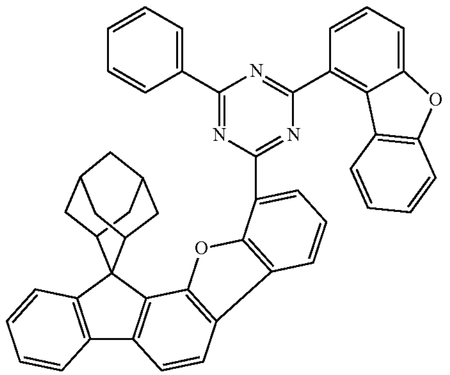 7 | 60 |

TABLE 5-continued
| Reactant F | Reactant G | Compound | Yield/ % |
|---|---|---|---|
| 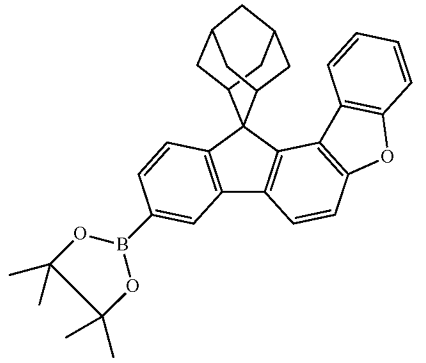 IM i-4 | 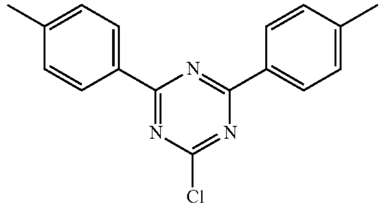 | 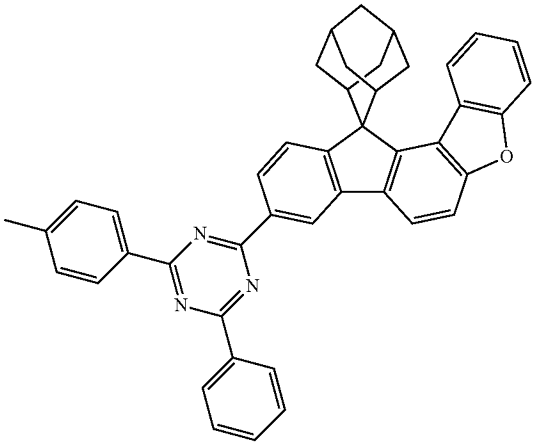 13 | 63 |
| 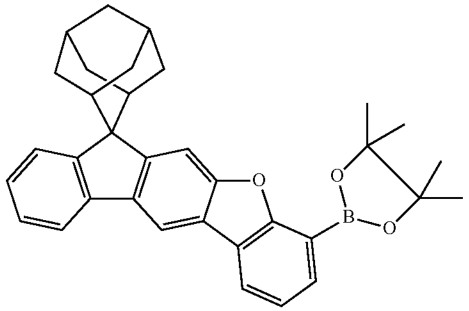 IM l-4 | 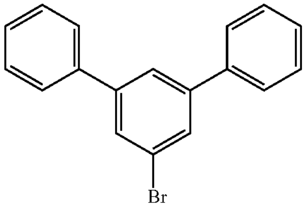 [SMILES: Brc1cc(-c2ccccc2)cc(-c2ccccc2)c1] | 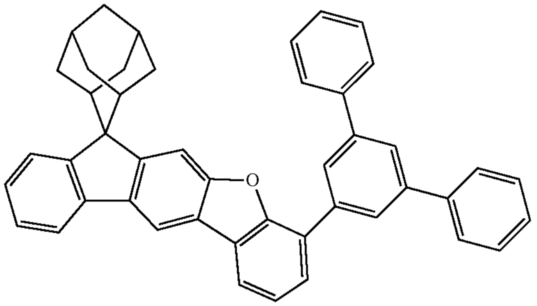 23 | 60 |

TABLE 5-continued
| Reactant F | Reactant G | Compound | Yield/ % |
|---|---|---|---|
| 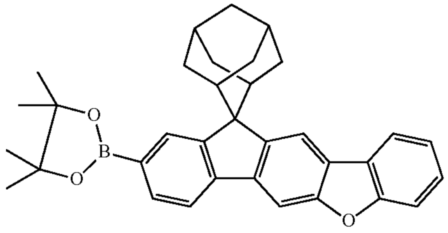 IM o-4 | 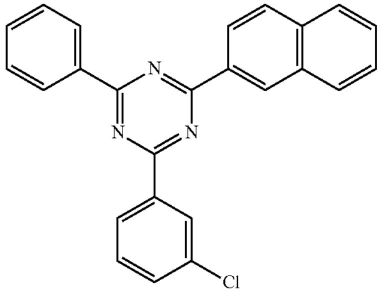 [SMILES: Clc1cccc(-c2nc(-c3ccccc3)nc(-c3ccc4ccccc4c3)n2)c1] | 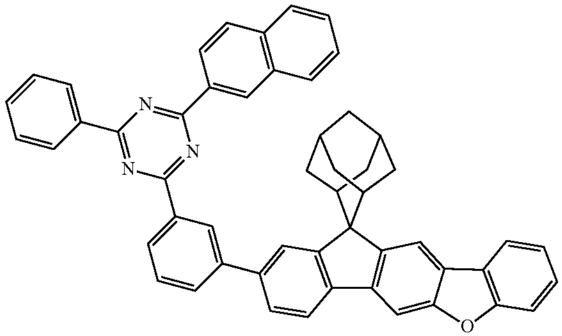 28 | 68 |
| 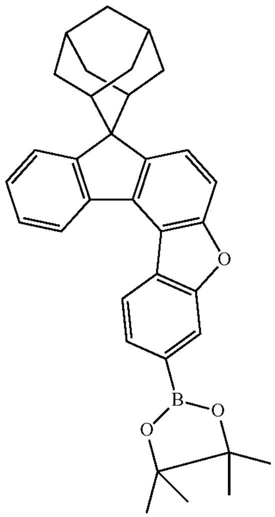 IM s-4 | 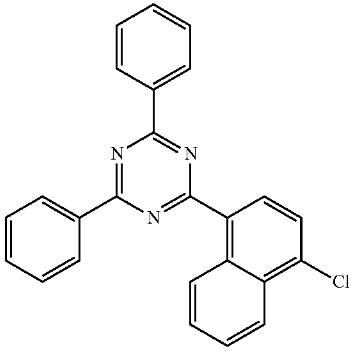 [SMILES: Clc1ccc(-c2nc(-c3ccccc3)nc(-c3ccccc3)n2)c2ccccc12] | 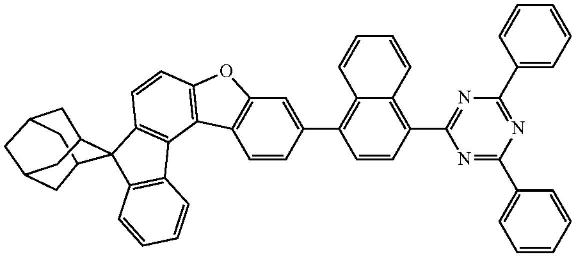 44 | 64 |

TABLE 5-continued
| Reactant F | Reactant G | Compound | Yield/ % |
|---|---|---|---|
| 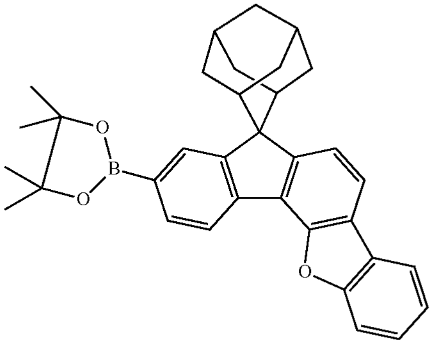 IM v-4 | 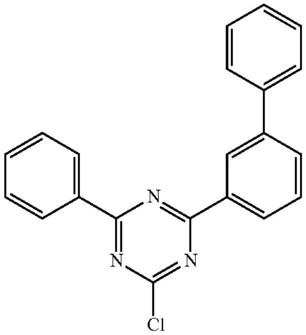 [SMILES: Clc1nc(-c2ccccc2)nc(-c2cccc(-c3ccccc3)c2)n1] | 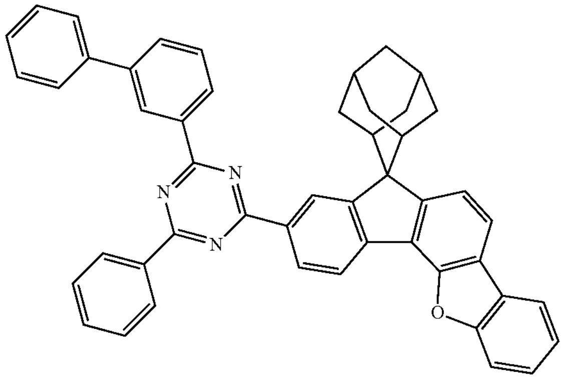 48 | 71 |
| 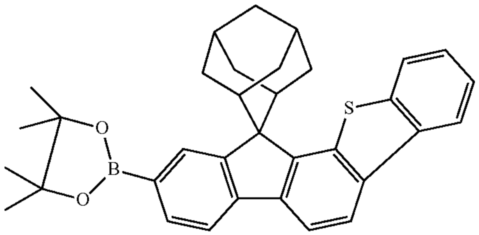 IM g-4 | 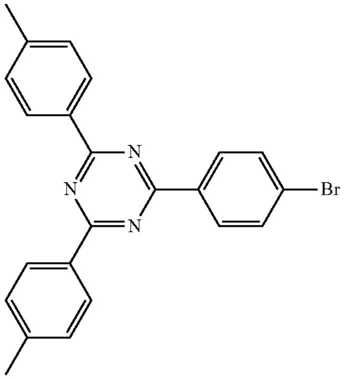 [SMILES: Cc1ccc(-c2nc(-c3ccc(C)cc3)nc(-c3ccc(Br)cc3)n2)cc1] | 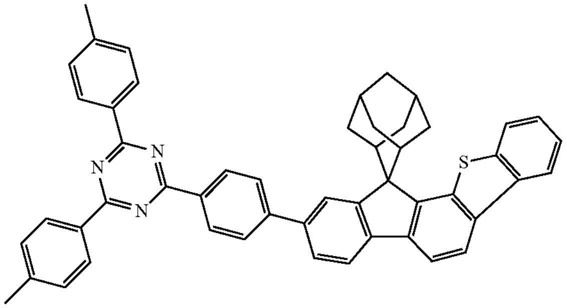 58 | 72 |

TABLE 5-continued
| Reactant F | Reactant G | Compound | Yield/ % |
| --- | --- | --- | --- |
| 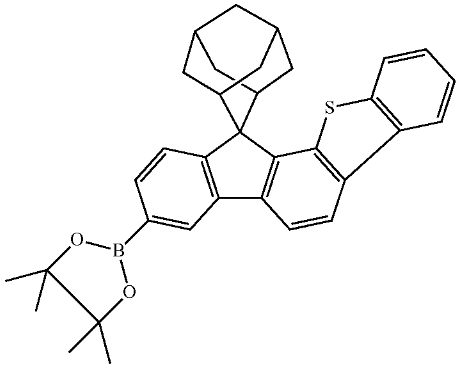 IM e-4 | 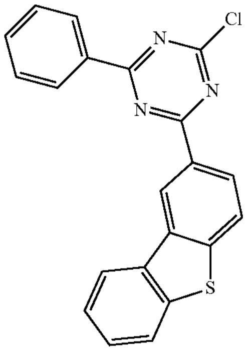 [SMILES: Clc1nc(-c2ccccc2)nc(-c2ccc3sc4ccccc4c3c2)n1] | 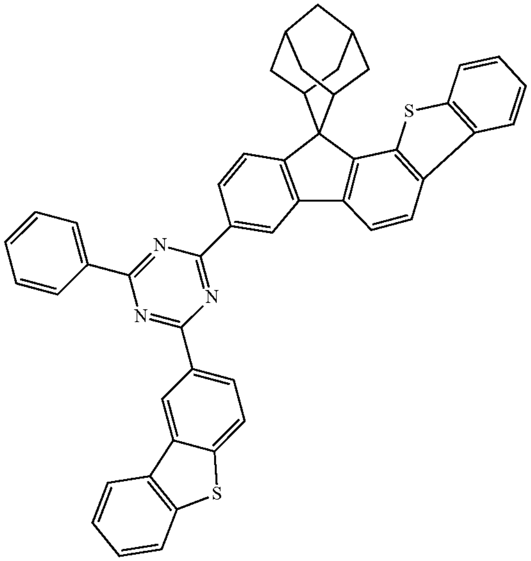 59 | 59 |

TABLE 5-continued
| Reactant F | Reactant G | Compound | Yield/ % |
|---|---|---|---|
| 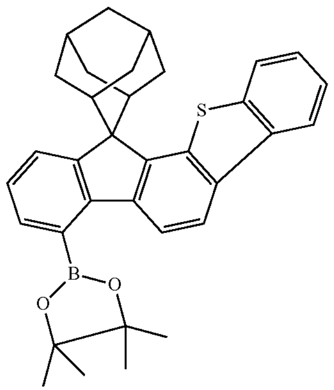 IM h-4 | 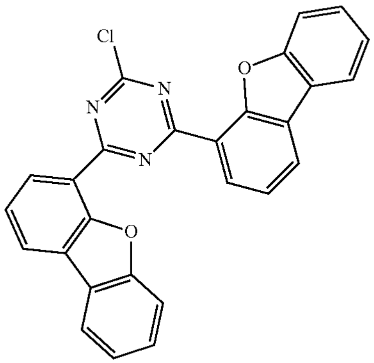 [SMILES: Clc1nc(-c2cccc3c2oc2ccccc23)nc(-c2cccc3c2oc2ccccc23)n1] | 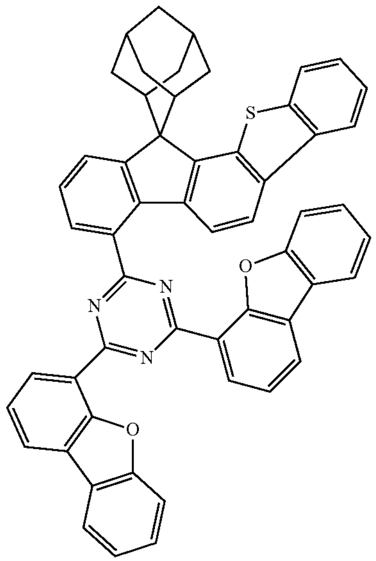 60 | 60 |

TABLE 5-continued
| Reactant F | Reactant G | Compound | Yield/ % |
|---|---|---|---|
| 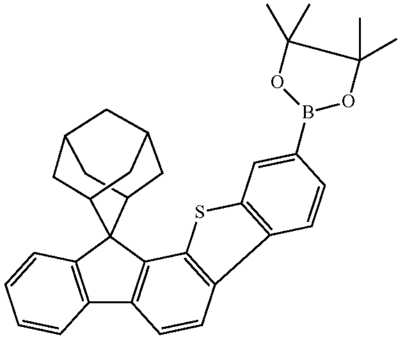 IM f-4 | 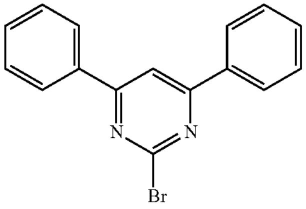 [SMILES: Brc1nc(-c2ccccc2)cc(-c2ccccc2)n1] | 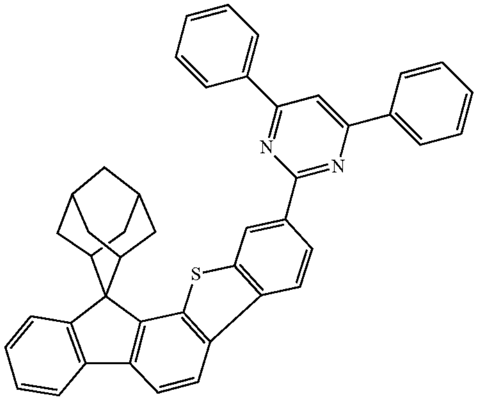 64 | 67 |
| 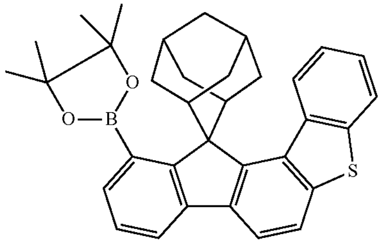 IM j-4 | 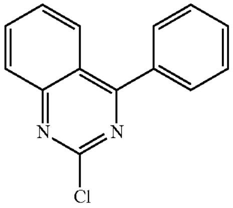 [SMILES: Clc1nc(-c2ccccc2)c2ccccc2n1] | 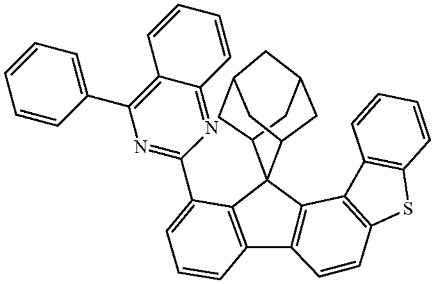 67 | 54 |

TABLE 5-continued
| Reactant F | Reactant G | Compound | Yield/ % |
|---|---|---|---|
| 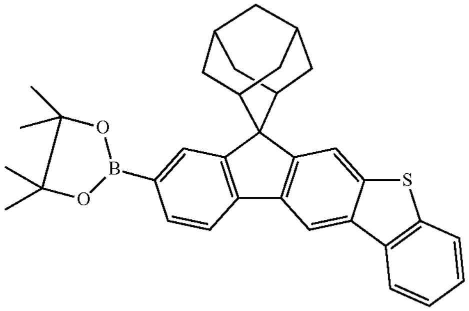 IM m-4 | 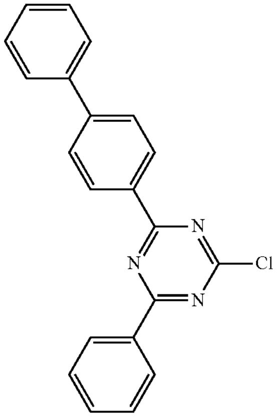 [SMILES: Clc1nc(-c2ccccc2)nc(-c2ccc(-c3ccccc3)cc2)n1] | 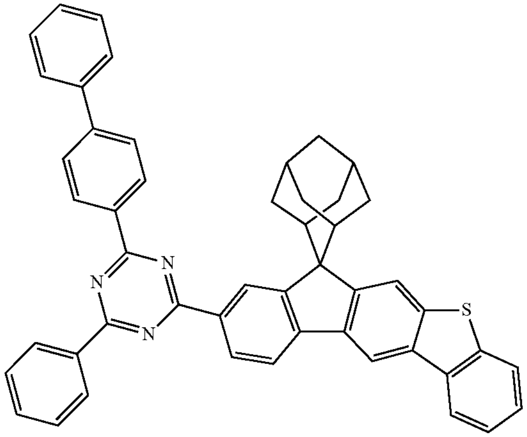 78 | 68 |
| 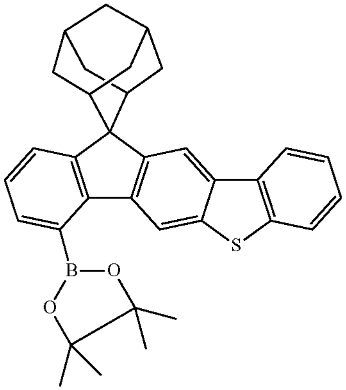 IM p-4 | 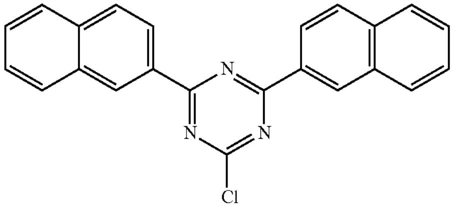 [SMILES: Clc1nc(-c2ccc3ccccc3c2)nc(-c2ccc3ccccc3c2)n1] | 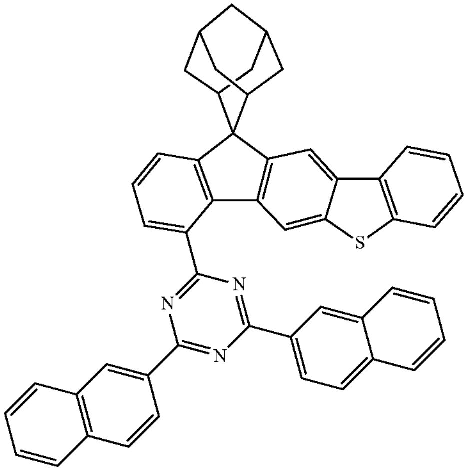 90 | 59 |

TABLE 5-continued
| Reactant F | Reactant G | Compound | Yield/ % |
| --- | --- | --- | --- |
| 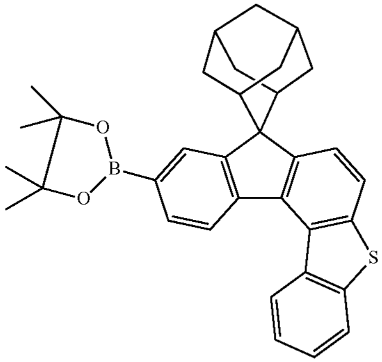 IM t-4 | 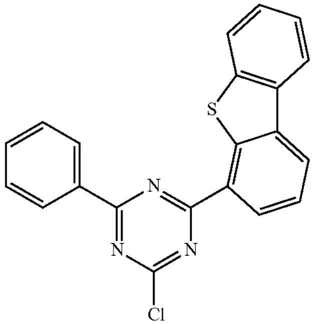 [SMILES: Clc1nc(-c2ccccc2)nc(-c2cccc3c2sc2ccccc23)n1] | 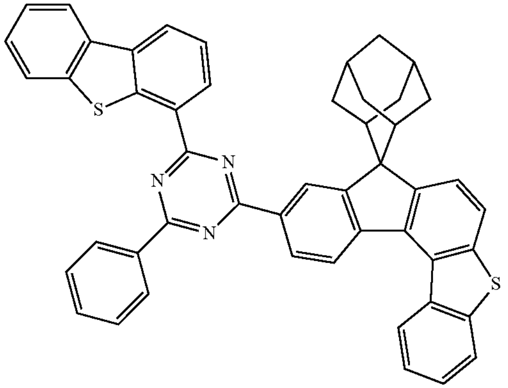 98 | 68 |

TABLE 5-continued
| Reactant F | Reactant G | Compound | Yield/ % |
|---|---|---|---|
| 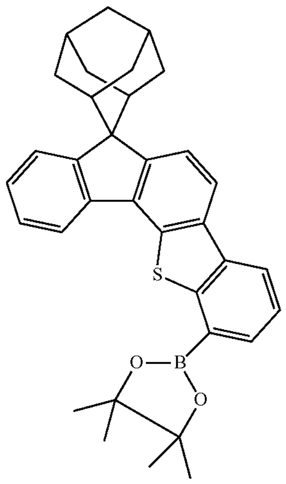 IM w-4 | 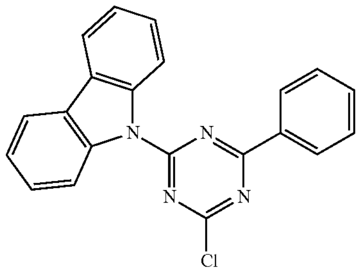 [SMILES: Clc1nc(-c2ccccc2)nc(-n2c3ccccc3c3ccccc32)n1] | 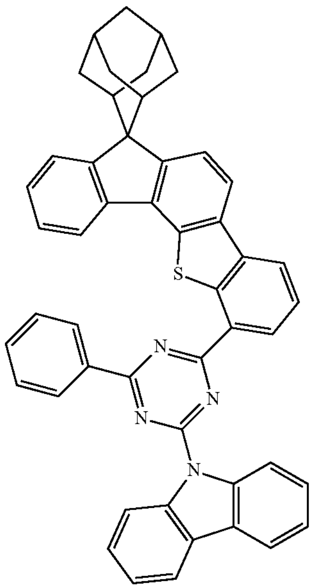 116 | 68 |

TABLE 5-continued
| Reactant F | Reactant G | Compound | Yield/ % |
| --- | --- | --- | --- |
| 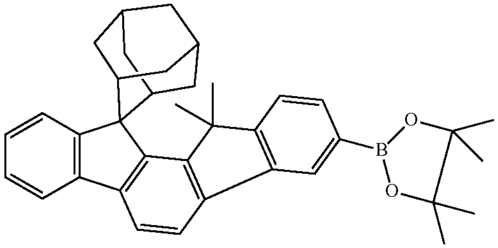 IM c-4 | 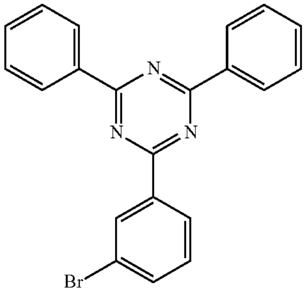 [SMILES: Brc1cccc(-c2nc(-c3ccccc3)nc(-c3ccccc3)n2)c1] | 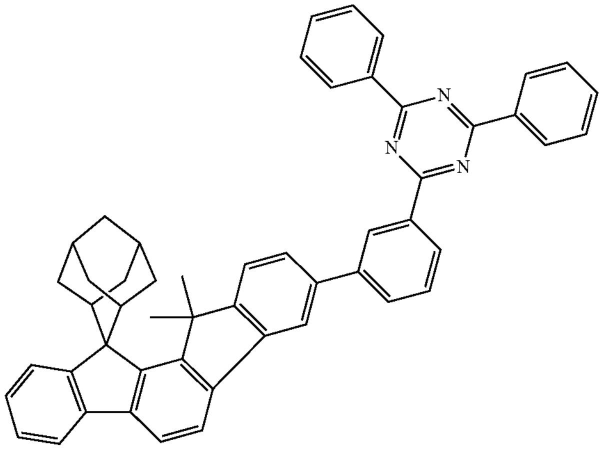 125 | 62 |
| 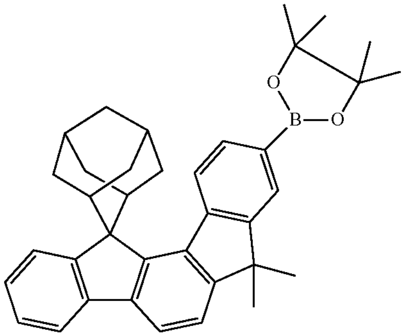 IM k-4 | 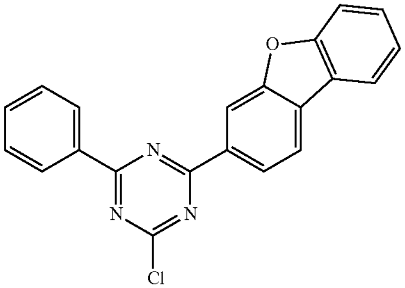 [SMILES: Clc1nc(-c2ccccc2)nc(-c2ccc3c(c2)oc2ccccc23)n1] | 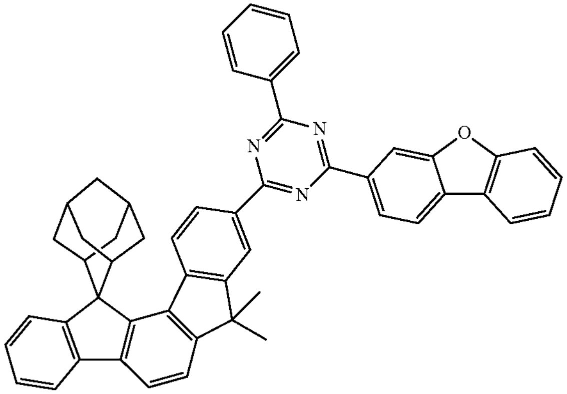 135 | 56 |

TABLE 5-continued
| Reactant F | Reactant G | Compound | Yield/ % |
|---|---|---|---|
| 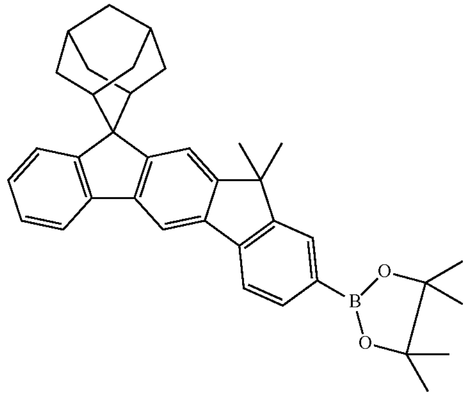 IM n-4 | 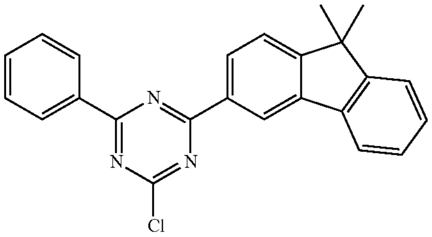 [SMILES: CC1(C)c2ccccc2-c2cc(-c3nc(Cl)nc(-c4ccccc4)n3)ccc21] | 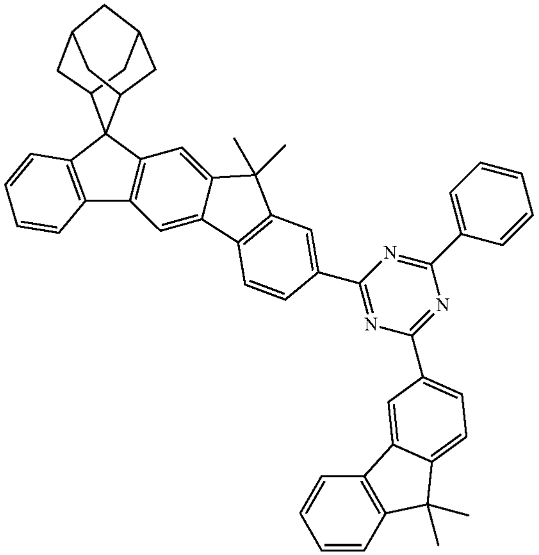 144 | 66 |
| 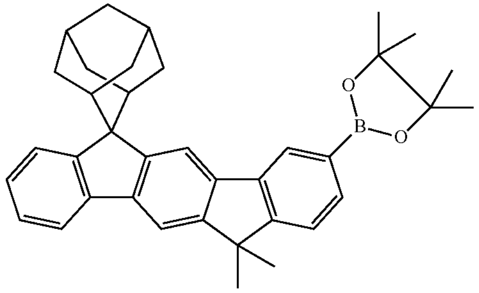 IM r-4 | 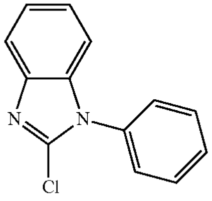 [SMILES: Clc1nc2ccccc2n1-c1ccccc1] | 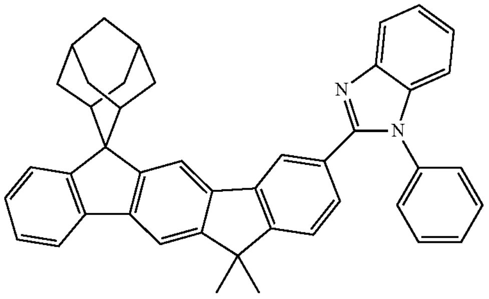 154 | 55 |

TABLE 5-continued
| Reactant F | Reactant G | Compound | Yield/ % |
|---|---|---|---|
| 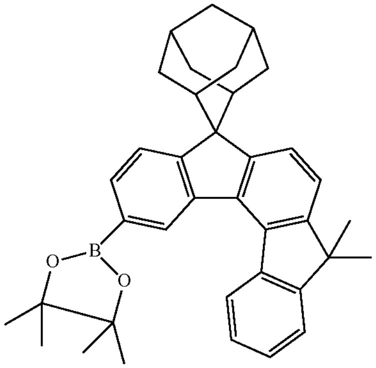 IM u-4 | 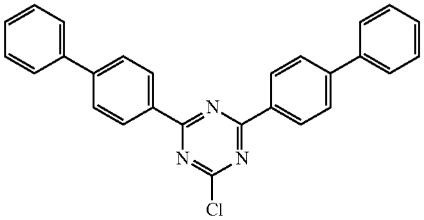 [SMILES: Clc1nc(-c2ccc(-c3ccccc3)cc2)nc(-c2ccc(-c3ccccc3)cc2)n1] | 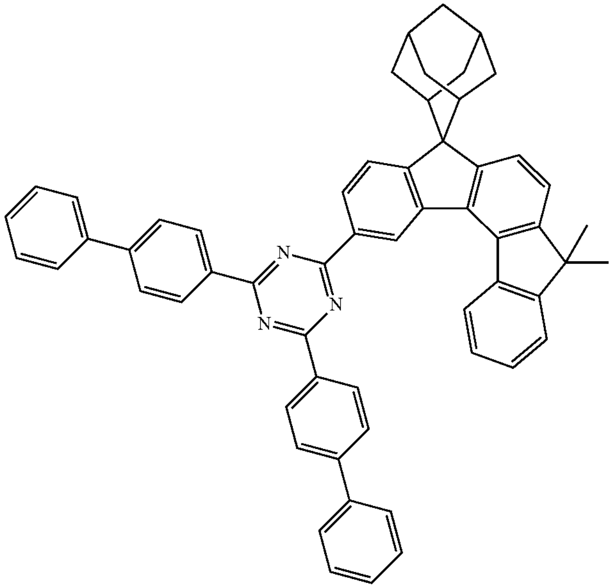 159 | 70 |

TABLE 5-continued
| Reactant F | Reactant G | Compound | Yield/ % |
|---|---|---|---|
| 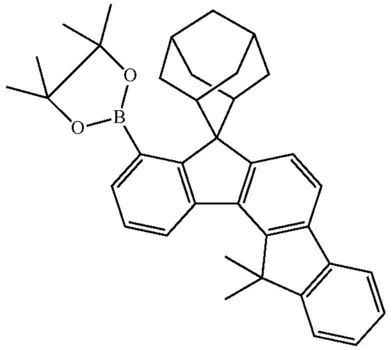 IM x-4 | 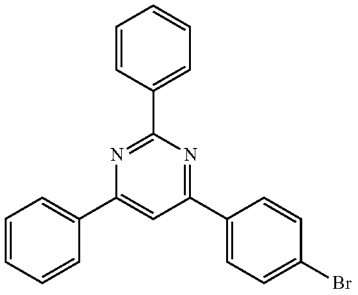 [SMILES: Brc1ccc(-c2cc(-c3ccccc3)nc(-c3ccccc3)n2)cc1] | 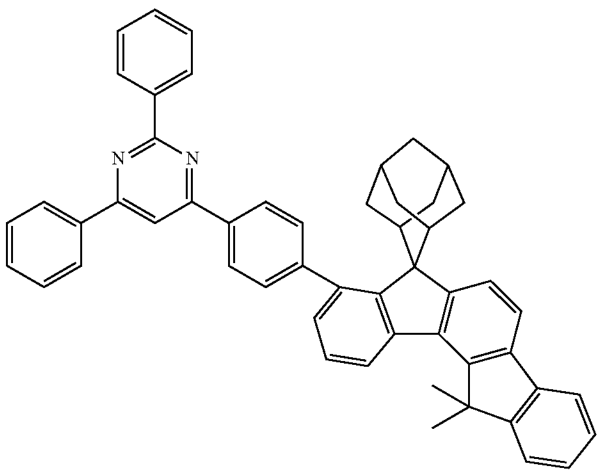 167 | 64 |
| 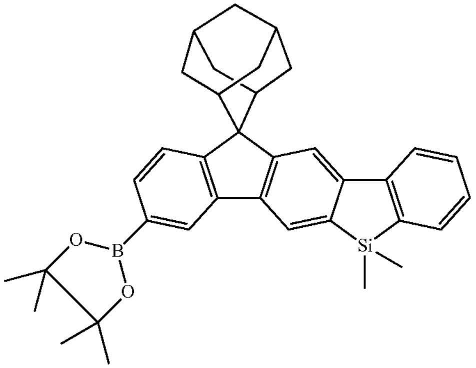 IM q-4 | 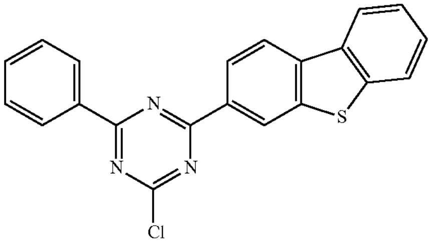 [SMILES: Clc1nc(-c2ccccc2)nc(-c2ccc3c(c2)sc2ccccc23)n1] | 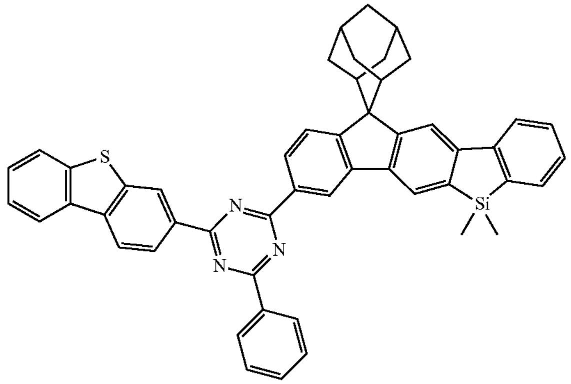 209 | 57 |

TABLE 5-continued
| Reactant F | Reactant G | Compound | Yield/ % |
|---|---|---|---|
| 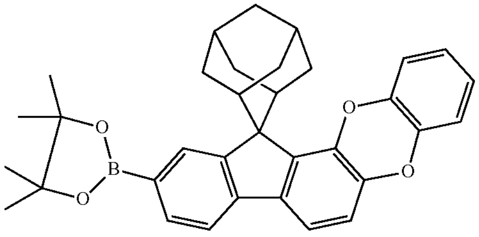 IM z-4 | 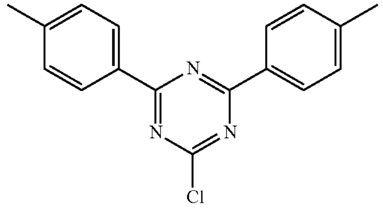 | 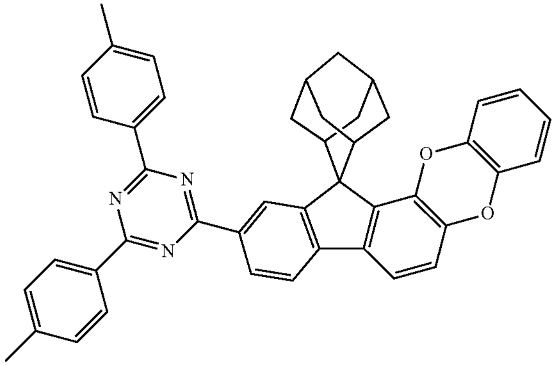 237 | 63 |
| 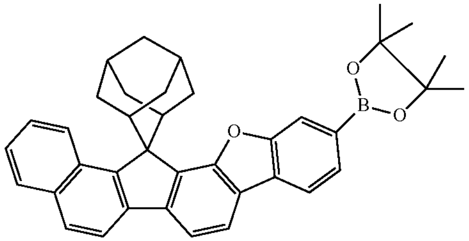 IM y-4 | 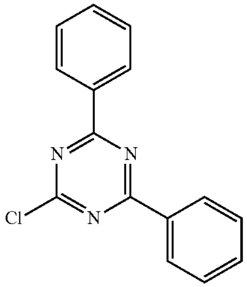 [SMILES: Clc1nc(-c2ccccc2)nc(-c2ccccc2)n1] | 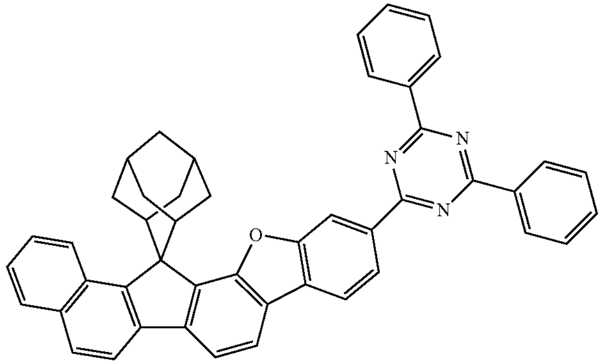 261 | 66 |

TABLE 5-continued
| Reactant F | Reactant G | Compound | Yield/ % |
|---|---|---|---|
| 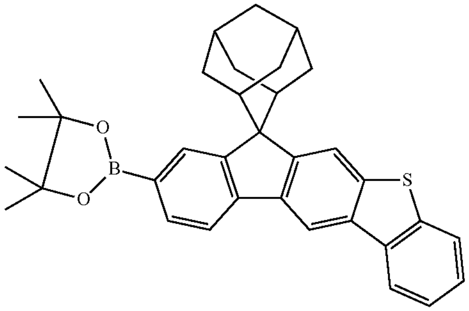 IM m-4 | 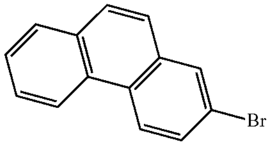 [SMILES: Brc1ccc2c(ccc3ccccc32)c1] | 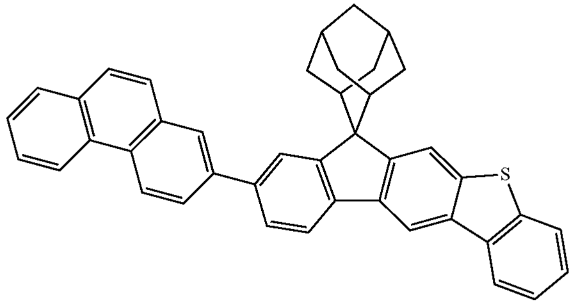 322 | 68 |
| 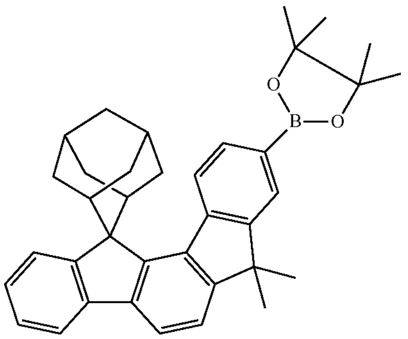 IM k-4 | 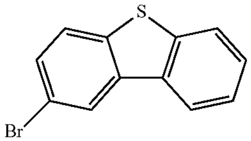 | 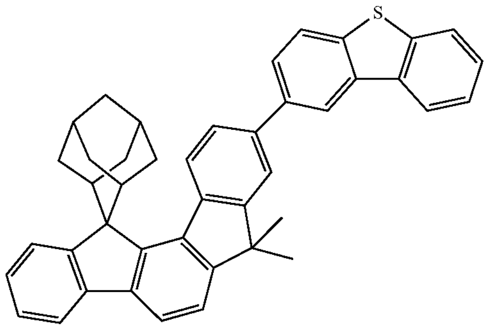 323 | 66 |

TABLE 5-continued
| Reactant F | Reactant G | Compound | Yield/ % |
|---|---|---|---|
| 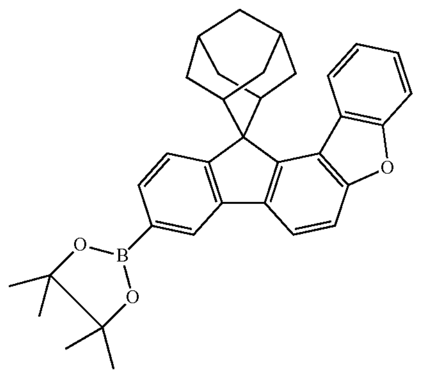 [SMILES: CC1(C)OB(c2ccc3c(c2)-c2ccc4oc5ccccc5c4c2C32C3CC4CC(C3)CC2C4)OC1(C)C] | 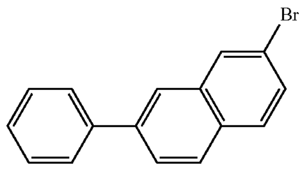 [SMILES: Brc1ccc2ccc(-c3ccccc3)cc2c1] | 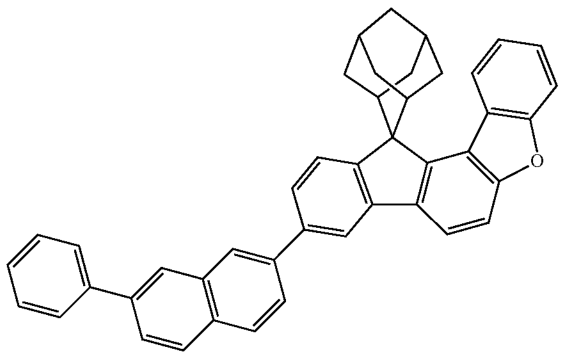 324 | 64 |

Preparation of Compound 374:

(1) Synthesis of Intermediate IM A

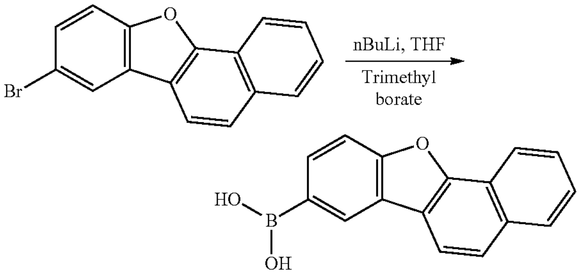

IM A

8-Bromonaphtho[1,2-B]benzofuran (50 g, 168.2 mmol) and tetrahydrofuran (400 ml) were added to a flask, and cooled to −78° C. under nitrogen protection, a solution (2.5 M) of n-butyllithium (72.4 mL, 181.1 mmol) in tetrahydrofuran was added dropwise under stirring, after the dropwise addition was complete, stirring was performed for 1 h while heat preservation, a solution of trimethyl borate (17.5 g, 168.2 mmol) in tetrahydrofuran (70 mL) was added dropwise while maintaining at −78° C., after the dropwise addition was complete, heat preservation was performed for 1 h, the system was heated to room temperature, stirring was performed for 24 h, a solution of hydrochloric acid (12M) (22.6 mL, 271.6 mmol) in water (113.2 mL) was added into the reaction solution, stirring was performed for 1 h, liquid separation was performed, the obtained organic phase was washed with water to be neutral, and dried by anhydrous magnesium sulfate, and a solvent was removed under reduced pressure to give a crude product, and the crude product was purified by silica gel column chromatography using a dichloromethane/n-heptane system to obtain a white solid intermediate IM A (24.7 g, yield: 56%).

(2) Synthesis of Intermediate IM B

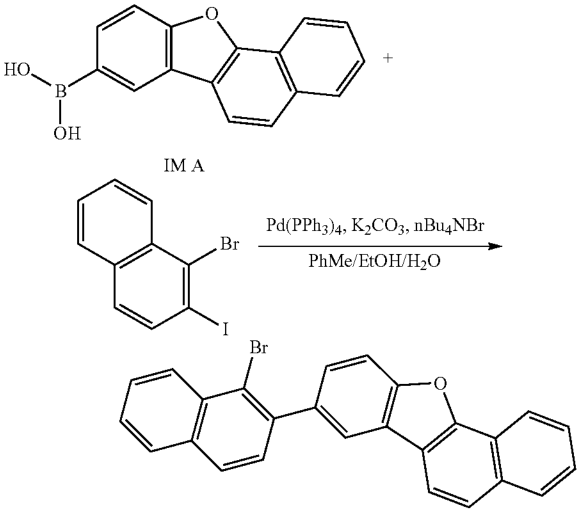

IM A

IM B

1-Bromo-2-iodonaphthalene (29.9 g, 89.8 mmol), the intermediate IM A (24.7 g, 94.2 mmol), tetrakis(triphenylphosphine)palladium (2.1 g, 1.8 mmol), potassium carbonate (27.3 g, 197.5 mmol), and tetrabutylammonium bromide (5.8 g, 17.9 mmol) was added to a flask, and a mixed solvent of toluene (240 mL), ethanol (120 mL) and water (60 mL) was added, and the mixture was heated to 80° C. under nitrogen protection, and stirred for 24 h while maintaining the temperature, after cooling to room temperature, stirring was stopped, the reaction solution was washed with water, the obtained organic phase was separated, and dried by anhydrous magnesium sulfate, and a solvent removed under reduced pressure to give a crude product; and the crude product was purified by silica gel column chromatography using dichloromethane/n-heptane as a mobile phase to obtain a white solid intermediate IM B (28.5 g, yield: 75%).

(3) Synthesis of Intermediate IM C

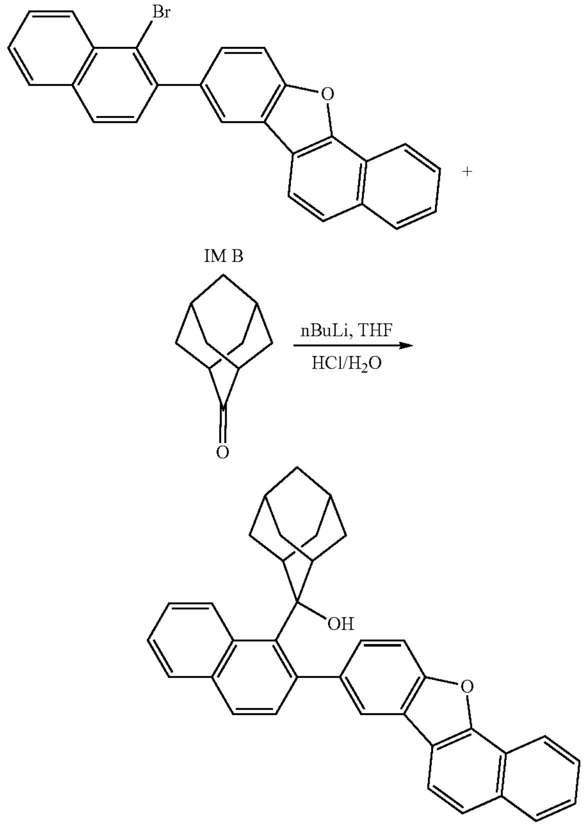

IM B

IM C

The intermediate IM B (28.5 g, 67.3 mmol) and tetrahydrofuran (230 mL) were added to a flask, and cooled to −78° C. under nitrogen protection, a solution (2.5 M) of n-butyllithium (32.3 mL, 80.8 mmol) in tetrahydrofuran was added dropwise under stirring, after the dropwise addition was complete, stirring was performed for 1 h while heat preservation, a solution of adamantanone (11.1 g, 74.0 mmol) in tetrahydrofuran (44 mL) was added dropwise while maintaining at −78° C., after the dropwise addition was complete, heat preservation was performed for 1 h, the system was heated to room temperature, stirring was performed for 24 h, 50 mL of hydrochloric acid (12M) (10.1 mL, 121.2 mmol) was added to the reaction solution, stirring was performed for 1 h, liquid separation was performed, the obtained organic phase was washed with water to be neutral, and dried by anhydrous magnesium sulfate, and a solvent was removed under reduced pressure to give a crude product, and the crude product was purified by silica gel column chromatography using a dichloromethane/n-heptane system to obtain a white solid intermediate IM C (18.3 g, yield: 55%).

(4) Synthesis of Intermediate IM D

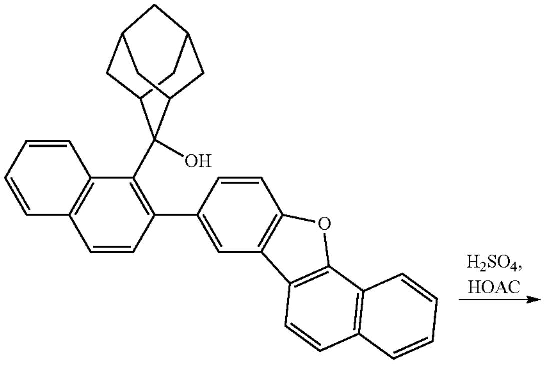

IM C

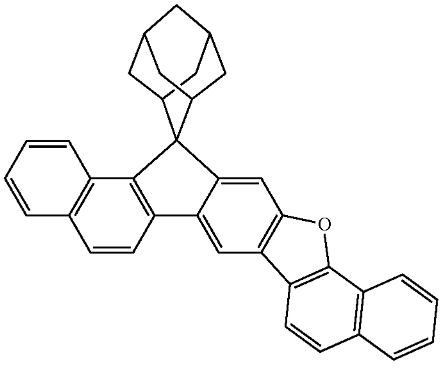

IM D

The intermediate IM C (18.3 g, 37.0 mmol) and glacial acetic acid (146 mL) were added into a flask, and a solution of concentrated sulfuric acid (98%) (0.8 mL, 7.4 mmol) in acetic acid (15 mL) was slowly added dropwise under stirring at room temperature under nitrogen protection, after the dropwise addition was completed, the mixture was heated to 60° C., and stirred for 2 h; the resulting reaction solution was cooled to room temperature, the precipitated solid was filtered, and a filter cake was rinsed with water and ethanol and oven-dried to give a crude product; and the crude product was purified by silica gel column chromatography using a dichloromethane/n-heptane system to obtain a white solid intermediate IM D (13.6 g, yield: 77%).

(5) Synthesis of Intermediate IM E

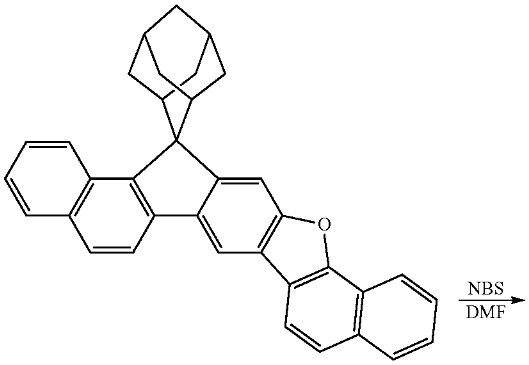

IM D

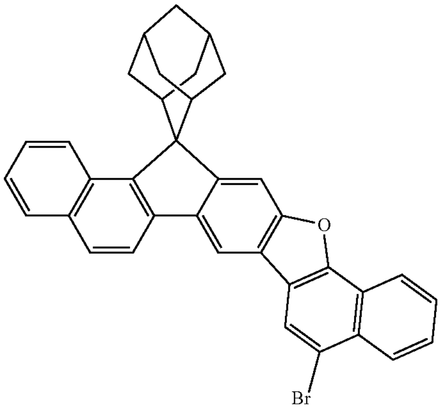

IM E

The intermediate IM D (13.6 g, 28.5 mmol) and a solvent DMF (N,N-dimethylformamide) (110 mL) were added to a flask, and stirred at room temperature under nitrogen protection for 10 min, N-bromosuccinimide (NBS) (7.6 g, 42.8 mmol) was added, and the mixture was heated to 80° C., and stirred for 4 h while heat preservation; after the reaction was completed, the resulting reaction solution was cooled to room temperature, the reaction solution was extracted with dichloromethane and water, the obtained organic phase was taken and dried by anhydrous magnesium sulfate, and a solvent was removed under reduced pressure to give a crude product; and the crude product was purified by silica gel column chromatography using a dichloromethane/n-heptane system as a mobile phase to obtain a white solid intermediate IM E (11.9 g, yield: 75%).

(6) Synthesis of Intermediate IM F

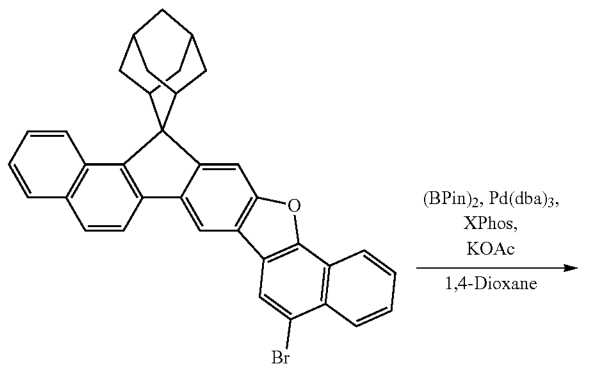

IM E

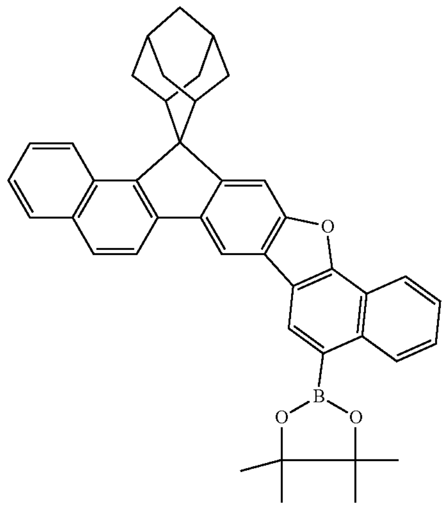

IM F

The intermediate IM E (11.9 g, 21.4 mmol), bis(pinacolato)diboron (6.5 g, 25.7 mmol), tris(dibenzylideneacetone) dipalladium (0.2 g, 0.2 mmol), 2-dicyclohexylphosphino-2',4',6'-triisopropylbiphenyl (0.4, 0.2 mmol), potassium acetate (4.6 g, 47.1 mmol) and 1,4-dioxane (150 mL) were added to a flask, and stirred under reflux at 100° C. for 12 h under nitrogen protection; the resulting reaction solution was cooled to room temperature, dichloromethane and water were added to the reaction solution, liquid separation was performed, the obtained organic phase was washed with water, and dried by anhydrous magnesium sulfate, and a solvent was removed under reduced pressure to give a crude product; and the crude product was purified by silica gel column chromatography using a dichloromethane/n-heptane system to obtain a white solid intermediate IM F (7.74 g, yield: 60%).

(7) Synthesis of Compound 374

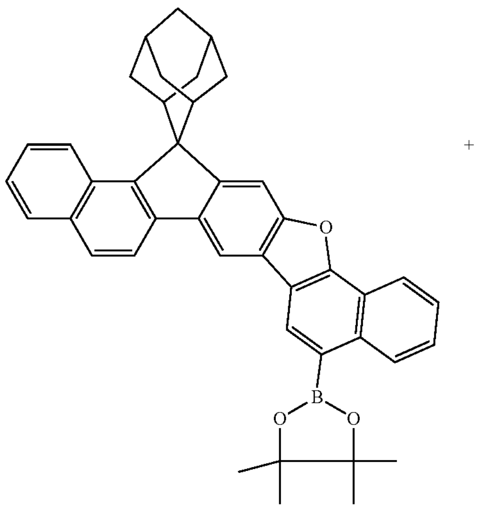

IM F

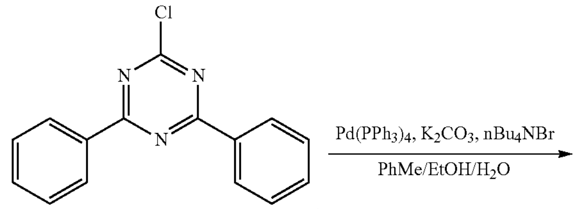

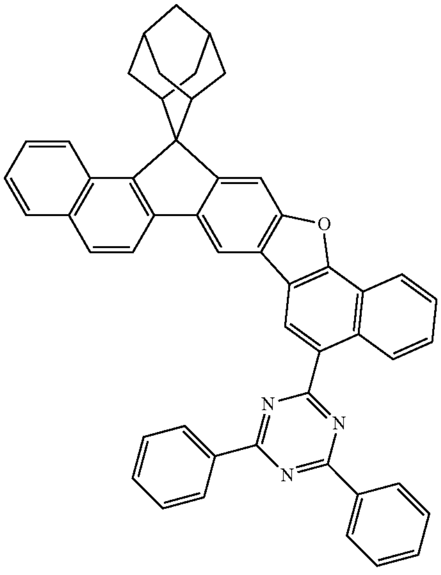

374

The intermediate IM F (7.7 g, 12.8 mmol), 2-(4-biphenyl)-4-chloro-6-phenyl-1,3,5-triazine (3.3 g, 12.2 mmol), tetrakis(triphenylphosphine)palladium (0.28 g, 0.24 mmol), potassium carbonate (3.7 g, 26.9 mmol), and tetrabutylammonium bromide (0.8 g, 2.4 mmol) were added to a flask, and a mixed solvent of toluene (60 mL), ethanol (30 mL) and water (15 mL) was added, and the mixture was heated to 80° C. under nitrogen protection, and stirred for 8 h while maintaining the temperature; then cooling to room temperature, stirring was stopped, the reaction solution was washed with water, the obtained organic phase was separated, and dried by anhydrous magnesium sulfate, and a solvent was removed under reduced pressure to obtain a crude product; and the crude product was purified by silica gel column chromatography using a dichloromethane/n-heptane mixed solvent as a mobile phase to obtain a white solid compound 374 (5.6 g, yield: 65%).

The above synthesized compounds were subjected to mass spectrometry and the results are shown in Table 6:

TABLE 6

| Mass spectrometric data for compounds | | | | | |
|---|---|---|---|---|---|
| Compound 2 | m/z = 684.3 $[M + H]^+$ | Compound 98 | m/z = 800.2 $[M + H]^+$ | Compound 4 | m/z = 608.3 $[M + H]^+$ |
| Compound 7 | m/z = 698.3 $[M + H]^+$ | Compound 116 | m/z = 713.3 $[M + H]^+$ | Compound 125 | m/z = 710.3 $[M + H]^+$ |
| Compound 13 | m/z = 636.3 $[M + H]^+$ | Compound 135 | m/z = 724.3 $[M + H]^+$ | Compound 144 | m/z = 750.4 $[M + H]^+$ |
| Compound 23 | m/z = 605.3 $[M + H]^+$ | Compound 28 | m/z = 734.3 $[M + H]^+$ | Compound 154 | m/z = 595.3 $[M + H]^+$ |
| Compound 44 | m/z = 734.3 $[M + H]^+$ | Compound 159 | m/z = 786.4 $[M + H]^+$ | Compound 167 | m/z = 709.4 $[M + H]^+$ |
| Compound 48 | m/z = 684.3 $[M + H]^+$ | Compound 58 | m/z = 728.3 $[M + H]^+$ | Compound 209 | m/z = 756.3 $[M + H]^+$ |
| Compound 59 | m/z = 730.2 $[M + H]^+$ | Compound 237 | m/z = 652.3 $[M + H]^+$ | Compound 60 | m/z = 804.3 $[M + H]^+$ |
| Compound 64 | m/z = 623.2 $[M + H]^+$ | Compound 322 | m/z = 569.3 $[M + H]^+$ | Compound 261 | m/z = 658.3 $[M + H]^+$ |
| Compound 67 | m/z = 597.2 $[M + H]^+$ | Compound 323 | m/z = 585.3 $[M + H]^+$ | Compound 90 | m/z = 724.3 $[M + H]^+$ |
| Compound 78 | m/z = 700.3 $[M + H]^+$ | Compound 324 | m/z = 579.3 $[M + H]^+$ | Compound 374 | m/z = 708.3 $[M + H]^+$ |

NMR data for compounds are as follows:

Compound 2:

$^1$H-NMR ($CD_2Cl_2$, 400 MHz): 8.81 (d, 2H), 8.20-8.17 (m, 3H), 8.04-7.97 (m, 3H), 7.86 (d, 2H), 7.66-7.56 (m, 4H), 7.54-7.39 (m, 8H), 7.31 (t, 1H), 2.83 (d, 2H), 2.71 (d, 2H), 2.14 (s, 1H), 2.06 (s, 1H), 1.89 (s, 2H), 1.73 (t, 4H), 1.46 (s, 2H).

Compound 23:

$^1$H-NMR ($CD_2Cl_2$, 400 MHz): 8.14 (d, 2H), 8.08-8.06 (m, 2H), 7.86 (t, 2H), 7.78 (d, 1H), 7.70 (s, 1H), 7.63 (d, 4H), 7.52 (t, 4H), 7.47-7.33 (m, 5H), 7.27 (t, 1H), 2.80 (d, 2H), 2.73 (d, 2H), 2.14 (s, 1H), 2.07 (s, 1H), 1.88 (s, 2H), 1.72 (t, 4H), 1.38 (s, 2H).

Compound 78:

$^1$H-NMR ($CD_2Cl_2$, 400 MHz): 8.79 (d, 2H), 8.34 (s, 1H), 8.29 (d, 1H), 8.20-8.16 (m, 3H), 8.07 (s, 1H), 8.01 (d, 2H), 7.86 (d, 2H), 7.75 (d, 1H), 7.66-7.51 (m, 8H), 7.43-7.38 (m, 11H), 7.30-7.26 (m, 1H), 2.84 (d, 2H), 2.75 (d, 2H), 2.12 (s, 1H), 2.06 (s, 11H), 1.86 (s, 2H), 1.70 (t, 4H), 1.36 (s, 2H).

Example 1: Green Organic Electroluminescent Device

A green organic electroluminescent device was manufactured by using the following method:

an anode was prepared by the following process: an ITO substrate with an ITO thickness of 1500 Å was cut into a dimension of 40 mm (length)×40 mm (width)×0.7 mm (thickness) to be prepared into an experimental substrate with a cathode, an anode and an insulating layer pattern by adopting a photoetching process, and surface treatment was performed by ultraviolet ozone and $O_2$:$N_2$ plasma to increase the work function of the anode, and the surface of the ITO substrate may be cleaned with an organic solvent to clean impurities and gungo on the surface of the ITO substrate.

F4-TCNQ was vacuum evaporated on the experimental substrate (the anode) to form a hole injection layer (HIL) having a thickness of 100 Å, and HT-01 was evaporated on the hole injection layer to form a first hole transport layer with a thickness of 850 Å.

HT-02 was vacuum evaporated on the first hole transport layer to form a second hole transport layer with a thickness of 350 Å.

A compound 23, GHn1 and $Ir(ppy)_3$ were co-evaporated at a ratio of 50%:45%:5% (an evaporation rate) on the second hole transport layer to form a green light-emitting layer (EML) with a thickness of 400 Å.

ET-01 and LiQ were mixed at a weight ratio of 1:1 and evaporated to form an electron transport layer (ETL) having a thickness of 300 Å, LiQ was evaporated on the electron transport layer to form an electron injection layer (EIL) having a thickness of 10 Å, and then magnesium (Mg) and silver (Ag) were mixed and vacuum evaporated at an evaporation rate of 1:9 on the electron injection layer to form a cathode with a thickness of 110 Å.

In addition, CP-01 with a thickness of 650 Å was evaporated on the cathode to form an organic capping layer (CPL), thus completing the manufacture of the entire organic light-emitting device.

Examples 2-10

The organic electroluminescent devices were manufactured by the same method as as that in Example 1, except that a mixed component shown in Table 7 below was used instead of the mixed component in Example 1 when the organic light-emitting layer was formed.

Comparative Examples 1-3

The organic electroluminescent devices were manufactured by the same method as as that in Example 1, except that a mixed component shown in Table 7 below was used instead of the mixed component in Example 1 when the organic light-emitting layer was formed.

The structures of main materials used in Examples 1-10 and Comparative examples 1-3 are shown below:

-continued
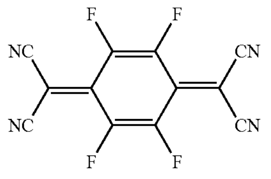
F4-TCNQ
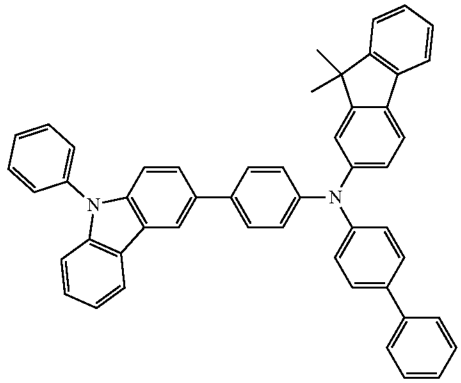
HT-01
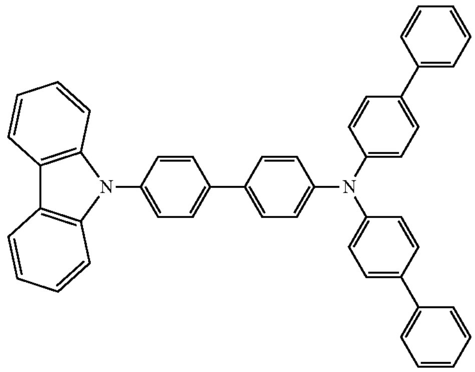
HT-02
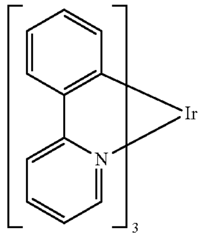
$Ir(ppy)_3$
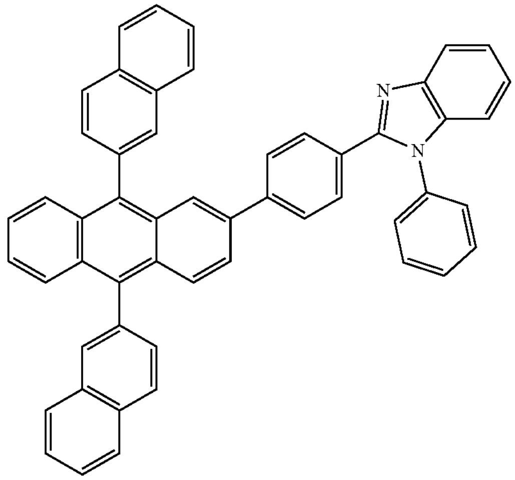
ET-01
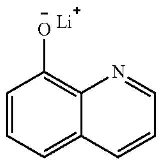
LiQ
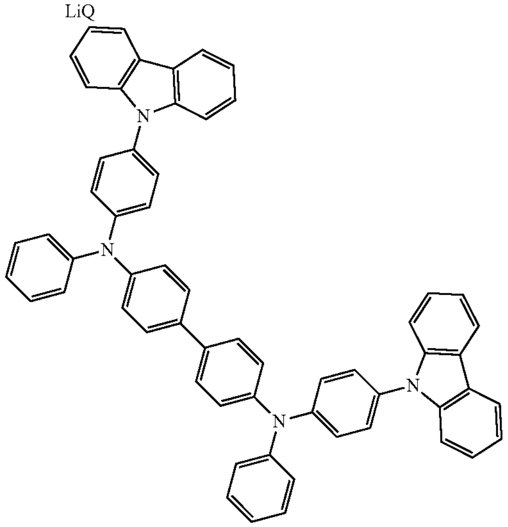
CP-01
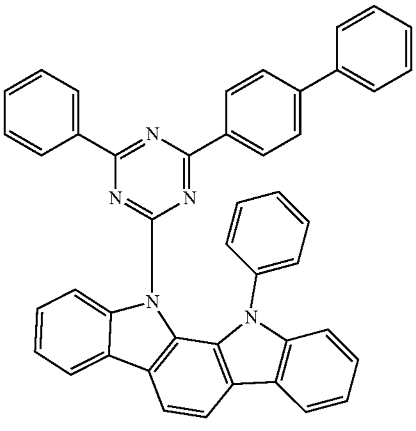
GHn1

-continued

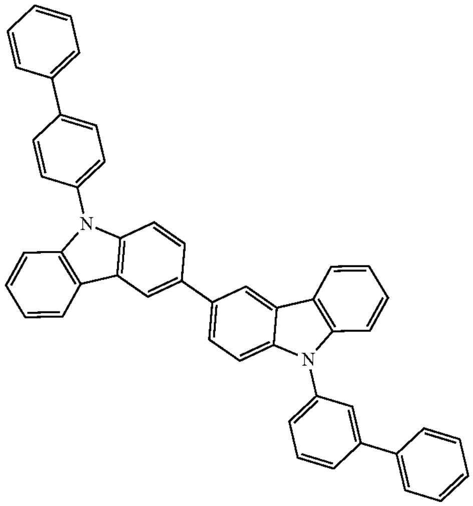

GHp1

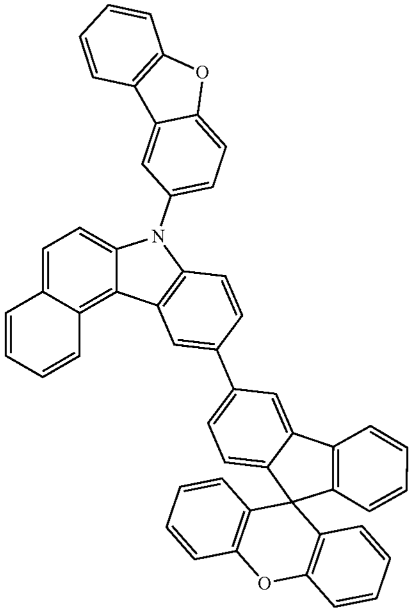

Compound A

-continued

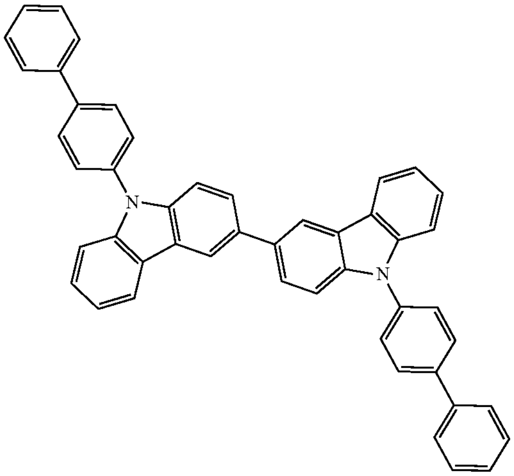

Compound B

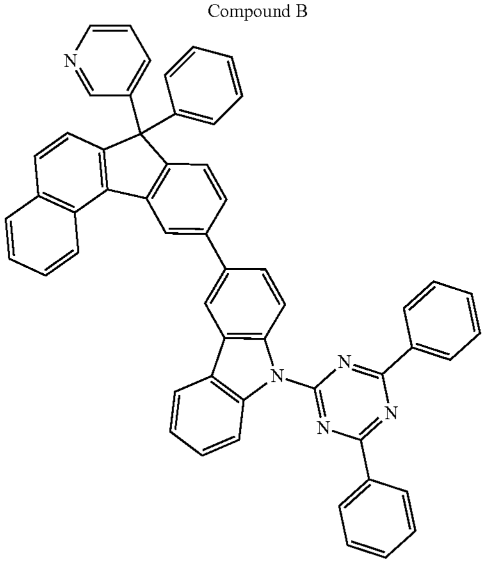

Compound C

The organic electroluminescent devices manufactured in Examples 1-10 and Comparative examples 1-3 were subjected to performance tests under a condition of 20 mA/$cm^2$, and the test results are shown in Table 7 below.

TABLE 7

Performance test results of organic electroluminescent device

| Example No. | Light-emitting layer three materials = 50%:45%:5% | Driving voltage (V) | Current efficiency (Cd/A) | Power efficiency (lm/W) | Chromaticity coordinate CIEx, CIEy | External quantum efficiency EQE (%) | T95 service life (h) |
|---|---|---|---|---|---|---|---|
| Example 1 | Compound 23:GHn1:$Ir(ppy)_3$ | 3.78 | 80.5 | 66.9 | 0.22, 0.73 | 18.2 | 216 |
| Example 2 | Compound 323:GHn1:$Ir(ppy)_3$ | 3.76 | 82.3 | 68.7 | 0.22, 0.73 | 18.8 | 219 |
| Example 3 | Compound 324:GHn1:$Ir(ppy)_3$ | 3.80 | 82.8 | 68.4 | 0.22, 0.73 | 19.2 | 221 |
| Example 4 | GHp1:Compound 64:$Ir(ppy)_3$ | 3.77 | 83.2 | 69.3 | 0.22, 0.73 | 19.3 | 227 |
| Example 5 | GHp1:Compound 67:$Ir(ppy)_3$ | 3.70 | 84.5 | 71.7 | 0.22, 0.73 | 18.2 | 226 |

TABLE 7-continued

Performance test results of organic electroluminescent device

| Example No. | Light-emitting layer three materials = 50%:45%:5% | Driving voltage (V) | Current efficiency (Cd/A) | Power efficiency (lm/W) | Chromaticity coordinate CIEx, CIEy | External quantum efficiency EQE (%) | T95 service life (h) |
|---|---|---|---|---|---|---|---|
| Example 6 | GHp1:Compound 2:$Ir(ppy)_3$ | 3.70 | 87.3 | 74.1 | 0.22, 0.73 | 18.4 | 232 |
| Example 7 | GHp1:Compound 4:$Ir(ppy)_3$ | 3.69 | 86.8 | 73.9 | 0.22, 0.73 | 19.1 | 236 |
| Example 8 | GHp1:Compound 7:$Ir(ppy)_3$ | 3.66 | 89.8 | 77.0 | 0.22, 0.73 | 19.4 | 240 |
| Example 9 | GHp1:Compound 13:$Ir(ppy)_3$ | 3.62 | 88.3 | 76.6 | 0.22, 0.73 | 18.8 | 237 |
| Example 10 | GHp1:Compound 28:$Ir(ppy)_3$ | 3.70 | 89.1 | 75.6 | 0.22, 0.73 | 18.6 | 241 |
| Comparative example 1 | Compound A:GHn1:$Ir(ppy)_3$ | 3.71 | 68.2 | 57.7 | 0.22, 0.73 | 16.4 | 154 |
| Comparative example 2 | Compound B:GHn1:$Ir(ppy)_3$ | 3.80 | 73.2 | 60.5 | 0.22, 0.73 | 17.6 | 152 |
| Comparative example 3 | GHp1:Compound C:$Ir(ppy)_3$ | 3.69 | 66.9 | 56.9 | 0.22, 0.73 | 16.4 | 176 |

From the data shown in Table 7, it can be seen that the organic electroluminescent devices manufactured in Examples 1-10 have the advantages that the driving voltages were substantially similar, the luminous efficiency was improved by at least 10%, and the service life of the devices were prolonged by at least 23% compared with the organic electroluminescent devices manufactured in Comparative examples 1-3. It can be seen that when the organic compound of the present disclosure is used as an organic light-emitting layer material of the organic electroluminescent device, in particular a host material, the efficiency performance and the service life of the organic electroluminescent device can be effectively improved.

Example 11: Red Organic Electroluminescent Device

An anode was prepared by the following process: an ITO substrate with an ITO thickness of 1500 Å was cut into a dimension of 40 mm (length)×40 mm (width)×0.7 mm (thickness) to be prepared into an experimental substrate with a cathode, an anode and an insulating layer pattern by adopting a photoetching process, and surface treatment was performed by ultraviolet ozone and $O_2$:$N_2$ plasma to increase the work function of the anode, and the surface of the ITO substrate may be cleaned with an organic solvent to clean impurities and gungo on the surface of the ITO substrate.

F4-TCNQ was vacuum evaporated on the experimental substrate (the anode) to form a hole injection layer (HIL) with a thickness of 100 Å, and HT-03 was evaporated on the hole injection layer to form a first hole transport layer with a thickness of 850 Å.

HT-04 was vacuum evaporated on the first hole transport layer to form a second hole transport layer with a thickness of 800 Å.

A compound 44 and $Ir(piq)_2(acac)$ were co-evaporated at a ratio of 95%:5% (an evaporation rate) on the second hole transport layer to form a red light-emitting layer (EML) with a thickness of 350 Å.

ET-01 and LiQ were mixed at a weight ratio of 1:1 and evaporated to form an electron transport layer (ETL) having a thickness of 300 Å, LiQ was evaporated on the electron transport layer to form an electron injection layer (EIL) with a thickness of 10 Å, and then magnesium (Mg) and silver (Ag) were mixed and vacuum evaporated at an evaporation rate of 1:9 on the electron injection layer to form a cathode with a thickness of 105 Å.

In addition, CP-01 with a thickness of 650 Å was evaporated on the cathode to form an organic capping layer (CPL), thus completing the manufacture of an organic light-emitting device.

Examples 12-18

The organic electroluminescent devices were manufactured by the same method as as that in Example 11, except that a mixed component shown in Table 8 below was used instead of the mixed component in Example 11 when the light-emitting layer was formed.

Comparative Examples 4-5

The organic electroluminescent devices were manufactured by the same method as as that in Example 11, except that a mixed component shown in Table 8 below was used instead of the mixed component in Example 11 when the light-emitting layer was formed.

The structures of main materials used in Examples 11-18 and Comparative examples 4-5 are shown below:

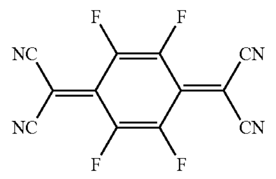

F4-TCNQ

-continued
HT-03
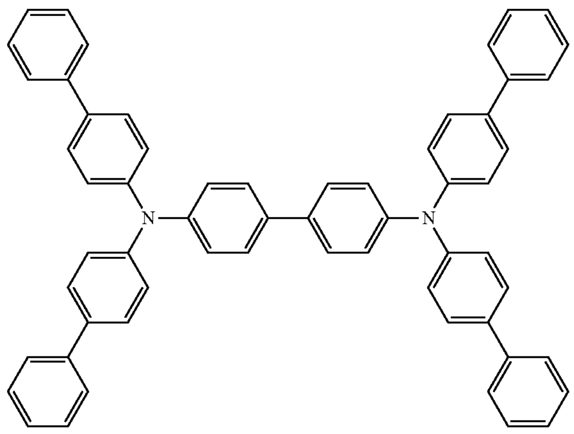
HT-04
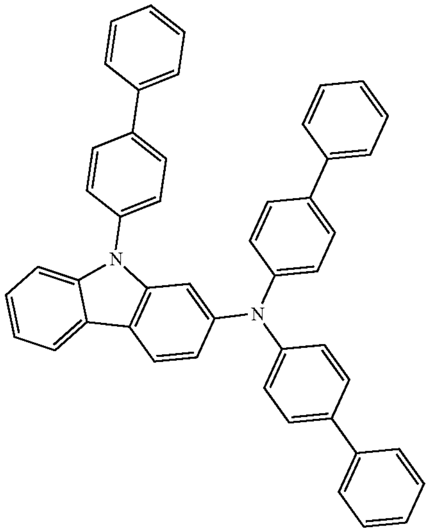
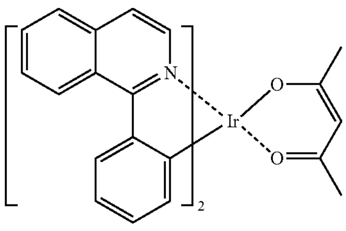
Ir(piq)$_2$(acac)
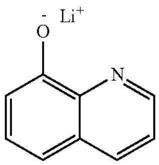
LiQ
-continued
CP-01
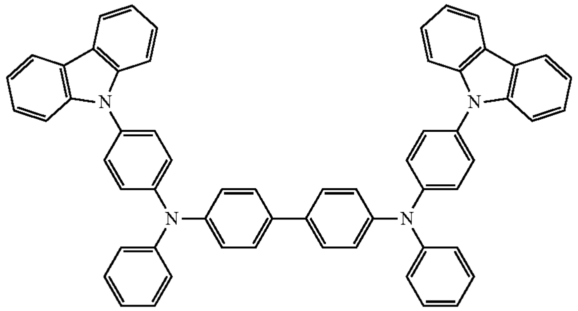
ET-01
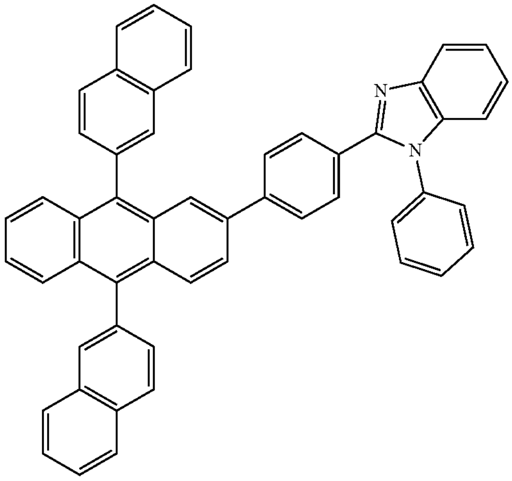
Compound D
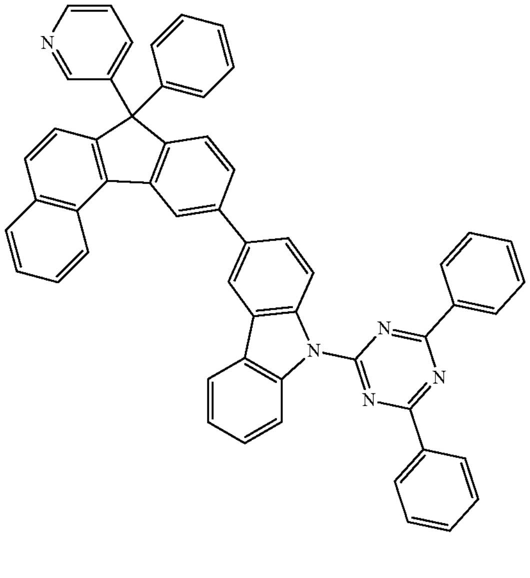

-continued

Compound E

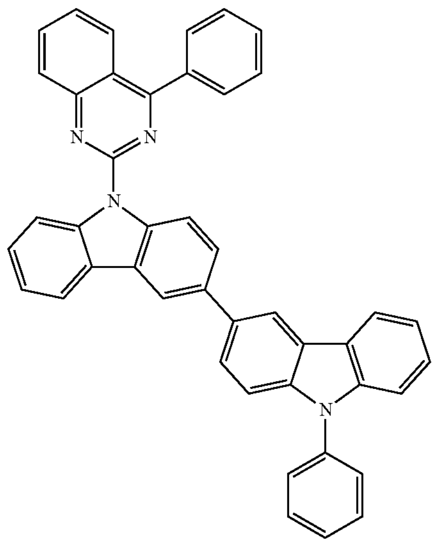

The organic electroluminescent devices manufactured in Examples 11-18 and Comparative examples 4-5 were subjected to performance tests under a condition of 20 mA/$cm^2$, and the test results are shown in Table 8 below.

TABLE 8

Performance test results of organic electroluminescent device

| Example No. | Compound:Ir(piq)$_2$ (acac) = 95%:5% | Driving voltage (V) | Current efficiency (Cd/A) | Power efficiency (lm/W) | Chromaticity coordinate CIEx, CIEy | External quantum efficiency EQE (%) | T95 service life (h) |
|---|---|---|---|---|---|---|---|
| Example 11 | Compound 44 | 3.78 | 39.0 | 32.4 | 0.68, 0.32 | 27.4 | 430 |
| Example 12 | Compound 48 | 3.74 | 39.2 | 32.9 | 0.68, 0.32 | 27.3 | 428 |
| Example 13 | Compound 58 | 3.73 | 41.5 | 34.9 | 0.68, 0.32 | 28.4 | 401 |
| Example 14 | Compound 59 | 3.76 | 38.6 | 32.2 | 0.68, 0.32 | 26.0 | 458 |
| Example 15 | Compound 60 | 3.71 | 41.6 | 35.2 | 0.68, 0.32 | 27.9 | 387 |
| Example 16 | Compound 78 | 3.70 | 40.8 | 34.6 | 0.68, 0.32 | 27.6 | 412 |
| Example 17 | Compound 90 | 3.72 | 38.9 | 32.8 | 0.68, 0.32 | 26.5 | 452 |
| Example 18 | Compound 374 | 3.73 | 39.4 | 33.2 | 0.68, 0.32 | 26.8 | 445 |
| Comparative example 4 | Compound D | 4.05 | 27.7 | 21.4 | 0.68, 0.32 | 20.2 | 270 |
| Comparative example 5 | Compound E | 3.78 | 28.5 | 23.6 | 0.68, 0.32 | 19.4 | 270 |

From the data shown in Table 8, it can be seen that the organic electroluminescent devices manufactured in Examples 11-18 have the advantages that the driving voltages are similar, the luminous efficiency of the devices were improved by at least 35%, and the service life was prolonged by at least 43% compared with the organic electroluminescent devices manufactured in Comparative example 5. The organic electroluminescent devices manufactured in Examples 11-18 have the advantages that the driving voltage was reduced by at least 7%, the luminous efficiency was improved by at least 39%, and the service life was prolonged by at least 43% compared with Comparative example 4. It can be seen that when the compounds of the present disclosure are used as an organic light-emitting layer material of the organic electroluminescent device, in particular a host material, the efficiency performance and the service life performance of the organic electroluminescent device can be improved.

In the compounds of the present disclosure, spiro[adamantane-fused fluorenyl] as a part of a core is a large planar conjugated structure, which has a strong rigidity and thus the compounds of the present disclosure have a high first triplet energy level, conjugated connection with a fused heteroaromatic ring in the compounds has a better hole transport ability, adamantyl is spiro-bonded to fluorenyl, so that the electron cloud density of the large planar conjugate structure can be greatly increased by a hyperconjugation effect, enhancing the hole mobility of the compounds, helping to promote the transport balance of holes and electrons in the light-emitting layer, and improving the efficiency performance of the organic electroluminescent device, and thus the compounds of the present disclosure are suitable as the host material of the organic light-emitting layer in the organic electroluminescent device. Not only that, the improvement of the hole transport performance of the compounds can improve the recombination rate of electrons and holes in the organic light-emitting layer, and reduce or avoid the transport of electrons to the hole transport layer through the organic light-emitting layer, and then, the hole transport layer material may be effectively protected from the impact of electrons, improving the service life of the organic electroluminescent device. Moreover, adamantyl spiro-bonded to fluorenyl has a large space volume and strong rigidity, thus, it is possible to reduce the interaction force between large planar conjugated structures, reduce intermolecular π-π stacking, and adjust the degree of intermolecular stacking, thus enabling the compounds to have a more stable amorphous form during film formation, and improving the film-forming properties of the compounds, and thus further improving the service life of the organic electroluminescent device.

Preferred examples of the present disclosure have been described in detail above, but the present disclosure is not limited to specific details in the above-described examples, and many simple modifications may be made to the technical solutions of the present disclosure within the technical idea of the present disclosure, and these simple modifications are all within the scope of protection of the present disclosure. In addition, it should be noted that various specific technical features described in the above specific examples may be combined in any suitable manner without contradiction. In order to avoid unnecessary repetition, the present disclosure does not further describe the various possible combinations.

What is claimed is:

1. An electronic element, comprising:

an anode;

a cathode, wherein the anode and cathode are oppositely disposed; and a functional layer disposed between the anode and the cathode, the functional layer comprising:

an electron transport layer;

an organic light-emitting layer comprising a host material and a guest material, wherein the guest material is selected from $Ir(ppy)_3$ or $Ir(piq)_2(acac)$; and a hole transport layer, wherein the host material is an organic compound consisting of a structure represented by Formula I and a structure represented by Formula II:

Formula I

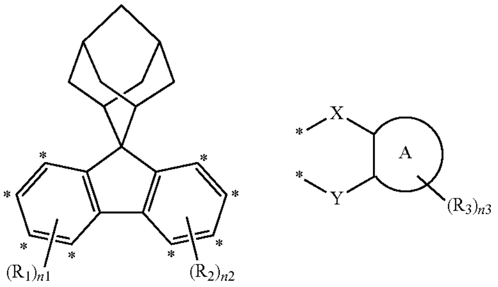

wherein the structure represented by Formula I is fused with one structure represented by Formula II;

* represents a site where the structure represented by Formula I is fused with the structure represented by Formula II;

a ring A is selected from a benzene ring or a naphthalene ring;

$n_1$ represents the number of $R_1$, $n_2$ represents the number of $R_2$, and $n_3$ represents the number of $R_3$;

$R_1$, $R_2$ and $R_3$ are represented by $R_k$, $n_1$ to $n_3$ are represented by $n_k$, and k is a variable and represents 1, 2 or 3, wherein:

in response to determining that k is 1, $n_k$ is selected from 0, 1, 2, 3 or 4;

in response to determining that k is 2, $n_k$ is selected from 0, 1 or 2;

in response to determining that k is 3, $n_k$ is selected from 0, 1, 2, 3, 4, 5, 6, 7 or 8; and in response to determining that $n_k$ is greater than 1, any two $n_k$ are the same or different; and optionally, any two adjacent $R_k$ are connected to each other to form a benzene ring, and the formed benzene ring is optionally substituted with R';

$R_1$, $R_2$, $R_3$, and R' are the same or different, and are each independently selected from an alkyl with 1 to 5 carbon atoms or a structure represented by Formula III:

$-(L)_m-Ar$ Formula III m represents the number of L, and m is selected from 0, 1, 2 or 3, wherein in response to determining that m is 2 or 3, any two L are the same or different;

Ar is selected from the group consisting of:

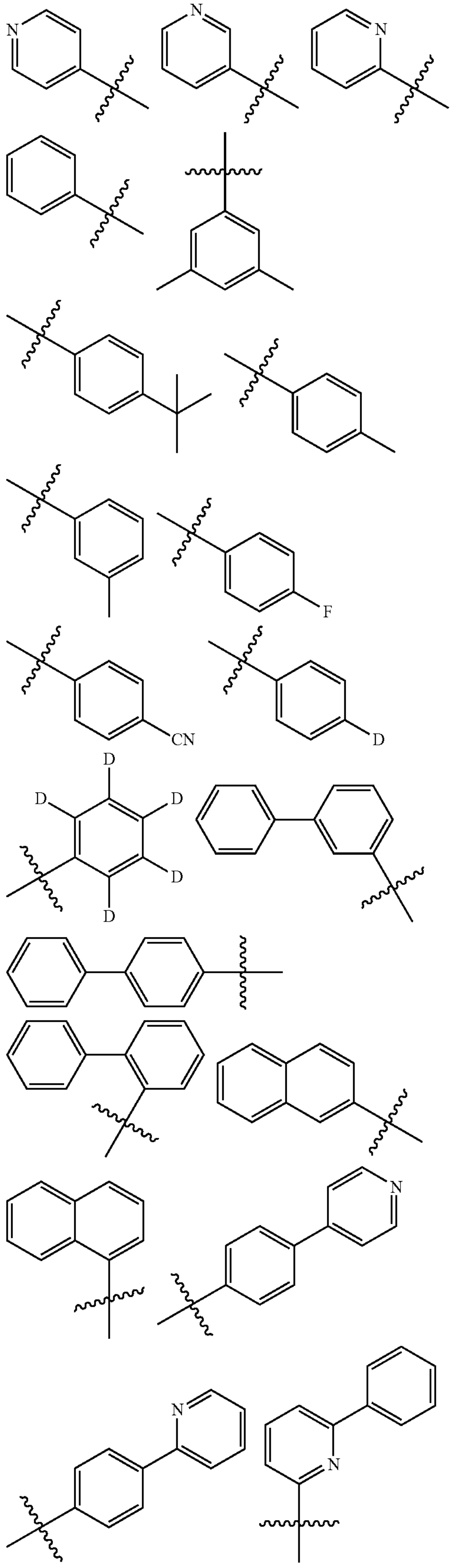

-continued
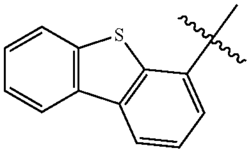
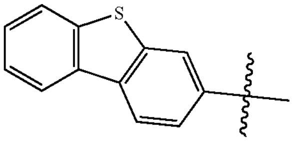
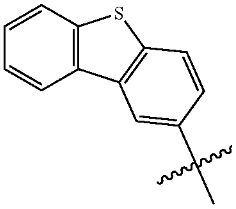
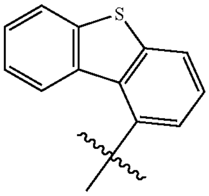
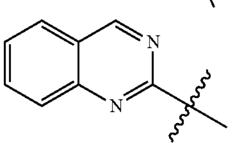
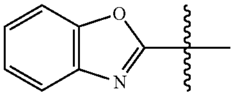
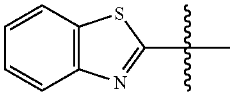
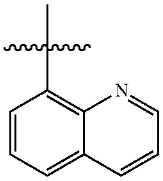
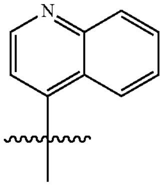
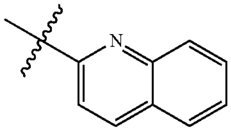
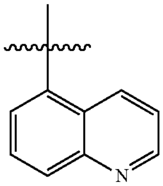
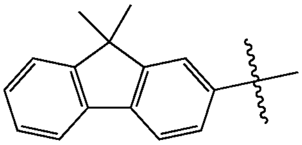
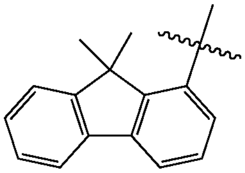
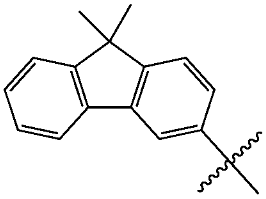
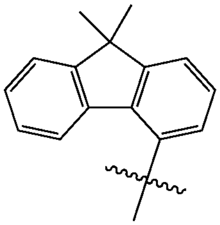
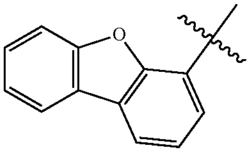
-continued
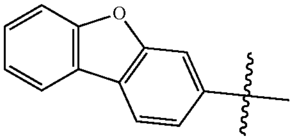
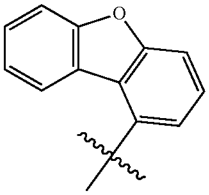
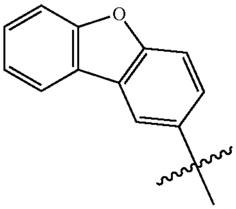
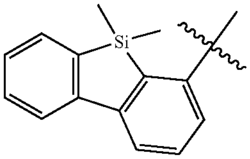
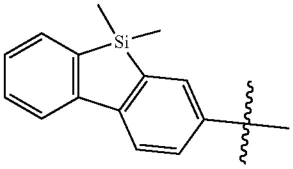
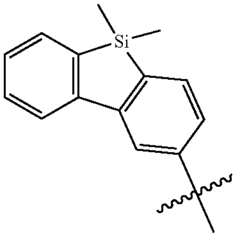
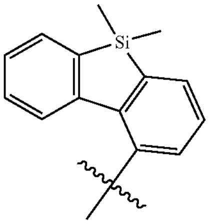
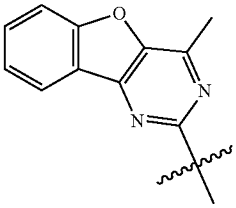
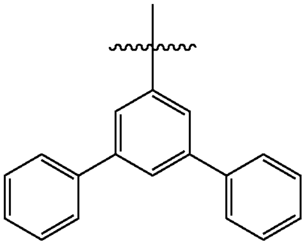
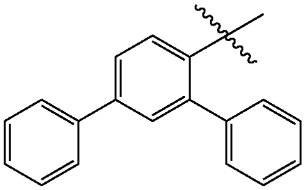
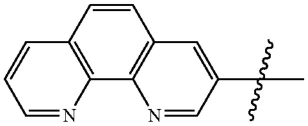

-continued
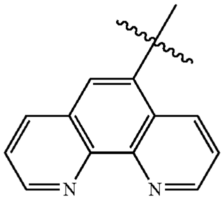
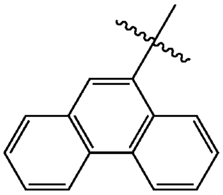
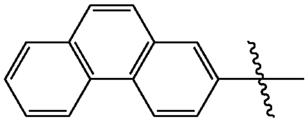
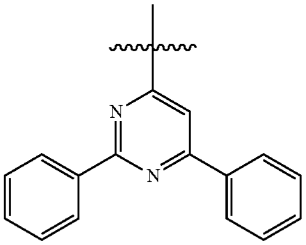
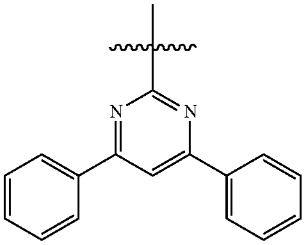
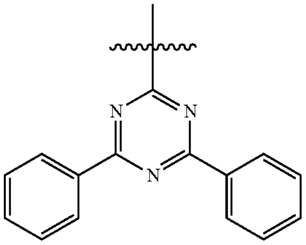
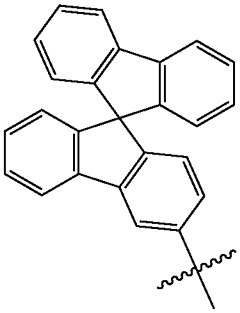
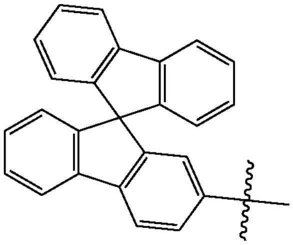
-continued
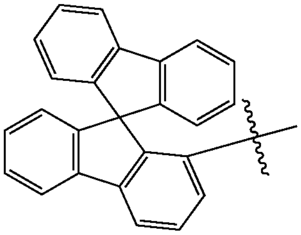
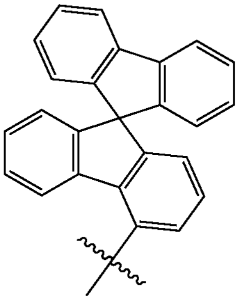
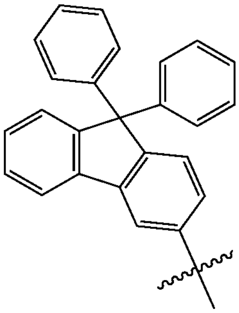
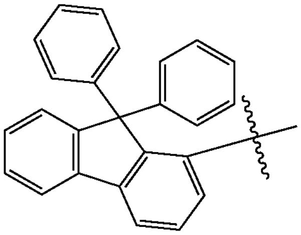
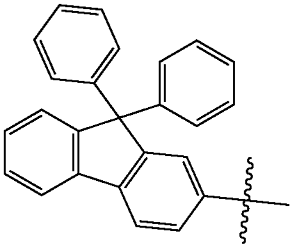
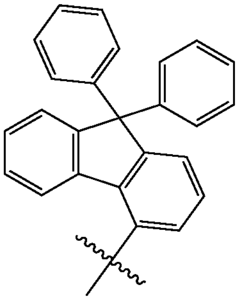
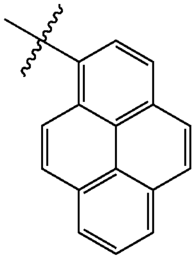
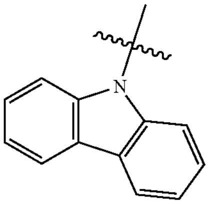
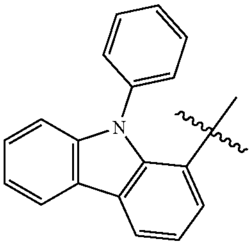

-continued
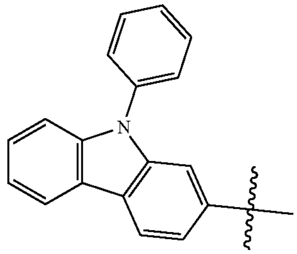
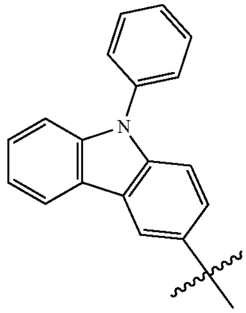
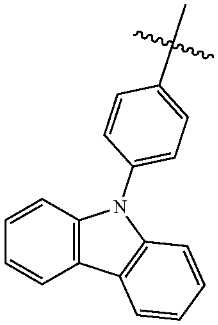
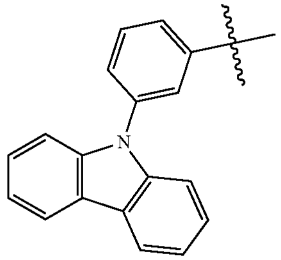
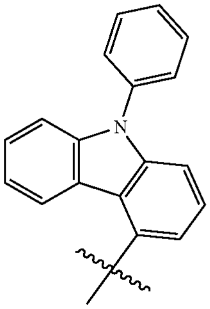
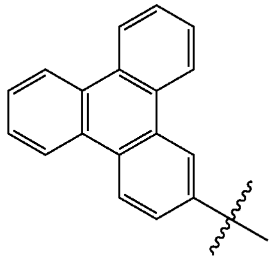
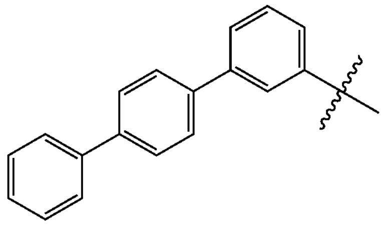
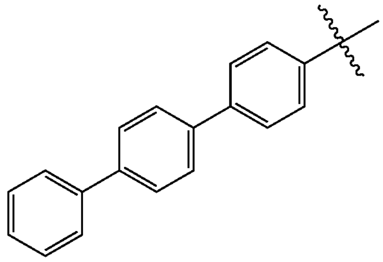
;
L is selected from a single bond or the group consisting of:
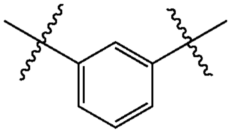
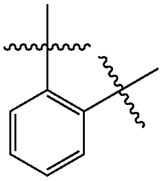
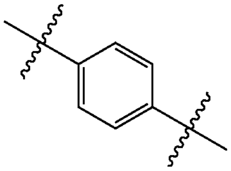
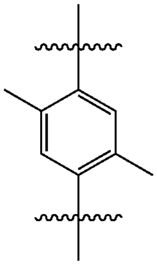
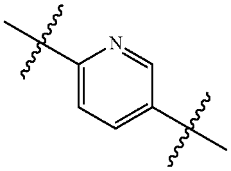
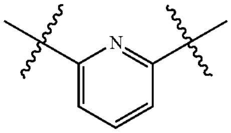
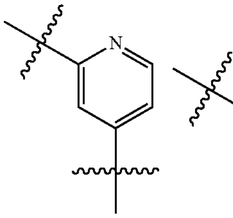
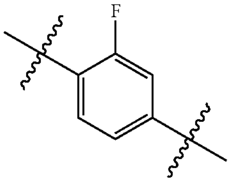
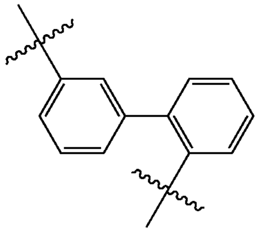
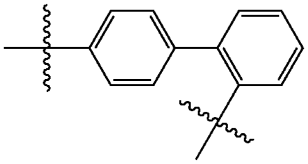
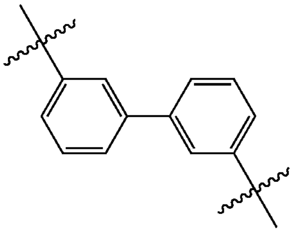
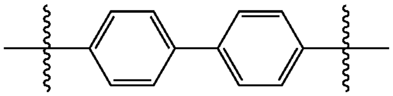

317
-continued
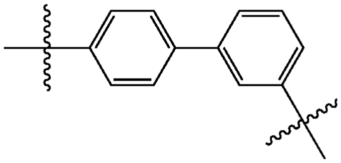
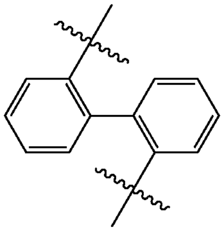
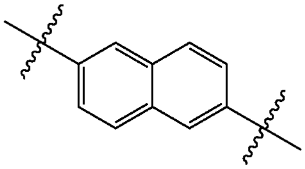
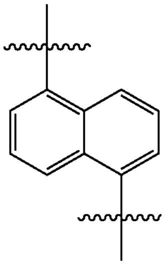
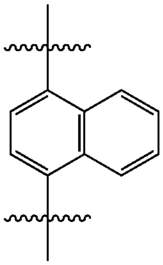
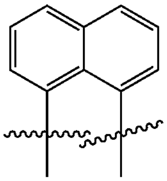
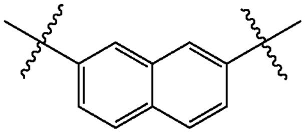
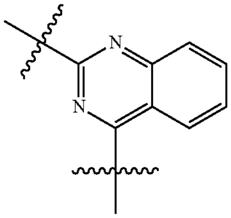
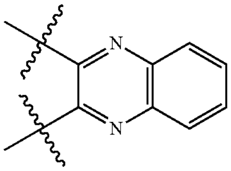
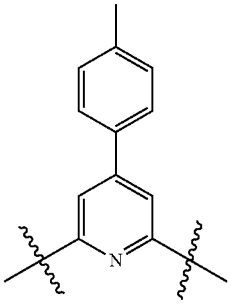
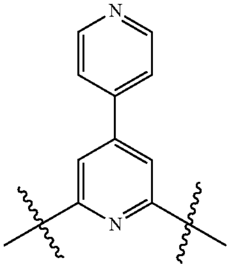
318
-continued
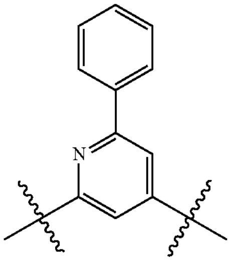
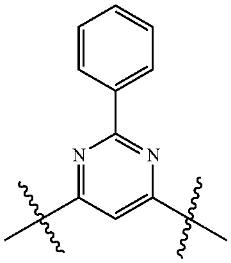
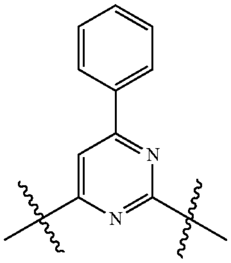
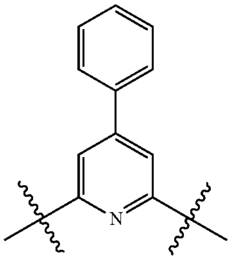
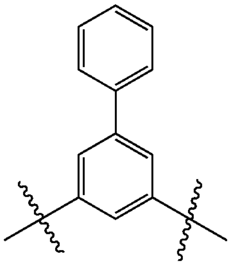
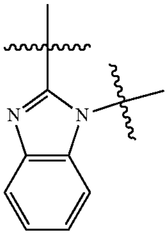
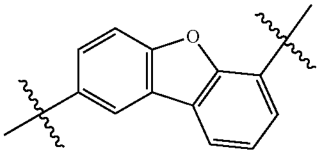
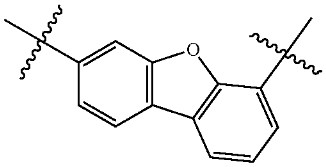
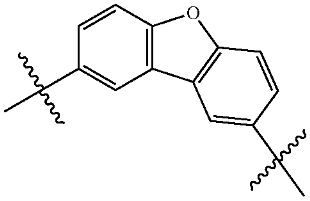
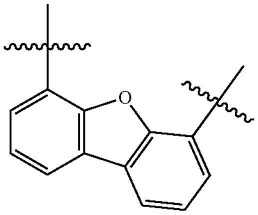
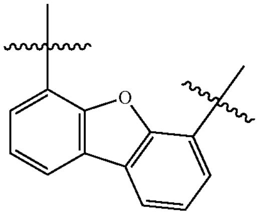
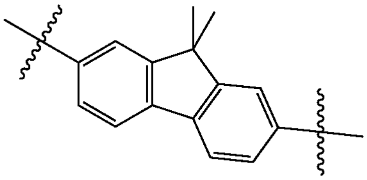

-continued
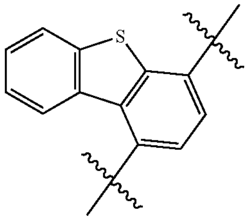
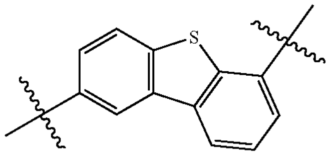
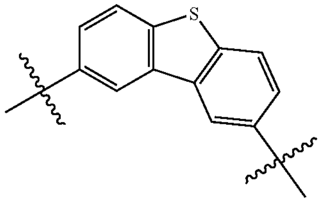
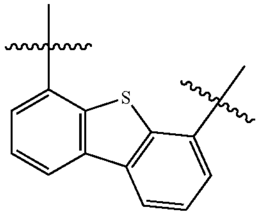
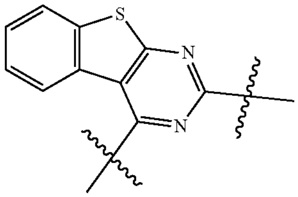
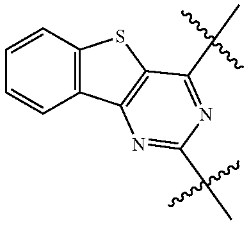
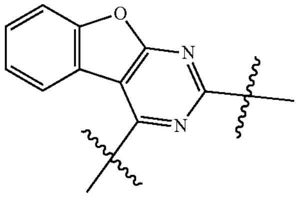
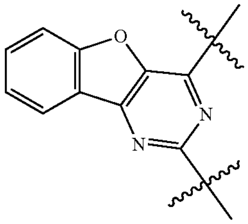
-continued
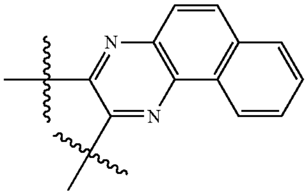
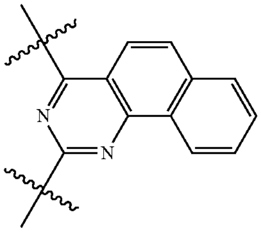
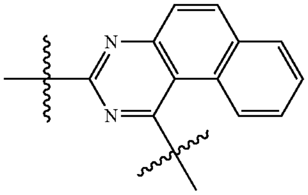
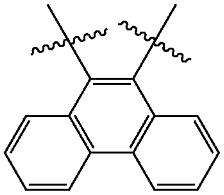
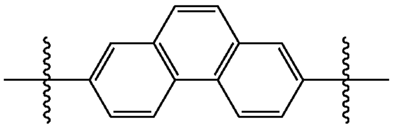
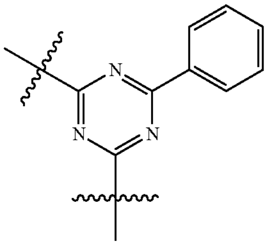
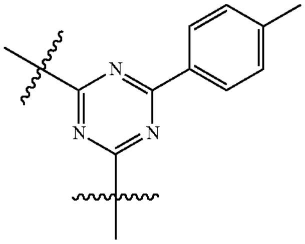
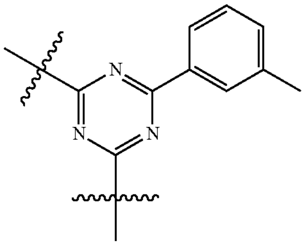

-continued
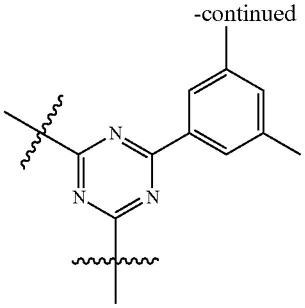
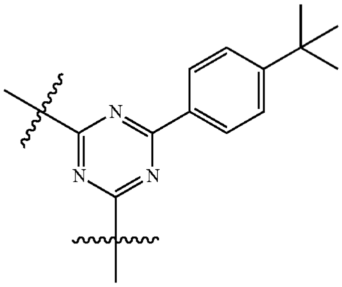
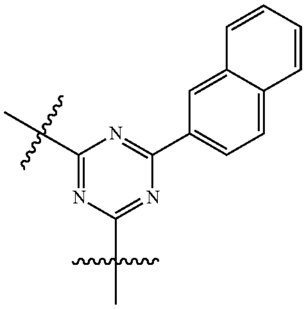
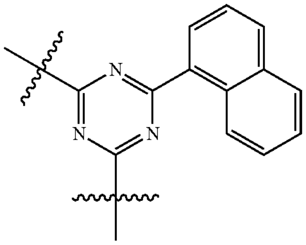
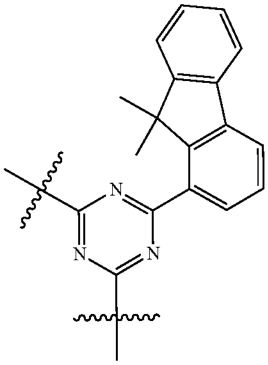
-continued
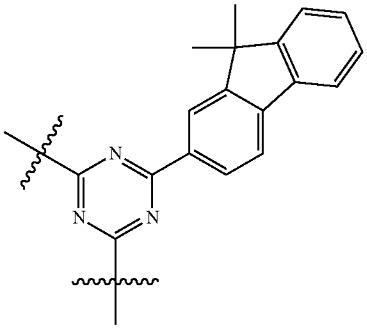
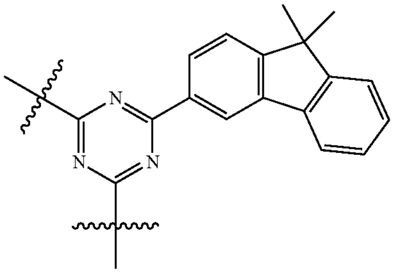
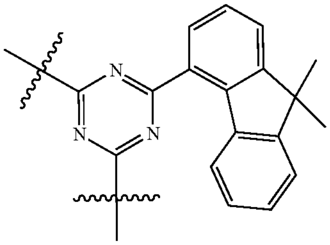
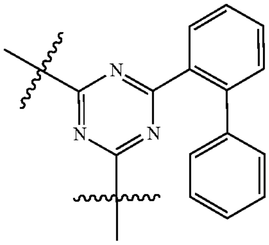
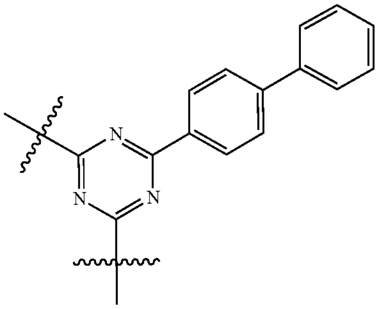
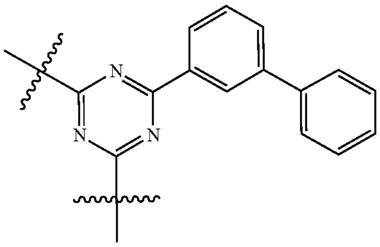

-continued
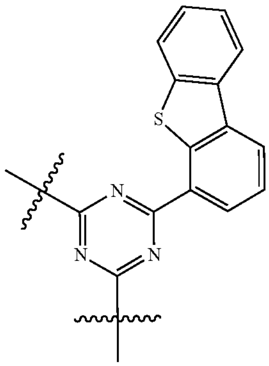
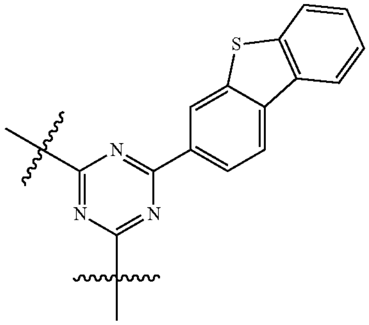
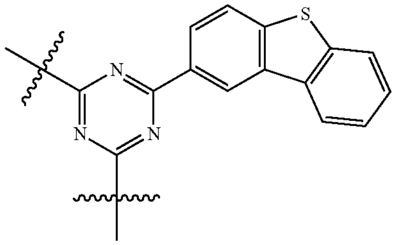
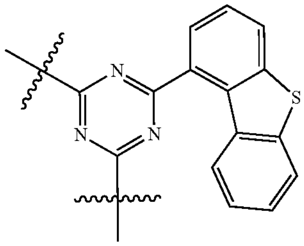
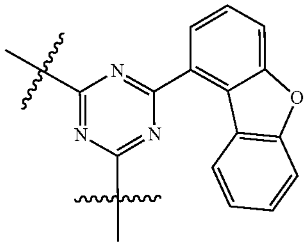
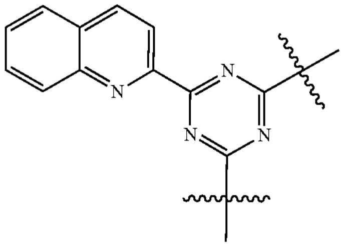
-continued
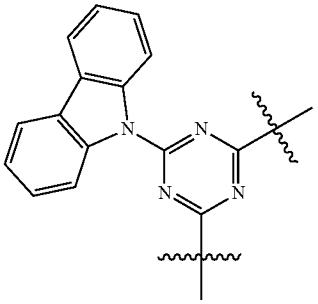
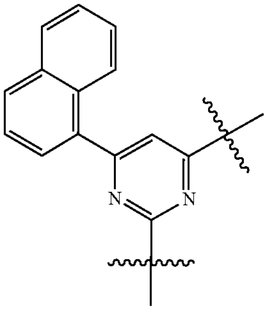
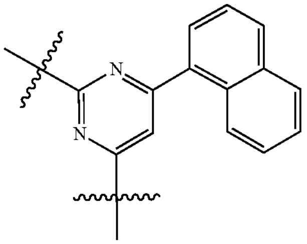
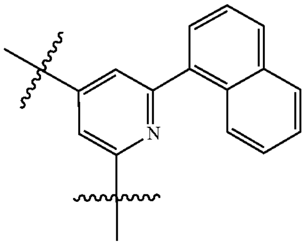
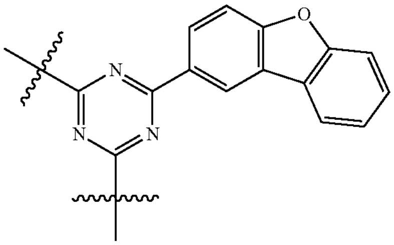
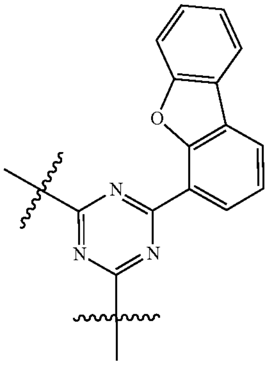

-continued
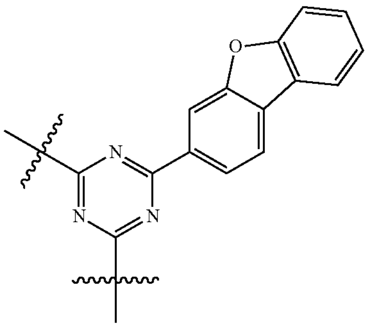
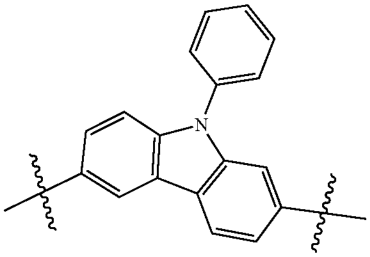
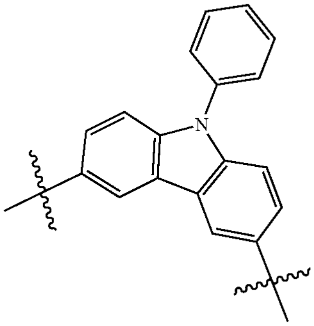
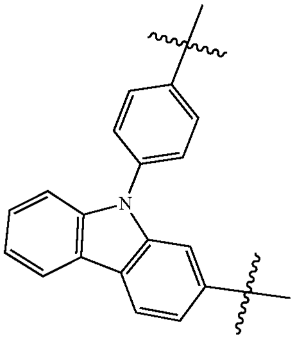
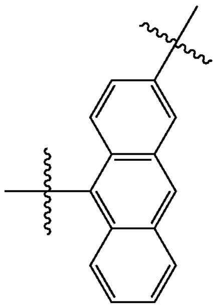
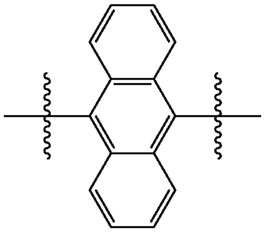
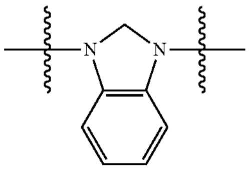
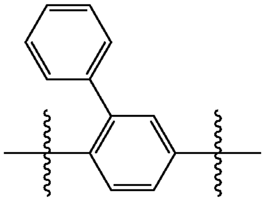
-continued
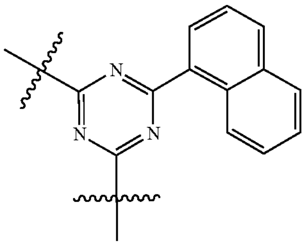
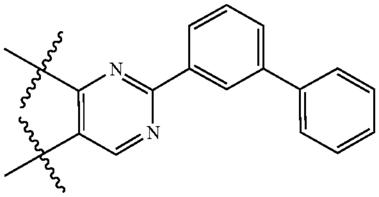
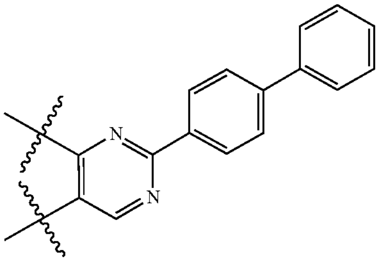
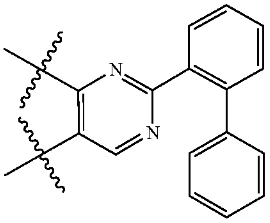
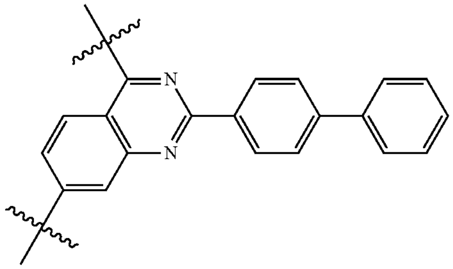
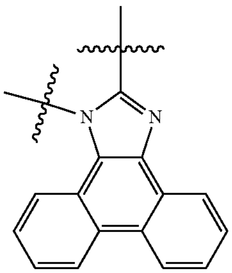
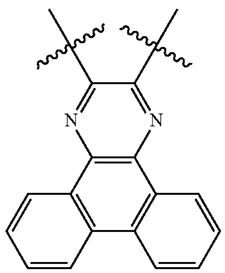

-continued

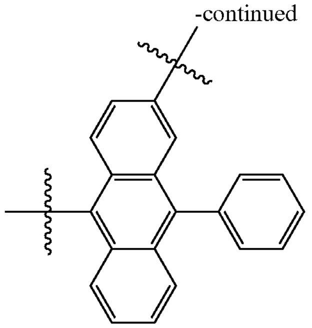

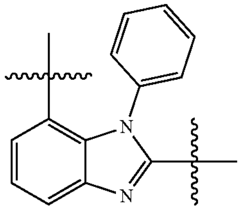

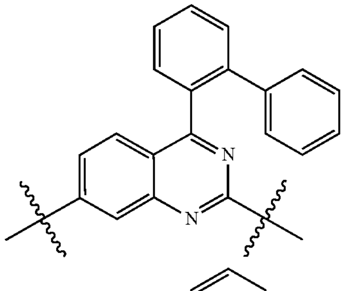

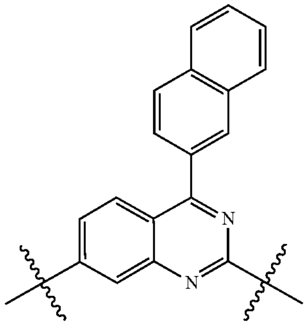

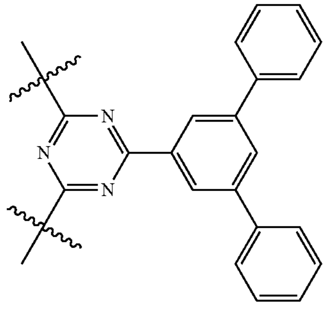

;

and

X and Y are the same or different, and are each independently selected from a single bond, O, S, $C(R_4R_5)$, and $Si(R_6R_7)$, wherein X and Y are not simultaneously a single bond; and wherein $R_4$ to $R_7$ are the same or different, and are each independently selected from an alkyl with 1 to 5 carbon atoms.

2. The electronic element according to claim 1, wherein the organic compound has a structure shown in any one of formulae 1-1 to 1-3:

1-1

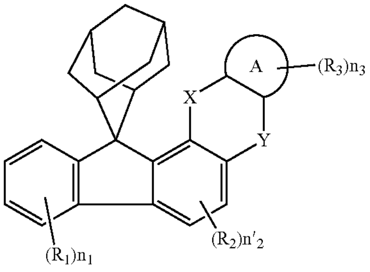

1-2

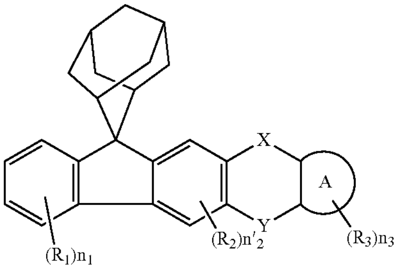

1-3

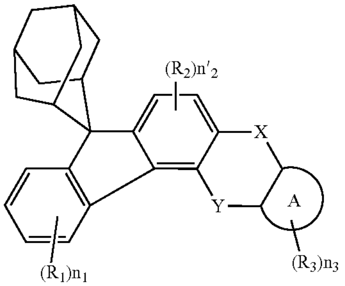

wherein $n'_2$ is selected from 0, 1 or 2.

3. The electronic element according to claim 1, wherein the organic compound has a structure shown in any one of 2-1 to 2-41:

2-1

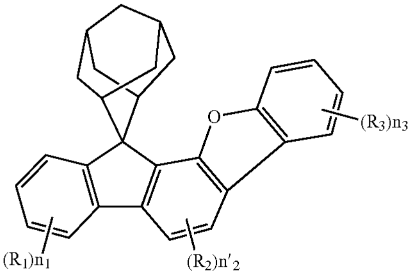

2-2

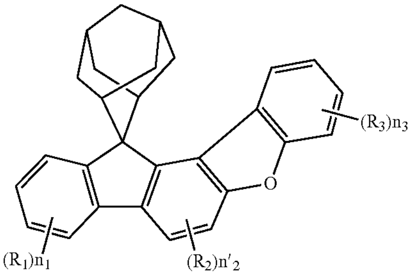

-continued
2-3
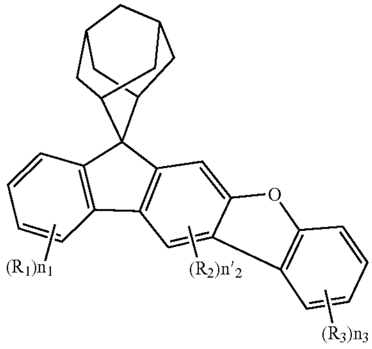
2-4
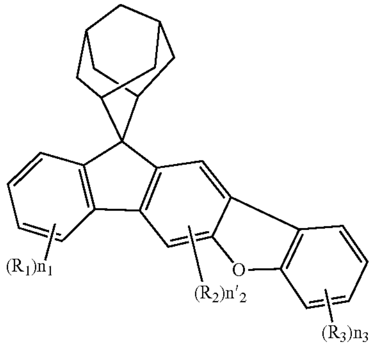
2-5
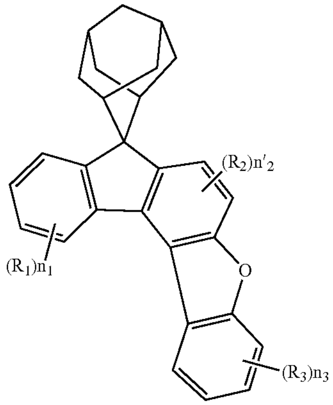
2-6
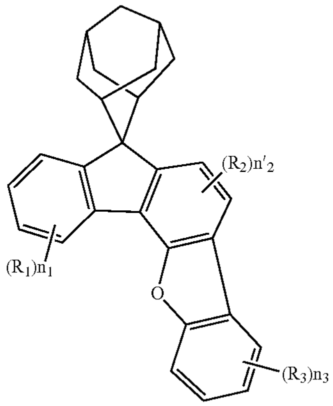
-continued
2-7
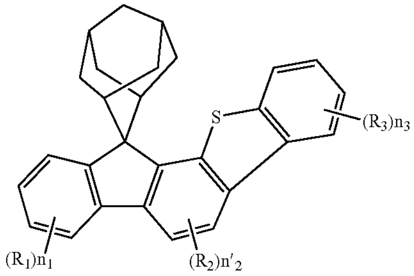
2-8
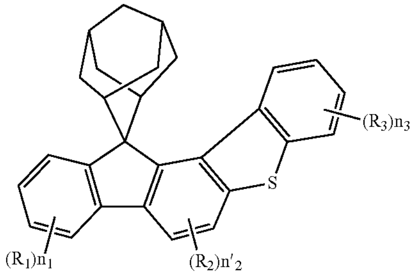
2-9
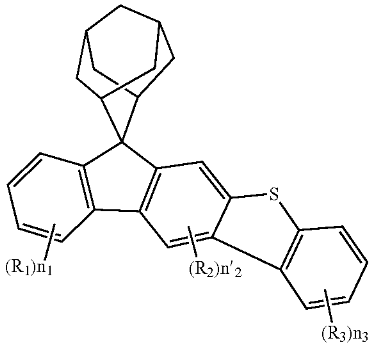
2-10
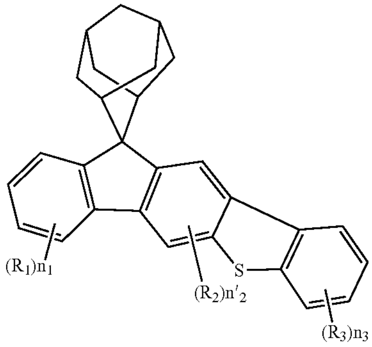

-continued
2-11
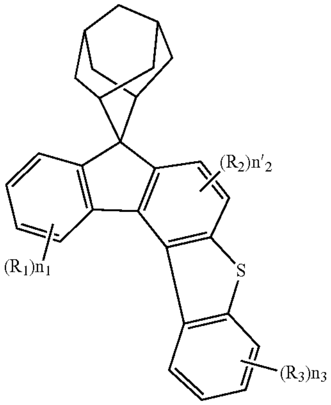
2-12
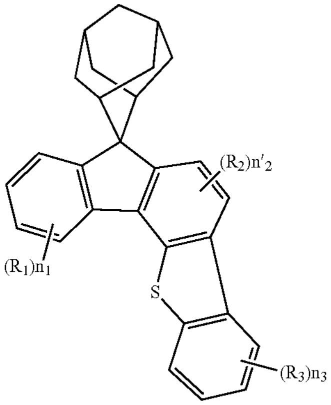
2-13
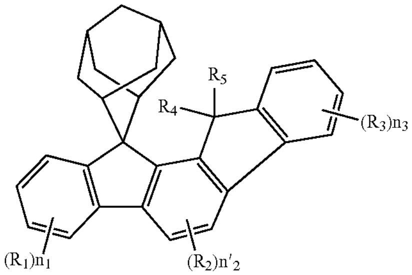
2-14
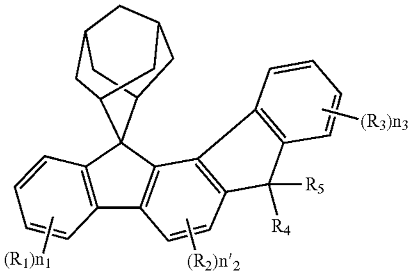
-continued
2-15
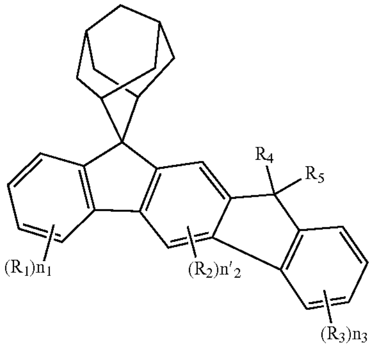
2-16
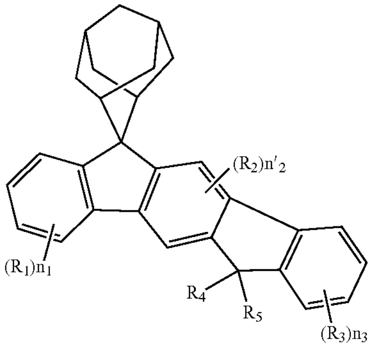
2-17
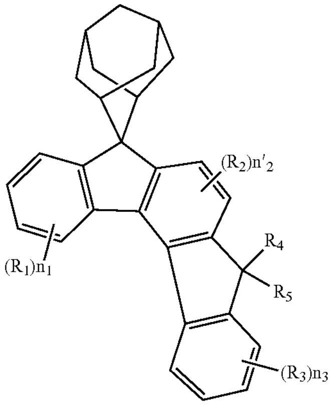
2-18
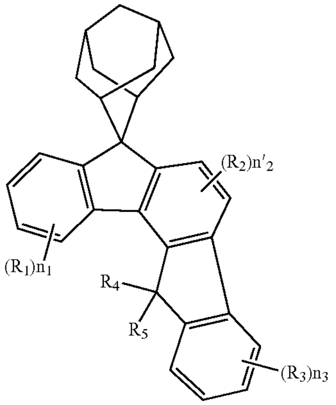

-continued
2-19
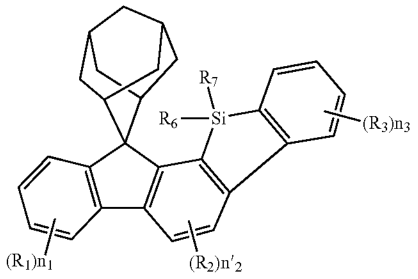
2-20
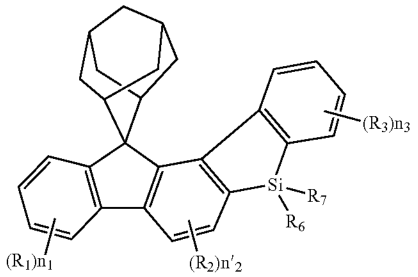
2-21
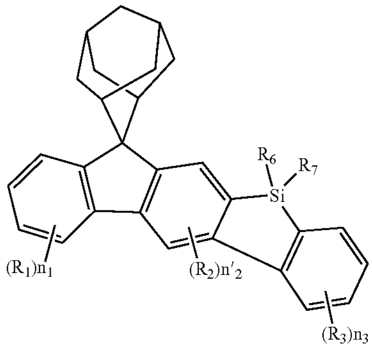
2-22
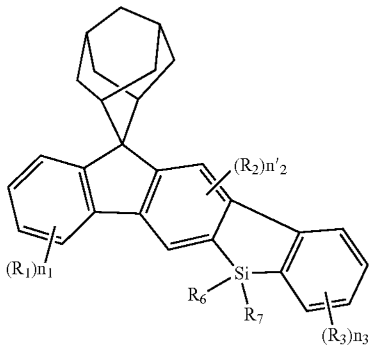
-continued
2-23
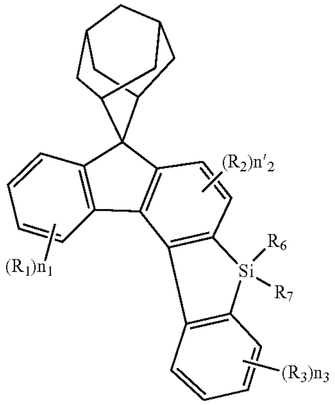
2-24
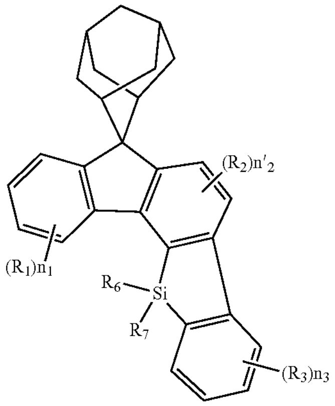
2-25
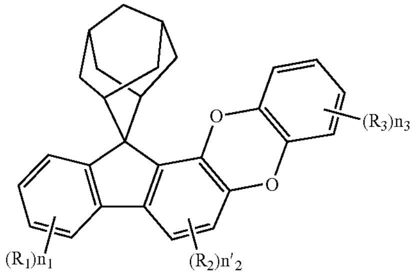
2-26
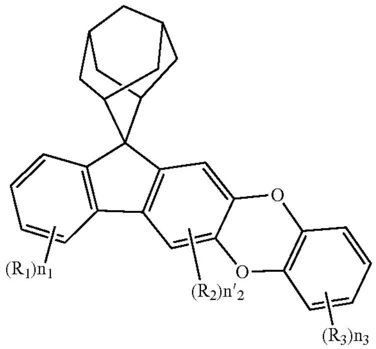

-continued
2-27
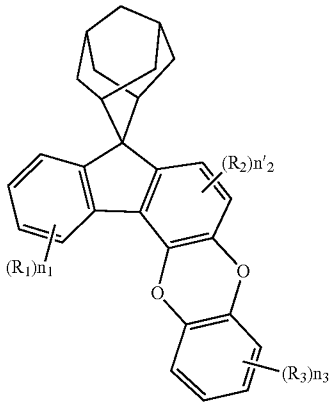
2-28
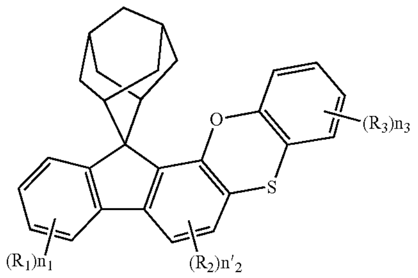
2-29
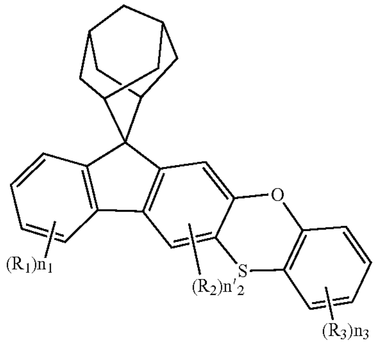
2-30
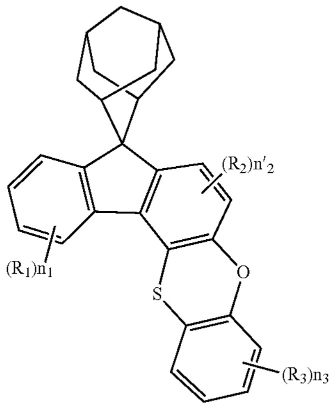
-continued
2-31
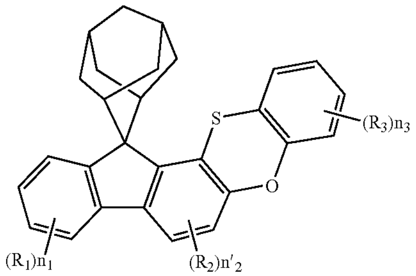
2-32
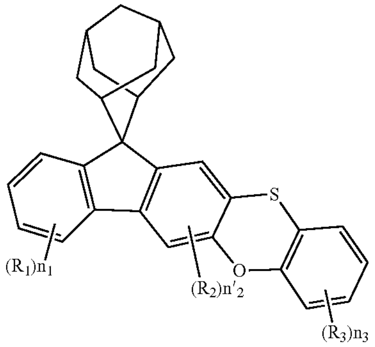
2-33
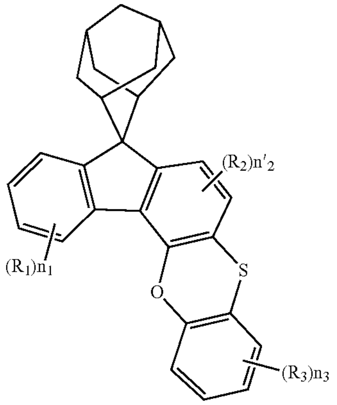
2-34
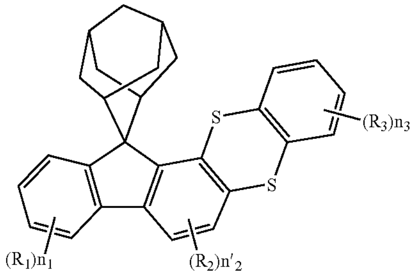

-continued
2-35
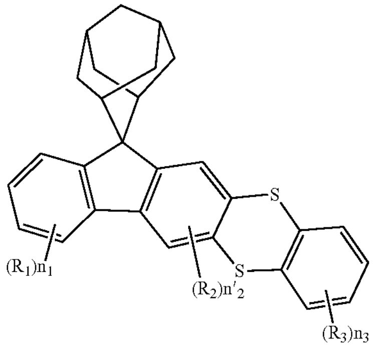
2-36
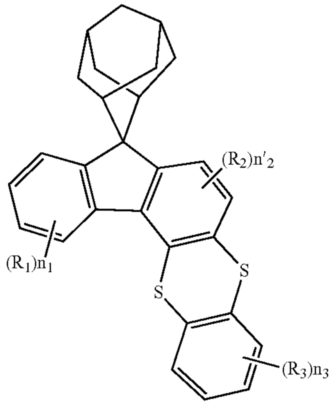
2-37
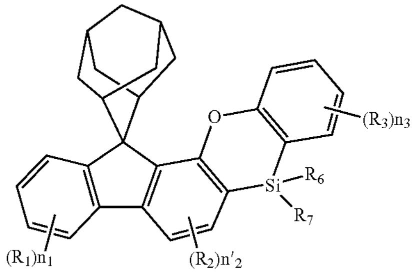
2-38
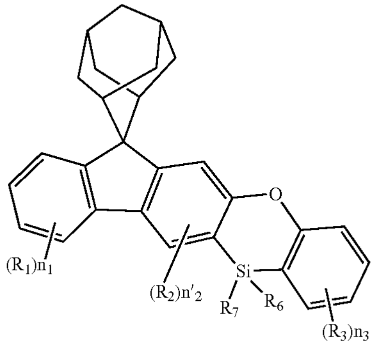
-continued
2-39
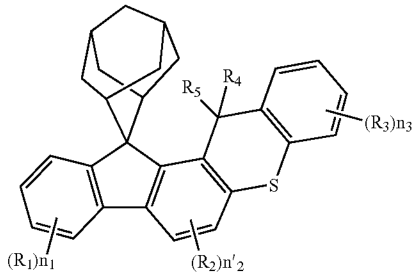
2-40
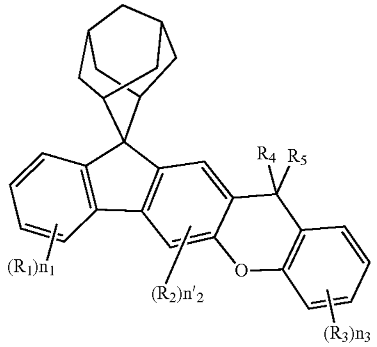
2-41
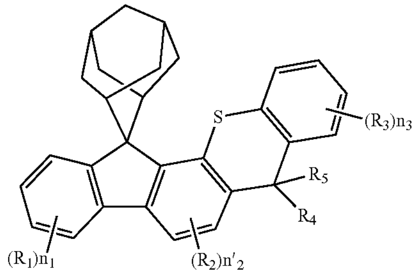
wherein $n'_2$ is selected from 0, 1 or 2.
4. The electronic element according to claim 1, wherein the Formula II has a structure shown in any one of formulae II-1 to II-11:
II-1
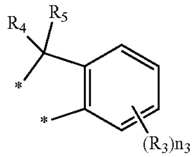
II-2
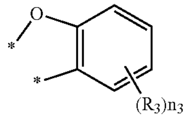
II-3
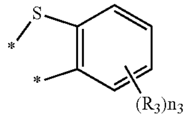

-continued
II-4
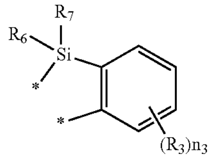
II-5
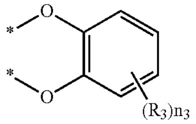
II-6
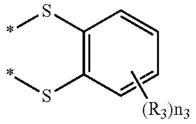
II-7
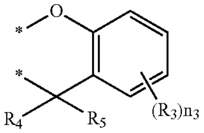
-continued
II-8
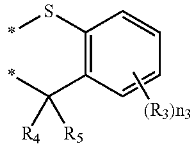
II-9
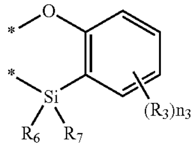
II-10
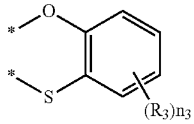
II-11
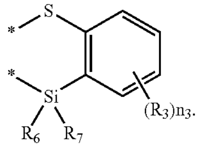
5. The electronic element according to claim 1, wherein the organic compound is selected from the group consisting of the following compounds:
1
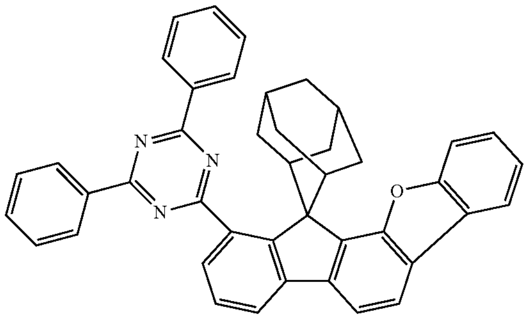
2
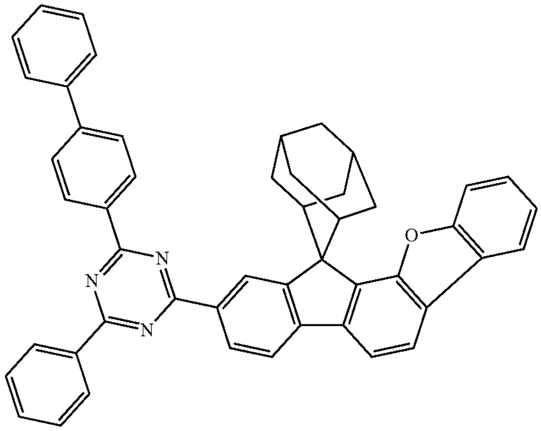
3
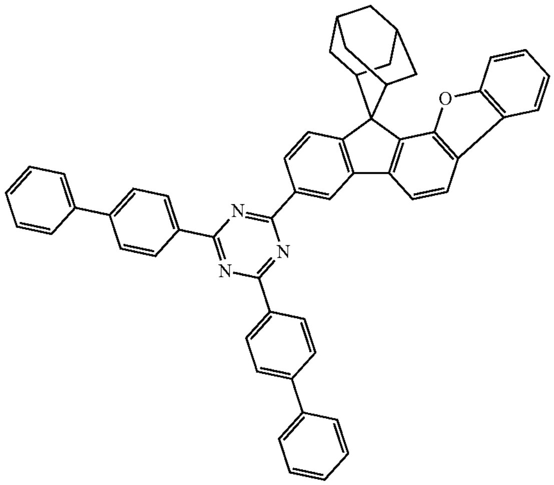
4
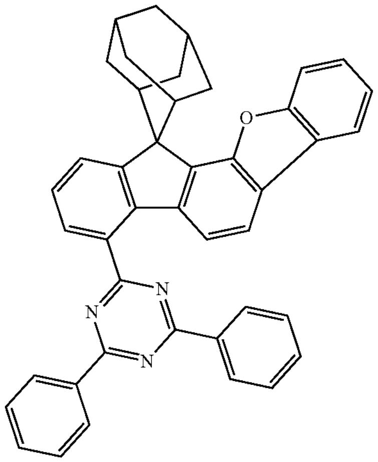

-continued
5
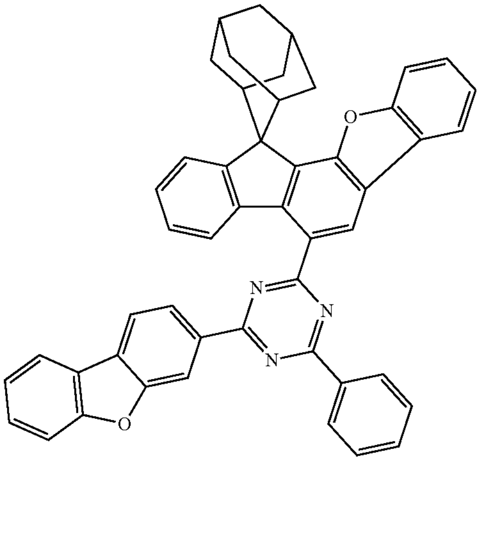
6
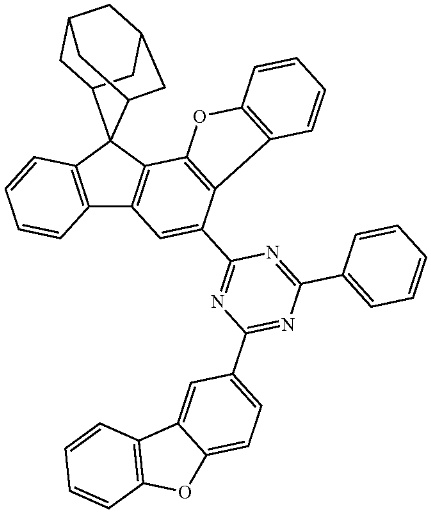
7
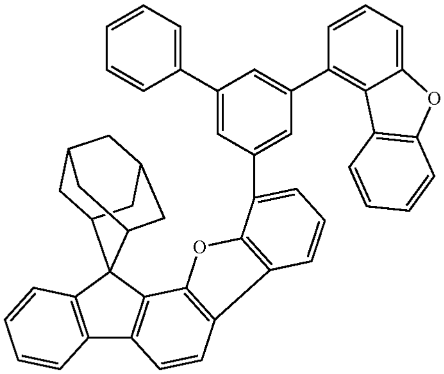
8
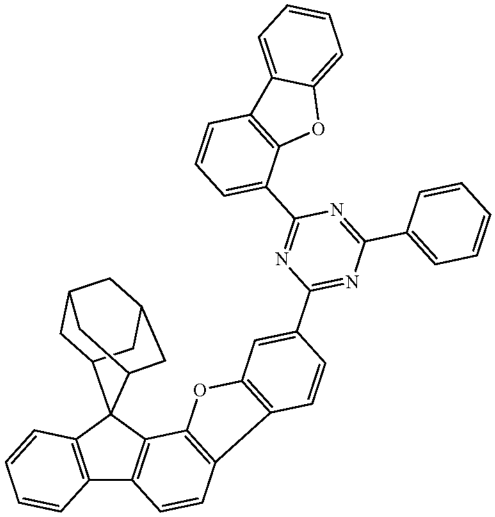
9
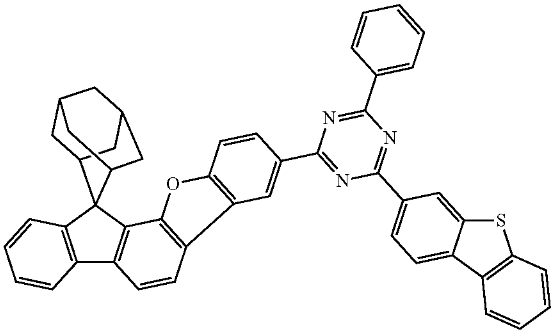
10
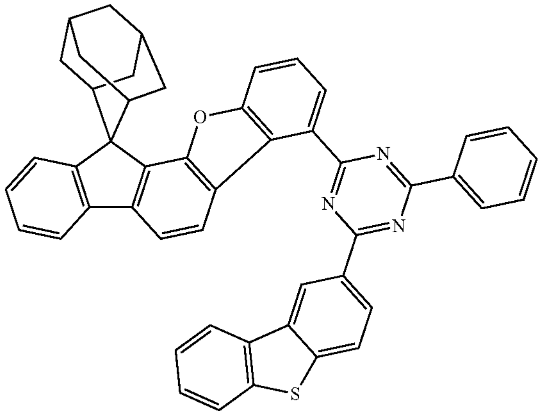

-continued
11
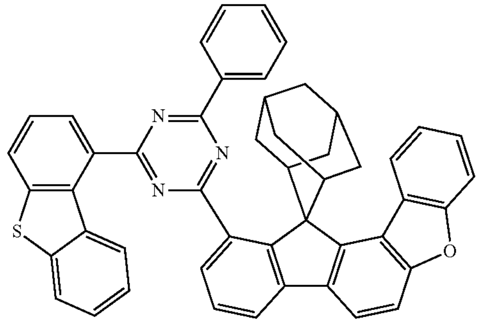
12
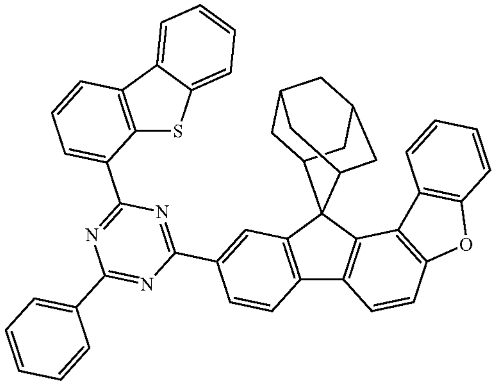
13
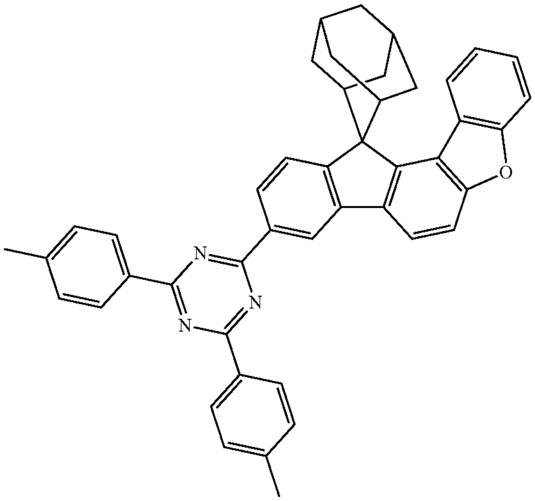
14
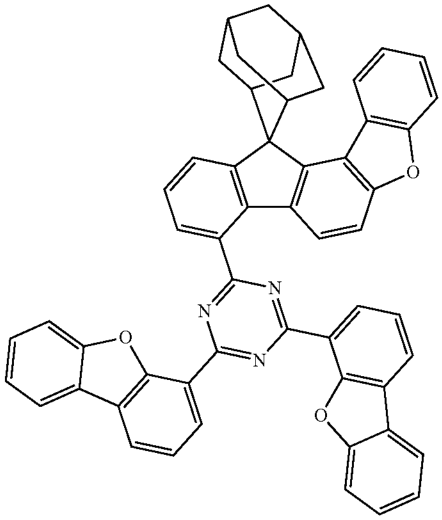
15
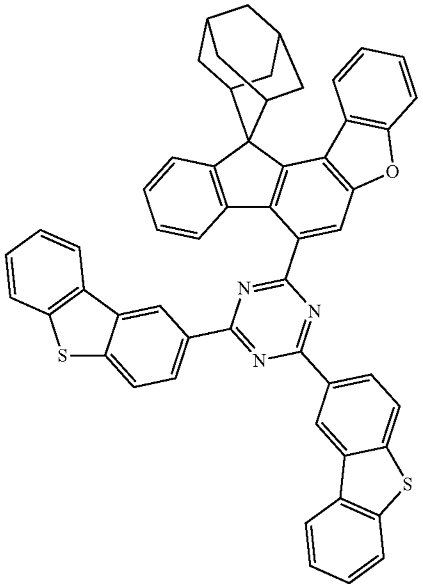
16
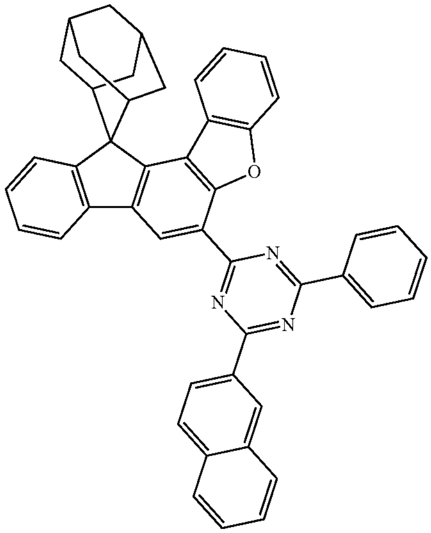

-continued
17
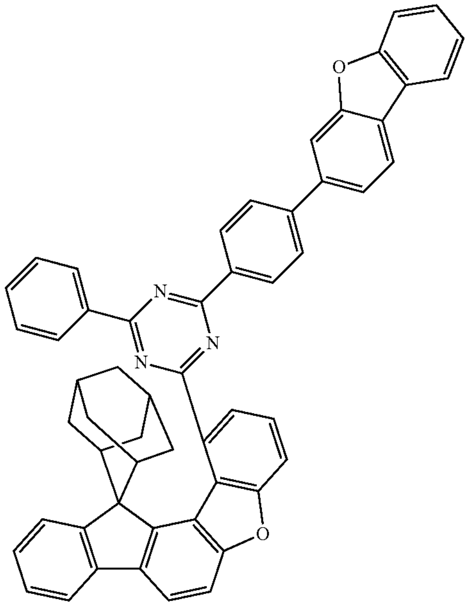
18
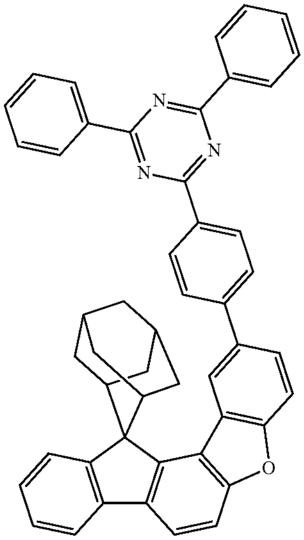
19
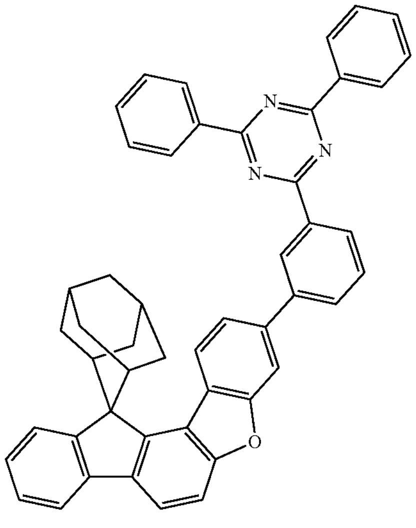
20
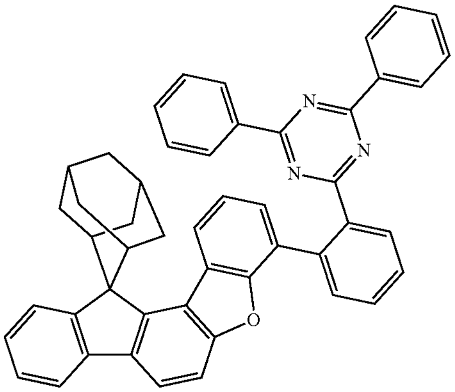

-continued
21
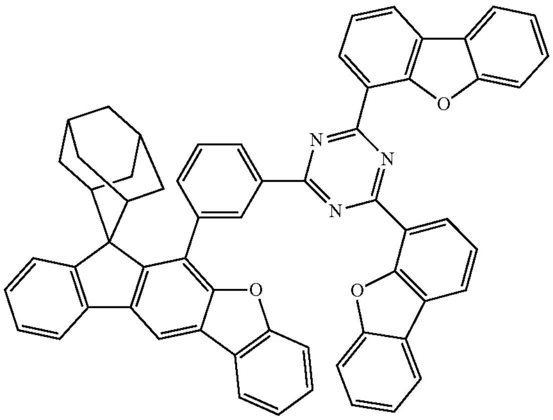
22
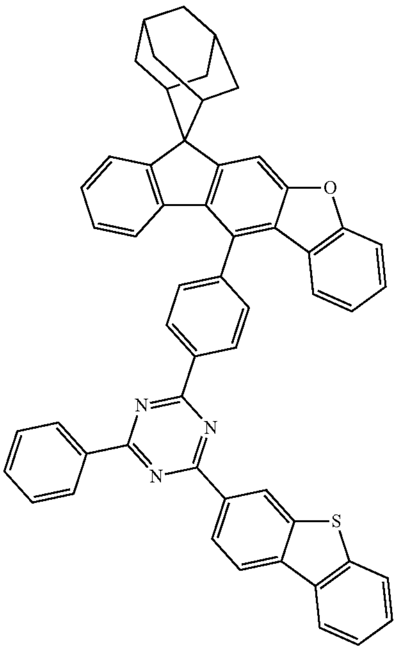
23
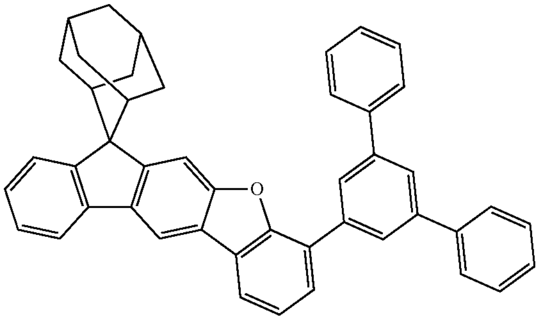
24
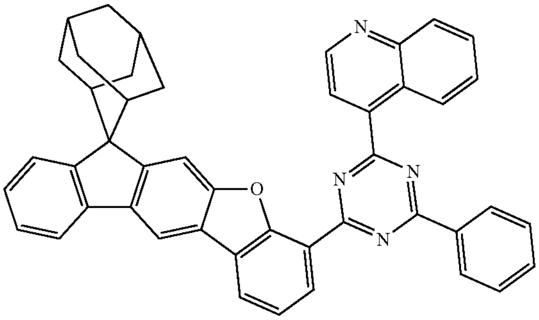

-continued
25
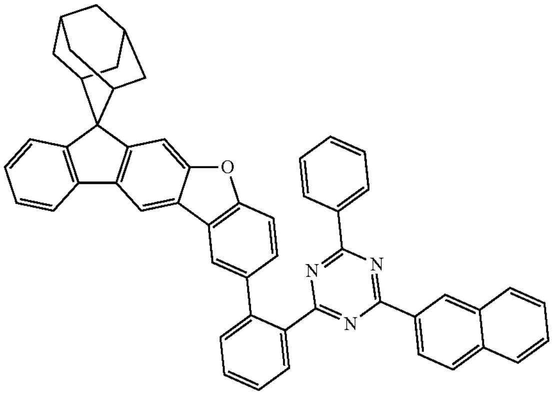
26
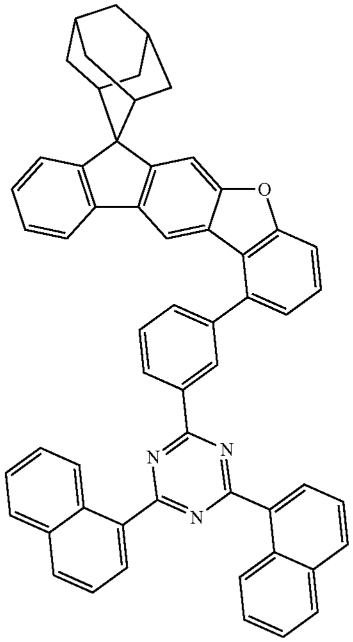
27
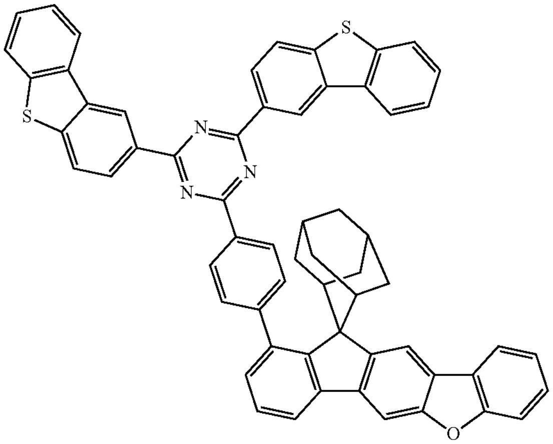
28
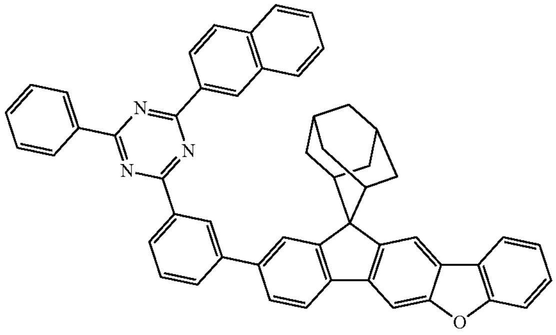
29
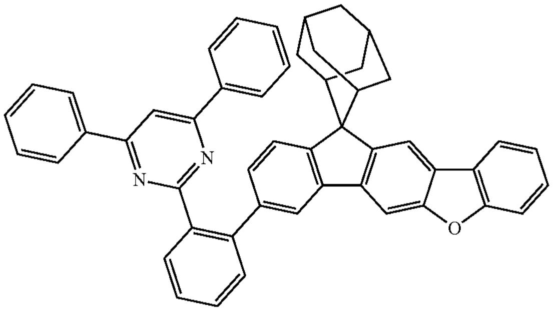
30
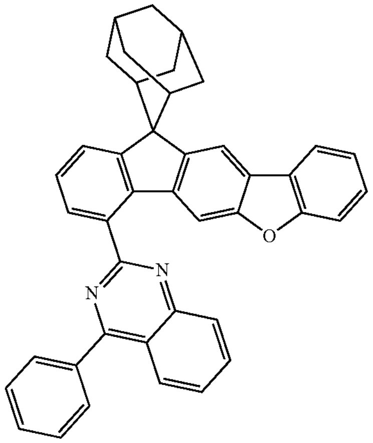

-continued
31
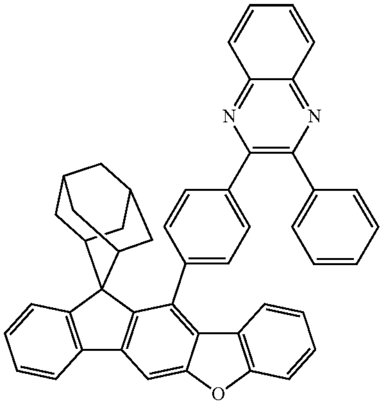
32
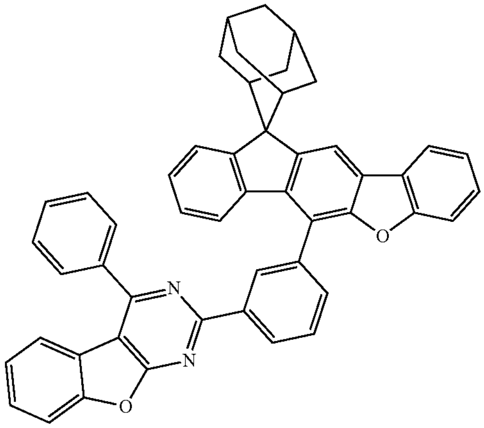
33
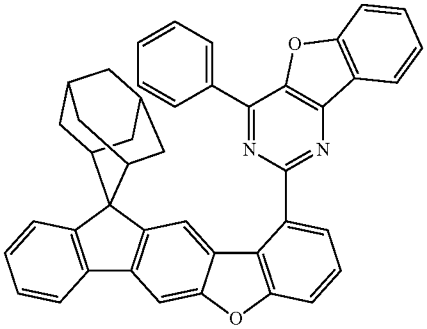
34
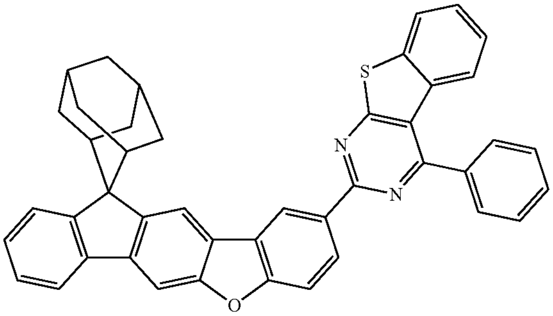
35
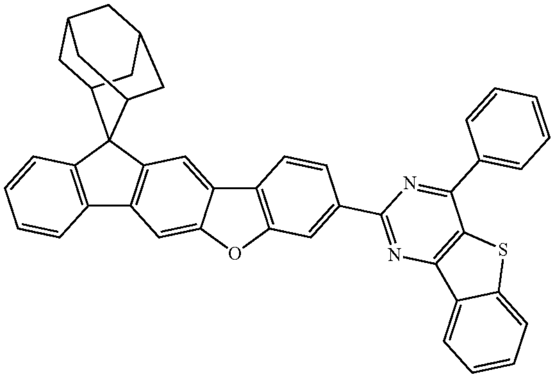
36
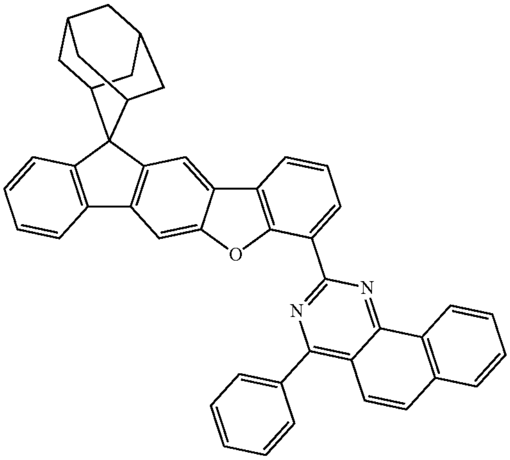

-continued
37
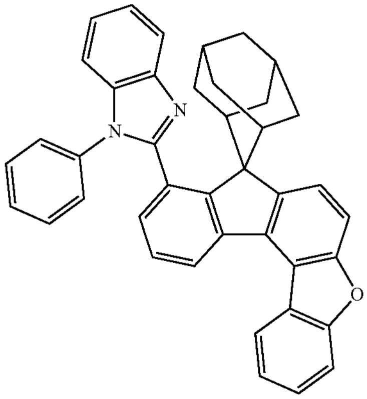
38
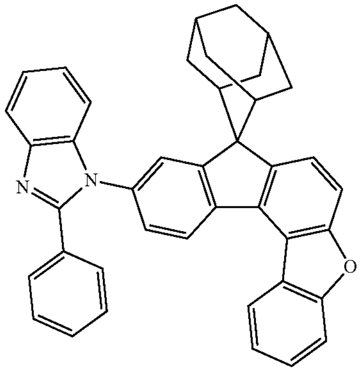
39
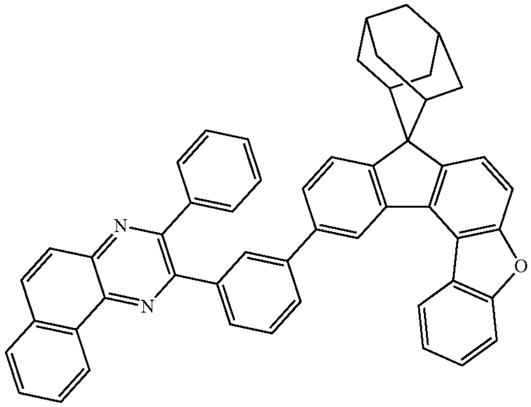
40
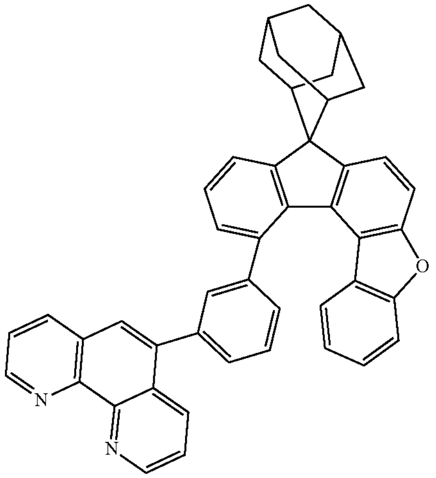
41
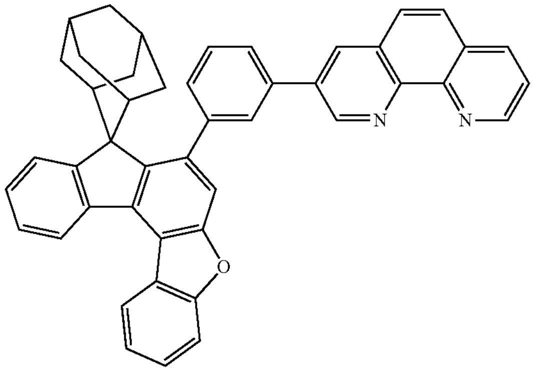
42
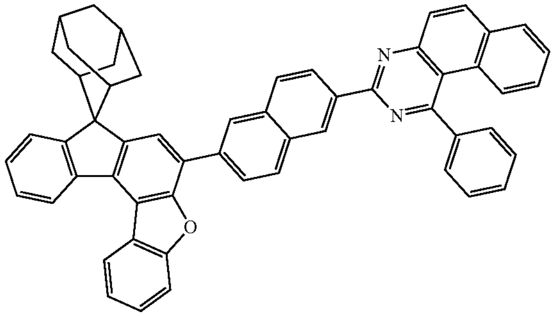

-continued
43
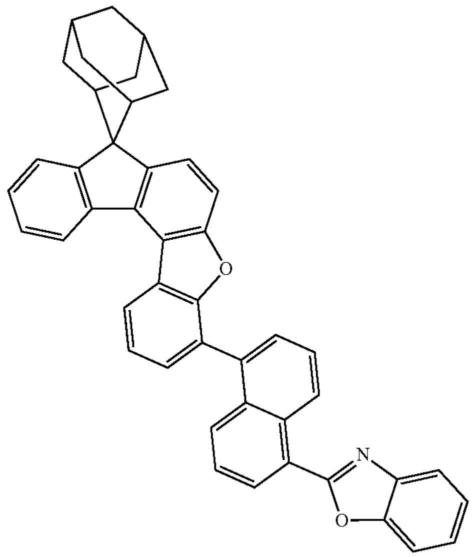
44
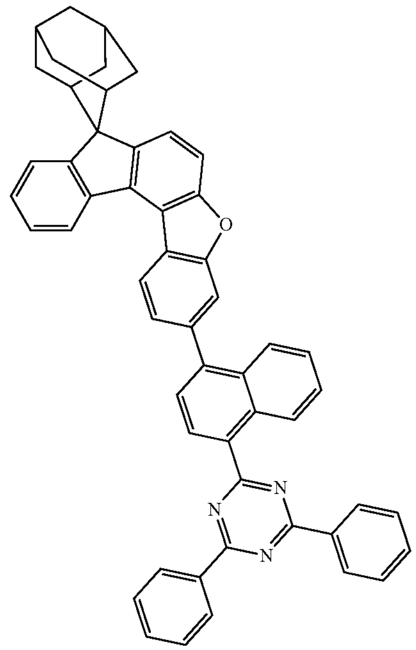
45
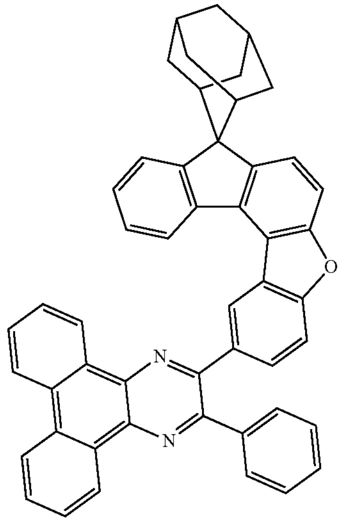
46
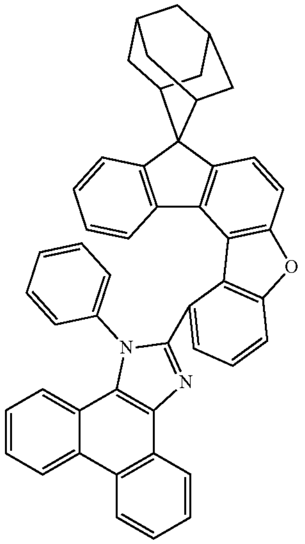
47
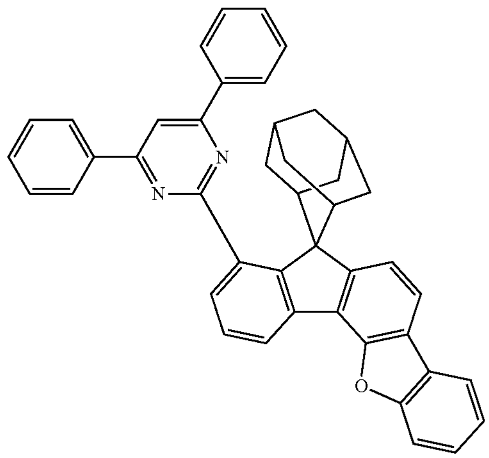
48
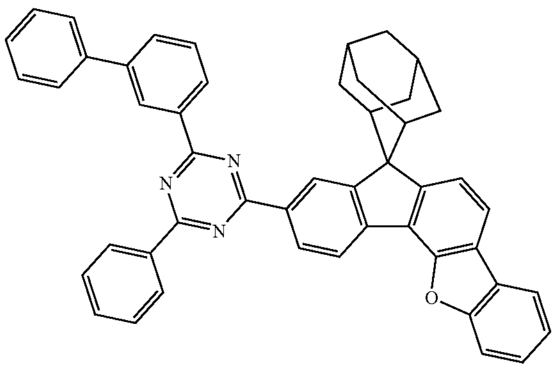

-continued
49
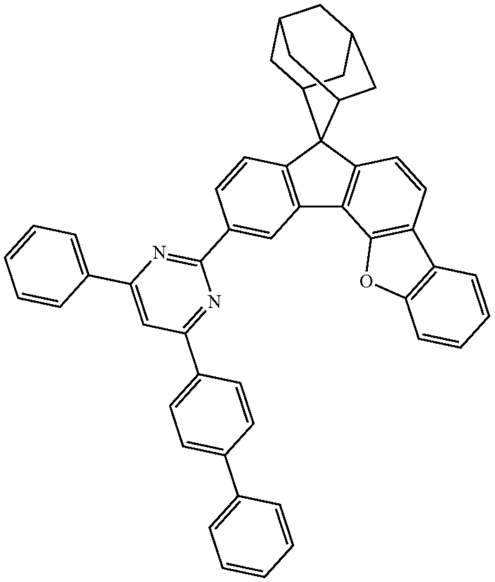
50
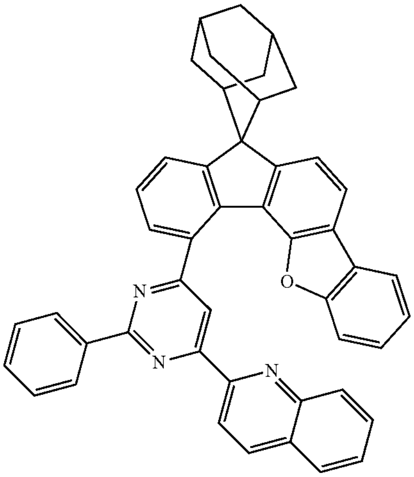
51
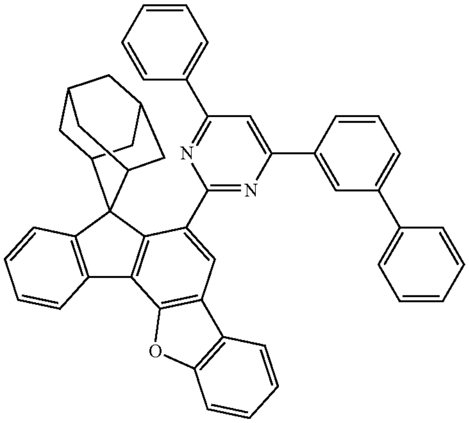
52
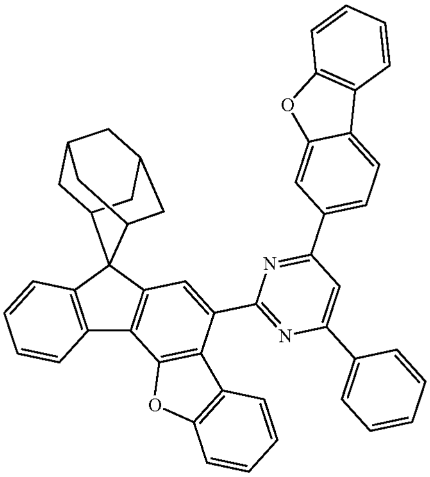
53
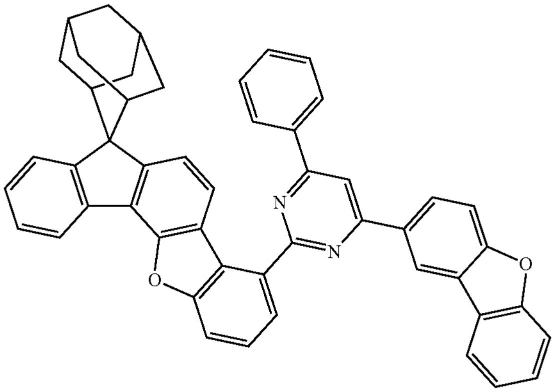
54
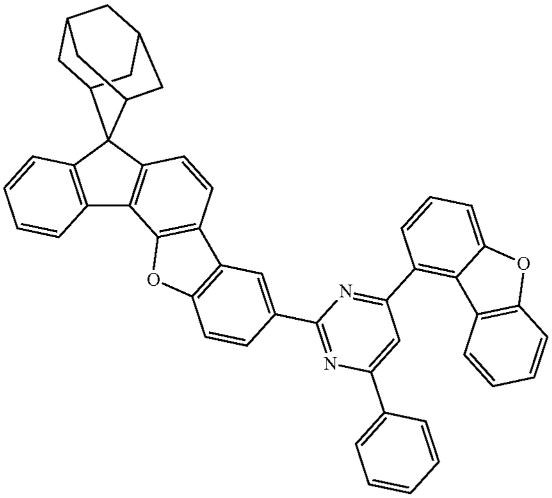

-continued
55
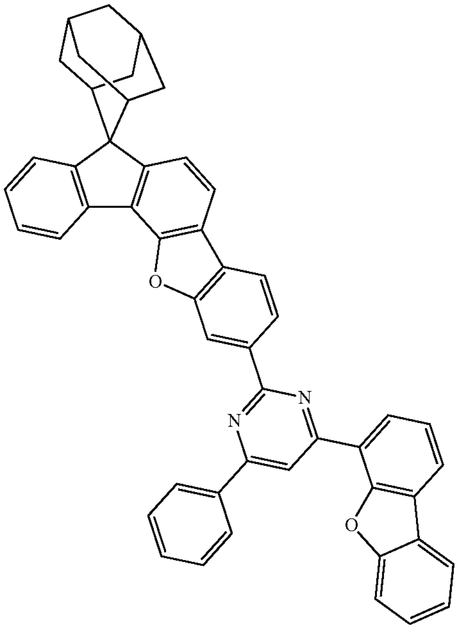
56
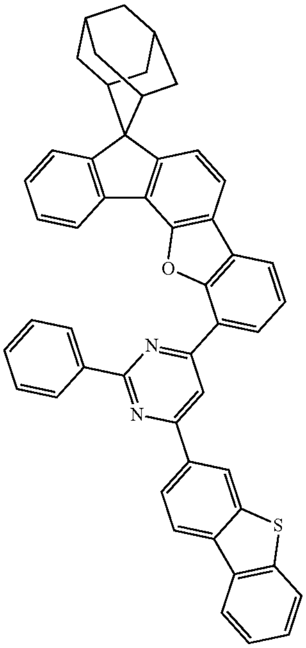
57
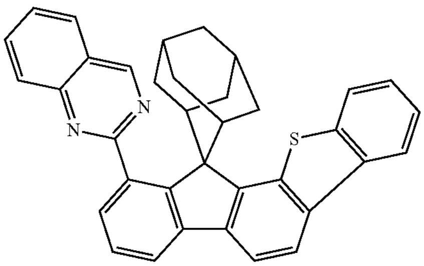
58
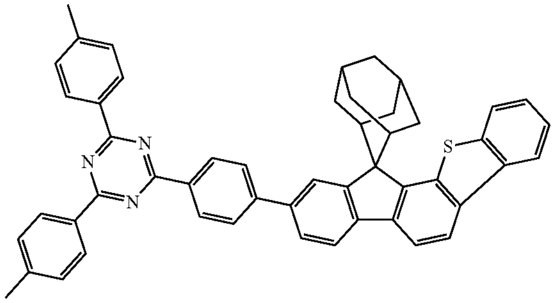
59
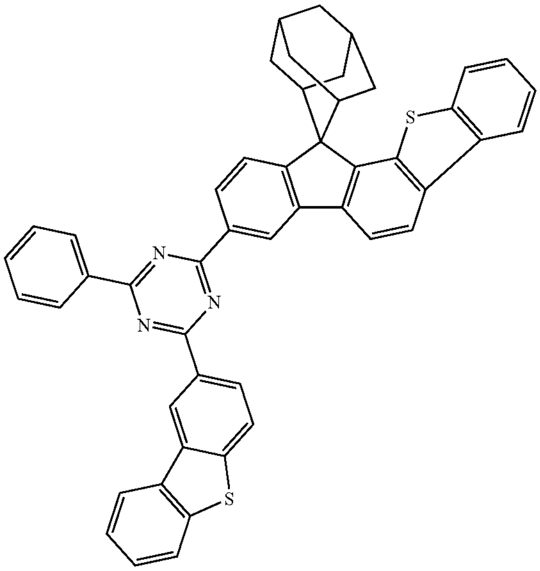
60
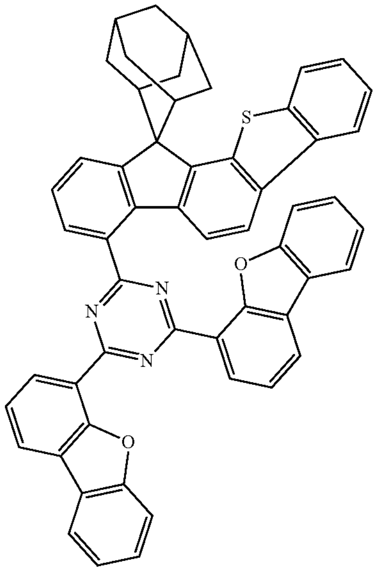

-continued
61
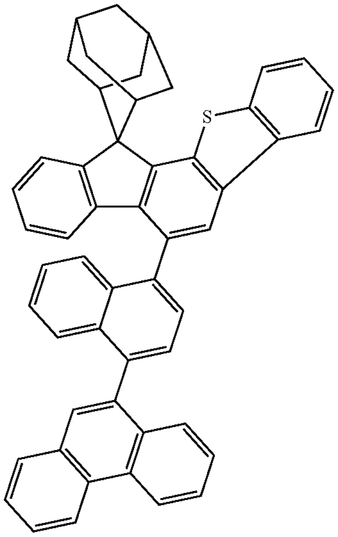
62
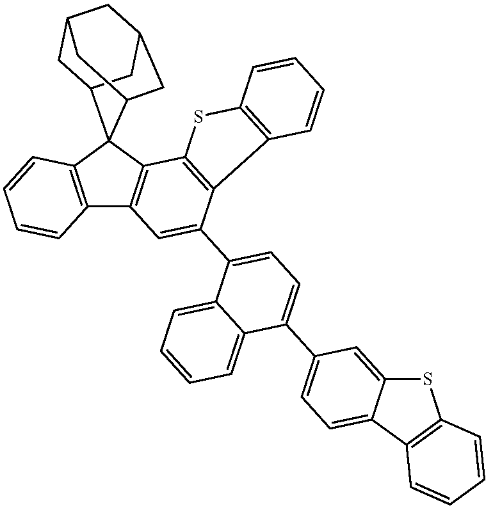
63
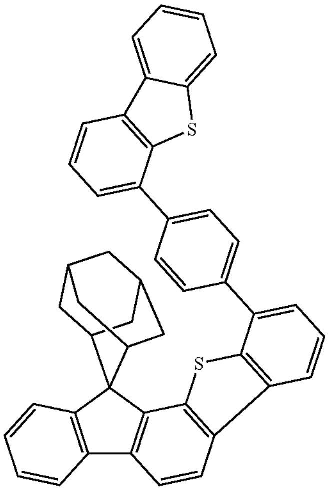
64
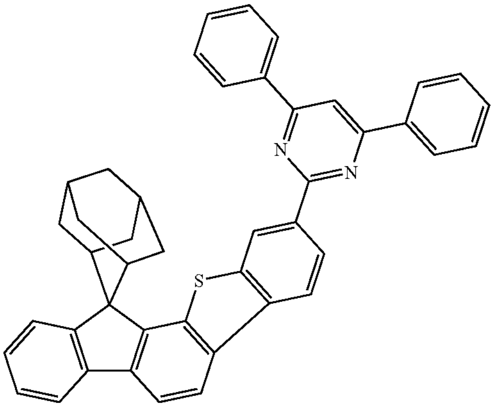
65
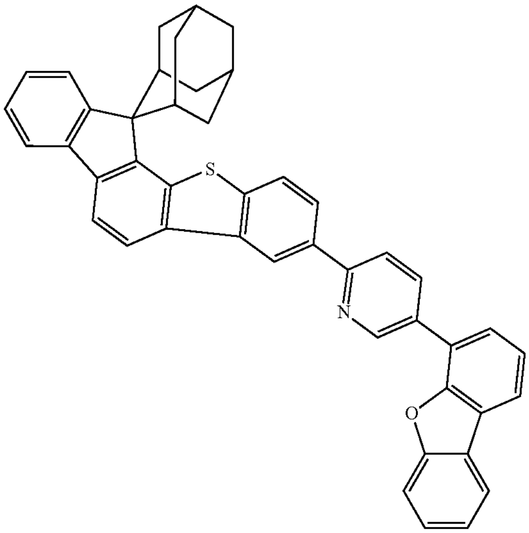
66
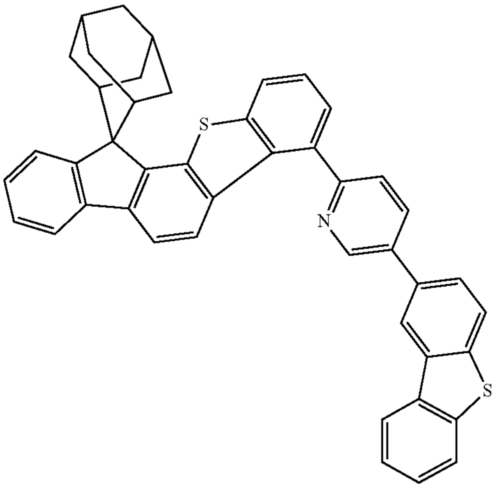

-continued
67
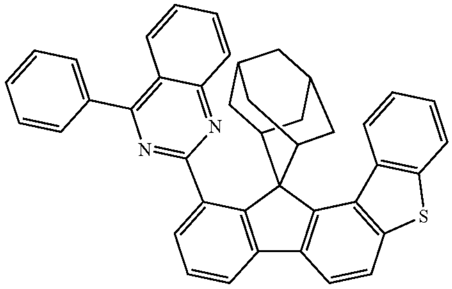
68
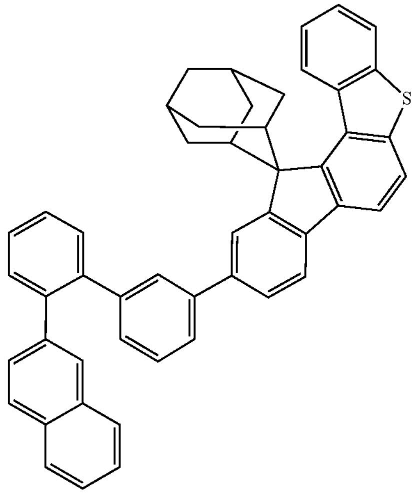
69
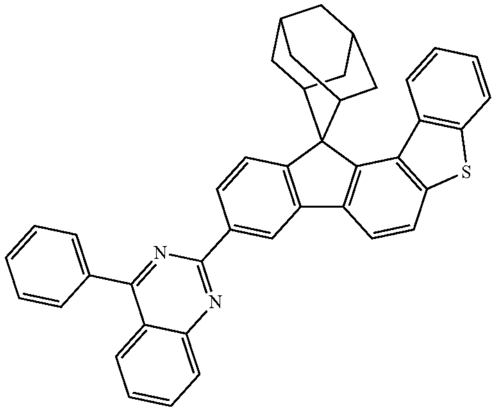
70
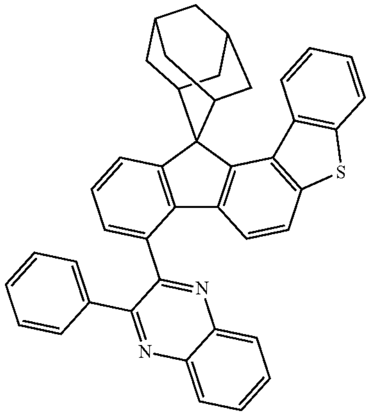
71
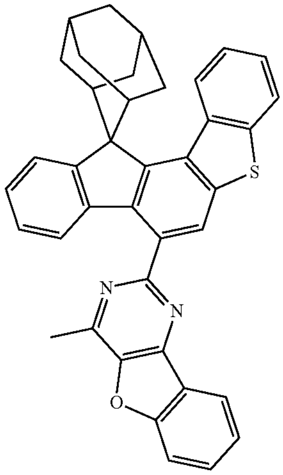
72
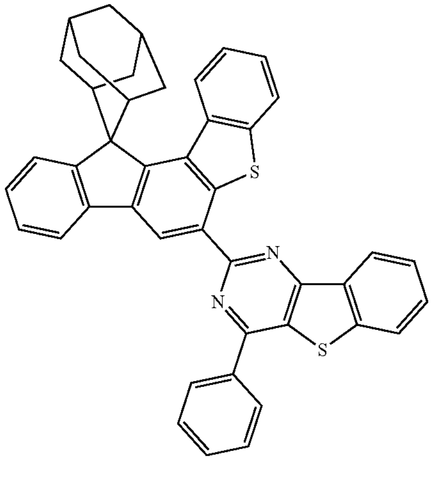

-continued
73
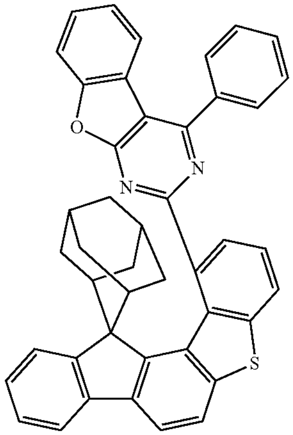
74
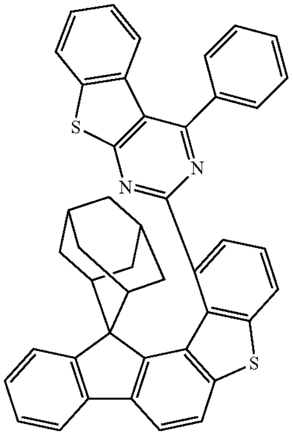
75
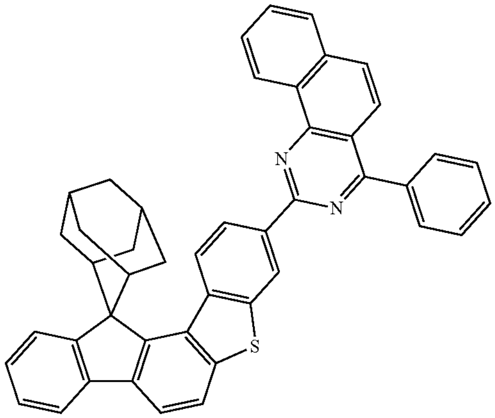
76
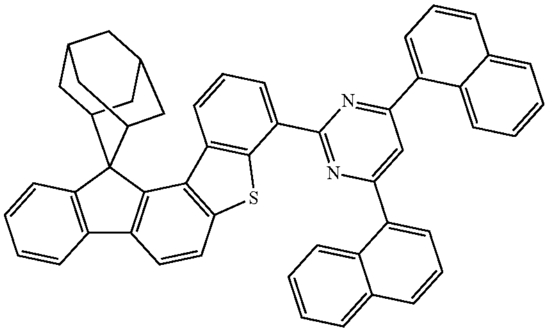
77
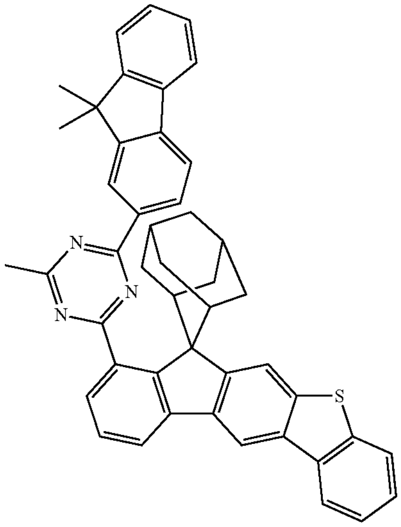
78
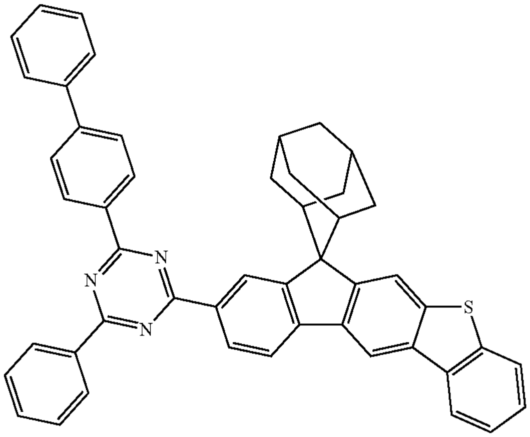

-continued
79
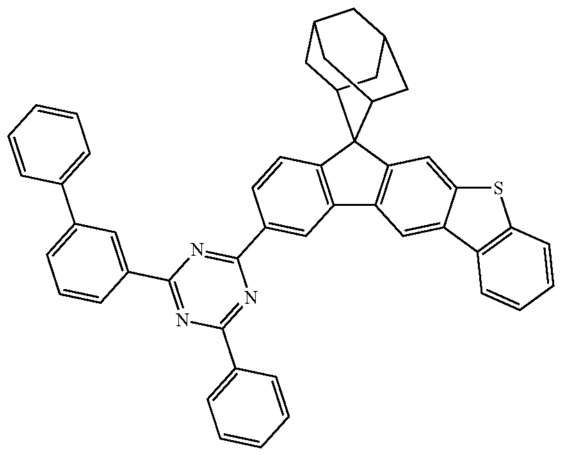
80
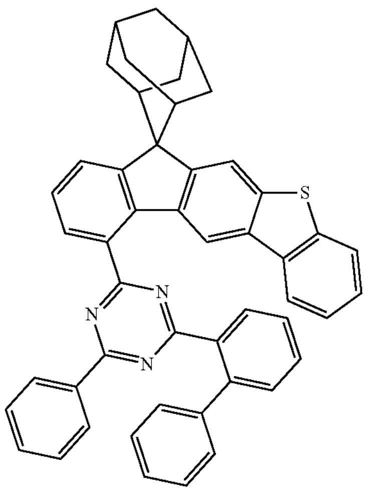
81
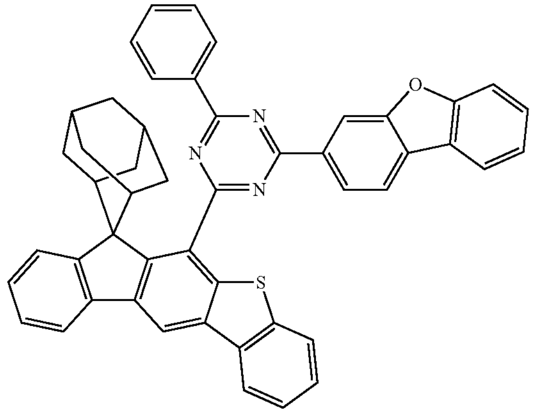
82
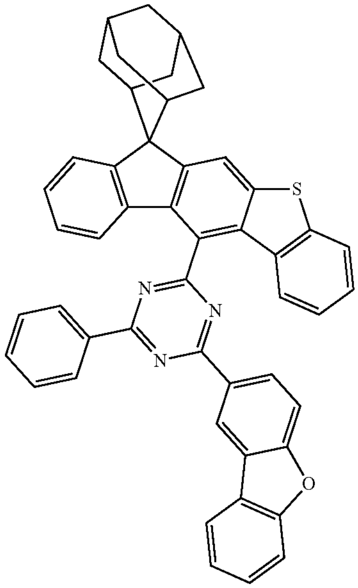
83
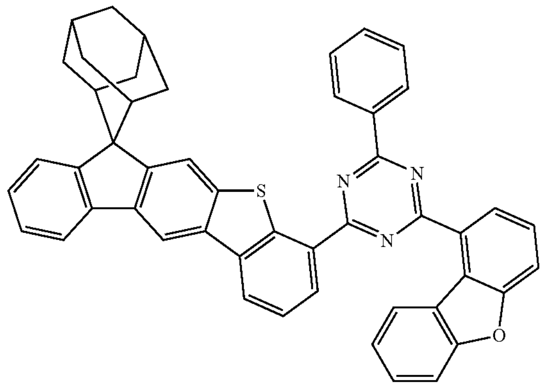
84
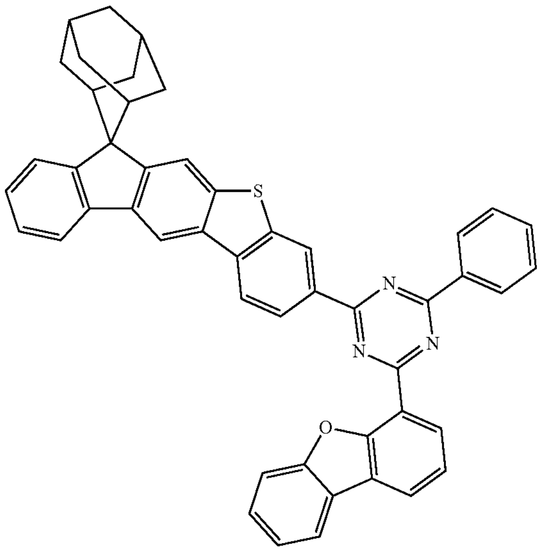

-continued
85
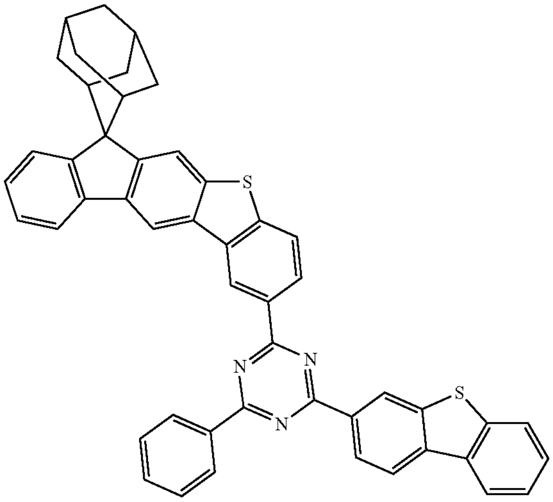
86
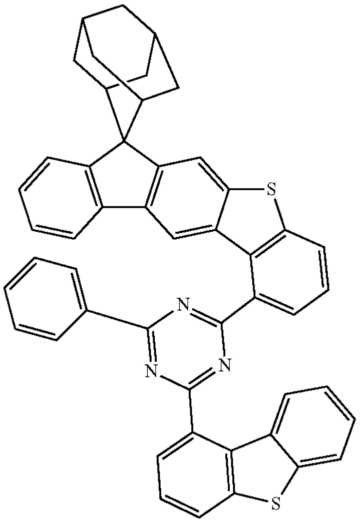
87
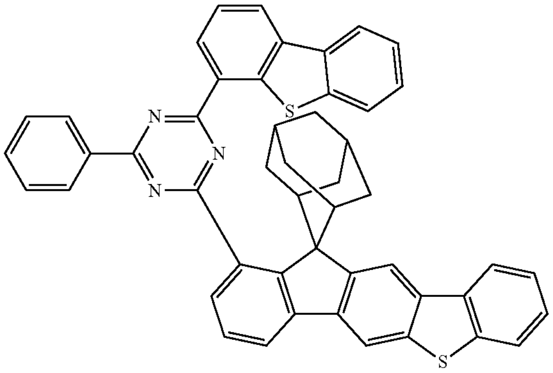
88
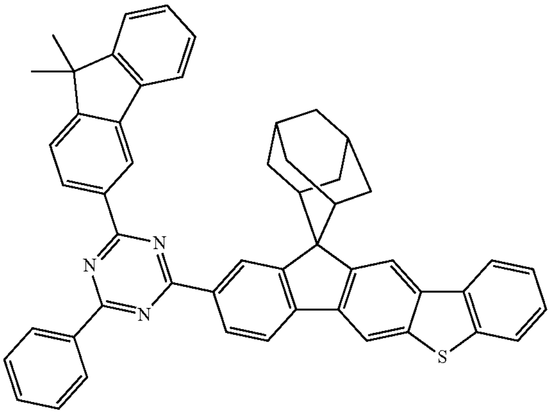
89
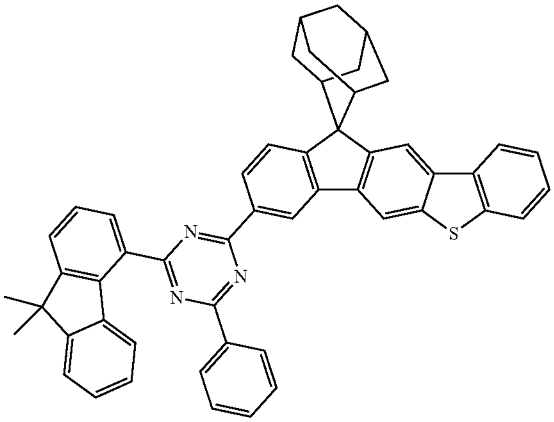
90
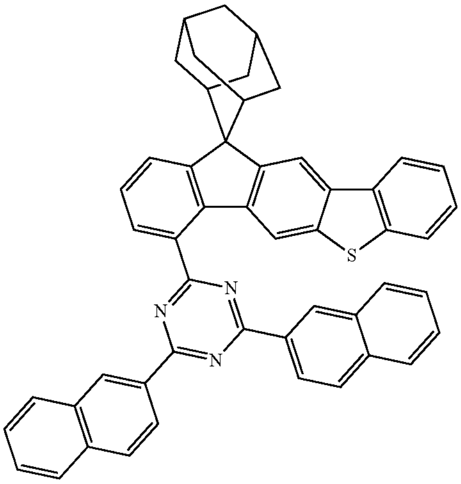

-continued
91
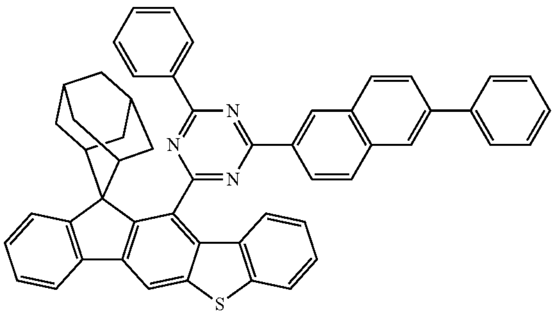
92
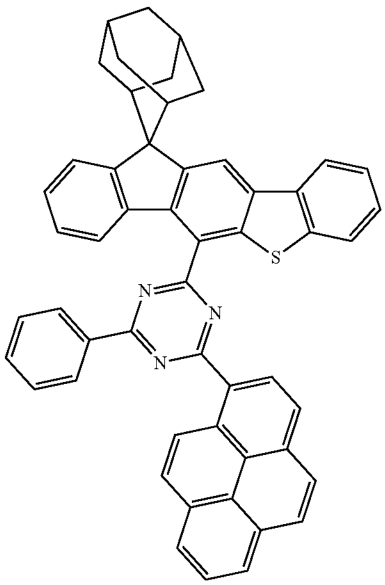
93
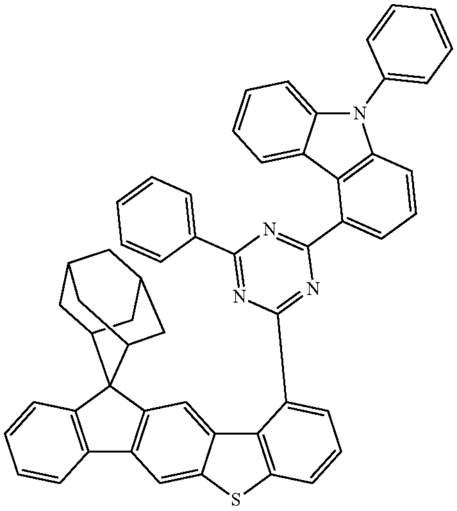
94
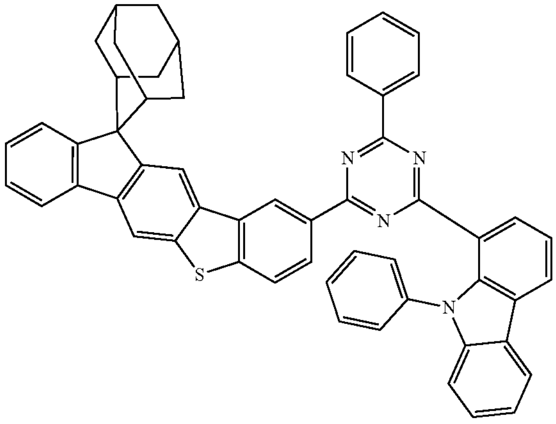
95
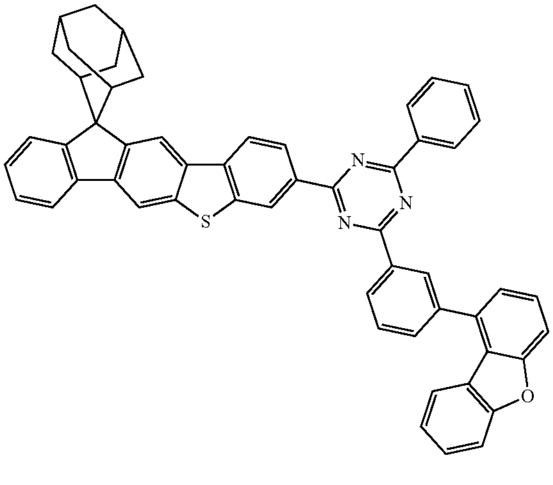

-continued
96
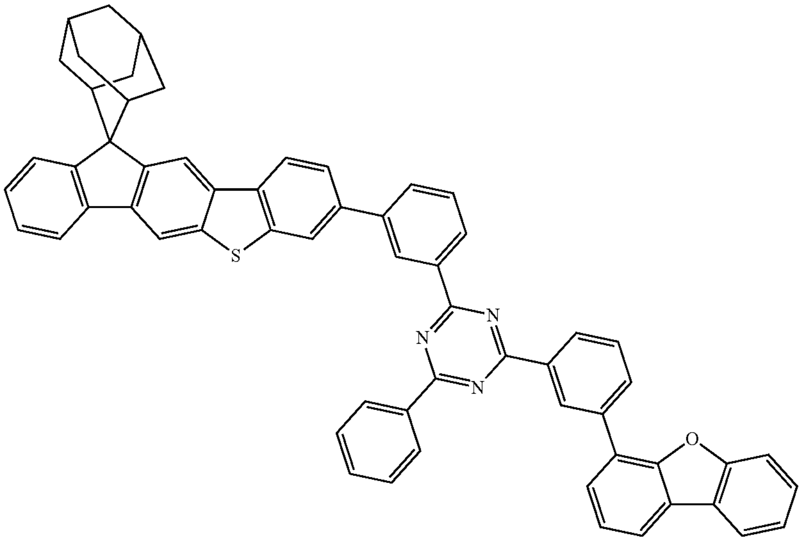
97
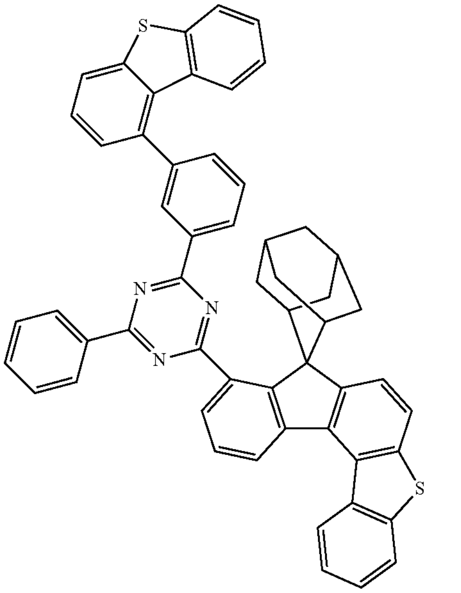
98
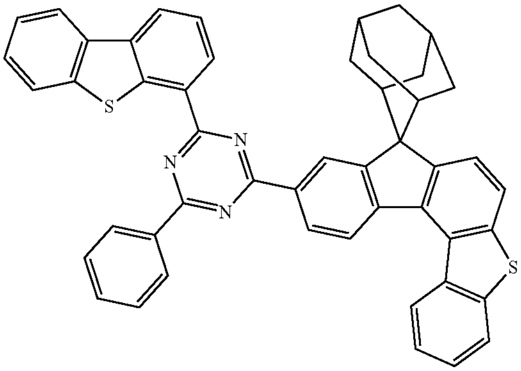
99
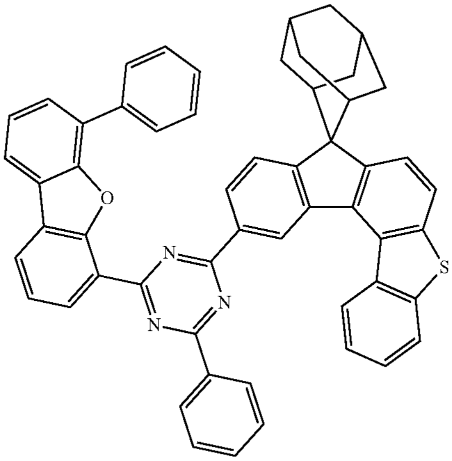
100
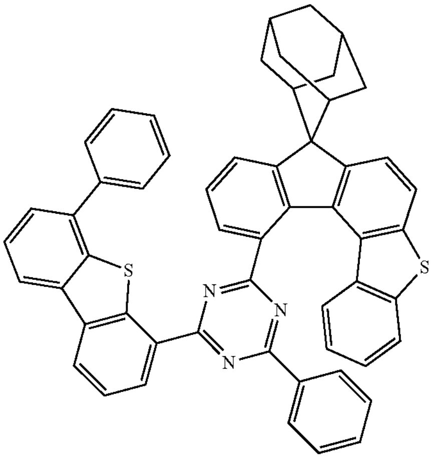

-continued
101
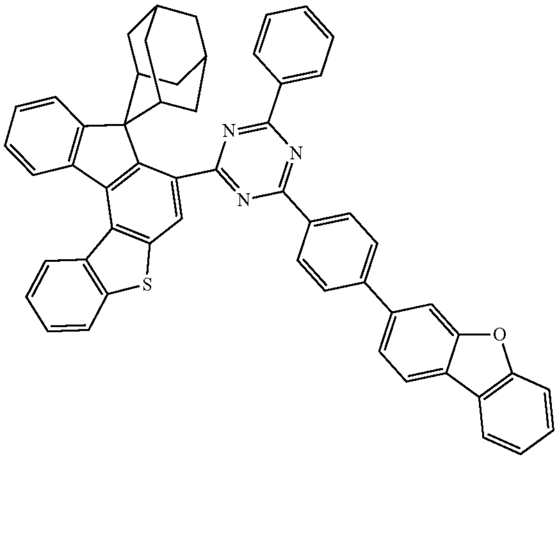
102
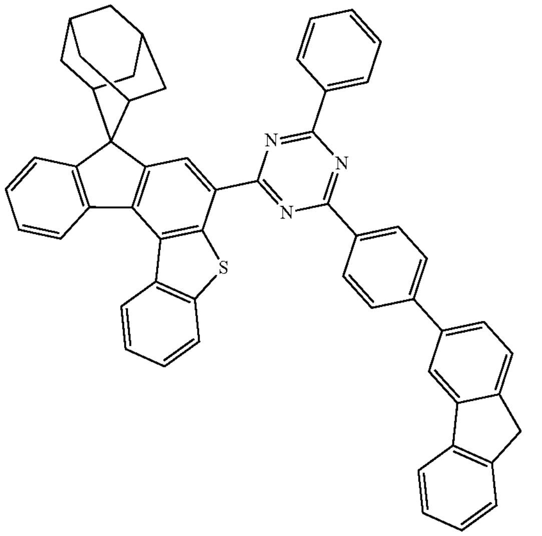
103
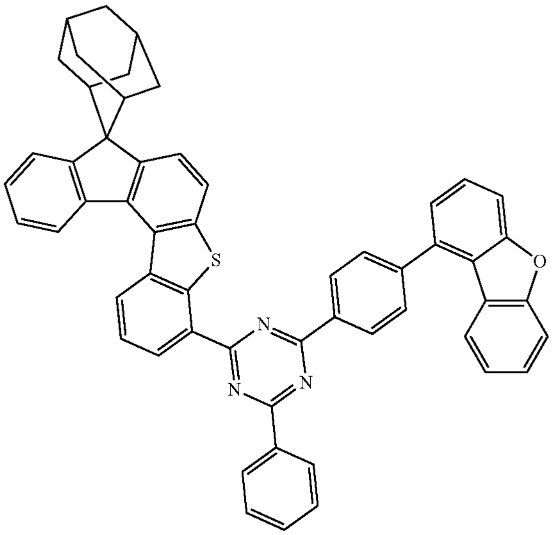
104
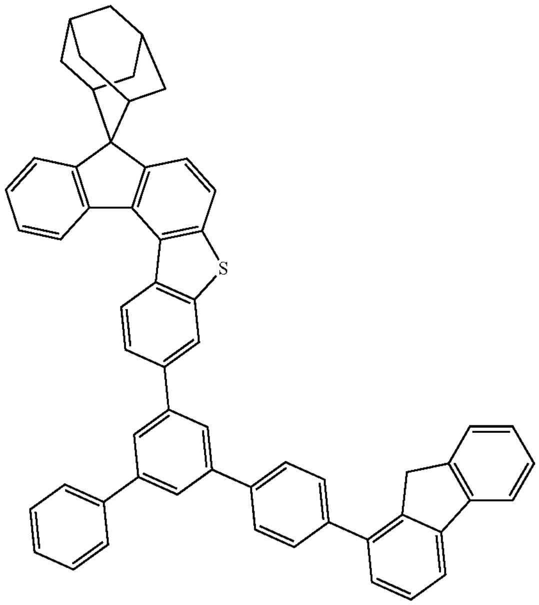

-continued
105
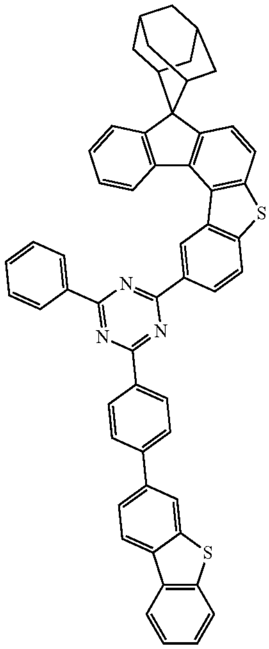
106
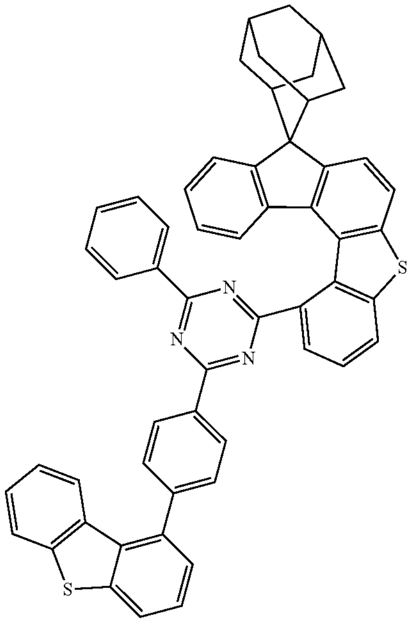
107
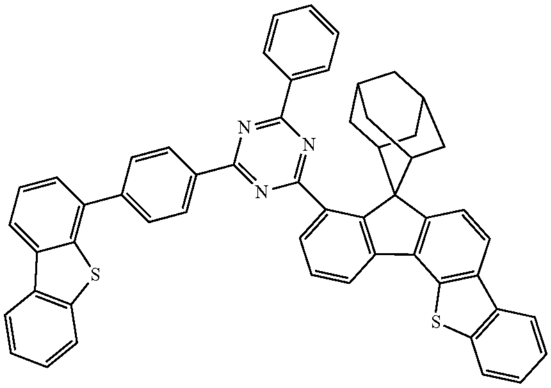
108
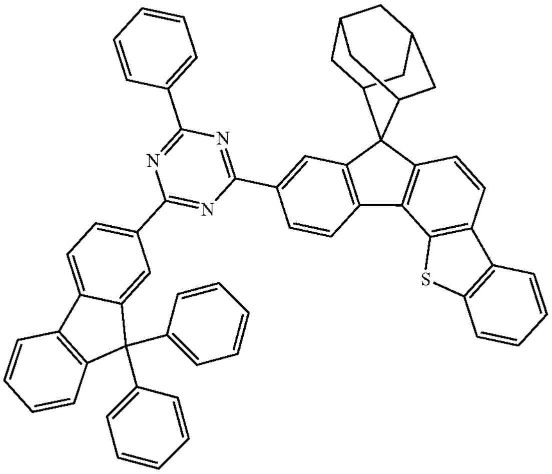

-continued
109
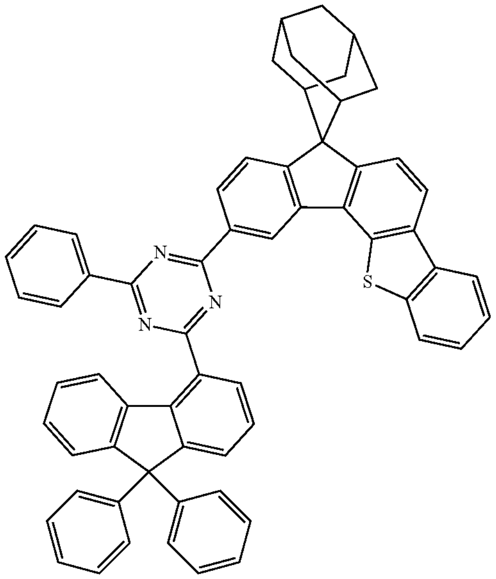
110
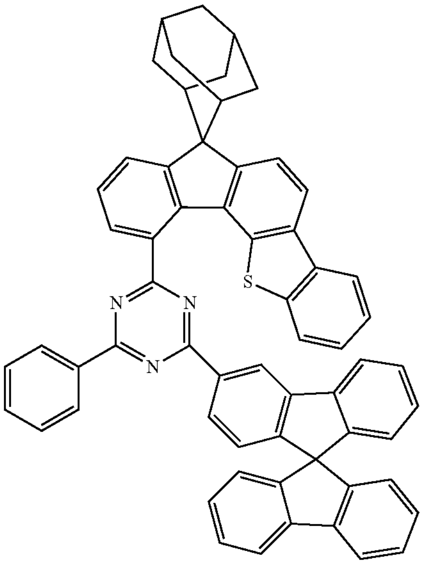
111
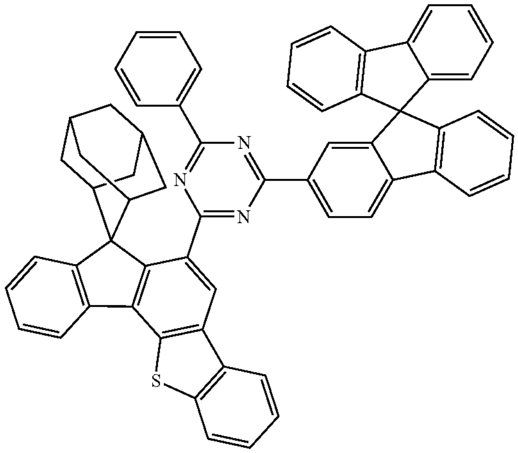
112
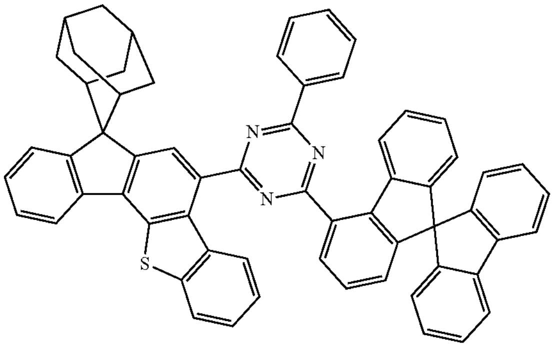

-continued
113
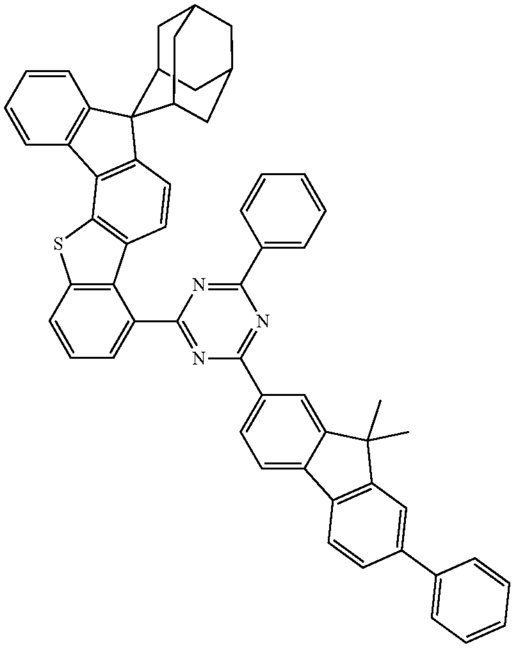
114
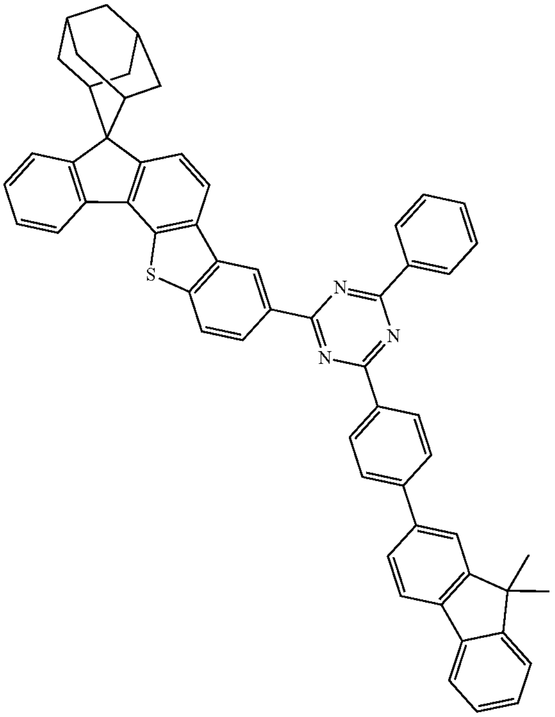
115
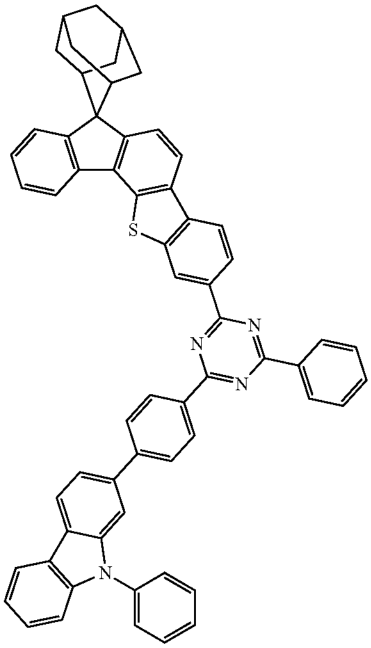
116
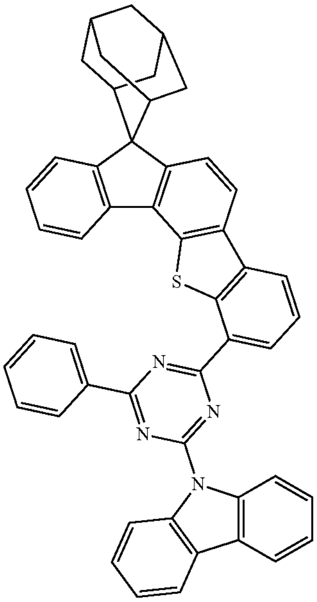

-continued
117
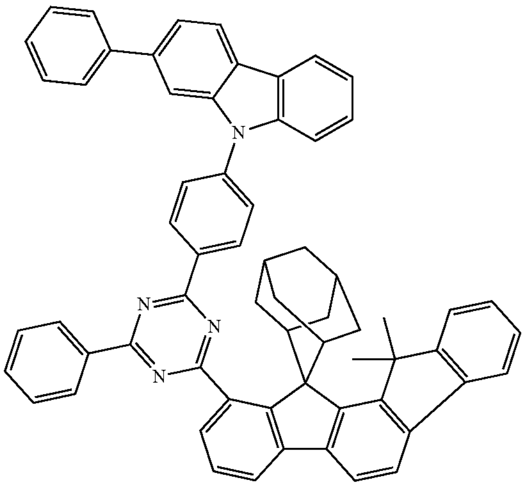
118
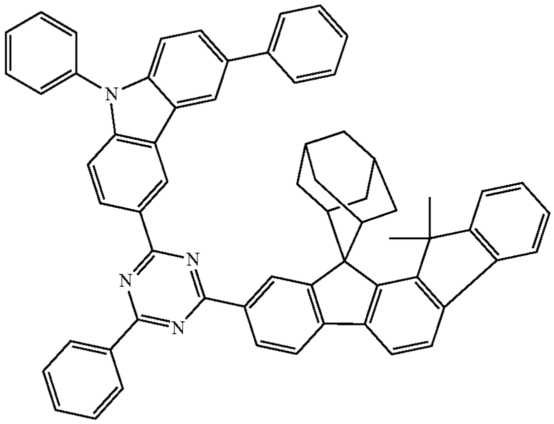
119
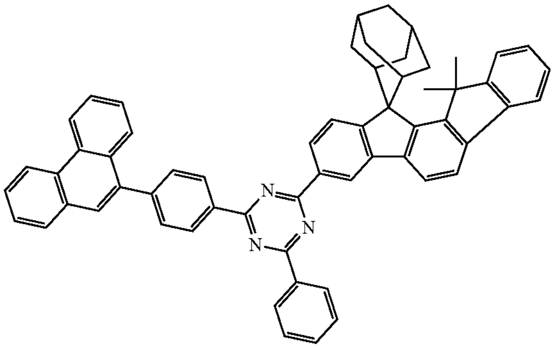
120
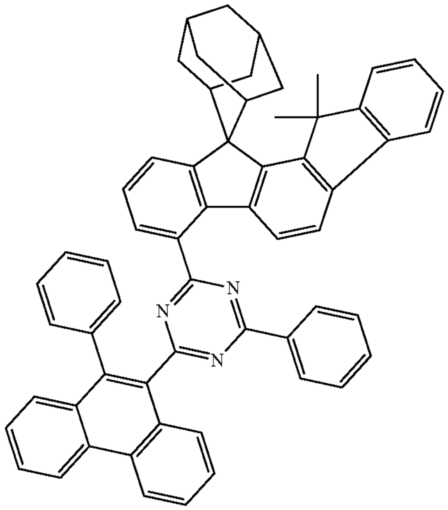
121
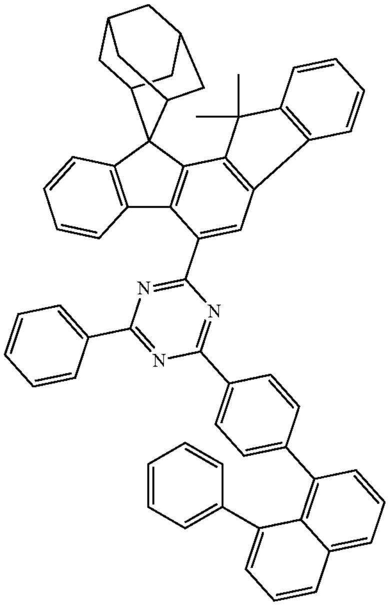
122
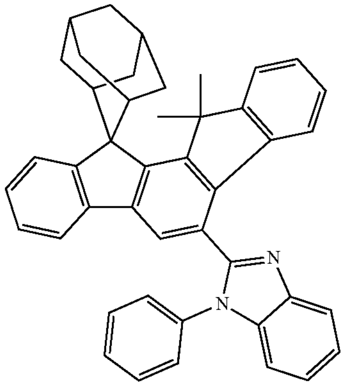

-continued
123
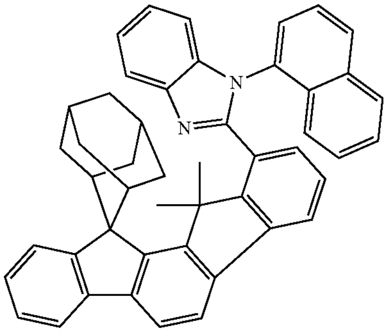
124
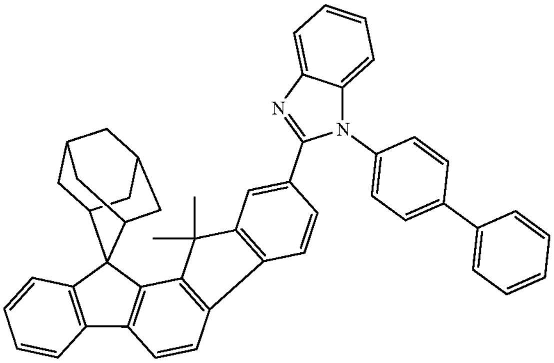
125
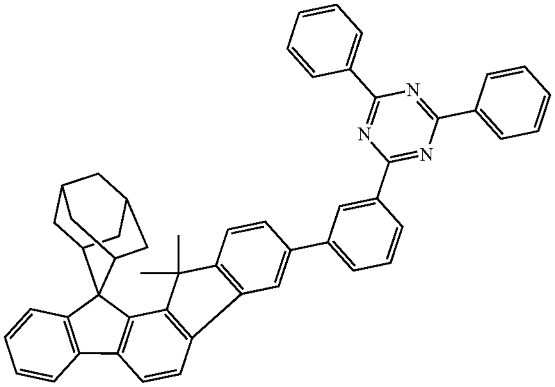
126
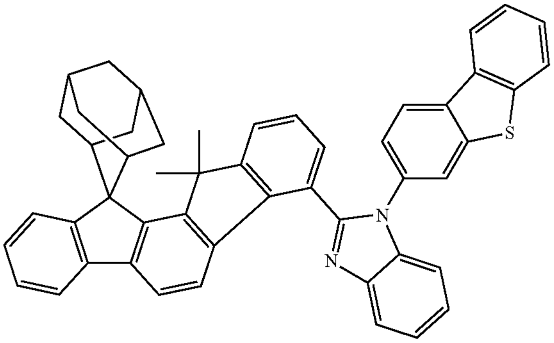
127
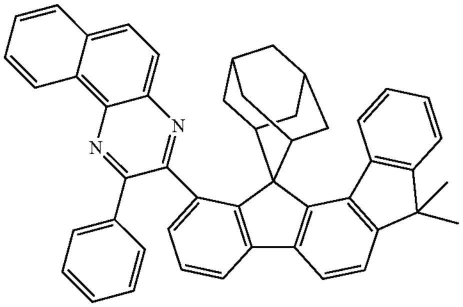
128
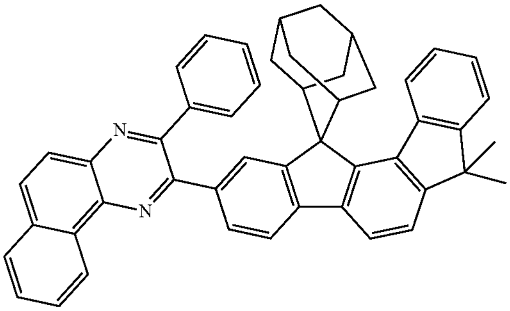
129
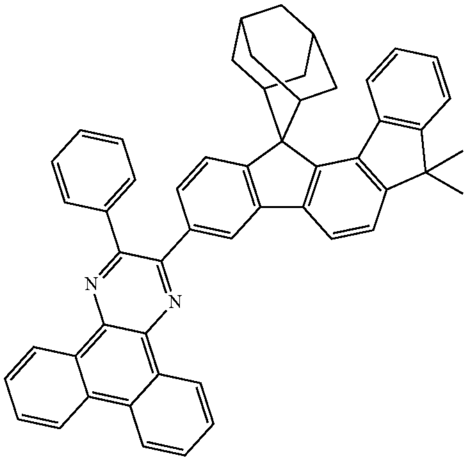
130
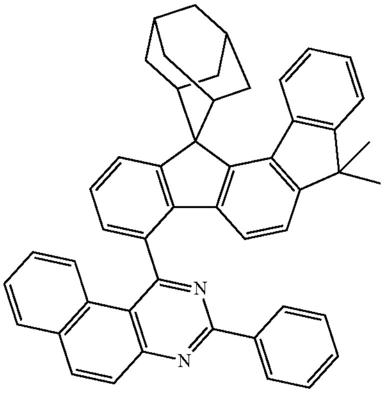

-continued
131
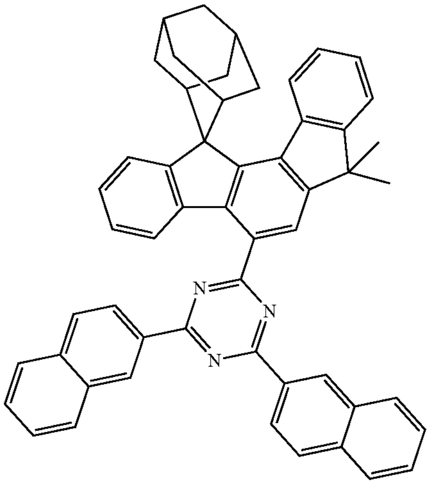
132
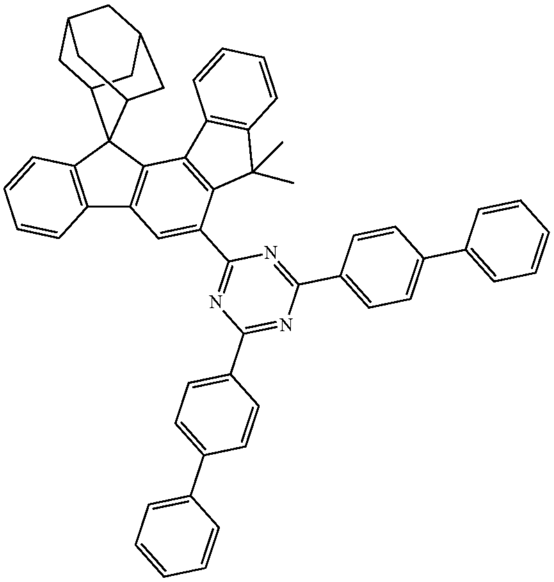
133
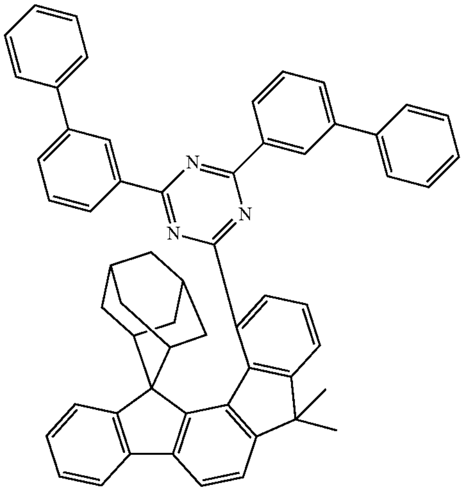
134
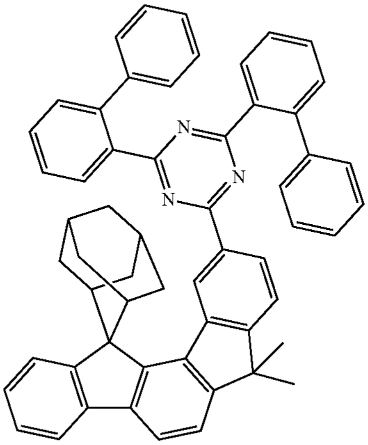
135
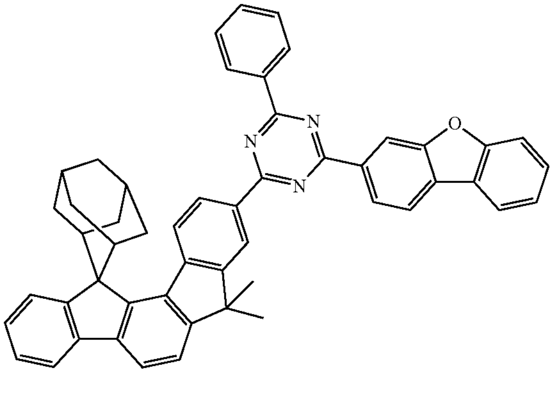
136
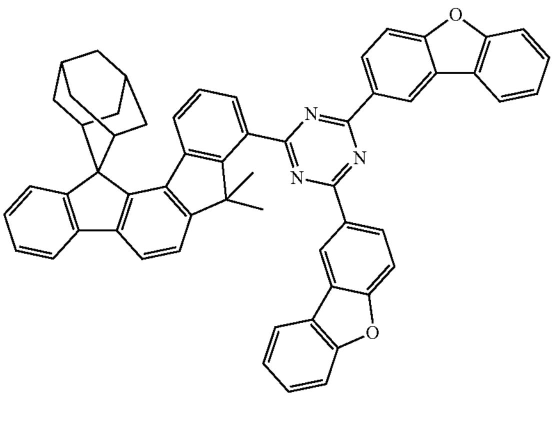

-continued
137
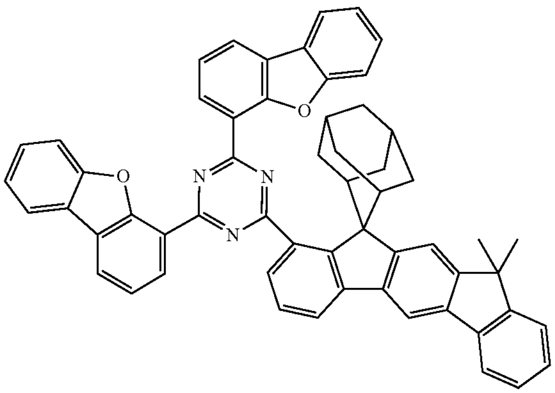
138
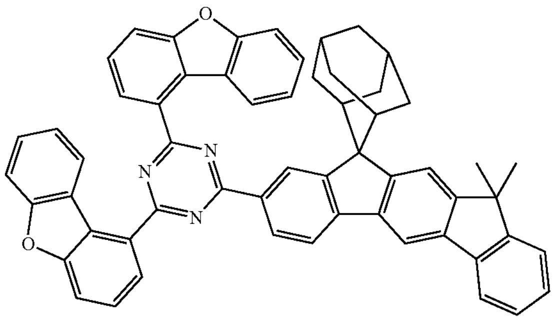
139
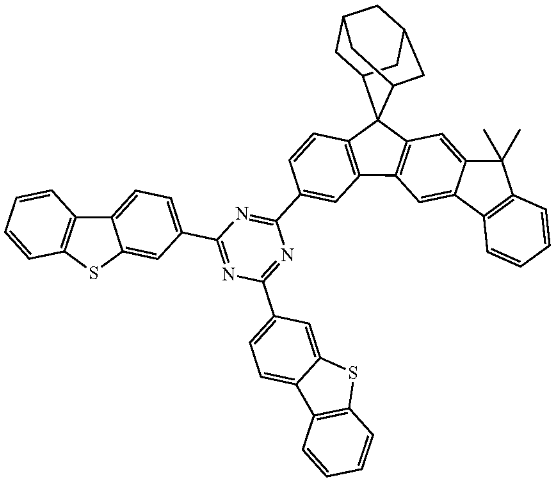
140
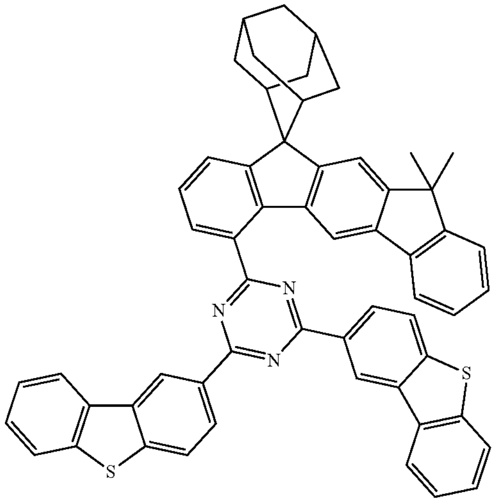
141
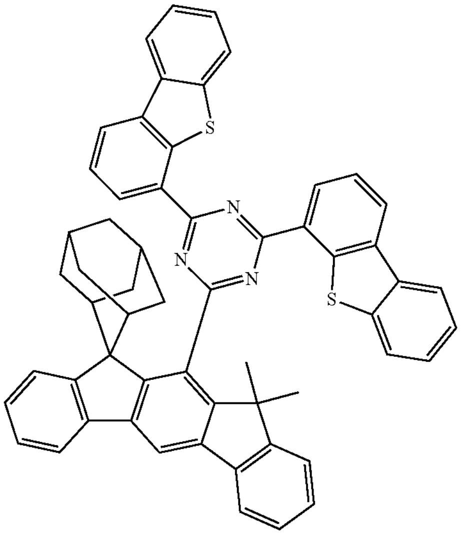
142
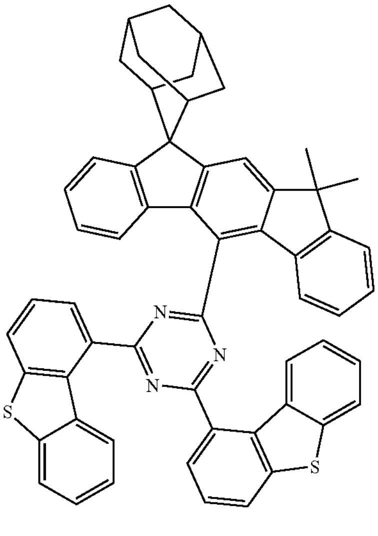

-continued
143
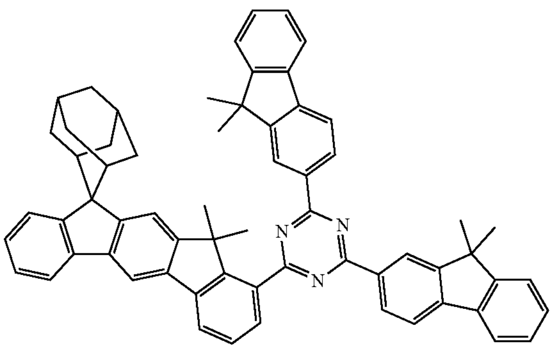
144
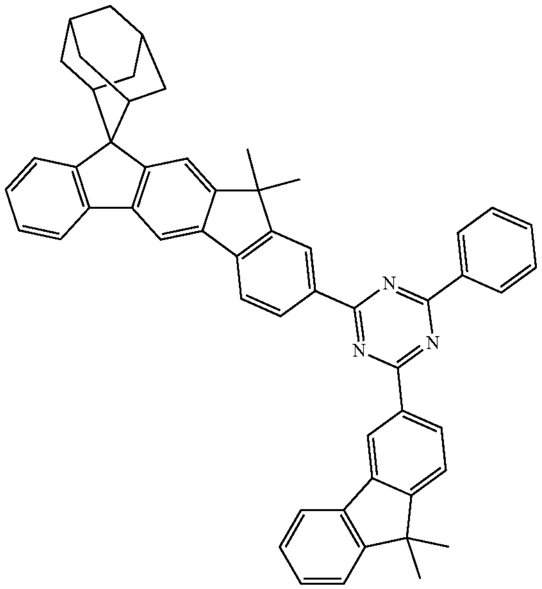
145
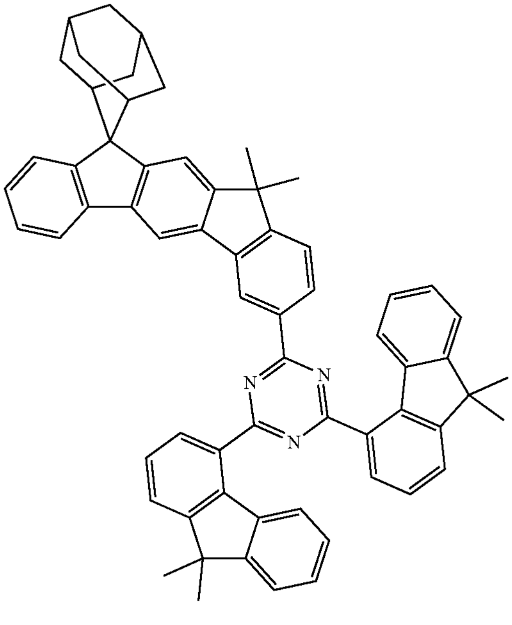
146
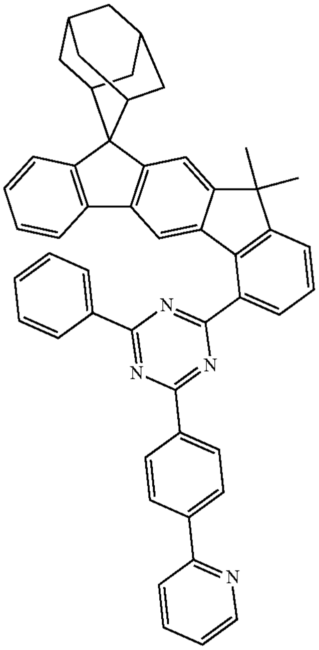

-continued
147
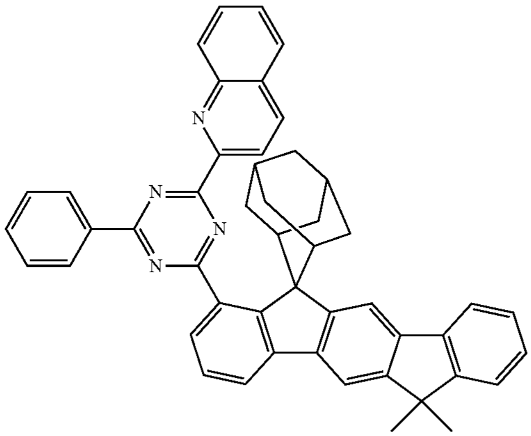
148
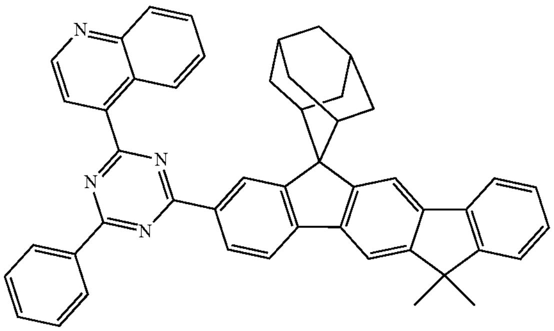
149
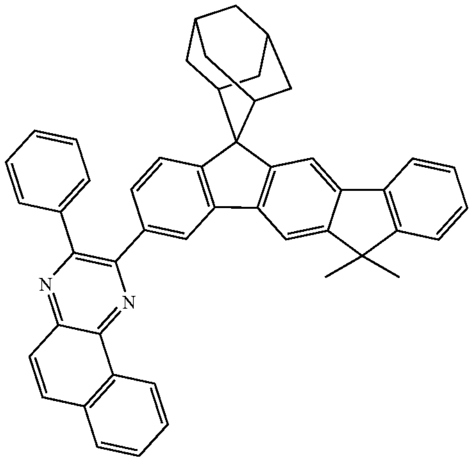
150
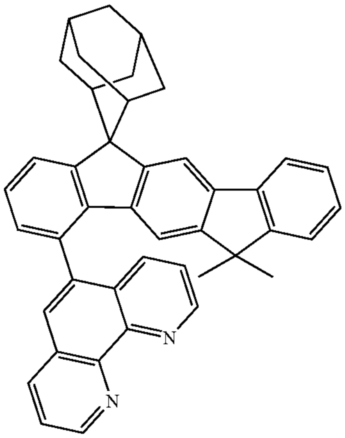
151
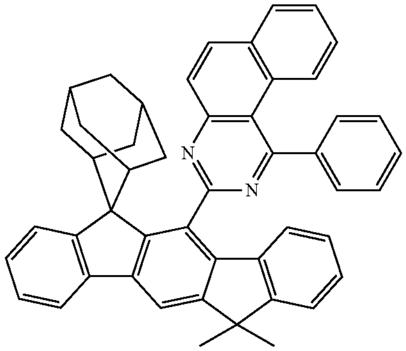
152
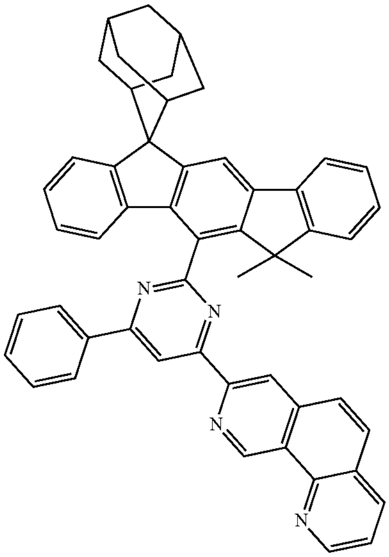

-continued
153
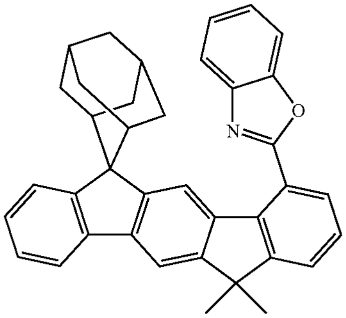
154
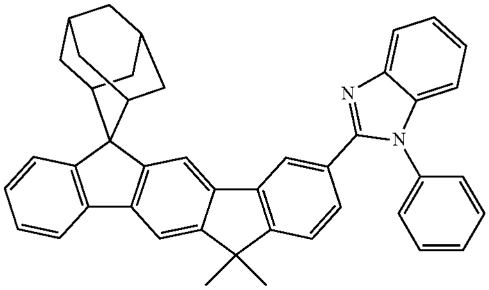
155
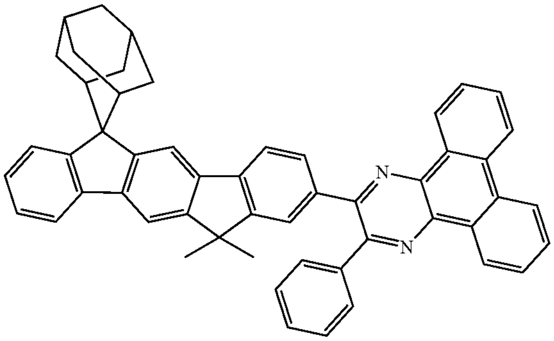
156
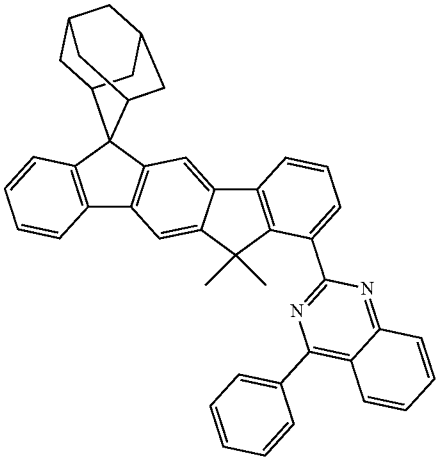
157
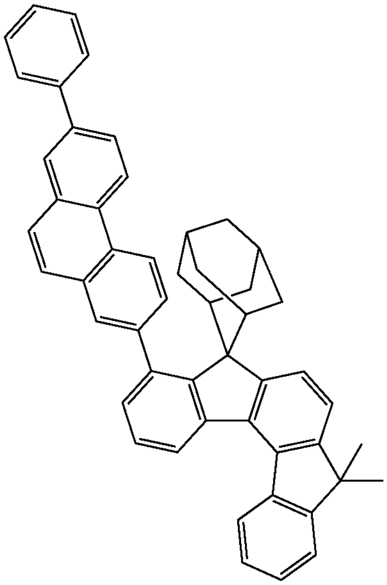
158
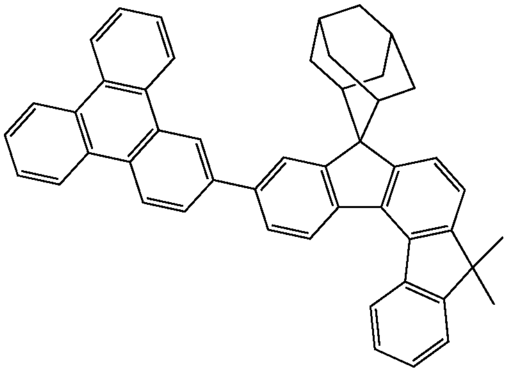

-continued
159
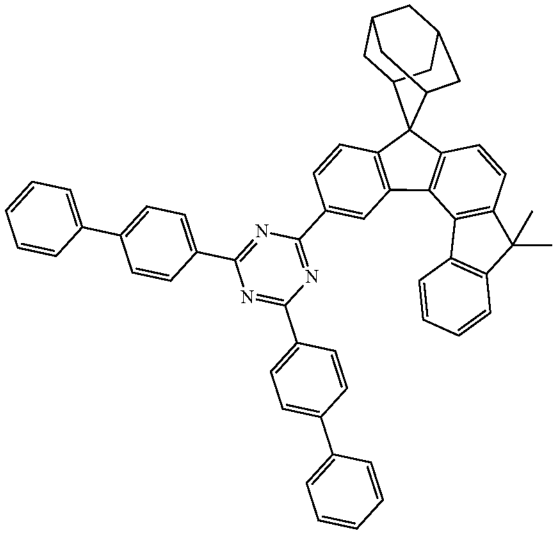
160
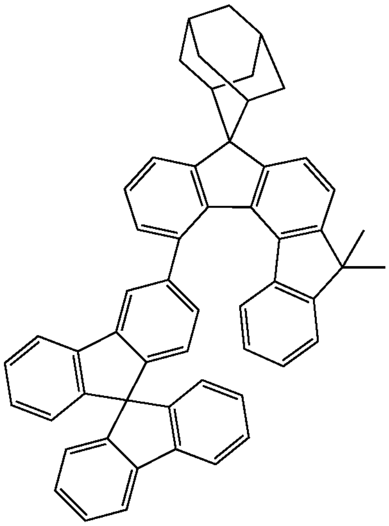
161
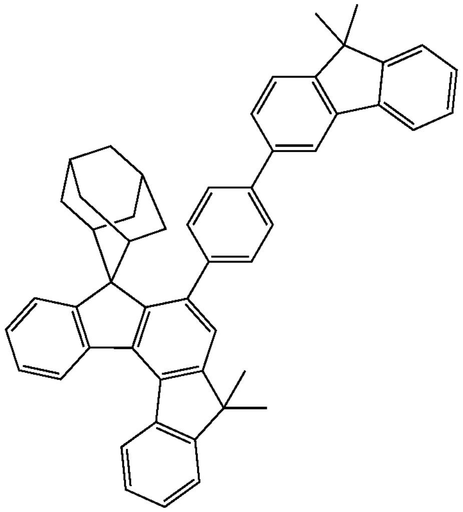
162
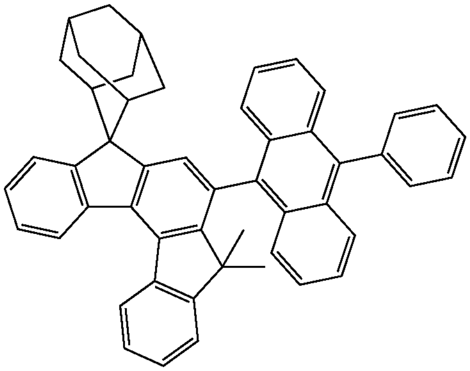

-continued
163
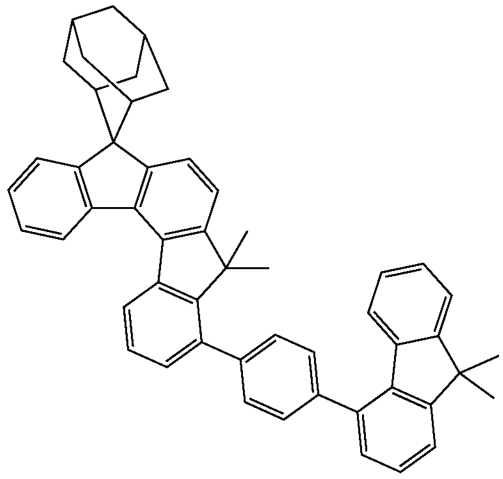
164
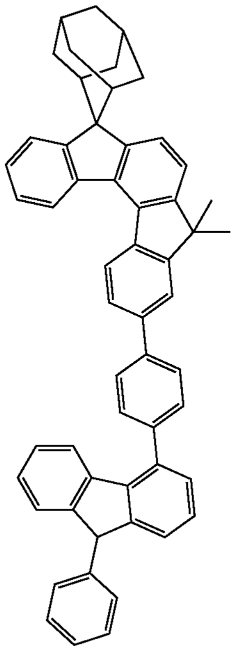
165
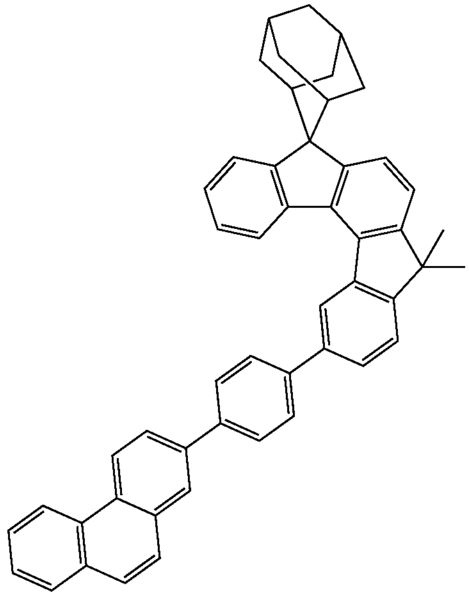
166
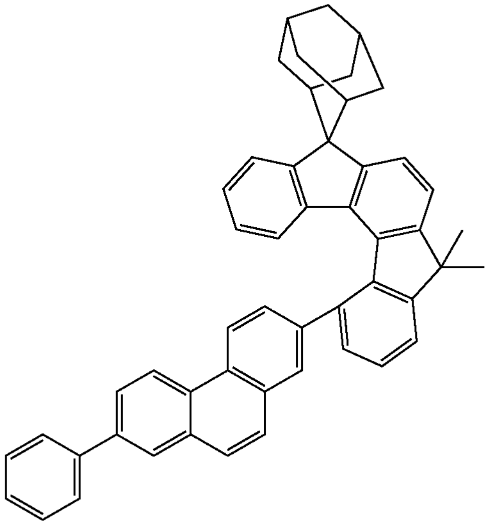

-continued
167
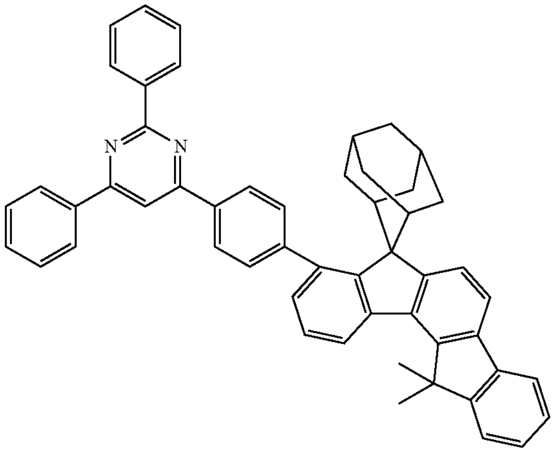
168
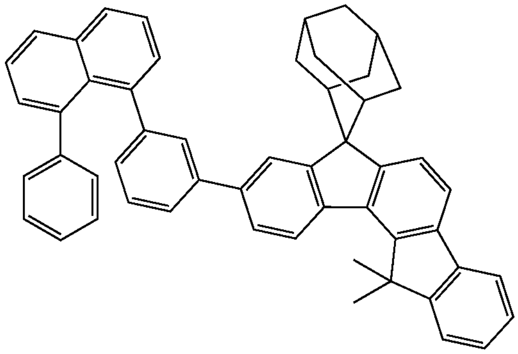
169
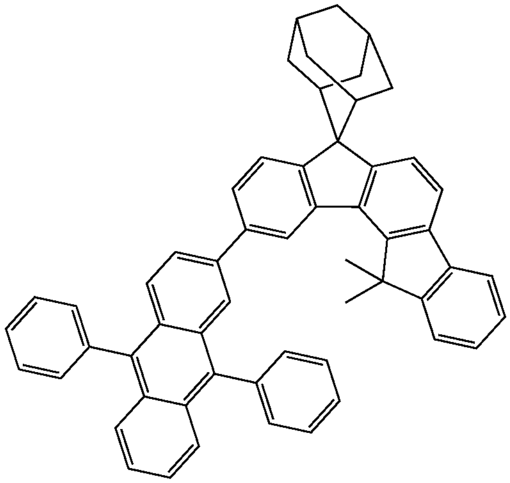
170
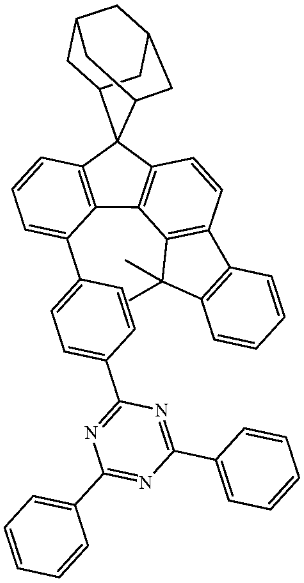
171
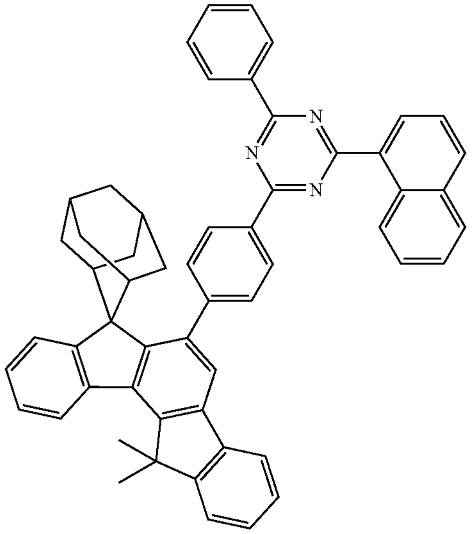
172
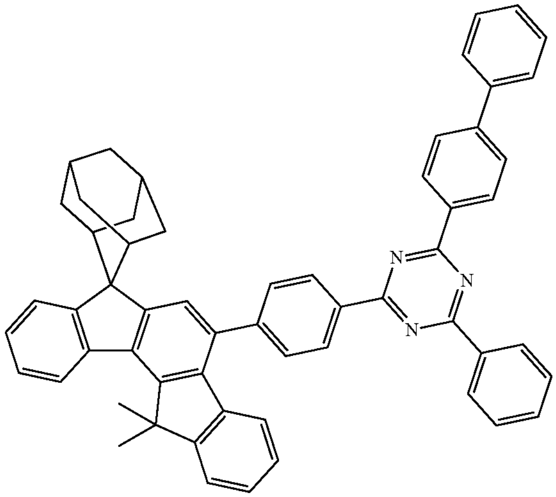

-continued
173
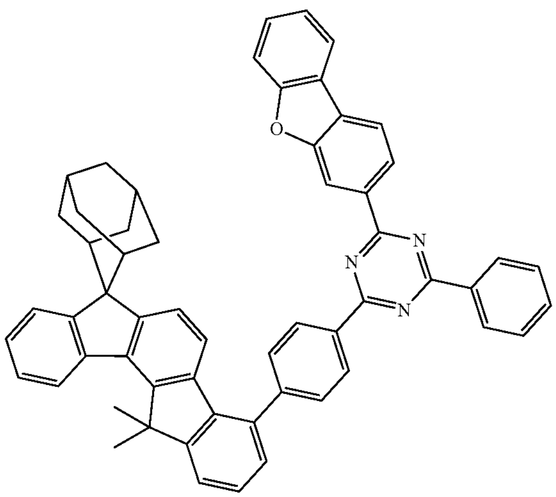
174
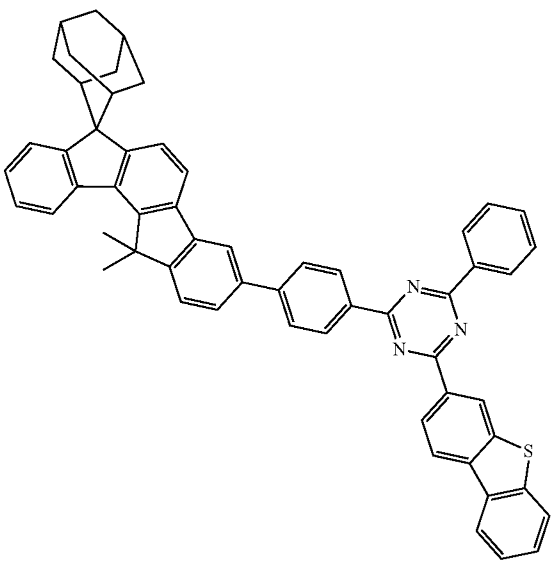
175
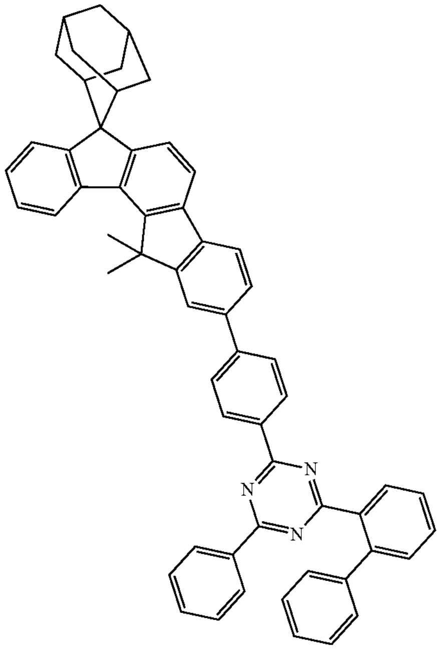
176
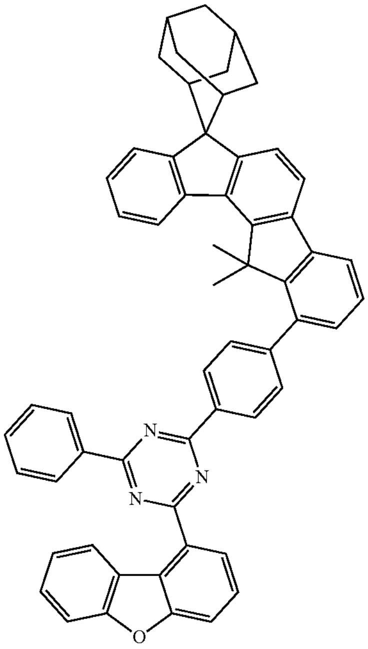

-continued
177
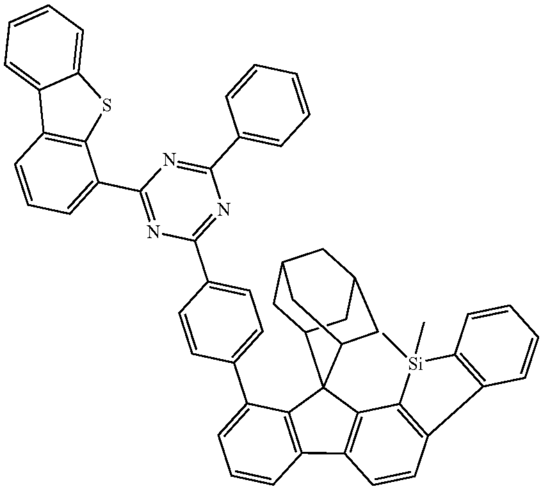
178
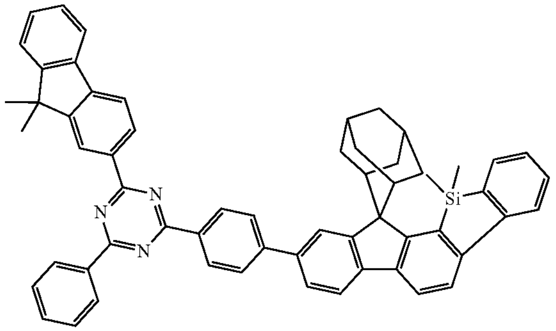
179
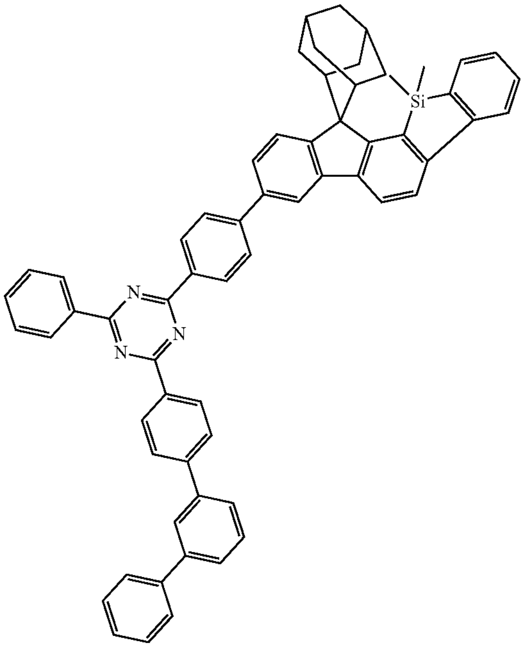
180
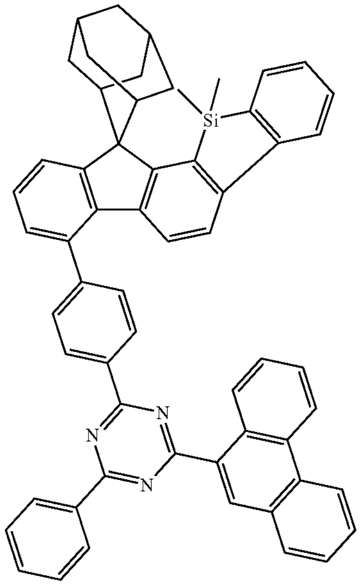

-continued
181
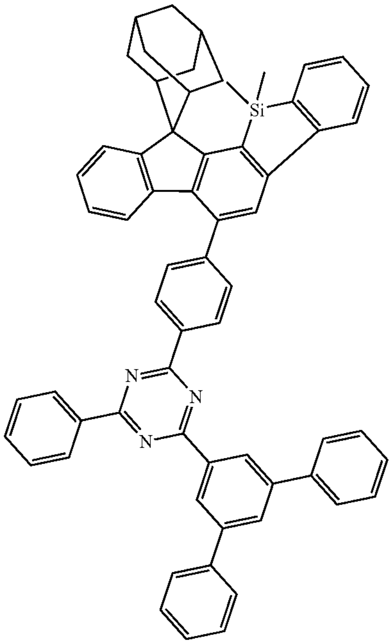
182
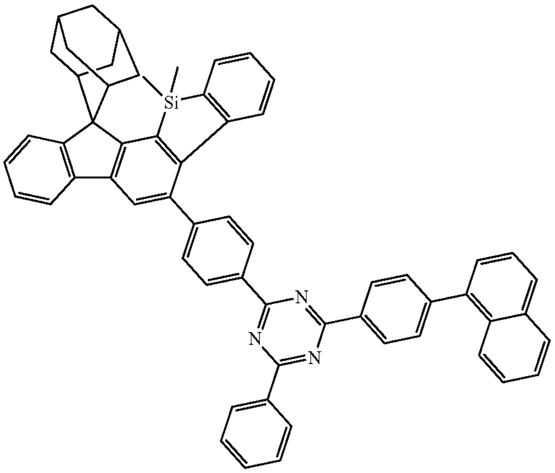
183
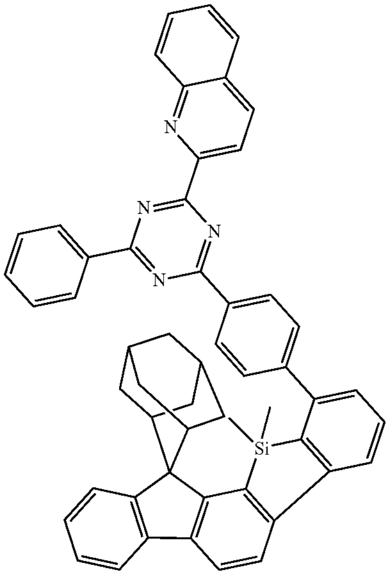
184
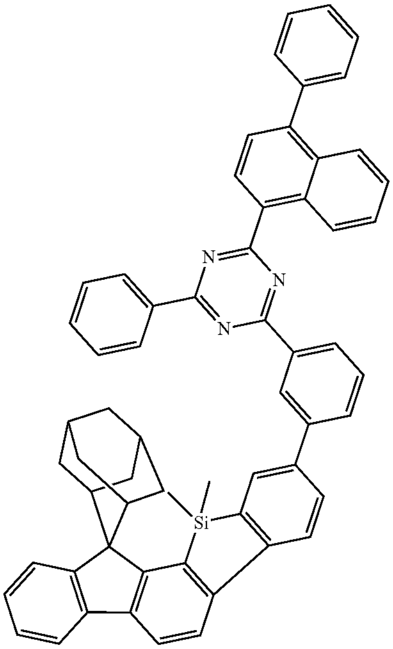

-continued
185
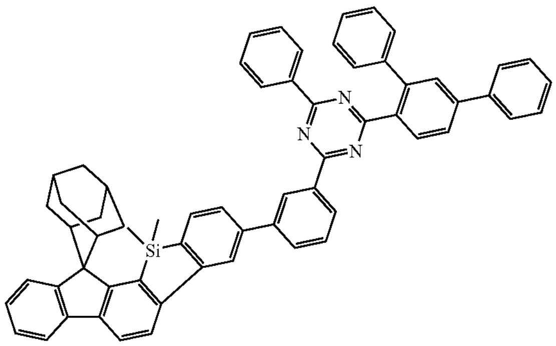
186
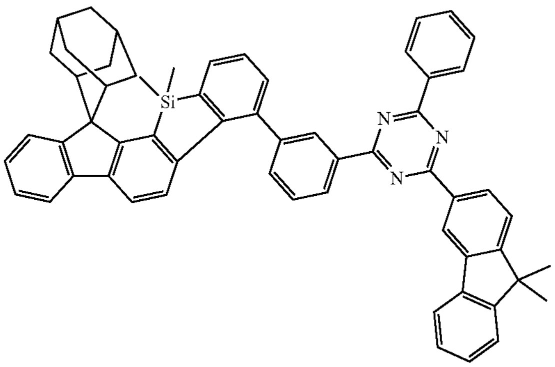
187
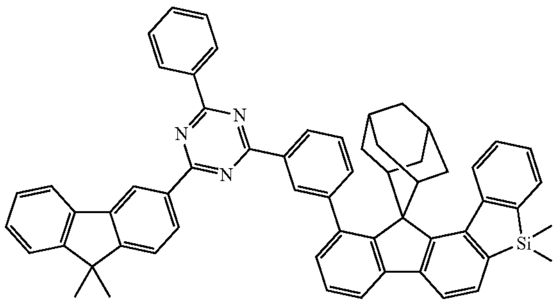
188
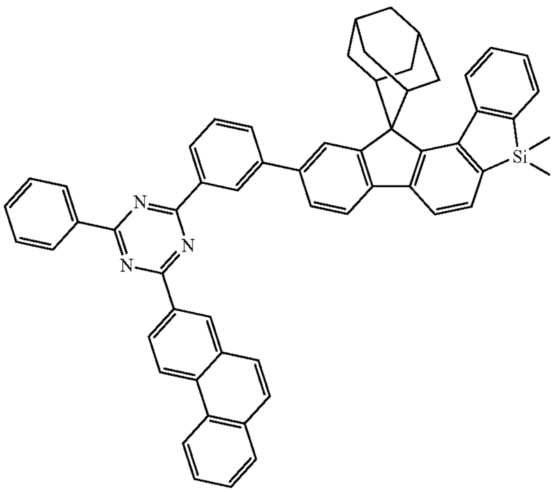
189
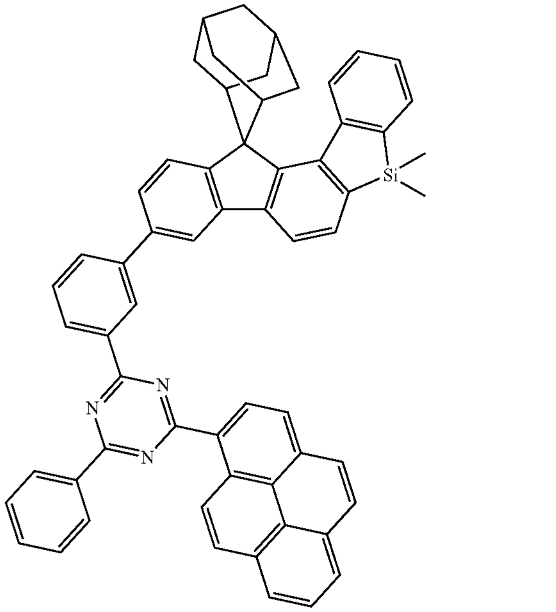
190
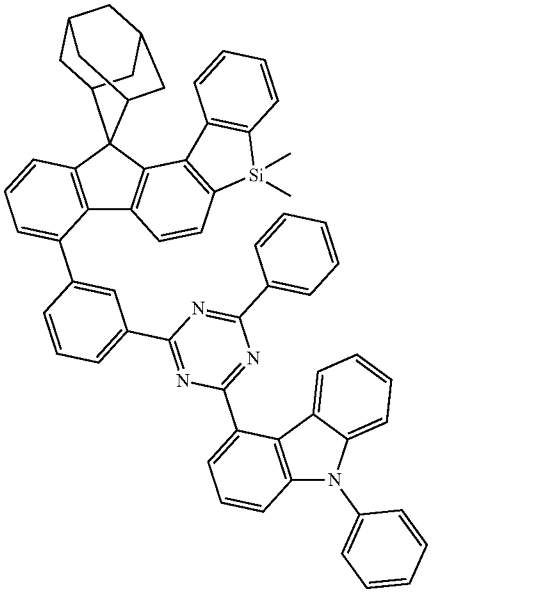

-continued
191
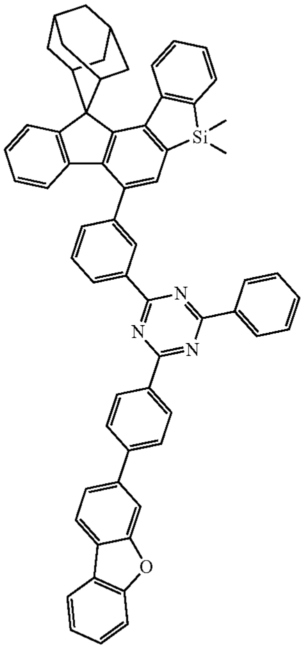
192
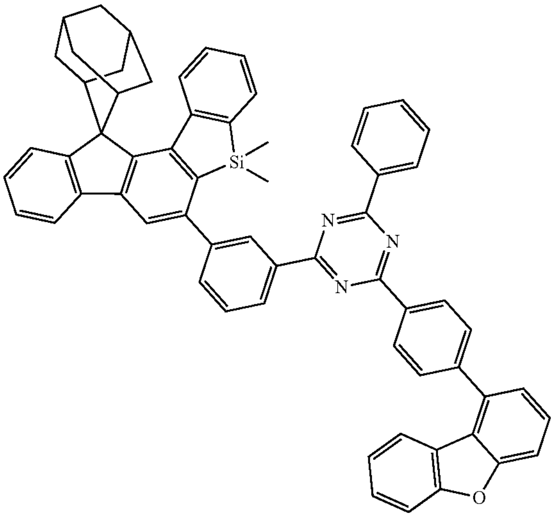
193
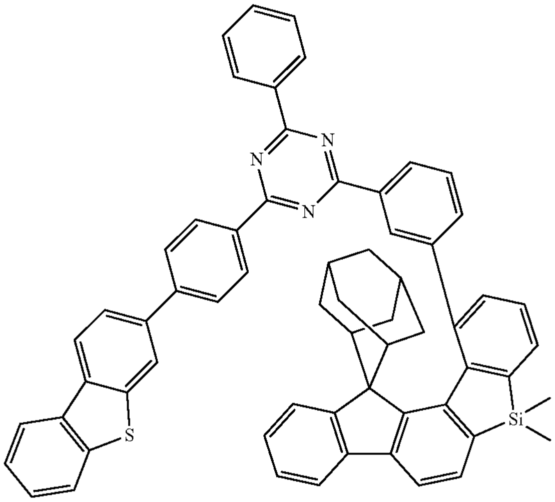
194
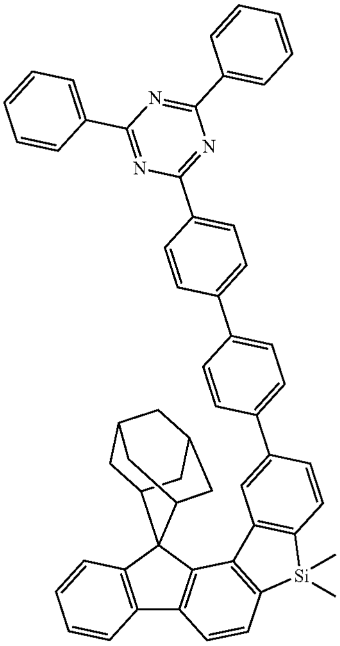

-continued
195
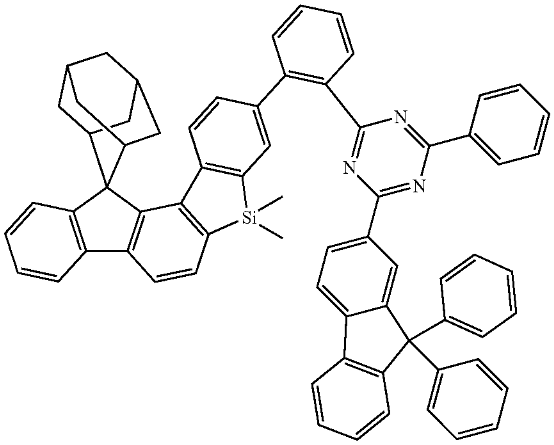
196
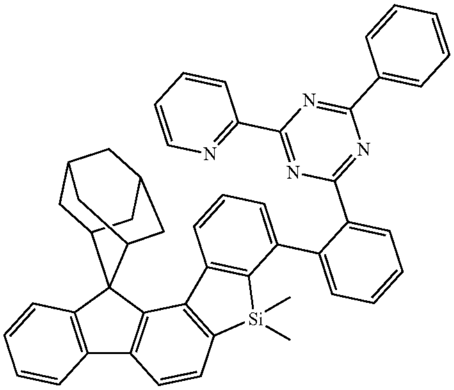
197
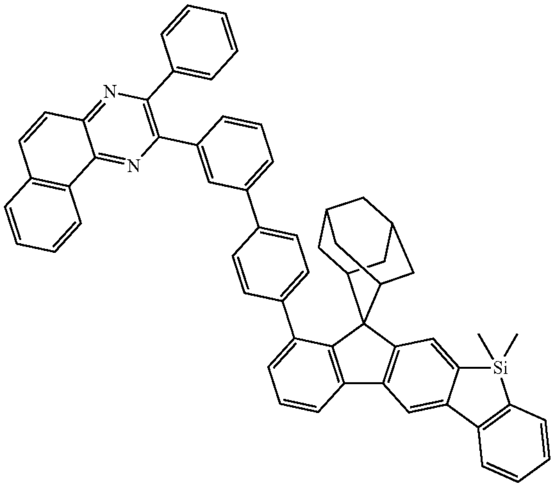
198
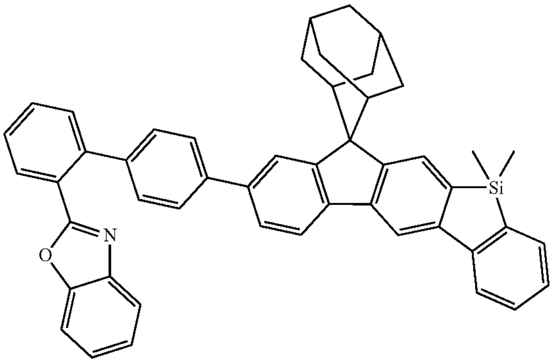
199
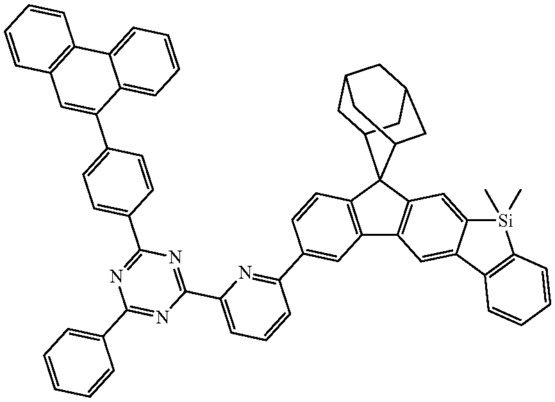
200
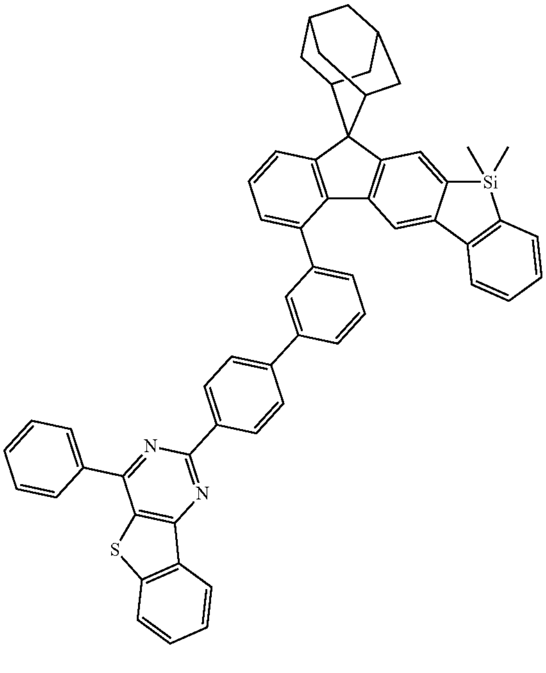

-continued
201
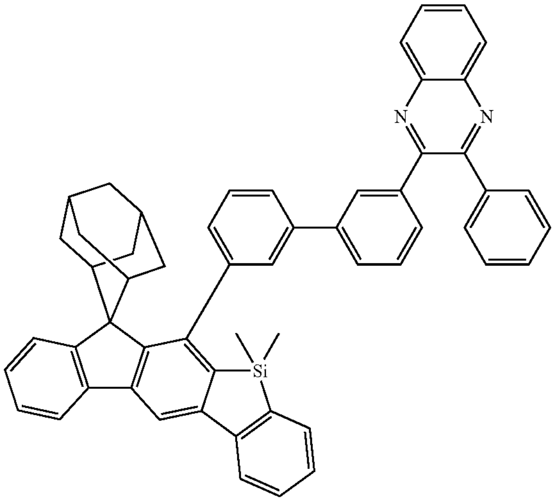
202
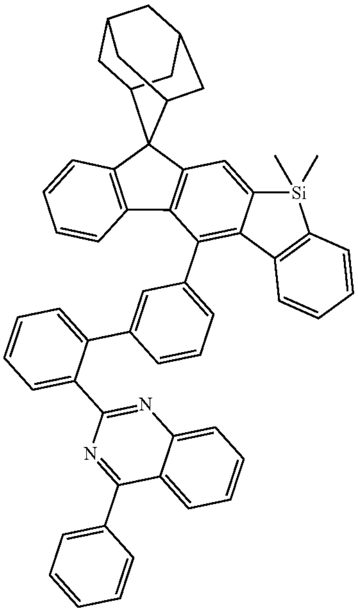
203
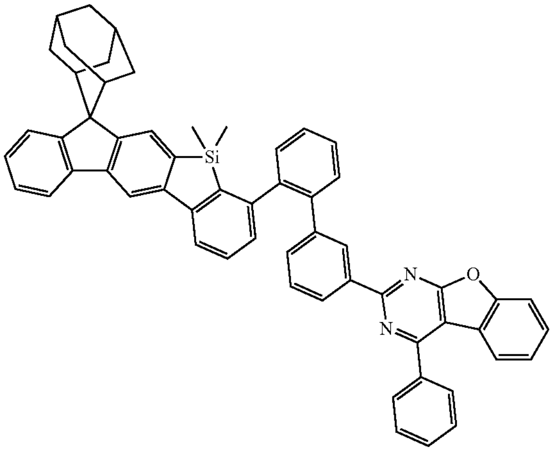

-continued
204
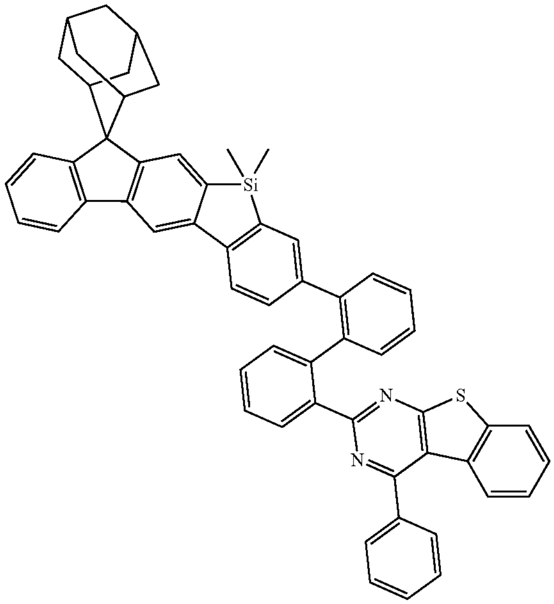
205
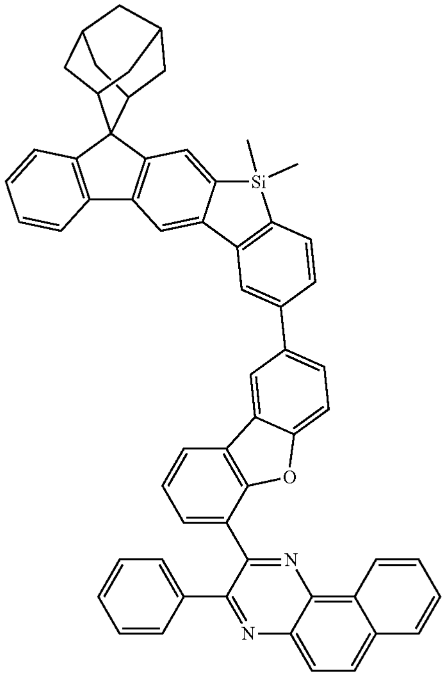
-continued
206
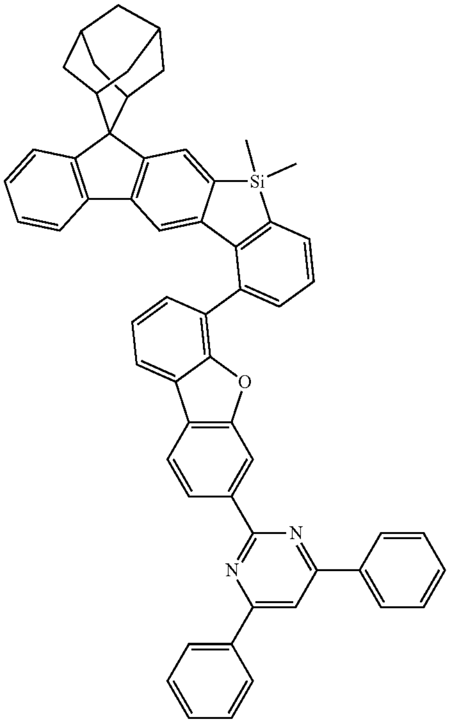

-continued
207
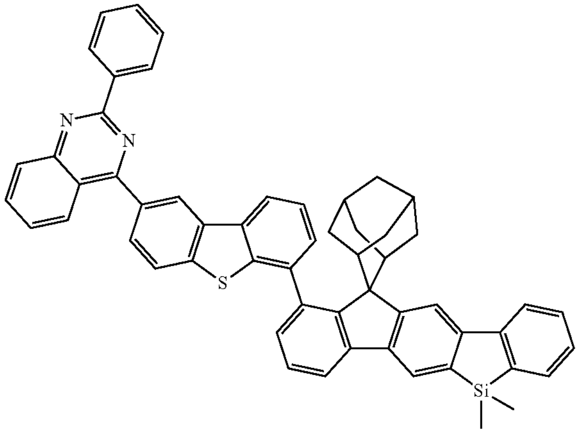
208
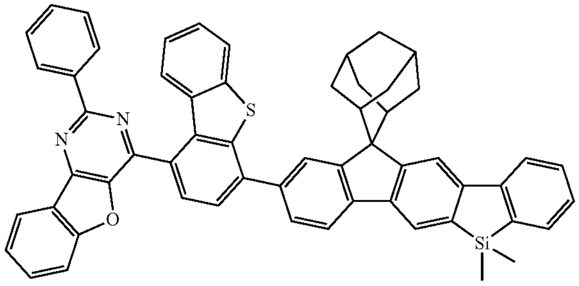
209
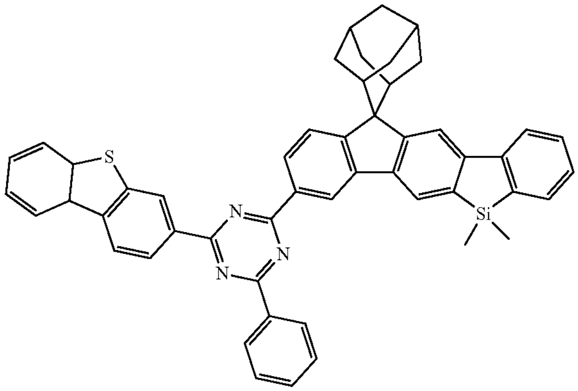
-continued
210
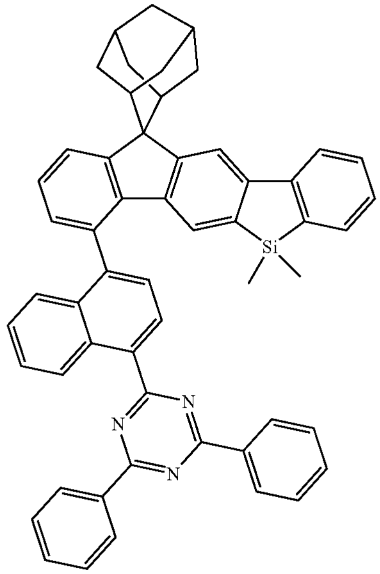
211
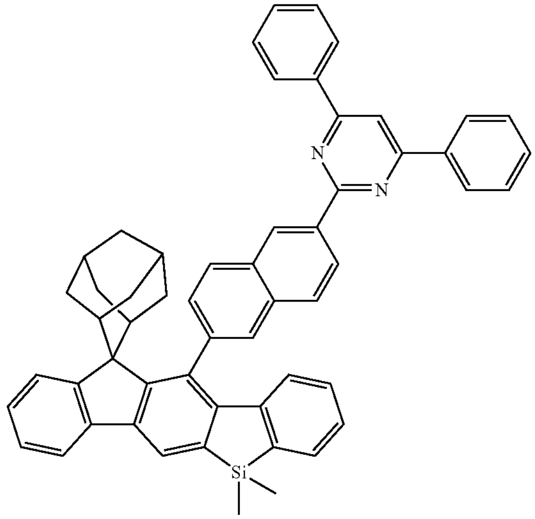

-continued
212
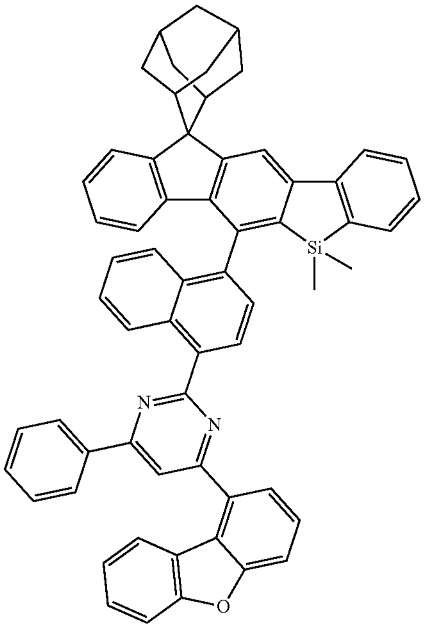
213
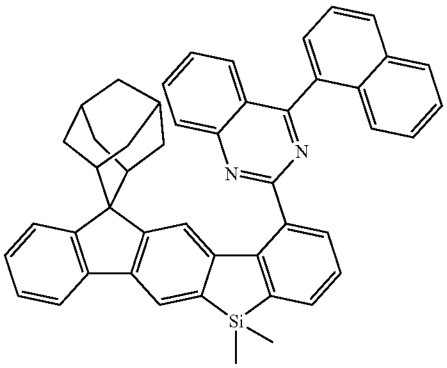
214
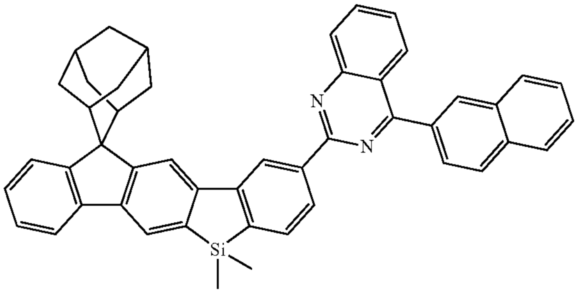
-continued
215
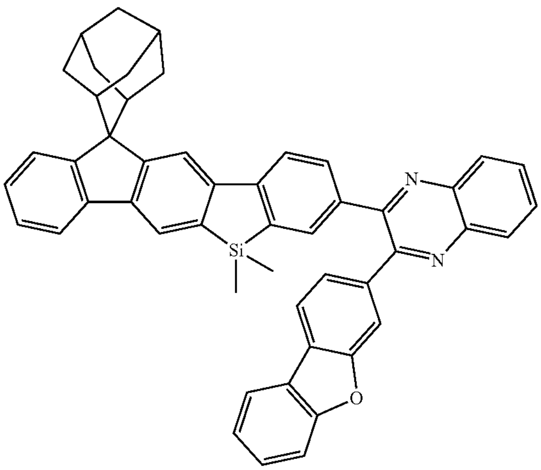
216
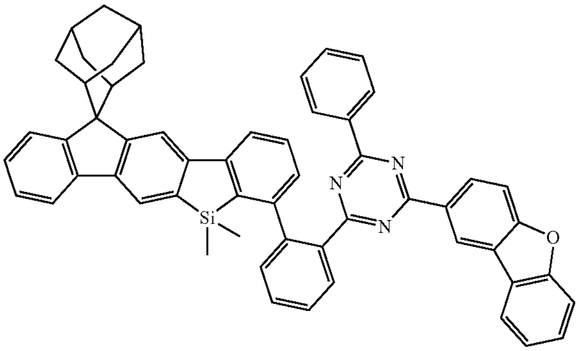
217
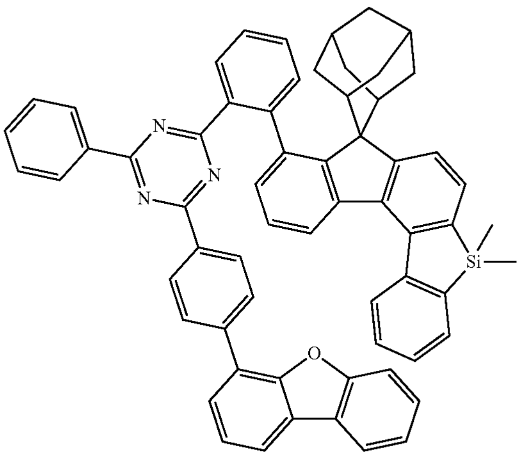

218
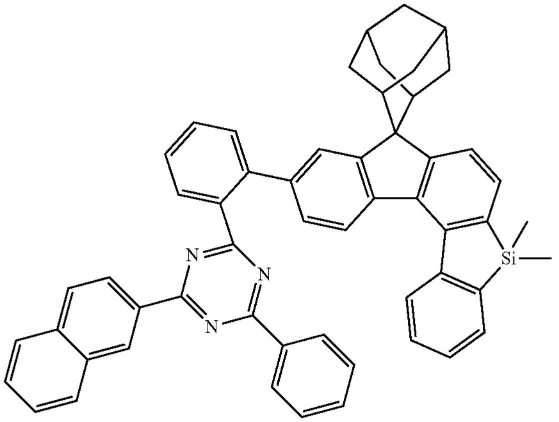
219
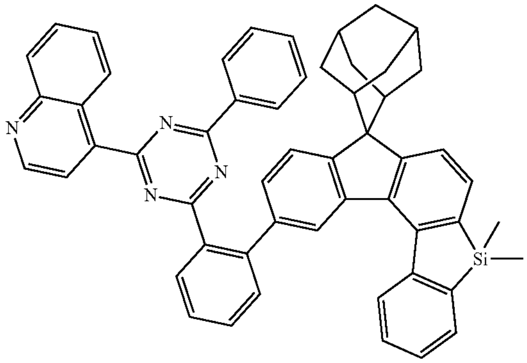
220
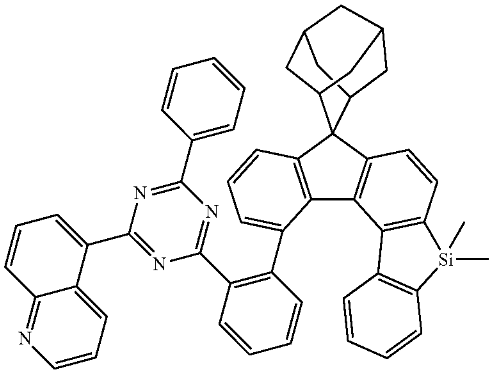
221
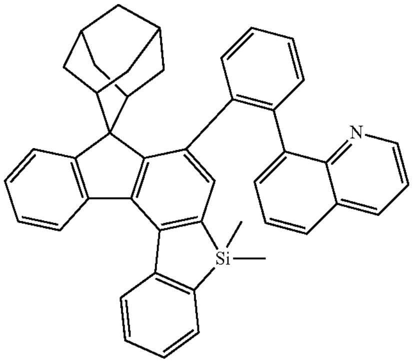
222
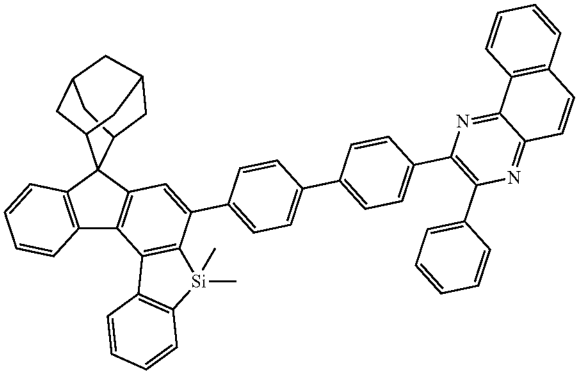
223
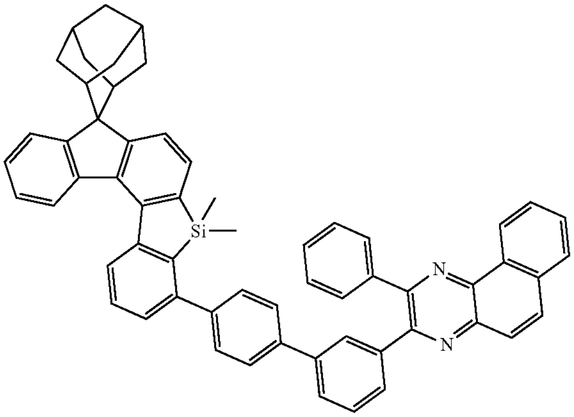
224
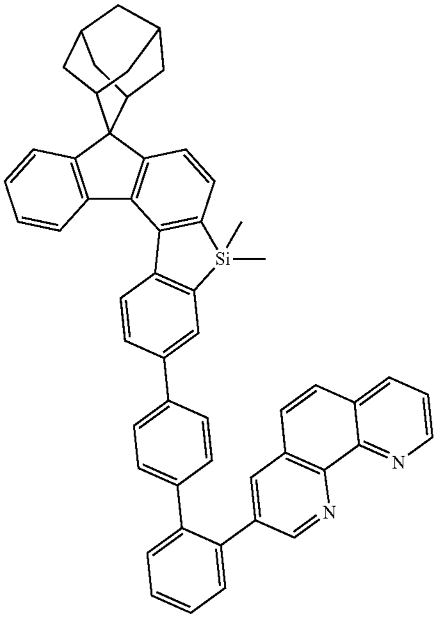

-continued
225
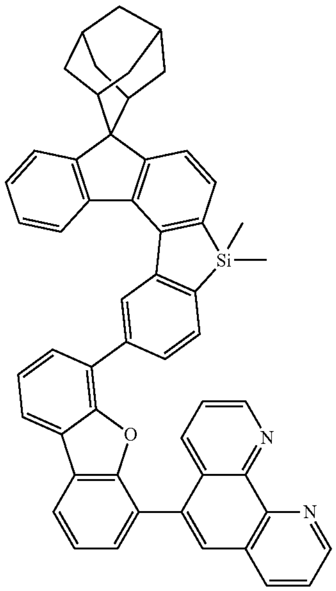
226
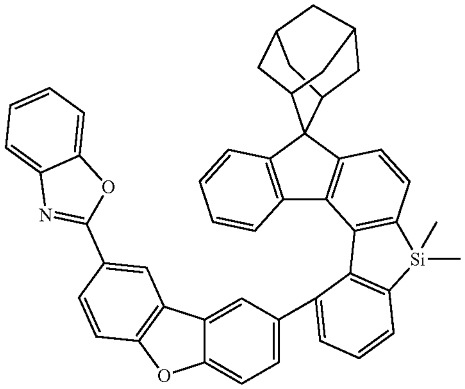
227
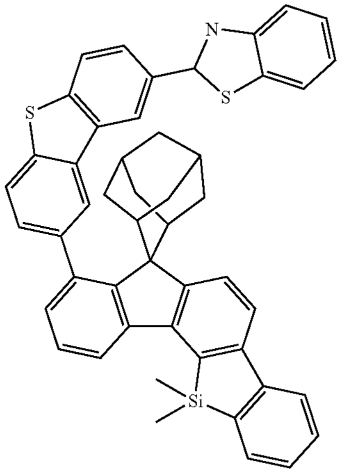
-continued
228
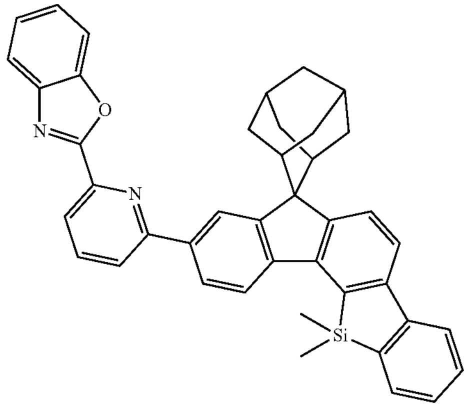
229
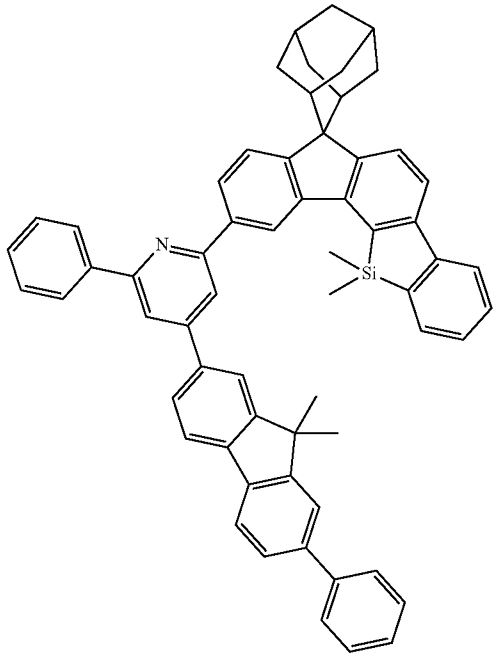
230
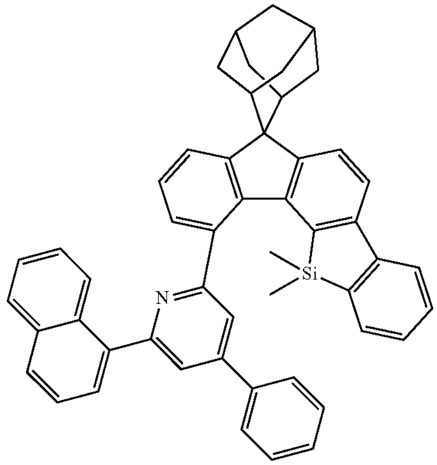

-continued
231
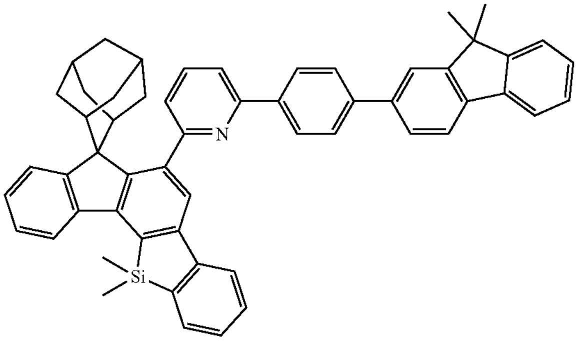
232
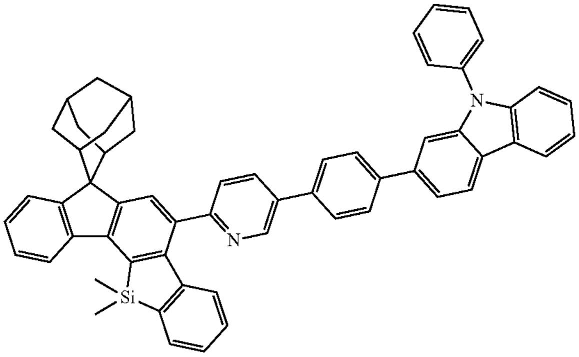
233
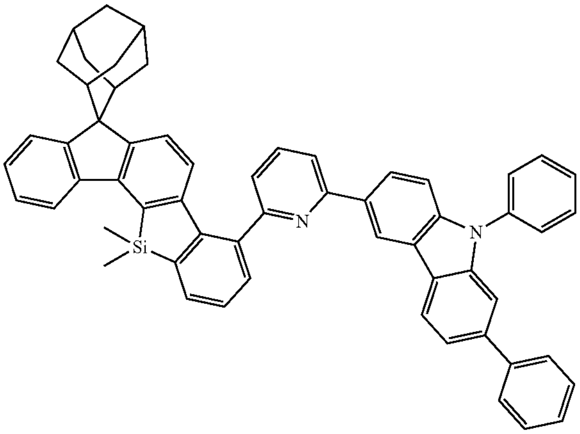
-continued
234
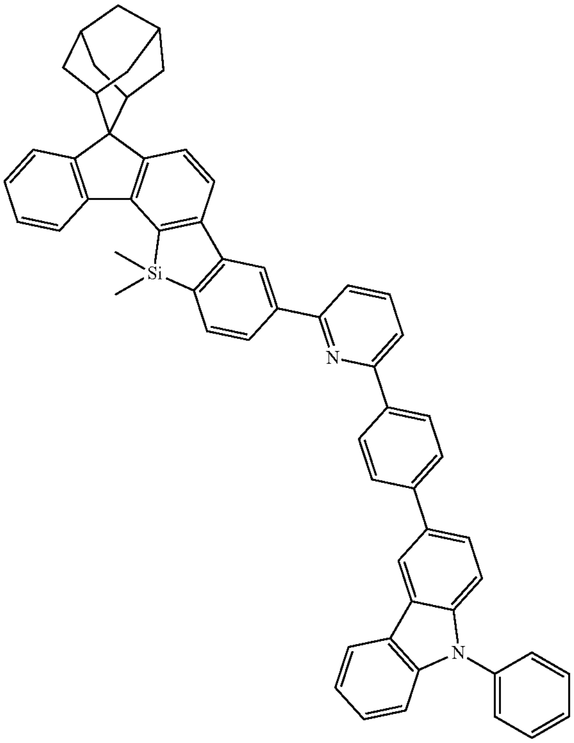
235
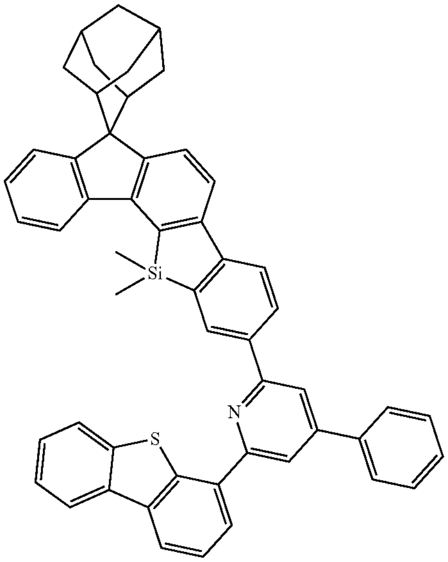

-continued
236
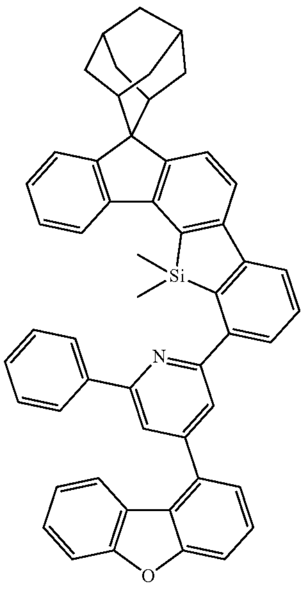
237
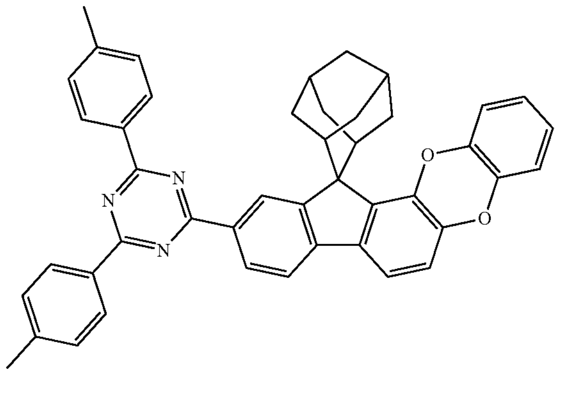
238
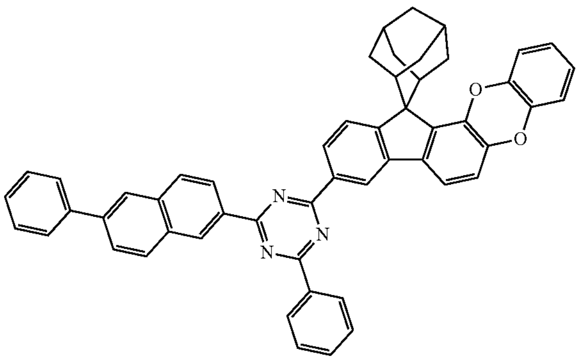
-continued
239
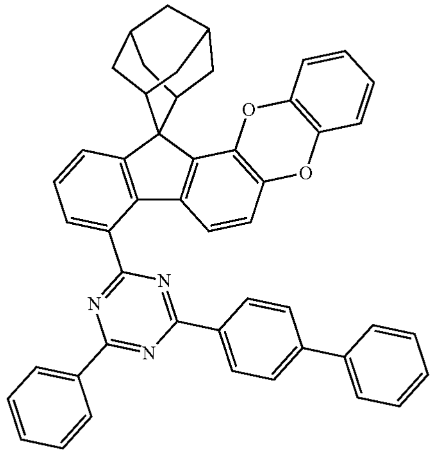
240
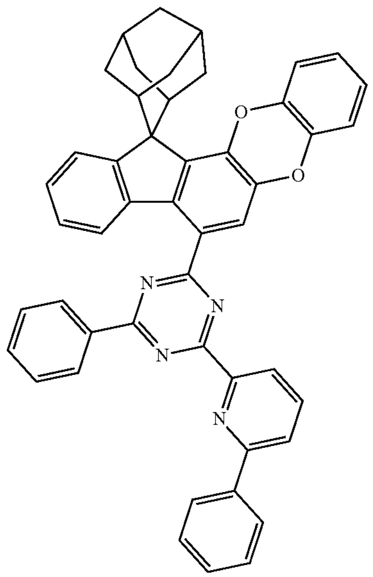
241
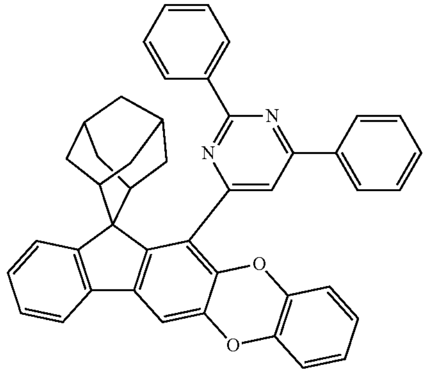

-continued
242
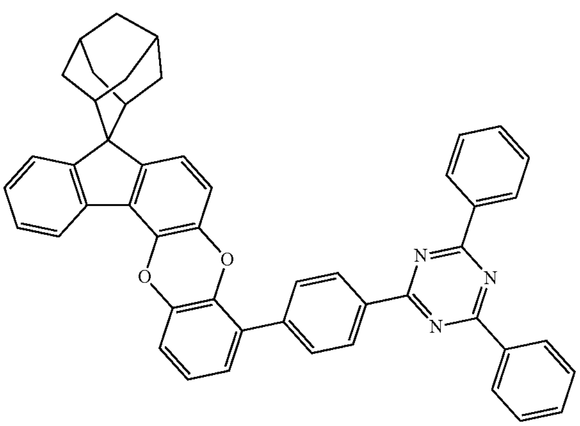
243
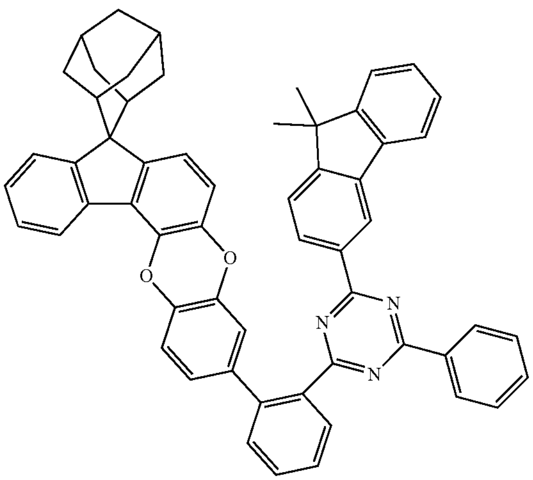
244
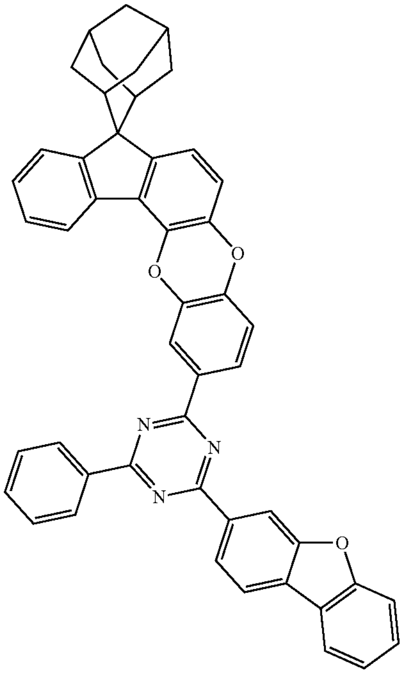
-continued
245
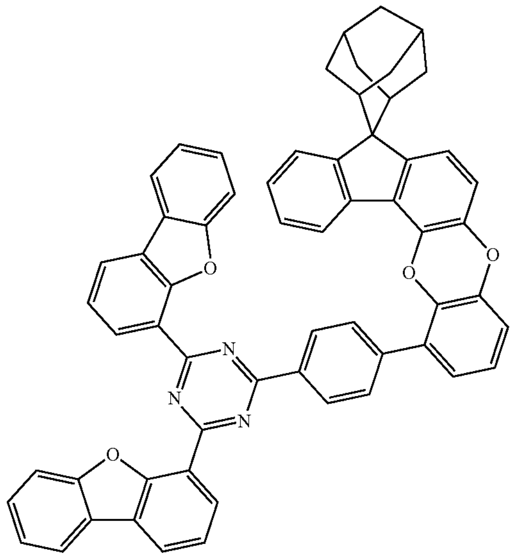
246
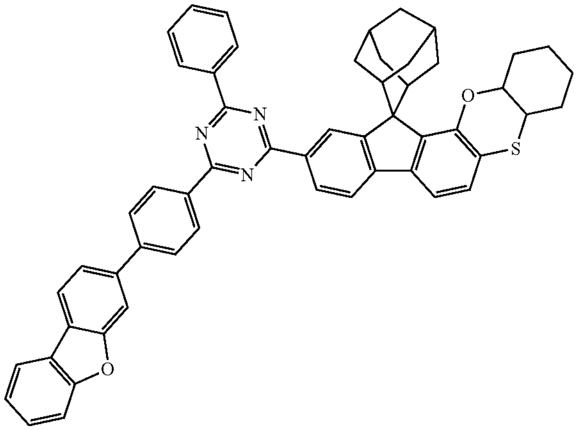
247
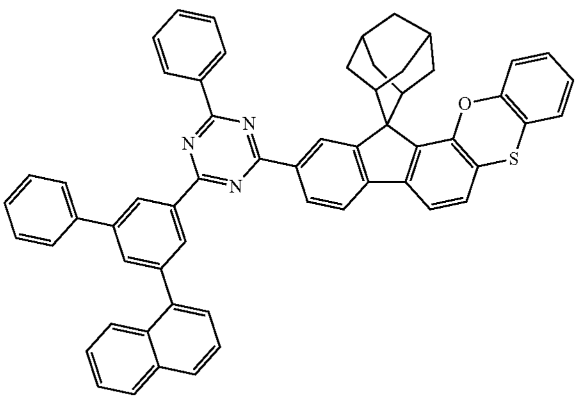

-continued
248
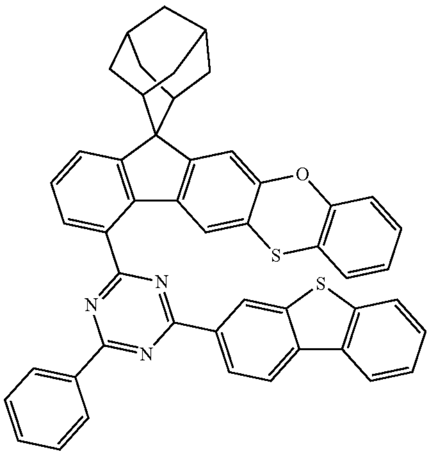
249
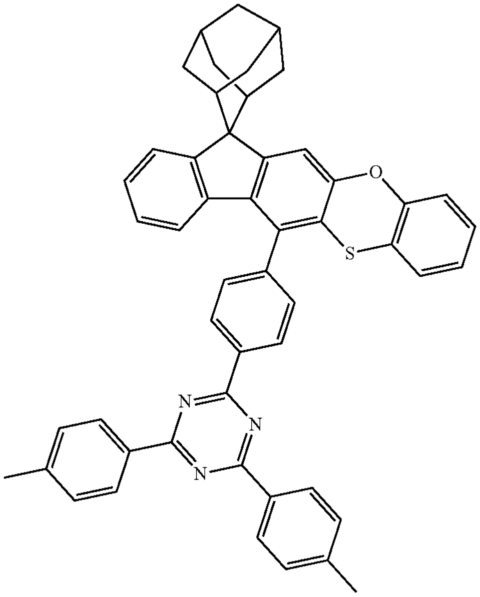
250
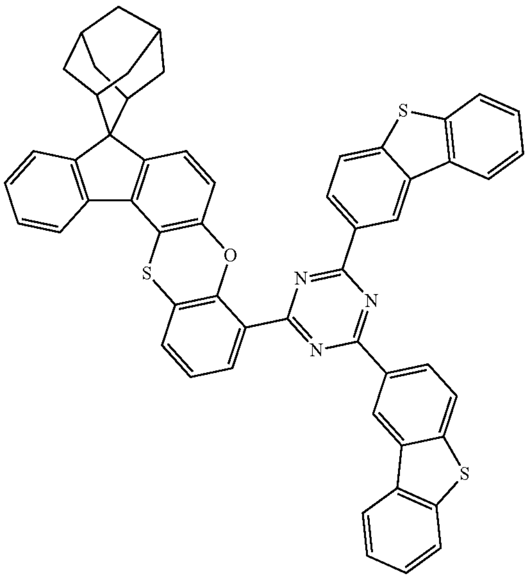
-continued
251
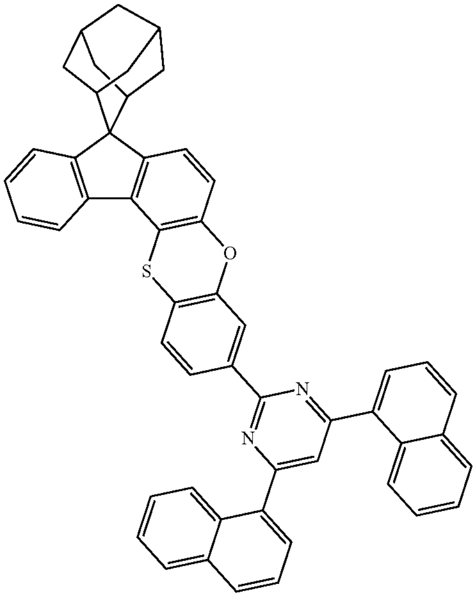
252
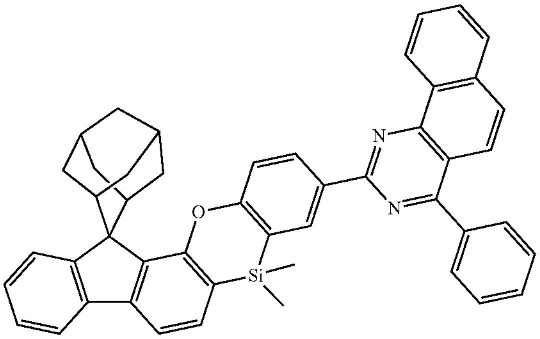
253
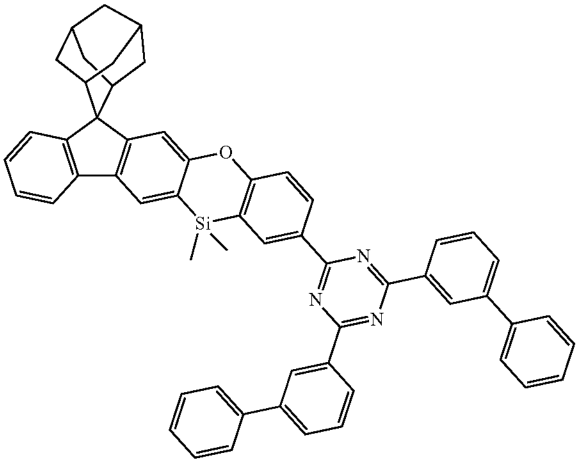

-continued
254
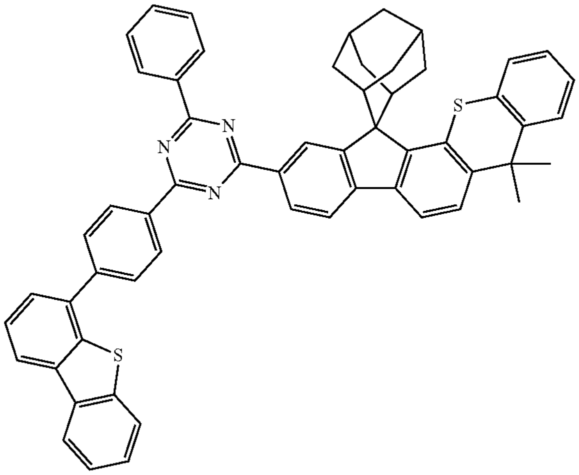
255
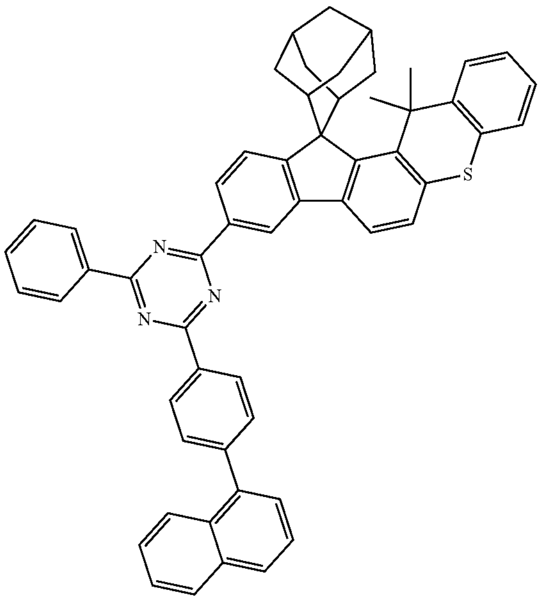
256
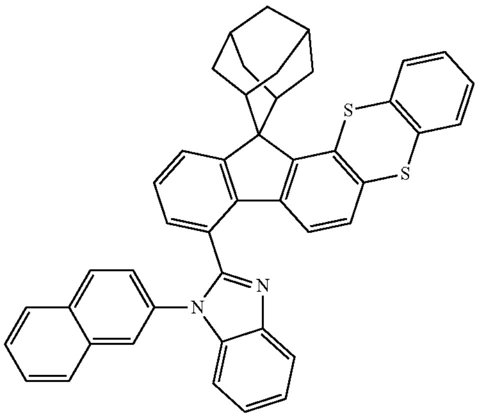
-continued
257
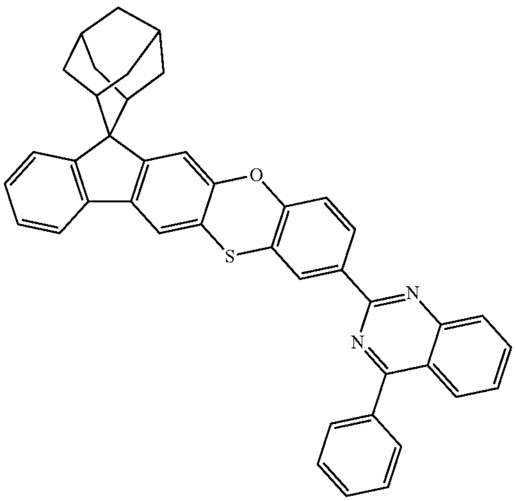
258
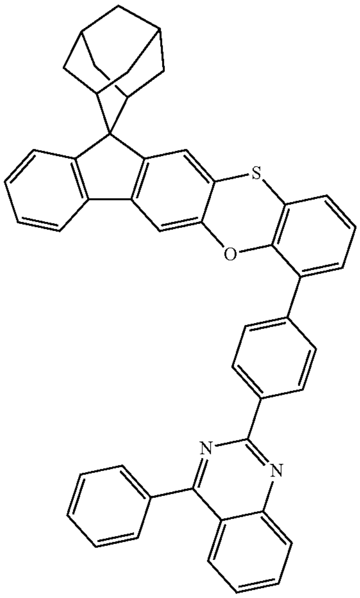
259
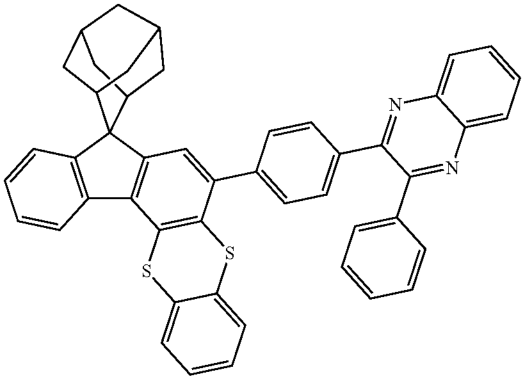

-continued
260
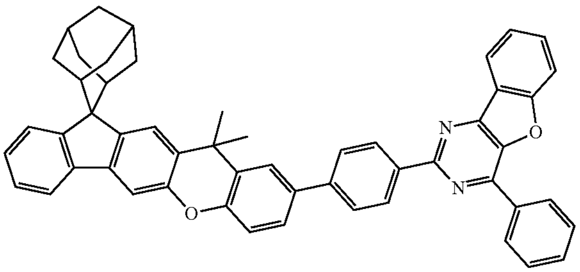
261
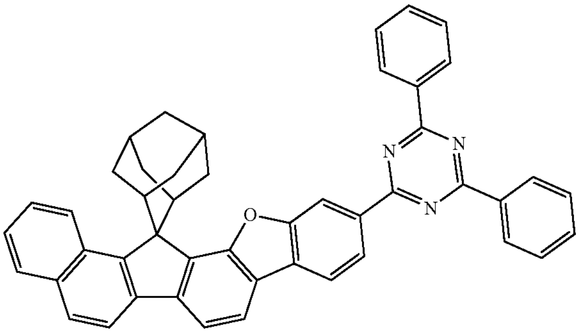
262
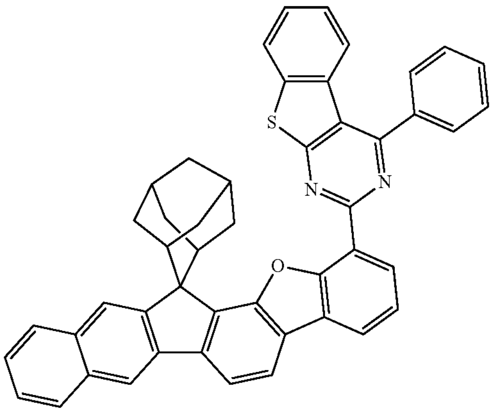
263
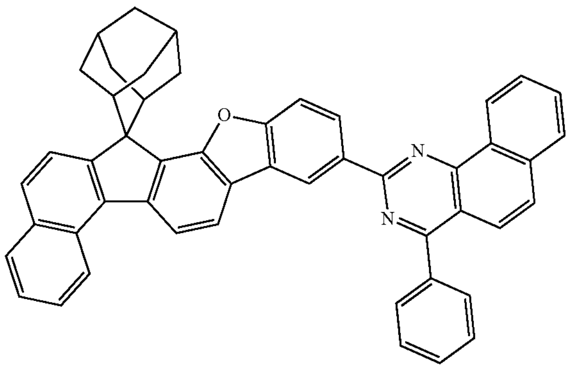
-continued
264
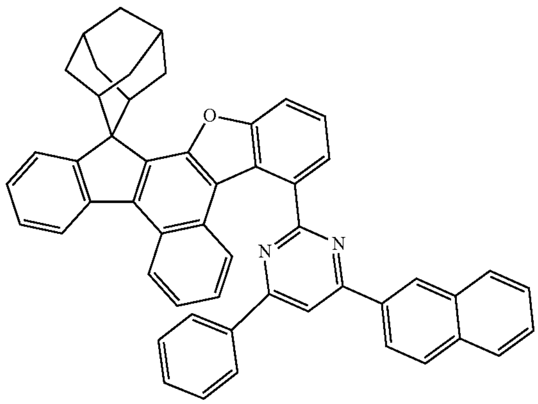
265
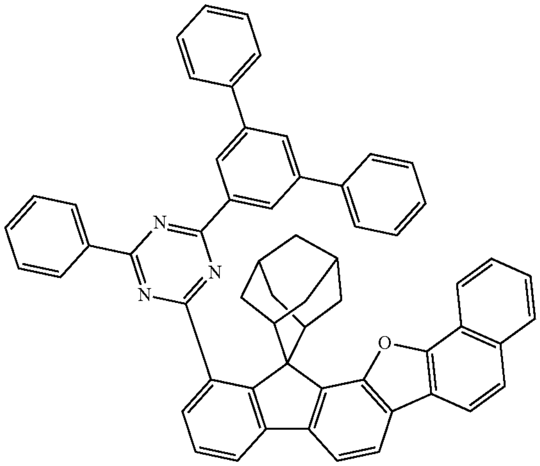
266
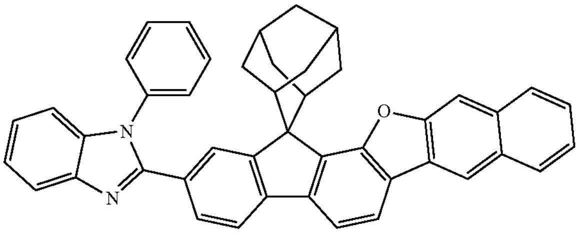
267
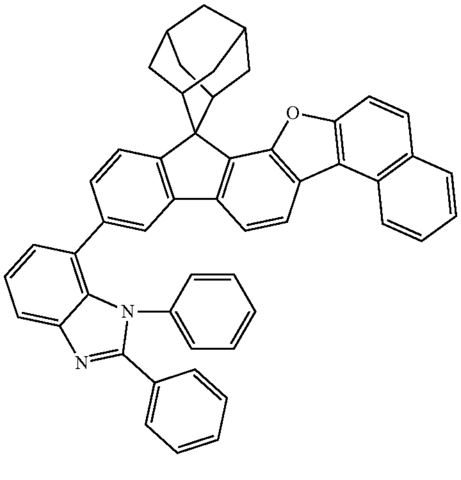

-continued
268
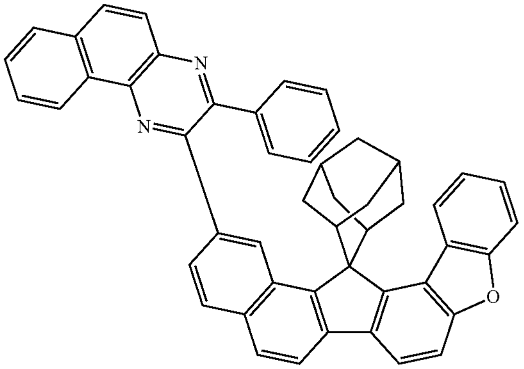
269
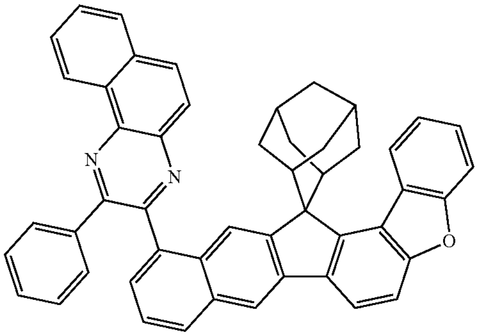
270
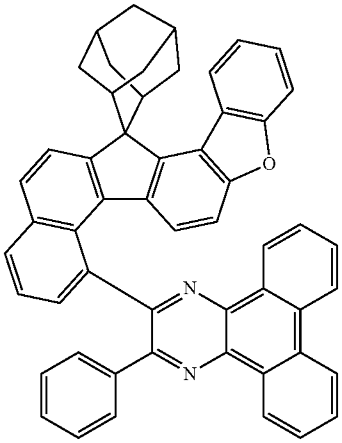
271
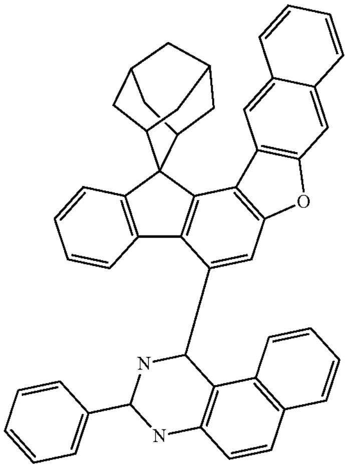
-continued
272
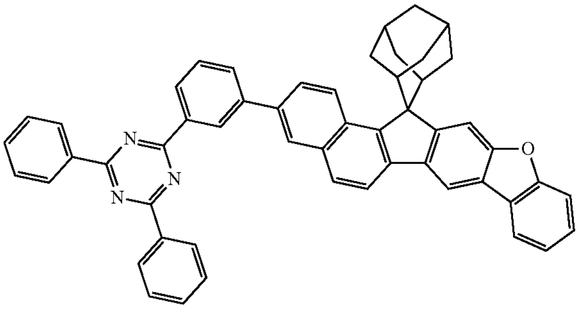
273
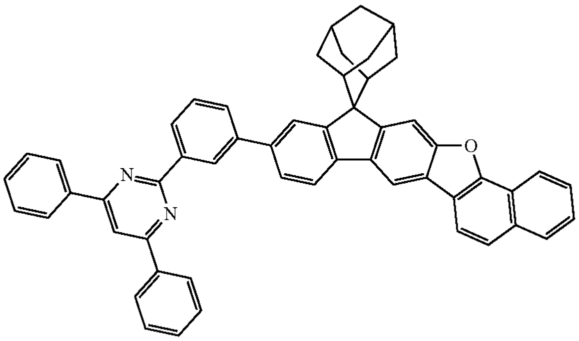
274
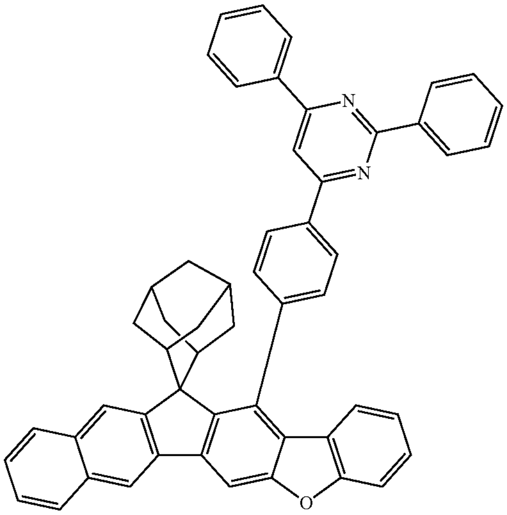
275
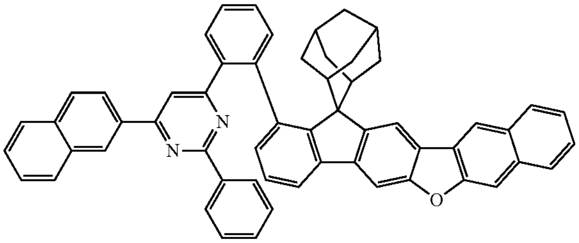

276
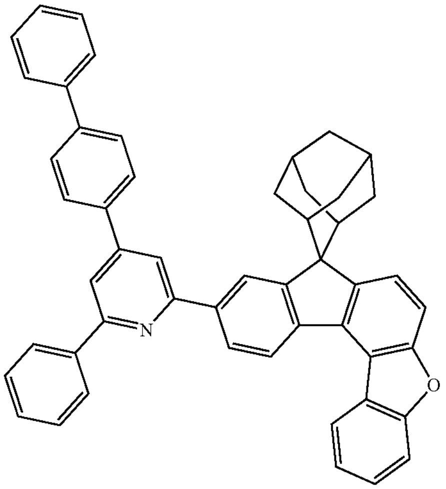
277
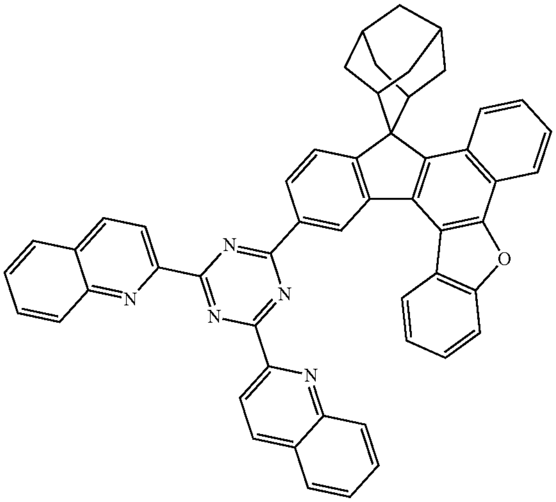
278
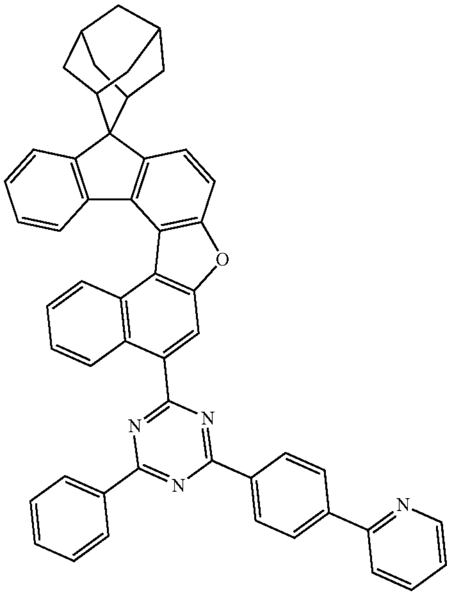
279
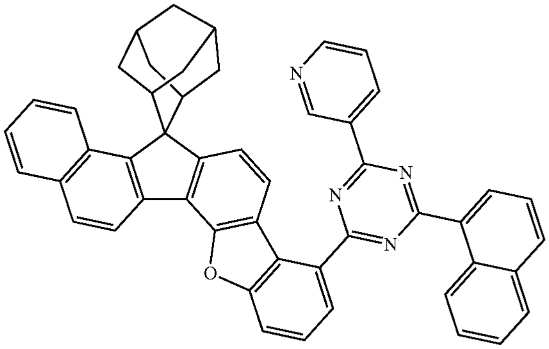
280
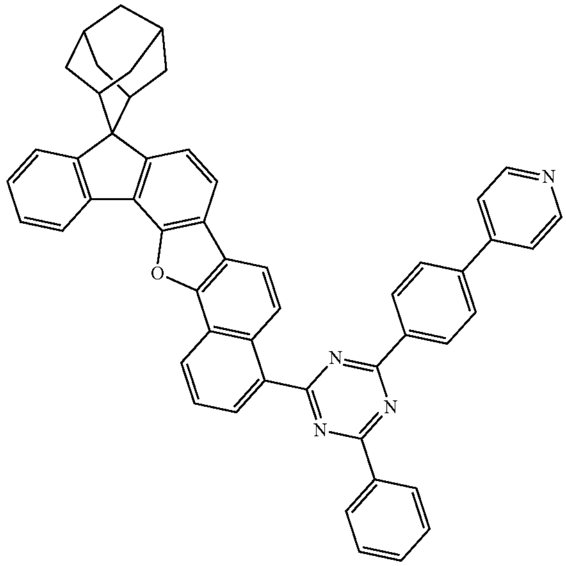
281
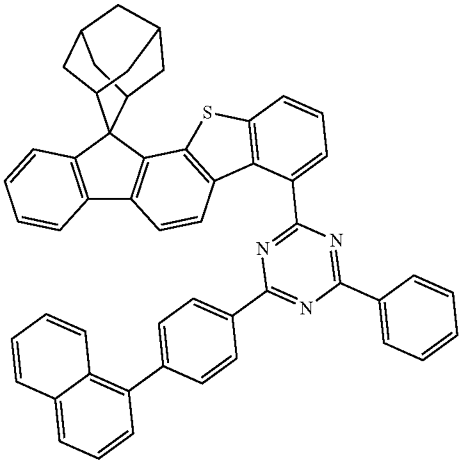

-continued
282
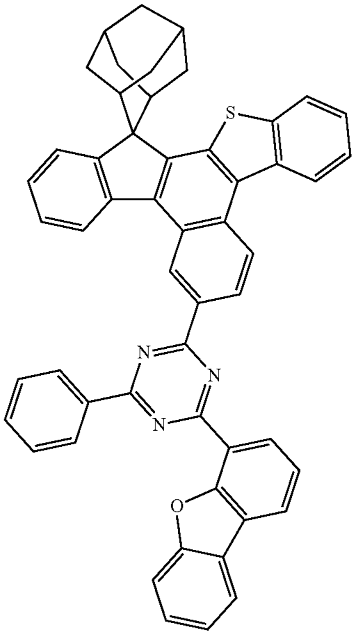
283
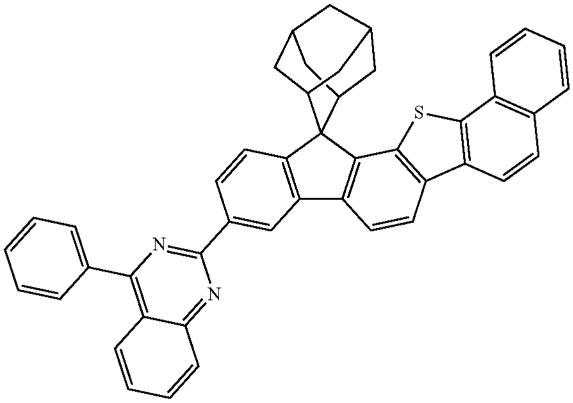
284
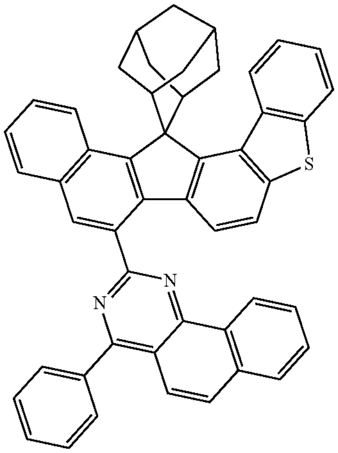
-continued
285
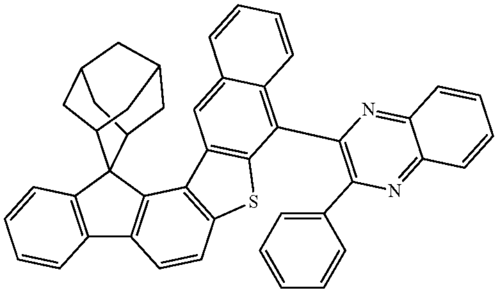
286
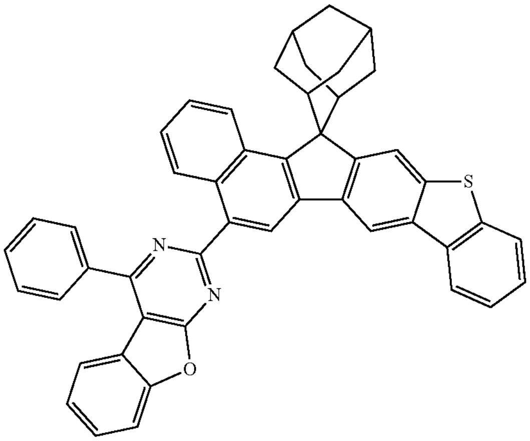
287
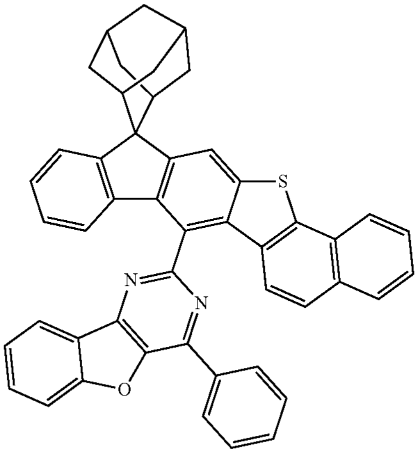
288
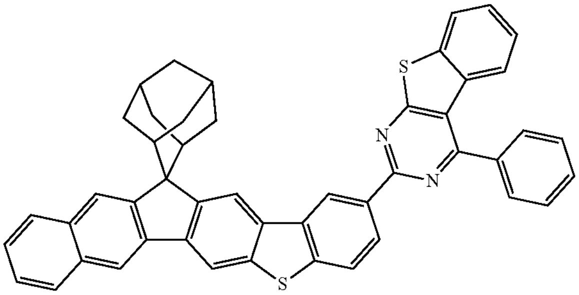

-continued
289
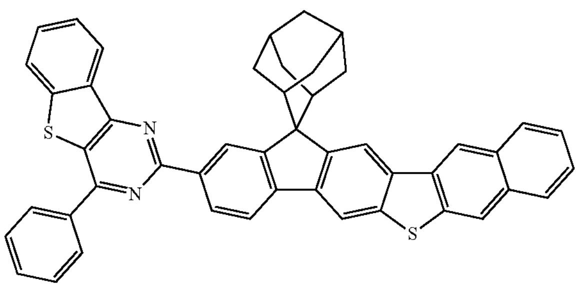
290
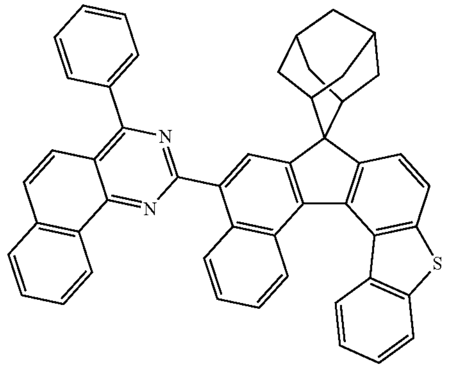
291
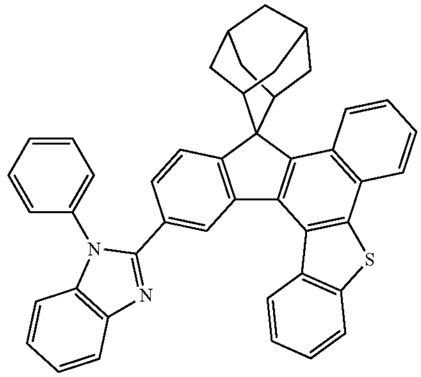
292
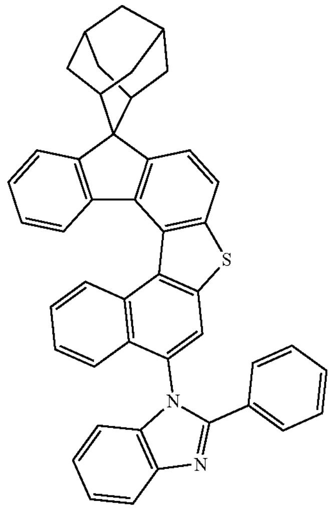
-continued
293
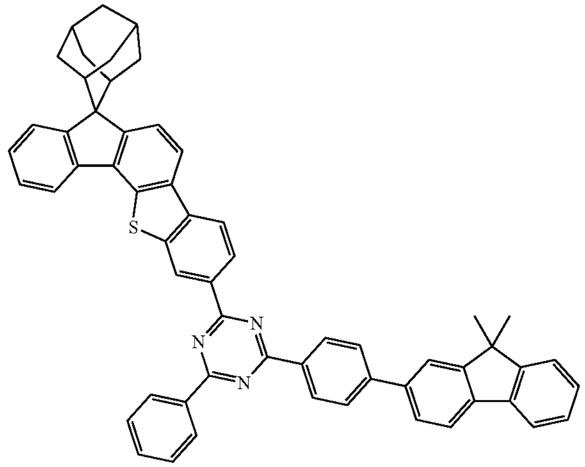
294
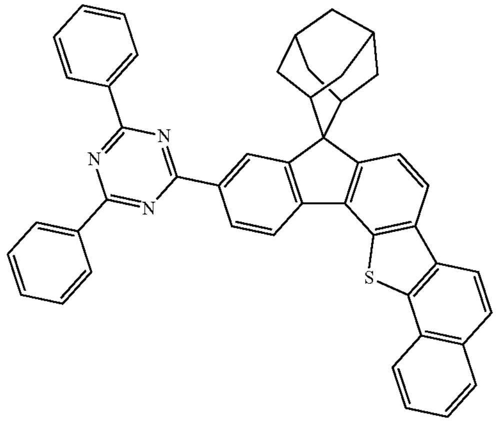
295
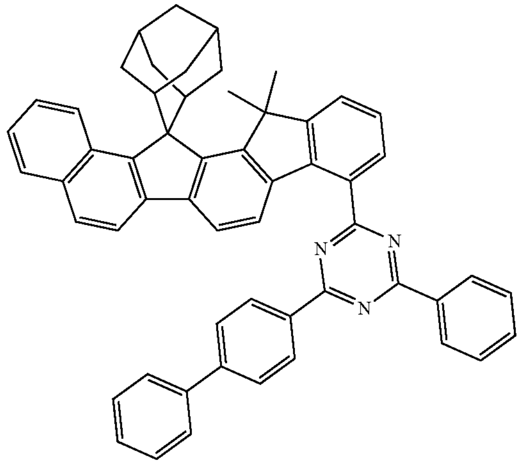

-continued
296
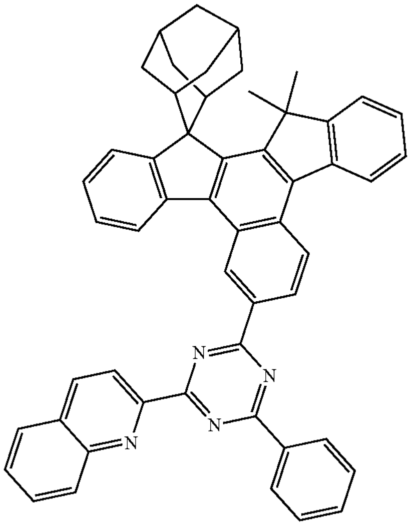
297
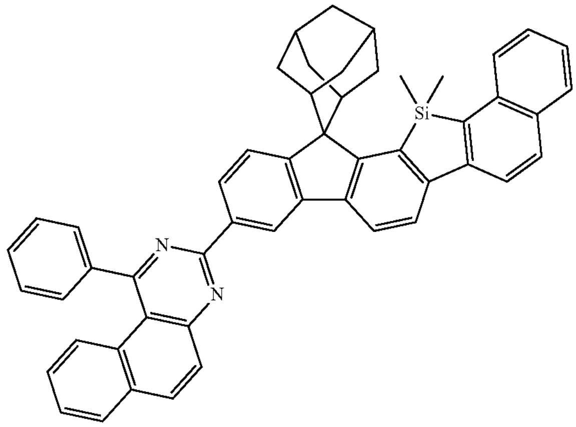
298
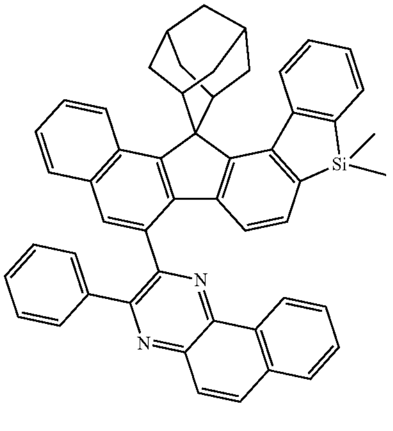
-continued
299
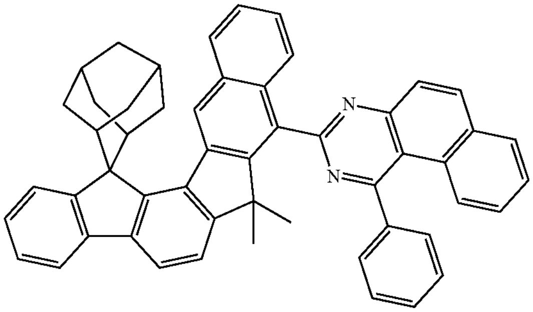
300
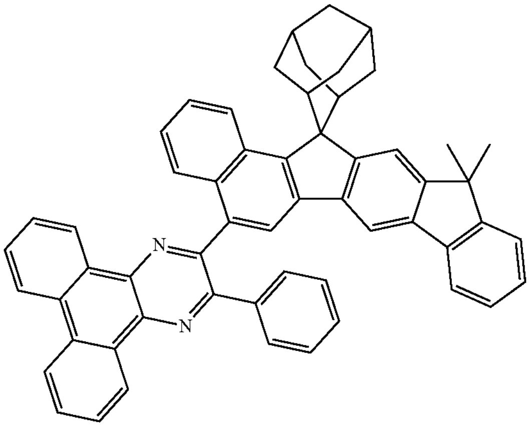
301
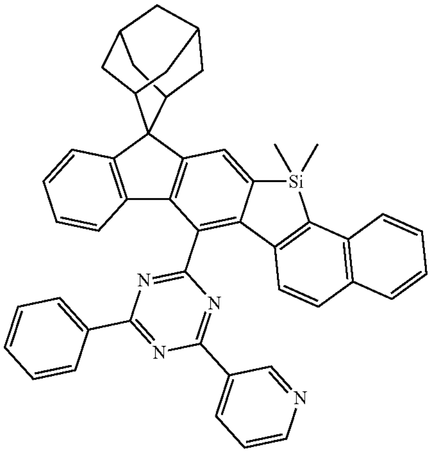
302
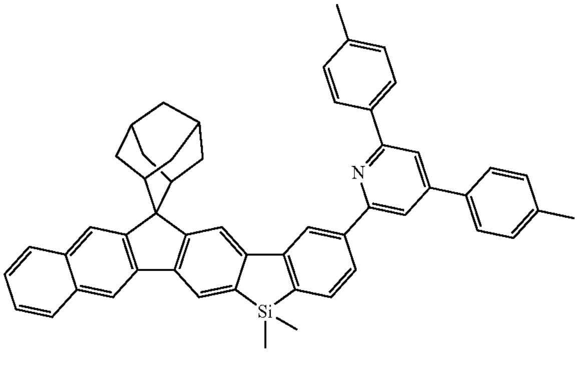

-continued
303
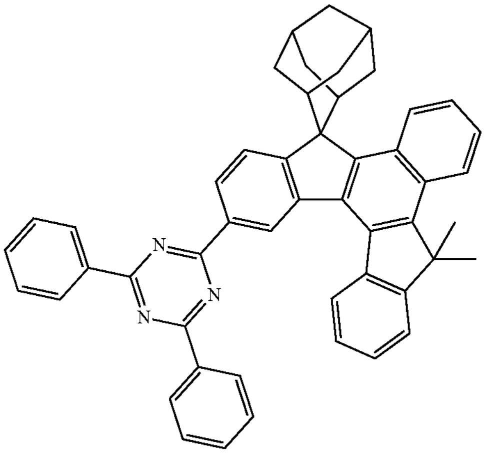
304
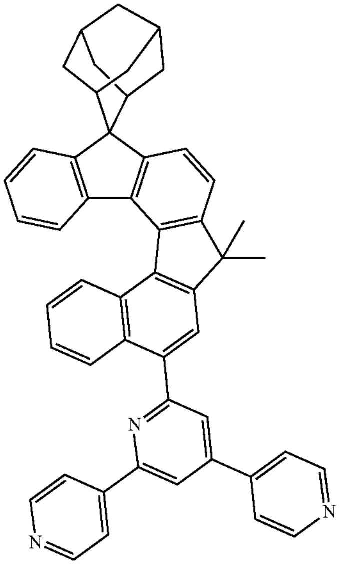
305
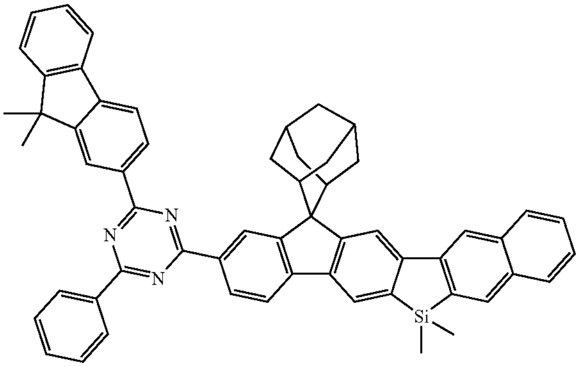
-continued
306
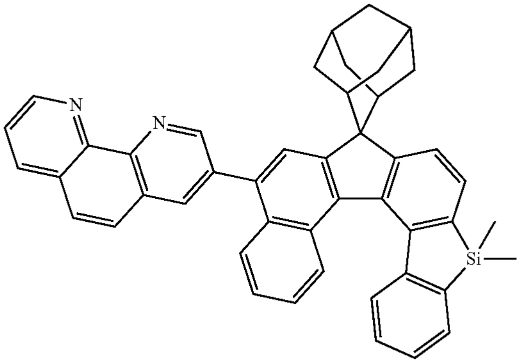
307
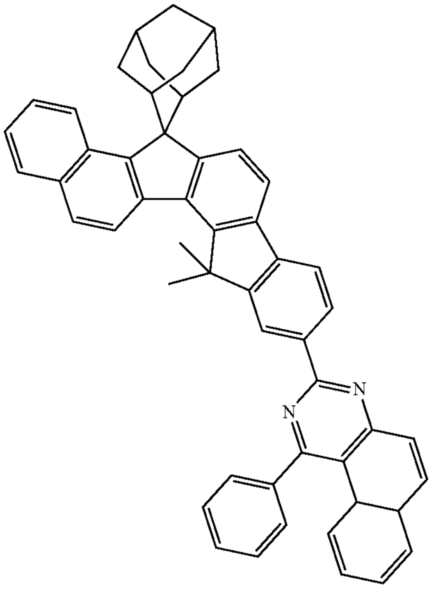
308
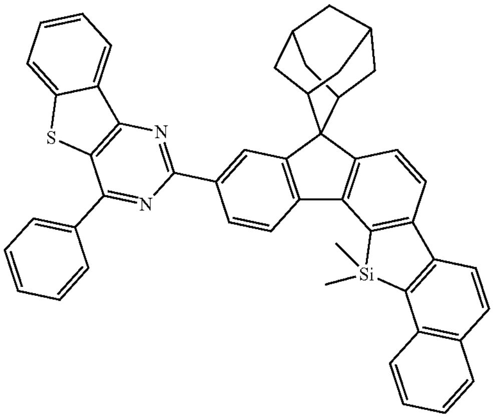

-continued
309
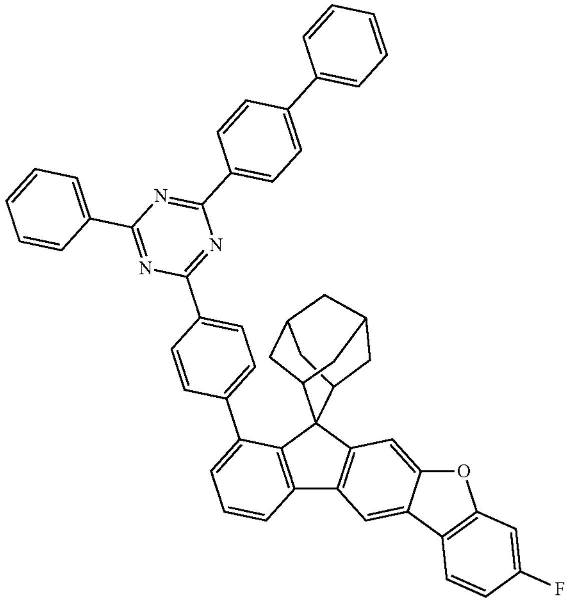
310
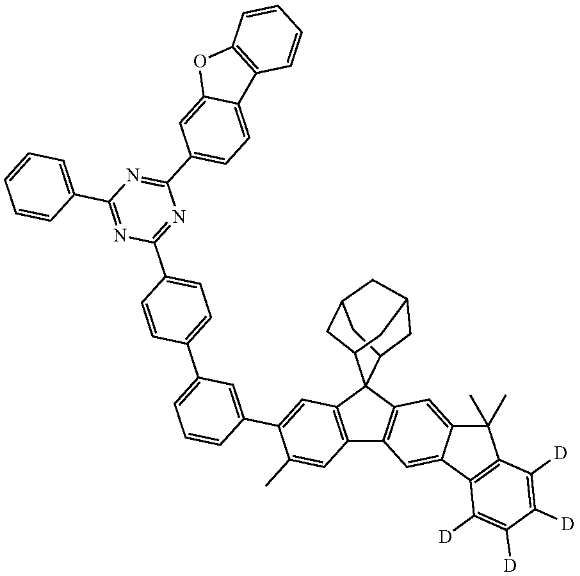
311
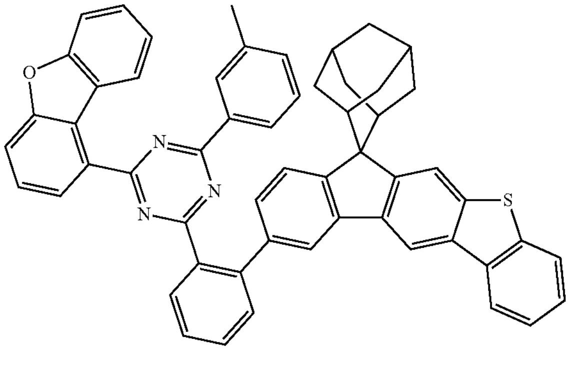
-continued
312
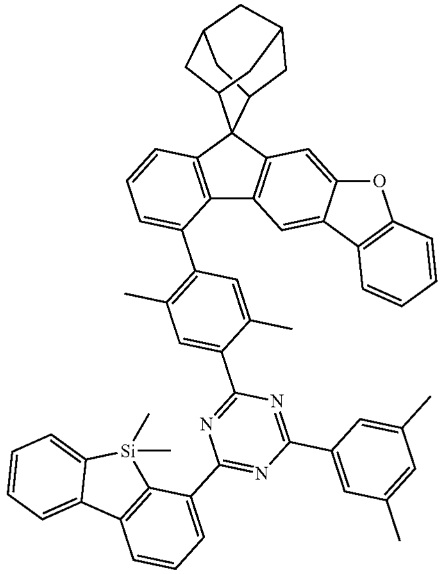
314
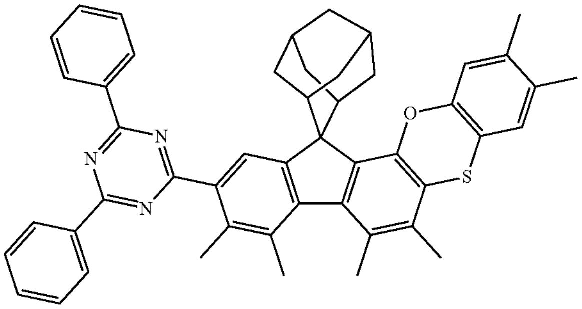
315
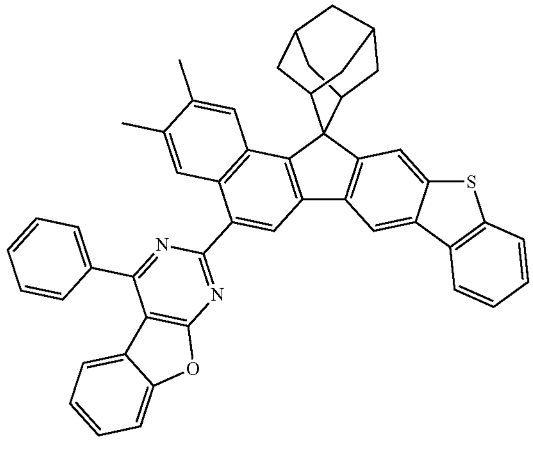

-continued
317
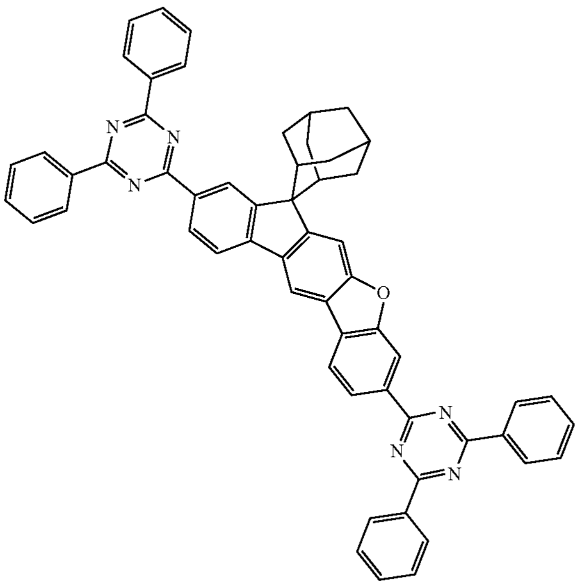
318
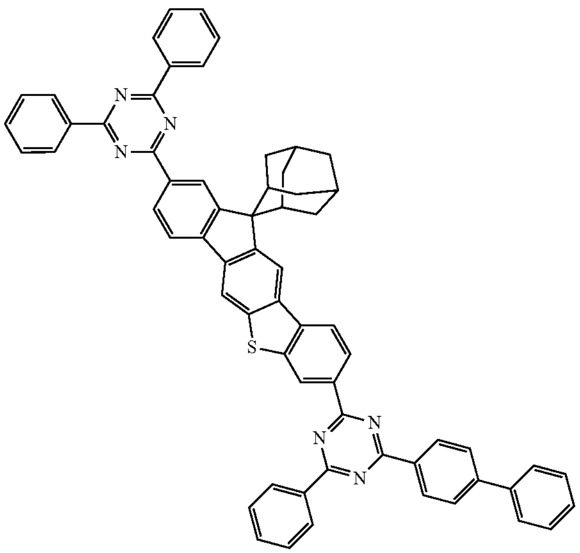
-continued
319
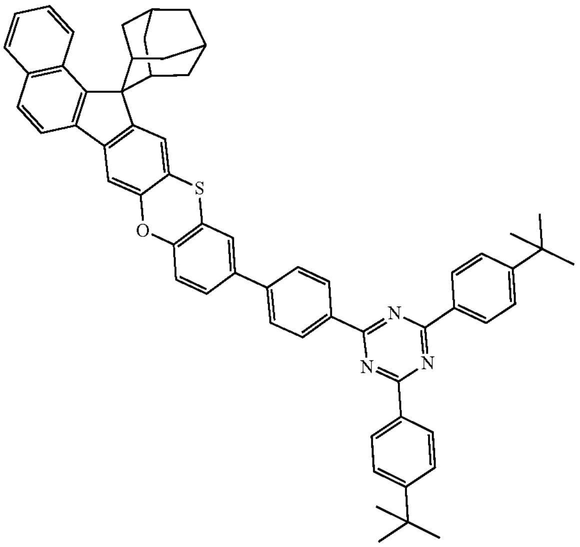
320
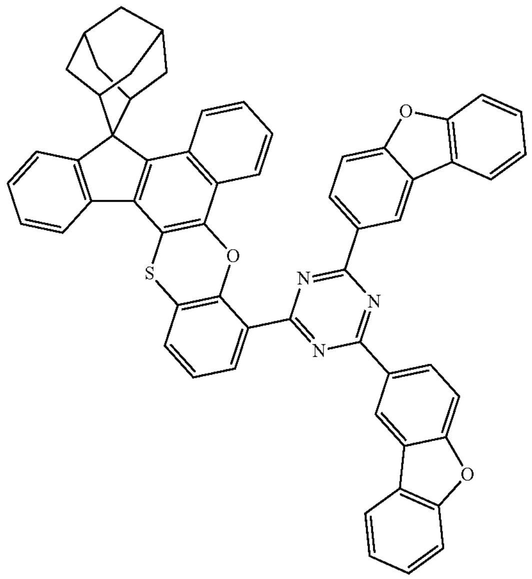

-continued
321
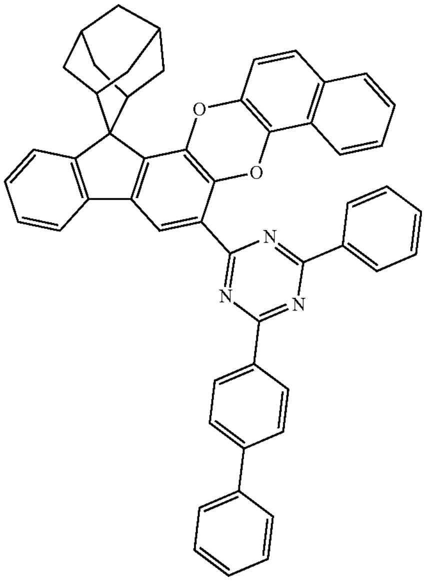
322
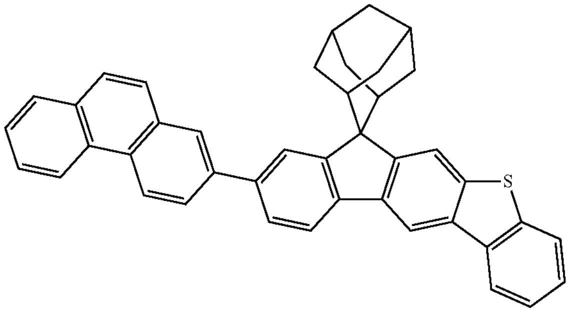
323
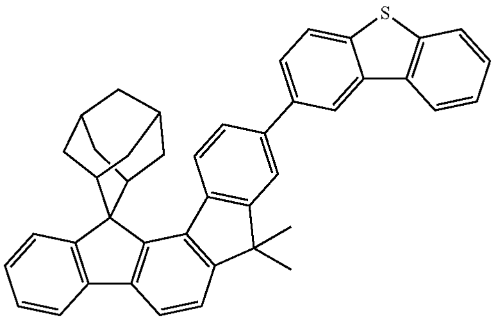
324
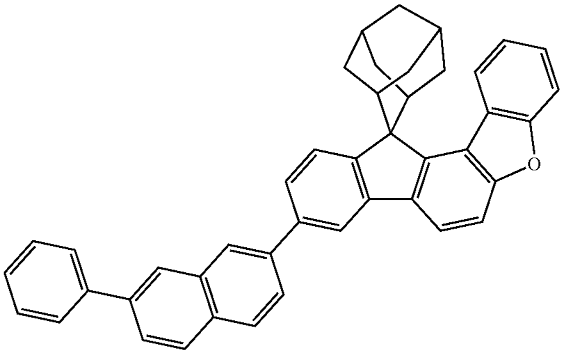
-continued
325
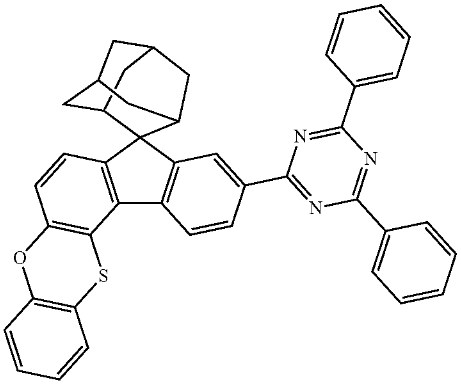
326
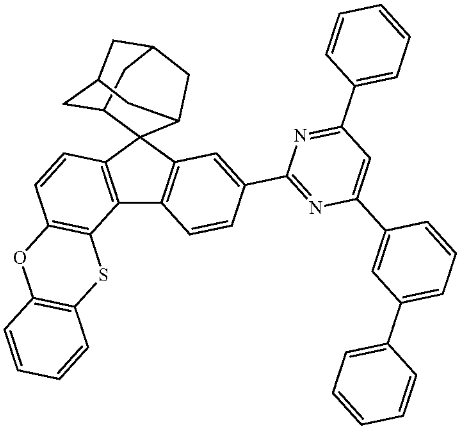
327
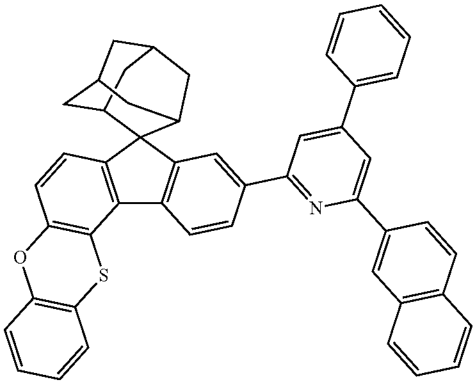
328
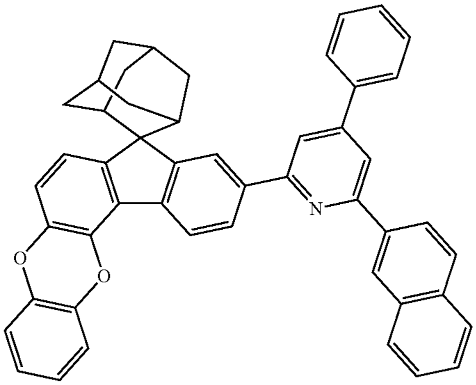

-continued
329
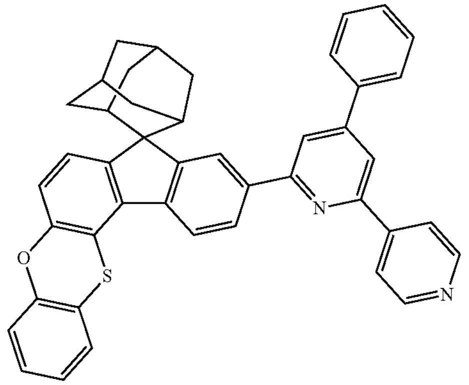
330
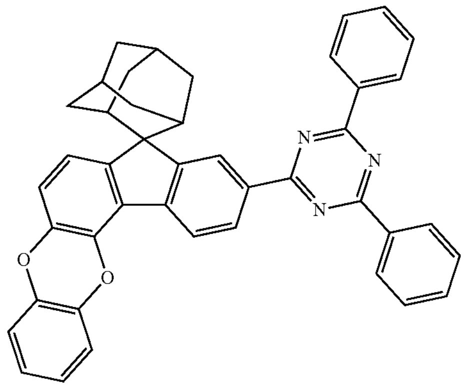
331
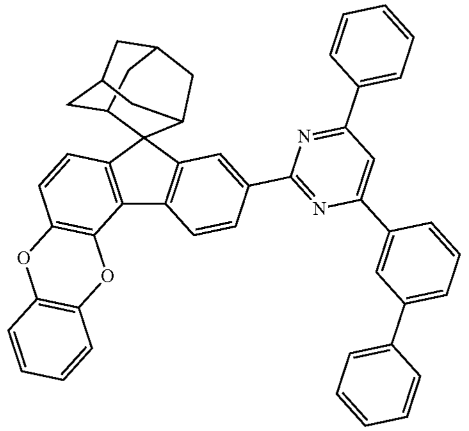
332
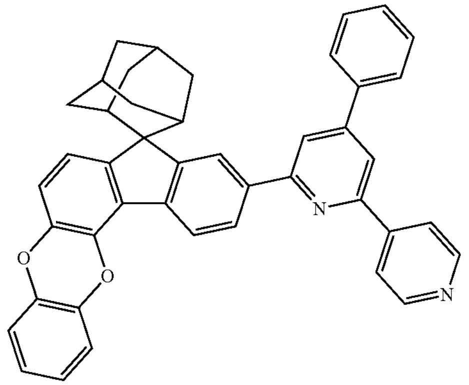
-continued
333
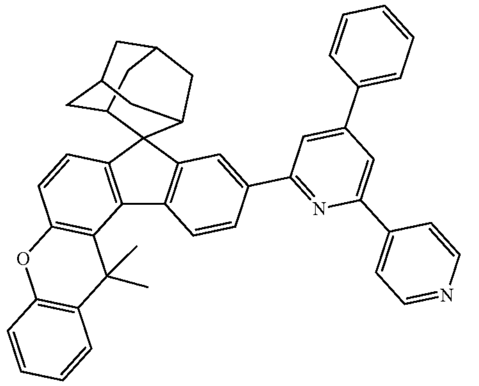
334
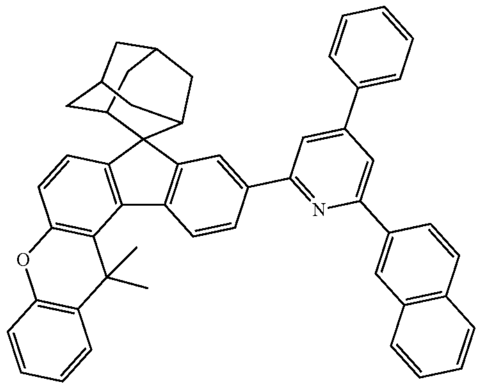
335
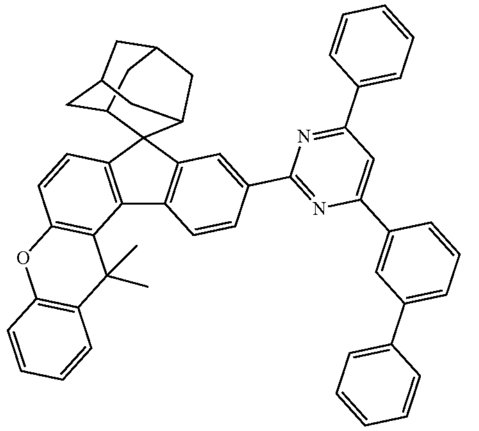
336
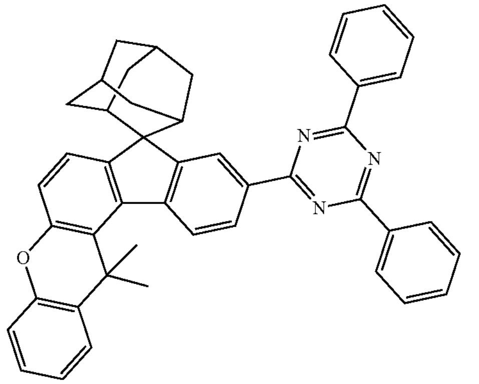

-continued
337
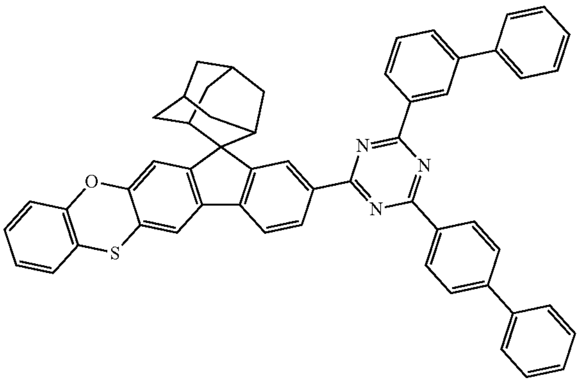
338
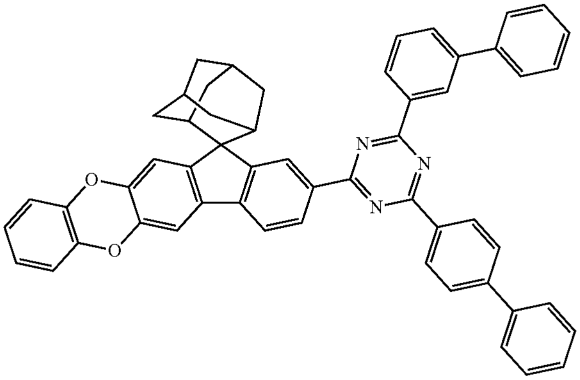
339
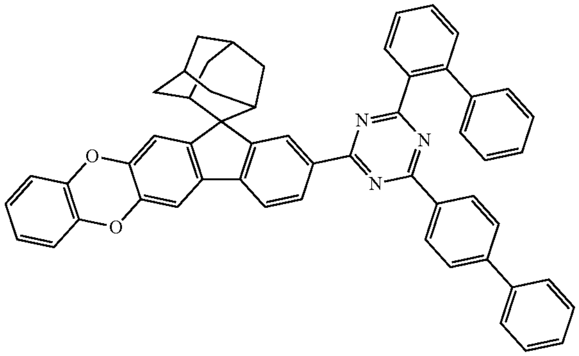
340
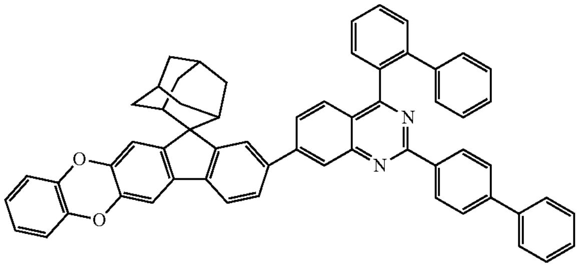
-continued
341
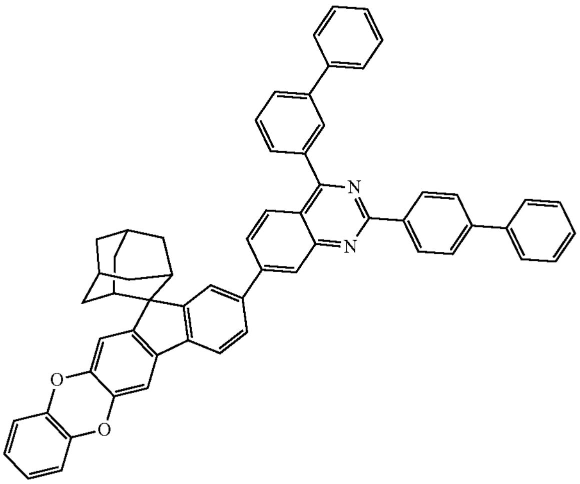
342
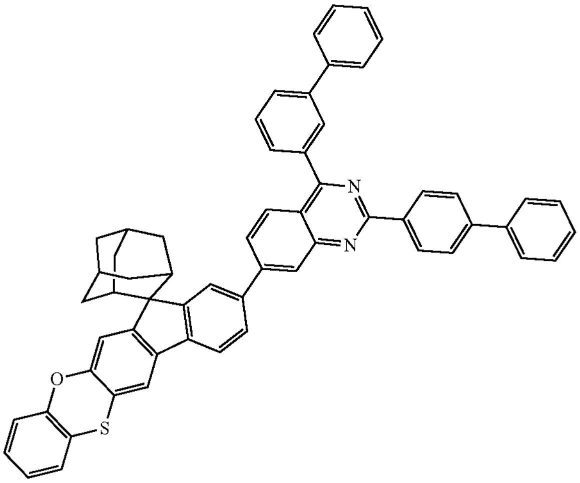
343
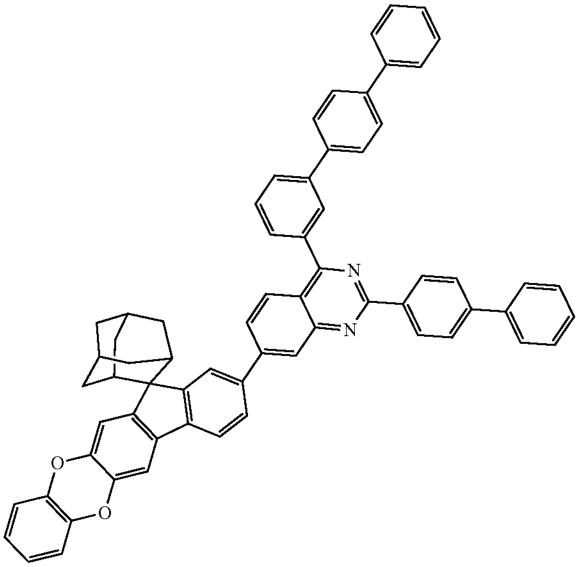

-continued
344
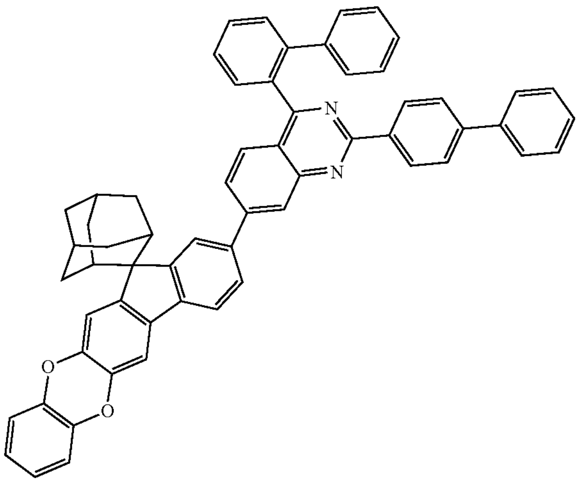
345
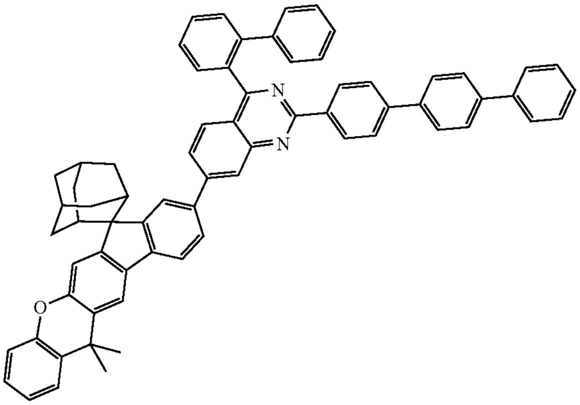
346
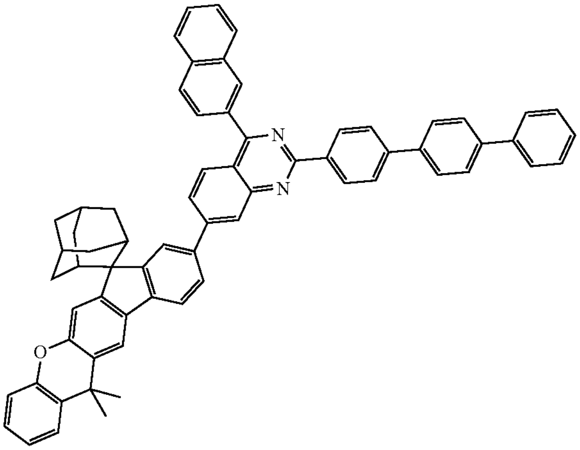
-continued
347
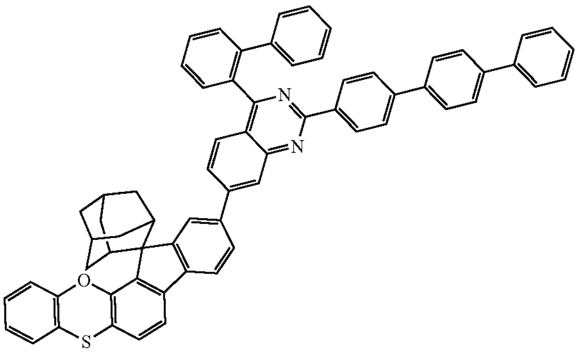
348
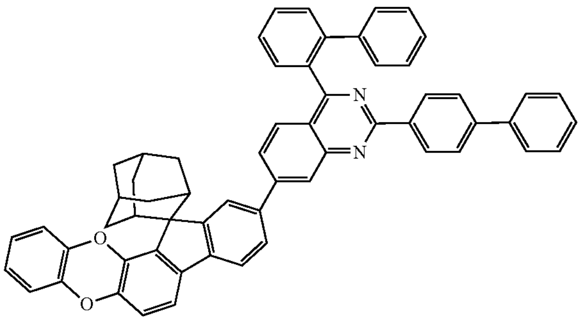
349
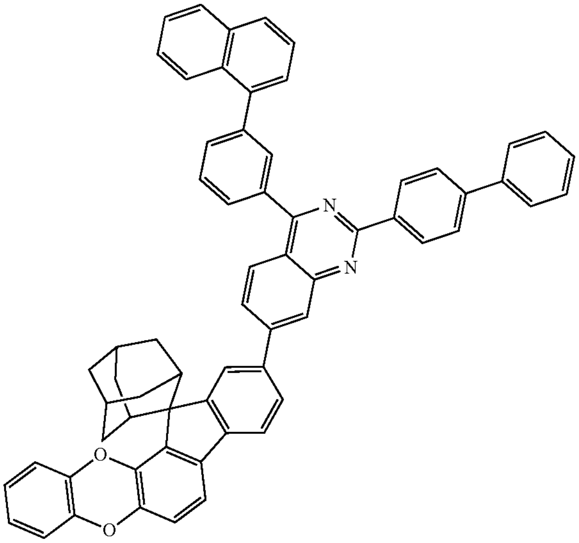

-continued
350
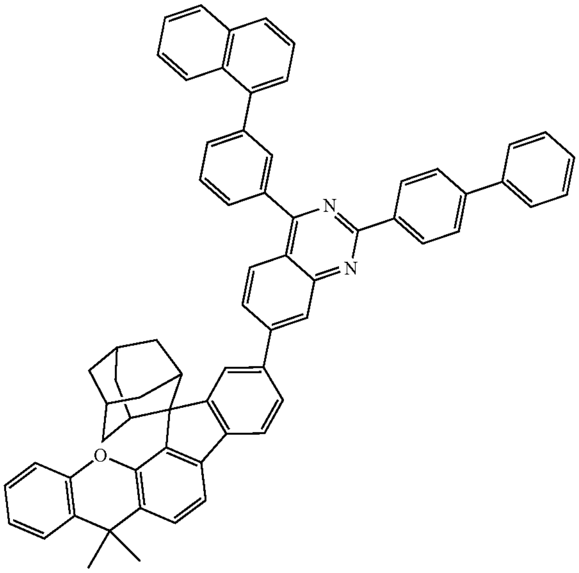
351
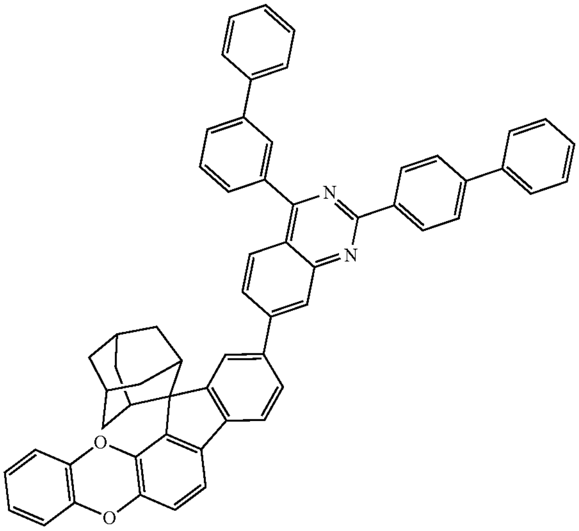
-continued
352
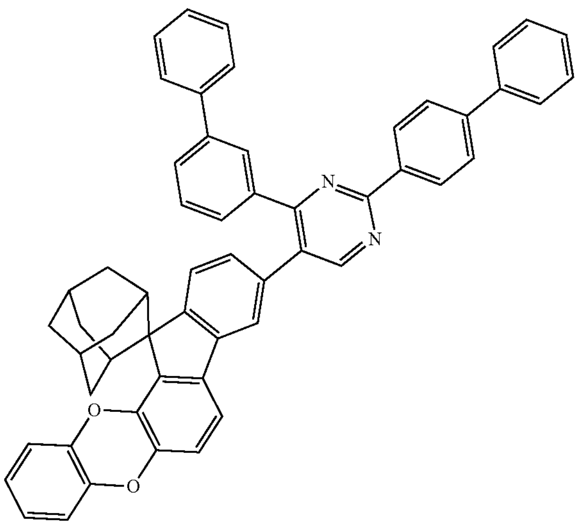
353
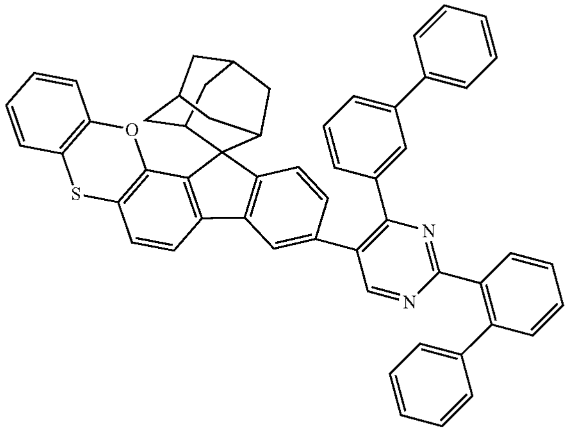
354
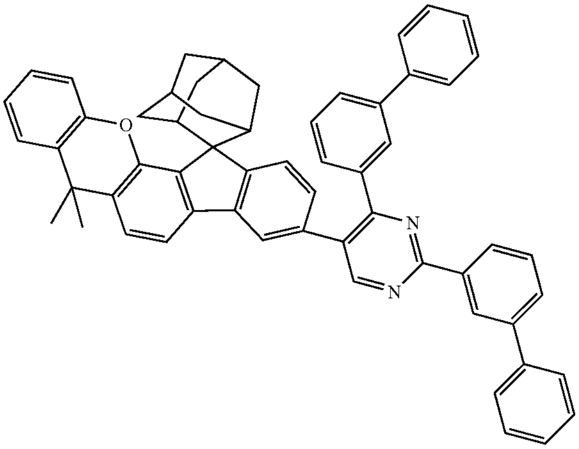

-continued
355
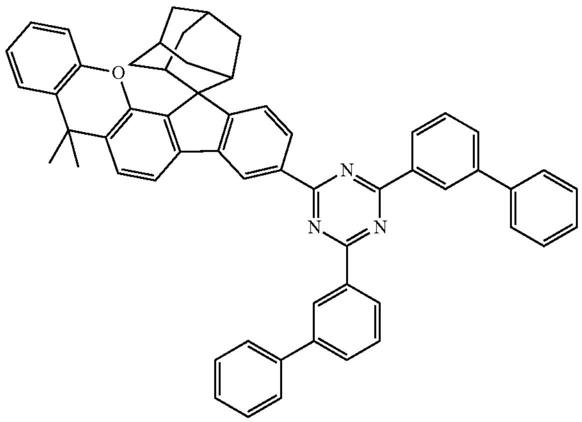
356
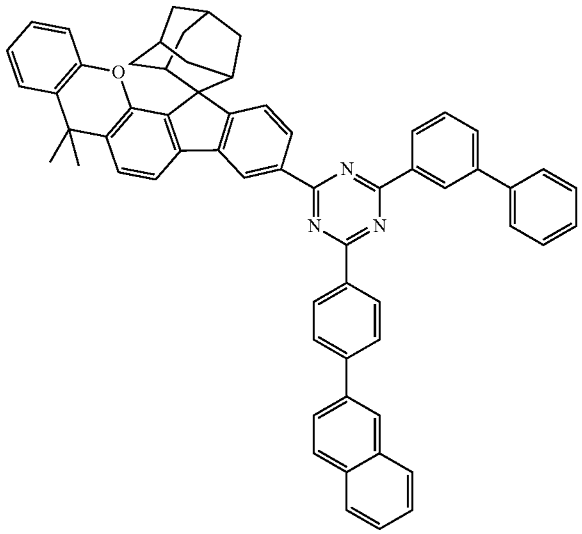
357
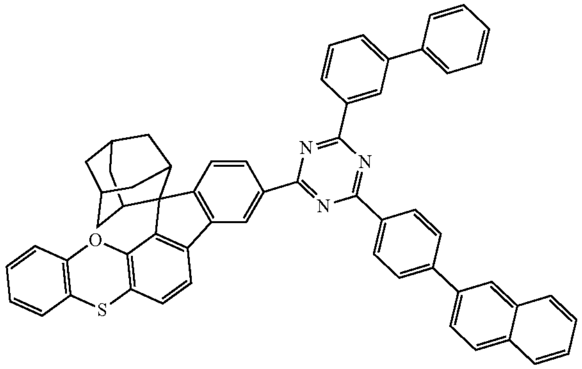
-continued
358
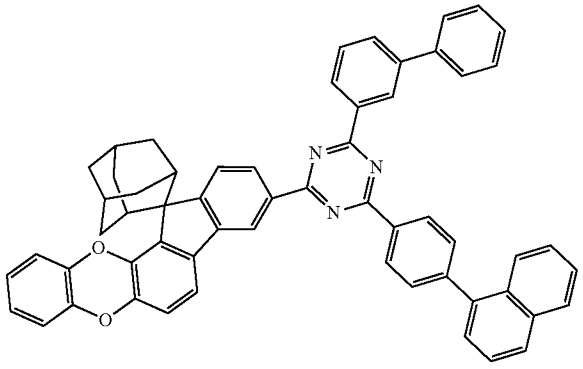
359
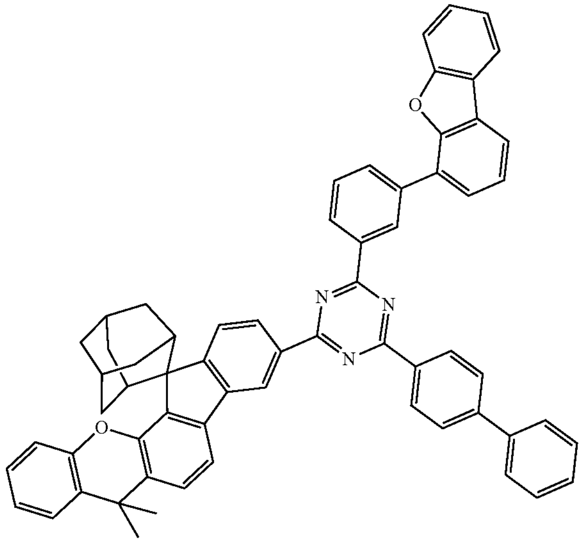
360
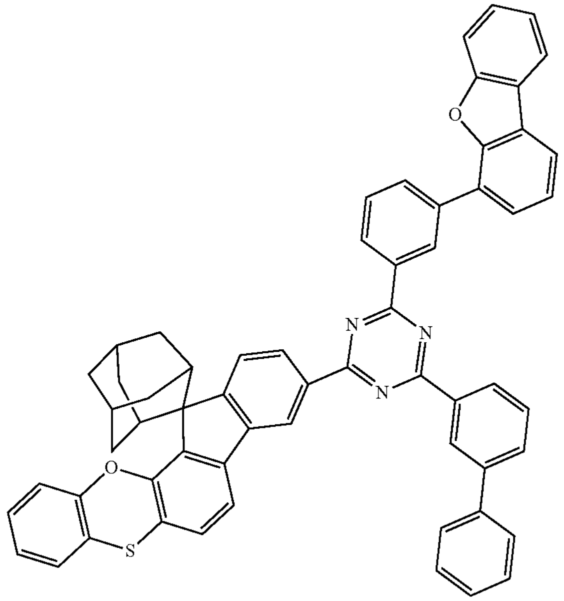

-continued
361
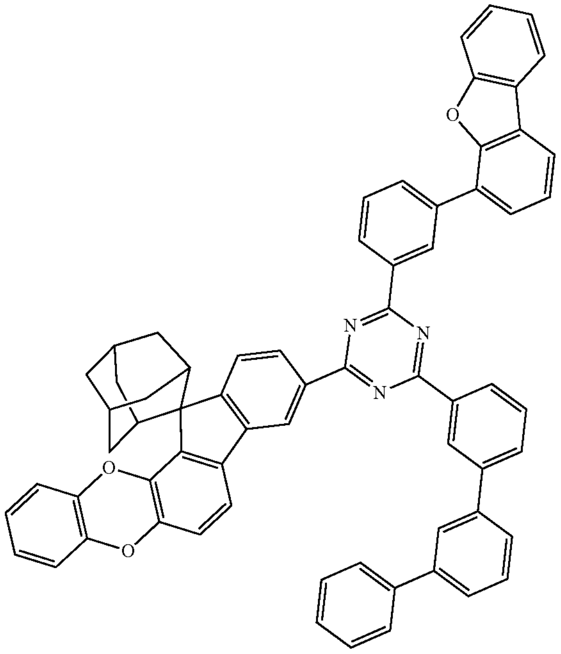
362
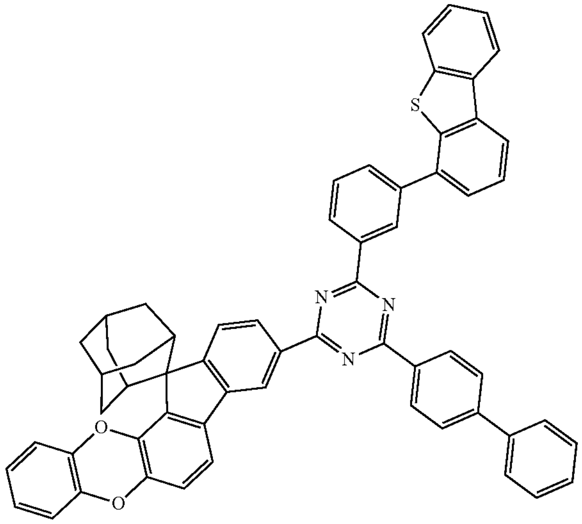
-continued
363
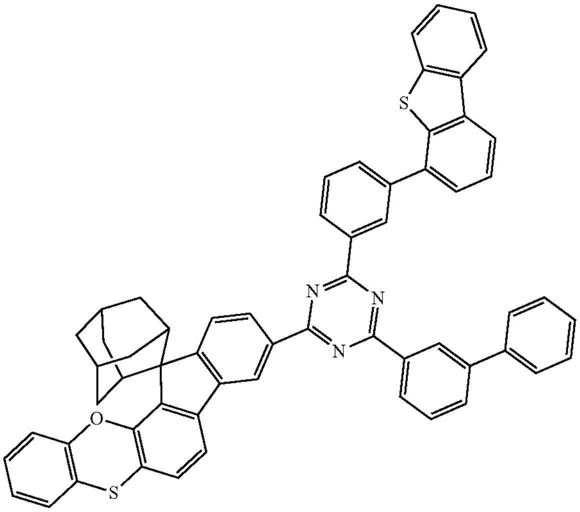
364
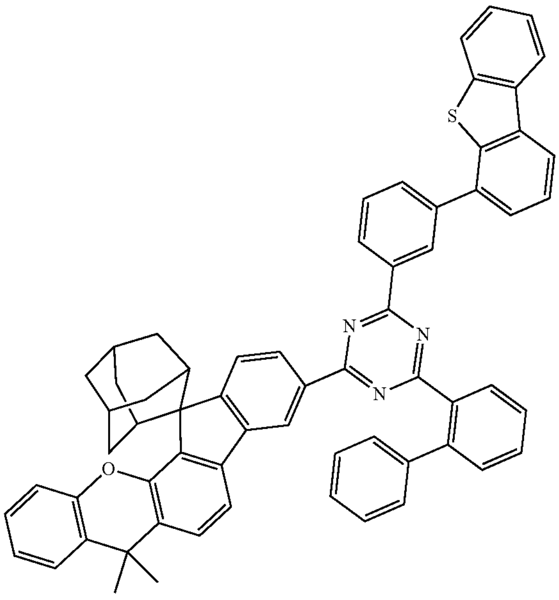

-continued
365
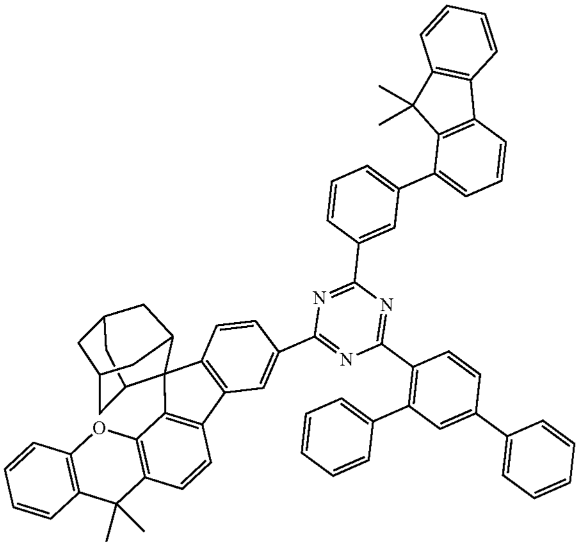
366
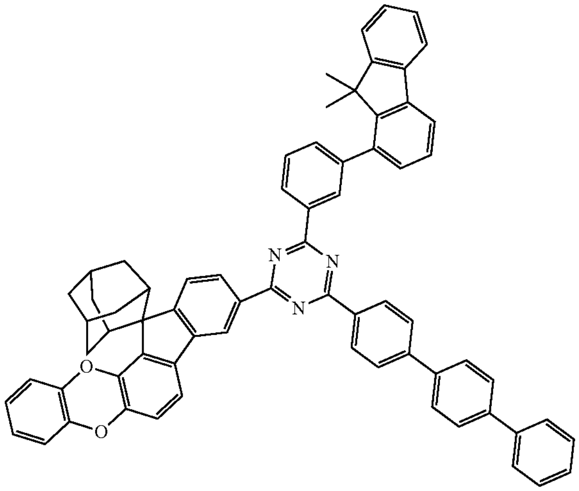
367
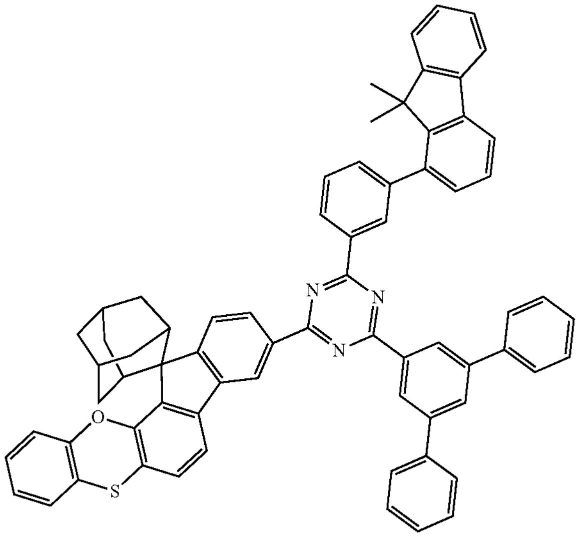
-continued
368
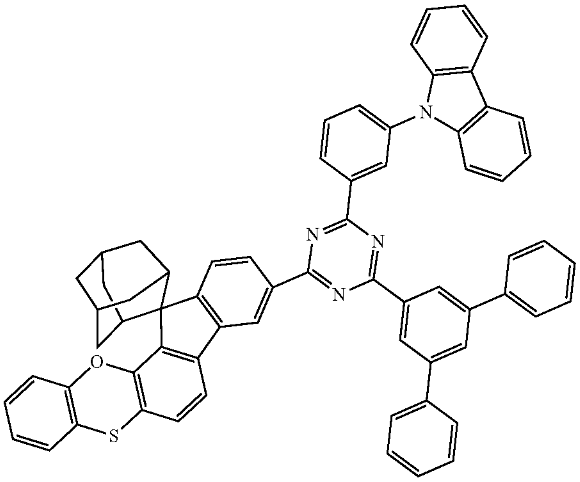
369
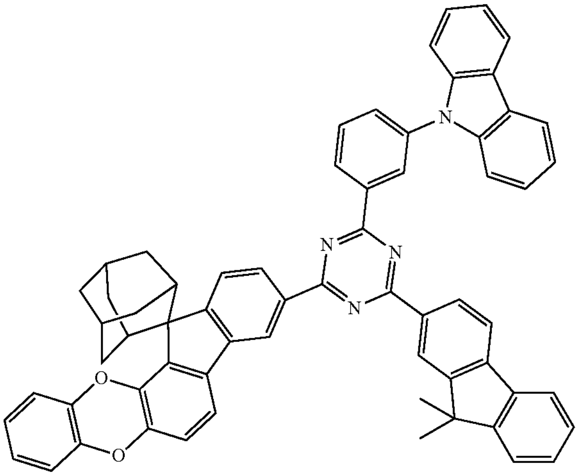
370
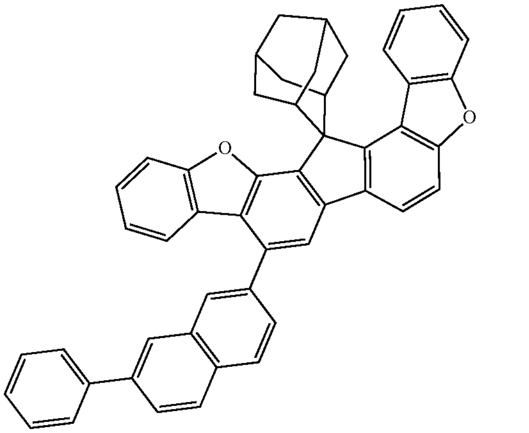

-continued
371
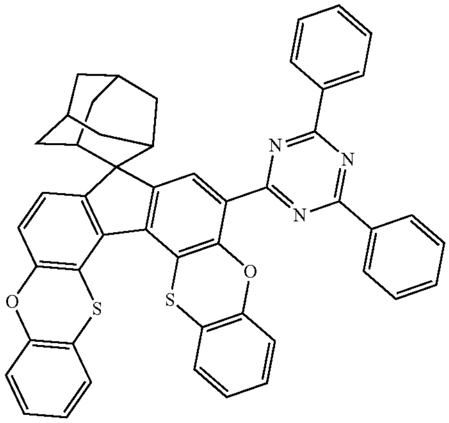
372
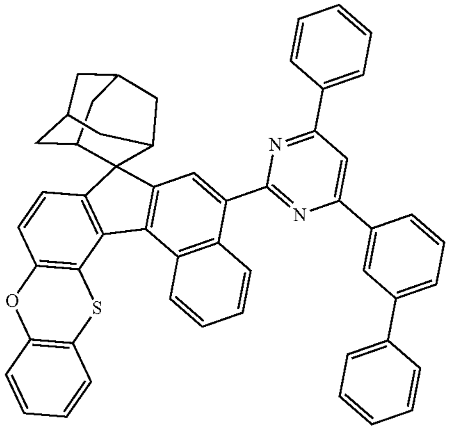
373
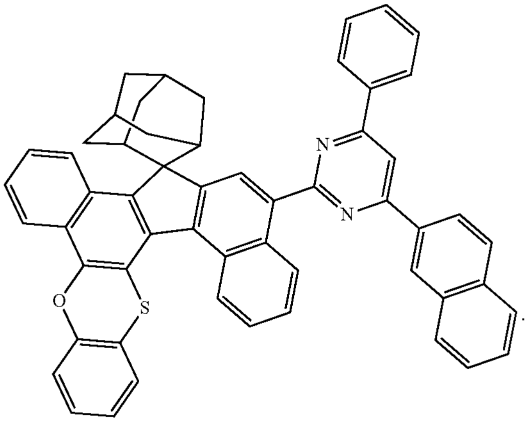
.
6. The electronic element according to claim 1, wherein the electronic element is an organic electroluminescent device.
7. An electronic device, comprising the electronic element according to claim 1.
8. The electronic element according to claim 6, wherein the organic electroluminescent device is a green device or a red device.
* * * * *